(12) United States Patent
Beever et al.

(10) Patent No.: US 8,158,356 B2
(45) Date of Patent: Apr. 17, 2012

(54) SCREENING FOR THE GENETIC DEFECT CAUSING TIBIAL HEMIMELIA IN BOVINES

(75) Inventors: Jonathan Edward Beever, Mansfield, IL (US); Brandy Michele Marron, Fithian, IL (US)

(73) Assignee: Agrigenomics, Inc., Mansfield, IL (US)

( * ) Notice: Subject to any disclaimer, the term of this patent is extended or adjusted under 35 U.S.C. 154(b) by 1493 days.

(21) Appl. No.: 11/549,888

(22) Filed: Oct. 16, 2006

(65) Prior Publication Data

US 2009/0239212 A1    Sep. 24, 2009

(51) Int. Cl.
    *C12Q 1/68*    (2006.01)
(52) U.S. Cl. .................................... 435/6.12; 435/6.11
(58) Field of Classification Search .................. None
    See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,683,292 | A | 7/1987 | Hahn |
| 5,498,521 | A | 3/1996 | Dryja et al. |
| 6,013,444 | A | 1/2000 | Dau et al. |
| 6,225,093 | B1 | 5/2001 | Grant et al. |
| 6,306,591 | B1 | 10/2001 | Cockett et al. |
| 6,759,192 | B1 | 7/2004 | Blumenfeld et al. |
| 2003/0203372 | A1 | 10/2003 | Ward et al. |
| 2006/0063191 | A1 | 3/2006 | Sutherland |

FOREIGN PATENT DOCUMENTS

| | | |
|---|---|---|
| WO | WO 93/16094 | 8/1993 |
| WO | WO 02/46465 | 6/2002 |

OTHER PUBLICATIONS

Marron et al. (Jan. 2005), "Mapping of the locus causing tibial hemimelia (TH) in Shorthorn Cattle", Plant and Animal Genomes XIII Conference, San Diego, CA, IDS reference.*
Everts-Van der Wind et al. (2004) "A 1463 Gene Cattle-Human Comparative Map with Anchor Points Defined by Human Genome Sequence Coordinates," *Genome Res.* 14:1424-1437.
Lapointe et al. (2000) "Tibial Hemimelia, Menengocele, and Abdominal Hernia in Shorthorn Cattle," *Vet. Pathol.* 37:508-511.
Marron et al. (Jan. 2005) "Mapping of the Locus Causing Tibial Hemimelia (TH) in Shorthorn Cattle," *Plant and Animal Genomes XIII Conference*, San Diego, CA.
Ojo et al. (1974) "Tibial Hemimelia in Galloway Calves," *J. Am. Vet. Med. Assoc.* 165:548-550, p. 18, line 5.

* cited by examiner

*Primary Examiner* — Stephanie K Mummert
(74) *Attorney, Agent, or Firm* — Greenlee Sullivan P.C.

(57) ABSTRACT

The invention provides methods, materials and kits for analyzing DNA samples from bovine to determine whether the animal is a recessive carrier of a genetic mutation that is associated with tibial hemimelia. DNA-containing samples are analyzed by genetic testing to determine whether or not a deletion mutation is present in one of the alleles that encodes Aristaless-like4 (ALX4) protein, wherein the deletion mutation is associated with tibial hemimelia.

24 Claims, 3 Drawing Sheets

SEQUENCE LISTING

<160> NUMBER OF SEQ ID NOS: 103

<210> SEQ ID NO 1
<211> LENGTH: 160958
<212> TYPE: DNA
<213> ORGANISM: bovine

<400> SEQUENCE: 1

```
atgaaatcct tgctgggtac aataatctgg gcggtaggtt attttcttcc atcattttaa      60
gtatgtcttg ccattccctc ctggcttgaa gagtttctat tgaaagatca gctgttatcc     120
ttatgggaat tcccttgcgt gttatttgtt gttttcccct tgctgctttt aatatttgtt     180
ctttgtgttt gatctttgtt aatttgatta atatgtgtct tggggtgttt tgccttgggt     240
ttatcctgtt tgggattctc tgggtttctt ggacttgggt gattatttcc ttccccagtt     300
tagggaagtt ttcaactatt atctcctcaa gtatttctc atggtctttc tttttgtctt     360
cttcttctgg aaccccctatg attcgaatgt tgtagcgttt aatattgtcc tggaggtctc     420
tgagattgtc ctcatttctt ttaattcgtt tttcttttat cctctctgat tcatttattt     480
ctaccattct atcttctaat tcactaatcc tatcttctgc ctctgttatt ctactatttg     540
ttgcctccag agtgtttta atttcattta ttgcattatt cattatatat tgactctttt     600
ttatttcttc taggtccttg ttaaaccttt cttgcatctt ctcaatcctt gtctccaagc     660
tatttatctg tgattccatt ttaatttcaa gattttggat caatttcact atcattattc     720
ggaattcttt atcaggtaga ttccctatct cttcctcttt tgtttggttt ggtgggcatt     780
tatcctgttc ctttatctgc tggctattcc tctgtctctt catcttgttt aaattgctga     840
gtttggggtg tcctttctgt attctggcag tttgtggagt tctctttatt gtggcttttc     900
ctcgctgtgt gtgggtttgt acaggtggct tgtcaaggtt tcctggttag ggaagcttgt     960
gtcggtgttc tgatgggtgg agctgtattt cttctctttg ttcagtcgcg ctgtggggag    1020
ggagggaggg atgctgcaaa caaataacac tggcgtgtgc tcgcagtgcc tcagccacac    1080
tgggtctgcc cccgctcacg gcgcgtgtag cctccctgcc cacactgctc gggctctagg    1140
ttgttccgcc gggaacaatc cgaggctggc cctgggttgc atgtacctcc caggtccaag    1200
ccgctcaggt tcaggcactc gggtagtcct cagaggcgca gactcagttg ggcctgagtt    1260
ttgtgctctt cccaggtccg agcagctcaa gtgatgaggt gtttggcgag cgccaatgct    1320
gcgacttatc gcctccccgc cactcggtta tctgggtgta aaaccggcgc atcttctcag    1380
gcagatgtta accgtccaga cccccaagaa gttttagtta gcaaagaagc ctgcttacag    1440
ttttatagat aatgtctctc tggggctgcg attgccccct tccggctctg gctgcctgtc    1500
```

```
accggagggg gaaggtctgc agccggctat ctccgttcag tcctttgttc cgtgcgcggg    1560
cctggcggtg tcttaggttg gggctggctt ttcgcgtggt agatatccca cagtctggtt    1620
tgctagccca aattatttcg ctcagatagt gctcagggta ttcaggccag attcttactc    1680
taagcgatgc agcccgcgcc gcgcctccct gcccagcccc cgcttgctaa tggcgcgtgc    1740
aggcgtctgc gctgcttctc cgctgaggga gttaccgtag ggctcgcaat cttcgagttt    1800
taattgttta tttatttttt cttcctgtta tgttgccctc tgtgcttcca aagcttggca    1860
cagattcggc agtgagaagg tttcctggtg tttggaaact tctctctttt taagactccc    1920
ttcccgggac ggaactccgt ccctccctct tttgtctctt tttttgtctt ttatattttt    1980
tcctacctcc tttcgaagag ttggattgct tttctgggtg cctgacgtcc tctgccggca    2040
ttcagaagtt gttttgtgga atttactcaa cgtttaaatg ctcttttgat gaatttgtgg    2100
gggagaaagt gttctccccg tcctactcct acgccatctt ggctcctccc aaatgtcaat    2160
ttctttagtc ttttttctctt ttaaaaattt agctttacag atcctgtttg gtttttaatt    2220
tgtgttttttt tttaattact taattacttc tatgtttgaa tttattttgt tgtgataata    2280
tctttttttta tgatatgtaa ctcattaaaa tttgtaaagc tcatatttgg atacagcttt    2340
tgttccctta gccccagttt tgttatacat gaaaacagta tgttttcaca ctgtgggtaa    2400
tagacaattg ggtggtataa tcattgtagt aggttatggc cagtatttta aaaaacggtg    2460
ataggataat acaagaatac agtgttcatc acatattcta tggcaaatac tgtgtactaa    2520
ggttaaataa gcgtcgtttt gtgaaactta tttcaaatgc atctgtgtct atgttagatc    2580
acaatacaga atgttgtttt attataggtt ttagtaaaaa aaaaaaaaag agcttaaacc    2640
actgtattaa aaggcagttt gtctaacatt tagtaaagat ttcaaacctg gctgcctaaa    2700
ataaacatgt gagggcttg ctattttgac acattctctt tttttttga cacattctgt    2760
gaccttattt taggcctgct gatacagccc tccagtgctg ggaccaagga ctctgtttta    2820
acaaactcta cctgtgtgat tcttacagtt cgggttttg agaaccactg attcaggata    2880
tagatagacc ttgagagcct gttgggctgt tgtgacacgg ggcttgtgga gagtacggct    2940
ccttgcatgc atctgtccca aggccgcctc ttttctagct ccggggggga catggggaag    3000
gaaggaaagc gatcagatgg gtccggtggt agtagggggtc ggggaccgcc tgtaaacatc    3060
ttgttcgttg ttaggatgac agaaaacatg aaatagctct aatgcctgca tttctgtcat    3120
ggaatcgatt agtgtatatt gaatggctaa tgtatatacc ccaaagatga ttatctttaa    3180
gcttaaaatg tataaacttt catacactag tccatgacaa tcatgttttt ttgatacatc    3240
ccagaccatg gtctcagata cagcagatac aagttgaaat cattaatgat cattcagcac    3300
attttacccc caaagctgat aatgattgca acattcaggg cttgacagga ccctactaag    3360
ctaggcagga agcagtttta ccatgtaggc atgattggag agaactccat ttagcaaagt    3420
gaaaatggtt cataaaccct aagatggtct atgagctttt caattgtttt cctttatatt    3480
aacgtgtgct cggtcactca gttgtgtctg actctgcaac cccattgact gtagcccacc    3540
aggctcctct gtacatggaa tttcccaggc aagaatactg gagtgggttg ccatttccta    3600
ctccagggga tcttcccaac ccagggatca aactcgtgtt gcttgcatct cctgcattgg    3660
caggtggatt ctttaccact agcgccacct ggggtttgaa taacttttct gaaagatcag    3720
agactagaat gagaccattt tgaagattgg aatcttgaca caaggaatgc cgaagtcact    3780
tgttgcagtg acgtgtctgt gatagatgaa ggaatcacgc tcaggtgtgg gtaggcatca    3840
ggtgttgggg ggcttgtttg gtaaggatct taatttgtgg tctacagggg cactttgcat    3900
```

-continued

```
tttcagctga gggctaaaga tttcttttta tgtctctgtc catgacgcat ggctgtttc    3960
acttttttct tgctatgtag caaaccacca caaaccttac aaacagcagc aacaatcgtg    4020
tgctcgctca ggattctgcc gtctctgcag ggctcgttgg ggatggttcc tcttggctcc    4080
acgtagtctc tgcagtcttc ctgagcttcc tcacagtgtg gccctggcc aatggctaca    4140
gggtctttta aagcctggtc tcaaaccccc cagaatcttc cctttgccac tttctcttgg    4200
tcaaagcaag tcccaagtct agcccggatt cgggtggaag ggaaagagat tccacgccgt    4260
gaatggacaa ggggcatgca cattcatcag tgggaagaat gtttagcgtc tgtctttaga    4320
gacagatcta cctcgctggc cttgcttttc ctccatctct cctttcctcc ttccctgttt    4380
ctttcttcat ttctcccttc catcaaaatg tgccaactat ccccttatta taaaacatca    4440
atatatcttt atttaaagat tagtcttttt ttctctaata ccctttttccc ctttcttgat    4500
attttcctag tggtattttt acattataca ttttgttata gttttgggta tctcattagt    4560
atctaaattc ctctaaggta gatctttgct ttccttcttta ggttctctat gaggtttgaa    4620
tgaatgaatg aatgaaaact ttagtatatc aaacaaaagg ccagtttgtc cagatgaagc    4680
atcagttttt gttaggcaag tatttaaaaa acaaaatgaa actgtccttt ggctgttcca    4740
cttctaattt tccttgcttg gtcagcgctc ttcttcttag gcctgatatt aaccagctta    4800
tgctttcaga gaatttgtat ttatagaata tattctatag taaatatata gcatattttc    4860
acatgtacaa atatttgttt actttatcag ttcagttcag tcattcagtt gtgtccaact    4920
ctttgtgacc ccatggacta cagcacacca ggcttccctg tccatcacca attcccagag    4980
cttactcaaa ctcatgtcca tcgaatcagt gatgccatcc aaccatctca tcctctgtca    5040
ttcccatctc ctcccacctt caacctttcc cagcatcagg gactttttcaa atgagtcagt    5100
tcttcgcagg gtcaaatgta ctggtccttt cggggggtcat ctgtcaccct gaaggcttca    5160
ttttcctctc ttctccgctg gtaaccagga gtgtgaggag gaggctgtcg gggtcattat    5220
gtgcgcgtcg gtcaagtaca acatccgggg tcccgccctc atcccgagaa tgaagaccaa    5280
gcaccgcatc tactacatca ccctcttctc catcgtcctg ctgggtctga tcgccacggg    5340
catgtttcag ttctggccgc actccatcga gtcctccggc gactggagcg tggagaagcg    5400
cagcgtccga gacgtgccgc tggtcaggct gccggccgac agcccggtgc ccgagcgcgg    5460
cgacctcagc tgcaggatgc acacgtgttt cgacgtctac cgctgcggct tcaaccccaa    5520
gaacaagatc aaggtgtaca tctacccgct gaagaagtac gtgggcgagg cgggtgtccc    5580
ggtgagcagc accatctccc gggagtacaa cgagctgctc acggccatct cagacagcga    5640
ctactacacc gacgacgtca cccgcgcctg cctgttcgtc ccgtccatcg acctgctcaa    5700
ccagaactcg ctccgcgtga aggagacggc gcaggcgctg gcccagctct ccaggtatcc    5760
gcaggtctcc cagaaactag gggcagggga gggcagagcc ggtttccagc cggcggctca    5820
tctcctgtct caggtgggca cgtgggtgag ccgctgactt ggaggaggac ccgcgctgcg    5880
ggcaggcagc cggtctctgc accaccctct gggccactg ctgtgggttc ccaacttctt    5940
cttcttcttt tttttttttt aattttattt tattttaaa cttacaaaa ttgtattagt    6000
tttgccaaat atcgaaatga atccgccaca ggttcccaac ttcttaacat ttagaagcta    6060
aggagggctc atcttcccaa tccttccttt taaatgtaaa tgccttttccc cacctcccct    6120
ctttattact cacatataca tattcactat aaaaagcttg aaaatacagt taagcaaaaa    6180
gaagaaagtt agagtcatcc cataagcctg cttttgacat aaccattaat attttgatgt    6240
tgcttctcag tcgtttctgt ataaaacatg tacaggggca cgcatagatg cattttagta    6300
```

```
tgtatatgca catgtatata cacatatcgg agaaggcaat ggcaccccac tccagtactc    6360
ttgcctggaa aatcccatgg atggaggagc ctggtgggct gcagtccatg gggtctcgaa    6420
gggtcggaca cgactgagca acttcacttt cacttttcac tttcatgccc tggagaagga    6480
aatggcagcc cactccagtg ttcttgcctg gagaatccca gggacggggg agcctggtgg    6540
gctgccgtct ctggggtcgc acagagtcag acacgactga cgcgacttag aagtagtata    6600
tacacatgtg tagttccctg gtggctcaga cagcaaagca tctgcctaca atgtgggaga    6660
cctgagttca atccctggat agggaagatc tcctggaaaa ggaaatggca acccactcca    6720
gtattcttgc ctgaaagtc ccatggacag agaagcctgg tgggctacag tccatgaagt    6780
cgcaaaaagt cggacacgac tgaacgactt cactttcact ttcatacaca tatgtgtatg    6840
tataacattt tgctcacaca gcaaagcgta ttcattttgc tgccttttcc ccttcattta    6900
ccatgcatgt gtttccaaat aatttcatct ttgtatgtca gtgctgtatg acatatacac    6960
agaatgtata tgtattcgtt tttacagttc tgtatgggac tccattttgc acacattccc    7020
taatgtcctt aattagcctt ctgtgtttct ttgtgttttt gtaaccaaat ggtgaacact    7080
gcagtagcgt tcagattttc atcagcgtaa gcagttctgc agtgcaccag cttggaggac    7140
acatgccctg gctttccttt ggaggagcca agccagtgcc cggagcgctg ttgcgatctc    7200
caggcatgca gtttgccttc ctgagaagtg accctgttac aggtcaggga tgcttgctac    7260
ttgttgtcca gcttcctttg tggctcatat ggtgaagaag ctgcctaatg caggaggcct    7320
gggtttgatc cctgagtctg gaagatcccc tgcagaagag aatggcaacc cactccagta    7380
ttcttgcctg gagaatcccc atggccagag gagcctggtg ggctgcagtc cgtggggtcg    7440
cacagagtca gacatggctg agcaactaac actttgactt gtcatccaga aactgacttg    7500
cctgtttctt cacagttgat gcgtgaattc tacatgttta ctctcttatt aggtgggata    7560
gaggtaccaa tcacctcctg ttcaacatgt tgcctgaggg ccctccagat tataacacgg    7620
ccctggatgt ccccagagac aggtaggtgt atttggggtt gtccacctga tgggtttctg    7680
aggattaagt caatgtagga ccctttttgtt catgtgaaat catatttcta agcccactaa    7740
gacataactt tgtaatcaga attgtttgtt caagtgtaaa attgtcctcg gtcttttcct    7800
ccctgagacc tggaagcatt gaaacctgcc agaatctgtc ccgggaaact aatggagggt    7860
taggttccag tggagcatct tagaggtctg tcttgtcttc ttagtccggg ttatgtgctc    7920
ctgagcacac ggtctttccc ctaaaaggcc tggttcatat cactggcttg tgtcagctct    7980
ctctacattt gggagcatta agtagagtct cagctcctga ggggagcagg cgtggccgtg    8040
tcattggagc ctgtaacgtc cgggaagtga ggcactctaa gtaccgctta ctctcttctt    8100
tccttccttc ctaatgaaac ttccaaacag gcagaagtgg catggggtgg ccacgatggc    8160
ggttcaagtt caggtgctgt gcatttggcc ctgttgtacc aactgcgtgg cttcctggaa    8220
acctcagaag ggaggtgccc ctaaggttcc tctcctagtg cttggcctga ggctccgaag    8280
agagcgggaa gtgtgggccc agcatgaggg tcctgggcag cagccacggg agggattac    8340 tgcaagttca gatatgaact catttatacc cagctttgtt gcagttgatg tttaattctt    8400
gaaatcattg ttactgaaag aggtgagaac agccttaggc ccgctgtggt ctctgcttac    8460
ttgaggccaa catcgtcatt tgtgaaaatc tacacttagt actgcttttc cccagaagat    8520
taagtctaag ccctctttgc ttttaagtgt ttatctagag tcagtattga gtttctatct    8580
ggaaagatga tcatcactag aaaagaccct agcgccatcc ctcagctttg gtgtagaaac    8640
cattttggac ggtagagggc agtcaggcca cacaagttct gtagaaaccc gctgaacaca    8700
```

```
aggcggtctc tggtttggct cttcgcccag cgctccggag tgcgttactg tctatgcgtt      8760
tgcttgttct gggaaagtga aatgtgttag gggacagaaa agggaaggca gagaggtgct      8820
gggaatgcag tgtcttcacc tgctgctctg ggtttagttt gaggagggtt cgtttctgtt      8880
tgggacatgt cggttcttgc tgacgctttg gtatttgtat ctgactggga gaaagatttc      8940
atttttatcg agtgcacatg ttacaaggag tttcatttct ctgcaggaaa gtgtcaagta      9000
atcaggagag agttgaagtt cttgctggtg cttaggtgtt aaggatcagg aagggtaaat      9060
cattttccct gtgcgtgtat ttttggaagt gattataggc agtcctgtag caagtaatga      9120
atcatcaaat agtcctcctt tatctttcca cgtgggaaat ttcattttga agccgaggtg      9180
gtcttcgact ggttggagta aggaatagta gatttgtttg ttaattttc tgacccttg       9240 tccttgctcc tggattcaga ggaggtaaga accatgcgtg taggatggtt ttagcagaag      9300
ctgcatatct ggttattcag aaattagaaa acaggctaga tttagaccgt ttctaagatg      9360
cccctgaaat ctaaagtcat aagtgtgatt tttttttttt tttttaagaa ttatctgact      9420
cagaaaaatg caaggaccag gactaaagca gatgtcagct cagcaaatac atctttcatg      9480
ctgtgtgaat ctgtgtttct ctttcagttt ttgaaaatcc tatgtgtggt acacatatac      9540
cttctgggta caagattgaa acagtgtgca agtatacaaa gagtaaagtg taaaaatatg      9600
ttttcaaatt ttcctctggt tttactcttt tactgagagg taatcattgt tctcaaatac      9660
tgtgtgtttt ttgagtcttt gatggatttc tagtcaaaca cccacatata ttcacctatc      9720
cattttaagt caaatgatag caaattatac ctcttcaatg cctgacttta ctgatctttg      9780
ttttctcagc tatattctgt aattttatta ctactttaga ttttattat cctttctttg       9840 caagtatctc tctcaaattt ctacttttgt ataggtgtat atttatttaa acttcttagg      9900 gaaaattta aacctgtat aaaagaagtg agccccacac aaccactgtc cagctttgtt       9960
aattgtcaac ttgattcatc tatgctccta ccttcttccc accagattat ctagaaacaa     10020
atctcagatg ttgtatcatt atgtccgtaa atatttccat ttgagactgc agaagaagtt     10080
tttgtgtgta actcagtggc tcagtcggta aagaatctgc ctgcaatgaa ggagacccct     10140
ggttctatcc ctgggttgga aagatcccct ggagaaggga atggctaccc actccagtat     10200
tcttgcctgg aaaatcccat ggacagagga tcttggcggg ctgtagtcca tggggtcaca     10260
aggagttgga cacaattgag tgactgatac tttcaacttt tttcaagggc ttttaaaaa      10320 atataactac agcactaata tcatacctac agcaattaac acttagttct ttaacatcac     10380
tagatattca ccaaatatct agccgttgct cagatatata tgtctcattt tcttttttta     10440
cagtttgaat ctgtaaacaa atgaggatag ccagtagagt tggtcagttt tttttttttt     10500
gcaaaaccta aaacttgaat cttttgtattt gagggattcg caggcctgat taaaaggaag    10560
caaaagatac acttgcagac aaaccgtgtt tagctctgtg gatactcaga tgggaggagg     10620
cgagctgtga gggcatctgg ggcagaccca gcgtagggac gagggtccac aagacaggga    10680
ggaagagggc tcagtgatgt ccctgggtct tcgagtcccg ggaagtgctg aagatgctgg     10740
cggacactcc cagcgacgga gcacctggcc tggggtgagt cgtggtgctc acagctatgc     10800
tttcttaggt gcaccgttcc cgttcagtct ctctcagctt tggaacagat ctccgatttg     10860
ggaaaacaga acgcgcttct cagcaattca cttttcagtc aatgtaaaac acatgtgctg     10920
taaagcaagg gaggcttaca ctattttctc cttggtaatg ttcaggaaag cttggcagaa    10980
gaagatgcgg tgatttggag tggaggtctt gtcagcagca gggccggtgt gaggcttgtt    11040
tgactaattg cagcggtggc tcctcctgag agctccagcg agattgcatg tgcgtgatct    11100
```

```
gtgacatgag gcatgcttcc ggttacctgc ttgcctcctc ccagggctta accccctccc   11160
tcagccccgg ggctccaggg agagagtaac agtgaaagtt ggtgtcatgt acacctgctt   11220
cctcaccaca gatgctcgcc ccttcctctg gggcgtgggt gtaattacat cacccaccac   11280
gccgcttacc tgggccgcct gatgctggta tattggatct gtgtttcctc ctctgcacat   11340
cgatcgtggg ggcccctgca gtctgcttgc catcatggtc atggaaccca cccaaattca   11400
tgttggacga gtcactgcc gaatgctaat caggaaaaat gagaccgtat gttggtacta    11460
cggctagtca ttaagtttta cagagcggac tggcagctgg agaggtgttc cagcctgcac   11520
attacctccc taaccagttc ttggtttcat aaagcttaaa caaacagatt gggatttcca   11580
ggggtggttt ggaaatcttt gaacttaaac tggtcatgta agaagggaat gtaggctgtc   11640
atcagggcag ggaggggatt ggtagcaatc aagattgcaa aaaatgtggc tttgcagttc   11700
atacattttg gctcagactg tgccgcgcat ggacctggca gcactctgcc ccagtaagtg   11760
atttgatggg ctcgggggcc ccccgggaca caataaccat aaacgttggt gtgatgtaca   11820
cctgcttcct ttctaatgaa gtgtcactgt attacttgct ggatccagtt aaagcagcgt   11880
gttcatggtt ttctaattaa ggagaataaa agctcgtgtg ggtggacttg caggagaagc   11940
actcgaggtc aagttctgga ttctgcttcc tgtggaagca tggggttgat aagactgagt   12000
agctggaatg ggtggtgaga gctggtagag gctacacagt gcacgaag ctttgggacg     12060 acagtgaaaa gaactgatct tgtgggaact ggagcgggct ggggcgcagg cagcgtgaga   12120
tggggtactt tgccgtcacc gtggcttttt ttttttttag ctcattgtcc cctgagcttc   12180
cgtcagtggg acggtaagtg actgccccag ccagtcctgt tgttattcgt attactgtaa   12240
atgtgtttaa gagtcagggc ctcctcggtg gctcagatgg taaagattct acccgcaatg   12300
cgggagaccc tggtttgatc gctaggttgg gaagatcccc tggagaaggg aatggtaacc   12360
cacttcagcg tccttgcctg gacaactccg tggacagagg agccttgagg gctacagctc   12420
atggggttgc aaagagttgg acgtgacgga gcgactaaca ctaccacgtt caccgtctgt   12480
gacttctcgg agaggtgaat gggatccaaa caaggtagca gaggggccgt tcgcaggctg   12540
tcctcctggc tgtgctgtat tttaaaatag ggaaagtaag gacagactgc ttaggacccc   12600
agaggaaggc gggtgactca ggacgaggat gcagcgagtg cccctgagat gctgtacaac   12660
gtttagcact gtgtctttct agaaaagtga cttggtaaac atcagctgtg gctgatactg   12720
ttatgaacat ccagctgccc ctttccacag agcttatcag aacgaagact gtctttcttt   12780
ctcaccgttt gacaaaaccc tttgtttttc agggctctgt tggctggtgg tggcttctct   12840
acgtggactt atcggcaagg ctacgatgtc agcattcctg tctatagtcc gctgtcagcc   12900
gaggtggacc ttccggagaa ggggcccggg taaggcgcct cgggcacagc cagcggtgct   12960
gagagatgcc agtgagggcc cggggggcgg gttgcactgc agtcgaacca tcagtgacag   13020 gccgggtcc ttgagggtcc gtcattcctg tcccacacca accttattta ccttcagtt     13080 ctctctctgt ctgtctctct tcagtcagt ttgcagcgct gtctaccaag ctccccaaat    13140
cagaaatcta gttgctgtcc ataagtcttt cctctccctt acttcctgtg cggaattgca   13200
ggcttccaga aggaaagcag gtgttcagca tcagttcagt tcagttcagt cactcactcg   13260
tgtccgactc tttgtgaccc catgaatcgc agcacgccag acctccctgt ccatcaccaa   13320 ctccccggagt tcactcagac tcacggccat agagtcagtg atgccatcca gccatctcat   13380
cctctgtcgt cccccttctcc tcctgccccc aatccctccc agcatcagag tcttttccat   13440
tgagtcaact cttcgcatga ggtggccaaa gtactggagt ttcagcttta gcatcattcc   13500
```

```
ttccaaagaa atcccagggc tgatctcctt cagaatggac tggttggatc tccttgcagt   13560
ccaagggact ctcaagagtc ttctccaaca ccacagttca aaagcatcaa ttcttcggtg   13620
ctcagccttc ttaacggtcc aactctcaca tccatacata accacaggaa aaaccatagc   13680
cttgactaga tgaaccttg ttggcaaagt aatgtctctg cttttgaata tactatctag    13740
gttggtcata actttccttc aaggagtaa gcgtctttta atttcatggc tgcagtcacc   13800
atctgcagtg attttggagc ccccaaaaat aaagtctgac actatttcca ctgtttcccc   13860
atctatttcc catgaagtga tgagaccaga tgccatgatc ttcgttttct gaatgttgag   13920 cttaagcca acttttttcac tctgctcttt cactttcatc aagaggcttt tgagttcctc    13980
ttcactttct gccataaggg tggtgttatc tgaatatctg aggttattga tatttctccc   14040
agcaatcttg attccagctt gtgtttcttc cagtccagcg tttctcacga tgtactctgc   14100
atagaagtta aataagcagg gtgacaatat acagcattca taaatcctgt catttgtact   14160
gttttcccct gaaatcgaag ttcccatgca ccagccaagg gccagccttt caaagaagag   14220
agccgccagg cccactgagt taagtctgtt ctgcacgggg cactgtgggc agctaacagg   14280
cggaggttgg tgatgcccta aacttctgcc atgcccaggg cggcccctca ccacaaagca   14340
tcattgggtc caaatgtcag cagtgctgtg gctggagaaa gcctggggga cacagggtga   14400
gcagtcttaa gatggctcag actaaactct ctttatcatc tactctcccg agtgtaatct   14460
aggtctctaa tgttggttga ggactggcac gtcccttaag atttaatcca gggaagaaaa   14520
caggctgaaa ggaaaagact gagagagatt gaaacgaagg agagcaaacc actctgaaca   14580
gtacaaatta ccttcaaata agtttccaag aattacaagc ttgctctgtt ggtggtattt   14640
tcttggtaac ttgatctcta attttttatgt gtaactagac tgaaatgact atccttagat   14700
ggtttaaggt tgctgttgat cttagagtc ctgagactct agaaactaga gaatcttaag    14760
cagtctgtct tccagagcag cagcaggatg ctcaagacac aaggggatgg tcctccccgt   14820
ggtggacaag cggtggattt ctgtggcccg atgcggaccc accccactcc gtttcccctc   14880
cagggtttgc agtgggccc tgtagttgtg ctgtttcctt tacaaataac actcctctgc    14940
ctcaggagag aaaaaagaaa agcaaagaca ggctctaggc tcatcacact ttccagggat   15000
ctgggaggag gcagtctggg tgacctcacg gcagcatttg gaatctgttg ctctttgtga   15060
gagttgattt ttaagggaat tcccacatct cttgagggct gcgtagagta gcaagggctt   15120 tgttttatt tttatttaa atgtctctca atattgtcca atgggaagct gaggattgtt    15180
gctattgata gcttcttctc acagatgtgt tggcctcagc tggaattctc gtcatttctc   15240
tctctaaaag gaactaaatt gggagtttac aacggttact atggagggaa acttggagtt   15300
ctcagcatga ttttgctgaa ccttcgatat cagctctgct gggaagaaac atgaaagtca   15360
tagctggtca ttttagtcct cgaaagaaaa acaaatccac cttaagattc tgtttgctta   15420
aaactaaaat gggcctactc caccagccca ccatctgcca ggtcagagcg agccagcatg   15480
caggcagggg gaacattttt agactcttgt tcacatctgc acatttatgt agaaaatggt   15540
ggtgttgggt ggggacccac tgagcgtggt gactaagtgt ctacaataga actgtgtttc   15600
gtaacagcaa aatcagccca gagtctttct ttactccaga gtttctttga gcaccacgtg   15660
ttagcatctg tacttgtttc tccgtcttac gtagatggc ccctctctct ctgtctatgt     15720
gtattgaaaa ccatgccttc ccgtcgctct ctcctattcc atccagtgct gcagggatt    15780 ctggctctct ctcttttccgt agctgtaatt tccttctcgg acagtgagga gtctagctcc   15840
cgttatcccc tgtatcttgc ttgatcaacc ctgtcgtgcg tgaccagagc cctgtggtag   15900
```

```
cctctgcccc tcaccgcgca ggtgtctatg cgccccactt gggctctgac cccctgtgcc    15960
gagctcctgc tteccgtcgt cacccegggg caggccccct cctcacatat cctgggctct    16020
gaccccccca cactggaggg gtgccgcccg tgccatcacc ctccccgtgc gccttcagcc    16080
tgggctgccc tcctgccctg acttggcctc cgcatcgcag gtggggaggc catgactccc    16140
tctgtcccgt ccccgctccc tctttcaggg atctcacagt ctgggccagg ccacctccct    16200 gctcttccccc caagaagttc tcccccagat gaggactaga gcactcccag tgggccagcc    16260
ccaccgcacg gaaacgctgc ctcccctcca ggacgccagc actgcacacc cgcctgcagg    16320
gaccccctcg gacaccagcg tggccgctcc tgttcgaggc agcctggagt gccagttttg    16380
tgttagcggc tctacttaaa taggaagtct ccagggaccc agcaagtccc agcgctctgt    16440
ggcagctgcc gtagagccag cgtcttgggg actggaaagg tctttagagg ccgtttagct    16500
ctcactttgg agaaggaaat ggcaacccac tccagtattc ttgcctggaa aatcccacag    16560
atggagaagc ctgagggct acggtccatg gggttgcaaa gagtctgaca cgactgagca    16620
actaacacta gttctgactt aatgtatacc ttgttactgt gatttcttcc tgaaaagttt    16680
tctgatttgt ggtgaaaaag actcaccacc tcacaagaca gctcatcttc aaatggcctg    16740
agttgttgag gtggtttccg tgcttgcgtt gagagtttga ctgtccatct tcctcctgtt    16800
ctaagcagac gagcttgatc acagaagtcc tccctttggg atgcctgaag aagactccct    16860
atatgtgatc ttcccatcat acctctcccc tctgaaaact gatgatttta cgaaagaaaa    16920
aatgattgag gctgagggct gggggtagaa ttcaagagtc tgtttcagtg gctagcaggt    16980 atgggtcac acacagtcgg acacgactga agtgacttag cagcagcagc aacagcagca    17040
gcagccaatg tattgttcag caaaatgcaa ttgaaggaga agttgtccag gatgagagaa    17100
gccagtctgt acggctgatc caaactgtct cccgacgggc tgctgttcgg tgtcttttt     17160 acgtctgctc gcctttgccc tgggctccgg gtctgcactg ctgtctgggg cagctctctc    17220
aagcaggact ttcagtgagg aaatgatctg tgtttagtgg ggtgccgact ccacgtata    17280 gctgttgagc ccttgaaatg gggctaaggt gaccgaggaa ctggatttta aaactttaat    17340
agatttaagt ggtctcacgt ggctaattgc tattgaacag tgacgttcta gggggtctgc    17400
ttgtccctgt cttccctgcc tgcctttgct ttcagttcga ctgtagagag aaatgaccgg    17460
aagagatggt tccggggact tgagggccat cagctgtggt gtgcgctgct ccatttgctg    17520
gagtcgagct gatctgcagc tgggagagtg ttcatttcct cactccctgc ttgctctgtg    17580
tcttttgggc gtgacgctta aagcttggga aagataacac tctctcagag agtgatttct    17640
ttttggccac gggtagatgt gtaaggtgtt ctccagctgg accctccaat taagcctgag    17700
aaacgaaagg aaaataaagc aatttccctt tctttctctc caaagcaaga agaaaagaag    17760
gtatggggtt gggttcagac tagagggttt gagtcctttc tttctcactg cttcttgtta    17820
gctcccctgg tggccttgcc tagagatggc tgtcttgggt gttatccttg gtctgtacag    17880
tttgaggaag atttgagtcc tgcttctggg tttgatgggg gtttcatttc ttctggagcc    17940
tgctttctat cattccttc ttcttcagtg atccctgctg gttcctttgc tgaggtcgtg    18000
tttattgccc ctgtaacctc tctgccttgt gggaatcttg ccttctcgga gagaattact    18060
taccttctgg tctccccagt gagttcacat tttgttctc gtggagatct gaatggtgct     18120
agacccttgg aaatcctttc ttcagtctgt tctctctcac gcatccttgc tatccgatgt    18180
taagactggt tccatccatt gacaaagcca gttttttcca cttgttctcc acgaccaagt    18240
ttggtcttcc tgaatccatc tggccttgag gatgggggct gcctttccct ggagctcccc    18300
```

```
catagcatag ggtgcccgtc agcagccgga agtaggctgc tttcacggtc agtgctgtct   18360
gttaagaccc cttgttttcc tctttgaagg ttgcagcctg ctctcagctg cttttcagag   18420
cagagaactc agatcgaact aatgctaacg ttggatgttc ttccaaataa tcaaccagtc   18480
agtcagtttc tctctttaca cacacacaca cacacacaca cacatacaca ctcacactct   18540
taaagcatgc tccctaagct tggcctatta aagcatttc  ctcaaaacgt taagaacttt   18600
tcctaaatga acccttaac  aacagcatga tgcttcagca tgtgaatgag tcattgcttg   18660
ccttctcagc atgtataata gtttaaatat tcagcagtgc tgagtgtagt ttccccagaa   18720
gtcaaggacg tgagtgaaga tgggtgagaa agcactcgta gccctaagct ctagacccga   18780
agttggcctc accgtgactc atgcagcggc ggccagggtc ccagtgcccc ccgttttctg   18840
cttcgcaggc cgcggcggta cttcctgctg tcgtcccagg tggccctgca tccagagtac   18900
agagaggacc tggccgccct ccaggccaga cacggcgagg cggtgctggt gctggacaag   18960
tgcagcaacc tctccgaggg cgtccctgcc gccggaggc  gctgccacca gcagcaggcc   19020
tttgactacc cgcaggtgct gcaggtgagt gctccgcccg cccctctcag ggcccgggct   19080
ggggctgagc ccagccgaca ggcgctccgc tccaagctgc actcgtcaag ctccctgagc   19140
ggagagcaaa accggactgc tctccactgc tgccccgtgg acttctggga gcttcagggt   19200
ctgcgtgccg ttagtgcaaa gccgcttggc ccctgagcgt tccggctcct tccacgaagc   19260
tcatcttact gcaaaagac  acaccccgta gatgtacaga ggagccgtgt agtcaaagca   19320
ggcacgtgta ttttgctttt attcctgtat tccttatcca gcccagagga gcttgcttct   19380
ttaagctgca gcttgtatcc tccaactgag ccagctcgcc acggccacag ttagttcttc   19440
ctgggagtgg gaggtcttta ttttttgtta ccgttttttc tcttggtgtt tttgcctccc   19500
tacatgtgtc ctcctggtgt cgtgggagtg ccagcacttc gtaactgcag gcagagtagt   19560
cctgtattat acttctgtat tataagcagg ctgtttgata ctccaagagc caggggggctg   19620 ggaaagcaga aattgagttt tgttcactct gctgttgtcc agtcactcag tcgtatctga   19680
ctgtctgtga tcccatggac tgcagcacgc aaggcttccc tgtccttcat catctcctag   19740
agtttactca aactcattgc tatccaacca tctcatcctc tgtcgtcccc ttctcctccc   19800
accttcaatc tttcccaaca tcagggactt ttcaaatgag tcagttcttc atatcaggtg   19860
gccaaagtat tggagcttca gcttctgcat cagcccttcc aatgaatatt caagactggt   19920
ttcctttagg attgactggt ttgatctctt tgcagtccaa gggactctcg agagccccaa   19980
cagttcaaaa gcatcaggtc tttggcactc agctttcctt atattttaaa tcttttgttc   20040
gcttaagtat ttaaaacaca aatagttcag ttcaaggaga gatcttaagg agctggtgtg   20100
attgtgtgtg atttttattt tttcaaagtc tccgaagaga accggcctgt gctgggattg   20160
ttaaaatacc ttcaaaaagt gctgcatctc ctctggaatg tctgactgat aacagtggtg   20220
atgtgagcag gagtatttat agtaacctt  gtctagacag gaaaatggt  tatcagcaca   20280 catgcccaca tctggacgcc gactcttcgg ggccggctga gcgtccacct gcccctctgg   20340
gcgccatgac cggtgcccct tctccacccc ctgccctttc tcatcgcttt ctcctttatc   20400
cccagaggaa tttggcgtat tgagttactt catatttctt ctgaactctc cttttctcta   20460
gctttaaaga ttaagtattt ttgctttaaa atttttttt  ctgttttct  cctggagagg   20520 caaaaactgg aagaaacttg agtattagag acgggagctt tccttatttt tttcggttga   20580
cctattacaa ccacctttt  ttcttgtgca tctctccttt tcccaaacag gcccacatcc   20640
agtgggttcg agggagtgaa tgaggaagac ctttagtgag gtcttgcttt tgttcagtt   20700
```

```
gtatctaaat agagcctatc tgccttaatg tgttttcgaa ggcatagcat tcatgagatg   20760
aatgtcttct gtatacaaag cacactgctg gatgctgtgg gggtaggaag atgaaaggag   20820
atttgatgct ttctgtgtag ggggtcctct caagagcccg atatgcccag tccaaataat   20880
tctagtacaa ggcaggcaga agtaagtatt ctgagccctg ggaagccacg gtggatatac   20940
acagcaccgc agggctgaaa gaatccagtc cgtgggaagt catgctgttg agtttccaga   21000
ggaagacctg gaggtgggtt gtgaacattt tcagaatcca agcagcggag gcattgcagt   21060
gacactcaag agtggaaatc cagagcattg caacctcttc agcttttcag tctcacccgg   21120
gtgagctgtt atcttttagc attttctgtg ttgcctggct tcagcccttg agagaacttt   21180
gtggtctgcc aggatcagag taagtggatc agcggaaccg gtttgtaatc ccctcctctg   21240
cctgtgttct gcaggaggct actttctgca tggtccttcg tggagctcgg ctgggccagg   21300
cggtactgag tgatgtgtta cgggccggct gcgtcccagt gatcatcgca gactcctacg   21360 tttttgccttt ctctgaagtc cttgactgga agaggtgagt gttaccttct gatgaacctt   21420
tatcccaggg ttcctgcatg gattattttt aaagtccccc agcagttgta atgcatagct   21480
aggtctgaga actgctcctt cagattttt tgctccatt ttccatcagg agagttcgtc   21540
catgaacctg cagcagaggt tggtcacccg aggccttgg gccgcatgtg gcatgctgcc   21600
agtgtctgta aataaagtgt tattgcatca cagcacaccc attcattgac acataatctt   21660
tggcggtttt tgagctccag tggcagttga gtcctgcagt ttaaaatgac agagattgtg   21720
tggccttgca tgtagtaggg cctccataaa tacatgctaa ataatgaat ggattgggga   21780 atacagccga aggagaagtc attgttaatt tagagtggac agtgatgagt gaagacgagt   21840
gtacctggca ggcagaactg gacacacaga ggccctgtgg tcgggcagag tgtggtgtat   21900
tcaggaggct gagagggtac ctgtgtggct ggagcacagt ggggagtgga cggaggacag   21960
gagaggcatg gagtggtgac ggggaggtga gagatgagc tcggggagc tcctttgcgc   22020 tggtcggtcc caaggaaggg agaggaaaga gggactgctc actgcgagga ccgtgggct   22080 gagggaggcg cggggcattg ttgcttctgc tcgtgagacc cgagcgggac acacatgcag   22140
ccgtgctttg tatgcagggc tgtccataca tccgctgtct ccctctcgtc tctagagcat   22200
ctgtagttgt gccagaagaa aagatgtcag atgtctacag tattctgcag agcatccccc   22260
gaagacagat tgaagaaatg cagagacagg taaggggcca ggcagccctg cgggggaggg   22320
ggcgaggggg aggtgaaagg tggccttgac tgcttggacg cagagcagta tccatgccgc   22380
tgagagcggg catgggattg atatcctcca ctgagtcggt cagccagact taaaaggaga   22440
aaacagcgtt agggagttgc atcagagagg cttggaataa taactgtcaa agattcagaa   22500
acgctcctga gcaagcctg ctgtgacagt aatgtcacac ctctgctatg tgttcaggat   22560
gcagagctgc ccatctctgg aaggccgttt acacagcagg tgagggctct ggtgactgag   22620
acggacatgg aagctggtgt gtttcagggt gatgcttctc aggagctttg accttgagtg   22680
ttgtgtatca gctagccagg gtccccacag agtactgagc agagtttcct gtgctatgca   22740
gtagggcctt attaattgtc tattttatgt atagtagtgt gtatacatca gtcccaatct   22800
cccagtttat tcctctctcc cttccaccct ggtaaccctg agtttgtctt ctacatctgt   22860
gactctgctt ctgttttgta aataggttca tttgtactat cattttagat tccacatata   22920
agcaacatca tctggtattt gtctttctct gtctgacctc actcacctct aggtctgtca   22980
cggtgctgcc aatggcactg tttcatttgt gtggctaaaa ccccatcgta tatgtgtacg   23040
gcgtcttctt tacccgttcc tctgtccgtg ggcatttagg ttgcttcctt gtcttggctg   23100
```

```
atgtaaacag ggctactgcg aacattgagg cggtgcctgc gtcctttcag atcatggttt    23160
tctccagttc ttttttcttct tttaatgggt ttttacaagt ttttattctc atcaaaatta    23220
tctgtgtagg tgatgagccg gagaagaggt ttggagggtt agggttaggc tgtagccgcc    23280
tccacacacc cctgtgtcta acttggtcgc aggaatgagc ctcaggtctc tgggagaggg    23340
cagggccgtc acccggtggt gtggaagtgg ggagggactc tggcttctga cggctgctta    23400
cacacgttgt ccgtctgtcc tcctgccccg agctccgcct ctcccccga gtgtgcgcag    23460 cggaacgcgg gggtttctcg gctcctctcg ggtgctgtct tgggcctgtc gcgtcagcca    23520
ccacctgctt tcctgcttcc acactttggt ggtgttagct ccttccccgt cctctttatc    23580
tttggttatg ccttcatttt agggttttag gagggagtta gtggatgtgt tcagtccacc    23640
tctttatttt ggacccagct ccttagacca aacagatggt acatcacaca gtggttgagt    23700
ctgtaggttc cgaccctaga ctgcctgtgg cgaatgccgc cttggccggt tactgactct    23760
gtgcccttgg ccaaggctct gccttctgtg atccccatg acctcatctg tcaagcattt    23820
tgacattccg atttgaaaac aaatcacatg ttaagtttag cctccccgta gtctatttcc    23880
tagcacaccc atgttcaggt ttctgggctt ccccatttgt tgcttaactg ctgacctcat    23940
ttgagttgta gtgaattaga aaatcagcct agagatctct atagtcttga tctgaacttg    24000
gggttcttac aactcatggg aagaaaaagt actccttgaa gggacctggt gtttatgctc    24060
tttgtgtttc attttatggc atcttgatt gttaacatag taaatagga atcatctgct    24120 aaatcaggta tcatctttta tagatttata aaaggctaag aaaacaccag ggaggtgaaa    24180
aggagcaaat tctgcccagt tatcttcccc actaccttcc tgttgggaag agaatcactt    24240
agtttttaga gcagagcacc cagggccagc tcacagaatg tacttttttcc ctgggaactt    24300 ggcttaggaa ccacagatct gagacgagcc ttgccagtct tttcaaatga caggttcaga    24360
atcagaacca ttgaagcaga gtgactaagg gttacttaaa acagtgtact tttaggttat    24420
ttgggctctg agagacacat gtgggtctt taaaagactc tggcttgagc cctgtgtcag    24480
tctctgttaa ttgtgtgact gtgacacatc tgtgaccaaa gctcctcaga cttcctcatt    24540
tatggaatca agggtgggct ggatcagctt tcatgttcca ttcagctgtt aaaaaacact    24600
gtgaaactcc tgtccttgac agcttttaata actgagtgat catctcttttc ccatgaccac    24660 ctcctgtcat gagggcctgt tactgtctct ggtggtgaat aacctgtatt atgtccactg    24720
gcagaataaa ggggatctca gtacttttcct gggcttccct ggtggcttag atggcaaaga    24780
atccgcctgc catgcaggag acccgggttc gatccattag ttgagaagat ctcccagaga    24840
agggactagc aacccactcc agtgttcttg cctggagaat tccacggaca cacgagcctg    24900
gtgggctaca gtccatgggg tcgcaaagag tcggatacga ctgagcgact cgcacttgca    24960
gtactttctt ccctccccta aatccccctt ctgcttgatg gtgctcttct ctctgctact    25020
ttcagatgtt ctgagatgct tcgctgccgt ggcccattta gtcctgctcc ctttctctga    25080
atagtctgca tccccaaaat gacctctttt cttctcccaa tgtcagattt ctagactgaa    25140
ctgatctcag ccagaggtga gattatccgg ttgaagcact tcccagagag ttcgaaagga    25200
tgactaggtt ccactcccag attccagtgg cacacctgac tcccagattg tgacaccttg    25260
aaacggctgc acatgttgcc agatgcctcc caaggcggca gaagtgctgt gcttgggagc    25320
cgccttcctg ttgataccgt ggccgtctct ctaagattag agacagctct tttgttctttt    25380 gcagaatgtg cttgtccttt atctcctgta tcccctccat tgattcagtc agaccttggc    25440
aggagtgact gaaaaaatag cacacgcttg gttcttggaa gttattacac ctcagtgaat    25500
```

```
tctctttagg gaggtccaat ttgagtcttt gtaagacagg gataaacttt taggggaaaa   25560
cctgttaaca tcagtagttg ataccttaga accctgggtt gcttatgtta gaatgagctg   25620
agactgagga gcagagggtc agattttctt gctcggcaac tcaggaccgg cccgaggggc   25680
tgcacgcaca gttgtaacca gcagagggct ccatccactt tgaagtgact catttccctt   25740
ctgagtagcc gtgtccaagg agtcctgagt gccatgagct atgctgacac cgttcctcag   25800
agccgctctc tagagagacc cgcttcttcc tgtgctttt agcacaggat tctgctctcc    25860
tgtgatggat cagagccaga cttctgaat ttgaccctg agatacgggt gggatcttgg    25920
tgaggacggt gatgcagctt cgagttcagg ggctataatc tgatcgatgg atacgtggtg   25980 acagcccta acatgaccca ggagttagga cgcacccaga gaggagggtg ttctgcctga    26040
caaggaagcg taacttttcc tcctcacctg agatgcgaca gtgaagcagc cgttaaagtc   26100
atatgcaggg ctagaacctg aagtaagagc tggatgtaag ctaagacttt tgaagtacag   26160
cccgcatctg tgttatctac ccctgaagac caatagctgg ctgtgttggc gtaggtggca   26220
ttggaagagc tggggtggcc tatagggctt tctgtggttt agttagaaat cagttccttt   26280
cattaataga aattaatagt tgcttttgtt gttgtccagt cggtaagtca tgtccgactc   26340
tttgcaaccc cttagactgt agcacgccag gcttccctgt ccttcagtgt ctcccagagt   26400
ctgctcaaac tcctgtccat tgagtcagtg atgccgtcca accatctcat cctctgctgc   26460
ctccttctcc tgccctcaat cttcccagc atcagggtct tttccaatga gtctgctctt    26520
tgcatcaggt ggccaaagtg ttggagcttc agcttcagca tcagtcagaa tattcataat   26580
attcagggtt gatttccttc aggattgact ggtttgattt tcttgctatc caagggactc   26640
tcaagaatct tctccaacat tactgttcag aaacaccaat tcttcggtgc tcagccttct   26700
ttatggtcca cctctcacat ctgtacatga ctactgtgac ccctacccac acatgcctaa   26760
tagccatcct ggggatatgt aggtataagg ccaaagaaag ctgagaagat ggtacagatt   26820
ttccaaagca tgttagtggt ctgaaatggg aggaagtctg ggttaaagct gttagggaca   26880
gatttattgg ggaggtagta cttgatggca gccttaaaga tggagggttc catccactat   26940 cttctcgtg ttggaagcca ggaagaagta tgcaactaag tattttccta tagtctcatg     27000
gaacattcac gtccccagtc tccttggaa tcacaatgaa aaagagggca acccaggata    27060
ttgaaaggct gactagacac tggactgtat ggttggcagt gtttgtgtgg atagggagga   27120
aggtgtaaat ggatcctcag tttatctgtt gagtggagtt tccaaacatt cttttattgg   27180
tcagtggctc cgccagcagt gacctctaac ctcagccaca ctaggaggtg gaagtcagga   27240
gcctgccttg cctttgaact cttctttgta ctcatttgac tgggaacctt tgaggtggca   27300
gaaacattca gcatcttctt tgctctctct ccttgaatgc ttggccaact taaaatacca   27360 gtttctttc tattactgac ccatctcagc ctgccttcat attttcccta ttatactaag    27420
cataccaatt atttgttctc cggaggagga cgtgaagata taatgggctg attaggaaaa   27480
agaacatgtc tgtcgaagaa tatgtggtcc cctctcctgg caggactgtt gtcaggcctg   27540
gctgtggtcg agcagagagc agaagagacc acagaacagg aagtgtgtgt gtccaccagt   27600
tcatgcactt tattcagggc agagaccca caggaggctg ctcttttatc ttgcatgtga     27660
tttcagcaca tccaactgtt tgcttttccat agacatggta gtttcgaagt tacatctttg   27720
aaggacagaa agactgtaag tgagggggctg tgacatgggg catctgccag tcaggcatga  27780
atagagaaga cagaaaggct gttttaaaaa tagaacttgg atggaatgct ctgtgaataa   27840
taaatcctgg agagggtgtg gagagaaggg aatcctcctg cactgttggt gggaatgtaa   27900
```

```
atcggtatag ccgttatgag aacagtatgg gggttcctta aaaaattaaa gatagagctg    27960
caatatgacc tggcagtccc actcctgagc atatatttgg agggaaacat gatccaaaag    28020
gatacatgtg ccccagtgtt cactgcagca ctgtttacaa tagccaagac aacctaaatg    28080
tctgtcgaca gaggagtgga taaaggtgta cagatataca atggaatatt actcaaccgt    28140
tacaaagaat gaaataatgc catctgcagc aacgtggatt gacctagaga ttgtcatact    28200
gagtgacata agtcagagaa ggagaagtat cgtatgatat cccttatata tggaatctaa    28260
agagaactgg taccaatgaa cttatgaaac agaaaggac ccgcagactc ggagggtaaa     28320 cctaggggttg ccaagatgag agatgcggga aagaatagct ggagagtttg ggatggacct   28380
gtacacgctg ctgtgattag aatggttagc caaggatggc cagcgaggac ctactgtatc    28440
gcaggaactc tgctcagtgt tgtgtggtgg cctggatggg aggggagttt aacggagaat    28500
ggatgcgtgt gtatgtatgg ccgggtccct gtgctgttca cctgaaactg ccctaacatt    28560
gtgtgttgat tggctatacc ccaacacaag ataaaaggtt aaaaaaaat gaacttggg      28620 gcttcttggc actccagtgg ttagcacttc accttccagt acaggctgtg tgggtttgat    28680
cctctgactg aggaactaag gtctcgcatg cgtcatggcc aaaaatccag aacataaaca    28740
acagaagcac cattgtaaca aattcagtaa agactttaa aaaatggtcc acatcaaaaa     28800
aaacacaaaa cttaaaaaat gaaaacagaa ctctcagcac tctggataca tggcagacgg    28860
cagaacgtgc ttctcgatat cctgggtgtg tcctcgtaag acggtagaat tccttggttc    28920
aaagaaatat gtacgtgttt gttttgcata ttttgggttt ctggcatcca aatgagtcct    28980
accatcactt tgattgttga atatagtttc tgttttgtcg ccttgaagct gtttctgacg    29040
gagcatctta aaatcgtgga aatacagaga tggctgtcct gagaacgccc tgcagtcttt    29100
tcagggaagg tttacgtttc gcgtatataa acgtgttttt aaaatactgg ctttcgcgta    29160
aagtattttc gaaagttttc tatctaaaat aatttgcttt tattttttta aaagtgtttt    29220
gtgatccgcc taaaggcgtc ggccctcgga tgtctaggac ccccaggaac ctggatggat    29280
gtgttctctg agggtcccct gcgcttggct gttgtgtccg ttgacggcta ggtagcagtc    29340
tgtgtccatt tctccctccc tccctgcccc caaacacaca caatttacaa agcaaacttg    29400
ttaaacagag cagtgagact aggcagtgag aggagcgatc tgaattttt ttaacgtgag     29460 gaaacggaag aagagccgtg aagcgatgct ccggtgatcg cacgacctga gagggacaga    29520
cggggaacat actgttttgc tgcccacagc ttgattcaaa tcctagagct ctgtggcctg    29580
gattgaggtt aaacgtcagg atgagcttcc cagcaattca ggttagctgc ttattggatc    29640
gtctctccta aaaagtggtt gcctgagacc ctggagactg gacacgtctc tggaaatatg    29700
aagaacgtgg aaaagacttc acttctgatt tccaagattt gacattgtaa cgtctgtcac    29760 tcttcccac tgcccgcccc cccatactgt ggaaattgaa aaaactttta atatgcataa     29820
actgaattct cagggctttg aaaaaaatgc caagtattcc cttcctcccc ctgctctcta    29880
gtcccagcat gccactccaa gctctgtttg ccgatctctg ctttcatact cgcccttaaa    29940
aaagctactg gatcacttac ccgtctacga aacacgttga ccttgatcct tggcgttctc    30000
ctggtgaaac agacaaccgt ggttctgata caaagccagg ctctttggcc agtgggagag    30060
ccttggggaa gagtgtgatt atgggatatt ttgagtttca taatttttatt tcaattttgt   30120 tactctgttg gagttttcct gaatgtataa atccatattg tgaaggagat cagtcaactt    30180
atgtttaaag caggataaaa taagggctca tttaattgga actcttaagg aagagcattt    30240
ttatgtgttt aacttttttt ttttttcaagt ttagcattaa gaaccttatt ggaaaaagac   30300
```

```
ttttgccaag tatctgatgg gaagccaaga aaagcatttt aatagaacgg tctcaaattt    30360
atagtacacc agggcctgta aataaatttc cctgtcttta aggttggggc tgatttgcag    30420
ttattttgta tagcttctga gatttaaatc ctcacagtcc agatggggag accataaagc    30480
tgctttcttt ggcaaccctg gcatacattg tccacggcga gctctgtctg taaatgctca    30540
cttaccgtat tgtgatgcca gtttgaattg gtttagcgac ttttcctaga gcagctcccc    30600
ccaccccaaa tgttctcaaa atcttggaga attaagagtc cttgatttca taatgcagac    30660
tagtcaaata agtatgtttt aagtaccggc ttttttgcta gaattgtata ggtatattaa    30720
aggagatttt tacaaagggg gaggggagga acacagatcc tgtcctcagg gtgctaggga    30780
gagcactttc agcaatagtg aacgaagagg gcggaagtgc tggccctcag tcgtgctgcg    30840
gaatggatca ggaggcgaga gcaggcttcg tgaccgggtg gcctcgaata gggtgagagg    30900
atgctctgag aggtgccgag ctccgcccag aggttggctt ctgtgggaag gactcggtag    30960
gtgaggtgga acagcctacc agcctgaggg ggaacttgaa ataccagcaa gagagaactt    31020
tctaggaagc tggaaggacg ggaaagtcag tgacaagtgg agagtaatga aaaaatgcgc    31080
gaggaaaggg gaaagcagta tcaattaagg agacagggga aaaaaaaaaa aaatcaaaga    31140
gctggaagga accttagaaa ttattcagcc ctttcttcat attttgtaaa tgaggtggaa    31200
gccctagcgt tcaagtgatc ttgaggatga attgttaggg cctgagcctc gcctcgcctg    31260
gaacccaggt ctgctgactc cagctgatgg attctgggtg aaggggggac cttgtgtact    31320
acagtatttt tcaatttagg gagtcttgag tggcatttta tttttaaaa aatgaaggat     31380
aataggaagg catcagagta ttacctagca agggtaaatc tttcctgaac tcttttttt    31440
gatatgtata tgtgcagtgt cattatttaa tgtatttgta tgtttcttgg tgtgggcccc    31500
agtccagaaa gtttgaggga tgttgatagt gagtggcaag cacacaggct tttgagttga    31560
ggagacctga atttgcatcc caggctgtgc cttctgtctg ccagctttgt gagcatgggc    31620
aagtcacttt gccaagcatc aatttttctta tcttagacct ggggataata gtccgactct    31680
ttgtgagccc acggactaga acctgccagg ctcctctgtt catggaattc tccaggcaat    31740
aatactggag tgggttgcca ttcccttctg gggatcttcc tgacccaggg atcgaaccca    31800
ggtctcctgc actgcaagca gattcttttac catctgagct acagggacgc ccccaataat    31860
acaatagagc agttgtgttg tttaaatgaa atccttgact taaagcatct agaggccggt    31920
ctgcctgctc tgtgttggct gtcgtctggg agtgctccgc ctgggtctag gtttgaacac    31980
tggcaggagc ctcctggttt ggagcttgga cttcaggaac cacagtaagt taccaacgcg    32040
gatgtattat gcatttgctt ctgggcttgg aaacttgaaa cagaacttat tcctgtgggc    32100
ctggtgtgct ttctacatct tggaataaag ggaggttccc ctctctggtt ttcagaatgg    32160
cttatgaaaa tcagtggttc tttagctggc cttaaaaaaa attcattggc acgtttgagt    32220
gccagaattc ataaagcaac gtttgggtca agtactatta cttttccccc tttccagtga    32280
gaacgatttt catactgagt cttttttaccc cgtcttttaa tgtatcctct gctggatctt    32340
gattttactc attttttttg agccagaaga ttaaaaaata agcataaaga gaaagtcaa    32400
aatcagaatt gacatttggg tggtgaacac ttggagagtt ggcattttac taggtatgta    32460
ctaaaaataa agcaacttt tatgtgaatt taagagggct ggtgagatac ctcttaggaa    32520
tagctgttgt tcgcctccta ctgaaagggt aatgagttgt atcatctggt tttcctggtt    32580
ctctgctgtt cccctaaccc ctgctgccct tcccccacc cctgctgccc ttcccccacc    32640
cctgtccagc cagctccatc ccatgtttga aatcccgctg gagagcgagt ggagcgcttc    32700
```

-continued

```
atccctagat gatttgggcc aggggctaaa acactgccat aaatctgcag ctcattttaa    32760
tgccacgtta aaacagtgtg agcggctggt ttccgtggcc cctgccctct ttctttatgg    32820
gcttctttgg ctcttcttta taaagaggcc ctgtggagtc attttaaagt tcttatcagt    32880
ttgctgacag ctatatgggc ctttctgctg agtccaggag ctcaggcagg cgtgtgaaac    32940
ttctgatatt aaaattgaag aaaaatgcca ggcagaaggg attggggagc gcagcggtga    33000
tttggaggtg aaagactagc gaggtaatta acctctgcag gtccggaact cgcccttgg     33060
ctggataagt tgctcctggt tggtgggggc agggcagcaa gggttaggcc agggagggct    33120
ttccaagggc ttttatttt atccccgatg agaaatgccg ttcagctggc agcctgtgct     33180
ttcaggcttc agcaagtgcg ttgggcagtc ctgaaaggct aagggagcca ggtttacaat    33240
gcagttttt tttcttttc ctaaaggccg tctgactggc tagacctcgg cttgtgagtc      33300
tctggcagct ccagctcact gtctctgtcc acagcatcgc tgttatcgaa tttaaagggg    33360
ctttcatcag tctgctccgc agccccttt agaccagctt gctaactccc agtgatcctc     33420
gcagagtgct tcgtggaagc gccaggccct ctataaatgt cagcctgcag cttagccctt    33480
cttaccctct cagttacgga gaggtagcct ggaagccgct cctccctctc ctccaccgct    33540
tttcctttct ctctttgctg gaaaactcta gcagcagaca gctgagggga aggaaaaacc    33600
attacctgga tcaaggccag gggcttgatg gagcctcaaa atctctggca tctcctgacc    33660
agagtgtttt tccaggcatt tcaaaaagta caccctcacc ctccgccagc tttcagcttt    33720
ccagccttga ttccaggtgg gctggcttgg gggcatcatg ccctcagaat ctgtatctgt    33780
ctgctcctct tctcctaact aaagcgttta ggaaaaggat agtagagata agcaaaatcc    33840
agtggacatg tattttaac tgccttgcac cctttggcg caaacacatt atttttcctt     33900
tttcaaatag ttttggacat gagtactttt gcaagtgtat tcaatttaaa atagtcattt    33960
aacttgaggt tgaagcaaaa gcaaagaatt tttgtagtta gtcaaattat atagctgttg    34020
atctaggatc aatgattttc attgagcaaa caataaaaaa taccggttcg ttttactact    34080
tgtgtggaag tagctcctgt ggggggagta attaggtatg aaaactgacc aagctataaa    34140
tcaaaataaa atacccccaac ctccaaagca atcaagctac ttttttgaac atttctgaca   34200
atatcaatag atattttggt attctgaaca atatcagtag aataaattga tattctataa    34260
ttagttaagt ttactgaatc agaagttttt gcttgtggta taattttaat aaatttacta    34320
aaaatatttt acaaataatg tactgaaagt tctcagtaag tatatgatta tgagcagtct    34380
tcattgtaca gcctttgcaa ggggtgtggt tatatcatat gaccagtttc ctctttgggc    34440
attggttgca gagctggctc tagagttagc catgggttaa tccttgtaa caagtcccca     34500
atatggggca ttgctttagg aaatggcctc tctaataaaa gtgttaaaca ttaatttgca    34560
gcctatataa ggattgtctg actctttggg gctggtttcc tacagagtgg aactatttgt    34620
gaagcatttc tgagaaataa ttgctcatta caggaagtgt agtgcaggct ttgtgaattc    34680
attatatatc tacttagaaa aatatctagg tttgtttaca aaagaataac ttataaatta    34740
ccaagtgtcg atacaagcat ttggtaaaga attcactatt gtcaggtctt cagtaagagt    34800
cagactgatc cattagattt ctgtctatat ttatgattat tttgtatttg aatgtatttt    34860
tctgtctccc tcagcattga agaggctgag agagtttgga gttgcctgac tactttgtaa    34920
taacaccatc ttgtaattcc atgctactgt tcttgggaat gtaagacaac aattgtgtat    34980
ttatttcatt ttatttgact agatgacctt taatactgaa tcagaccaga attggtacag    35040
aaatagcttc ataaagtcat ttctggcaat gtagttctct ctctctcccc ttatagttta    35100
```

-continued

```
aaggttaatt tgtatttaaa tgtgcactta tttcccattt tgataagatt tcagtagtaa  35160
gcaagcaggt catttgttat ctttcagaat tcagtacttt ttattaaaag gagcaagcgg  35220
tttgtcttca agtgtttgaa gcccatatat gtatatatat atattgaagt gttctgaatt  35280
ctctgaatat atattggcca ggtcttgatg attttatata tatatatata tatatatata  35340
tataaatttt gtattttaga gagatctttg agttttttgtt tgaagctaca gactgagggt  35400
tgaattctct caactctctt gctctcactc agattcttag atgctttctg gagtggggaa  35460
tggggacata aatttctctt gagaatcctc gccgtgatga acctctgcta tgcttactca  35520
taggtaagaa agggcgcggg gtaaagatga gaaccactca cagagcaagc atagctcttt  35580
caaacttctc cctctgttca gagtcccaat ttagggaacg cacattgggg tttccactca  35640
gatcaacagg agagcgtgtc ttaatacctg ccacgtgatc agaccaaggc acttcccagc  35700
tgcaagcggc ttagggaggg ctcccgtggc tccggtcagc tggaaccggc attggaccca  35760
cactattctc aacttctctg tttctgggaa tgtgtgggga cagtggagag ggctcccatg  35820
cgacctgact gcgtctgtat aatatccaca gccagaaaaa taaataaata aataaataac  35880
ctgctaaaga atagctcccc agccttcttt agaattgtta ctacctggga agcagatgga  35940
ggggggaaca tggccctgat gtggcaggat gtgggatgaa acgagccctc aagttctgtc  36000
ctcggtccct tcacacgtgc tatctgcgtg tgtgtcttaa ttaaaagggg tcggcctttc  36060
aagtgtgccc gctgcagtga gacttgtttt atatttacct tttctgatca aacaagcata  36120
cagctctctc cctgttttgg tatagcaaac atggggaatc tcaccccagg cggattcctt  36180
tacaacgaac tgacccaagt tgtgctctta tttatttatt tttgatgaca gatcctgatt  36240
aaaggtttcc agtccaaacc ttttagctgg tccatgaacc cagccaggag agagggctgg  36300
tcagctgctg attgccaaag aagctccccg acctgaccga gggaacagtg taattcagag  36360
gtgtgggtaa ctggggaacc gggcacagca gaaatgaatc tctcgtctct ttgctgagaa  36420
ggtttgacca aacacagttt tattggtcag tggctcctgc tttagtaacc tttcacccccc  36480
atggctcttg gaggtgtaag ccactggccg gccttgcctt tgaactcctc atggctcctg  36540
ccacctcaaa gactcacagt cggagcttgt gttttgcttg ggatctctcc tcacagcagg  36600
gcatcagcag ttgggaaaac tgatccaccc ttagagcctt gacatatttg aaggtgatac  36660
ccctgagact tgaaacctat ggcttttctat ttcaggagct gcctgtcaca tgtcaagaaa  36720
cacgacacag gctgcccact ttgctcctct gtccctcctg gcttcccata ggacgggaga  36780
tagtaacatc tgagcacacc ctgcaagtat tcaccgagtc ctcccctcat cttcaagctc  36840
ttttacccat ttttcttctg acttgtccca agtagagtct attttgaaat aagttttctt  36900
ttaaataagg ctaaaacgtg caaatctagc cctctttggt gtctgggaac ttgatgcagg  36960
tgaagatgat gcagtgaaag tgtcacaggg cttacattga cacgttcagt cccagtgcgt  37020
ccaggtcaga tgagccctac ttttaagatg gcccagcttc cttttaagat gggacactct  37080
cccctgtctt cttgagtcat tctacgttct ggaaaaacta gatcttgcaa gaagagatag  37140
aaatagcatg gattgctctc ccacatctgc ttggcttcca gcctacggaa caagagtgag  37200
agctttagtg ttgagaggcg aatccaggga cccatggtta ttgggtgact tcagtaaagc  37260
ttctttggca agaaatcaaa cctcatattc aaagaatatt gagttgaaaa atgccttcta  37320
cttatgatgc cgttagctta gcaaaggagt aaatgatctc cattgagttc ctctgctttc  37380
ctagaattca ggtagaacat tactgataat ccttagcaga aagaatactc tggcagggtc  37440
tttttctgct tcagagtaaa ggttgagttt ttagcaggta cccaggtgtc agaaatggta  37500
```

```
gcccactcca gtattcttac ctggaaaatc ccatggacgg cagagcctgg taggctaccg   37560
tccatggggt cgcaaagagt cagacacgac tgagggactt cacttttctc ttcaggtgtc   37620
agaagaggca ggcctggttt ttctgctgtc ttattctgtg gtcgtgagtg tggtcatgag   37680
cttgagctcg acaaagggaa ggttgacaaa gggatgagaa gtagcattta tgttaactcc   37740
catgtctgat aactgacctc atgaaaatct gatgaggcag ttgtagttct tctcattttt   37800
acaaagaggg aaggtgaact tagaggctaa tggctggtct gtagttacaa aactttagtg   37860
gcaggcttgg gactgggaag aatttgtagc acatgattaa aaagttcact tttctcacct   37920
ttcctctggg ggcatttgcc ttttacactg aggtaagtat gtctttgaga tgagtataaa   37980
ccatcatcaa tacattaatt gctgtattga tgatggttta taggttgctt ctccttgcca   38040
ctattttctg ttttttttcca cctactggga aatttagttc tcccatttct aaatcctatt   38100
gcatgactta gaggaaggaa tttgaaatcc cctttcttca cttgcctctc tttgtcccat   38160
gttccagttc tttctctgta tccttgccct gatgataact cagattttc aactctttat   38220 gggaatcagc cgtgttatat gatgttatat gatgccatgt aagctgataa ggaacctgta   38280
catatttgat tagcctttgg gaaaaaaacc cacgtcgtct aattaaacac tgtgcactta   38340
actgagcaca ccgccttgct gtcagaaagt attgctctgg gcctcatcct cctgacctct   38400
tccttacatt tttgtcattc ttcttctaaa aacatgttta cttctctatc tggctttgct   38460
gggccttggt tgcagcacgt gggctctcct agttgaggca tctgagctcg cagtcatgcc   38520
ttgtgggatc cagttccatt tgaacatggg ccccccttcac ggggagccac tggaccacca   38580
gggaagtccc tcgtgattct taacaaatat atgctggaac cgttttctct ggtaactata   38640
ggcggaacta actgcatgtc cattctttaa tcactcccca taaatataaa tatggaggct   38700
ggagatgaac agaaggacat cttttggttct aaatggatga catgcgctta catataggca   38760
tttttggaat tttctatgca actctgtatc aaaataggat ttgaatgctg gtccacatac   38820
ttgcttgttt tctaaccttt gaatgactca gggttttatg tgtaagagca aggtctagaa   38880
ctcctagaaa taagcacaag tgggtgtgct cagctcttcc tacgaggctt gggctgcggc   38940
tggtgttgag aagcctttag cggttggtgg gagcaggcta gggggggagct tggcctggaa   39000 gactgtgtaa agacctcttc ctctcagcac caggaaaagg ggattacatt gagggaagtt   39060
aagggatggt taacaaaaat ggtacgcggg gagagagaga aaactagatt taaaggctga   39120
gtactctgca gccagccaag gggaaaggct gtgagcaagt tctcagagtc ttcaccaaag   39180
ggtgagaagg ggaagaaagg gcgccttttg catggcagag gttcataacc atttgtcatt   39240
gtttatttgc taagtcgtgt atgactcttg cgactccatg gactgtagcc cgctaggctc   39300
ctctgtctat gggttttccc aggcaggagt acgggcagga agggattgcc atttgcttct   39360 ccagggggatc tccccagtcc agggattgaa cccatatctc ctgctttgac aggtagattc   39420
tttaccactg agctaccagg gaagcgttca taatgatagt cgctattatt aaggtgattt   39480
tatgtttctc ttcactacct atgtgccaac tgggtagaga ttattttaaa caagacacaa   39540
ctacaacaaa cctactgtgg attctgaatt ctgatatgtt tttagaaggc tgggaatgcg   39600
gaagaatgta aaaataaaaa taaaatagag attaaatcct aggagagatt aaagtcctaa   39660
caagaatcat caggttctat atgagatccg aggagaagag caaaaatgtg ttcattaggt   39720
gtgatacatt agatctcgca ctgggtagtg gctgcatttc acatttaata tggttctcag   39780
ctgttcccct gcaatgacac agctgaaaat agaggccttg ctggttaagc caagtctagt   39840
cagtcctgct tgctgctgct gcaggggaaa atgagacatt gagaatggcg ctcagtcccc   39900
```

```
ttagtctgct ccagtttctc gacactcggg catgactcta gaggaactgt aggataccag    39960
cgtaaagaag ccacgagaac ccgcggaaac ctactgcccc aactctgtag tacttatggg    40020
ccaagttttc aaatccttgt ccttgagtgg ggcccagcag attttggttt ttactgaggg    40080
ccaccagaga gttttcagtc taactaggaa gataagtatt ttcacccat gagataacag     40140 tagggcagag aatagatgct gactcttgtg tagaaattgt cagatgaatt ggaaaagggc    40200
ctcagtatgc tttcaaggag ataaaacttg aagcccaggt aggattttt gtttttaat      40260 tactaaattt taaaaggta tttatttaat ttatttagtt gccctcgtc ttggctgcag      40320 ctcgtggaat ctttagttgt aactcagatc gtaatgcaag ctcggttcgc gttactaaga   40380
gtcgcagcgt gtgagctctt agtttcagca cgtgggatct agttcactgg ccagggatcg   40440
aacccaggcg ccctgcactg ggagctcgga ggcttagcca ctggaccacc agggaaggcc   40500
cttaatcact aagttttatt tttcagagca gttttaggtt cacagcaaaa tcgagcagga   40560
ggtagggaga gttcccatac accctgtgtc cccacagacg catagcctcc cacactaaca   40620
gtgagccaca gtggttcatt gttagagtgg agcctacact gacacagcct tctctctcag   40680
agtctgtagt ccttgttagg gtttgctctt ggggttgtct attctgtggg ttttaacaa    40740 acgtataatg tttcctccat gtcactattt ctaatttaat tccattgcgg tctgggagca   40800
gacatcatat gacttctttt catggttgtt caagtatgct ttatggccca gaatgtagtc   40860
tgtctcggtg aatgttacat gtgagcttga aagaatgtg tccaatctgc cgctgttgga    40920
tgaaatagtc tacagatgtc aattatttgg tgctgtgaat acattcaact atgtcccttta  40980 ctgattttct gccttctgga tctgtgtgct tctgacagag ggcagctctg ggagaggatt    41040
catctgtttc tccttgaatt tctaccagtt cttgcctcat gtgttttgat gttcttttgt   41100
cggttgcctt gaggagtgtt atgttttctt ggagtattga cctctttatt attgtgtatg   41160
ctactgttta tgtgttgtaa ttttcctcgt tctgaagtct tctttgtctg aaattaacat   41220
agctacctat actgtcttca gattagtgtt agcatgctct atctttctcc gtctcgttta   41280
atttatgtgt atctgtttat ttaaagtggg tttctcatag acaagatata gttgggtctt   41340
gttttttcat ccaccctgac aagcttttaa ttgtagtatt taagccatta gcatttaaag   41400
taatgattga gatacttgaa ttgacattga ccatatttgt cactgttttc tatttgttgg   41460 cttgttctt ttttcctgtt aatatttttg tcttctacac attttatgtc ttttgtggtt   41520
ttaattagta gtttatatga ttttattctc tgtgttagca taccaattac actccttttt   41580
aaatactttt tttagtggtt gccctagagt ttgcacttta catctatatc aaatccaaat   41640 ccatttttcaa atattcctgc ttcagtgata gtgcaagtac cttccttatg ttaacacagt   41700
aatcctggtt ctcttgtccc ttgtatcgtt gctgtcactc atttcacata tacatatata   41760
tatatatata cacacacaca taatcaaatt tgttgctttt atagattatt atatgttaga   41820
tcaattaaga ataaggaaaa tgacgatttt aattttacct tcacttagtc cctctctgat   41880
gcttttcctt tctttatgta catctgtttc tgactacatc attttccttc tctctgaaga   41940
acttctttta acatttcctg taagcagaaa tactggcaac aaattttctc gattttttgct  42000 tgagaaatta tttatttctc ctttacttct gaagggtttt ccagggtgta aaattctgtg   42060
ttggtgcgtt ttttctctta acccttata gctgtcattc cactttcttc ttgcttgtat    42120
ggtttctgag aagtcagatg taattgttac ctttgctcct ctatagctaa ggtgtttttt   42180
tcccccctgt ggcttctttc agaaaatttt taaatatttg ctttttctaaa gtttcactat  42240 gatatgcaca ggtgtagtgt ttttggtatg tatcctaccc agtgttctct gagcttcctg   42300
```

```
gatctgtggt ttggtgtttg gtattaattt gaggaaattc tcagtcatta agtttcctct   42360
cccattgtat tctttctttt tggtgtttgt attacgtgta tgttacccct tttatagtag   42420
tcccatggcc cttgggtatt ttgttctttc cctgccttt ctctctttgc aattttggaa    42480
gtttctgttg caatattgcc aagctcagat tttatctttt tagttatgaa aactcacaaa   42540
tccagggact gcacgcaaac tgtgtcacat agtgtccgtt gtcacatagc ctccattgct   42600
acaagaggct gggtaatata gtattttaag ttgattttgt tagtaaagat gaacgagata   42660
ccagatactg gggaggcagc ttaatgtctg tctggaggac taagaataat ctggatgtga   42720
gaagttaggg tagtgagatg agctttgtct tttttgatt gtgctgggtc ttccttgctt    42780
tgcgagggtt ttctctagtg gcagtgagtc cgggctactc ttaggatgca ggagctcctc   42840
actgtgacgg cttctcttgc tgcagagcac gggctctagg cacatgggct tcagtaattg   42900
cagtgcttga gctcagtagt tgtggctcgt ggaccctaga gcacacggct ccaggagttg   42960
gggcacaagg catggggaat cttgcccaac cagggatcga acccacgtcc cctgcattgg   43020 caggggatt cttttccact gtacgaccag ggaagtccag tagaacgagc tttgccacta    43080
actctgtgtg tgtgtgtgtg tgtgtgtgtg tgtgtgtgtg tgtgtgtgta tttgtgtgta   43140
aaatctcact gggaattgct ggcatagaag agtcttgttt tttgttttat ttattttaca   43200
aattattttg tagctggcca ctttattaaa cttccttatt agctttgatg gatttttagt   43260
tgatttctta ggattttctt aatagaaaat caatggaaag ctcttggatt tcttttcaaa   43320
tactcttcct ttgtctgttt tcttattaat tactgctact agattcctta ggttttttt    43380 cctttcttc ccaaattatc agattggggt gcttacttta tttttggatg ataattctgt    43440
gtatatatca gagtaaaatt aaagtatgag attagaagca gttgaaattt agaaatattt   43500
gtggtctcag tagatttcat ctctaagatt tttagtaaaa actggctaca tgcttttctc   43560
ttttcagtag ctaggatatg ttatcaggct tcaacttaac atttaaggca tatgtcagat   43620 tttttgttt agtggaatta ttcaagaaag aaaatgtttt atacttccct aagccacaaa   43680
tacctagagg cttaaggatt ttaatagaat cctgttctgt atatacgtag actagctgtg   43740
tgtgtgtgta tgcacacgtg cgtgcacgct actcagtgaa tggaatttca tagttttaa    43800 ttcttttaaa caacactaaa aacagtatgc tatttctctg atactacctc ctccgggatg   43860
taaagcttaa ttatcttctc tttgaatatg gtctgaacat agtgacttgg ttctaatgca   43920
taggctatga gatggggatg gtaactttac catggagaaa cctggaagac ctcacctta    43980 actaggtgat taaggtgaac ttcccctgta ataagtcacg ttgatcccca ccatgtgtcc   44040
cagttacgaa ggaaagagaa aggcacgtca tctgtgtagt attctccaaa atccataacc   44100
tcagtcttaa cagttaaaga acctcagacc aaccagacag agggacattc tacaaaattc   44160
ctgaccacat ttggcaaggt gttaaggtca tgaactatag ggaaagattg aaactaagga   44220
gccatgacag ccagaagcaa tgcagtgtcc tggataaggt gccggatcag aaaaatgacc   44280
ttagaagaaa actaggaaaa tccaaaaaga aaacaaaagt ctttagctga gttaatagaa   44340
ttaacctaac attaacatct tagttttgat cattgcacca tggagatgaa agagactaac   44400
attaggagaa ctagtgaggg tattcagagc tctctgttct actgttgcaa ctattctcta   44460
agtcaaaaac tgtttcaaaa tgaaaagttc aaaagaaagc gattacaagt cggcctggta   44520
aataaaaaca tttttatat ttatcaaaaa ttgtaaagtg aagtctgcta ctgttaccag    44580
aacagatgtc tgtggctttg tggaagggtc agtgaatggt gggtgtgggc gcctcaggtg   44640
ccaggatcaa gtaattgaga taacgggact gggaagaccg tggtaggtgc cggagaagtg   44700
```

```
cttccggggg caccagggac aggtcctggt gcaggatgct ggtgtggcga gggcgagtga    44760
agtcactttg tgagtacaga agtgaagaaa agcactctca tgttttacgg aggaaggcat    44820
ttcagttcag ttcagtcact caattatgtc cgactctttg taaccccatg aaccgcagta    44880
cgccaggcct ccctgtccat caccaactcc cggagtttac tcaaacttac ctccatcgag    44940
ttggtgatgc catccaacca tctcatcctc tgtcgtcccc ttctcctcca gccttcagtc    45000
tttcccagga tcagggtctt tgctaatgag tcagttcttc acatcaggtg ccaaagtat    45060 tgcaacttca gcttcaacat cactccttcc aatgaacacc caggactgat ctcctttagg    45120
atggactggt tggatctcct tgcagtccaa gggactttca agagtcttct ccaacaccac    45180
agttcaaaag catcaattct ttggtgctca gctttcctta tagtccaact ctcacattca    45240
aacatgacca ctggaaaaat catagccttg acaagatgga cctttgttga caacgtaatg    45300
tctctgcttt ttaatatgct gtctaggttg gtcataactt ccttccaag gagtaagtgt     45360 cttttaattt catggctgca gtcactatct gcagtgattt tggagcccccc aaaaataaag    45420 tcagccactg tttccccatc tatttgccat gaagtgatgg gaccggatgc catgagctta    45480
gttttctgaa tgttgagctt taagccaact ttttcactct cttctttcac cttcatcaag    45540
aggcttttga gttcctcttc actttctgtc ataagggtgg tgtcatctgc atatctgagg    45600
ttattgatat ttttcccggc aatcttgatt ccagcttgtg cttcttccag cccagcgttt    45660
ctcatgatgt actctgcaca gaagttaaat aagcagggtg acaatataca gccttgacgt    45720
actccttttc ctatttggaa ccagtctgtt gttccatgtc cagttctaac tgttgcttcc    45780
tgacctgcat agagatttct caagaggtag gtcaggtggt ctggtattcc catctcttaa    45840
agaattttcc acagtttatt gtgatccaca cagtcaaagg ctttggcata gtcaataaag    45900
cagaaataga tgttttctg gaactctctt gcttttgat gatccagcag cacttaaatt      45960
taattaaatt aacaaatgat ttaagtaaag aaaaaaatgg tgtgctgata aatcctcgat    46020
atgttgacct cttttgcttc agaaatctct tattttaaag cagataaacc ctatttatga    46080
ttgttcgttg gaccactgag taaaagtatc aaatgtcagt gagcttctcc tttagaaaag    46140
ctgacagcct ggggctagta cattttata aaaccttcag tccttgagga ttgccccgag    46200
gggatgttgt tgattttgt tttttttcct ctccctgttt ctgttgtcag ttaaccctct    46260
ggtttataaa aatggagtca gcgaaagaat aaacaagaag ccagtcttgc agtaatgctc    46320
cactgggaat caggacaccc tgattatccc tcgacctcac cattgtgtgt gttttcagct    46380
gccaggcgga ggctgtccat gcctgtctcc attgcctcca ggctggccat ggggttagcc    46440
acaccccgga agtgaggtca gcaagaaggg cactcggctc cctgctcggg ccctgtcacc    46500
tgcccaggaa ggtggcgggg aagagagccc gtgtgaccct gcagagcttg ccgtgtagga    46560
ggctcagggg ccgtcacagg catgctcact ggctccattt gtcacagcaa agaaacgaaa    46620
aggagctcgt ctgccggtgg tacgttaagt gcttggaaag cctcggaatc cctttggaag    46680
ttttcagatt caccttcaga cacagctttg aaaaattaat ccatgaggcg tggaaatatt    46740
ttccagccct tcacctgaga taaatgttct gtcagtgcag tgagctgaga gaaaatctcc    46800
tggcctcaga tcccccggaa tctcccaggt tgctgctcag aggcagaagg gcttctgcgg    46860
ctcgaacggt gcagctgttt ctcaaacttc ctgagggaga aggcaaatgc tttatttaat    46920
ctcccttggt tctctgtgct tattcagtcc gttttattgt ttttcattaa tttgggaaaa    46980
ctcttagcca ctatttctct aaatgtatct gttgccttgt ttctgaaccc cctctctgga    47040
actctggctc caggtactgt taggacattt ccatgtggtt ctacagttct tggacgctct    47100
```

```
attttcttgt actcttttc tctttgcatt tcggtttgga tcatttcttt tttatttcca   47160 agttactac  cgttttcttt tcctctgctc tattgtgata agcacacttg aagaaattct   47220
atgatggtat gcttttatt  tctagcattt tcatttggct ctttgtttac agatagtttt   47280
catctgtcta ctgaataagc ccatctgttc atgcaggttg tccactttt  cactagattc   47340 tttcacatgt taattatagt tattttgaag tctccatctg gtagttccaa acatcttggt   47400
catctttcag cctagttctt ttgacggggt tatgttatga cagtggattg ttttctctcg   47460
tattttgttt ctgataaact ttgactgagt gatggactgt gttagaaaaa caggagacct   47520
aaagtaaatg tcgtgtccag cagtgggcag accttctgtg agccattcgc atgggaggtt   47580
gactcaacct agcatgtaac tgggatgggt ctgagttttt ctgtcgctgg acttaccttc   47640
agcaccgctg actccagatg ctgccagtgg tctcctcgtt cttgtgtggg gcacagggta   47700
ctggggcttt tctcagagtt ccagctccgc cctccgcttc cagcaggccc tgcccccctg   47760
cactacacag ggagccgtgc tcccgtcggc gggtaggtag acttctgttg cttgtatgtg   47820
gtgccagacc tgtggtgggc caggagggtt ccattcccct ggtccagcct cagtcttgca   47880
ggcttgtttg ctggggccgt ggaaggggtg cttttctcagt gttcctgggg cagctggagt   47940
ctgccctttg tctgtggggg tctggggttg gagggagtct cctacccctc ccttgggagc   48000
agaggctttt gcttcgaccc cagccacagc tgagccttct aggagctgga agggttcctg   48060
ccctccgagt gcggggcagg ctgcctgtct ccccctctcc cagaagccga ggatctgcat   48120 ccgccttttgg gggtgagggc ttttcctgct aaccccaag caggtagaga tttggctttg   48180
gatgaaaaaa aaagatttg agaaagggac agggctttct ccctgtgtgc cattgaaggg   48240
aatgtctctg gtttcttctc ctgccctcct ctttctccag aacatccagc agaaaagggc   48300
tcgaaagtga gtgcagattc tgcttgtgtc cagaactccc aaactgccct actagcccac   48360
actcagtttg aagaatttgt taaaatgtta gctggttttg gtgactgcct ttatagcagc   48420
cacccccgcc ttctctgctc ttcccgagct ggatttgagt gtcccatggc tcctggatgg   48480
cgctcttaga aatcgggtgt ccctgattgc cttctgaccg cagctctccc acgcgtccag   48540
ggcaagttac agtgttggtg gtgtatctgg tggctttttc tcatggttac tgtagattcc   48600
atgtttcttt gcgactttct acatcccaag cagaggcaga tctttattc  tgtggccaac   48660 cagtgggtgg gggtgggggaa gtagagtaat attggggtac ctactgatcc accgttacgt   48720
gtttggacag cattgcctga tgaggtttga cacagaggca tcaccggctg gtatatttttt  48780 ttattttgtg gttttcatta gaaatgtcct tttaatatat taaaacgaag tctgttggca   48840
tgggtcacat tcaggagatt ctgttggaaa gggcagtgcg cagttggttg ccgatgaaag   48900
ggtgttggag actcgtcact gtgcttggga tgcagtcgcc cttggactac tttgggtcc    48960 tggggttctt ctgtgtaatt tcttcatggt tagatatcct ggacacttcc aggtcagact   49020
tgcaaggcat agttctaacc actgattctc tctcgtggtc tatacacaca caatataagg   49080
gacacccatg gtcccatttc tgccttgcca tttcacctag aaacacgttt tcctttttt    49140 tccccctca  aatccactcc ctgccccatc ttttcccttt taaaattctg catgcacgag   49200
gtgatccttt ttatgaactg acggttttcc tcctttaagg tcatgggctg gtgcttagaa   49260
gatctggaga gttctgtgag atgcctgtgg tgcctgtgag ggagatggat ttgttctttc   49320
aacaaacatt cgactgtcca gtccttgaca ggcgctgtgc taggggctgc aagaccagtg   49380
atgagcaaaa ccagatgcgt ccccactctc acggtctgca gagaagtgct ggcctctgcc   49440
ttggaagctt agagattcag gtagaagaga catgttagtg ggtgagatat tttccagtat   49500
```

```
taaggtctgt catccttgta tttattttta ttatacctac ctcccttctc tgaccagttg    49560
gattcttttc ctggcttcaa gaattgaaat gaatggagtg taaccttaga atcccttctg    49620
tctctcctct tccctgtct ccctccccgc ccccaaatca cgcagaatgt agtatatact    49680
gtaagtgacc tcgaggggca ggatgggtgc aggtgtggag gagatgttct gattatctgc    49740
tctgcacagg gcgaggagct ttacaaacct catctcacgg aacctgcagc tccaagagaa    49800
aggtggtgtg gtgtccatcc cctagattca aaaatagag agggttaagc tgcttaacag    49860
agaaggcaat ggcaccccac tccagtactc ttgcctggaa atctcatgg acggaagagc    49920 ctggtgggct gcagtccatg gggtcgatag agtcggacat gactgagcag cttcactttc    49980
acttttcact ttcatgcgtt ggagaaggaa atggcaaccc actccagcgt tcttgcctgg    50040
agaatcccag ggacggaagg gcctggtggg ctgccgtcta tggggttgca cagagtcgga    50100
catgactgaa gcgacttagc agcagcagca gtaagctgct aaaatcgtg caagacactc    50160 atcaccatga ctcttctcc catattgtac ttgcttcctt taaacacttg ttattgctag    50220
tcctgttggc tttatgttac tgaaaatcaa agaaattaaa ccacagtagc agttttagtt    50280
tgaagtttgt gtttgcttga gatagtttta agttggccca atccttgcct tttgcttcat    50340
gattctaatg tttgaaagtg tcataggaac tttagttcct gtgctttgaa atctgctttt    50400
acaaaattac tgtggtatca gtttcatgaa gaaaagttaa atgctttgtc ggaggttgtt    50460
ggtatgacct tttcatatat gacttagctt tcagctgtgt agatgcatag aatagagcgt    50520
gtggggaatc tgcaggtttg tggaagaatc cctcatttca aattttcaga tagagataag    50580
tgtggcccat gttgatgggg ggaaaaatct caaaacaaaa taagtgtttg catttagctc    50640
actggatggg aatggtggtg ctttcatgta tatcacaaca gagctgaaaa ctccttcctc    50700
tctgccaaaa agtggcctat gctgagtcct gggggggctg taaattatgc cttctaaatg    50760
ctgcaaggtg ttaaagaggt cctgcagaaa taattaagcc tgtgaagttc acttatcctc    50820
aggcggagac acttgagctg tgattattgg caaggcttgc ttccttccca ggagaactgc    50880
aatttggtgg acaggatgag atgatttgag acatcttaaa tcagagtctc tgtcctacac    50940
ttgtgcctct ggctggtatt ctaggtggat ttgttcccag tcattgtttc atgtaaatcc    51000
caaacgctgc tgtctccact gtgattaaat gtgaatgcaa agctttggaa tgctcgagtt    51060
tgagtgtggt gtgatttgaa attaaaacaa acaaacaaac atatgacgat gaaccccattt    51120 gcgtagaaaa ggaggtaaat atttaagctg tgtttatgtg tgggctcatg catcttggtg    51180
ccttggtaga ggaccatttc cttactctgt gctggtactc ttcatattct agaaggaggt    51240
agaaggtctg actttagagt tagtattcac gggttggatt ggtgactttg ccacttaata    51300
gctcagtttc tcacatataa aatgaaattt gtatctgcca cccgaccccc aaaagttaac    51360
aaacttggtt ataaagagca gatgagatca tgggtacagt agtgctttgc agcaggcaaa    51420
acattctaac gtttgtaagg atactaatga ggaaaaaaaa aatgccagtt tccacagcca    51480
agaaattcac agtgtagctg gagagagaaa agtggtcatc tgaaatgcca gtaaagcagt    51540
gttagaacgg tgtatcagag aactaagcca taaggtaaag gctgtgaatg cggtgggatg    51600
tcttagtaag ggaagattgt tgatgttggg ggtgctcagt aaaggtttca cagagaaggt    51660
aggttctctt aggcctcatg aactgtgat gctttggctg gatgatggga ggggaagcag    51720
cagcatggct gagcaggaaa gagactagag tgagtagagt gtatctacga agcagcagca    51780
ggcagccaag aggccccccc tggctgtacc cagatggcaa accgcaggac ggctcaagtc    51840
agatgcccct ggaagctaaa tctgtttttg attttctctg aataggagaa attctcattg    51900
```

```
tgatgctttg ccttctcctt attgttagtg gaaacaatag tcgtcatata actcagaagt    51960
tatccaaggc tttaactaat agaggacttg tccaggaaac agacccaaag tcagtaagtc    52020
tagactagaa agtgtctttt tttcctctcc ctattttggt tatgcttcca gtttctcatg    52080
ctaaacttgg atatgtttgg cccccttgca taaatgcaaa cagcctctga ttttgagtgg    52140
gatcgtaggc tgaatgaagc tggagaggtc atcggcgtca gcatcctgct ttctttagga    52200
accgagttta aactctgctt ggataagaaa ctgtcttctt tcagaagact ctgacagagt    52260
ggctggtttg ggagtaaccc tcctgtcaat aaaagaaaaa gaagtacaga agctcattat    52320
aatagatgaa acaacagttc agagagcagc caggacttga gggataattc ctgagagaca    52380
ggagcaccct gagaatagct gcctgttcac tctgatgcca tcccccgagg acttctaatt    52440
cacagtcatg ggtatgggga cttcacagga acagcagcc ccacagggct gacaggctgg    52500 ggttagggg ttcccagagt atctgggatt tgaaggacaa aagtctcagg agaaagggaa    52560
tcatggggaa ataaacaaaa aacgagcatg cagtcttcca ttaaggtctt tgccaactcc    52620
taaggtgcac acgatcagag caagactcct ggagtccctg cagaaagaag cggctgggag    52680
cctaaggagc tgtgcagcta tttcagtaac catatatagt gctaatgaga caaaggtcca    52740
tgttcagggc tggccaggat ggaggggtcc tgggaaatac cccaggcttt agttgaaggc    52800
ccagaaggcc acaccttcag actatgggca agctgaaaaa agtcctgaca aaagttgaag    52860
ctgataggat taaagtgttc tgactgcatt ctctgtgcct gcaagcagaa tgtgttatat    52920
tcttaagaga aagataatct ggattgtcca gaatctctat aattttaat gcagaatatt    52980 ggtatctaat aaaaaattaa gatgcaagtt agaaattgaa accaaatgac caaaatgaag    53040
aataaaaaga gatggcagaa agagacttaa agtttattca gatattggag ttatcagtca    53100
ggaactaaca atactcaata atacagaagt gaaggaggat ttcaacaaga tacaaaatct    53160
tcttagccaa gtggaattct ggaaatgaaa aatataagaa gtgaaattaa cagttcaata    53220
catggattta atagcagttt atagacttac acacacaaag gataaaggat tattggaaaa    53280
ggataaagga ttattggacc agaaggaata ttagtagaaa aatacacaga ttgaagcaca    53340
cagagaaaaa atacagaaaa gagaataaga gacatacagg acatggtgaa aacattttac    53400
atacacgtgt gtctggagtt gtagaagagg agagtgtgat agaaccaaca ttttaaaaaa    53460
tactgacaga gttttctaga agcatcagaa gacataaagt cacagattag agaagctata    53520
cagttctcag taggataaat acaaagagct acactgaggt acatctgtgg acctctgtgg    53580
acaaatagaa tgagcaaaca cttaaactca actgtatcag aaattacatt aagtataagt    53640
ggactgtatg tacaactgaa agccaaagat ttttaaatgg gataaaatat taaaatccat    53700 ttatatctt ttatgagaga taatctttag acaaacttta agggcagaaa tttgaaagta    53760
aaaattttgg aaataaacac acatacacgc gtgcatacag gcagagagca atcaataaag    53820
gtatagaata tttagatagt actaaataat caacttactc tgcttgacaa gtgtaaaaca    53880
ttacactcat caacagcaag atgctctttt taaagtgcac gtagatcatt gacaaaaata    53940
aataatgtgc ctggccataa atcaagttta aataaattgc aaggttttga ataacttgt    54000 atgttccctg actacagtgc aaagtagaaa tcagtaacag ataaatataa aatctgagag    54060
tgtttggaaa ttaaacagta tacttctatt aataaatgcc ctttgggcca aagaaagtgt    54120
tacaatggaa attaattttt tttacctaaa ttgtaatgaa aatgatatgt aaatgtgtgg    54180
gatgcattta aaatagtgca tagaaataaa tttacagctt tgtatttagg tattaagaaa    54240
gaagaaagat tgaaatatct aaacttcaat ctcaagaatc taaatgcagt atggattaaa    54300
```

```
gtcccccaaa accaaagaaa gtaaaaataa gagcagaaag gagcaaaata gaaaaaaagt   54360
taggtgaaga attaagtaag taagatacca catagttgca ctcatctcac atgccagcaa   54420
agcagtgctc aaaattcttc aagcggggct caacagtat gtgaactgag aacttacaga   54480
tattcaagct gtatttagaa aaggcagagg aaccagaaat caaattgcca acatctgttg   54540
cagagagttc cagaagaaca tctacttctg cttcattgac tatgctaagc ctttgactgt   54600
gtggatcaca gcaaactgga aaattcttaa agagatggga ataccagacc accttgcctg   54660
cctcatgaga aatctgtatg caggtcaaga agcagcagtt agaactggac atggaacaat   54720
ggactggttc caaattggga aaggagtaca tcaacgctgt attttgtcac cctgcctgtt   54780
taacttatat gcagagtaca tcatgcaaaa tgccatactg gatgaagcac aagctggaat   54840
caagattgcc gggagaaata tcaataactt cagatatgca gatgacacca cccttatgac   54900
agaaagcgaa gaggaactaa agagcctctt gatgaaggtg aaagaggaga gtgaaaaagc   54960
tggctcaaaa cttaacattc aaaaaattaa aatcatgcca tctggtccca tcacttcatg   55020
gcaaatagat ggggagacaa tggaaacagt gacagacttt attttcttgg gctccaaaat   55080
cactttagat ggtaaatgca gccatgaaat taaaagatgt ttgctccttg aagaaaagc   55140 tgtgacaaac ttagcatatt aaaaagtaga gacattactt tgtcaacaaa ggtccatcta   55200
gtcaagtctg tggttttcc agtggtcatg tatggatgtg agagttggac catgaagaaa   55260
gctgagcgcc aaagaattga tgcttttgaa ctgtgttgtt ggagaagact cttgagagtt   55320
agtcagtcct aaaggaaatc agtcctgaat attcattgga aagactgata ctgcagctga   55380
aactcccata ctttgtccac ctgatgcgaa gagccaactc attagaaaag accctgatgc   55440
tgggaaagat tgaaggcagg aggagaaggg gacgacagag gatgagatga ttggatgaca   55500
tggctgactc gatggatgag tttgagtaag ctctgggagt cagtgatgca cagggatgcc   55560
tgcctgctgt agtccatggc gtcgcaaaga gtcagacacg actgagcgac tgaactgaac   55620
tgaagatgaa gaaaatcaac aaaatgaaat ggaaaagatt aataaaattg ataaacatca   55680
gtaagactga tcaagtacaa agggaaaaca cagatgatca atatcaggaa tgaaaagaga   55740
gatattacta cagattttat aggcattaaa tagacataca tttagtccaa acatttaaca   55800
gtttaaagtg aacatattcg ttgaaaaata ccacctacaa aactgacatg aaaatatgca   55860
gaatcttatg tctgtggaag aaaattcatg atttaaaatc gttacccacc ccaccctccc   55920
aaaaaaaaca caaaacctta gatggctttt ttgatgactt ctcagtcttt caaggcagaa   55980
ataatgccaa acttggctaa catttgtcaa agaatagaac tttttctact cacttttcaa   56040 ctcctttat gaggccagca taacctgaca ctgaaatcca atttaacat tacagtgttc   56100 agcaaaagag gtccgacaca aaagagtaaa tactgtttgg ttccattaat atgaaattcc   56160
ttagtgggct aacagaaatc agagtaggga ttactcttgg aggggtgaga tactggctgg   56220
gtgcagcaga gaggactctc ctggggtgct ggaatgttct atatctttat ctggatagtg   56280
attataggag tactgaatgt actttatgtg cactttagta gtaacattaa aaaaaaaga   56340 ctataaactt gatacttcat tcccatgtag tttcttttct gtctaaattg ggttccgtgt   56400
gcattgcctg cgctcatgtc ctgtttgact gccttggatg aatgcccatt ctgatggagt   56460
tgccttgcac agcaggcagg cttttgcctt gggcttgctc ttctttgaga ataaggaaat   56520
gaccccgacg cagaggtgcc tgtgatggag cctctagttc ttccctcact gctcatttca   56580
cgcagtgtgg ttttcttcac aggcacggtg gttttgggaa gcatacttcc agtcaatcaa   56640
ggccatcgcc ctggccaccc tgcagatcat caatgatcgg atctatccat acgctgccat   56700
```

```
ctcctatgaa gactggaacg accctcctgc tgtggtgagt aaatgctggg gtgagccacg   56760
tcaggtatag gccagaggcc aggacgatgg aacatgtact ggatttgtaa aggtgattta   56820
agtttgagct ttctaagata taagagtgtg ctagaatatg tgggacccaa taggaccagt   56880
tttggtcttc cctgttggct cagatggtaa ggaatctacc tgcagtgcgg gagacctagg   56940
ttcaatccct gggttgggag gattccctgg aagagggcat ggccacccac tccagtattt   57000
ttgcctggag aatccccatg gacagaggag cctggcgggc tacagtccac ggggtaagga   57060
aagagtagga cacgaatgaa gcgacttagc acacacgcac gcaggaccag tttaattttg   57120
aaatgaccaa agtaacaaat actgaagcag cagtttgttt taaatgtgct taggaaggca   57180
gtgtgtttgt ttattgcaga aataaattgg gaggcctggg tcttgttgga aatggaagac   57240
ttcctgatga cttttgcaat ggtggtgctt tgaactcttg aaaagattct ctaagcaatt   57300
agtgatggct tatattttga gccctgcctc ttgtgcttta tgctaactaa gtgctttgca   57360
tggatgtcaa ttaacattca ggcccctgct aggggacatc atcagcaaaa atgatagaga   57420
ggcattaggg attgctcagg gtggccgaga cccctcggtc cttccagcag caagatgggg   57480
tgggcagatg ctgctctcag agcttcgtcc ttaattgcag gagtcatgag gtacctgtgg   57540
cctgggaggg acaagtacct gaagctgtgg ggggcacagt ctctgctctg gggcacacct   57600
gctctctggc tcacagaccc cgaggcctct gcgtgagaga gctagactcc tctccgctga   57660
atcattgctc ttctctttgt ggccagccgt ccttgtctcc tgactctacc cgctcttaac   57720
agtgctgtat gctgccacct ggtcggtctt cttttcccct ccccatctcc ctcctgcctt   57780
tcttaagggc ttattgtgtg ccagtgctcc accaggtgct tagaaagcag aggaaaccag   57840
gccctgccct cagaggaact cagtgctaac ttgggaagcc cggaaggaag ggtattgtat   57900
gagttgccct gcagtggagc tgagggtgga attcccaggg agcccgggc aagggcgggc   57960 agtgctcctg aaccgggagt gcccgagagg aagtaaaacc gtcaaggcaa gtgaaacagt   58020
agcaaacacc tcctttctgt tttccttgag ggaagatttc cttctgtcca tctcttccct   58080
tgacttcctt gccaaaggta accttccaga atgtttgtgt tcctgtatag acatactgtg   58140 taatttttaga atacaaatgg ggtcacacga tgcatattat tctcaacctt gccttttta   58200 ctttaaaact agatcatggg cttacttcca tttcattctg tatagggata cttcagtttt   58260
aaggactgct gtaatcatgt tttggccttt tggctaagat cacgtgttgg actgctgtat   58320
gtgatcccat cgcttaggtc tatcttacag gcaaatctgt tttcaacagt aatagggggg   58380
atgcatatta ttgcatccac acagcctttc aggtgtgtat gcacataaat gtgtgaatgt   58440
atctgtagaa ttagtaatag cagagaaata actagaagaa taggcacact ttaagtgttg   58500
atcagtcaat cagtctgttc aattgctcag ccccgtctga ctcttttcaa ccccatcgac   58560
ttgagtgttg atagatttta acaaattgct ctttcaaaag actacaccag tttataattc   58620
caccaataac atttttggtta ttctgcttct tcatgccttc agtaaccctg agtacttgaa   58680
tttttgctta cttggaaggt tgatatctct ctctgttgct cccagaatac aaatataaat   58740
cctatttgaa ctgtgattga taaccctgac tttttagatt gttttggca tgtattcatt   58800 cagcgggtat ttcctgagtg cctatttgt tccaggcagt gttcttggta cttgagatat   58860
gtcagtcaac aaagcagaga aaatccacg ccactgggga gtttacagtg cagtaggtct   58920
tgctatctgg aagcaaggtt tgtctttcta gtaaaatttt aaagctttct gtatactggt   58980
cctttacaag tcttgcaaaa ttttttctta ggtgttttat cattcttaca ctccgataaa   59040
ggaattcatg ctttctgaca ttttagttcc taactgatta cttttgtatg aagacatatt   59100
```

```
gttggctttt atgtataaac ttgtaatact ctgagttctg taattgtttg acttttttca  59160
agttgattct cttgtgtctt ctagatgtac agtgatacct gcaaatgcta attattcttt  59220
tttccaacac ttgaaccttt tgttatcttt tatctaattg ccttggctgc tgcttccaga  59280
acaatgttaa atgaccatca tttaatgttg ttaagtgtta aaagagaagg gcgggtgttg  59340
tgtgagaaag ggggaagtta gatttccccc tcccacagct tacctggttc tctggaggac  59400
agagactcag gcaagtgagc gttagataca gggaggggg gggccaagaa tgatgaattt  59460
tggggtttct ggttccatcc agaaggagaa gcaaattcag gggtcagagg gacaagagaa  59520
cacggcggct tcaggaactt tgaggggtc agtgtagcag gagtgaaggg tttgtgaggg  59580
agatgcagaa ggtggagcct tctgagggcc cagattgcca aaccctggc atcttaaggg  59640
aggtgctgga atgtttccgg tgggtgatgg gagatcagca gagcacctcc acagaagtca  59700
tgtgctgaga ttgcatttcg ggtcattctg acatcagtgt ggagggtgct tctgttgtag  59760
gaggacaggg ccaaaggcag gagactgttt caggaaccag gtgagaatta atggaggata  59820
aatgtgagtg atggggcttc cctggtggct cagtcggtaa agaatctgcc tgcaatcctg  59880
gagactgcct gcaagacagg tgacctgggt ttgatccctg ggtcaggaag ttccctgga  59940
gaaggaaatg gcaacccagt ccagtattct tgcctggaaa atcccatgga cagaggagcc  60000
tggcagacaa cagtccacag ggtcgcaaag agttggacac aacttagcga ctagaccacc  60060
acccaaatgt gagtgatacc agggaccacc tgccgtgcta actgggaagg cgtttaggaa  60120
gagtgaggag gatggtgttg tctattgagt gcgagtacat gggcatcgcg ggccaggtgg  60180
tgttggagtc caggcatggt ctggcagcag ggccttccac cgtccagcgc caggcctcct  60240
ttccagcctt atttccttct gttccctttt ggggagcact aggtttctgg ctccacaatg  60300
ttgtccttcc tgtgtttgct ctctgctttt ccttcctgtg cccttgtgac cattgcttct  60360
ttccctggac gccgttcttc accatcacct ctggtcttat gcattttatt caggggccct  60420
ggccatgtac cccttttctcc atgagatttt tcctggaccc cttacaaaaa gtaatctttc  60480
cttcttgtaa atcttaaagc gtattatcta tttctttcct gtcatttaac atacatagaa  60540
gtacaatttc ctgtaaaatt ttaagtttct taagggaatt tctgagttat cttggtattc  60600
cttataatat ttagagcaat ttaattcagg taggaagccc tttatacata agaaggaag  60660
gagggattga ggagggtgga atttccagga cttgaaccat ccaaagctca gtcgcatgct  60720
gacgtgacag ccttttatttt atttgacctt caccctattg ggaaggtgag aaaagtgaaa  60780
gattccctct catgtctaaa gcagacctaa tgaggctcac agagcctgat gactcgtcca  60840
aggtcgcata atgggcaagt tgtgtaaaca agcaggaacc cgggtcttct acccacagag  60900
tgtcttgact ggcttatgca gtattatggg agccattgag cctcctccag gctgaaacat  60960
ttccactctt ctgagcatat ggtacaagct tgagacaaag aagatcacat ctgttgctct  61020
gcaggagaat tcatacaggt gggataatca tgacccagct agagaatgtg gagacagtgg  61080
gcgctttcct gtacttttat ctaaagctcc aagaaaagtg tttgaggata aatggttggg  61140
attctggtct ctgtctttca taagaataca gactaggaga aaatagtata tgaagtttta  61200
tagttttgaa ataggcatat tttaattgag gacaaagcag aatgctggac tcaatttggg  61260
aaagaagatg agtataaaaa gcatagatct gaataagcaa ctggaaacta tattatttat  61320
ttatttattt atttttcttt cttaagggga atttagtgtt taagttctag gagctcaggt  61380
gatgagagcc ctgatttaaa gctgtaggtt gtacatttct gcttcttcag tgaaagcaac  61440
tgacagaaag cctgaatagc attgatttat ttatagttac ctcccccgcc cccgcccct  61500
```

```
tcagaaatac ttaacctgtc ctagatgtgg ttactatgag cccagcctgc aggggagtct    61560
cccctctaga ttccatcaaa tttaccattt caggcacccc gaggtgggag ttggtgtgga    61620
tctcagtcag taaatcaagg gttggcctgg cttttcaaa gatctgcagt cagggcctcc     61680
agccatggct ctgagcttgc tcagctggag aggagggccg agagcagaga gccctttttt    61740
ggccagatgc cactgcctga gtttaacgtt aaaaaaaaga agaggcttgt gtgtggatgg    61800
tgaaaacagg gaggggtggt ggccggccgt gcagaaaccc ggtgcctggg ccaccagatg    61860
ctctgccgtc ctcatttgta accggagcgg ggctgattgc attatccacc ttttgctaca    61920
ctctcaagat ggtgaaagcg tgtgagtagg tcattctgga gcacaacttt aaagtggcac    61980
agtggtccag tctggagaga tgggcccttt gtcttgaatc ttctctttgg aaggaatttc    62040
tcaccaaatg gaagtttctt tgtgagagat gacacatttg ttcttaatca ttaaattttt    62100
tagctcctct tgtcaaggat gcctgcattt tacggtctct tgaggttttc atttctcccc    62160
cccccctttt tttttttttt gcaagtctca gcaaaacttt accatctccc caaacactcc    62220
ccgcctgtgt cgcttctcag gcgtgtgcca tttctggtct cccccttggc gggcctggtg    62280
cctggatctg ggcctggcct gggtggctgg ggtctcttc agacagcctc ccccagctta     62340
cctctggtcg cctgcagggc acgagcttgt cgggaggaca cagactgagg cccgggagca    62400
ttgagaatgc cgatatggag cgggccaaga gccgtgaggt tttggatttc tggcctgtgc    62460
caacaaagcc atatcctctc ggtaaaatca cgtagagtgg agtattttcc catattattt    62520
ttgtacagcg tgattagaag gattatctcc accttatcgt gtgctaacgt gattgagtag    62580
tggtggtagt gtcagtcgct cagtcgtgtc cgtctctgtg gactgcagcc cgccaggctc    62640
ttccatccgt ggaattctcc aggaaagaat actggagtgg gttgccatgc ccttctccag    62700
gggatcttct caacccgggg atcaaaccca ggtctcctgc atttaaggtg gagtctttac    62760
catttgagct acccaagaag taaactttat ttacctagtt ccttctggca gtgttttttca   62820
gatttgttgt catagataac actagtatag ataacccagg ttttttttt ttttaacact     62880
gactatactg gacctagaac aacagaaaag ggagacagca ggggtcccat agctattgac    62940
aaaaaacctg acaaactgac gaggaaagtg gggaagtgac ttaaaacgga ttgttgcgcc    63000
cagcataaga ataaggctga cagcaaaaac ttgttcctat gaaatctagc ccttgtggca    63060
gcttcgctgc aagccaggcc tcaggtgcgg gttatatgca ctcacctagg catcctgtgg    63120
agaaggcaat ggcaccccgc tccagtactc ttgcctggaa tatcccacag atggaggagc    63180
ctggtgggct acagtccatg gggttgctaa gagttggaca cgactgagca acttcacttt    63240
cacttttcac tttcatgcat tggagaagga aatggcaacc tgctccagtg ttcttgcctg    63300
gagaatccca gggacgggga agccttgtgc gctcccgtct ccagggtcgc atagagtcgg    63360
acacgactga agccacttag cagcagcagc agcaggcatc ctgtaagcct gagtccagct    63420
tttgaagata gaggggggaag gctcagcagg tgggaggcct gtagaagagc acttgcttgc    63480
atggcagtcc tcacccacga ggggcagggt cagagctgtg gactcggtgc agcagagcct    63540
gctgctgtcc ctagttcttg gggaagcggt tctccaatgt caggaggttc tccaatgtca    63600
ggacgtgtca gaagctcctg aaaggctcgt gaaaatgcag attgctgcca ctccacccct    63660
agtctcagat ggtgttggtc tgggtgaggt cctcggattt gcatttctag caagttccca    63720
agtagtgtcg atgcagctag tccaggggct gtgctttgat gtgggattgg ttcactgtgt    63780
gtgtcctgac tcactgcctg gagaaggcac tccctctccc cccatccagt gcctcttctg    63840
catccctgga acttgattag aagcttccag agcctgggct aagcccacat ctgtctcagc    63900
```

```
tacaagaaga actcagggct accggtactt agatgtccag acggcagccc tcctcattca   63960
cagaggttgt ggttgtataa gctgctgaaa atatcactca gctgtaaata ctaacaagct   64020
ataaatcact ctgcaggccg aaggagcgcc agctcagatg cctggagcag aaccccgagt   64080
ctgtttaact ccactccctg ccctttaaca tccaggttgt ggaatgtgtc tctggaattt   64140
gaacacctcc cctgctcacc ccctccccca ggaggccttt ttggcttatt ttctcccctt   64200
tttcctccca ctgcccagat atggctgaag tatgtatgga attcagaaat tttagcttga   64260
attttaagta agtttaagcg ttttggagtc ttttgttttt agaggtgcca catttacagg   64320
gtcacagttg cacagaaggt ccgccttcct gcccccaatg ccaggccttt ccttgagttg   64380
ccttcgccat tgaactgttt cgtagctgta cttgcttctg tggaaacaag ccggacagtc   64440
tcaggtcatg gagtaaagaa agccgagttg ggtctgtgga gcgagagacg caggaagatc   64500
ccaggagctt gacccggggc cccatgccaa gaattctgat ggtcagatag taacgtggga   64560
aagatgaggc cgcaggtcag atccaggtgg ggaggataag taaagcacag gaagggccag   64620
actcggggt gctgcggagg gggtcctgtc aatcagagca tccttcctgg agagggagac   64680
tcgtgtaccc ggggttgccat gtgtgcatgg cgactccagt ggtggcggag gtcgagccgc   64740
acgtgcagtt tctctggatg cagaccttcc tcacccaccc gggcttttgt agagttcact   64800
tttatgactc tggcatttat gagtcaaccc ctgtctgctt ccttacgtcc cagagaggag   64860
ggcagcgagt ggagtaggtc ctcggggtcc atggagcttg gtctggcagc agatgaattg   64920
aggacacctt gggtattttg gcaaagccat ccttcacaca ccagctgtca ctcaccggca   64980
catccaattc cctttcccct tgcttcaggg cccactttct ttctccctcg agtcagttta   65040
agaggttcag tagcagaggt tactgggaaa atgagttgtc gggtatccca acatcagggg   65100
taatgaattc tatttctcgt atcctatact gtttacatag acatatcaat taatatttga   65160
gtgtaatttt tctaatgaga gggtcattac agctgcagag tagaaaaatt tccacattgc   65220
tccagctgga gtttgagtct tgattttggg ttctgtctta tctttcagct atatttctta   65280
atttcatgtt taagaaaaaa atagaatggc ttaacacatg aatggtttaa aaagtaaaat   65340
cataaaataa cgcctgtaaa ttaaggccca ttcccgaggg gcagctgctc tcagctctcc   65400
tctgatattt attttcctac cttctcataa aatgctgata gtgctgtttt tttttaattt   65460
ctctatctca gacattctct cttttacttcc atagagttag tgctttgttt cctgttcctg   65520
cctcttcctc tgcacgtttc tcttccctct catcttacca gtggggcagt gtcatcattt   65580
ttcattagag caatgtttat tgttgcgtca ttaggactat ataaatgttg gtgtcagtgg   65640
gaccaagtaa taaaacatgg ttatgttttcc tttcttgcat aacttttttt attttccagg   65700
gagtaaatgc atagctgtct taaaaacaaa acaaaacaaa aacactctct tagctttcca   65760
tgttcctatc actgcttttt actaacttct ccaacgaaga gtgaaatggt caagcgcaag   65820
tgaactatgg gctgtccccc gccttcgctc tctttccctc cctcccaccc ttctcgtaca   65880
tagcccgcac ctgcagctcc agtgtggatt gactgctctc taggtctcct gtacagaggt   65940
cagcctcaat tctctgttca ccatgattct tgcaattctc ttcttttctc ttctttgttg   66000
gattttgtt ttcaagttct aacatcctct ttcttttgg gttttttttt tttttaatc   66060
cagtagcttc cccagaaaag ggactgttgg ggggtaaatt tgctgtcacc ttgtgtctct   66120
gaaaatgcat ctattctctt tcaccttgat gaatagctgt gtgcagtgct gtgcttgggc   66180
tggtataaaa ttctggtcca cgtggctttt cttcaaaatt tcaaaggcat tgcttcattg   66240
tctgctgatc ttcctgtttt aatctcaaga gatgtcattc taattcctga tcctttttgtg   66300
```

```
tgaaactttt aatcttcctg aaaaatcctg tgttctgaaa ctaatgatga tacaccctgg   66360
tatgagtgtt tttttgttca ctggatactg atttgggccc tttataaggg aattttcaca   66420
ttttctatct cccccgcccc gcctcgtttg ctctcttttt cgcttggtgg aacttgggtt   66480
accttgatga tgaatgtgct agactgaccc ttatttttct tatctttttct ttctgtctta   66540 atggactctt tgttttaatt tcttagatat tttctcaatt ttatcttcta attttttcatt   66600 ttaaaattt tgttcacttt taatttctaa gagttttttc ttgtcttcta cctaatcttt   66660
tttatagctt cctattcttg ttttaaggat acagtacttt ctctctctga agatatttgt   66720
ggttttgttt ttatttttta ttgtttttat ataaatttat tttaattgga ggctaattac   66780
tttacaatat tgtattggtt ttgccataca gaaacatgaa tccgccacgg gtgtacatgt   66840
gttccccatc ctgaaccccc ctcccacctc cctccctgta ccatccctct gggtcatccc   66900
agtgcaccag ccccaagcat cctgtatcct gcatcaaacc tggactggtg attcgtttca   66960
tatatgatat tatacatgtt tcaatgccat tctcccaaat catcccaccc tcgccctctc   67020
ccacagagtc caaaagactg ttctatacat ctgtgtctct tttgctgtct cgcatacagg   67080
gttatcgtta ccctctttct aaattccata tatatgcatt agtatactgt attggtgttt   67140
ttctttctgt ttttatttgt cttaagctcc gtgtattgtt tgtttccttt gaattccatc   67200
atcagggctt tattttctgt cttttcacatt ggaaactttc ttcaaatacc tgatgttttt   67260
cagcagtcta ttcttatttg ggtgaggcac tgaaaactga tgggaagccc tgtgtgcatg   67320
gtttggcttg tcaacttttg ggctttactg aggtttatgg atggggactc aactgtttac   67380
cccgttgttg gtactcttca gttcagttca gtcgctcagt cgtgtccgat tctttgcgac   67440
cccatgaact gcagcacgcc aggcctccct gttcatcacc atctcccgga gttcactcaa   67500
actcacgtcc atcgagtcag tgatgccatc cagccatctc atcctctgtc gtccccttct   67560
cctcctgccc ccaatcactc ccagcatcag agtcttttcc aatgagtcaa ctcttcgcat   67620
gaggtggcca aaagtacttt taggttattt ctgttggatt ggttcactga cccaaaggat   67680 aatcttctg cccttgggag tagggcgagg atgatagta agtctgggct gcaagtcttt   67740
ggggaggaga acgggggaag gagactggtt cttatccttc atacagtaga tgatcactga   67800
atctgccgta tttggtgtgg cgcctcatcc tgctggccgt ccgttgtgtc tctggagtgt   67860
ggggtctctc tagttcattt tctccagaga ataaacctcc tgctaagatg cagtgggtgg   67920
agaggacagg gagggcattg acctgcctgt gcacgtaggt ttaagggatc tcagaaccaa   67980
cttttcttat tcctgttttc agagtccgtc ctccctagac acctaggcct tcccattttct   68040 cagtctgcta accatcatcc ttggaaggat tagcttccca tgctttgcta ggcagtttat   68100 gttccttat ctgcctttg tttgtttgct taaacagacc tacaattctg tatatttttt   68160
aattttctat tttgacataa ttttagactt aaatttccaa aaccagtgca tcgtttctgc   68220
acacccttca ctcatagtca tcaaacacta atatttttgcc acctttctttt tattcttttc   68280 tgtgtgtgtg taagcacaca caaacatata cattcatatt tatgtatttt tttcctgaac   68340
catttgcaag ttacagatat gaggcacctt tactcctaga tctttctcag aaaatcaccc   68400
aaatgatcgc tagtggtaaa gaacccactt gccagtttag gagacataag ggatgcaggt   68460
tcaatctcta ggtcgggaag atgccctgga ggagggcatg gcaacccatt ccagtattct   68520
tgcctggagg atccccatgg acagaggagt ctggccggct acagtccatg gggtcacaaa   68580
gagctggaca ccgctgaagc cgctgagcgc acacatacag accttattta gattttgtca   68640
gttatcttca ttatgtccat tacagcagaa gattgcaggc agtcattgtg ttcagttgtc   68700
```

```
atgtctctgt agcttctact agaacagttt ctcgggtcct tctttgtctg gcatgacagt   68760 ggccttttg aagagaacat gtcagttatt ttggaaggta tcctttgatt tggatttgtc   68820
tggtgctttt gtgttaaatt atgcattcca tttcaaatta ttgaaattca ggttaagtat   68880
ttttggcagg aatgtcacaa aagtaatgtt ggttcttggt gtatcacgct ggaggacacg   68940
tgatgttggt ctgtcccatt ggtcgtgacg ataacttcac tcagagcttt ctccagtggg   69000
aggttacttc cttcttttag tgtgtcttgt tcggacgtac tttgagactg tgtaaatatc   69060
ctgttactcc tcaaaccttt actagggtta gcatccacca atgatttctt gtctgaatca   69120
attgttataa tggttgccaa atggtaattt taattcccat gctctatctg cttttgagag   69180
tgatttttat tctttaacct gagggttcat gtcttttaat cagtgttgga atattctgcg   69240
tcattttctt gttgaatatt atgtatctgt cattctcact gatcttggaa tcctattaaa   69300
tgcatgttag acctctttaa ttctgttgtt gtgtctctca agtttgtttt ttttttttccc   69360 cttatgtttt acacatttt aactctttgt gctgcatgtt ggaaaatttt ttctcatcta   69420
ttttgctctt tcctttggcc atgtccaatg tgtttttacc catccagtgg gattaaaatt   69480
tcagtagtta tttctagaag ctctgactat ttttcaaatc tgtctgcctg atctttttc   69540 atagtatctt tttttcccta tgtattttca cttccctctt ttgtgtgtta attatttgag   69600
atactcactt tatattctcc agtaattcaa ttttaaaatt tctcatagct tctaaccctg   69660
tcgtttgcct cctgcctgtt gctcttgttg cattatttcc ttatatgttt tgcaatcttg   69720
gaatgtgagt ttcatctctg gtgaggtttt ctgtggaaat cttcgccacc tgagtgtaag   69780
aaggtatttc tccagagagt ttgttcttgt tttgtggctt ctgccagatg ttccaggagg   69840
tattgcagag ataaatcact ttttaacatt agtttctcgg tcagaggttt ccatactgca   69900
cagggagggt ccatttaaac cccacaccag tgcgagggct agcctctgtt ggaagcatcc   69960
cccgtccaaa ctcaggttga aaaggacaga tgattttctg tatgtccatg ttctaggagt   70020
gactttcggg accaccttt tactgattgt acaggccttc aagggttcag gcttggtatg   70080
taagtcccac cgcctgcccc ctctgccccc gtgcccaaag ctgtgctcct cgtccaaagt   70140
gggtgtgagt gtccacgccc tgcgccgctg ggcccagtga cagcctcccc gcggcgcctt   70200
cagttctttg cagtttgctc atcgatttgg gttcctggca actttccatt tcctgaatat   70260 tttttttaa ttttgttata tttatcccta cgttctgtc tgttgtccag caagagacgc   70320
tgtctttttc gcctccccag atacgttgag ctcctgtcca ctgttgtttc cttgcctgtt   70380
ctttgtgccc tgtgggttta tgctccccct cttctccccc caggaggaag cagggctaaa   70440
acacagtaga caaaacatac accttattgg aattccggag aagttaagaa atgattgcat   70500
tttagaggtt gttctttcca ctttgtattg accttaatac tcctgtcagc tcaaaactgt   70560
acaaaagctt tgattttctt ggtcataact gtgtaggtat tttgagcttg gaggccacaa   70620
gctataactt aatctttccc aagagtgtct gtttaccaag ctagtgatgt cttccttcat   70680
accatagctg acctctgaaa tatagtcagc gggccgccag caaacatttt tatgcccagg   70740
ccaaagaagg agcctgtctt tcgaactgag tatttcaggt gtgggatagc cagatgaaac   70800
tataaatttg tttcacctct catgagaagt agtgctttga gccaccatta gcattcttga   70860
acactttgga ttatagatca gcctgtttgc ttgaatcaga gaaattacta gcttttcac   70920 tgaagttttt ttttgttgtt ttttttttta aagtgttttc agtatacttt ttaagtaaca   70980
gatccaggga tgaggatggt gaatttgaag actgtgtctt aagaataatc cacattttt   71040 actatcaaac gactgaactg ttatttttaa catacaaagt taagaaccag taaaatcaac   71100
```

```
aacatgttgt atgtgctcct actttattgt attcacccat ttaattgatt agacagtatc    71160
ttaaaccatt ttaccacaga tgtatttagt gaaatttatt acttgcagac tgatataact    71220
catgaattat taaaagcatc agcatatgga accttctctt tctcatctag attctttgaa    71280
tacggcttag gttgagccat ttaactggct tctgtccatc ccactgatgg aagccacagt    71340
cagatgaggg ttcttataaa tgattggctt cctttccgag caagaagagg ataaaatgtc    71400
agcttttttcc tctactacct gaaaagcaat caggagcagc cctcccactc ttcttgacag    71460
tagtttggct ttatagaaga agggcaggca ttgagccaaa tgtgaatgtc agtgctatat    71520
aaagaaaaaa gttaagtagc taaaactccg atagtaactg gaatttttag agcagtattc    71580
agatgggttt accctgtaag ctttcagaaa gctaacaata actcagcctg aactgcaagg    71640
tttaatccct tctttcctgg tgatgatccc agtaaattga agttacttac cgaatgtctc    71700
ttcacagcga tttgctcatg tgtaggactg ggtttagggg gtaataatag tttcagaaga    71760
atagggtagt ggttagtgac tgattaccaa ttactaatca aagccattga aaaggacatt    71820
ttggaatcaa ccggagttcc agaccattta ggagcctgac attgtgcttt cttatctctt    71880
taaaatttgt tatccttacc tgtaaaatga actattactt atttcatagg attattatga    71940
gacagtagtg aagtaatgta tgtaggagca ttttgtaagt ggtattgata aggctgctag    72000
tgtaacgttc tatcacatgg aaacatacac tctagaattg ggtgggactc tggagaacaa    72060
aactgaaatt tacagagggc acagttttat acccagatag gctctgttgt gtattttctg    72120
ttgttgaatc cttgcatccc caaagtagca ttctgctagc tccattccta cagatgaaga    72180
aggggagtct tgtttatttt taagatctgc gtctccatca tcccatttca tacatgagga    72240
aatggaggtc tgcagaagtg tggtgacttg tctgacgcag agattctcag tccatcattc    72300
catctgttat aataggttat gatgttgtcg cagtaattgt ttttgtattg cacacagact    72360
tggccctgaa attaatcagg aaatacaata gcacctaatt caattattag cgtaaatata    72420
gaaagacttg tgtcactggc ttcttggtgg attaggtatg ctaaatgacc ttcccaactg    72480
aacaacaaaa atattgaatg aagtatgata aagcctgttg ctaagttgag tgaaaagtaa    72540
gatacttgtt gaccctaaac aaagtgaagc caggtgtcct gggaggtgct ttcactgcag    72600
acatttgcag agttcggtgg cgtagagcct cagcctggtt gactgtctga agcagggagc    72660
aggggagcgg gagagaaagt gtgtggcctg agcaagttgg agaatctatc gggagcttcc    72720
tgggtgaagc cagggagcta aaagagcctc ttgagtgaag gggtgaagaa gcgcaagtct    72780
gtattgaccc tgctgttgag cactgcattc ataagccagc ttcacatggt ttgtggtcca    72840
tgttcgtact acaggtatag tccaaacaaa ccgtaagagg agaatttcct cggaggtggc    72900
catgagttgg taggggccag cagaagtgga cacggaccct ctctgtaggg gttcgttttc    72960
agtccagctc tcaaatgatg aacgtgtctg tggaaaatga gcagctcact gtaaaaaaca    73020
aaacaaaaac cccacgatca gaaataaggc aaaccctatc aagaaataag gcagtatcac    73080
gagcgagaac cagcagaaac acagctgcaa ggcttgggca agctccagaa gatagtggag    73140
gacagcgagg cctggcatgc tgcagtccgt ggggttgcaa agagttagac gtgacataga    73200
gactgaatga cactttagat gattaaattc aaagaaatgg tttggaatgc agcccaaaga    73260
gacagaaaat attaacgaat tgaagttacg tggagagcag agggacaagg tccaacatat    73320
gtctagtcag agttccagga cgaagagaga caatggagaa gaggcccatt tttgaaagaa    73380
taatagctga cagttttcca gagctgttga atgatagtag atctcagagc taggaagacc    73440
agcaaaccgc aagcaggaca gtcgtagtga aactgcagtg cacggaagaa aaaggagctt    73500
```

```
ttaaacacat ctagatgttc aagctcgttt tagaaaaggc agaggaacca gagatcaaat    73560
tgccaacatc cgctgggtca tggaaaaagc aagcgagttc cagaaaaaca tctatttctg    73620
ctttattgac tatgccaaag cctttgactg tgtggatcac aataaactgt ggaaaattct    73680
tcaagagatg gaaataccag accacctgac ctgcctctta agaaacctgt atgcaggtca    73740
ggaagcaaca ttagaattgg acatggaaca acagactggt tccaaatagg aaaaggaata    73800
catcaaagat gtatattgtc accctgctta tttaacttat atgcatagta catcatgaga    73860
aatgctgggc tggaagaagc ccaagctgga atcaagattg ccgggagaaa tatcaataac    73920
ctcagatatg cagatgatac cacccttatg gcggaaagtg aagaggaact aaagcgcctt    73980
ttgatgaaag tgaaagagga aagtgaaaaa gttggcttga agctcaacat tcagaaaact    74040
aagatcatag catctggtcc catcacttca tggcaaatag atggagaaac agtgaaaaca    74100
gtgtcagact ttattttttt tggttccaga atcactgcag atggtgattg cagccatgaa    74160
attaaaagac ggttactcct tggaaggaaa gttatgacca acctagatag catattcaaa    74220
agtagagaca ttactttgtc aacaaaggtc catctagtca aggctatggt ttttccggtg    74280
gtcatgtatg gatgtcagag ttggactgtg aagaaagctg agtgccgaaa aattgatgct    74340
tttgaactgt ggtgttggag aagactcttg agtcccttgg actgaaagga gatccaacca    74400
gtccatccta aaggagatca gtcctgggtg ttcattggaa ggactgattt tgaagctgaa    74460
actccaatac tttggccacc tgatgcaaag agctgactta tttgaaaaga ccctgatgct    74520
gggaaagatt gaaggctgga ggagaagggg atgacagagg atgagatggt tggatggcat    74580
caccaactcg atggacatgg gtttgggtgg actccaggag ttggtgatgg acagggaggc    74640
ctggtgtgct acagttcatg gggttgcaga gttggacaca actgagcggc tgaactgaac    74700
tgaaacacat ctagaggaaa aagaggctaa cagtgaaaag gtctggcttg ctcctgtgac    74760
cctcagttag tctcagtggc tcagtttctt tggatattaa agagtcacag taccagttta    74820
ctccagtcca cccagatgtg gttagacccc ttccaagacc aacatacaga aaactgattt    74880
gtgaggacat tactgtaagt aaattgtagg aattctaagt tgataattta actatcttag    74940
ttttgtctac agcactgaaa gggatttctg gccttcgatt ttcatctctc atgtgtctgt    75000
ttaatgtcaa gtcagggaga tttagccatc agcattctcc ttattttcca gagcggtcag    75060
gtatttttta atgggtggga tgaggcaaag acgcagtgta acaaatagac ttcaggcttg    75120
tccctgaatc ttttcctct caatgttaag agagcccgct ggcacacatt ctttaggtct    75180
ctcatcctcc agcttcccaa gtcagcgcac acccagggca gtgctgtgct gcagagagaa    75240
gctgcagagg gttaatgatt aaggcaacgt gggccgcgtt actgattgcc cctttcagat    75300
cttccagcac ccattaacat aaatatcatc tcaccatttt ggacagggga caccacccctt    75360 atgcacgtta gtaatgcgat gctaatgctt aacccttca ttgccctctc tgcttcaaag    75420
gccttgccct atgtccattg ataggagggc tgtttgaacc tcaaggcaaa atgaaaggg    75480 ttaactcctt ttggttttgc cctttgacca cttcaggatg agaggcatga tgaaatactt    75540
ttcaaagtct tcagtggaaa cacatcatgc ataattggag caaaaaagaa taaatcaaag    75600
cttccccccc cccctttag tctggtaatt cataattgaa accacattga ggtaagggtt    75660
gataacttca aaacaaccat gaaaactgcc ctttcgatca aggtagggat aggtaaggct    75720
gctcataacc aggggcttga aagcttctgt ataacaagcc tgtcctctcc ttttcctttc    75780
tcctctgact tctcactttt ctgttctggc aaaataccatt catttaaatc aaatgtgggt    75840
tgactcaaat atctgcttaa ttctcttctt gtcacaggac gttatacata gtgacataaa    75900
```

```
aaaaaaaaaa cctctgctat aataggtgtt aaattttgga tcatcctgct ttgaatgtga   75960
ttccttctgt gtgggttttg cctagtgtag gttgagagag tcctttcgtt gatattagaa   76020
tgtgtatttt ataatcctcc tgtagttcca gcaagaccct ttcagaatgg ctctagcagt   76080
ttgcccacca gcttcctcca ctttctgtag gtaggtaact ttggccagga tggttttggt   76140
taaggctcgc gtaggactcc catgaccttt caaccaagga agtaaaacag gattgcagga   76200
agggcccaga caacttccct gtgtgtgagc ctgcccaagg cacaccagtt agttgagttg   76260
gaatcccctg cttgaaggag aagacccctt tgaactggtg gtgggcttta agcctgatct   76320
cccaaggctt ctcttcaag agatcctgcc acccgaaccc acaagtccgt ctcgctggct   76380
ggtctgttcg ctgttaattc attcaccagg gcgctccagg ataagagatg cggtagaact   76440
tctcgaaagt gggcgtggtg atgtgacagt tgtcatggct gtcgtggatt aagttaacag   76500
tctgagtttc tcagcttccc tgaagaatgt ttgttctgag tgaggagtgc agtgggggga   76560
gggtgagtgg tggaggaagg aggtatttgg cctcaacgcg ccgtgcacac actcctcctc   76620
tggtatcacc tcccatcttg gagtgaagag tttcaccgag cataccggaa agttccttga   76680
gagccagggt tccgggctgc agctgcggta gcagggctca gccttctcct ctggcccctc   76740
ttttgctggg tgcctggttt cgtgccccat cgtgccatga ttgagattta atcaggccgc   76800
cgagttaatt gccagtgctg tttgcctttt ccctggcaga agtcagagtc ttgagtaaat   76860
tatggaggtt taaatttgct tgatttcctg cagaaagtgg ggtcaggagg tcccagactg   76920
tagacactct ctttggtcag ccagcagggg gtcagtcctt aacggtattt cagaggtgac   76980
taaacgctgt ttttgaaatg tccttctcca gtaagttttt ttttcctctg ggggttggtc   77040
tgttgacctt accctggcgg agtggagtgt ctgtatgaag gcacacaccc cgttaaagct   77100
gcctttctcc tccccatcac cgggctccaa aggcaaatgg aatcatgttt gcggacggag   77160
aggcacccag cacagaagcc cagctgcaga tcagcatttc ctgtttctga ccttttgaga   77220
cacaatgtga aggtagccgt gttaatttat cagtaaaaca atactctgga caagaaagct   77280
tcaaaacaaa tcaacagaaa accaatcatg agacttaaaa agaaacttct gtcgaatggg   77340
cttttcatga tgtggcttta gtcttgagtc tgaggtccgt tgtctgtgct cccctcccctc   77400 cctcctcccg accttggccc tggcagagtc tgcccctagc cagcgaggaa gcaggtctca   77460
gcacttgcca ctcagcttgc cctgcggctg tttgattagc tccgtcccct cctcacctcc   77520
tccaggaaga tggaggtgat tctgtggatc ttctgggccc acgggacttg aggaccttgt   77580
tgtttgcgtt ataatttgtc tttttaccta gctgtcttcc ctaccagatt ctgaactgtt   77640
tgaggagaag gaatttgtct ttgcgtcttt aaccctattc ttggcttata gtttatgctc   77700
aggaaatgtt gactgaatga atgagcacca aaaatcatac tgatgaaaag attgctgagc   77760
tgctaatact gttgttttgg cagatgagaa tatgaattgg agcgagctag ttttttgtgt   77820
ttacttacaa ctaccattcc tagttttcct gatagctcag ttcattcagg gcttcttgga   77880
tagctcagtt ggtagaatcc gcctgcaatg caggagacct tggttcaatt cctgggtcag   77940
gaagattccc tggagaaggg acaggctgcc cactccagta ttcttgggct tcccttgtgg   78000
ctcagctggt aaagaatctg cccgcaatgc gggagacctg agttcgatcc ctgggttggg   78060
aagatcccct ggagcatgga aaggctaccc actccagtgt tctggcctgg agagttccgt   78120
ggactgtata gtccacaggg tcgcagagtc agacacgact gagcgccttt gactgtcact   78180
tcactttctg catccctgga gctctgtgtt gagccctggg ctgagggcgc acgtgcatca   78240
tctggaggga ggtgctgtca ggctctccat tttacaggtg aggaagctga gagtcacaga   78300
```

```
ggaggttttc cacaccacag taaatgtcag catccagggt cacactgttt attaaatatc   78360
ctaatacact tcttcagaat acttagcacg ataagattgt ggatgcgtat tttaaaatga   78420
atgaactaag ttggaaacca tttcagagct ttgatgtcac tcatttgaat gtacattagc   78480
tgttcacacc catgcacaga aacagaaaag aacacaattt aggcttcatc attttaaca   78540 agttttgtt gagtcgcacc aagcactgtg ctaggcgctg agtgttaata gcggttatga   78600
ctctggtttt catgacgctt tcaggatagc taaaatataa tgaataggac agaaaagaga   78660
aaaactttga aataaaaag tgtatttgga gaggaagaag aatccaggag aatccaggta   78720
aaccaggacc ccagagcatg gtgaggtgaa ggtagagagg aagaagggat tcatttaaga   78780
tcctagtggc tggaagatag ctcatgatca cttagccacc tcccacctgc ttttgagacc   78840
tgcggaaagt gaatcccagg gaaattgctg ttcccataag accatctgtt ggcttccttt   78900
atcgagtgtt gctatgtgtc aggcactttta catttattag cttgttactg ttattaacag   78960
catctagatt gttaagaaat aataagtaag acatgttaat aatttagtta ttgtgttaag   79020
taacactacc tagaaaagag cctccctcat agctcagtgg taaagaatct gcctgcaggg   79080
cagaagaccc gggttcgatt cctgggtcgg gaatagcccc tagagaaggg aatggctacc   79140
cactccagta ttcgtgcctg ggaaatccca tggacagagg agcctggtgc ccatggtgtc   79200
acaaagagta tgacacaact gagcgactag cacttgtact tgtgcctaga taagttgtag   79260
ttttaacgtg atcttataga ttcagaaact gaggtgcaag agaggttaag cgctttgccc   79320
aggccacaca gctggtaagt gaagatcctg ggttctgatt aaggacatgt gattctaaaa   79380
ctgacctcca atgtgctggc tcactttttg aaggcatgtc ctacagtaaa gcgtcaggct   79440
cataacacgg tagacccatg ctcagcggtt tctgtgtcgc ctccatgttc atctcagcgc   79500
ctgtgtttta tgggaaagcg ttggcaagat ttcagagctt gttgcgcttc tttacgtgcc   79560
ctgtctcccc cagtatgctg ccgtttctgc ttctccagtc ttcaagccct gttggcacac   79620
aagtgagcgg tgtggaaaaa ttgagagcca agacaagtta ctgtccgttt cccacccatc   79680
cttcatctcc tcccacatcc cataaccatc cgcttcccga agggagctgg cataccagat   79740
gagacaggat ctgctgtctt gccagagact tcgtttcttc tcctggcagt gctgtgaaac   79800
cagagctgtg atgcctttcg gggggtttaa attccaaggg attcattttc tgaaaccaag   79860 cttttgcatct ctcagggaat tttcccctc ttttgaatgt catagaggca tgcgagtgta   79920
ctggcgttcc ccacttctcc cgaagaacag acctcatttt gttggaggtt taatagtttt   79980
tcctcctgtg ttagaggtgt atttacccttt ttaaatttat gtgctcccttt tgtgtcagtg   80040 ttatgtatttt ggtgtgtttt tattccatgt accctgtgaa atcatagtgt ttaggtgggc   80100
tcttacttat tggcccagat ttgatcatca agaatcaaga aaaccttcag catttctctt   80160
ctcttctctt ctcagaaaag agctacaagt aataagctct ggagtttccc acagttccag   80220
agtctgtaaa tggtgatgct tacctcaaac tggggaagga ccatgaaaca ccacatcctg   80280
gtgttctgga gtcagacagc ctgggcgctt tcctgctctg tcatgtatag gttatatgac   80340
catgaacatc attcactatt tcttctttcc tttctggact ggtaaagcaa atgaatagac   80400
atcattcact attttgtaatc ccacagtttc atcatctgta aaatgagagt ggtagccatc   80460
tattttgggg ttgtcatgag gctcaaatga gataatatat gtacagcaca gtgcctcaca   80520
gtaaagtcat tcagtctttta ctgaactctt tggaacccca tggactatac agtccatgga   80580
attctccagg ccaggatact ggagcaagca gggattgaac ccaggtctcc cacatttcag   80640
gcggattctt taccagctga gccagaaggg aagcccaaga atactggagt gggtagccta   80700
```

```
tcccttctcc atcagatctt cctgacccag gaatcgaact ggtgtctcct gcattgcaag    80760
cagattcttt accaactgag ctgtcaggga aaccaaagta cttagtaaat cttgactatt    80820
ttgatatcac atattaaatt attttacata cttctttaaa aactttttt gcttttccat     80880 ttaaaatggt gattttcaag cacacaagtt ttgtgttggg aggggttgat gagtgggctg    80940
ggttggtgag ggcagagaga ccacgaacct tagtgattaa ctgtgactta gtagcacagg    81000
gctacttccg tttccataca agtcaggaaa ctgatgagta agataggagt agaaaatgaa    81060
aaggtgttcc tgcaaaggtg atcggatgca gggtggaaac acgaagatcc aggccccgtc    81120
ctaaaaccac agcttaatgc ccaagagtga tattgtggaa acaaaaagtc agccttagga    81180
ggatactctt tcctgtggtg tctcttggtt gtgaaatctt aattatggcc tgttgtggac    81240
attttggcgt taatatcctg atgacattag gactccagga atcccattcg gtctcctgga    81300
gttcccatcc atgtgcattc catgtgcgtg tgtgcatttc ctgccccaca ctgtcacatc     81360
tggcaaacag ctgctgtcat atacgtggtg atggctgtcc gtcagtgata tggatggggg    81420
tgatggggga aaccttggag atcccagagt atgaaaagac taaggagcgt gagcagccag    81480
aataacaggc catttcatat tcagcctcct cctggtgaag ctgaagttag gtcctaaagt    81540
taggcttttc atgtaaaagc acgtgaatgt aaatgtaact catgccactg aaatgtacac    81600
ttgagtttga aatggcaggt tttgtgttat attttaccag ttttaaaat ttagcagtgt     81660 aatataccaa agccattgca taccttaaat agatgcattg tttagtacat aaattattgg    81720 gcttccctg tggctcagct ggtaaagaat ctgcctgcaa tcggaagac ctggttcagt      81780 ccctgggttg ggaagatccc ctggagaagg gatagcttac ccaatccagt atcctggcct    81840
ggagaattcc atggactgta cagtccatgg ggtcgcaaag agtcggacgc agctgagcaa    81900
ctaaaccacc acccctcggc ttcttctatt gtctctgttt tctctgactt cttgtgtttc    81960
tttctgttca tttgttttct attgttcatg ctgaagatgt tcttgaaatg tctgattcta    82020
gggtctgtgg aagctctaaa aagctgatca aaagcttttt gtttaagaga agcttgttac    82080
ctggagggct ttgctgtgag gtgatggggc ctcgctgtaa ggtgatgcgg cctccctgtg    82140
aggtggtggg gcctcgctgt aaggtgatgc gggctccctg taaggtggtg gagtggcaag    82200
taaaccacat ggctgctagt gtttgggttg ctagaagggg aggaagctgt agagctcatc    82260
attcaaaatt taggctctaa ctgcattttc ctctcttcag tacctatgtt tccatgtcta    82320
gagctttagg ttttcagag aatcaacctc ccttctgtag cgtgggtaag gaagaagcgt     82380
agttttctgg ctgagtgggc aggtggtggg aacgcttgtg ccctgagcct gtcgctgctc    82440
cttgcacgta tttcagctgt tcctcctgtg ttcgccctcc tcctcttacc tcgtgaggcc    82500
cgccgagcac agcccctggg ccgttgtggg gctggcagtg ggacttggct gccttgttgt    82560
ctcgccaccg cctttgtagc acttgggttg cagctctcag ccttctgctc cgtcaccact    82620
tctccagccc ctttcagtct ttcagaagca tgttgctgct gctcatcagc tgctgtctct    82680
gttcccattt cattgtctgg gtagatttat attttttatc tattaattgc catttagtg     82740 ggtttgggga gggaatggag ataaacgcat gtgtttaatc tgccatgttt aactagacat    82800
ctcctcttag ctgcaaagat tctctgattc ttttttttaag ggtatcagag ccaaactcag   82860
ttaaacagca tcagtacaga ttttgaggtg gggaagactt tgaacagttg cttgcctctt    82920
ggattggtca tggtagaaac tacatcgagt ctcccgtgtt ccggtttatt ggtcatgctg    82980
agaaagagac cagcaccatt gttactagat ccttctctga cccatattaa tctgttctct    83040
tgcagaagtg gggcagtgtg agcaaccctc tcttccttcc cctcatcccc ccacaatctc    83100
```

```
aaggtttcac ggccatcgtc ctcacctacg accgagtgga gagcctcttc cgggtcatca    83160
ccgaagtgtc caaggtgccc agcctatcca agctgctggt cgtctggaac aatcagaata    83220
aaaaccctcc tgaaggtaag acgagcggag agacggtgtg tccaggaaag gcccggtttg    83280
gacgttttgt gttcgtctca atgggatcga gttttttga tggacaaatg atttgcagcc    83340
tttgtcttaa atgaactttc ctgctttgtc aacagtaatg ccattcctga ggcagcatga    83400
ccctggtttt ctcagtcatc ttgttcttgt tctagggtgg ccggtttaac tcttagccca    83460
tggcatgctc tgtagccaca agtgtttgag ggcttaggag tcataggat caaaggccat    83520 cagccttggg aaaacagatc tcagcttccc tcaaccctct cagctgattt gtttacatga    83580
aaagtcagtt taaaaggcat tagttttctc cttccttatc tcggctctga tactgtgctc    83640
ttcttcaaaa aggacggcct cacctctgat gggcagagtc agcaaagtgc gccctcccag    83700
gcttgaatca gctccttaaa gtgacccctc actggaagtt cccaccagct catccgtaat    83760
cactctgtcc cttgccttgg ccaccccgt aatctgctga ctggcagctc gggctgagcc    83820
tgtttgattc attggatttg tttttaattc aggacgcata atgtacgttc cacctgcatt    83880
tcgtttctca ttcagtccgt ctattatgga tcctaatccc agggacttca aagcccctgc    83940
cctttatagc ctattaaagc caggaagttt ctgatggatt agagcaagga atgagtttga    84000
agtttgtaat gtgcaccact atcaccgata aggtctagtt tattgcctga cagtagtatc    84060
tgcacttttt atggctgttc ccgtttaatt ggttatcctg aagtcgggat agtcaacctt    84120
ggaaaaccca gtagtagatc cctagtctag gctgggagaa gaatgtactt ctgtctgtga    84180
ggcaaatcag gatttaaatg ccctcttgag actttaaaat ttttccttg gtgggactt    84240 tgttctctgc atcagtactt gcttttaga ttcaggggc cacagtttag taaacaaagt    84300
agctctttta tgtgaaggcc catagtactc cctgaggcac acggcgttta ttatcgttgt    84360
tgctattctc atcttttgtg ccgggttgtt ttcctcccag cattcttgga ttttttttg    84420 tttgtttgac tctcaataaa ggggacagaa aagggtagaa gaaaagagg atgttggcac    84480 cttctcagag ggagagagga tgaaactgac gggaaggggg aggaggagga ggccgacggg    84540
acagaacggg acagcaggga ggctcttcag agccccgggt ccacccagag tgagtggatc    84600
ggaggcactg cattgctcat ctgagtcttc attcataaag gatgggttgt gtttcagaag    84660
gaaggctgtg tgtcccttgt tggagctgga acagctgtgt gtcgtatctg cagtcaccct    84720
gctgcatgcc gaggccacca gcttccaggg cgggagcacc ccagctgcac cccacccctc    84780
tgcccagaca ggcagtgctg ctgctaaatg cagaagagac gtctccttag aaacccgggt    84840
tagccacttt gggcataagg tgacttattt aatgtgactt tgagtcactt ctttagagca    84900
agtatcactg caaactgtga ggaaagagaa ctagttttct tccttcttgg tctaaggtcc    84960
tgcctacatt gctgtcacta aaagcaagag cacaaaccta ggttctggag ttgggtgttt    85020
agttttaatt tttggtacac cctaccaaag tgtagtggtg aatgtcatga ccaagagtgt    85080
agtttatttt tgaaatattt tggctctaga gaggaaagag ccctcaactg atgaggccca    85140
aattttgaca cattcagggg ctggaccagc ttttttccta acagtggttt ttaggtcagg    85200
gctctggttc tggcgttgtg gttgtttggg gagaacatga actgtgttta atcttctgtg    85260
gggtgtttgt tcagttggta aatgggctg tcagctctgg ccctcgtgcc agcaaaggca    85320
tctgattttt catgtacggc attagtaaca tatatatttt ttaaaagaca agtccaaggc    85380
tttgaaatat tagaggcaaa agtgatgtt ttcactttct ctacatttac taaaataaat    85440
attgtggtta acatgtctgc tgctgggagg attagtgtag gcagaaatcc ctcccctcta    85500
```

```
cttttttttt ttttcactct ccaacccaac caaatagtat tttcttttg gttacattta      85560 agtctaaatt gctgggtttg aagtttaagt aaatacttag actaggcaat agaaatttcc      85620
agcgagcttt cgtcacgttg ttttgagct ctgtcagacg aaacaggcga gccactgccc       85680
tcctccgacc tcagctttc agtttccgg cttgatggat atagaggttg ttaggcttgg        85740
cccctggcct cagcctgaag gaagctgtta catcgtacat ttcagataga tttaactcag      85800
ccttctgttt taactgattt cagttttaa atttgaattg atctcaggga actccctat        85860 ggccacccca gcttcgggtt gctacttcca cagttcttaa taggcaggat gggattggct      85920
gagcgtttca gggcggtctg tcgggatgga ggccatcgag aagcagaagc aggagtgccc      85980
ttccttccag ctgaattcag ggaccgtggg gagtgaggct ctggggaccc gctgttcacc     86040
aggcaggttg aggacttctg gagggagctc aagatttgta cagagataac ctgatggttg     86100
attttgtgaa tctgtggttg tgtttgacag tgatccccag gatggacttg gggtcatcgt     86160
cggacaacct gaacatttcg tagtaccttt gccaagttgg agaattctcc tagctcacat     86220
ggctcctggc atccaacttg gagaaaactg ttaatcaata catgtttta aaaaaatcct     86280 taacacaagg agttcttttt ctccttcaag ttggactaaa gctcagaact gtaaagttat     86340
caggtcagtt ggctcagctg tttgttttc ataaatttgg caatgttttt gagaaatctt      86400 attttcaga ctactttgtg tgaatggaag gtgacatttc tgttttgcca gctatagatt     86460
cgcaggatga gacacaagct acaattcatg cagttccatt tagaggttaa aagaataagg     86520
aaaagacccc acctgggcca agcagtggtg gaagaacccg aggtttctag ctgtgacact     86580
gtttccttct gcgtgctaag gagtcaccac ctgttcttct gtctacaccg cttcaaaatg     86640
tcagaggcaa agtgaagttt gtaagacctt acaagaatcc atttgtgaag atgcctgggt     86700
aaggaagatc tcctggagga agaaaatagc agcctattcc cgtattcttt cctgaaaaat     86760
ctcatggaca gaggagcctg gcgggcgaca gtccaaagga ctgcaaagag tcagacatga     86820
ctgaaccact acgcacatct gtgaaaatga gaatgataca gtgttgttac aacatgtatc     86880
gtgtaccttt tatatccaag gaatgggaac tgtgctgagt gctttacacg tattgtctct     86940
actgcttata caaaactga aagaagctga tattatcccc atttacaaaa gtgaaactca     87000
gattaactga gtaatttgcc ctagggctcc cctggtggct ctaacagtaa agaattcgcc     87060
ggcagtgcaa agacccgggt tcaatcctg ggttcggaag atccactgga gaagtgcatg     87120
gcagcccact ccagtattgt tgcctggagc attccatgga cagaggagcc tggtgggcta     87180
cagcccatag catcacacag agccggacac gactcaacaa ctaacacaca cacgtcagag     87240
gtctgcagaa atgaacacaa gtctctctgg atccaagctc atgctctgtg ccccgagccc     87300
cactgtgtct attcagattg ctgtttagca gcaaggagat catgctttgt caggtctctg     87360
atttgggatt atgcagatca accaggttct tatcaggggc tcgaagagag gcagaaaaat     87420
aaatcttatt cttttggaag tactaacgga aagaaaaata caagtcttct gttctttctc     87480
acttacgttt ttctttccta ccttgtattc ctgtcctttt tttttttttt ttcccaaact     87540
gtatcaaaat cctatatcag aattaccttc tttaaggcag ggagtaatta tactgcttct     87600
ttggctagcc actttcttgt tcccgtgttc cacagaaggg atacaaaagc ccaaggaagt     87660
tggatcccct ccttagagcc ctgttctatt tgaagctgtg aaaacaagca actgggagtt     87720
ctacttggag tccttccttg tggtcacagt ggttcatagg gagctggacc gttgagctgg     87780
agacttcttt taccaaagct gcctttggct ctccaggccc aactcaggac aggaaaaggt     87840
aatcaccttt ccaagaaagc cacgattcat tctacatttc catctgtacc catttagctt     87900
```

```
tcctcacttg ctaaaacttc cctatcaaag accttatcaa ggaaggttgt ttttagacat   87960
tgtcttgagt aattttctgg ctacacatag gaaaagaatg tggaaaactc tctgttgaag   88020
atgttgtgca cactccctgg gtgagaggga ctctcatcca gggtcgagaa cattgacaca   88080
tcatgcaagc agctcacctg ttttctagcc tctttctgta ttgcagaaag agaggctgtt   88140
tgttgccttg tgaaatttcc ttggcaagag ttccatgttt cttgccaacg gaactgttgg   88200
caagttaggt tttttcagtt ctagaggatt aatggcaggg tttccgctag tctcaaagtg   88260
aactttgaag ataaaagctg aggacatgcc actagactgt tggagtgatg tacgagatct   88320
aacgtgtgcc tctttgccac cactacctag ggttcatcct ttggtctgta aataggcaca   88380
gacttgcaag ggaaagcaca gccaacgttt ggtggacgtt ctgccacgtg ctgggcactg   88440
agctgctaaa agcattcctg ttcctcctca cgccttgcca caggtggaga tggtgtcact   88500
atcccatctt catagtcaaa gaaacaggta cagaatcacg gacttgttca agatcacata   88560
gctgataagg aatacaaaca cctgagattt gaagctcttt ccaaagactg ttctctctgt   88620
gaaacgtgac tggccataca gtcctcagag gtgtcttgtt tggtccctga agttggtaca   88680
tttcacgtgg aagagcacat agcgttgctg aaggcatttc gttccatcag aacattctta   88740
ccgactttga gcctgaatcg gtttccctgt aactttcacc caggcgttgg tcacgcttct   88800
agcttcagaa gccatagaga agccattcag aagcctttca tctgggaacc cttctgatag   88860
ccctagtgtg ttagtcaagg tccaggtggg agacagaaac cacacagcaa cttgaccagg   88920
aaaagttcaa gttttaacta ggaattgtta aggaggacta ggagattggt ggctaaaggg   88980
tgaagagagc tcccgggata taggaaatca gcttggggat tgagagcgct tccccaagct   89040
cggtctgaga ttcagaccca ctgcatggtg aagctgctca ggtgccacag gctgagtctg   89100
gcaaacagga aaccagcagc ccctttggat acccatggaa ttcaatggga agccatccgg   89160
ggggtgttat tggactcaga ggggtactgg cgagggcttc agttcctgag gaaccacctg   89220
agggcagaac ctcagctgag ttgctgctga aggtatcaca gaacttgcca ggaaactgcc   89280
tgcagaggag ctgccagact ccttcgggag cctgttgggg tgtctgtaga acctgctggg   89340 agcctcccctt gggggtgccg tctacatgtg ctggagaggg gtgctgctgc ctacctgctg   89400
gccaagtacc gaaggagcaa gtgaaaaagg cacaccagaa ccaggaagca aagccctcac   89460
ctcccagcgt ccctccagca cctgctgctg acgtgttaac atcaagtcag tgggcaaagg   89520
ggaaatggtg atggggctgg ctgccagtat cacccccagg gcagtgaagg gtgaatttgg   89580
agctgagagg cagtgcatgg catattcagt ttaaagagat cctggatccg aggacctgta   89640
ctgtcctcat caactccgcc tatctcccag tttgttggtt cttctgtaag tgtttgtgtg   89700
ctggtcgctc agtcatgtct gactctttgc gcccccacgg cctgtagtcc tccaggctcc   89760
tctgccaatg gaattcccca ggcaaggatt ctggagtggg ttgccattcc cttctccagg   89820
gaatcttccc gacccaggga ttgaaccctg gtctccgaca ttgcaggcag attctttatc   89880
gtctgagcca tgctgggcag ctctattgca gtacccaaat ctaaatacaa ggtctcatac   89940
agaggttctc aaagtgcagt ccggggactg ctgagcatcc ctgaggtcct ttcacagggt   90000
tggtgaggtt gaaattcttt ctctgagaat gctgagtcac cctgcgttcc cacgcttata   90060 tttttttacgt gtgcatagtg gggttttcca gggactgccc aacatgggat gacatcacca   90120
ctctactggc tgatggaggg tatgctcgtg tgtcctgggt tttaaagttt ccttggtttt   90180
cattcagaat ataataaatt gtgtgtgtgt gtcctacata aataaaacct ctttggggat   90240
ctcaacagtt tttaaaagca cgaaggaatc ctgacaccat ttgagaacca ctgatctaaa   90300
```

```
gataaccact gatctagtta gagctataac ttccttcact tttagatatt acaatttatt    90360
catgttttct aaggatttgg atttatgaca gggatttctt ttacttaact ggaagaggga    90420
atgggaagca gagaagaata aggatgattg tttttgttcc agatccagag aaacatgaca    90480
ttttcaagct gcagtaaacg gtgcaggtcc tatttggtct ttgatgctaa acagacttag    90540
attcaaatgc tagctgtatc atttagccct aaccccagcc aatgtactta acctctctga    90600
gccttgtgaa tcctactctg taaataattt ctgctctata gacttgtcag gaggatgaat    90660
gacagtgcac ctgtaaagta tctggcatat actggttgct taatgaaggt tcccttctct    90720
ctctccactt attcttaccc tgagaataag ggacctgcct aagaacccca tgggaaatgc    90780
agaactcagg tctccagtct cttagtcctg tgcctatcca tttattctga agacagtttt    90840
tgattatgtc attctggacc aggttaagta ttgattaaaa gggactgacc cattggatca    90900
tttctttggt ctccagtcct ttctcaaaca tgctttttt tggagttgaa cacatttta    90960 gaccctaagc ttttcaggc tgtgaaagtg ttagtcgctc agttgtgtct gacttttgt     91020 gaccccatgg actatagcct gtcaggctcc tctgtccatg gaattctcca ggcaagaata    91080
ctggaatggg tagccattcc cttctccagg ggatctttct gacccaggga tcgaacctag    91140
gtctcctgca ttgcaggaaa actctttaca atctgtgtca ccaggcactt taggccctag    91200
gcttatttag aacttaagga ctatcttctc catatatata tatatatata tatatgtatg    91260
tatgtatgta taggaatatc ttctttaatt acagggcctc gcactttcac aggcctcttc    91320
caagaaccta ggagcacctt acctggacac attgtaaatt atgcagaagt aagatatttt    91380
atatgatgtc tgttagagca accttttttc ctcctgattt tccctcagtc atacttatcc    91440
ttcggtatga taacttcgga gtggccacag gcattttggg gcttcaagac tcacaaaact    91500
agaccatccc acaattatgt gttgggtttc tggaagcaat atgatacctt tccgtgctca    91560
tctgacaaat gttgtgtgaa gaacaaactg ccctctgtaa agaaccctga ggtctatgga    91620
cataggtcct gtaccaaaga agtgttaatt ttattctgtg ctaaatgcat cacttttaaaa   91680 tgaggaacct gaggttgaat tgcttcaaag tagaatggga aaaatgtaag gcgagtcaca    91740
agttcgtggg tcttcagtat accagaaaat cccatgtaat cggacctaga aatttgatat    91800
ttactctgta aattggtcat gatgagaacc caaacccagt gagtcaggag agagcggctg    91860
ttgagcggtg aggtgctgag ttaggaaagc tgaactcatt cagggcaacg gttttgtgag    91920
ggtggcttcg gcggccttgg gagccgttgg tggtggaagt gggcactctc atcttctttc    91980
agcaaatgtt tccagagggg gctgcaggca agtttgggc tgggtgtaca cacccggaag    92040
gattatgcag aggtggccag gtggtcgagt cctggtgttc aaaccatggg cctgagaatg    92100
aggcagacag ggcccatgcc tgctcctgcc ctgtccctgt gaccttcatc aagtcgttcg    92160
gcacccccca cccccacccc cggcctctca gttgtgcctt ggagcctgtt tgtggattct    92220
ggttaagaca gcattgagca gcagcagtgt tgtaaggatg tagagagaag agaagtattt    92280
atgatatatt ataaaaattc atctttaaga atgtcctcct gtagttgtgc atgcggttat    92340
tgttttttcc ccatattctt atttattttt ggctgtgctg ggtcttcgtt gctgtacggc    92400 cttttttctcc agttatggag agtggggggct gctctctagt tgcagtgcga gggcccctcc   92460
ttccagtggc ttcccttgtt tcctagcgtg ggctccaggg tgcacgggac ttcagtagtt    92520
ggggctcccg ggctctagag cagcggctca gtagttgtgg cacacgggtc agttgctctg    92580
tggcatgtgg gatcttcctg gatcagggat tgaacccaca tctcgtgtat cggcaggctg    92640
attctttacc actgagccac cggggaagcc ctgcgcctgt ggatttcatg agagtcacag    92700
```

-continued

```
ctttgagttg cttcttctgt cttatttgtg agacatggct tttaccagtt tatcttttca    92760
aagaagttag aagagtcata aataccttgg ttttttttttt ttttttttctt tttccagatt    92820 ctctgtggcc caaaatccgg gttccattaa aagttgtgag aacagctgaa acaagttga     92880 gtaaccgctt cttcccttac gatgaaatcg agacagaggc cgtcctggct attgatgatg    92940
atatcatcat gctgacctct gatgaactgc agttcggtta tgaggtaagg aggtctcaaa    93000
cagtgcgttt tcatatttaa tatttattgc ccattattgc ttgtcttgcc taatacagag    93060
ggttatattt cattctctga agttgtgatt tgtaatagca cccaaaaacc gtgtttggga    93120
gcgtgggtca cgaagctgtt ctttagagct tcgtggaacc cctattccaa aatgacaatt    93180
gtgctggctg ccagtttggg gagctcccaa ggagggtccc aggggacatc ttcaaaagag    93240
catctatgag atttaacaag cgctttactg atgtctccat gaagagcact gcccagactc    93300
aggcagctgg gcatggccac aataaaaaca tcagtaagtg aagaagctgg cgacactgac    93360
aaacagaaag cagacccgct gctggcttgc cttctgagtt tgaagtgcag aggctggctg    93420
cctgtctttg gggaggagca ttctctatca ccgttcattc agggaggctg atggattagg    93480
ccgggttcaa gggttaagta tggagaccag gaaaggtctc cccaggggaa agtgccagag    93540
ccgaggcctg gtgaaaagca ctaggaattg atgtgtcctg tcaggggat gtccgcgaga     93600 cgcgtgatgg cgacaggcag aggcccgggg ctgcggggc gagtcggggg tatcagagcc      93660
aagcagaaca gtgtgcacat caattaacca cagccggcac cagggaaagt gggggcattt    93720
atccccaaga ctcatcctgc tttggggaga gaggtaacca tcttctttag ttgactcagg    93780
atctgttaaa tttgaggttc taagaaatca tgaaactttat tttaatgaag ccatatttgg   93840
tacatgtgtt atagaaattt attttctaag ccttaaaagt ggattttttct ttcttatttt    93900 ttaaattatt aaagtaagat aacacgttta taggagactt agaaaataca gaacaaagtt    93960
acatatagtt ctgctatata ttacagttct tttttttaaag taggtaaatt aagattttta    94020
gttggagttt caatatcaga gtttcaaaaa ttaatagaat gaatatacag aacagtagaa    94080
agatattgta gacctgaaag gcaccatgaa ccaattcagc ataattaaga ttcgtacaac    94140
tttcacacaa taataggata caaattctgt tcaagttccc atagactgta aactaggagg    94200
cattggaaca tagccaggga cataaaacaa ggtgcaaaaa tctcatggtc taaaggtatt    94260
gaaatcatag agtctgttct cttaccactg tggaattatg ttagaaatca tattttttaaa   94320 gttatgaaaa taattcacct attttccact gcagcatgac atttaccaag agatatcttt    94380
gatttagcca ttaaaagcct caataaagtt agaagactga aaaacaatac agttattgca    94440
gagaagaaag catttaaata agaacttaat atcaaagata cttttagaaaa cctcatgtat   94500 ttggaaattc aatgtccact gaaagtggat tttaaaggga agaaatagga atccccctg     94560 tgaccaccag caccaaaaat tagaagctta tatttcccca ggtgtaatcc catggaccgt    94620
agcttaccag gctcctacgt ccatggaatt ttccaggcaa gagtactgga atggattgcc    94680
atttccatct ccaggggatt ttcccgaccg agggattgaa cccaggtctt ccacattgca    94740
ggcaaacgct ttaccctctg agccaccagc gaagtccttt ttatatatag acataaataa    94800
tttaacatat atggaaatat atataaataa ttatatataa tgcatattat atataaataa    94860
ctatatatca gttcagcgct cagtcgtgtc tgactctttg tgaccccatg gattgcaaca    94920
tgccaggcct ccctgtccat caccaactcc tggagcttac tcaaactcat ttccattgag    94980
ttggtgatgc catccaacca tctcatcctc tgtcatcacc tcctcctccc acccttcagtc   95040 ttcccagcat cagagtcttt tcaaaggagt cagctcttca catcaggtgg ccaaagtatt    95100
```

```
ggagtttcag cttcaaaatc agtccttcca atgaacaccc aggactgatc tcctttagga    95160
tagactggtt ggatctcctt gcagtccaag ggactctcaa gagtcttctc caacaccaca    95220
gttcaaaagc atcaattctt cagcactcag gtttctttgt agtccaactc tcacatccac    95280
acatgactac tggaaaaatc atagctttga ctagacggac ctttgttggc aaagtagtat    95340
ctctgctttt taatatgcta tctaggttag tcttaacttt ttttcaaga agcaagcgtc    95400
ttataatttc atggcagcaa tcaccatctg cagtgatttt ggagcccaaa accataaagt    95460
ctgccactgt ttccactgtt tctccatcta tttgccatga attgatggga ccagatgcca    95520
tgatctttgt tttcggaatg ttgagcttta agctcaacat tttataatta tacataatgt    95580
atattatata ttaaaatata tttatatatc cattgagtat aaaagaaatt gttgtgaaac    95640
aggctggtat gtgaataccc tggtcgacat cattactggc cagtgaaagg catgaatgta    95700
gctagtacat agactcacct tcctgggttt atttccattc atagagatgt gtttcctatc    95760
atcacaccta aggtgttggg gattttcat acactatctt tccctttttt taaaaaaagc    95820
aaattactta tttctatagc caactcatgg caaacagacc tggtttttt cttgccaatg    95880
ttttctctct ccattatata taatggcttc aaactatatc cttgtgtttg tttttgtggt    95940
aaaaggaagg tgggaagtag gaacatttca atgaggaaag gtagccaaga tggacagagt    96000
gctgcctctt tgctatttgc agtcggtcta aatgaagtct gataaaagaa aggtaccctg    96060
gaagaattcc tttcaaccat ggcttaaaat cttgggatct caggaatatt gcagcctgaa    96120
atctctttca accttgagtt catttagagc gacaaaaagt gtattgatga gaggaagtgc    96180
aaaacccaga gggactgagc ttaaatcttc atctcttccc tctgaggccc tgtgtttact    96240
ccacgtgacc tctgaagcag tcaactgtgg atcaagaggt aggggcaggg acacccttca    96300
tctctagtaa tgggggtctt ctccagatgc taagacagga gtaacttccc taaccaccat    96360
ctatgtgctg cttactgtgt tgctaccggt ttgctggctg tttacataca ccagtggaga    96420
ccagtcctgg gtgttcactg gaaggactga tgctgaagcc gaaactccaa tactttggcc    96480
acctgatgag aatagctgac tcatttgaaa agaccctgat gctgggaaag attgagggca    96540
ggaggagaag gggacgacag aggatgagac ggttggttag cattactgac tcagtggcca    96600
tgagtttggg taaactccgg gagttggtga tggtcgggga cgcctggcgt gctgtggttc    96660
atggggttgc aaagagtcag acatgaccga gcgactgaac tgaactgaac gatcttttcc    96720
caaacctcct aggcagttat tgggttttgt tgggttttgg ttttttgtttt tgttttcccc    96780
tttcttact gagactaagc aagattagat gacttcccta cagtcacaca gctaaataag    96840
tgggagagtt gagatctgaa tccaagtttg ggtgacacta tattgtcttc cttgaggatt    96900
ttaccatgtc agagactact ggtcctcaaa agtagtcctc agaaccatct tctatcactt    96960
gtccatcact aaattacctt ggtactaaag aaaacaaatt tatttctcag gcatccctac    97020
cactggtgct ctagggtgct gttgtaaagt tacctcttgc ataataatta atactatgaa    97080
aaaagttagt gctggaccca agtttctgtt ctgtcaccgt ggacgactta tgtaatctct    97140
ctgggttgta gttattctt ggacagaatg gtgctgacag tgtctgcttc gctgggttct    97200
catgtgcatt agataagatt gtgtagcgga gaaggcaatg gcacccccact ccagtactct    97260
tgcctggaaa atcccatgga tggaggagcc tagtgggctg cagtccatgg ggtcgctaag    97320
agtcggacac gactgagcaa cttcacttc actttcact ttcatgcatt ggagaaggaa    97380
atggcaaccc actccagtgt tctcgcctgg agaatcccag agacggggga gcctggtagg    97440
ctgccgtctc tggggtagca cagagtcgga cacgactgaa gcgacttagc agcagcagca    97500
```

```
gcgccagtgc acgggcagcg attagaaagt gcatgttctg gctggtgggc tgcgtgctct   97560
gctctttatg agatgcttca tcagctgctc taccatgact gctgccgtcc ttctcgtgat   97620
ccagtgattc atggggaggg tttgtggttg ttttcatcat tcagaaggga tagtgctctt   97680
ctggggaggg tacccagttt tgtgttaaaa tcagaagaca gaagaggatg gtactcctaa   97740
atcctgtttt ttttatgcca aagcctggga ttattttcat gtagacttga tggattaaga   97800
gaataaacaa atcagttaat aaaaatttat gtcctagggg ggttatgttg gagcccagaa   97860
ctacttcttt gtcacagtta ccactgtgtg ttaggattat atctatcttg ttgactgttt   97920
ttcgtccttc agcactcaga tcaaaagaag ctttcacaaa gtctccagac tggagcactc   97980
aacctctttg taagcaaata attgtgaagt gtgttgttta gtgtctgctt ttcttctaga   98040
atggaagccc catagggaca gaaatatggc catcttattc attgctgtat cctctgtgcc   98100
taacccagct cagtccattc agcagttagt aatatttgat aaatgaacaa attttcatta   98160
ccagcatgca catgaaagat aggagacaga tgattctggc ccgcatgcct ttccacttta   98220
ctgggatcca taacctagat gcaaccgttt cagcaaacag tttggtgttt aaaatgttga   98280
ctgtaaatct acagtgtgac cccaccgttc ttcccacaga gatttaccct agagaaatga   98340
gagcatatgt atacataaat agttgtacgc taatgtaagt tttagtgttt gtatttgcag   98400
tgtttatttg taaaagcaaa aaactggagg aaaaaaatct tatcagaagt tgaatgaatg   98460
aactaattgt agtgtctcca tacagtagag cactacttag taataagtag atgagctatt   98520
gatatgtaca atatagacgt atttaaacat gattatgctg agtgaatgaa gcaaggtgaa   98580
aaagagaaca tattttatga tttcatttat aggaaacaca aactaaatct tcagtgattg   98640
aaaggtcagt ggctgcctgg agaagggtag ggcaagtcag cttgaaaact ttagtaaaac   98700
gtgtgcccca tcggttcaat gaaaactagg aaacattgct caaagaaatt gaacagcttc   98760
ataaatggaa agacgtatca tacatttgaa tccgaaggtt cacaattatt aaggggtaag   98820
ttctccccaa actgatttat agattcaaag cacgcacagt caaaatccca gaaggctttt   98880
ttaaaaagtt gaagttgaca gcagttctaa ttgaaatgga aacacaacgg acctgaaaaa   98940
gccacaagcc aaagttttaa gaaagaagga caaaattata agacggcctt atgttaagac   99000
agataaagct aacgtaatca agactctggt attggtgtaa acttagacgt gtagatcaat   99060
gaaacagaat ataagattc tagaaatagg ctacatgtgt ggtcagtcag ttttctgcaa   99120
aagacccgag tcaattcagt agaggtggaa taggcttttc actacatagt gctggagcaa   99180
tttgatatcc atatgtcagt tcagaataga tcttgtccta aatacaagaa ctaaaactat   99240
aaaaacttct tcaaggtaac agtgaaaaaa gttctagtgt gcctgagcta agcaatgatt   99300
ttttttttaa agtaggagac aaataacata atttataaaa gaaatcattg ctgctgctaa   99360
gtcgcttcaa tcgtgtccga ctctgtgcga ccccatcgac agcagcccac caggctccgt   99420
gtccccggga ttctccaggc aagaacaatg gagcgggttg ccatttcctt ttccagtgcg   99480
tgagagtgaa aggtgaaagt gaagtcgctc agtcgtgtcc aactcttcga gatcccatgg   99540
actgcagcct accaggctcc tccgtccatg ggattttcca agcaagcata ctggagtggg   99600
gtgccattgc cttctctgaa aagaaatcac tggatttcat cagaattagc aacacttaaa   99660 aagcacttc taagaaaata aaaggcaatt ttatagactg ggaaaaatat tttcagtata   99720
tataaagaac tattcacacc tctctaatga gaaacaagt caattaaaga tttgagcagt   99780
tacttcataa aataaaatat acaggtatag actaacatat ggaaaaactc tccacctcat   99840
cgtcattggg gcagttctac agtaaaagca cagagggtca tcaccataca cccactgctg   99900
```

```
tgactaaaga aaactgcaaa tgctgacagt gctgcatgct gggggatgt ggagcagctt   99960 agaactctcg tacgttgttg gtaaaaatga gaagtggtac agccagtttg ggaaaatgtt  100020
tagcagattc tcataacgtt taagaaaaaa aagtttcact tttctatgac ccagattcca  100080
aaagaaattc atagcgtcac tcataatata gaaaacctag atgaatcaac ttgcaaatag  100140
agaaacagta tggaatacct gtgctgtgaa atatcattca gcaataaaaa gaaataaact  100200
cctgatatat ccagcaacct ggataaatct cagaattgtt atactgagag aatgaagccg  100260
tgtgcaaaag accacttact gacatgttct gtgcataaaa ttctaggaga aactgtgttg  100320
ccacgggcga gggcagacct gagaacaaaa gagcagaagg aacttttcac aggatggaaa  100380
tgttctgctc tgattgggat ggtggttata ggactgtgta cttttatcaa cacagacttt  100440
gaactggtga tttttattgt aagtaaatta ttttcccaac ctgaagaaaa attgtggaaa  100500
gcagttctta ggggaaattt ataacaagta aacgcatata ataggagaga agaaaaggtt  100560
aaatgcagtc acctaaactt tgttctattt taaggagcta aaaagaaga gtaagttaaa  100620 ctcagagcaa gtagaaggaa agaataaaga taaatgctaa taaaatctag gaaacagaac  100680
agaaaattaa tagaccccaa aactgacttt ttgaaaaaat taacaaaatt gataaatccc  100740
tagccaaacc actcaaaaca aaggaacaca acttatcatc attaggaatg aaaaggaatt  100800
aaggaaaggt tgtcatagat cctacaggca tttaaagagt attataacaa agaagggctt  100860
ccctggtggc tcagatggtt aagaatctgc ctacaacaca ggagacctgg gttcaatccc  100920
tgagtggaga aaatccccta gagaaggaaa tggctaccca ctccagtatt cttgcctgga  100980
gaattctgaa agatgactgc cagaaaagta gagctcatca atgaatttgg taagttgca  101040 ggatacaaaa ttaatgcaca gaaatctctt gaattcctat gcactaacaa cagaagatca  101100
gaaagagaaa ttaaggaaac aatcccgttt accatcacat caaaaagaat aaaatgcctc  101160
agaataaacc caccaaagga ggcgaaagac ctgtacttag aaaacagtaa gacacacttg  101220
aaagaagtca aaggtgacac caacagatgg agagagagac catgttcttg gattggaaga  101280
atattgtgaa aatgactgta ctactgaaag cagtcaacag agtcagtgcg attcctatca  101340
aattgccagt agtatttttc acagaattag aacaaaaatt cttacaattt gtatggagac  101400
acaaaagatc ccaaatagcc aacgcaatct taaggaagaa gaatggagct ggaagaatcg  101460
agctccctga cttcagacta taccacaaag agatggtcat cacaacaata tggtactggc  101520
acaaaaacaa atatggatca gttgaacaga acagaaagtc cagagatgat ccaggtacct  101580
atggtcacct gatctatgac aaagaaggca aaatataccg tggaggaaag acaagctctt  101640
cagtaagtgg agctcggaaa actggcctgc ttcatgtaaa agactgaaat tagaacattc  101700
cctaacacca tacacaaaaa taagctcaaa aggattaaag acctaaattt aaggctggat  101760
actacaaagc tcttagagga agacataggc agaactctct ctgacataaa tcactgcaag  101820
atctttttca atctactgcc tcgagtaatg aaaataaaaa taaacaaatt ggacttaatt  101880
aaatttaaaa gcttttgcac agcaaaggaa accataaaca aaacaaaaag acaatccaca  101940
gaatgagaga aaatatttgc aaaccaagtg accaacaagg gattaatctc cagaatatac  102000
aaacagctca tgcacttcga tgtcagaaaa acaaacaact caatcaaaaa agtgggcaga  102060
agatctaatc agacatttct ccagagaaga tgtacagatg atcgagaggc ataaaaaac  102120 atgctcaaca taactaagta atccaaacat cactagaaaa atccaaatca aaactacgat  102180
gagctatcac ttcacattgg tcagaatggc catcatgaaa aaattcagca acagtaagt  102240 gctggggaag atgtggagaa aaggaaacct cctgcactgt tggtgggaat gtaaattggt  102300
```

```
acaaccatta tggagaacag tatagaggtt ccttaaaaaa ctaaaaatag agctacccat  102360
gatccagcag tccgactcct gggcatgtat ctggagaaaa acatgatctg aaaggatcgc  102420
accccagcat tcattgctgc actgtttaca gtagccaaga catggaagca acctaaatgc  102480
ctattgtcgg aggagtggat aaagatgtgg agagatatat atacacacac acatatatat  102540
ttttttcccc acatatttat gtggaggcag aggacgggat ggttaaatag catcacagac  102600
tcaatggaca taagtttgag caaactctgg gagatagtgg aggacagagg agcctggcct  102660
gctacagtcc ctggggtctc caagagttgg acacaacaca gtgattaaac agcaaagtat  102720
cactgagtta gtgagtcaca ccaataagga catgtagttc gtatcagtgc agttttcccc  102780
ataccaggcc agctgtaaag atcatgtagt tcgtatcagt gcagttttcc ccataccagg  102840
ccagctgtaa agatcatgta gttcgtatca gggcagtttt ccccatacca ggccagctgt  102900
aaagatcatg tagttcgtat cagtgcagtt ttccccatac caggccagct gtaaagatca  102960
tgtaattcgt atcagtgcag ttttccccat accaggccag ctgtaaagat catgtaattc  103020
gtatcagtgc agttttcccc ataccaggcc agctgtaaag atttcattgt gtaactattc  103080 cattttgcc tctgtgccac tcaaacccat ttgttcagaa cctcttttg gtgaaggtaa  103140 aaacacctga acattttgtt tcatatttta atattcacaa ataatccata tagtcaggaa  103200
aacagaatct atactaatgg tttcaataga atggatttaa tgtatgaaaa tttctaatac  103260
atggtattag agagttgaga gggcaaaaag cgaatactga aaatacaaag agttaacaat  103320
tccagagtgt acccaccacc cctaggatgg gagaagcaaa ggaagagagg gaagaggttg  103380
gggttgttag aacctggaag catggaggag acgccccatc ccactccctt cctgccagag  103440
ctgggcctta gacctctgag ggggtgggcc actggctgcc attgctggta attccacggg  103500
gtcaagatga agttggttct gccagaagag gttagaacca cctgccgaca tgggtgaaat  103560
gccacgctgt cggggaaaag caggcaaaac agaagtagtt tccttctcct ttgctccagt  103620
tttctaactt ctatctggtg cccctgttga cagaacctaa caggaagtca cctagcaaag  103680
gtgagatgtt tgctgagtct cagccccac atcacaaggc agaatctagg gtctacgagc  103740
tgcaagccca ccaccccttt ggctactcca cagccccatg cacaccttc tccgcatgtc  103800 gctacttcca cgcagcagca actttgttct tccactgaga agatgtaact atcctttatg  103860
cagagagagg cctcacgttc cccccagaa ggggagaaac aaagtcccga tggtcataat  103920
tatcaacgtc tgtgtaattc cttcaatgaa aagtctatga attccttctg taatttagtc  103980
acaggtctcc ttaacatttt ataacttaat taatacattc caggcttcca attctggaca  104040
tgattgagca agcacatccc accctgtttc tggaaaagaa agacagactg gttagggtcc  104100
tcaggactta agagatgttc cagcagttcc cttggatttt ttttttccct tcctttcttc  104160
ctccatttgt ccctgcctct catataacctc agcctcagag ctagagatgg ctatggcaca  104220
gggacaggta acatgctaaa caaacataca gacaaccatc ctccactttc tcttgtaagg  104280
gctgggaaga acccagagat gcagatggaa cccttctgac catcccgct tgacgccagg  104340 caaacgccac caaagaagcc aaatgtaccc ctgccagcta gaggctgtgg ttatggagat  104400
tgtctacaga gccctgccat ccatccccat cctgcactaa ccggagacag gagcagagac  104460
ggtgctcctg gcctgcctct gtccactctg gggactgtga atggagccca cctgaccatc  104520
catgtcctcc atgaagcgaa tgtcagtgaa gaggcagctg cagagactgt tgcggggtgg  104580
ggagggaaat ccagcctgca ccagacaagc aggcagcaag aggcagcatc gcatcccctc  104640
ccagctagag tggagggaag gtcgcgttag ggagggggttc tttaaatctg tgtgtgaagt  104700
```

```
tccgagcaca ctggtgctcc tctcccttca aagcagcccc tgcatgaaac tgactcgaac 104760
caacacaaga aaagctatga gaactaaact gtggtgtaga atactgccca ggctccagag 104820
tggccgctgg gtggcataca agctgggtag accagaatag ccccaatata gtctttggaa 104880
attaaattga tattcagccc acagcccaca gaagtggatc aggacatgca ttctgaacct 104940
aaactctgtg ctaaaattga acacatgcaa ggcagcagca ttgcatagta acactcaaca 105000
tgttcaggaa aaaatccaac attactcttc ataccaagaa ccagggaaat tgcaaccttta 105060 ctgagaaaag ataatcaata gttgccaaca ccaagatgac acagatgttg gaattcttga 105120
ccaggatatt aaaaccgcta tttaaaaaag aatcctctaa taagcaatta tgagcactgt 105180
taagtggaaa aatagaaagt ttccactttc agcaaagaaa cagaagatat aagaaaaaac 105240
cagatggtaa tttcagtact gaaaatttca gtaaccaaaa tttaaaactt gatgggctca 105300
atcagtgaat gaaagtaaca ggaaagaatt ggtgaacttg aggatgaaac aataggaagt 105360
atccagtcta aatagcacag agaaaataga ttgggaaaaa aaaaaaagtg aacagacact 105420
cagggactgt tgggacagtc acaaaggata tgacattcat gtcatcagag ttgcaggaga 105480
ggagaaaaaa tgtggggcag aaaaaatatt tggtgaaata atggctgaaa gcttgcaaaa 105540
tttgtctgta aggtcattaa acttatagac tcaagaagct gaggaaacca caaatatcca 105600
aagaataagt tgtataaagt atgtaccttg tatgtaccga gtaaatcctg gcagtaattc 105660
ttgtatcaaa tagtcatcgg aagagaaaag gagacaaata aattgggatg tatatgcata 105720
aggaaagaag aaaggttcat ggctgctact tccttgcttc tgcagcttgg tcctgagcag 105780
ctacccatct ctccctttgt tctcagccag cactctagca ggtgctggaa actgggttta 105840
cagacccagt ttcttcaatg gctctggtac tattcagact ctccatttct tcttgtgtta 105900 gttttttttga taagttgtgt tttccaagga ctccgttcat ttcatctaaa ttgtaaaatg 105960
cattgctata aaatcatcca taacattatc ttgttattgt ttataaattc tatagatttt 106020
gaaatgatgt gttctttttc attcttgata atttttcattt tctctccttt tcttgatcag 106080
ccgtggtgaa ggaatgtcaa tgtcatattc tttgcaaaga atcaacttttt gatttttgtta 106140 tacacttttc tttagtgttg acttgttttta tatttagtaa ctattctttt cttgattaat 106200
ctcttcctca gtttcaggag tttaagttgc tgttactttt ctaacttttt gacttgatag 106260
tttagtgatc tcaatattca gttttctaat atatgcattt caagctgtaa atttctcctt 106320
aattagggct ttaggtaccg ttccaggttt tgacttgttc tatttttatt atcaagttta 106380
aaatattttc taatttctgt tgtaatatct tcttttgaccc ataaaagcat taatatattg 106440
catacttttg tcagtttttta aaattatgtt cttattgatt tctgatttgg ttccactgtg 106500
gtcagaaaat gtactgcata tgatttcatt gttttgaaat ttattgagtc tctatggctc 106560
agtaaaaggt ctattttggt aagtgttccg taggcccctg aaaagagtag acattctgca 106620
gctgaagatt taatgacctt agtaggtcag ttaggtaagg ttaggtacat tggcacctttg 106680 aatataatca aaatttttta tttgattatt tttattcttc tctagaatag gcaacttcgt 106740
ttcttctgat ttggtttggt tgtgtgtgtg tgtgtgtgtg tgtgtgtagc ttttgtcatt 106800
tctgtagtag ttacaatcac aatcttcttt taaatgaaaa atggtttaaa cagtactgaa 106860
tatgtgggaa tcaaggggga accatgcggc agacctttct tactgtgact ccagagacag 106920
aggcgcctcc cacttgggaa ttttttccgaa aggggcagcc agcggccctc cagcatccaa 106980
ggtggtttta ctagtcctgc ctggagccga aaaataggcc agatgacttc ccccaatccc 107040
tcagctgtaa tgaatctaag agatcagaag tcaggcagat gtgtaaggtg gggtttcatg 107100
```

```
tgaaatagta tccaatgcta tgcgtaggaa gtgtcagact ccctctgagg acccaggggt  107160
atttggaggt ggtgccagca gcacgttagg agtggaaggg agaactggcc gctgccttag  107220
cggaggagag tgtggtgacc ggggcctgtt tggatcatgg ttctgctgtc cctcttgaga  107280
cctaacacgc aggctcaggc cccagagtct ctcacaaacc acagggcaat ctcacaaaca  107340
agcatgtctc tcaccaaccg gagggcattt taaagcagag ctgctattgg agggttggaa  107400
gcatcactcc acagagtggt tttaaagcac caggctccac gggttgctta aggggcttgg  107460
agcagaggct gaaggcagct ctgtgatggc acactccctg cctgagctgt gagaaagaaa  107520
ggcggcccca tgcagggatg aaagagcagt gatgggggaa gatctctgct acctgggctg  107580
ttagcttgaa accggtcagg acctctggaa tcccttggca gttgttggag ccacagcagt  107640
gctcagccag cctctgtgaa accgtagctc acgaagggaa tgttgaggct gtcccaggat  107700
ccgccaacaa ggctgctgca ctgacctggt tcagagggga tccgaacctc tgtgcggcgg  107760
gctccattca tagcgcccca ggcagaaagc tctctgtctt ggtatcagaa tgggaaggga  107820
accttggaga ccattcagtt acttcatgct ttattgctga gaaaactgag atgtgaagag  107880
gttaagttac ttctctaagg tgttaaaagt acgttgaata taaccctta agggacaccc  107940 tagcacgttc ttgggactga aaggccagat cctgtaagaa aggcttttt ttttttcctt  108000 ccagtgtctg tgacttgagt acacagacat ttggattagg caatggcacc ccactccagt  108060
actcttgcct ggaaaatccc atgggcggag gagcctgttg ggccgcagtc catgggtcg   108120 ctaagagttg gacatgactg agctacttca ctttcacttt tcactttcct gcattggaga  108180
aggaaatagc aacccactcc agtgttcttg cctggagaat cccagggaca ggggagcctg  108240
gcgggttgcc gtctatgggg tctcacagag tcggacacaa ctgaagtgac ttagcagcag  108300
cagcagcagc agcctgggta tcattattca tttaattgga agaaaacaca ggggtcattt  108360
gcctgtttaa atgggtcgta ttccctgttg gaaggcaaag agctttggga aatgtcacat  108420
tctctagcca gccccgaaat cagaagcaaa agagtgatct tctctggccc tgcatgtttc  108480
tgacttgttt gacaagctct agtgagctac cagatgtgga aattcttttc agcctgggat  108540
aatttattta tctgtttatg tattttacca ggaaagtatc tattgagtat cttgatactc  108600
atttgcaagg agctcctggg ggaacagtag cagtgtatag tgttactcga atgtttgatt  108660 cccccacc ccgccacgt ccgtctgctt ttatttcaaa cctaaagagc tgagaaataa  108720
aatgcaactt gttcctcctc ccctcccccg cctttcagag aggccgttta aacatgtgg   108780 cagaaaatga gccatgcaga cttggctggc tgtatgaacc cggaattta ttttccttt    108840 cgtactttga tcctcatttc caaccataaa aattattagt agcacttaag tgttgaacat  108900
ttttcacctg agagatgtga aacactcctg gccaataaca ctggttataa agtcagtcgt  108960
tcacgtgggg ctgagaattg actatgagca gccatgtact gttttgtgca caaagtgctg  109020
atcccttcct ctgctcctct gcatcccata ggtggcagcc tctgggtaaa cagcttggc   109080 gctaataaat tatgagaatt tatctgtgtt attttgtcca caactccaca aggtgatggc  109140
aagtaaagaa tcaggagaag atagcaaaat agtgtggaag gccccacttt tttttttct   109200 tgaggacacg aaaccatccc gagtgggttt tcctgctgta aagcaccaa gagggaaagc   109260 acctaagtta gaacacgctg ggtgagtgtg ggcgcatggg ggactccaac gtcgattgac  109320
gtggtgggga cggagcttgc gtttggggtg acgtcggaag ctgggttggt tcacccacgt  109380
agggccaggt gatggacagg ctaagaggtc agctgaaaag tcgaaggcag taagaggtg   109440 ttgtaggttt gcaaagaggt atctggtcca ggcagtgaga tcacaggatg aattagaggt  109500
```

```
gacaggttga dacaggaaac gccagttaga taatggtcgt ggtagcttaa tgttcatctg    109560
ggttgaagaa cgaagggaga agggaaagac gggcgccgcc agggctcgaa tttgattgct    109620
gatgagggag cttggctagt tggagaattc cagagctgag cctctagtat ctaacagtta    109680
cattttaaat agaatcagtt aactttaaag gtctctatat attcatccag ggaaagatgg    109740
tatattctgg gattctaagt aaactatccc acttttctc ttctcactag aagaacagaa    109800
agatggaaac aacctatcat agacttcata ataaccttc taaaaagctg gtgggtaact    109860 tttaagagg aagaaagtgt cactgtcctc ctgtgtgccc ccgctgagcc gcctgcagcg    109920
tcaagaccgc agacaccgcg tcttgggctg gtctcacag acctgtggct gtggtccttc    109980
cgacggaatt aactgctgtc cttgctagac ttcagcccta gagtcctaaa tctgaaactg    110040
tgctcaagag ttgttgggaa tccaaggagg gttttcttta cggtacttgg agccaccgt     110100 ctcatcctgc cgtgggccct acagcaggcc ccaccacacc ctgtggtctc acctagggca    110160
ccaagaagct gggttcttac agcccgcacg gatgaaaaca aggcctccct gaaggagagc    110220
ccagatgcag ataacagcac gcagtgggag cctgcgccac gggttcccat cccttggcac    110280
atggtctgac ccagtggctg cctggaagga ctggggccc gggtgttcct tctcctctcc    110340
ggatgatggg ctgcagcggc agcgccccgt ggagcccgtg caggagtcgg tccacacggc    110400
tgctcaggcg tcccagcgag ccaggcctgt ccctgtctgg acatgggca aaatcgaacc    110460 ttgctagagc ggttctggat cagcattcat ttgtactggg tctacactaa agctttacaa    110520
tagctagatc cattttgcca aaactgagct tttttttgg aatgtaattg ctctacagtg    110580
ttgtgatact ttacagtgtt gtgttagttt ctgctatacc acaacatgaa ccagccatac    110640
acacacacac acacacacac acacaccctc ctaagagcct ccctcctacc cacccgtcc    110700 caccctctg ggtcctcatg gagcaagaag ctgagctccc tgtgctattc agcagcttcc    110760
tgcagaaagc tgagcttttt gaaaacgaga agctgtctgg gacttgcagt gacttctcta    110820
tttagggtct gaagaagctg gtgactggaa gctgtctgtg agccttgtgt gttacatccg    110880
agtgggggac agttctcccc ggagtgcctt tcttgggcct ggccgccctg caggtcaata    110940
gaatgcggac tgttgaaagg acatctgtct gtccttttcc tttcctttta ttcacgtgaa    111000
gcgttgcctt tatagagact gttgtctcga gacaagagaa cggggtggaa tggaaggacc    111060
cactggtgag ggagtgactc gttctgtgag ggtccctgcc caccaggttc agtcaggaga    111120
cccgaggaag actggggttg gagggagtcg tcctccctag agcatgacct ccttggggtc    111180
ctcgccacat cgcttcaggc tcctggtctc cagcctgtag gagccctgaa tcctctgtta    111240
ggcctatgct gtctccagcc tgcactgatt tgcacccgga ctctcggggc ctggagagag    111300
gctagttctc aagtgctgcg ctgtgcacga gctgctgaaa gcagacccca agcagcaggc    111360
ccgggcccac ggaggtgctg agagaagctg ccatgaggtt tgacctcttg gagctttcct    111420
aaagcaccca gtccccatcg gagagtaagt caaacaaata ttaagggaag gaaatcgaat    111480
atgtctgctg aactttgaaa taacatctga tggtttaaaa aaaaaaaaaa gcacccaatt    111540
gggaattaca atagagtgac acttttttcct tccccactga gcagagtaaa acagcaggcc    111600
cagaatttgt ttgcctagcc gttaatgaaa cagtaaatgg aggactcggg ccccttatcc    111660
cgaagaggag ggcggtgctg cccactggca cgtccaacca ccgaagggcg tctcctcgca    111720
gtctcccatc ccacagaggt gatttcgcgg ttgtccgtgg agctctgtgc cggtgaggga    111780
agagctcgct gacctgccca ctccctgccc tctgtgcccc ccgcgcgccc ccccccaac     111840 ccccacctca ccatctttc tgtccgcagc actggcaggc ccacctggct ctgcagttct    111900
```

```
ctgcctcaaa aacgaatgct tgtaatgtgg aatcgttatt ttaaagaggt gttggtccac   111960
ttgatggttt aaagaatcct ttccctcccc ctgttctaaa ggagataact gtcatgatat   112020
tccagccctg agaggatcca tatgtttgcg ggttattgtt ccaaaacctg cctgttgttt   112080
ctttgggatt gattacagac cttggctgcc ccaggaatcc agagcttcag aatttggttt   112140
atgatttggg gatagggga atttgtcttg catgggctgc ttctctgcct tgattttgat    112200
ggagatgctt agaggaggtg tgtgggcagg acttggcatg ggaccagggg aaatgaaacc   112260
caccacagct ctctcaggag ggcagtgccc gcagcctccg agcaggattc tgtggtgtgg   112320
ttcctgagtg tgaagctaca ccattcatcg ccagttataa agctgcttgc aaagtcagga   112380
cttggaaaca gtggttggtg ggtgtcattg cattagacag agcaattcct ggttttgaaa   112440
gaatagaaag aaagaaaact ttaaaggaat ggaatactcc cctaatctta aacatgtcac   112500
acctgggaga aggaatctca agaaagcaag gtggccagtg ggtgtgatat atacaattca   112560
cttctcagat cagatttatt tctcggtgct ccagaattgg tgtgtacggt tcacgtacgg   112620
ttcacacacg tataatcgtg attataactg ctactgtctg ttggctgctt tagagtaaga   112680
gttggcagcc tttaaaagta agatttctag gatcccatct agacctttgg gttgggctgt   112740
agatttgaga ggtggggcag aggtcctgat cacatgtgga cactacccct agagaaggaa   112800
ggaaggggct aacttcttat aaccaaggtc actaattaca tccacgatat agatctgggc   112860
tagactgaca aatttccctt gagcacggcc cgaccacaca ggcctgtccg cctgctttgc   112920
tggtgtctgc ctagagcttg acacatacgc ggtgctcagg aaatacttat tgaccgagtg   112980
gacttaatgt gattggacat tgaattttct tttatatagt ttctgtgagt gaaattataa   113040
ggtgtttttc aaagttaagt gattccatat tttgtattca gggggagata tctggtcttc   113100
tctgtgttaa cctgctaaat agcaaagagt aaaactttgt actaattatt tatctgattg   113160
agggaagtgg agatctcagc tgaactttgt aatttaataa ctttcttttc ctttctcccc   113220
ttaaaattca tgaagctttt tccttcttcc cgctttacca cccccgactt aactcttttt   113280
tttgttgttt tttgtacttt ttcctgcatg cttaccttat ttcatcttca gttttttaat   113340
gtatatgtca ttagtttttc taaatagtaa gctccttagt agcaagatat atgtgttatt   113400
tttgtattca ctctttgaag tgtaattcag tccctaaaaa tagttgggggg cagctgattt   113460 ttgcccaaag gtgcaaatgc aatttggtgg aagaaagaca gctctgttac atgatgctgg   113520
acaaactagt catccgtagg taagacttta accttgacct aagcctcaca tgaaattaaa   113580
agacgcttac tcctcggaac gaaagttatg accaacctag atagcatatt caaaagcaga   113640
gacattactt tgccaacaaa ggtccatcta gtcaaggcta tggttttttcc agtagtcatg   113700 tatgatgtg agagttggac tatgaagaaa gctaagcacc aaagaattga tgcctttgaa    113760
ctgtggtgtt ggagaagact ccggagagtc ccttggactg caaggagatc caaccagtcc   113820
attctaaagg agatcagtcc tgggtgttct ttggaagaaa tgatgctaaa gctgaaactc   113880
cagtactttc tttggctacc tcatgcaaag agttgactca ttggaaaaga ccctgatgct   113940
gggagggatt gggggcagga ggagaagggg atgatagagg atgagatggc tggatggcat   114000
cattgactgg atggacgtga gtctgagtga actccggtag atggtgatgg acagggaggc   114060
ctggtgtgct gcgattcatg gggtcgcaaa gagtcggaca tgattgagcg actgaactga   114120
agcctcacac cttatagaaa aattaactgg aagtgaatca tggacttaaa tgtaaaacat   114180
aaaattgtgt aacgtttggg aaaaaagttg agaaaaatct ttaggatcta ggactaaaca   114240
aagagaaaca tgattcataa aaggaagagt tggtaaatta gacctcatca gatttttaaaa  114300
```

```
cttttgggct atgaaaggcc ttgtgaagag gattaaaaga gaagctgcag attgagacaa    114360
aatatttgca aacgatatat ctaacaaaag actaagcatc taggatatat aactctcaaa    114420
attcggtaga agaattcagt agattaacag tagaagacga acagtccagg tggaaaatgg    114480
acaaaggaca ggagcagtga tttcactgaa gaggatatgc agatagcaaa taagcccatg    114540
aaaagaggtt tggcatcctt aaccattaag gaaatgcaga ttaaaatgag aattatgtaa    114600
cacctgtcag aatggctaaa attttgtttt aaatagtgac tacagataaa gatgcagaga    114660
aacctattga agacgctgag aaactggatc tctcgtacat tactggtatg aatgtaaaat    114720
ggtacagcca ctggaaaaat aatttgttcc acttcttata aaaccaagca tgcaactacc    114780
atacgactct gcagttgcac tcttgggcat ttatcccaga ggcagtaaaa tttatgccta    114840
cagagtgggc acaatgaatc ttcataataa cttcatttgt agtgccaaaa aatgaatcag    114900
cccaggtatc tttcgtgaat gaatggtaaa ccaactgtgg tacacccaca ccgtggcata    114960
ccactcacca gtgagaaggc acaaaccgct gacatggtac atccacaccg tggcatacca    115020
ctcaccagtg aaaaggcaca aaccgctgac atggtacatc cacaccgtgg cataccactc    115080
accagtgaaa aggcacaaac cgctgacatg gtacatccac accgtggcat accactcacc    115140
gatgaaaagg cacaaactgc tgacatggta cacccacacc gtggcatacc actcaccagt    115200
gaaaaggcac aaaccgctga cacacagcca cttaatccca aaagggcata tgctgtgtgg    115260
ttccactgat acacagcctt cttgaaatta tgaaattgta gagacagaga acagattagc    115320
aattgtcaga gggaatctgg atggggagga tctataaaag gtcaatagga gggaccctcg    115380
gtgatggcag tgctctgtat cctgactgta tcagtgtcaa tatcatgtgg ttaagtcaca    115440
ctgtagtttt gcaagatgtt accattgggg gaaactaggg aaagatccag agaaggcaat    115500 ggcacccac tccagtactc ttgcctggaa atcccatgg gcagaggagc ctggtaggct     115560
gcagtccatg gggtcgataa gagtcagaca caactgagcg acttcacctc cacttttcac    115620
tttcatgcat tggagaagga aatggcaacc cactccagtg ttcttgcctg gagaatccca    115680
gggacggggg agcctgatgg gctgccgtct atggggtcac acagagtcag acacgactga    115740
agcaacttag cagcagcagc agcagggaaa gatcatacag gatctctctg cattatttct    115800
tacagctact tttgaatcta caattatctc aaagcaaaat gttgaattaa aaaatcgtga    115860
aaactcagta agtatccaag ggttaaatgt gtaaatgaat taataaatag gaacactcaa    115920
atttcttcat ccctatacta tgacttgact ttgctgtggg attgcctttc tagcacttca    115980
tagcaggatt aatatctcca agatgggtgg aataccatct tacaattctt gaattttaa     116040 agaaaagctg ttgagggcat catctgtttt gatggtttgg actttattct agttttgcc     116100 ttttgtagta aactgtccca aatcattttt ggggatgtag atggggtcga aataaataag    116160
gaatttaaaa gagttcttcg gcttcttgat tctccaccaa gatattacgg agtttaggca    116220
cataaggagg ggactatggt ggattaaaga atcagttcag aaccacattt atatttcaga    116280
gtcagccagg attatagttt gtggtcaatg ccgtttcctt cctttgcaca agaagaagac    116340
aacaagcctg gccagttcca ccgtgtcttc tgtgacagga gagtgatctg agtccccagg    116400
gcagtggctt gaagtcacga gagtttctct tgctggatgg agctggtgtc tttagtcccc    116460
agtcagtcaa agcaagcctc accaagatca acttgaaatt ttgaaggctg ggtaatggtt    116520
atttacatta gaaatagaag ctggagtgtc tgtttatacc tcttgcagga tttaaagaga    116580 atagccatt ggcttatgat cattgttctc cttttagctt cattcagtaa tcccctggga     116640
ctagacttag aaacagtatg acccccactg gagttgaggt tatggaaata aaaatgattt    116700
```

```
cacgtttagt agatcttaag gagcgcaaaa tttgaaaacc catgacccaa cgctgacccg   116760
tgtcttcctc ctcccatccc ctcaaactca catcacatct ccctgcctt tctgtattct    116820
ttctcaagag attcattgcc tcatgaaaaa tacgcattaa gtttaatctt ccgttcagct   116880
gctctttgct tgtccttccc tcccggcccc agagtctctg ggtcccaggg ttccagtagg   116940
tgctcagggg tcctgcgtgg catctcactc acttgctctg caggctcatg cgagttcctt   117000
ctctcagtgg gtgagcctct ggcttctct gctgaatgga aaccgcgttt gcgacgagcc    117060
tcaggctatc agaagacagc gctgagggga gcagaaggtc ttgttgtttt ccccgccacc   117120
tctctctccc tgttctgttc cctccctgct cattccgcat gcatgtggga cccgtgacca   117180
tctctgcccc cagctgagca cattgacact ggtgtgacct cagacgccgt cacctggctt   117240
ccttgacaag tgagggtctg agctgggaa gaggaggtgc ttttagaac cacgagagca     117300
ggcgaccaca agactttaag agcagaggcc ggacgggaag ttaggcggga ccatgtggtg   117360
tgacctcggg accgccgcct cctctccagc cctcatttcc catctgtcca gggagggat    117420
accggaccaa gtgacctctg ccgtcctggt gacccgcgag ttagtgtgga cggggctcca   117480
cagctcagac tgctggagcg tgagtctctc cttagcatcc accaaaggcc tgtgggccct   117540
ccgtccgggg agagagtgac tgttggagcc ccctcctcag tgtgtatgca tgagactcac   117600
tcagtcacgt ctgactcttt gcaaccctgt gaaccgtgtg tgtgtgtgtg tgtgtgtgtg   117660
tgtatcactc agtcgtgtcc gactctttgc gacgctatgg actgtagccc accaggctcc   117720
tctgtccatg ggattctcca ggcaatgata ctggagtggg ttgctgtttc ctcctctgcc   117780
tctccaatga tgccctccta acagtggtag tggtgaaagg tttactggca cacagtcctc   117840
ttaccagctg tggccagccc tggtctgtct ccttagcttc gccactgccc caggcctgat   117900
ggaagggctt gagaggaatg gtgatcatgt accccagcgc cagagcactg cgtccagcca   117960
gactggggtg aatagggctg ctgccaaaac ccagaagcct catggtgctg ctcttgcttt   118020
ggcttatttt aagcagaacc ccaccttggg ttggaaaggt ctctgggca gactgaagtg    118080
atctgtctaa taacaggtaa agcttaatac acaacgcagc atgtacatga gtttgtcaaa   118140
acccatcagc attagggcac tccagatgac agcttcaggg ctcaccggct ctaggtgccc   118200
agcatgaaca tttaatggtg ttggtgatgg acagggaggc ctggcgtgct gtgattcatg   118260
gggtcgcaaa gagtcggaca caactgagca actgaactga accgaataac cacccttgac   118320
gaaaagtacc atccgccatt gtaattaaaa gcatgaactg aaaacaaggc cagtcagtcc   118380
ctccattcca cttcatctca ggaaattcca aatataaaag gtgagctttg ttcccagagg   118440
gccgagagtg agtccaataa ccagctcctc tgtggaaacc agctagaaat tggaaccccg   118500
gcagcctccc cctctcccat ctggggagca cgcaagacaa gcccgacggg aaggatggcc   118560
actaactccg aggtgttcgc acgtcgggtt cctcgcagcg ctgccctgac tcgcctgcgc   118620
acgtggccgc agggtgtggg ctgggtcata gcgttctgtt ccgctttgct ggtcaggac    118680
tgacacaatc aaggggatgt gtgcaaggag aggaatgaat cctagccccg cttggggtac   118740
cttgggccca ccgtccccg tttccctcac cacttcttag tccgtctctt ggttcacgag    118800
tcccagtaca cgtggcgttc ttctcacgca gtggcagtat ccctgtggag ctctgccttt   118860
gaaagtgtga tgactgcagc ggccacttca gagagtccct ttccccctgg agctaacccg   118920
tgagctcctc agcagacatc ccagatgggt gccacctgtt gttataccct cccaccccc    118980
ccacctcccg acccctgggc tgtttcctga atctgactgt ggttagcaca cacccctgagt  119040
ttaaaatgca ctcgcttagc tggcttagaa tatagtgcat tatcctcttt tcaggaacat   119100
```

-continued

```
ttgttgggta cctgtatgtg tatggcattt taaaaacaaa gttaaataat gcagaccagc    119160
aactgatcac tgttgctgaa ttagtttcct tggaaatagg ttagtgggga agaagatata    119220
agaatttagg cctgaaagtg cattagaggt catttaatcc aacccctcat tttgcagagg    119280
gcagaaagaa atcagggcaa cttgaatagg tctggggcac aactcatcca tggcagaact    119340
gttcctaggt atacactaac catgtcctgc ggtgcgtttt ctataggcgg tagtcagggc    119400
tgcctccttt gccttttcaa aaaggtaga acatcttagt tttatcctct aggagtggga    119460
agccacaaaa gacctcagga agcttacaaa agaaaaaata tatataagta ggtaactctg    119520
aaaacagaca catgagcaca gctggcagtc cagagaggag aggagatttc cataatccag    119580
gtaagaagtg gttgggacca agattataaa aattagaacg gaaggacata ggatggcagt    119640
ctgttgttac catctttgtt ggaatagtga tattgtaagt aaaaagtgaa agtgaagtcg    119700
ctcagtcgtg tctgactctt tgcaaccccca tggactgcag cctaccaggc tcctctgtcc    119760
atgggatttt ccaggcaaga gtactggagt gggttgccat tgccttctcc aggagatctc    119820
tccaacccag ggattgaacc cgggtctccc gcattgtagg cagacacttt actgtctgag    119880
ccaccaggga agccctcttt gttggaagag cgatatggaa taggcttcaa atgtaaggac    119940
tgtttggatt tccctagtgg ctcagatggt aaagaatctg tctgcagtgc acaagaccca    120000
ggttcaatcc ctaggtcgga aagatcccct ggagaaggaa atggcaaccc actccagtat    120060
tcttgcctgg ggaatcccat ggacagtgga gcctgaaaga ctgcagtctg tgagtcgcaa    120120
agagtaggac acgactgagc aacacacaga cacagacaca cacacacaca cacacacgca    120180
tgcacgcaca aggactgttc agattactgc caagcccctg atcgaggtgt ggggtttgtt    120240
ttaacagaca tgcgcctctg tcttcaaaga tgtgtgcaat ttaaaataga tgacacttta    120300
tacaaaagat gttgatagga caggcaggca gttgaatgat ggctttgtga cttgaacata    120360
ttaatagctc tgggagcact attactccag ctatcgggat gtaatgtgaa gtttcaaatg    120420
cctgcactac aatatataaa ggcatctgtt agtaatgaca aaaggctgac cccagagcat    120480
ttccccgaag taaaagaaa aaagtggaa ttagggcggg aggtggggag cgatgaggga    120540
aagggggttg aagtcgggtt cccgctctct ggctgggaaa atgctttact gtatacctaa    120600
tcgggcttcg tactacaccc gggctctggg agagagggcc cgtccccttc cgttccgctc    120660
cgttttgatc ctgcagtcag ctgcagagtt atagatgaag tgacaaggat ggtatcttga    120720
ttgcatccag ctgcctggag taagtcaagg gcagagaggc cccgcctgag gagccgcgct    120780
tgccgaagcc tccaaaggcg tctgggagcc aggacaccgt ggggctttca gagcggcgac    120840
attcagcgtt ctgtgaccca gtgtcaccaa attaagtgtc cccagagaga agcctggtaa    120900
gtggcttgag ctcacaggaa gaggactgaa atcaaaacag ccttcgaccc taaaactgag    120960
cctgtgttgt tatcattgct gtcaactagg ggcttgaaaa gaagaacccc ttgggaaggt    121020
gatttcaccct tccttcacat ggattagaga gctgtgctgt gctgtgctta atcgctcagt    121080
cgtgtccaac tcttgcgacc ccatggactg tagcctgcca gcctcctctc tccatgggaa    121140
ttctccaggg aagaatgctg gagtgggtag ccttttcccctt ctccagggga tcttcccaac    121200
ccaaggatca aacccaggtc tcctgaattg caggctgatt ctttaccatc caagccacca    121260
gggaagccca ggaataccag agtgggtagc ctgtcccttc cccaggaggt cttcccaacc    121320
caggaattga accggggtct cctgcattgc agttggattc tttaccaact gagctaccag    121380
aaagccccag attagagagt tgactcaaat acatgtgggt ggggggagat gggattcagc    121440
ttctatccag cagaggtgcc aactgaatgg atgcccccca ccctgcccct tctcctctac    121500
```

```
cttgcctgtt gctggtgctg agtgcagttg cttgtgctcg tagccctcca gaaacctctt   121560
tcatcccatt gagacgaatt gatgatggtg gttgtgatgt ggcttgaaca ggcaggtggt   121620
tagtgccaag cagagaaacc tggctgtgca ctttggtggg gtctacccca gtctgcaggc   121680
cagatagaag ttaggaccca cagcctgtgt tgtggctcca taatagtatt atattaatct   121740
gctgaaatac aaacccaga gtagagagaa cacagccgca gcattataca tctgaggaaa    121800
tgtttgacac tgattcattt gtctgcagct attatgatga cgcctgtggc cgattagctc   121860
agttgattac aacatggtgt tcatgaggcc aaggctgtgg gttggaggcc tgttaggtga   121920
gctggttcca cacaaaggaa acctctttcc gccattccag accacgttca agatcccagt   121980
cagacatccc atgaaagcag atagacgatc acaaagactg ggcaagagag tgtaatgact   122040
cagcaaatgt cccttacctg ctcctggaaa agcgatttaa aacacgtgct ttagcgatgg   122100
tgagttgtta ctgtggtctt ctcacacaaa ggctatcaca ttattacgaa cgatgactgg   122160
tgatcagtac tgttgcaggc ctcctttctg aatgaagaag tgtactagct ctggctgtga   122220
agaaaacagg aaggggcttt ggtccccttc tttcctgctc agcttttcc tgctgaggtt    122280 ttgcctgtcc gtctgtgcct tcagcaggtg tgcgtggaag gctgtcatgt gctctgtact   122340
tggaatgcca ccgtgaacct ctgtcctcat ggagtttaaa ctctgcagga ggaaaagaga   122400
taataaaaaa aatagatgat aaataaccag tgcagtttca tgaaatggaa gtttgatgca   122460
gaagagcatg gagtgagggg tctaatgaag aatggctggt cagggatggc gtttaccttg   122520
gatgggaggg tctggaaagg cctgtcagag taggtgatag ttaactagag acgtgactga   122580
tgggcaggaa ccagccttt gaagagctag gggaacagcc cacctgagaa atagcaggtg     122640
cagaggcctt aaggtctagt cacggttgaa ggacagggaa gccctgact cgtcgagaac     122700 gtggtaagag agaggctgga gggaggaagg ctgtttagaa catgcgtagg agttagcgta   122760
ttattcttaa gaggaagcca tcttttgttt tgttttatgg gtggagcatt ttttaacgct   122820
cttgtcgaag gggatgttat ggattgaaca tgcctaaaaa aggtattccc ttttttacct   122880
ttcaccaaaa gtcttccctg gtggctcaga cagtaaagca tctgcctcca ctgtgggaga   122940
cccaggttca atccctgggt ggggaagatc ctctggagaa aacagtggca ccccactcca   123000
gtactcttgc ctggaaaacc ccatggacgg aggagcctgg taggctgcag tccaggggt    123060 cgctaagagt tggacatgac tgagcaactt cacttcttca cttcaaaaag ctgaaatcct   123120
aatccttagt aaccttactg gaaatagggt cttttcagag gtaatcaagt taaagtgaga   123180
ttgttagggt gggccctaat ccagtttatc tggaatcctt ataaaaagga gaaattcgga   123240
cacagaggca cacactcaga gaagaagtcc ctgtgaagac agaggtttgg agtggtgcgt   123300
ctacaagcca aggaatgccg gagattgaca gccacccacc aggagccggg gggaggcagg   123360
caggatcctt tccccggggtg agatggcccc accagcactt tgacttctga tttctagatt   123420
tctgttgttt taagccaccc actttatgtt ttaaagcagc cctgtgctcg gttgctcagt   123480
catgtctgac tcttttgcgac cccaaggact gtagcccacc aggctcctct gtccatggat   123540
ttttccaggc aagaatactg gagtgggttg ccatttccta cttcagggga tcttcctgac   123600
tcaggaatca aacctgcatc tcttgcgtct cctgcattgg caggtggatt ctttaccact   123660
gtaccacctg aaaggtgtgg gcaggcgggg ggtcctagca tgctgacttt gggaaagcag   123720
tgacgcatcc tccctggtgg ggcaagcctc tgggtgctgt agcatgcatg accataagac   123780
ttagatacat gtgggtagat agataatgaa tatatatata aattaatagg atggcacccg    123840
ctggttgaat taccctgtaa agcataccct actcttcttt tagaaatagt cctttgggg    123900
```

```
atgctctgta aatgatggtt tggaagggca ggggtggaag cacacagatt ggaagcctgc    123960
tgcagtaacc cgggaatcca cagtgacctg gtaatgacgg tggtttgagc tggggacagt    124020
gtagcagaag cagtaggagg gcgtcagaag tagagtcagc agcagctgct agaggactgg    124080
gtgtggagag agaggaaaga aggaggaaag gctgcccag atagtttact gaggcaggaa    124140
atactgagag gatggctttt cccaggctgt ggaatcaaga gtcatgcttc ggacatatta    124200
agtctgaggt gcctgttgtt aatccagctg aaggtattaa gtaagtagtt ggttgtatca    124260
gaaacattca gggccagacc tgcatttaga ggtcttcaga gtctagatgg tatttaaaaa    124320
gactgaagct agatgttgct tgtggggaga gtttaagagg gtatagctct ccgggactag    124380
gccctcagga actccactgt gtagaggtct gggcgaggat gaggactccg tggtgctgag    124440
cagaggctcc aggacagctg gtaaattgtc agtattcact aatggttagt agtttaaagg    124500
ctaaggaaat tgtatggaaa tacatggagg aaagtactgg atgtacccca cccttgtata    124560
ccaattctgt ttaacaaaac tatatctcag agcctttcca aatgtggaaa taaaattttt    124620
gttttcagta aaatcaggca acatctctat gcctaaggct tccaaaagat cgtaaaaaat    124680
gtctttgtgc tccagatagg ttttttttct ttttcagaag cagagacttt gtaagtttcc    124740
acaatcatca aaatttacca taaatcatgg tttcatttat acttcatttg tgcgttcatt    124800
aagagtggaa cctatttcac taatcgcctg ttgagagatt ataccttg gcgcaattca     124860 agaaactgtt agtctacatt acttgaaatt tccaaataca aacccgaaag ttttagagga    124920
aattagaatc aacatttatc tttgaatgtt ggcagaagaa ctagcacctg ttggatcgaa    124980
tttcttcaga agcccattct gctcttagtt tgtgaagatt tgaatgcagg gattctgtca    125040
tttaaagagc tgagcactgt acttgcttat tgtctgaact ggggattgat tgctgatgtg    125100
tttctgtcct caggtctggc gagaatttcc tgaccggttg gtgggttacc cgggtcgcct    125160
gcatctctgg gaccatgaga tgaataagtg gaagtatgag tctgagtgga ccaatgaggt    125220
gtccatggtg ctcacggggg cagccttta ccacaaggta aggtgggac gagcctgaag      125280 caagtggggc cgagctgacg aacacgagag cgtgatactc gttttgtttc gccgaaacta    125340
aatttcgcca agtttaggga aaatgttccg ttcagagagc ttaggaaggc catgctgtgt    125400
gatttaaaaa aaaaaataaa gttatttttc taattattaa agtattacat gctcaaatat    125460
ggaacaaatt tattgtataa gaaaaatcac ttaaagttct atcataggat tgctgctgct    125520
actgctgcta agtcgcttca gtcgtgtcca actctgtgcc accccatgga cagcagccca    125580
ccagactccc ctgtccctgg gattctccag gcaagaacac tggagtgggt tgccatttcc    125640
ttctccaatg catgaaagga aaagtgaaag ttgccatttc cttctccaat gcatgaaagg    125700
aaaagtgaaa gtgaagtcgc tcagtcgtgt ccgactctta gcgacccat ggactgcagc     125760 ctaccaggct cctctatcca tgggatttc caggcaagag tactggagtg gggtgccatt    125820
gccttcttga tcatagaact aatggtagag aaactactgg gttggccaaa agtccattc     125880 atatttttct gtaaatctta tggaaaataa tgaatgaact ttttggccaa catagtatta    125940
ttatttaggt gtttttttcca atttgtcttt tttatttatt gattcacaca tacagtcata    126000
aatattctca ttagctttt tgcatgtatt atgagttttt tccttatgtc attaacattt     126060
ctttataaac aacctctact taacataatt gctaatatac cattatatta atattccata    126120
gatcatatac agctgtttct ctgttattgg atatttcagt tcagttcagt cgctcagttg    126180
tgtctgactc tttgtgactc catgaatcac agcatgccag gcctccctgt ccatcaccaa    126240
ctcccagata tttaggttat atctaatttt tttttgctag ataatgcttt gtatcaaatc    126300
```

```
cttaaataat gatcagtatc cattttcata actgcctata cttatgatct ttatgataga    126360
ttcctagaag aattataaac attttgggga ggctttgttg tatatatttg taggttctca    126420
gtatcgtttg tgccagttta cattctcacc atactctttc ttgcatgaaa tacatttttt    126480
aaaaaaatca aacttagcta ttttgctaag tgaaaattga ttttattgat ttcactttga    126540
tcacgtgggg tttgcgattc cttttgtgta tttagccttt tgtattcctt ctgagaattg    126600
ttgctttatg ttttttgactc ttttttatta aagggagaga ttgaagggta tacattgggc    126660
tttagaatat tatgtttggt ggtggagtgc tccctgggag tgtgtggctt aattgaacag    126720
taatgttcag ttgtcagcag tggcataagg aattgatgtc aggagaaaga tgggttcagc    126780
ccagtgcagt taagttgact tcactgtcag ttgtcagcag tggcataagg aattgatgtc    126840
aggagaaaga tgggttcagc ccagtgcagt taagttgact tcactgtatt tatatcggct    126900
gcgtgttgtg atctcagcac tgctgccctc atattttttca gggctctcga tccagaaatg    126960 agttttttt ccttagcaaa gcataaataa atatataagg tttataattc ttggggctat    127020
gatagactga taaatgcctt tttggcagat gtatttctgt attataccac aaatttctgt    127080
attatttcat acatgtaggt tatggtagtt ttggaattgc ctcattttg ttgtacttta    127140 acaaagaaca tgtctgcaat gtcagtccac catcaatata tctctgttgc tatctgcagt    127200
ccatgggaag aagataaaaa acggcggagc actgtgactc agagggaagg attcagtaaa    127260
gctcagtatg tagtgtgtct ctgaactatg tttattaaac acatctgtta atcagtccaa    127320
agggcctgca tcttacaggg acttcatact gtaccgtatg ttcctctgct tacaataggt    127380
gattttttaa agaatgacag tgttaaagac agttggtcac ctgaccaaaa gcattctaat    127440
acttcccttg gcctttgtat tgatccaaca ttgtgactca tcttatgagg gaaagcttgt    127500 cccctgtca tggctcagtt gctctttgtg tatcagccat agggaactgc tatttgaata    127560
tgtctcctct tttgtctcac ctggcagtat tttaattacc tgtataccta caagatgcct    127620
ggggacatca agaactgggt ggatgctcat atgaactgtg aagacattgc catgaatttc    127680
ctggtggcta acgtcacagg gaaagctgtc atcaaggtag gaggcatcta tggccagctc    127740
tggggcacat cttgggcacc tttctgagtc tccaaagtgt tcatagctat aaatgaaact    127800
tggaatagat gaactttcag ctgccttta gctttaatat tctatgatgg atatttcaca    127860
ttgtgaaatt gaagctcaac gtattttctt ttgttatata aaattgcttt agttatagtt    127920
ttttaagtac caggatcaga aagtaagtct ataatggtta atctacaaat tgtgtttgtt    127980
tcaaaaatgt aattttattc tcaacactga tttggaatct agttcttgta aagaatgcaa    128040 ttatgtctttt cttaaggtag ctgatttttt taaaataaat gttgaaaaga tagtatactt    128100
tgtccaatta tactggtagt tgtcctaaac actgttttaa gacagtgatt atcaattttt    128160
aaaagaacct ttcccatagc atattaaaag cagagagtat gtaaagatca tgtggggatc    128220 tttgttttcta taatagatgt ctattcctaa aatgtaggtc ttgcccaaat cagggcccta    128280
taaatgtaga aaaagtatac ttctttatat cagtggagtc atcttgacct ttttttcttt    128340
ctggattaga ttccacatgt aaaaatggcc aatgcttcta ggccagaatc ctatactgga    128400
agcttatatt ggaaacgtgg tatgacattc cagaatgatt gctcatgcta ttaatattaa    128460
tcgatgagag aagccagatt aaagcagtga ctgagaacag aggaaaagtc actgtccaga    128520
cttgatccag tctttacact atccctcggc tctctaaata gctcagtgaa cagctcactg    128580
cagggacaat taaagaatgt aaattgcaag acgagtttta aaagaactcc tcttatctcc    128640
aaattcattt tttgacattc ttcaagacat tctttagctg tgcctttact ctggacagta    128700
```

```
attcctcgag tctgtatact tcttagccga gtctcagctt agccgggtct tagctttctt   128760
ccccacccac cctctactgt ttacttatct tcgctgggtt acgatagcag ccttccctga   128820
gtttgctaga aaatattcg aagtttgagg tgtggggaag gtggtgggga gagtcagaga    128880
aaaggattca gagggcaaag gacccctgga ttttttcct gacttaaagg ggttgcaaaa    128940
taacctgaca tcttcaagag catggtgccg cccgtagctt ttgccattag ctggaaggag   129000
aaagagcgcc tgttggaact aaggttacgg tgaaagttat gggaagctgt atttcatcgc   129060
ccttatggct gcaagaacaa atggtgttta tacaaggacc ttggcagtga gaaaacagtc   129120
attaaacagg aattaaggag cttgtcatca ccacttcttt ccagttacag aaggcaaaag   129180
ccctccaagc ctctttatt gggcccttgt gagttctgcc ttggccgagc cagacagaat    129240
tgaacggagg agcggtgagg ggtgtgtgtg tgcgcgtgga gagggagcag gcatctcagc   129300
ttacagaaca gaagcatgca gagtggcatc acaagcatgg ttttattgtc cttagcactg    129360
accgccgggt atattttgt gctcctctgg caggtaacac cacgaaagaa attcaagtgt    129420
cctgaatgca cagccattga tgggctttcg ctcgaccaga cgcacatggt ggagaggtga   129480
gtgggcctct agacaaaagt ctgccctggc ctctgatccc catttcctgc tttgggcctg   129540
tttatgggac tttgttgcag atataaggac agcagctggt agccatagtc acctcctttt   129600
gcacatggga attgggttag ttcaagccca ggtcacccaa agaattaatt tggaatgcta   129660
ttcactcaat atgtaatggc tggaagggtc ttaaaaatat agctggcctt aagctccaga   129720
agccagattc tccatgtgga ctaagcagtt aaccatccac agtcactcaa ctggaagtga   129780
gctaattcca aggaaatcct gggttgtttt tcagggtagt atctctgtgt tacagtaaaa   129840
gttcgattag agagaattat taaaccaaac ccaccagagg ccagattacc tttgtggaca    129900
cactaaaaca cctaccaaga acagaattga aagcacagct ctttacattt cagagagcga   129960
agcagggccg ctctgaaata cctgctttat attgattcgg tcacttagcc aatgagcacc   130020
catttctgtg gatgtaatac agggccttgt aggtgagcat gaaggaagtg ggagatgtct   130080
gtctgccctc aagaccgtct cacttgtgtc ccaaaggccc caagcttcaa atctcctgaa   130140
tcaaacctaa ttcttccaaa aggcagcctc ttacataaga cagcgagctc tggcaaccaa   130200
tggcattttt gtcaagggac cagaatgcat tcagagaatg ttgtgatagc tgtcagagtg   130260
agatatctag ttcgggtctc cctgggtctc atgcgtctgc gtgcagcact catttctgaa   130320
ccctaccagc tgcatcaggg tccttcaagc ctggaggacg ttgtacaggg ggctgtttca   130380
gttggcctgg acccttctat aatgctttac tccttcttac gcattctctc taaataatct   130440
ctttcatatg taaatatctt acccaaatga cttgactttt accaactgtc aatatgaaat   130500
tatagacatt atcgatatta ttatatatca caatatatat tatatatatt atcacaatat   130560
atatataatt atatatcaca ataatattga tacaattatc ggtattattg tgactttgaa   130620
atatctgtca ctggtatcaa gtaatcacct agtcaaggac agtgacattc ctgacacagc   130680
tcatttggaa gagaccccaa ttatagttct gtggctgctg ctgctaagtc gcttcagttg   130740
tgtccgactc tatgcaaccc catagacagc agcccaccag gctcccccgt ccctgggatt   130800
ctccaggcaa gaacactgga gtgggttgcc atttcctcct ccaatgcgtg aaagtgaagt   130860
cgctcagtcg tgtccgactc ttcgcgaccc catggactgc agcctaccag gcttctctgt   130920
ccatgggatt ttccaggcaa gagtgctgga gtggggtgcc atgttagagc acatgaaatt   130980
gttacttaaa cctaccccca ttctgtgttg agaatttcat agcattaagc aattagtttg   131040
attgggctga gttacatggt ggggttttat ggtctaagaa gaattgtatt tagaaaattt   131100
```

```
cacccaatac tggccttaaa gttcatgcta aagctgaaaa actgagataa caaatgcaat    131160
gagaaagatt taagttaggt ataattatta tttaacactg aagtaagtaa ctaagggaag    131220
tgtggaagct tcctctcggg aaaagggttt tgaaaataga ctaggcactg cccagatgtt    131280
ggtaggcttg attttatcag atttttataa ttaacaacag tagataacac acatgtgtat    131340
gtgtgtatcg aacctaatcc gaagctatat gtgataagtc aaaggaaggc tcagaatgtt    131400
gtaactggtc agaggaaaga aaagtgactt cttactaggt tagtcattat gaatgatttt    131460
gtaagaggtg gcacttgaag tgagccttcc aagattgcta ggattccagc tccaggcagg    131520
aagaggagat cctcggcagg ggaaaccgga tggtccaagg tgcatttggc aagcagtcaa    131580
gatagccagt tttgttagag cagaacatcc tggcctgtca gtgccaaagg cttttttct    131640 ctaggtaagc cgtggaaggt ttttgaatag ggaagtagtt tgattagagt attgttttaa    131700
gattgatttg gaaggagtac atagaatgaa ataagggtga gattgaagaa agaagaacag    131760
ttagaaggct tgaactaagt tgagtgtgga gaggaagggt tgaagtaaat tacacggttt    131820
tttccttttt tctcccaaag gagactgtgc tagcatttga tgtccagctg aatggtgtgg    131880
ggaggtcttg gaggagttga ctgagatagg aagaatggta gtacctttaa cggtggaaat    131940
aatatgatta ggagggatgc taagtagggg aggggaggac atggatgttg tagctttcac    132000
agtgtaatta atgaggccag gagattttaa tggtgtgtca agttggagag caataaggca    132060
ggtgcgtttg cgctcttacc ctctgtatat gcagatatag atatagagca agcagttgga    132120
aatatagaac gaggacttaa gaaaaagatt aaaacaaaga tggagatttg gaaggcatcc    132180
gtccagagat gacaactgat tgaagaaaag ctatgggtag aatcttgaga aattcagaca    132240
gttaggagac agagtaattg aaaagagaga agcaggcact agagagaggc caggagagaa    132300
ccagggtctc cagtgccagc agcattggag actttggaaa aagtaatgcg tagggtgagg    132360
ggctgaaggg cggtagcgtg ggagctgaca gtgaggacgc agggtcagtg acagcaggct    132420
cccctttgga gaaatgcgat ggagaacaga aggaaatcgg tcttgaatta attggaaact    132480
gcgagcaaaa ctatttggat taaggttaaa tgactgaatt attaaataag acacttaggt    132540
tgggtgggag ggggtatga tttaagccct actggatagg ccaagagatg gagttacaac    132600
tgcagaattg ttcacttgtt tcgaaatagt tcccttgcg gaatctgcat ttttgcacaa    132660
aacggtgaga agagttaacc gctctgtacg ttctgatctt tgttgagtt gtgtgcttca    132720 gtaagcttat ttattcttat gtttggggtc tgggatcaga aatctcagct gtggaggaga    132780
gtactttaac tgcccttcct ccatttccag gtcctgctat tagttaattt aagaaaaaga    132840
agattttgta acttcttttt gcccagtagc tttacccacg tcgagacaat atggcagaca    132900
aacaatgccg atttaagaaa caaacgttgt attttgattc aggtcagtct ttgttcaaat    132960
tatgaattag ccatttatta gctgtctgac ttaaggaaat tgacttacct tatcctgaac    133020
ttccaatcat ttcatctctg aaaatagata tattaactgt catattactg tatccattca    133080
ggaattcaac aaatatttat tgagcatttt tgtatcagtg ctaggaaagt ctgtaccctg    133140
gggcctggca aggttagttc acttcccagt ttccccagca ctgaccctca agctccttgt    133200
tactttaggt aatagtatga gtttgaaagg aaaacagaaa gccattagtc ttttctcccc    133260
agcccttgca gcacttcaga gatagacatt ggctgttctt agcctatctg ttggttagaa    133320
aaccaagcta ggggaacagt tactgacata gtagctggac ccccaagaga acaactcaga    133380
tagacccacc agcaaccagc ctgactcata atctacccta acttgttccc cacccaggt    133440 cccctgcatg aaatgacggt aggagacact gtcggtacct ggcagtcgag gacttgtacc    133500
```

```
attcagcatg gcagtcgctt ctccagggtg ggctgcgtgg agagaaagga ggactcagta    133560
gcctgggtca gccaggggca gctgtcagca agccgagctg gcctgagccc cagcggcctc    133620
tcgcctgtgg cccggcccgg ccggccggtc tagttacaga ggagatgttg tcctcggtgc    133680
tccccaggag cccgtagagc caccagcccc tgccaggagc cgtgagtctt ctttcatcca    133740
tcctcgctgg caccctatgc tggacacggc tgggctttgc tggccggagt ccacaagcag    133800
aatcactgga aactacaaga atctgtccgt gtttataggc agaacaactg tcaaagtgag    133860
accttgggga gatttgactt agtctgccgc tgtcttgacc ccgtaattta aggtgagaag    133920
agctgttggc cagtgcttgc ttcctatcat tttattaaaa cctctctcag tcttttcccc    133980
agtctcctgt cattttggaa cctgagactg cgacctcctg ggtctcgaaa gactgccaac    134040
aggagggag ctcagtgatc tgtgggccat tgtagaatgt gatagaaaga cccaggcctc    134100
tcttagcaac gcaagcctgg gtttgaaccc agctccacca ccttccggct cagggtcctt    134160
gggaaagtcc cttagcctct ctcagcccaa atctctcaaa tcacacaaac cttcgggctt    134220
atggaggggg atacttaaag gaatcactgg gtcgtggatg taaattagct ggcacttaat    134280
aggaaatggc aacccattcc agtactcttg cctggagaat tccaagttca gaggagccag    134340
aagcctgaag ggctacagtc catgggattg caaagagtcg gatacgactg tgcgaccagc    134400
tttcactttt tcagtaggtg cttaacagtt gttaatttcc agcttctctc tttggaccct    134460
agaataatga taataaataa atgtgtctcc tctcatagtg aagacttcag cctcagcaac    134520
cagagtgcct ggatttggct ctgctctttc cggttatttg gctttggtcc tgtctctgag    134580
tctccctgtg gtgtgcctct gtctccccag tatgccgtgg gaaggatagg aggcctgcct    134640
cgtgagcttg ttgtgagggg agacgtgagt gactagtgca cgccaagcac ttttaacaca    134700
gcccggaaca tagcgtaaat ggtaggtgcc gctgctctgt ggctgtgggc acagtgatgt    134760
tattagctgg aagagctcac agtgagatgg taacaccttc tgagcagcag aataagtgca    134820
agaaaagaat tgacaataac tggcttcttt attaattggt ttcttgctga agctcaaagg    134880
actcaaataa aagctgtgga ctgaaatagc ttgaagcaag gcttacagtc tttccgagga    134940
cagaagagcc ttgcagtctg tgtcttgaaa ttcggccctt ccccgggaac cggttctcag    135000
gtgccatggg cctgactgag gagagagaat actgacctcg ctgaaatcca tccttgaggt    135060
cccccttaact tcaaaagcgg tctttgcggg ctcgttttcc cccttggtc tgatgccgaa    135120
atgtcctcat caccgctgt cacactcagt tggcctgatt gaccagagcc ctttcctgcc    135180
cgtgtgtctg agccgctccc ctctgagggg gctgctcacg aggtgggggt gaggggctgc    135240
accctcccct caccctgcgg tgctaagttg cttgttgctg ttgattctaa cacgagaaca    135300
gctacaatta tgaaagctgt ccagtgtgaa cttcagctct cacagaggag cttatggaag    135360
tggactgata attcccagag attgccactc acagccctcg atagatgttg gttgaatgcc    135420
tgaagtgttt gaaattgagg ttcacggccc ccgttgtctc ctctgccttc catcgcccca    135480
catgtaagag ccttccttct ccctttaag ctcaagcgag ctgaagccaa gatccaaccc    135540
tttgcctcct cccttttgcct tctcttcagc tggcagggat ggggttaagg cttgttggca    135600
actaatccac ctaggttaga ggcctgcttg taaggagctg gaggaatgac tggaatttga    135660
gggggagggg aacgatactc tgacctctgc aggcccatgg ccttcgaaca gctcaaacag    135720
catccctggt tcccttttctc cctctgaact aatagagtac ccccgatcac tttgttcctc    135780
cacagcctcc cagccgtggg aagaacccgg gagcatgctg gggaaccttg cgtttctctg    135840
gccagtgttg aatacgatat attttttgctc tcagctctca gcctcttgaa cgttttcttt    135900
```

```
gttccccacc cctgtccctc tcatctgccc cactgccctc cccaattccc caggtccgag    135960
tgcatcaaca agtttgcttc cgtctttggg acaatgcctc ttaaggtggt ggagcaccga    136020
gccgaccctg tcctatacaa ggacgacttc cctgagaaac tgaagagctt ccccaacatc    136080
ggcagcttat gaagcaggcc gctggtggag gtctcaacac gaatgccgga cagaggaaga    136140
gaactcggcc ccccagccct ctgaccccg  gatttcagag tggaagactg gcacctcctc    136200
gcctgaagag cagaggcccc aggaggacat ctgagcacct ctggcatcct ctgatgctct    136260
caatgggttt tctgaaaact ctaggtggaa gcctgtggca ggctccaggg gaaggccaga    136320
tcaggctttc tttgtctcca gctccagtac agtgatctga gaggaactgt ccctggctct    136380
aagactgctg agaagcctcc agcagatctg tgatatcatg gaagagctac cggactcact    136440
ttttgttatt tcacatcagt gggttcttca gaggaagagc cacacccaga atttggtgca    136500
cgatccaagc atcttagtgg cgtttgatgc cttgggagca ccagctgctg agttgggacc    136560
cgtaaattcc atgaaactct ggtttggctt ttggatatga ttaaacttat ttttattcc     136620
gtttcatact acatcttaaa tattgactgt ggaactttgt gcgtatgtaa cttgcatctt    136680
ctgacctcaa ctccagcctc cttcccaggt ctgggaagac agtcggccgg gaggcgtgtc    136740
tggtgccatg tgtatccagc agagaagaac ctccaactac aaatattctt agcgtcccca    136800
gacctacaaa ggagtctctg tgcttgctga ttagatctag atatccttgg gggaaagcag    136860
agggcctctc acagccatac gctgagtcgc tctgctggta ccacattgta aaattgagcg    136920
agttgtgacc ctcgtcccaa ggggatgcca aaatttccct cattcttttg gtataaacct    136980
aacgttagcc agggaggctc tggctaatgt taaatgctgc tataacaact gctttgcaat    137040
agttgccggt atatttaaat cgttacattt cagcatttag taatactgca catgtgtgaa    137100
ttatacctct ttaagctcag ttgatgaaca aatctactct ggcaaatgtt agatgttaag    137160
gattcgaaac agatttatct gactctaata ttaagattag ccacagtttg gctttagcc    137220
ataacatatg tccccagaac acaaaataca taacaatttg cttggaatat ggatataatt    137280
actgaaactt agttgtgtgc ccggtccaag tcactaaacc accactcatt gttctgttga    137340
gtgacacgga ggtgagctgg tctcatgctg gtgttttcag acttgcagtt ttaaaagaat    137400
cacttcaaat gtgttcccat ggactttgag aggccaaaga aaattttcag aagtagcaca    137460
attgaaagtg gaaatcttga gtctgatctt tcatatttag gcctggtggg atggcaggct    137520
gttcttggca gaagggataa gataacatct ccaggtcatt cattttgcag ttgcagacac    137580
tggagcagtg atttattcat gtgttgctgc tgtgaacact ggtgcttaat caatactttt    137640
gatttgaata attatatcct agccagcagg ggagatggga aggcattttg gcctcatagt    137700
actggggggta tacggtaga  aaccaagaga aagggttttt ctcttgtcac ccagatacca    137760
gtagctgaca cggcgagtag gaacctctga tctttccagg ggttcccttg cttgttctcc    137820
aaggtttggg gcaagtggaa ggggaggagg acctcacagt taaattctag ctaaaatcta    137880
agaactgtgc tgacattgtc tactgtgtga cgtgcgttga cgcacaccct cggcatgtat    137940
tagtagcgct ctgctccttt cagatgacca gctgcactgc attagtggct gctttctaag    138000
ccacctcccc ctctcaaaag ggccaccttt cctcctcctc cttcctgccc tccttctctc    138060
cctctctatt attcctttga ttctggaaga gaaatgcttc agtagcaggt cattgggggc    138120
ccaaggggac agagccagtg gacctttatc accttctcag aagacattgg tcttctaagg    138180
gcattaaaac tccatttcga gtacctaact accccagaa  atattggggg ttagattttg    138240
caccatagtg tacaattttc ttttattatt attatagaat aaatattaca tcctaggcac    138300
```

```
tgaaagcaaa cctcaaagct tctgtcctag ggaaagagag agggtacagg tcacagggaa    138360
aaattcagga caggagtata gcaagtgctc tgattcatgg gttcagaggg gactaggagc    138420
tccaccctgt cctgtgtggg tgtatttctg agctgctcac cagcaagcct cactcataag    138480
cttgggccag gatcatctgc ccttgggatg ccataggttc tggtttcaga agcggaacaa    138540
taatgctaat taaaatgtca tattctggcc tacaacagac aacagctggt tttagattaa    138600
gaaatctttt ttaaggaatt gcatcgtact ggcctgcacc gacgatgaac ctgagctggc    138660
cctggccttg ccacacatgt atgtactaag tcgctagcct ttgccctcag ggacctaact    138720
gggatgggcc gggctgcgtg gaatgccagt gttgactggt gcgtgctcag ttgtgtccga    138780
ctccatgacc ccatggactg tggctcacta ggctcctctg tccgtgggat tatccagtgg    138840
gttgccattt ccttctccaa atgccaaggt tggaaaccct tttttgctag ttaagtttag    138900
gtagctatac atattcttat ctgatgtatt ttagcaaggc tcacacatgt ttaggcaaaa    138960
ccctcctttt ctgggaaaat taaggaggaa aatatccact tttgtcctca gactctctgg    139020
ttccttcctg caagtgatgc tatcctgtct cttcttactc ggcatcgtga aggtcagaac    139080
tctggcttct ctgctgaacc ttctatgctt ccagcttgtg ggttttagga gttttctctgc   139140 tgcctctgga gagagtggcc atcatcctgg cctgtgctga ccaggaccgg gagctggaag    139200
aggccaccag cctctgtgct ctcacttgcc aaagggtggc tggtagctct gtgatccggc    139260
ttcctcctgg gacagtccct gaggatcctt gccactgaag ggccgcaggc tcctggccac    139320
gaattctcaa ggtgtgattg ctggactcaa gtccaagacc ccttggtggt agaattaaga    139380
agtcaatgaa gcagagtccg ggtcaggaag tggttcactc ctgggggggac tcttcctgac    139440 tctacagtca cagaacccgg ccaagagggt ggaggtctcg aaggttcccc attgtctagc    139500
ttccctgagc ctggtgggtt tcctctgctc tcccagtggc ggctccgggg taagctgttt    139560
tctccagttc tgttggtcat cttctgctgc agcagctgaa gccgcagtac gccattcccc    139620
gaggagccct ggctcgggga ggcagaggca gaaaacaccc aagtggcccc acgccacttc    139680
ctgaggagcc atcctggtgg aagtgccaac cggattggca ggcagcggcc gtcgagggag    139740
gctctggaag agacttgagc tttccactga gggcccggag gcgtgtgaac cctggaggct    139800
ggctgctcac ctcaccccag agctctgtcc caagccccag ggctcctgtg ctaggccagt    139860
gtttgcttct aaatgaaacg ggggcagctt ttggccccac tctgccagcc aggcccggtg    139920
agatgatctg aaccggtttc actgagctgc tcctgacagg acagtgaggc aggccagatt    139980
ctgctctcac ttgtgaggtt ttcctctctc ctaagctaag gggttccctg gtggctcagt    140040
ggtaaagaat ccacctgcag tgaaggaggt ccaggttcaa tccttgggtc aggaagatcc    140100
cctggagaag ggaattccaa cccactccag tattcttgcc tggagaattg catgacagga    140160
ggagcctggc gagctacagt ccgtggggtc gcagagtcgg acatgactta gcaactaaac    140220
aacagtgaca tcatcctaaa cgaagctcac agcctctctc ccacctccat taaatagact    140280
gtcagggctc cccagcctca ggctttgtga tgtccagcct ctctcccacc tccgttaaat    140340
agactgtcag ggctccccag cctcaggctt tgtgatgtcc aggttctctc ccacctccat    140400
taaatagact gtcaggcctc cccagcctca ggctttgtga tgtccaggtt ctctcccacc    140460
tccattaaat agactgtcgg agctccccag cctcagactt tgtgatgtcc aggttccctc    140520
ccacctccat taaatagact ctcaggcctc cccagcctca ggctttgtga tgtccaggtt    140580
ctctcccacc tccattaaat agactgtcgg agctccccag cctcagactt tgtgatgtcc    140640
aggttccctc ccacctccat taaatagact ctcaggcctc cccagcctca ggctttgtga    140700
```

```
tgtccaggtt ccctgggaca gggtgtgggc tgtctaggca acattgtgct acagcttttt   140760
catgtccagc tcaccactgc ttccaacaca aggcaggtga cggggcagct tgcccctct    140820 cccagctttg caggcatctt tccttttcaa gaaattgttg agtcacccac ctctgtgtct   140880
ggcatctcaa atttaacagc ctttgtaggg tagagttttt tcctttcttc tgctcccaac   140940
tggttgggcc catggttaca cttctttgca gcctccctga agggcagagc tgtcaggcgg   141000
agacgaggaa agggaaggat gtctgggtgc cactcgagag gtactaggca gctatgtctg   141060
ataagaggtt ttcccagcaa agcacctgct cacccacagc atcttgggag ctgcctgtgg   141120
agacagctgc caacggagct gggactggaa tctgcgtgtc ttggacccaa gcctccagcc   141180
actccatcca cccttcagag ccttcccttc acagagtatc aatgtgagct cttatttata   141240
gctgccaact tctatcatta actactatgc ccaaagaatg tctggttttc tggtaatcac   141300
agctgaagaa caaccaactc gttactgacc aagatgaggg aataattcag tcattcggtt   141360
ttctaattgt tcattcactc attaaaatgt actctttgct agaacctgtg ctgcgtctga   141420
gacagagtgg aataaaacac agtcttgacc tccaggaact tgggttcccg tgagagttct   141480
tggctctgta agatggtgtg agtccctcag aggcctaggg ctccacacac gtacgtttga   141540
gtcctgactg cgcaggaaga gtccattacg tgaacaccac cttcgctggt gcccagagga   141600
cgcaagcatt gtttgtttcc cgttctcata gcgccttcct ttgagttgag ccctgggcct   141660
tcctcggcct tgagggattc cactcccttg ccttactttc ctcaaccaga aattgaagat   141720
ggcaagagtg tttcgacccg ggtggctgag aggcagtgat gtatcagatc tctcccctct   141780
ctacccagag ccctggccag attgtacctg gtggtgctgg cagccggccc tcttccggcc   141840
cctatttctg ctcaccctgt taccagagag cctgggggtc tggatcctat ccggcccgt   141900 cagggtagat taccagatga gtggctcttt tgccccagtg cctttcctgt gctataaata   141960
agccccgtgt ttattttcta atgttattga aatgagcact tgggattggg gcctcttgac   142020
tagtccggag agcgtccacc cggtgcctgg tgagggccct gtgtggctgg ctgctgtctg   142080
aagctatttg gagtcctccc cctgtgttgt ggatgtggct tcatttcaat agtaagggct   142140
gtatgcagcc ctgtatctgc tgattttcag gtttcagctt tctgccagcc tcactgcctg   142200
cttagaagta aagctgtgtt tctcattaag gggataacag ccacaattga gataattaac   142260
gaaaattgta tattggtggc agcaggtcct ataggatttc caatagtcta cctagtagat   142320
cctgaggggc tttaccttca tctcctccct tctgcctacc ctgtgcccaa tctctgttct   142380
tgttttctgg gtatagtccc agtaatttct ctccatacag ccttgttctt gtcagcagtt   142440
tggtttgatg tactgacaac ttgacccaat gaagatttcg tcaactgcct cttctccaag   142500
gcacagaaga tgcaaggatt tccccccacc accaccacct tcgcaaagta tctcccattt   142560
gctggttgta ccttggatat aagatgaata tccattaata acagatagac gttcccttta   142620
gtactatggc tgcaccatct cagtgggaca gtgctgagac agaatggaaa cgtaacagcc   142680
cagtgcaatg tcttatatgc tatgtggttg tctaggaact aggaagtgtt ccgaattagg   142740
atttcctcag gagtggtttc ggagaaggca atggcacccc actccagtac tcttgcctgg   142800
agaatcccag gggcagggga gcctggtggg ctgccgtctg tggggtcgca cagagtcgaa   142860
cacgactgaa gcgacttagc agcagcagga gtggtttcta gctccatcag gctttgatga   142920
tgcatcagac atatccagtg agactgagca ggacacagca ttgtctatca gaacttgagc   142980
taaagatcgt tatctactgc tcaggaggga ttattctgat aagtcactcg gtagagaaat   143040
gtttgcatga acaaaccaga acctatagcc tattcatgag cagttacatc taacaaccag   143100
```

```
atttaattca ctttcagaca tggaaccaga agaaagtgaa ttttttactca tgtgttttta   143160 gtctattgac tcctaaagat cctttttctct taaaaagtaa aaagtctttt gtgatggatt   143220
catatttatt gagcgcttat tatgtgccag atactgttca caattatgaa gacgctgcat   143280
tgaacaaagt gcctgctcct gctaagtgta cattctaaga aggaagacaa ccaaaaaaag   143340
taaatgaata caatttcaaa tggtaaaaaa atgctatgaa aagaacaaag cagaataagg   143400
ggagatggtt agtgacttga gcatgctgct gctgctgctg ctaagtcgct tcagtcgtgt   143460
ctgactctgt gcaactccat agacggcagc ccaccaggct ccaccgtccc tgggatcctc   143520
caggcaagaa cactggagtg ggttgccatt tccttctcca atgcgtggaa gtgaaaagtg   143580
aaagtgaagt cgctcagtcg tgtccgacta gtagtgaccc tgtggactgc agcctaccag   143640
gctcctccgt ccatgagatt ttctaggcaa gagtactgga gtggcttggc attgccttct   143700
ccatgaggag atatttaaga tgagttggtc agaagtggca tttaaacaca gatctcagtg   143760
ttgaggagtg gagacagggg gatgagctag tataaagtcc ctcagatagg aaaaacctca   143820
gcttgtttta agaacagcag gaacccctgt gtggctgcag tgtattgggt atggagcgca   143880
gggtagagat gatgccagga aaagtaagtt aaggccaaat tgtgttggga tcatgcagga   143940
cagaagggtc ctggattttt attgtgagtg agatgggaag acactggaag gttttaagca   144000
ggggattggc atccgaatgg gattttttgtt taaagagtca tttcagctgt tatgtgaaga   144060
acaagaatgg aagaaaggaa atagagaggc tgcgttacag agagagatgg cagaggctta   144120
actagactag gatggtagca acagagaaag tgaggagttc cattgggaac agaatctgtt   144180
ggacttactc acgatttggt tataggagat gaaaatagga ttcacagcta agtactaggt   144240
ttttgttgta accgagtgac acagttcagt gaagtagagc cgactgggca gggtaaggac   144300
agagaaatgt gagagggat atcaagagct ccactttgga tgggttaagt ttgagatgtc   144360
ttttggtcat ctagtggtac tgctatttaa gcagttagat atctagagct taaggggaaa   144420
gttaaaactg aatatatagg tgggatgtaa aaccacagga tagatgagac tacccagaga   144480
gtcagaatat gtagagacaa agaggactgt ggcctcattt acggggagag aagaaaagag   144540
gaaccagaaa aggagattga ggcattgcca gtgagttagg aagaaaacca ggaagagatc   144600
tgcatgacag actgtgatga attagagata cacattgtaa accctgaagc aatggctaaa   144660
aacagtttaa aaggaagcac agctaataag acaatattgg agatagagta tgataaaaaa   144720
tattcagtca gaaagaatgg attgaagaaa aaagtaaact aagaatagac gggacacaaa   144780
aaagtaggag actagactta aactctaaca tgttaataat gacattaaat gtaaatgatc   144840
taaatgttat aattaaagga aagagacttt cattctgaat taaacatcaa gggcaatcat   144900
atgctatctc tgagtaaagc actataaaat acagttgaag taaaagagta gaagaaatta   144960
tactagacaa atatgaatca caaggaactg gaagtgattt tatcagtaaa ggacaaaata   145020
aacttcaaca caggaacatt tccagggaga aagaggaata attcataatg ttaaaggtgt   145080
cagttcatta agaagacata acaggtaatt ctaagtaagg taggcactaa ataacaacac   145140
ttaaaaatat atacagcaaa attgacaact gaaaataaaa tagaaaaatc cacagttata   145200
tttggatgtc tcagcactcc cctcttagta attgatagaa caagtggatg gaaaaatcag   145260
aaagagagag atgactggat aatgctgtca accgctttgg cctagttgac agctctgaa   145320 cacttcaccc accaataact aagcagatat tcttctcagg tacacagaca atattcagca   145380
cctgtgtgtg gcaccataaa aagtctccgt tttagaggaa atgaaaatac aagtatgttc   145440
tctgatcaca atggaattaa atcaataact gatatctggg ggaaatccct aatagaaatt   145500
```

```
aaataacata tttctaaatg catgggttaa taaagacaca aagcaaatta gaatgtaact   145560
ttaggtgaat gaaaatgtgt ctaaatgtgt caggtggagt gctcagagat ctgttcttga   145620
agggctagtg ttagaaaagc agaaaaaact aaaactaatt atgtaagctg ctactataaa   145680
aaaattgaaa acagcaaatt aaatacaaag taagtggaag gaagaataaa gacaagcttg   145740
gaaataaaca gaagatggac aaacaatgga gaagaatcaa ctaaacaaaa cctggttctt   145800
tgaaaagacc aacaaatact ttagactgtt ccagggggaa aaaaaagagt atataaattt   145860
accagtatca taaatcaaac ggggagcttt ggtacagatt ctaaaaatat tagaagtgaa   145920
atacatgaga aaactttata ctgataaaat ctacaacata gatgaagtag ttgcaaactt   145980
tgaaagacac aaagtgataa aaactacctc aagaagaaat agaaaaatct aaatagccat   146040
atccactaaa gcagtcaaat ttgtaattta aaacttcaca caaagaaaaa cctaagtcca   146100
catagtctac tgacatatca aataattaag aaacgacacc aatcttacac aaactctttt   146160
cagaaaatag aagacaaaga gatgggtccc agctcatttt atgtggccat tattaccctg   146220
ttatcaaaac cagacaaaaa tcttacaaga aaagaaaact gcagacttaa agccctgctg   146280
agcatagaca caaaggtctt tttaaaaatt agcaagccaa atcaacatac aaaaaagata   146340
atacatgact aaagaatatg gaaggaaagt tatgaccaac ctagatagta tgtatattca   146400
aaagcagaga cattactttg ccaacaaagg tccgtctagt caaggctatg gttttcctg    146460
tggtcatgta tggatgtgag ggttggactg tgaagaaggc tgagtgccaa agaattggtg   146520
cttttgaact gtggtgttgg agaagactct tgagagtccc ttggactgca aggagatcca   146580
accagtccat tctgaaggac atcagccctg ggatttcttt ggaaggaatg atgctgaagc   146640
tgaaactcca gtactttggc cacctcatgc gaagagttga ctcattggaa aagactctga   146700
tgctgggagg gattgggggc aggaggagaa ggggacgaca gaggatgaga tggctggatg   146760
gcatcactga ctcaatggac gtgagtctca gtgaactccg ggagttggtg atggacaggg   146820
aggcctggca tgctgcgatt catggggtcg caaagagtcg acacgactg agtgactgat    146880
ctgatctgat ctgatctgaa agaatatgaa gtttgaaaat gtattttata tttgaaaatg   146940
taattcacaa tagcaataga ataaaggaga atagtcatat gattatctca gtagttttta   147000
aaaaaaaaaa aaaaaacaga aaacatacat ccacacgaag acttgtatac agatgctctc   147060
ggcaggtttg ttcatgatag ccaaaacctg gaaaaaactc aaaggttaaa cagcagatga   147120
gtgcatagat aaattgtggt atatccatac aatggaatac atctaggcaa taaagataat   147180
aaactactga gacacacaca aggatgtgtt tccaaaatag gtgagcaaat aagccggacg   147240
tgaaagagtg catacttcac atacatagct tctatacata cagggattcc ctggtggtcc   147300
agggaaaggt gaggttcacc ctcaactgtt cagtcttacg cagtagacag gacccttaat   147360
ggcttctctc ctgtattagt ttgcctggga tgaggctcaa gggaacttt gggagtgagg    147420
agaaggtttt atattttgat cctggtgatg gttacatata tatatatata tatatatata   147480
tatatatata tatatttgtc taaactcatc caactctaca tgtaaagttg gtgcgttctt   147540
atctaagtaa tacctcaata aagatgatta ttttttcagt gatagttaaa aactgtcatc   147600
tttcacagtt cctttgcttt gtcatggacc agcatcccct ttccctcctt tacctggagg   147660
tttgcttagg gcctcagggt ccaagctgcc tccagttctg tttagtgttt tctatcgtgt   147720
tttgacatgg aatgcagatt tgccagccat ccagctgata tttatcaagt gcttgctgta   147780
atactctacc aaatattgca gataaacaat gaagccgttt ctgccttata atcaaactaa   147840
cacaggagat aagtccctaa tagccctgtc tactctgtaa gactgaacag tggagggtga   147900
```

```
atgcacgcat tccctgctgt ggaaggagca tgtgatcgct tctgacttgg tgaaggggtg   147960
agacttgagg tgtactttgg agaattcatt ggtagagaca ggcactgtgt ggatagggt   148020
gtgctgggag gttgggcagt cactttgacc tgagggggt gaaaggaaac aagaagatga   148080
ggaagtgtac tgatacccta gatttgtagg agcactaact cgaggttggg actttacaaa   148140
ttatagagct ggataggggt ttagggctag acaaagagc taaaatgttt gtgggcagtg   148200
tgaaggcttt gcagatgatt gttctggttg ggagcgtgat cagagctagt cttaggcact   148260
cccactttgg catcagcaca gatgagcggg tggagcagag agggaccagg aatgggacgt   148320
gaccacttag cagtagccta ggtgataagt gacaaggaac cgagcccagt ggctgctgga   148380
ctcatgtggg agcttgctgg acctgttgag atgctttggg atatgaagtt gagaagagca   148440
gtcacttcac ccatttaaca cataccagcc agtcttcttg ttacagacta aattatatcc   148500
tccgtaaaac tcatatatag aagccccaac ccccagtgtg acgggatgag gagatagggc   148560
ctatgtagag gtagtcaagt ttaagtgaga tcataagggt gaggtcttaa ttcattagga   148620
ctgatatcct cagaagaaaa ggaagaaata gcagagctct gtctctgcat gagcaaagac   148680
cacgtaagga cacagtggga aggtggccgt ctacaagcta gggagagagg cctcaccaga   148740
aaccagatct gcagacacac tggtcggagc ttctagcttc ctgcagctgt gagacaataa   148800
atatctgtaa tttaagccac ccagtgtgtg ctcttctgtt acaacagccc agacagacca   148860
atgcactgct caccaccaga ttcctcacca cccgccttcc caattcccat aaatagaata   148920
ttgagggttc ctggtgcttt atattctgat gacatacttt tgtgaaacag tacccccaatc   148980
tctggcttcc ttctcttagc cgttcgggta caagtcaacc ctgctggccc ttcccaaccg   149040
tcagcgtgtg taattcctcc tgtctctaca gctcttaatt atttccaagt attttaactc   149100
gtttggattt cataaccact tgtctcactt cctatgacat aagcaggcaa gagttggttt   149160
gaccccattt tacagatgaa gaaattgaaa atcgggattt tcgtggcttg tctaagataa   149220
ccaggaggag ttgcaaagtc agcccattaa atccagctct ctcacttcac cacacagctt   149280
cctggcctgt gcttttctat gactttgtct ggagagagct ttctgttcaa acctgtcttg   149340
gagtggagat gtgggctgcc tttgggcttc cttcttccct tccttccttt gtcctcccag   149400
catgcacaca cacacacaca cacacacata aacacacaca tttattttcg ttctctctcc   149460
atagtgtagc ttggccttaa tgtcatagga acaaggagct cctccttttc ccgcagagcc   149520
taaacatgac agatcccctg tgggtagagg acaaagaagg gatgggcaag gggcttacga   149580
tgcaaccaaa agagaaacct cggaaggcgt agcaagaaca ctgtagcccc tgggctgtct   149640
gaaccgcatc ctggccaggg ctctgggggg catctcctgc gggccccaca gtgggtttgc   149700
tcccagctaa cagttaaggc agcaccttaa cacatggtat gcacatggtc ataaaccgaa   149760
gctcctttcg gaagtttgcc cttcctcaag gctgttggtc tgtgttgggc taaaaaaga   149820
aaatctgttt ggaatcacag aattcctggg aaaatgtcaa ctctcacacc ccattgtctt   149880
tggagctggc atgcatcttc tcacttctga gccctgtttt gaggggcggg gctgtttgcg   149940
gagggcctat tgttcctgag cagctgagca tgcaagtctg ggcctgtgtg tgtgtgtgga   150000
gaaagaccac cactaccgta tcaccccca ccagccgaat caaggatttc tgctgaatca   150060
cagagcagcc cgcttgtggc gccctgaggt tggcaactgt tcttgtagca agacctggga   150120
caatgggatt ggtgagaaag attcactggt ggttgaggca gagcagaggt ggggaaggaa   150180
ggtttagagc atgaggggttg tcgagggatg acatggggaa aagcaggctt tgagcccaag   150240
gataaatggg aaaacctctg agatgagcac tctcagatta caacacctag ccatctcgag   150300
```

```
gagctggcct catgccaccc aaaccccaag aacactaaag aggttaggct tcctgtcctg    150360
accttggctc attggggatg catatgaccc ctgaaggaac aggatggaca gagtccacag    150420
acaagcggag gctgtgagtt cacaccaggc tcatctctag ccttcctctt cctatcctga    150480
accaaaaaca gagcctctcc gcattcctac cttcccattc attctcccag tgaattgcag    150540
ttactcagtg tactaatttt ctgaaggatt cattcagaaa cagaattggc ctgtcttttc    150600
ttggcacttg gaaggcagct ggggcagtca gacagataca taagatacta ttataaacag    150660
ttctgtggga gcatggagcc gcaaccactg gcctgggggt ggaagttggg acggggcata    150720
gagttaagga agaacttcac gtagcacatt cttattagga ggaagccaca gaggatgacc    150780
aggagtcctc ctggtagagt gggctggtga cagggcgcag gcattctaag gaaacagatg    150840
gcaagtctac cactgtagcc aagtgaaagg ccccagatgg tttggggaag caatgagtgg    150900
tcctggcacc cagacaggga agggctgagc cacagctgat gttcaaggaa gccctgctga    150960
caggggagtg tcctcccag cgatgctcct tggaggcaca catcccagga atgggttact    151020
tgagtcccca gggaggacca gatgacccgg cagccatcct gcccttggt gggagcactc    151080 atctggactc cagatactgt tggggttgct aagcaaggat ttcaggcagg cggcttccca    151140
tgcacaagaa atttctccct ctgcttccat tcccaccttg ggacttggca gcgacttggt    151200
gtggagagtc caagagctgc catgaccctg tcagatggca aggtcactt ttaaaaacaa    151260 gttcctagtt aaagtcaacc taaagccatc tgggtctata gtgaatgaaa acttaccct a    151320 gaggtacggt tgcagaaaag gggacccctt ccagggccca agagtgggct cttgtctaac    151380
actcggaaat gaactgtcca aggagacaca tgtgctacca aagcaagaga cttgggacgg    151440
ggcacccagg tggagaatgg cagggtaagg gaacccagga gaacggctct gccatgcagc    151500
tcagtctcgg gttttatggt gacggggtta gtttccaggt tgtctttggc caatcgttct    151560
gactcaggtc cttcctggtg gcacctgcat tgctcagcca agctggatgc cagcgagaag    151620
gactctgggc ggtggcggga caggtggcag ctccttttgg cctttccaga actcttgcag    151680
ttggtgatgg cttgttagtt ccatgttcct tactaggacc tcctgtcgta acgtaactct    151740
cacagatgat tcctagccag gatgggtggt ttcagtcaga gtgcttcccc taacggaacc    151800
aaatctgaga tgtggctcca ggaaagcagc atttacatag tcagagaaga tgaaaaagag    151860
tttcatgtcg gactcagagc tggtagccgg agggtgatgt ctttctcccg ggaataatca    151920
tagcccttca tgtattgcca catcagctta caaagcccag gcataggcca tctcacgcat    151980
acctccccat gaactgggaa actgggcaga gacaggcttc ttcccctcct tcagatgtga    152040
gagttgatgg tcaggcaaac aaggatgcct ccccttcagc ttacataggg gtccctggga    152100
gactaactgc ttgagtcacc tttaggctgg aaagcaagga agcacctctt gcatagcaaa    152160
atccaggcct ccagcttggc tttataatta gtatattagt gctttgcttt aaaaaatccc    152220
caggccttac ctcctgcaag ctgtctcagc cactaagcgt tagagctggg acagagacct    152280
gcctctcctg gaagcctatc ctgcaccatt tgtcccaagc agccaggtct ccctaccctg    152340
acctccaggc cctagctggc ccctcgcttt cagaacagac cccggaaacc cagatggtac    152400
cagtgatatc gaggggccgt gatgagcgcg ctggagacgc aggggcggcc cctgatttcc    152460
ctccactgct tgtctgccgt ggaggcaggt ccttt gggat gactgggggg ggggtgctcc    152520
agcccctcgc aggccatgcg cccctctttg tgcaggagcc ctggccggcc acctgttgtt    152580
aatctagccc tggtaatcca ttctgtactg tgtcagcagt tcaaaagggc attgttagta    152640
ttttttgccg acttcaatta acgtgagatt tcagaggccc ctctgatcac atttcatctg    152700
```

```
tcacaagtta ggaacaaaac agacaggttc cagttgaggg gaggaaggag aaggagttta   152760
ttgcaaacaa caaccaagcg gacagtgtgg gccgtgccca gacaagggcg ctctgcgaac   152820
gcgcagcggc gcccacgctc cacgcggccc cacgcctgga ccccgacgcc ccctcctcat   152880
caacagtcca gcagtcctcc cctccccca aagatgtacg tgcaataact tactttaaaa    152940
ggcaagaact ttttttttta atattttgct ataatgtagt tacatggtgg tataggcagt   153000
aaaactttat ggaaccgact tccttttttt atacattttt tttctgaatt tttaatgtct   153060
ttttcatata tacttttaat attccacccc aggccattaa gctaaaggaa aagttgcatt   153120
tatacagggt tacaatatct tacaaggaga acagtcatta ttgattgagg ttcatgttcc   153180
ttccagcact cagctctctt ttcaacccac tgcacaccaa acagactatt agacattgaa   153240
aactgtcctt caaaatcagt agtataaagg cctagctctg tgtgtgtaag tgcagggaa    153300 gaagggacag ggcagggcag gttaatgttt ggttgactgg gacaccttc ctcccccca     153360 gcatctttac agacatcacg tgggctcccg ggaacttgag gagtggagtt ttccttgtct   153420
tcccagtttt ctcttttgtg gtcatggatt attatcctgg gggcccgttt gcccagccat   153480
cctcagtccc caccaggccg tcaagcgac cggaagcccc agaactgtcc agcccagggg    153540
gagaaaagcc gcagaagcag gattcatggt cgtttgcatg gaggagttcc tctcgtcgac   153600
ccagccgaaa gacggcagag gggacactgg cgctgggccc gatgtggccg cggccacgtg   153660
tactagggac ccacctcacg cttgctaccg ccacccctg gcagtgtctt tgaaccaacc    153720
tggccgccat gcttcccac gctgggggca tggtagtgag agccgagaat caagtatagt    153780
ggaaagaatt caaggaaagt tccaaagccc gtgtcctcca agtgccgtcg aagactcggg   153840
gacaagcctc tccgtgcgtc cccggagccc cctctcccca cgctgccctg ggagcagcga   153900
cggcatctga gggtggtagc agcaccgtag tgtcaagcct tggccgccga gactggttcc   153960
cagcaggatt cgggggggctg gcagcgtgag gaggctgccc gggggcctgc cagccaccca   154020
ttatttccgg ttttgtgtgg ccatctctgt tgagattta ggcaaagagc aaaggaaacc    154080 ccacctctt tagcttattg gcttaacagt gaccaccgga gccatccact ctcccctgta    154140
cctgccttca tgagaccgcg ctcctgagga tgccgccagc ccagagagtc cacccaagc    154200 ttgctttagt catcacagga gaggctgcgg gatacctccc accccagcag ctgagaaggc   154260
agaaggccta ggcccagccc cccaccctgg ggagctccac gcagcatcag tcatcagagc   154320
ccctctctta gctctgcctc aagtgaaatg tggctcagga tgatgacctt ccccactggg   154380
gactggggtc atctccgttg tgaagggatt gggcaggcta gaagttttct gatcccttcc    154440
cgctcagcga ttctgtgatt gttggagtgt caggcaggcc ctagggtctg ggacaggcca   154500
agggcaggcc taggggcagg cagctgcccg aaggagatg cagaggtgtt tcaggccgac    154560
attttaatcc taaatactta gctgcgttgg tgggacgggc ggtcagcgcc aaagagcctt   154620
cttctatcgg aagattttc ttctcaaggt ttgggtgga atttgcctga ctgaggtctg     154680
gcccaggtgg aaagcagaca cacagcggaa ctgatcgcca gaagtcccctt ccagaaggtt   154740 ccacttaaga gccgtgtctc tcccttccct cccctcggt gtctatcctg ttctctctc     154800 tctgtctgat tctcacccag gtgagaacat acctcccagg tctttccagc catgatggca   154860
tttaaggagg aactggggg actgtctcca tcctgaagcc atttcttcct tccttttcct    154920
agattttggg agtcttgagt tgtttcagcc aagcttagaa ctagaaaagc cttcctaaga   154980
gttattccca gatcctcaaa catagaaaac acttaaagct aagtctccaa gaacattcaa   155040
ttcagtgtcc aagatgcttt tcactttgag aagatcaact ttagagctac gattcccaaa   155100
```

```
gaggtctgac tcttactagg gggaggttga ggccagctcc ttccatagtc ctgtttctgg   155160
agcacatgag gacttgagac acagctggag atggccacgt ccccaaaaac ctaagcaggt   155220
caaaggggga gggtctcacc cctccccacc cacccaagag gctgtgctga gtccagtccc   155280
ctgggcctgg tagacctagc tctcctcact gacaggattg gggtagaagg gataaaaagc   155340
agacccttct cctcggggat acctgcaagg gggcctccca gcgctcaaaa ggccggcctt   155400
ggaggatggc tacccatgc cccgagctta gctgacccct gggccctgga gctgaaactc   155460
aagctgcagg ctgcatgtca gacggaaatg cagccccct gagaaggagg cccttcctg   155520 caggcaggga gattggcttc cagaaagcac tgtgtccaga acagagcaag cgaccccaag   155580
gagctcagcc ccacatgagc cctctggagg ccagaacaag ggaccggggt cacccatgcc   155640
acagggcaga attgccaggg caggcgctct ctgccctacg cccagaggac tgcacagaag   155700
gctctgggca ggtgtgatgc aggaggccgc taaccgggaa ggctgtctga ggccgcgtgg   155760
gggccgacct ggtgcccgga ggccgggtga gtgtgccctc gtcgtctgcc agaccccaca   155820
acccgctctg gaccctctgg caccgtgccc ccaggcccta gcggctgtgt caaggtgcga   155880
gtccttctgc atcaggacac tggcccaaca gctccagcaa gtgaccagga tcttcagatt   155940
ccacctggag gggccagact ggacagggta caaagctacc cagacctgcc ccctgccacc   156000
atcatcctgc ctgaggtggg gcgtcaaggt ggccggagag ccgacgtgtg tgcacgagcc   156060
cctgcctccc caggacgcct ccctgcagcc ctctcggctc ctagaagcgt gcttccagca   156120
ccgtggggcc gtgggcagcg ggtctccttc cctgcactgt tcacccagat ccggagcctc   156180
agggtccaag ggggccagtg tggctgggtg acggcgggct ccttcggctc cagctcctct   156240
ctctctgccc tgtccctccg ggtgcgtcca gcacagggga cagtcagcag gacgggggct   156300
cctcacgtcc agggtaaagg cgaggtgggt gccttggatc taggaggttg gagtccatgg   156360
gctttgaggg agagcacagg agatgggatg gcagaggctg actggcagg gcatctgttc   156420 tccagacacg gtcaccgggc tggtgatcgg ggaccacaca gcagagggaa ggacggactt   156480
tgacggaacc gtagccacag ctggtccagg tgggaatcta gcctcaactc aatggtcaaa   156540
ccgggcaggg cggaggagca ggagtgggga gaaagggtct tcagcttata atggatgcaa   156600
agctgcaaaa ctcgtgccac ctggctgcct ccactgcctc tggccgggag cggggcacc    156660 tggcctcggt gccgctgcc cccttccctc cccacagtcc ccgggggcct cagacttggg   156720
gcggctgaaa gtgctgaggg tcaggctcct gggcccaggc caggtgccta agaggggagt   156780
tgagtggggg gcccggggggc ctgggagca tgggcatggc cagtgccaca gggcagggga   156840
gggcgcaggg atgggcggg gtggccctgt catgtggccc aggagatggc cgcgctgtgc   156900
tccttggcct tcatgcggag ggccgcgatg ctcgaagtct tgcggtccgg ctccccgttg   156960
agctcatagc cgttgaggcc cgggctgagg cccgcagctc caaacaggct gcccatgtgc   157020
gtctggccca cgtggctgcc agccccgag acgctcagga agtcggtgac gccgctggcc   157080
ccggagccgg gggggtgggc gtgaggggac atgcaggcgg gcaccgggtc acagggcacc   157140
acacaggccg gcacgggcga ggcggcccca ttgttgccga tccaggacgg gttctgaatc   157200
tggggagagg ggagggagac gcgtcacagg ctggctggac acagggtgc tttcctgtcc   157260 cacacggggg acctctcttc acttacaaac ccatcctgat gataaaacca ttcctgagtg   157320
tttacctggg aggctttcca aacctgcctg gccacctagc cccctaggag cctcggggtt   157380
ttatgctctg gttcctccgt tcccaggtcc aggagagcag tggacagaaa ctccgttta    157440 aggactgaac tccgaattcc atcaagagtc cagtgaaagg gtcgtcctgg ggcacagctc   157500
```

```
accagctgag ggcagcccct gattctgttt atttatttga ccacaccact tgcagatctt    157560
agttccctga ccagggatcg aacctgtgcc ccctgcggtc agagtcctct tcattggacc    157620
gccagggaat tcctggcagc cccggatttt agacacagag gcagactctg tctctccatc    157680 catgaccca tttagggtca gcacctgggc ctcaccctgc tccggctcct ccccaggccc    157740
agcacgccct cgtgacttga tccatgggag gggacacgag ctcagagagc tctggcatgg    157800
caacgtgggc tccgaggctg tccactctga gagtggacgt cgggggggcc tcaattctct    157860
cagaagccaa ggtcagtagt ggaggtccta ggggccggtg cccttgaggc ttcagaagta    157920
actcagggtc tgaaagggct gccttgagag gtggtaagtg gacagataga gccaggcggg    157980
atgcccacag gctctaggct ggggcagaga caggtggagg aggtggaagg tgctcgggca    158040
gcgggtgaag ggttgaactg gacactttgt cttgtatctg cacggctaaa atcctttccc    158100
cctccccagc ttccagctct agaccccact ttgccccagc atttatgtgg aggcagaact    158160
ggggactcag ccagaaatgc atctctcctg ggtgatggga ggcaggggg ttggtgggca    158220 ggatgggctg tgaggagatg gtgcacctct cggccacgtg aaagggcttc tcagtggtcc    158280
tggagcagca tctgccggcc tgcccccctgc ccccagcgtt tggagtacat tcagagaagt    158340
ctgtaataaa aggagtgaca aggcggccat gcccccagat gccatggtga ctgcagtgac    158400
aacaagaact gcttgcaggt tcgggtgatg gggacccct ctctcgaaag gcctagggga    158460
tgtggtgtgt ggtgctgcat ggaaaaaatg agcatgagcc cctctggtgt gtgagctcgg    158520
gcagcagagg tcaaggccag gggagtccggg ctggaggtcc atcctcccag ggacagaggg    158580
aggctggctg gggggacgga gagaggagag aaagatatgg gcgggcccag gcttggagca    158640
gaaggcggag gccacagcac aaggaggcct gagaggaagg aaccggctgc ctttgcaggg    158700
caggttgagg ggcgtcagga tggtactcag ccccaaatgc acctctccaa gggtcctggc    158760
tgcctgactt cacctacatc gcttcccgtc ccttgacatc ccactgagga cccaagtggc    158820
accaggaagg ggactgaagg acagccgtag aagaagatgc tctggaaggg atgggaagaa    158880
atgggccaga tgcctgggag agccacagac atacgaagca accttcctaa aaccatgtaa    158940
ttcacaaagc acttttgcac aatctaacgt agaccttcca acaaccttgt gaaagagctg    159000
aggcaggtgt ttttttggc cacatcgtgt gggatgtggg atcttagttc cccgactagg    159060
ggttgaacct gaggccccc gcccatggaa acacagagtc ttaaccactg gccagggaag    159120
tcctgaggca ggttctttta aaagacccaa ttcctaggtg aagaaacttg aggctcagac    159180
atgtgacttg cctgaaggga gaaagctctg gagctgggat gacagcctaa atcctgggtc    159240
tgagaatccc acgttcattc cagccttgcc tcactcacgt cctcgaactt caggaacccc    159300
ttcttctagg aaaacactctg ggtggctccc ggtggcctgg agggccctg gccttcagca    159360 ttcctcggtt ccgatgcccg tcaccgaagt ggccgaagga aaagtcattc tcaagcttct    159420 ccccagtct cccttccct aaagtccagc caagcctggg tcaacgctta tgggggcag    159480 agagaattct gggcctccca catcctggag acacaagtgc actcctggaa cgggcctgaa    159540
gcggggactt agagccccga gctctctctc caggaaggt gttcctccta agggcccag    159600 agcaggcagc tgggggcagg gactcacctg ggcatagttt tccgctcggg tgaggagggg    159660
cagctcgtag gctgtggaga agtgggtccg aacctgctgc atttgcccga agcgttccct    159720
cttcctccac ttggccctcc ggttctggaa ccagacctgc aggacagagc agttgtcgcc    159780
agggtcaggc ccggagctgg ggcccccgtg ttcgaggcag cgccaacctt gccctcgagc    159840
ccctctggct gtagttataa ggtcaagact gtggggctac agattacaca tctgccttgg    159900
```

```
tctccgtgct caagagctga taatctggaa ggatcgacgc tgagagccgg gaaggcagtt   159960
cacaccccag tcgtaggcgt gacttcgggc caataggttc cttttctga  acttcagaac   160020 ccagagcagg caagtgtcac aagcacacgg aacacgtcac cagtcatctc agcggtcaaa   160080
taaccagccc tgacatgggg cggcccagtc ctctggggcc acagactacg gcagaatctg   160140
atgacagccg tgaaagcttc accagagagt cattctcctg ggtggccaag tggtaaagaa   160200
cccgcccgcc aatgcaggag atataataag atgccagttc catccctggc caggaagat    160260 cccctggagg agtgcatggc aacccactcc aatgctcttg cctggagagt cccatggaca   160320
gaggagcctg gtgggctaca gtccacgggg tcacagagag tcgacaagaa ctgagcgact   160380
aagcacacac agaggatcac acacgtgtgg ttttccatt  gttttccact tcctgaatcc   160440
cccatgcagc cttttgtgga aagagtctgg accccctggg ttacagcttc tctgggagac   160500
agggctttag ccaggctgtt ggaggacagt cagggacagc tttgtggagg aaggtgggg    160560 gctggaggga cagaagtcca ggctgagttt agaaacggcc cggccacgcc accagctggg   160620
agagtgatgg gagggaagg  atggtggaat cagatggtag gggccctcaa atgccaggtg   160680
ggagggtcac cttggtgttg tgaagagaag ctgctgcaat ctcaggcccc caagagcagc   160740
gtgatgccag ggaggagggg aggcccagct gtcactcagc acggggtgg  cacattggct   160800 tgaccagggt gctctagggg agtgtggtct ctgagtcagg tgtgtatgag ccagggtctt   160860
gtttcatact taggaaaaaa attgagaacc ttccaacaaa agctattggg cttaatggaa   160920
gcttcctttg caaagagcgt ttctggcagg ctgagaac                           160958

<210> SEQ ID NO 2
<211> LENGTH: 85941
<212> TYPE: DNA
<213> ORGANISM: bovine

<400> SEQUENCE: 2
actccttcct cagcctccca gggttttctg ggcaggaggg gaggccaggg cgataaagag     60
aagcccactg gaagcatcta gatatacgac tggactgctt tcttcagggc tgaggagaag   120
cctagaaaaa agtgaggttg ccactgtggt ggggccgcc  cccttgagtc tctgtggact   180
caggtcctac agtgggagac acacagggct ggcaaagggg gcctgggggt gagggcagga   240
gcagagcagg ggtggtggga aaggggggcg gggacagga  gatggaatgc cggcgggcgg   300
ggcggagcgg ggtagagggg cgacctgggt tatctgggaa gacagatgag ctgggggaga   360
ggcagctgag agcgctcggc ctttgggaag ggagtgaaga gggtcaggca gaggggtttc   420
tttgcaggtt aagatggaga tcgtgggagg cggcacggct gtgggagca  ggctgggggg   480 aacagaactg cccacctcca gcccttcct  ccctgggcc  tcaccctgca gatgaggctg   540
gagcttttct gcccagataa ggcttaagct ccattagctt cctggtcttc actctcatca   600
tgcataaact tgggtggtgg cagggtatc  ctcccgggcc ccatctgtgc tcacattcat   660
gggcccccaa ggcttagagc atcctcccat ttctgaccct tggagcctgg ggtgctgaca   720
gctgcgcccc tagatgccct gggctcagg  ctctgcagcc cataggcttg actccactgg   780
gcaaccttgg gcaggagaag ggacccagag gccccagcct tcccttcagt gcgtcacagc   840
agcccaggac caccccgctc ctgggccacc ctggcctgga cccgctcagc acgggcctct   900
ccccaaggaa ccaactgtct tggcggaggc ccctgctaac cgcagcccat ctggggccag   960
ggcggggtgg ctcagggcgg ggaggcctct gccttattgt cttcagacac agctgcgtag  1020
attggaatcc cagacagcac agaagaggcc cctgcagccc cctggagcgg ctccaaactc  1080
```

```
cgggtttctt cccaggaaag gtccatctcg ggggcggggg ggcccgtccc tgtcccacc    1140
gtcactctgt gccaggcacc tggcttccca tcagctgagt atgggccccc aacaaactca    1200
tcagaggcaa gcaggggtt ccatccccac ctccccccat ctccagggca ctgccaagcg    1260
caacccagag gtctgacgca cctgccaatc ccaccaaccc tgctgccttt atacaaagta    1320
aagtctcaga caattaggc acgtgttcct ggtgaggcaa actacaggaa aagcactgga    1380
aagggctgga actcagggtc cctcattcta ttctcagcac ggccacccca tcaccttcc    1440
tgagtcacct ggtcacaggt gatggtttcc tgcctctggg tctcttcctc ctcgatagcg    1500
aatgagagaa cgaggtggtc ctctccagca ctagccttct agaattctgc ggtctcccc    1560
tgagatgata agacaggcag cacatcacag ttcccctttt tgctttggcg gctgggaagc    1620
tcagcattga aatttgcgct cagtgaaatc taggatcctt agcttagcct aggtctttga    1680
cataattacc ttcccatttc atggcactgt tattgttcga ggatgaagat aaatcttta    1740
agtgtaagct gcccccagctc cttttttggaa gtaggcataa atgtgtgtgt gtgtagagag    1800
aacactcctg agctgtactg tggtgcctga agaatgttaa acatgctctg gcgtcatttc    1860
gtgtgtggta ccagaaggat catcctatca atgctaagcg aattctactc ctgggcactt    1920
ctgtccattt gttagggaca cacacacgtg tgtgcacaca cgtgtacatg tgtataccct    1980
acagaaaacg gacagttcat tttgcatcaa cacagcacct acaggaacat cccatagcca    2040
gctgctctct ctccaccgac tccttacgct cctctcaaat ccactggctg agctgaggcc    2100
agaggctggg gttcctgtcc agagtctggg gcaccagaag tctcaggtga cacagtgggt    2160
gtgagaaggt ttctggaacc acagtgaggc ctcagctgcc tgtcttcctt ccccaaacac    2220
tcactgtgag ctggagagga ataaggtggg aagcttgctt tggggaattt atgaataaat    2280
gagctgaccg ttcagagttc cctggtgttt ctggatggct gtgtattcac tggcaactac    2340
cagtctcttt tacactttag ccattttaga tgatctagtt tctggaccat gctattaata    2400
caaatgtctc tgccttgtta aacaaagact ggtgagcctt ttattgacac cgtagggggtt    2460
ccctggtggc tcagatgata caacttggc ctgcaatgct gaagacttgg gttcgatccc    2520
tgggttggga agatcccctg gagaaggaaa ctgactactc actccagtat tcttgcctgg    2580
aagaaccacg gacagagaag cctggcaggc tacagttcaa ggggtctcga agagttggac    2640
acaactgaga gatttttca cttttaggaac actctacttt cctggtagct taggtggtaa    2700
cgaatcctcc tgcagtgtgg gaaacctggg tttgatccct gggttgaaaa aatccactgg    2760
agaagggaat ggctacccac tctagaattc ttgcctggag aattccaccg acagaggatc    2820
ctggcaggct acagtccatg gtgtcacaag agtcaggcgt aactgagcga ctttcacttc    2880
acttcagaat actctgcaga agattcttta gtgaaaaaag gcgagaaggg gcacccttgg    2940
ggtctgctga gtaacagggc tctcagtcct ggcaccgaaa ggaccccagc tgagcttgct    3000
gctttttaa aaagactcct ctttgctctt aagctgttga tttctatagc ccacgggaga    3060
gggaaacact gttatctgca aacacttgat ttgctatttc aacatgattt gggctgggaa    3120
ggcaggccaa acgtggcgtt catttagtgt tacgctgaag cctgagcttt atcttgtcat    3180
ctatggttgg ggtgcttaga ggactttgca tcctctctgg tttttccttt gttacaattt    3240
catgcaggga ggggagacat acctctctgg acaaaggagg tcagttggtc cacatatatt    3300
tattttttgc cttttctgat cttagttcag ccttctctaa ttggtgggaa ttatagtgat    3360
gaagaatcag accgtacctg ccctcatcat attctagtga gatgagacaa acagatgaca    3420
taatttaagc caatcataaa ttctaagata aaatagcaca actggtagaa ggtgacctgg    3480
```

```
tttgtttgtg ttgtattagg ttgagttgtg ttgggttggg ttgagctgta tggggttcca    3540
ctgtggtgca ctgaattgtg ttgggttgtg ctgagctatg tcgggttagg ttgcggggtg    3600
ttgtgttgtg ctgagctacg ttgggttagg ttatggtgtg ttgtgttgtg ctgagctacg    3660
ttgggttagg ttatggtgtg ttgtgttgtg ctgagctatg gtggactctg ctggcctgtg    3720
ctgggattag tgttttggtg gtcgggtgat ggtaggggggc agtagtcatg gtgattggga    3780
agacttctca gaggaggcat actgagctgg gacctgaaag atggaggagg aggcagccag    3840
cttgggcaaa gagaagagtt ggattgtctt ggtttctgcc catgggtgc catggatgtc     3900
ttgtaagttc atcctgtttc ctttctaaga ggtaggcctt ccagagcaga gaccctcat    3960
cgtcatcacc tccttcgcaa gagagcctgg actcacacac cacacagaac tcagaagcat    4020
agctgacggg ctgcctgccc cttccctggg agccccgccc tagcccctgc caaccagagc    4080
atgaagcagg atgggaacgt gaacaaaagc agacctgctc tggttacggc aggggcgcga    4140
ggggcgagct ccttgagctg aggtgaagaa agccctggtg cgcctgggga cgggcaagcg    4200
gccctgtctc gggccactgg cggaagggc cagccccgct ctccccgcct tccctggcac     4260
cctcactgac ctgcacgcgg gcctcggtga ggtcggtcct catggccagc tgctcccgcg    4320
cgtacacatc ggggtagtgg gtcttctgga agaccttctc cagctcctcc aactggtagc    4380
tggtgaaggt ggttctgttc cgccgcttct tgcccttgtt gctctccgag tcggccttct    4440
ccattgggct ggggaggtcg gcgctggccc ggtcctgggg ccccttcacc ccagcttcct    4500
tcacactgag gtagctgctg tccatcccca ccgtgtcaga gtcgggtggc aactctggct    4560
cacccaggga gctctctttg gctgaagggg gaggaaacaa agtcaaaaaa gcaatggctg    4620
aacccagccc gagaggtagg agggacgggg gagccattcc ctgcttttcc cttctcgggg    4680
aagcatggga tgcaaggtcc ggaggcctgg gttctaaggt cattaatgtg ctttgtgacc    4740
ttggctaagt ttcttttccct ctctgagcct cttcgccgtt acgtcagcat gggccccttt    4800
tagcaccgtg tcctgtgact ctgggccagc caatctgact tctataacat ttaccctccg    4860
cccccactga cccagggctc ctccctctag gactcccctt gccagaactt ctcctttggg    4920
tgttgaggat gttgtctcag tccttcggac tcaaaagctc agccagcagc catgtctggc    4980
ccaactggcc ttagggtgag gaggagaggc tcctccttgc ctggcctgat tctgtttggg    5040
gttcagcacc ctgccccctc caggtggggg ctgtttacta aggaaatagg gggtcctccc    5100
cgtgacatgc ccaggatgct gagctgggag gcccagcaga tttacacaaa gctcatggcc    5160
ccggggccca cagccaccgc tgtctagcag aacgggactc tgccggctga ttcctggacg    5220
ctcagagctg gcaaggacca gttatccagt gcaggtcaag gtgaggagac agagggaggg    5280
cagggagggc gagctcatcc ttgttcagat agccccatca gtgccctggg cagacacact    5340
cgccccaggg cggaggttag gggacaggcc ctgcaactgg cctcagggtg tgagtccccc    5400
cccatgtctg actcctgagc tgtgtgcttg gacctttcgc tgagcctctc tgtgcctcag    5460
tttccccctc tatgaaatga gggcacagat acttggatct ccctcacagg gacttccctg    5520
gtggctcaga cggtaaagcg tctgcctaca atgtgggaga cctgggttca atccctgggt    5580
cgggaagatc tcctggagaa ggaaatggca acccactcca gtattcttgc ttggagaatt    5640
cccatggacg gaggagcctg gtgggctaca gtccatgggg tcgcaaagag tcggacacga    5700
ctgagcgact tcactttctt tctttccttc ttttctttca aagggtagct gtgggattaa    5760
aatgtcttac aggtaaagtt gctccctgtt ctggtctaga cttgtgagca gcagaagagt    5820
ctagccctgg aagagtcctc ccagtgggca ggccctccct ggagtccccc agcccaggag    5880
```

```
tgggtgcgga tggggtgcga gtccctctct gagccaaatt ccactgggga ctctgacttt    5940
acttatagag tgaaataaca tacgggataa taagacatgt gtggggagca ttggataaaa    6000
cttttcatgt gtgaaagctc tgatcataac aagcatttgt ggtctgtatg ggcttccacc    6060
attctgactc ttggtctcct cctctgggaa tagatctgag ccccaggtgt taggtgtcag    6120
gacggtgcct ctagccccgg tcccttgatc ctgaccagat cctggggccg aagcttcgga    6180
tccgccctcc tccctggcac tctgtgttta ctggggggctc tcttattgct ggggagctga    6240
gagggacagg ctgcccaagg cggtgaggaa agggagtgga ggtgaatgct cagagtgggc    6300
ctggaagcag cttcaggagg ctgttcctga gggccactgg cagcatgggc gccagcaggc    6360 tgggggggccg gcccttgggc accacggatg acacccatgt gagtccaggc acacgcagac    6420
cgccacggct ttggtgacag cgtcatgcaa actgcagctg gcagctgggc tgagagcttt    6480
cagcaaagat atttatcttc ctggcagaca aatacgtttt gtgttttggt tttttttttt    6540
ttttaaagag aagaaatccc acccagtctc accaaaaata aacatctctg ttatgcaacc    6600
tcctggaggc cagactcggg gagcaggcag tggctgcagc cctgcccct tgtgcccaag    6660 ccctgctgcc cagaccccat cccatgaccc caaggaccct tcccgtatcc tctggcatcc    6720
agcctgggct caggaccacc ccacacagca aaaggggctg ggccgagcag gggaaactcc    6780
atgttataaa tatcaaggga cggtaggga taaactcctt gtgttaattc agggggaaaca    6840 gaagccagag agagtaagaa atgtgccaat agggacaggg tgcagcctct cagctctggg    6900
tcagtccttc tcttctaccc cgtggtcttg gggccttttcc cagggagaga gggaaaacca    6960
gaaggaatcc ccagggcctc acgtaatcaa gaggtatggt ctgcacatca aggaggcaga    7020
gaaccagtcc ccgaggatga gagagtgagg atgtggcccc tgggagaagc ccacccccgc    7080
tgagctggtt ctaggctcac tgcgggtgga gctggctgaa cacccagtcg tccaagtaga    7140
gaagcttccc cacctccatc cacccactga aagggtaggc atgggggggac agcatggtgt    7200 ggggcgcagc atgggagacc ccaggcccaa ggtgcggaga tctgcctcgt cccagctctc    7260
ccgaaatctg cctgtgacct cagaggacgc cttccaagtg ccagagcctc ctgtgccgat    7320
gggagcaggc aagccctgtc cgcagtgggg agtgcaggca ggaatggcat ctcggccctg    7380
tggggcagcc ctcccgcctc agtctccagt gggaccttcc ccttgggacc tggagtgggg    7440
agaggctggg ggcatatctg tccaggcaaa cgtcagctaa ctagaaaggc ttcaagattt    7500
caagacggaa gggattctgg caaaccgagg cctctctggc cctcgaagag ggacgagacc    7560
ttccaaatct caagtcttga ttattcttgc tttaggtggc ttaggcggta aagcgtctgt    7620
ctgtaatgca ggagacccag gttcgatccc tgggttggga agatcccttg gagaaggaaa    7680
tggtagccca ctctagtact cttgcttgga aaatttcatg gatagagcag cctggtaggc    7740
tataggccat ggggttgcaa agagtcggac acgactgagt gacttcactg acttcacttt    7800
aggttctgag gcttggcccc taattgagac agcaaaggaa aattccccaa ggttctgacc    7860
caacccatta gaatgacaag ccaaggtact catccctaaa gtgccaggct gggggcatc    7920 agttcccacc tcctgccacc ctataagcat ctgcacccag tgctgtcact caagctttgg    7980
tgacggagct catcgccccc aggaccactg gaccgtctgt ccaaaggtcc agcctgtgtc    8040
tgattcctgc ggtctggctc attggcatgg gttccaaacc tccatgggcc ttccccaagg    8100
cagccctgcg gacatctgga gatggctacc atgcctctga gtgtcccatc ctcctgaata    8160
aatatagctc tcactgctgt tctgtaggag gccctgagtt taacaggccc gtgtgagaca    8220
ggtgaatgcc agggatggga tgggtggtgg tgctgggctc tgggcaaagc cagcagatca    8280
```

```
ctctccaact agaggatcca gagaggctgg gtagagactt ggcaccatgg cccgagacct    8340
gggcctggtc aggatccagc ttgctccgta aggccctcct caacaagacg gccgctgaaa    8400
acagagggcc tgagactcag gctgactcac tcctgaacaa aggaaaccac tgagctcctt    8460
gctctccctc acctcctcct ctgtccacct gtctggaacg cccctctttt ccagctgacc    8520
tccaaggtcc agtcaagcac cagctcctcc aggaagcctt cccaaactgc ggcaatcata    8580
cagaccccct ccatctagtt gctgcctacg ttttaatcaa accctgaagg tccagcttct    8640
cctcagggaa ccagttccct gagggctgga accttgggcc atttgtccct gctcagccca    8700
ggatggggca ggcaggaggt taccgaggaa tcaatggcca atacaaacat tatcgagctc    8760
tcaccctgtc cagctacctc tgtgtactca ctggcagtac ctacagggta cgtgcagaga    8820
cgtctgctga acaaacacat cctcggagac aatggagaaa gctggtgagg gtgcatgaaa    8880
gagaggcatg cagtgggtag tgcctccatc agaactgaca gctgaaacag gaggaagagg    8940
tgagatcacc gaacgacaag aggggaagag ggcagaccga aaggaggcag gaggaggaag    9000
aacaggcaga cacagatgat gtctccacac agtgagcaag ggggacacgc tgggggaggc    9060
cacgcaggag caccgaatgg gggctctaga attgacgttt ccagaaaccc agtccaggat    9120
ctgccaggaa ccagctctgc atttactgca ctgccacacc aggagacagg aaaggcccca    9180
gctaacccct ttgccgggcg cgccttcttg aggccacatg gcatccgctg ctggcatgaa    9240
gctgaacgac agccctcact aggaccaggc cacctgcctg cccggctggc ttccccacat    9300
cctccctgga gcagccctc atggtctctg gccccatcca gagcgggaag ggaccccctgg    9360
gcgggctttg tcccaggctt tgggggccca agacaatgtc ctcgcgagct gcagcttgcc    9420
ccggaatgtc ttgatctgga aatacatccc agactaccca gaggaatcat gtattgtgca    9480
cagaacgtcg agaatccaga gtgcctgccc ccagggaggg atgcacaccc ttcagagact    9540
cccatgacca cttctgatga gtgggcggcg tttggttcaa ggcttactgt tcatcaggag    9600
tcacagacac ccttgagcct ctgcctgttc tcctcctggg gaggaggcct cgcctcttct    9660
gagggccaac tggtctgtgc cggacagcct tggctgttgg attttaagag ctacaagaaa    9720
cggggtacct ttcttcattc tcttgtgtgc atgctttgtc actcagtcat gtctgactct    9780
ttgcaaccgc atggactgta gcccaccaga gtcctctgtc catggaattc cctaggcaag    9840
aatactggag tgggttgcca ttccctcctc cagggacctt cccgacccaa ggatctaacc    9900
caagtctcct gcatttctgg tggattcttt actgtccgag ccaccaggga agccccttag    9960
cttctatcta ctcatcctgg ttgaatccta gggtgttgct ccaacctagt ctaactttt    10020
ttttttttga catgaaaggc cttgaaagat ttccaaagtt caccttaatt tttttttttt    10080
tttccatgac tgtgattcca agagaattat ttctgtgatt gtgatttaag gagaatgagc    10140
ttctgaagcc atttggggag aggctgctgg agccctttct gcgtgtatcc ctttcttgtg    10200
cacggatgtg cgccttcggg catgtagcac aagcctgctg ttgtgaatgg gtgtgggcag    10260
catatgtgta gttgcctgcg gataggtctg cggagcgtgc aggcttgtgt ggtcaagggc    10320
aggcacacca gtgggcgtgt gtgccagtgg atgtgtgctg ctgtgtgtgt ctgtgagtga    10380
gcgtgagcct gcagacagcc atgggtgggt ctggacatga gttgtgtgta tgtgtgtgtg    10440
tgtgtgtgtg tgtagctgtg cacacactct gacgtatgga gcgtctgtct aaggggctgg    10500
agtaatttta tcctccatgg ttttgattat atctatttt cctccaaaca tctgctttgt    10560
gggggacaca ccgctcgccc tgttctcggg tgagccagcc tcacgcgccc tgtggcagtg    10620
tgcacagcgc caatgcaatc tccttaaaga aaacaggcca gcgtgaggcc ctttcctgct    10680
```

```
gtttaaaggg caccgagtaa acccatcgct gtccaaacag ttgtgcgggg gtgggggcag    10740
aggttaaagg tgagccatcg atcacgtccc cagcccacct tatctgccac tgggctctgt    10800
cccgagttca gcttggatgg cccgagtttt aggtccaggc ccaataaaat acaccaacgg    10860
gggagcccat gctggggcca cctttcagca gacacacgtg gagcttatct gtgcgtaccg    10920
ggccgagatg gactgtgttc ctgtccggga ggaactgcca ggcggaagag gagaggtaag    10980
ccagggactc agccagccac ccacgaggtg gggtaggcac tcctgccacc aacacacacc    11040
cacccaaggc ccaaacgtgc ttctccaaac aaggcaagtc tgagaaactg tcacacgtca    11100
caggaggctg agacatggag gactaaatgt gatgtggttt cccggacagg gtcctggaac    11160
aacagtaaaa agcacattag cggaaaacta gtgaaatggg aataaagcgt ggcacttagc    11220
aggtagatgg gtaaactatt tgaatggaca tttcacccaa gaagatatac atctggtggt    11280
tcagatggtg aagaatctgc ctgcaatgca ggggacccag gttccatccc tgggttgcaa    11340
agatcccctg gagaagggaa tggctacccc attcccttgc ctggagaatt tcatggacag    11400
aggagcctgg ggggctatcc tgaactcaca ggatcccaaa gagtcagaca aggctgagca    11460
actaacaaat ataataacca gctcaatgta ttaccaatta gagattattt actagggata    11520
ttcatgagat atggctacac accaacagcg atggaaataa aactggatga tacccagaga    11580
tatcaaggaa ctgaagggcg tgaactcgct tccatcagtg gtgggaaaac agcgcagcag    11640
tgccttatac catgaaacac actctcatgg ctcgagccag acatcccact gctaggcatt    11700
cgccctcaag agacaaacac ttcttttcag ggcaaacctg tatgcaaata tttatagtgg    11760
ctttgttcac aatcgcctca aactggaaac agcccaaatg tcctttaaac catggaacag    11820
ccatgcaatg ggatactact cagagataaa aggagaaaac tagtgatgtg aactgtggat    11880
gactctcaaa gacagcatta ctgtctgtaa aagaagccag tctccagagg tatatggtgc    11940
ctggctccac ttgtttattg catgccattc tggggaaggt aaccgactca gtggacgtga    12000
atttgagcaa actccaggag acagtggagg acccaggagc ctgacgggct acagtccatg    12060
aggtcacaaa gagttggaca cgacttagca actgaacaac aaacaaacaa acagtcccag    12120
gacagagagc agatcgctgg tggcctgggg ctgggctggg gtggttttaa ccccaaaggg    12180
ctggtgtatg ggactatccg atcctgtatc ccagctgtga ttgtgagtac acggatctgt    12240
acaggaacgt gttcaaattc ataaaatcac gctcctcagt ttaaattttc agcatgctat    12300
ttaaaaaata aaaatatgc aaactacagg gcttccctgg tggctcaggg gtaaagaatc    12360
tgcctgccag tgcaggagac acgggttcga tccctggtct gggaagatcc cacatgctgt    12420
ggagcagcta agcccatctg tctgtctgtc agttgctcag tcgtgttcaa ctctgcaacc    12480
ccataaactg cagccgacca ggctcctcgg cccatgggt tttccaggca aggacgctgg    12540
agtgggttgc caaactgcaa cgtaactatc gagcctgcgc tcttcgagcc cgggaacctc    12600
aaacgctgag cccacgtcct gcaagtaccg aatccaaggt gcccttgagc ctggactcca    12660
caaacagagg agccaccacg gtgagaagcc cgcacaccgc aacagagaaa agctcgtgca    12720
gtaaggaaga tccggcacag ccaaaaataa ataaaaatat taaaaaaata aaaatatat    12780 aaaactatag agaaaataca aaattgggtt taaatatagt aagaaaaac taagcaggta    12840 aaatgtttgt atgtcttcac ccaaaaatct cacctctagg gatttaaaga cagaattatg    12900
gatagacaca aagaattaac tagagagaaa gttcctcgtg gcattttat atgggaaaat    12960 tgaaaataag caaaatctct attaatagga gattggtcaa ataaaggatg atatttccat    13020
aagtggaaga tccttcctgg tttctttat tctacacact gtttctctct tggtatttaa    13080
```

```
cacatattat tttgtattta tttgttttt ccttcattta ttgtctctct ctcccttcca   13140
taaaacaggg aatatatctg aatatatttg tttggcttag ccttttggtt taatgcctag   13200
tattgcggct ggtatgcaga aggggttcaa taaacactga tgaaaatga aagaaactga    13260
tgtccaagaa tagcatttta ttacctgaaa gttgttcatg ttacagtaag taaaacttat   13320
tttgaaaaaa ggggaggtga ggatgcggtg tctgttctta gaaaattcta gcagtttcca   13380
gaagtaaaga atatcagtat ctgggtttag ttgcttttt gtttctagtc tgacttaatt    13440
ttcttatttg tcctaccata aacaggaatt tctttcatca ttttaaaatg ctatgtgaaa   13500
gcagcagcta gaatcctgaa tggtgccggc tcggtaggtt tgggactggg ctgtgtgatg   13560
ggaggcggag ggaagcgctg cagggaagca gaggaggatg gcagtgatgc ttcagagaaa   13620
ggcccttcc gaggtgggac tagctaccgt cctcacaaac tgggcaccgc ccccacggc     13680
tctgaggcct cgtgggtgct ggagagtccc agagctctgg cttacgttca gacctcaccg   13740
gttcctctgc cctcagatca ccacgctcca ctacaaccgg agacagtgtc taagacgcac   13800
actgctggtc tagggccacc ctgtctaacc cagagctctc cttgttgttc agtcgctaaa   13860
tcgcgcccga ctctttgcaa ctccacggac tgcagcacac caggcttccc tgtccttcac   13920
tagctcccgg agtttgctca aactcatgtc cattgagtca gggatgccac gtaaccatct   13980
catcttctgc cacctccttt ccctcctgcc ctcagtcttt cccagtatca ggggcttttc   14040
caatcaggat ggtcagatag ggtacagggt gctcagttaa attagaattt cagagaaaca   14100
ggagtcactt tttaagtaaa agcatgtccc aaatattgca tgggaaatac ttatgcacta   14160
agtcccctac gaacaaacct tcaagttgca gactttcaaa gatgcgaacg tgcattccct   14220
cagtgtcaga cccgagtgaa actgcagctt ggccctacc atctcctata gctgacgatc     14280
cttccgctct actgtctccc acctcctgtc cctccctcca gccagcaact cttcttgcct   14340
gtgtgctgga ggccagctcc tctatgccag ctgttacact gtgctactgc acttttcaag   14400
gtactgtact ggaagatgaa aaatgtttaa ttttttctgt ttgttttat gtattgatat     14460
tatttgtgtg aaaagtatga taaacctatt tccgtacagt actacatagc cgattgtgct   14520
cgctgggttt ctaggctaac ttgcttggac ttacgaacca agtgaagtta cgaactcgct   14580
ctcggaatgg aactcgtttg tatgtaaggg acacaatgta ctgaacatta ttcattgttt   14640
atttgaactt caaattaaat ggaacatact ggttttgttg ttagattttt atttatgta    14700
tttattttt ttgctaaaac cgccaatgct cgagtcaggc tgactatggc attcaggatt    14760
ccccaggcag gaccggccac tgtcccctc acagacttac gtcttgccac acccgccct    14820
ccacctcgct tccggtcccg ctgacctgcc cgcacgcccc caacacactg ctcgagcggc   14880
ttcaggcttc cccaccttg catccttctc gctgggacgc cctctgccct tcgtgcacct    14940
ggctaactcc tactctccct gggtatcttc ctctgtaagc ttcgtggctt tcctcccac    15000
ccccactaca tacagttatc tatgttctat atgaagacaa gcccaaagaa gaaaactata   15060
atacataaac agaaaaggga aacataattt tttataaaag tcttttgtaa aacctatcac   15120
tgccctgtac atctttccat cctgttctat attcttctgc taatacatca ctttaatgg   15180
ctgcatagta ttccatcgta cagacaaact ctatttcctt tcctcagtcc ttactgttgg   15240
gtatacggat tgttgattgt ttgaaatagg aacaggcctg tgatgaatac ctttatagtt   15300
aagtcccttg acatttttgt ggcagttacc tttgcaaaag ttccaagaac tagaaatact   15360
gagtttggtc acagtcacac cttaagagct ctgataagtg tgtctgctag aaatgtgccc   15420
atttttcag catgcctgcc tgcttcagga caagtaccaa tcattacact gtttataaaa    15480
```

```
agctttgcca gtgtaatgga taaaagtgaa atctcatttg aatttacatt taaaaaaaaa   15540
aaaacaaatt tgggcttccc aggaggctcc ggagaaggca atggcacccc actccagtac   15600
tcttgcctag aaaatcccat ggaaggagga gcctggtagg ctgcagtcca tggggtcgct   15660
agagtcagac atgactgagc gacttcactt tcacttttca cttcatgca ttggagaagg    15720 aaatggcaac ccaatccagt gttcttgcct ggagaatccc agggatgggg aagcctggtg   15780
ggctgccatc tatggggtcg catagagtcg gacacgactg aagcgactta gcagcagcag   15840
cagcaggagg ctcagtggta aagagtccac ctgacaatgc atgtgacatg agttcgatcc   15900
ctgggttggg aagatctcct ggaggacgaa atggcaaccc actccagtac tctagctgaa   15960
aaaagtccca cggacagagg aacctggcag tctagagttc atgaggccac aaagagccgg   16020
acgtgactga ggccgagcgt gctcacacac acacaggcac atattactag tgaagttaac   16080
ctttaatgtg ttgcatttct tcttttgtga attgtttcta ctgagcttcc aaggttcagt   16140 gcaaggtga ctccttcttc ctctctgacc ccagggtcgg gcttctctct taaaggctga    16200
attccccact ctgaagcacg gcggtgtggt gtggcctccc gttcgaccga gagctgttgg   16260
gaatagggct gccctgatgc acttcggggt cctgaactgg gccccggctc cttctgcctt   16320
tggtagcacc aggcagctct gcgtgccctg ctgagggcga caagggcacc cagaggaagg   16380
gggcccagga ccatgaggct gggctccaga gcagggtggg gggctgcgat cccccagcac   16440
acactgctgt ggggtggctg tggcatgggg gtggaccttg gtccttgtgg ggtgatgggg   16500
ctcagagaag ccggccacgg ggcaggtcgt gtaggaccaa gccccatgta gctccagaca   16560
ctgctatggc ctcaggcaag ggttttggct tttctgcttc ttcacgtcag caagccctgc   16620
ctggtctcct gccagggaga ggagaggagg gttacagagg aggtgcagcc ctccccggga   16680
agccaagact gggatgttct cctcacccac agggcaggtt tgtgcgggcc cctgtgtgaa   16740
ggctctaggc accccatcc  tgccagtcag gatcaaggct gcagtagctc acactggcca    16800
ccaggaggca ctgcagtccc aagtaccttc ctcagggcca gaagtgaggc cccagggccc   16860
cgccgcagat gcttctccca gtttggttaa agacccaggc ccctcccgg agggttggcc     16920 aaacaagtgg tgattcagcc ctactatgtg tctctgatat cccagccctc cacacagtgc   16980
tgggtgagga gggtccctgc ccttctccac agagctcttt cctcctccgg ctctgagggt   17040
attcacgttc ttgacttgta tcagtccccg tcttgagcgt cctcattta cagatgggca    17100 aactgaggct cagagagagg gaatccacta aacgtcacca gccactgggc agccggcctg   17160
acccgagttg ctcttattcc ccccaatctc ttccctttgt ggagacctga ggggcatcgc   17220
tggccctccg gatactgaca ggtaagccat gccaggcta cccgaccctg gttttgccaa    17280
gtcggctgtc caggcagctc gtggatttgt tgctggctcc tctgtgggct cttccccagg   17340
gaagcttcag cagtctcggg gactgcaggc tcttcttccc atcactccac actgagggga   17400 ggggttttcct gtgagccaga ggatcgaggg ggctccccag aatcaggagg gaaaaggact  17460
caaccctggg ctctcactac acaccaggag cttcatggtt tactaacatg ctctcactgc   17520
tgctgtttac aacagccatg tgaaatatgc ccatttaca gctgcagaga ctgaggccag    17580
agggcgtaaa ggacttgtct aagaatgcac agctgctgag aggcaggatt tgaacccaa   17640 gcctgggca tcttcctctg ggccctcctg gagtggatac ccagtgtggg gctgggacag    17700
ggcagccagg agacagagtc agggaagaag gggaaaaaaa agtgggagcc acaggaaaat   17760
tcctcctctc tgatgcctct aaatctgccc aacatatcca accttcagtg ctggccctgg   17820
tgaaactgtc ctgatagaac ttcatagaac atctgggacc tccagtgtgg accaaggcct   17880
```

```
tttctcggga ccttgctttc agggtcactc catcccacag tttacattca actaattttt   17940
tcttttcctc ttcctgacac tgggtctgga tttatattca attctctgct aaataccgaa   18000
gtatttaaaa gtaaaaaggc ttatgtctgc gacttacccc caaacagttc tgaaagaaat   18060
aatatgtata tgtgcatctg aatatatatt aatatataca tacagaaaga acacaaaaga   18120
gagtgagggc aataatgcaa atatggtaaa actttaagat atggaggatc ggtgtcaaag   18180
ggatctggga atcctttgta ttctacattt aacttttcct ggtgtctgaa aacatgtcaa   18240
atgaaaagct tttaaaaaga acaagaatgc agacaaatgg gaagaaacca ctttatccag   18300
gaatccaagt tctgaaaccg gcatttgtta cagtttgaaa caggacccag actagagtct   18360
agtaagcaat ctctctgcct ccctctcacc agcaccatcc acaacttcta caaacgggct   18420
tgcacgctga aatcaaaatc acaaggcaga tcaactcaag ggacaaacgt atactccgta   18480
gtcctatgga aaccctcatt tccatccccg gaagcaaccg gagacccat taaaacatgc    18540 ggttcttcta aggccgtagg aggcagtatt ttgttagctg aggtcgagct atccttggga   18600
cttagaagta cttggtactg tttgagccta ttctaatttc agctccctta cagttagtcc   18660
aagcgggtac ggcttccttg cacccaaaga gaagtggtta aaaaggaagc ccgccgacaa   18720
tagctggcac atgcaagtga ccgtgttcat cggtgatgaa cctccacaca gaggaggatt   18780
attcaccctc agaaaggagg gaaattctgg cacctgctac agcacggatg agccttgagg   18840
acatcgtggt gaatgaaaca aagcagtcac aaaaaggcaa atactgcacg attccacgta   18900
cacgagtccc tggagcggag acagaaagta gaacaatggc tgccagcggc cggggcccag   18960
gagggtgcgg agttggtgtt tcacggggac agggtttcgg tttgacaaga tgaaaagagt   19020
tatgcggctg gatggtggtg atggttgcac aacattatga atgctcttca taccgctgga   19080
ccgtacactt aaaaatggtc atgatggtaa atttatttt tacttgtatt ttaaaattct    19140
tttaaaaatt ggagagaaag aaaagaaagt ccactactgg ctagggtccc tgcgggcctt   19200
catccggcct tccttcagtc cccacggtcc tctccgtacc ccagcttagg ccccagattc   19260
ttttctcttc tcttctccct gacactgtgg cttgggttgc gtctattcat tgcactcatt   19320
cgttagttga cttgtttgtt cattcaccaa gcacctcccc agggcctccc tttagacatg   19380
gcctcaccaa agggacagac gacaccacgg cctgacagca agagccctgt gacctgggca   19440
aggcaggctc tatgggagga gtggccggtg ctggctgaaa aggtcaggag aggctttagc   19500
aaggatgtga acttgacctg agtactgaca tctacagagg ccttggcaag gcccggtaac   19560
cacattttat ggcaaaacag gacacccagc tttcagctga actggtccta aattactaag   19620
tgagaagccc caggggccct ccccagggc tggtgacaac aatgagacaa tcatacaatt    19680
gcttgcgttg cagcagttct gacccactca ctgtctcatc tgatctcctc agatccctaa   19740
gaggtccgtg atgaggaaac tgaggtccag agaagcttga cttgctcaag atcacaaagc   19800
gaggaggggc agagctggga tttgaaccca gatggtccga ctccaagcct ggtgtcccgt   19860
ccacggcctc tcacgtgtct cctggacaca ggcaggcagt cttgggggt ggggcgggca    19920 ctggctgact cggtcttgtc tttgagtgac acagttgagc ctgaggagaa atttccatct   19980
cagaggaata acctcaacag agctctgggg tcaccgcgtg ctggttttgg tggtgtagtc   20040
actcagtcgt gtccaactct tgcgacccca tggactgtag cctgcagggc tcctctgtcc   20100
ctgggattct ccaggcaaga atactggagt gggttgccat ttccttctcc aggggatctt   20160
cccgactcag gaatcgaacc cagatctcct gcactgcagg cagattctct actaactgag   20220
ctacaaggga agtccatggg tcaccatgag aagccccatt tatggtctaa cacttggaca   20280
```

```
tcacctggtg ctgttctctg gggtgggctg gggtcatgac ctcagtcagg gactctaact    20340
accctgtga acagccctcc tcatggacac tgaggtttcc cagctcccg cttcctggcc      20400
cagcccaggt ctcatcccca agccctgcct cacgaggctg gagggatcc agagacccag     20460
caggggaagg ggcagcggcc caggctgggt ctactcccag agaaacagaa ggaacctccc    20520
ccattctccc ttcagcccaa aagaagccc cagagctcag gggccaccct gggccacccc     20580
tcctctttca ggcaggatac ggagacccc gagtgatcac atcgcctgtc agtggaagga    20640
ctgtcttctg atttcagatc agctcagtgg tctgcctgcc ccttgtcccc ctctaccttt    20700
acagaaccat gtggccttgg gcacgtcctt atctccttga tccctcagag cctccgtctc    20760
tcctctgctt cagaaaatct gcattcccaa gcatcccctt ggggacactg taataccacc    20820
gttgtattca agggaggcaa gatggagaag ctcagatcct gctctaggtg aaatgaatga    20880
ggagtccttg gagcaggacg gacttgggtt gactcctgaa actgcccctg acttgctgca    20940
tgcattcatt cagcagcatt tctggagcgc tagttatgtg cagggcaaag ctccaggaga    21000
tggaaacaaa gtccaagaaa gcatggcccc tcccttacaa aagccctgct tcatgaagga    21060
ggcagtgatt atggcggtgg aggtggatac ggcaggggca tctcggccag cctgcgcgg    21120
gaagcagtgt ttctggggcc tctccagatc tctaggcagc gatctggttg gagggtctg     21180
tcgaagctgt gtacagctag ctctgtgcat acgatgaaga aatgtcagct ctccccatca    21240
aagaaatggg gaaatttctc agggagattg tttaggaggc ttccaagcca ctcatgcctt    21300
ggcaaagtga ctttggcctc tgtgtgactg ggtttcctca tctgtaaagt aagggggagg    21360
ggacccacct cccagcatgt tgtgggctc tcagtgaggc caagggcgag aaggcacacc     21420
tctgcctgac acccagcacg ctgtctgtca acgggaatcc tccacgggag attaacacac    21480
ttattatttg gagggaagtt aggccagggc gggaggagac cgcagaagag cccctcaagc    21540
tgcagtgtct catcctcccc ctgccccgc cccgcccca ggtatatgct cttcagctca     21600
agtttcccca gctccagctg cccagaacat tccacagacc tccgtcccaa ggagctcccc    21660
ccacccagt cccttccaa tcaaggctca tttccacgta catataacag agaaataaat     21720
ggggtgaaac actgaaacta ttttgtttgt catttgttat agatatttaa aagtgctagc    21780
tgatgttcaa gaaagcccct tccatacata cattttgacc caggctgcaa cttgtagtag    21840
aggcatgaaa ggaggactct aattttaagc gctgcatcga agacagtgtg gcttatgcgc    21900
cagttgacaa aggtcagaga ggctgtgagc tcctttcaaa aacctcgctc ctgcttagac    21960
acttggtaac atctggacga ctctcctatg caggcacacc aatatttaac ggctccagaa    22020
gaatttctc tgtgggggcc ttcgctgtcc tccacccagc ataccaccca aaagctatct    22080
ggggtgggg agtgtcgaga gggatcgttc cagaaatgaa ccgccactcc cactggcgct    22140
gctgtctgct gtcctataga aactaacctt ggtgattcgg ggctatgtca gggccctttc    22200
tgccagagaa acccaaatca catttccagg cccgagtctg ttaccacttc ctctttgtag    22260
atttcctgcc atgccctcct ccaaactctc cttcttcttc tgtgaaagtc acttagtcgt    22320
gtccaactct ttgtgacccc atggactata cagtccatgg aattctccag gccagaatac    22380
tggagtgggt agcctttccc ttttccagga gatcttccca acccggggat caaacccagg    22440
tctcctgcac tgcaggcaga ttcttttacta gctcttcacg agccacaagg gaagcccccg    22500
aactactcct aataattcga ctgctttca caaagcattg ccaagtgtgg atgcatggca    22560
ccctccacca ttagacagtg tcttcatcac aggcagggaa aaagtcttgt caaactctgg    22620
tccgcacatc tggcactcaa aaaataccctg ctgaacaacc aactcaacag atacctgaat    22680
```

```
taaatgaatc tggttaagta actaaatgtc tcagtctgtg gaacgaccac atcggcctag    22740
agagaatgtt tttcccacca aaatcaaggg ttttcttcct ccagatgtgt tcatggtaaa    22800
ctaaacaatc atttacaagc cccaaaagca agaatatgtt ttctcccctt ggacaagaag    22860
ggaaaaatta tggctggatc aattgtgagg ttgccagtta aagttttctg aggttgataa    22920
agatggataa gattattcag ggtttcccag gtggtggtag tggtaaagaa cccacctgcc    22980
aacacaggag acataagaga tgcgggttca ttccctgggt cgggaagatc ctctggaaga    23040
gagtatagca acgcactcca gtattcttgc ctggagaatc ctattgacag agctgcctgg    23100
caggctacgg gtccacagag ttgcagagtc agacacgact gaagagacag cacagtgctt    23160
gtcaggaaaa tgactcatcc catgaaacag tgagaatgca ccttatggag cacaaaagtg    23220
gcttcctgta atcttatccg aggggctgag tcctgggtag ctcattaggt aaacctggcc    23280
ctggatgtcc actcaggcaa ggcctctcca aggcagcccc tgatccctgg cacagaacca    23340
atgccgagcc aacgaggagg ccgttccagg agcggtcatt tcttgcgagt ttaaggaagg    23400
gagcctaaac tccccagcag acatggcttg aggggtctga ggggcctagg actacccttc    23460
tccctccctt gatccctcca gcccccatgc tgggcagaca gccagcttat accctttttt    23520
catcactcat ctgcatttta aaatgctttg tcaaccacac aatatagact cagcaataat    23580
ttgttgattt tcaattttta tgcattcaag tcaaccataa ctgtctgtca aagtttccgg    23640
cctcacctac tcaaagttcc agcaacatcc tattatcaac aataacaact aacatttatt    23700
gagcacttct gctgccgtaa gctctttacc tatatcaccc tcctcaatcc tcacaacatt    23760
ccttcatggt agataggatt catatgccca ctttacagac aaggaaaatt gaggcaagga    23820
ggcaaagagg tcaactcatt tgccgagggg cactcagctg gacaggccca aatctgtttc    23880
caggtcctgg ctatactggc ctcactgaac caaaggcacc tgaagatgca ggcagccggt    23940
gcagcctgac tgtagcatga acacagtttc tataagattc caaggcatta gaagctgcgc    24000
ctgttacttg cctttgggct tccccgaagg ctcagaggat aaagaatcgt ctgccacgca    24060
agagacacag gagacatggg agatgcaagt tcaatcgctg ggcagggaag atcccctgga    24120
ggaggaaatg gcaacccact ccacctggcc gggagaccag gcctgtgttt aaccaactgg    24180 gctgggggt cccgaggcag gatacactgg tctcatgagc gagcccctc tggggctctc    24240 actgctccac tggtagcggc agccaccgt ccgttgcccc ctgccctct ggttacccac    24300 caggggcgcc gaatcctacc tggtccctgg ctgagccact ccctgggcag agcttgggat    24360
gaccagggtt gggtacaggg agcagcagat gcctctgatg aggaggaagc agaaaatctt    24420
caggacattc acgggcccag gagtacagag cagggtgggg tgcatggact tccctccagg    24480
ggctcctccc agccctgtgg ggagagggct ctggggtcat gttatggaag ggagtcctct    24540
ccgatctggt cctcttaggg ggtagtgtga ggaccctaag agcacatcta ccccaaggcc    24600
atatcctcat gggagactca gctgatggac acggggctc ccaagtatgg ccacaggcct    24660
agtcagaggc cagggctggg gcgtgggcac cctcgccact agctctgccc tcccccactt    24720
ctcatccgct ctggctgctg aaaaacaaat gtgtcccaga gccgaatctc tttggcgggt    24780
cagtcgttgg cctggaggtg aggagttgag caggatgact taatgaagtt ccttatattc    24840
tagaactctg gaccttcatc tcaggaggcc atgccacact ggggacattg actagtggta    24900
cagaatagag agcccagaaa taaattctca aatacatggc caatggattt ttgacaaggc    24960
agccaagacc attcaatgga gaagggcag tcttttcaac aaatgatacc gggaaaagtg    25020
gatatccgca tatgaaagaa taaagattga tccttatcct ataccatcta caaaaattaa    25080
```

```
ctcagcgtgg ttcaagacct aaacttaaga gctacaacta taaagctctt agaagaagac   25140
ataaggaaaa tcttcctgcc actggagtta gcaatgattt cttggctatg acaatgaaaa   25200
cacaagcaac caaggaaaaa attgataaat tggatttttt caaaattaaa aaattttgtg   25260
catcaaaagg acactatccg gaaagtgaga agacaacaat agagaaaatg tttgcaaatc   25320
agatatctga caagggatta tcatatatat atatatatat atatatatat atatatatat   25380
agggctccct ggtggctcag atggtaaaga atccacctat aatctaggag accagagttc   25440
gaccectagg tcaaaaaaat gccctggaga agagaatggc aacccagtcc agtattcatg   25500
cctgggaaat tccatgaaca caggagcctg acgggctaca gtccatgggg ttgcaaagag   25560
ttagacatga ctgagcgact aacacacata tatagatata tccagaatat acataaaact   25620
cctacaactc aacagcaaaa gccaagaatg caattcaaaa atgggcaaat agatatttat   25680
ttataaatat ttgccccaaa atgggcaaat aaatcttctt tctccaaaga aagaagttgt   25740
cagaataaag gtcaaagata aataaataaa gattgtcaaa gaataaaggt caacaatggt   25800
ttgacaaaat ggtcaaacac agaaggacaa atattgtgta attcgacatc tatgaggtgc   25860
ctggggtagg aaaattcaga gacagaaagt agaacagagg tttccaggga atggggagag   25920
agggagatgg ggaattattg tttaatgggc ccatttggga tgatgaaagg gttctggaaa   25980
tagtggtgat ggtcacacaa caccacgaat gtacttgatg ccaatgaatt gttcattta    26040
aatccttaaa atggtaaatt ttaagttacg tatatgttac cacgggcttc ccaggtggca   26100
ccagaggtaa agaacctgcc tgccaatgca ggagacgcaa gagatgcggg tttaatccct   26160
gggtggggaa gatcccctgg aggagggcat ggcaacccac tccagtactc ttgcctggag   26220
aatcccatgg acagaggagt ctgacgggct atggtccaca gggttccaaa gatccagaca   26280
tgacttagca cagcacatat tttaccacaa taaaaattat ccctaattaa aataaagatt   26340
tgaatgttga agaggctgc actaagtctg gggacgcagc ctctcactgc actgctcaga    26400
ggcttccagg gggcttccca aagtctgaac ccctcgtcag aaagtgaatg gccccctctg   26460
ctttgcccac gccgttcttc aggctgattc ttgcctctac ccatcatgcc ctcgcaagtc   26520
acacacctgc tctttcccag gcattccacg cactttcctg acctagttct ctctgactct   26580
agagtgctgt ttccagctct tccagctgga gaactcctat tcaacctcca aggcccactt   26640
ccaaatgccc ctacccacta agtcccagtc cattcgcact tttcctgaga accgcgatgt   26700
ttgcacattt agctccccgt gggcaggaat cacctgactc gctgcccagt gttccacacc   26760
caacaacaca gggcacaacc cggcagcagc atgtgtcaga tgtgaagggg agcctttgg    26820
cagcacacct ctcacagccc cgtctatgcc caactccttc tctacagaga gacgggggga   26880
gcccttccat agagtctcct ccgcctttgt tggccgccac ctgtgagagc tgactccaac   26940
ccaggctcag gtctcagtgt ttcttctcat ctgggctgtg agctcaggac ggcatatagg   27000
cccgagcgga ggggggcatc ccctggcggg gggaatctca gaaccctggg gaggggcagg   27060
gctgagtgga ggggggagga cctagggaag agcgtcatca gaagaaccag ggccccaaa    27120
ctcactgcag ggaaggggggg agccctgagg agaggagggt gtgtatgggt gggtgagggg   27180
gagacggccc aggagactgc agccacggtg ctcctctaac tgcaggagcc tgagaggaca   27240
ccaggcctgt gcagaacaga gcaactcaag gtctccttct accacgcttc agaggggtcc   27300
ccgcaggaaa tattttttcgc cagggtagaa gagaactaga agtcgggttc tcacccatgc   27360
ccacgcctcc ttcaaaagga ggaggaaggg aaggaggatg ggaaggttcc ctccctcctc   27420
cctgcctccc tcccttcctc cctacgttcc caaaattcac tgagcgcctg ccctgtacag   27480
```

```
caagccctgc tctaggctct gggaaaacag tttgaaacaa aaccgttttg taagacaaaa   27540
gcctcacaag gtctcacaaa ctccccagga ggcaggtatt tcctcctgtg gtcttcagct   27600
ccaccctgcc ctgatcagag gttctggcac gatcctggaa cctctgggac ttaagatgca   27660
atccctcaca acagttatga ggcaccgatg ccacacctga ccccaacaca gcaggacact   27720
tgaacaggga agaaactagg cccaaggaca cagggtcagg tctagactcg gacctaccgg   27780
ggctccaagc ccatccttga cctcctcccc agccaccgcc accccacccg ccaccactgc   27840
acctccagac aggaggatgg gaggagctct ttggggccat gtttgtaaac ccatgtcatc   27900
tgagatagga tgagctgtgt ttagtcgctc agtcgtgtcc aactctttgt gaccccatag   27960
acttcagcct gccaggctcc tctggctcct ctgtccatgg ggattctcca gacaagaaca   28020
ctggagtggg tagcctttcc ctcctccaag gggatcttcc caacccaggg atcgaaccca   28080
ggtctcctgc attgagggcg aattcttcac catctgaacc accagggaaa ccctggata    28140 tcagggaggc ccacaaaccc aggaaggccc cagtgtttcc tttcttaccc tgaaacctga   28200
tcagaatacc cccctggccc ccaactgcca ccaccattca acataccttc atcatctgca   28260
agatgaaatg agaaggcagc atcccttagt ccagactttg gccaccttgc aggataaccc   28320
tgcaggcata tcagctctct gcatcctcac atttcctccc acagaggcgg gactgcccca   28380
cacagccccc gttttgcaaa cgaagaaata aactaaagag ataagcagac catttcaaaa   28440
acacaggcaa tttccaggga agagccaaca catgaaccca gagctcttga tgtccagaga   28500
agccatggag tggggaagga gaaagcaaag aagcagctac tcagccacca gagaagatcc   28560
aggtggtctg tggcaactct aagccctccc cttacggggt aaagctccac ccacctggga   28620
gcgggctgcc cttctccgcc cagcctctcc agcaccaacc cattaactgc agtgaaccaa   28680
gctactagtc tgtctcccca tcccgacctg aaggcagagg ctgtgtccag ggcctcacag   28740
aatcccccag gaggccggga acagggacag gcaaagtctg gtgaggagct ggaattaggc   28800
atttcagtcc ccttctctgt gaaaactggg catttgggcc aggaggcgtc tggcgtctct   28860
tccaacactg ggcgggacac ccatcccgac accaggaccc atcatgttgg agggttgact   28920
tccgggcctc aaccaaggtc cctgacctgg caggtggtca gcctcagagg aggaaataag   28980
tcatgtggcc tcagctaaca cccttgggct ctcactgccg ggtttccaca cacttaggaa   29040 acaaacccg ggtcagggag cccagcagag agcaggagtc cctgccccac tgggtcacat    29100
ttggggatga gttcctgcaa tcccatcagg tgctcttctg ttgccctggc aaccccagga   29160
gctcccagtg gagcccatct catttctgaa ggagggggaa agggcaagca tctgctgtgc   29220
atgagacaca gagtgtgtgg ccaactggat ggattacagt gaaaggagac ggtaggagaa   29280
ggggcacagg tacccagct ccttcttcct tctccaccct ctgcagtcct tccttccttc    29340
ccactgactt gcctgtgggg ttccattccc ctttaggcct cagtttgttg ttgattagtg   29400
gctaggtcgt gtccgactct tgcaaccctg tggactgtag cctgcctctg tccatgggat   29460
tttcccaggc aagaatactg gagggggttg ccatttcctt ctccatgggg gtcttcctga   29520
cccagggatc gagcccagc ccgcgtctcc tgcatcagca ggtgggttct ttaccactga    29580
gccaccagag aagcccaggc ctccgtttgc caagacggtg ctcaggctgg tttctcttcc   29640
tcagaactga ggaaatgctc aagagctgga ggtgggagga ggcccactg cggtgtgggt    29700 gggctgggtg agagctctag gaagcctctg gggcttgttc caccccaag ggtcccaggg    29760 agactctgcc tccccgggga gccacaacca gcaaccggga aggccacagg tcatgaagca   29820
caggctctta gtcaccgcct cctcgcccaa gactctggtg gttgcacaga ccacaagcat   29880
```

```
ggtccatccc ccggggaggg ggtcgcacag gatcccatgc aggttctcat tctcacctgc   29940
acgctgctga ctatactggg tgcatccttg caagtgctag ggggcacgca aggcttccat   30000
ataggcgtgc acatgaattg gtacgcatgt atggtccctg gaatcaccct gggacagaca   30060
ccctggtcca ggacagatga gtgtgagccg ggaacaccac cccacagtca cgcgggactc   30120
gggctcacac ccactcccag gcctccaccc gcaccagtaa aggtattggg atgtgctcat   30180
agcttccttc cggacaaaag aaaagtgagg agggtgagga ggaccaggaa attgggtggg   30240
cgggggagcg gggagagtcc aaattggtac cagcacagta accccctagag ggcctttgga   30300 aactgtccaa actcccggtt tcgtagaaat aaaatccgga tccagaaggg gaaggggacc   30360
caaggccgtg cggggagtta agaacagcgt ggtggagacc cgccaccatc tcaacctgga   30420
ccttagtgcc tgccccaaac cttccacagc ctctccatct tctctgccat agccttgccc   30480
tcggacagct tgggaaacct gctgctctgc cccgacccgg gaccccggca gtccatcttc   30540
gaggtgcttg ggctgatgc ccaggttcct gaacccctag tttggaagga aatccgctct   30600
ccaggacaat ctgctttaag aatccgatga aatgcgcact gactccctct ctttctaaaa   30660
cgcacagctg caacgcgccc acgcccagca gccccaattc tgtggttccc aggacacgac   30720
caaccgaggt gcggtcgtag ggaaagcagg gtagttggca ggtggtggca cctccgtcag   30780
tgaccctcca cgcggggggg ctatgatatc tcccgtaac cctcctctca cacgccgtgg   30840
tgaccctgct agctgccccc ggagctgaat tccgaaaccg cccgctgccc agtccccagc   30900
ctttcgcagc tccgagcctc ctctttgcac gtctctttcc ctccccacca agcctcagct   30960 cccccttccgc ggctccctct cttccttgga gctgccggtt ggggtgggga cggggcagag   31020
aagagagtct tggctacggc ggcagaatgt tcaggagg cgcggggtgc acggccgctg   31080
gtgtgtctgg ggtctcgcga ccctccgtg gacacactgg aggctccggt cgcactcttg   31140
agtcagcttt gctggagaga acaacgtcca ggcagcacgg cgtcggctgc ccgcggccac   31200
cccagggaat ggaggtgggg gtgttaccgt ccatctgtag gcgaaagaag agggcacagg   31260
ctgcacctct gggtgggagg cccctgggag accaccagga actcggatgg ctgagaagca   31320
ccagcttatg gctggaaggt ttgttggcca gacagaagtg tttctctaaa aaggccctgt   31380
tttgaaggaa ggccctcttc tcaactctct agtctggacc agccgtctcg gccagtggtg   31440
tccacagccc cagaccaagg ggtggggagc ggggttgggg gggggagggt gcctttcact   31500
ctaaattcgc tgggtggtat catcccgcag ctgagtaccc ccctgtctgg gttttcgaat   31560
ctgatgaccc gccttgtgac cgtaatacct cctggggaac cgggtagcga gcgggagcat   31620
gtggccaggt ggcacctggg taagctgggt ccagatacag gaccaccctc ccaccgccag   31680
tgcctcagtc cttcggtttc ctggtgggga gtggagggtc ctgggagctg aggacgcgga   31740
ggttgcctcc agccaggcat tctcccagat ccatcccacc aactcccctt tcccggccgc   31800
aaaaggcgca cccgctgcag ctcgggcttc gcggtctcc accccaagcc ctcggagccg   31860
ctggggatcc cggcagtttt cctatccttt ctcctgccgc cgcttcgggc accctggacc   31920
agaggtgaac ggaaaagtcc aagcccctga caaacgccgg gaccccctccc tccctccccc   31980 cagcccccgt cgacgcgaag gtcgttatat ttccatttta tatttcaatt tgtcaccgaa   32040
acaaagccgc acgcagattt gcgggaagag agaaaagggc tgggaccaag ggataaggta   32100
tgatcacggg gcagcgtgcg cgcaactgct ttctgaaacg aaagttctca tggagcatgg   32160
cgacatttta cgtttggtac tgttaacttg ttttcctgtt gtggcccctc tctgcagcgc   32220
accaaactcg gggcttcagc gacttcggga gagcctttgg cggcaaggtt tctggggcag   32280
```

```
ccggcagttc ccagcaagag tgaggactgc gcaaatgccc gacaggcaag gttattctct    32340
ggagaaacgc cactatcggg agaggggcag gttctctggc tcccccgaag cctcttctga    32400
aatttccttg aaacaactga aaaaaaatcc cccaccctag ttttcgttta gggatacaat    32460
atgtaaatgg tctgtatctc catccacgtg atagttatac ctggagcaag taattaacaa    32520
ttcttccaac gtttcattaa ccgggtgctt cactgtatat aaattataat aaagacacat    32580
cgactgtttt aaaataatag gagacctttta atccaggtct gttttttctat ttaagatgct    32640 atgtgtttag gctgaactgt ttcagcagac tgagggctat agaaattaac aaagtaaaaa    32700
attaaaagca tctttcttct tctcctcccc acccgcaact gactgggat cctggacgtc     32760 acagctccta cgcttgagtt ttcccttcat catcccacaa tcatccatgg gttcttaagg    32820
ctaatgcgcg cccctcagtt tctccctgtc ttttggggggg atccctctta cacaaagcac   32880
accctggttc tttggcttaa tttgactatg acccacgtgg agtttacata tttcgtggtg    32940
tgtggattgt gtcggtgctg gtgggggggaa taaatatctc tagcattcaa tcactgcgtc    33000
taattcgaca aatcaaggcc agcccctcgg tggcgcccca ggggtctccg gccgggctca    33060
ggtctcccaa gacctctgcg cggagagcac tgccttcacg cgccgggatg gaaggtagc    33120 aatcggctag caacgaaaac ctgcgtgcac caaatagaaa gcgaaagaga aggaagtagc    33180
aagactgctt tcggaagcgt cccggcgcgc ctggccgagg cctggggtgg cgagcgcggc    33240
ttggagagtt ggcccccgtt tgcgagcgag atgccagggt cccgactcct gcagggatga    33300
ggctctttga gcagctgaaa aacactgggt ctccaacctg gcaggtctcc tggggtacaa    33360
gccgccaagt atgggccagg atgggcgggg actttggaag ggcgacgtgt ggccccaggg    33420
aacctggtgg ggttgggatt gcagaaggca ggatacggtg gggctcttgc ataaaatagt    33480
gaatgtgtat gcctgaaggg aaccgtgact ccacggttcg ggaccctttc agtaccgacg    33540
gggaagcagt ggaggcgcag ttaggggcag gaacttctgc agcctggatt cgtgtctccc    33600
ctccaagttc cacatctcca agcagcaacc ccccaactc cccacaggag gctgcaggcg    33660
gcttcctgct ccaggctctc gggctgcggc cccagtgcag cccccggacc cacagctctc    33720
ccgtcaagga gcgcttgtat ccaagcactg gctcccggcg gaggagacct cagaccctca    33780
cttttgctcc gagcagttac acagatggag gaactggcct ctggcccccg gaccaacgga    33840
gctgaaaagg tggttgccag gccgaagccc cactgggtgg cggcccgagc cacagtcagc    33900
ctggcaccaa agctgagtct gcctctgcct ttcccaagct cctgggaacc tccgaggctt    33960
tttccctcct actcacttac tttccccctt tggggtacac actctcacga gtgtaggggag   34020 agaaccatgt cggtgtgtgt gtgcttcaga gtccctgcct gctgccagct ccaaaggtct    34080
tctgcgcaac cgcctctctg ggcggcagaa cctcacctct tggtgcctcg gttccctcct    34140
tttgggccta atgtgccttt cccccccaacc cccacctaca agagccagaa atctcctcct    34200
ggccagagag acagcagctg ctgagagaag gaaacgaata agcagagctg tccatagttt    34260
gcggccgcac cctgagcagt gcctccatct tggacagccg ggagggcag tcctgttggt     34320 gttttccaag ctgccgtttg tcccaacctg cggctttggg attttaccag cgcagggtca    34380
gcgcccgccc tgtcctcaca agcgggtgct tacaggttcc cagtgcagca cagaggccga    34440
cggaagaaac gtgaggggg caggctagac tcctctgtct ctctgggctg ggggccgtgg     34500
gggtgtgtgt gtgagacatt tactacccag tgaggcctga ctgtcatctc cctgggatgc    34560
aggtgaggaa atgggctttt agagaagctc ctcacacgca ggtcagcggg gagccccatg    34620
gccactgccc atcgagggtg cattatggag actggcagtg ggggcccagc agggctcaga    34680
```

```
ggtggtgctc agaggggtct cacactttcc ccctttccct ccaaagccga aaacatttcc    34740
aaatgagaca ttgggagcca cgtagaatct ctccttacct actttctcag acgccttgct    34800
ggggaatttc tctaaaacat gaaaaaccag tgcagaggga gggaaaactg tccgtggggc    34860
gttccgtctg ggatataccc acacctaacg ttcccaaagg acaggaacca ggagaggcct    34920
ggcgggggag gaagcctgag tcccaggggg caggggggc gtgcaggcag gggcacgtgg     34980
acagggtgaa agcccctcgc tgcctgagtg tggaagaagc atctgtgcgg agatgcggct    35040
gtgattcacg ccgcctgaac tcattccaac aggaaggtgg agaggcgagg tagaggaagt    35100
ggggagagcc ccggagctct cagcctgctg ttctctgggt ttgagaggcc acacgagtgt    35160
actaggcgtg tgtgtgagcc tgctgctcct aaggaagagg ttgtgtgtgt gtgtgtgtgt    35220
ctgtgtagaa tccaagtgta gacaagagta cgaccctgtg aatgtttgtg cgtgtcaaca    35280
accacttagt ggacccctcc tgagcctgtg gggagccagc tccaggcaga gggtaaaaaa    35340
aaaaaaaaaa aaagcatcgg ccgaagttgt ttcctaacgt tattccagtc gccaaggcct    35400
ccaccccgtc tcacctctgt ccccggggcc cggtgtctca tcccgcctgg atcagtgcag    35460
ccaaaccact gtactgtcag aaccagctcg tttccagggc cctttgtgag ggccgtggcc    35520
caagggggag cgtgtgaacc cagcgctcct agcccagaga ttctcccatc cgtctcagtt    35580
tctctccctg ccagactgga gctcaccagt gccgatcctg tagcagaaaa ggttctggcc    35640
gcaggccttc cttgagaagc cctctcctcc tctttggtcg cggcgctccg ggcccaggc    35700 ctgtgtcccg tggccgcgtt caaggggct tggaggtcat ttaggcctcg agttcccgtt     35760
gggcccaaat caggacccag aaccttccct ctggcccagc accgcgccgc ctggagctct    35820
gtggcttcct gttttcccag ccgctcggtc ctaaagcgtg gttcagaggc cggccgcctc    35880
ccgggatcgc ccaaggcgaa gcgcttggga actccgattc gctcgcctcg cctgctgcga    35940
gccaccccga ttcgggtcat ccgcggcctc gggcgtcttc gaacccgcac ccagctggct    36000
cccctgcgcc accgcatccc cggcgcgccc cgccggctgc gcttcaggct cccggccggg    36060
ctccgcacct gcgatgctcc cacctgcagc gccgcccgag gagccttcta gccggccagg    36120
agtcaggcct cagcggcccg ggaacccgga gcccaagcgt tgtgctgcaa ctgtttcccg    36180
ccgcacgccg ggagccggtg ctgcgaagca tccgcttcga agccggcccg gcaagcagcg    36240
caaagcaagc ggtttgcgga aacggcgaaa aggaggagaa acggactccg ggttgagttt    36300
taacagccaa cgctccgtgc ccttggccga aggatcccaa gggggctgga cggattcccc    36360
cggtcccttc agagcggtcg atccccattt tccgacccaa agtcacaaac cgctcggccc    36420
cacgcctccc cagcccgcca actctcgcct ccagcaagtt gatcgcgttt cgaaggtccc    36480 ggagcccgg gtcagggggt ccccagcccc gagggattcg cacatgcact caccgtagca     36540
ggggacctgc aaggccgcgt tgtggccgcc gccgccttcc tggagtttga ggctgccgtc    36600
cgggggcgtc ttgcaggcgc ctcgttgcaa gtagagatgc ggctgcggcg cgggcggctg    36660
cggctgcggc gcgggcggct ggggctggaa cttgctgaag gagccccgcg ccccggcgcc    36720
gctctccaga ggtgctgccg gtcctgctg ccccgcgccg tagcgggccc ggctcttggc     36780
gtccccgaat ccctgccctt tggcggcggc tgacaggaaa gttgtgctga acttatcacc    36840 gccgggtat gccctaaaag gcgacgagcc ctccggctc tgcgacaccg ggctgtagta      36900
ggcgtccatg gcagcagccg gcgactcgca gtaagagacg caagtctcag cattcatgcc    36960
tggctcgcgc gggcgacggg cggggcgcg agcgggagcg cgaggacgcc accgcgcgcc     37020
ttggccggga gttaggagag gccaggaggc ggtggctgtg cgctgcgcgc gggcctgctc    37080
```

```
gctcccccte ctccccteca cgcctctctc tetggctcct cacccccteec tttetctece  37140
ttetccectce ccacagctgg ccaagggaaa gaaccgagga ctgtaaaaag attcagatgt  37200
ttcggaaagt tgaccagatc tcccaaaccc tcttaaggtt tttgaaccgg aaaaagagag   37260
tgctttttt tttttttce cccgactctt tcttttteec ttecgtctece ctctectect    37320
ctctgcctac tecccttete cctcacccett acccegtctce ccttectte ttttaaggag   37380
gtgctactaa ttcggtcgcc actccgaggg gattttacgc ggagccgccc gaaggccttt   37440
tcaagtcaag gcggggccag ggaggtctct ggactccccg ggctcccgag gctaggtggg   37500
tccaagcttc ggcctatggg aggggggcat gcacaacttt agtgatggat taaaaaaaca   37560
aaaacgaaaa acaatccaaa aaatctgaca gggtttgaca tttggaggca gaggggccgc   37620
taacttctgg gtgcaggcaa gtcgttgggg cacatccctg agaatttagc gcgcagctgc   37680
tacggtaaat gtagcgcgca actttcctgt cttcccaact ggtgcctttt gctctatttc   37740
caacccettt tccctattgt cggttcctcc ttgaaagtaa cacagtcaca cacacacaca   37800
cccgcgcgct gcagtcaccc tgcgcacggc cactttcttg ttaactgttt tcctcccttt   37860
aagggcacgg gcgagggttg cggaggaatc catgttcact cagacactgg agaaccagca   37920
ggctgctcca gtttctgaag ctttgcgccc agcccaggag attttctggc tgggttaagg   37980
gcgctttgag agtggggagt tgagagaccc gcacctcacc gctgcgcagt cacctgctca   38040
ctgctcaggt gggggtgaga cagtctaatc tctggcctca cagtccccac tagaaaagta   38100
atggcctgga tttgacgggt tgtgtgcgcc tcagggccct ggaaccggcc acagcaaggg   38160
aacaggactt cactacagtg agccgcgtcc cttctacacg gctaatcact gattgcgcct   38220
cacagcaacc gtgcttggtg gaaatcgggg tccccaaatt ttccgatgag caaaccgagg   38280
ctcagagagg tatgagcccct tgactgaggt cacacagctg ggaagcagca gcgcctgcct   38340
tgaaacccac gctgaggctc gtccctccgc cgatctggga tgacgttgct gacagcgaaa   38400
acgaaaccac gcagaacgga ggaaacggag ctctgactgt aggatgactc gggtttggag   38460
gagcccatta agagcagtcc tggataaact gcagagaaaa ggatagaaga catatctcaa   38520
gggaggctgg gagtgggtg aaaggtgaag gggcaaagta aaatgagaga gggcctgagc   38580
gccctgaacc caggaatgta ggtcagaagt caatcttctg cacctaaaag gtctccctaa   38640
gaagaaatat cggggggggg ggggcgtcat gcttctaccc ccaaccttat cctagctaat   38700
cctcaccccc acccctctcc cttggtatct ctgctccttg ctctgccgcc gactgcgcga   38760
tcccacatct ggtttccatc gcggcttacc ttgaagtgct cgttaataaa gatattctgc   38820
aaaccgtggc caggggtgcg caggcctgaa ccccctccccc actgcccata gggacccgca   38880
cctctctggc tcacggccca agccaagtga ggatctcata tatactgagt ccttgttgtg   38940
ccagaagcca tccacaggtt gtctcttggg gctaccccag caatctgggg atgctggtcg   39000
tctcctcata cccattttcc agatgggtag actgaaactc aaagacacca actaattttc   39060
caacctcagt tagccaaaag tgagtgagcc tgcatcatcc caaattctcc tgttcagccc   39120
tagtttcttt tagttcttag actctgccaa gttctggaat tccgtctctca tccctgtgct   39180
ttttgtcttg ctaataactt ggtattcagc aaagagtgtc tcctccagga agtcttccca   39240
tcttcccag tcgaagtgca tctctgtttt ggacttcagg tttgtctggt tgccggttca   39300
gtgttcatct ccatcgcact agtctgaggt tgcaagaggg cagcttctgc gctgcctggc   39360
gccccacaaa tatttacaga ataaaatatt agagcctggg ttccttccac tgctcagcga   39420
ggcagttccc agcgtatttg gtttcctcta gccaaggacg accggctgct cgccctcccc   39480
```

```
ctcttcatga atcaagcgac aaaattaaga gtacgctggc ctctccctgg ccgcacaaga   39540
acagtgagtt ctctcagaga aggggccagg cctgtcttgt tcactgcagg gcttggcaca   39600
tcctaggtgc tcataaaatg cgcattgaat gaatgaatga aaacactgag cgatccagtc   39660
tgagatctta aaggtgcatt ttcgctaagg tgttccaagc tgagaaggct actccggtcc   39720
cctgtgcccc aaaactggct actagaaccc agatgatgtc tgcgatcctt ctacttctct   39780
cccctcattt tccaattcca ggagtagaca caagggggaa actaagagaa gtgagctata   39840
tggggtgggg aatggtgact agacaggtag aatggcaatc accatattct ctagtaactt   39900
ctgagctgct ctggctgtca atgcaaaaag acaaaaccaa aaaacaaccc tgctgcgatc   39960
cagaaagctt tctttgcatt ggtggtatag tggttagcat agctgccttc cagaaagctg   40020
tctttgagtg ctgcctcctg ccacctaccc accccacgat cttatcacca gtttcatcac   40080
tactccatta tttaaccttt tcctggccac ccccacccc tcaccctca cccagggagg     40140 aatttcagcc tccagccct ccaggcacag actctggcgt cctcagtcag aagccctcct    40200
ggtgcactga ggtcatggtt cttggaacca gcagggggc cttctacctt tcaaggtacc    40260
ttagaggtga actcagaaag agtgagcatc tgcctgggcc tggaatgtgc atgtgggttt   40320
gcctgtgacc agtgagaaca ttctgggcat gttgttttcc ccatgaaaac ctccacagac   40380
cccctgccca agtcccttca aacacgtctt ttctaggaga atgagaagca tagctggtta   40440
tttctgtgtg cgttaagtca tttgcaggtt gatcagccca tgcctcccta tctcccttta   40500
tctctccctc catctctcca tccatcaatc tatccatcca tccctctgcc atagctgaaa   40560
gccaaggctc tcccacccag ttctcctgca agggtgcggg gcatctttcc agccagaagt   40620
gaggtggatg actctgaagc ctggttctgg tctttgctct ccccttgcat tatttcttcc   40680
tcggctaagg ctcctccggc ttgctgattg tccctccatc actgatgtgt ctggcagtat   40740
ctctacactt ctgatcactt taatgtgcca ggaatagtgg gtgcagccag tccctctgct   40800
tcaagtcctg attcctgtcc ccagccctgg cagacacacc ccttggccat cccttctctc   40860
tcccagtggc actgtcccac ttcaccctct tggaagcggc ttccccttc gatgggctcc    40920 gcacacagcc tgggaagggg gagtggtgac aaagtctttg tcaaggccaa gtgctcagtg   40980
tcacctcctc ttggaggcct tccttcacca ccctagcatc tgcctggtta tttccttgat   41040
cgtctctatt ctgacctgac attttctccc acatttatca acctacttgt tttattgtct   41100
gtcttcctac cagaacgtga gcccatagct acactcgccc caggaggaaa atacagggct   41160
tggcacatag caccactcag cactcgataa atatctattg agcgagtgac taaatgagtg   41220
aatgaaccag taagttgaat gaacagatga agaatactgg aggagaaatg cagtaactgc   41280
ccagtcccta tggctcaggg cgggagctct tgaggctggg gtgtagaact gagttggaga   41340
acggggaggc atggactgga agttcttttct tttaaagggg aggacggatt cggagccacc   41400 cccttttggtc tgagctccct ccactccatc cggcgctgca gtctccacct cctacagaca   41460
gtggagctgg ggaggggagc agccctgctt atctgctact tgacttctcc tgacagtgcc   41520
ccaagtcttg gccccagtg tgggtaaaac cgggaccata cacacctcag cgagtcacgt    41580
actacttggc ttgcacttgc cactttgtaa atgccaggag gcagcaaaga ttgctcgaaa   41640 ggttgggct gctgaataga catttttggac atctgcagag gggcaggaag agtcaggata    41700
tgaaggggga aggccaggga tcttacaaat cttgggcaga aatgcttctg ctctgcagac   41760
ccgggcacac agacctcaca ttcccagcaa gacataaatt agcaactgtg ttttggacaa   41820
ctgttaaaag tcagctcttg cacacagatc ttagcagtcc ttgaaacggc ccggtgatgg   41880
```

```
tactattatc ctcgttttac aatgattaaa aaaatatata tcgaagcaca gagaagtgaa   41940
gcgactgctt acagtcacac agcaaagcag acgacttggg attcgaattc aagtgacttg   42000
atctcagaac ccacgctctt aaccactgcg cgttctctga gatctctgcg gcgacgcggg   42060
tggaaaggtt cccgagtcct ctcggcctac cgggcgctca gagaagctcc cccttcgcca   42120
gtgccgcggg catagggca aggggctggg ggcgctcgcc agcctcggcc gcacgcgcgg    42180
accctggtcc tgtggcggag gaccaggcta tcgccccgag gtctgtgcca gcgttcgcca   42240
ccggcgtcca gccttccagc gtctgcccga tctcccagga atgcagacac ctagtcacct   42300
tcctgcattc ggctccagcc cccgcgcagc ccccgggaca gccgcgcctg ctgtgggatg   42360
gagcccggga gggaggcact ccccaccaac attctccgaa gactccaagg ccacgcggcg   42420
tgggcgggcg cacccccggc agtccgcacc ctagtgcgct aggctgcccg gggcaagaag   42480
cgagggtctc ttaggcgttt tgagccgagg gaggacctcg cgaggggcca ccacgctccg   42540
agagcgccgg gtcgcctgcg cttcctcctg gtccacggcc cctatctctc acccggaccg   42600
gtactccccg tttaggtgtt tagcgttcgc ggagtctggc ccctggtcgg ctccctggtg   42660
gcgcacgata ggggattcag cgcggggaga ggccccagaa ggacctcctc ttccccattc   42720
tccgctttct aaggccgggg agcgagggtc caaaaggagg tctgcgttca gggacgtatc   42780
ttcattcaca tgggaaaaac actaactccc gaaatgcggg taaacggggc gttctcgtgg   42840
gttctagacg cttgcacaac tgttcggtcg ggagggtcaa tgaaatacaa agctggaggg   42900
atgaaggttt ttaaaatgac caggcgcgac gccccgaccc gcaggaacgc atccctccac   42960
cgcccttccc cgcccccacg gtgcgtttct gggacctgcc ttcccagtcg ccctggtact   43020
tttcagcgtg ggactggggc tcctgtctga acgcgcggtc caggcgcacg acagaacctg   43080
gttccctgct ccccacttat ccgcagggc agagcaaaga gctcagggca gggagagaga    43140
actgagaggg ccacagctgg cgaaactgca gtctggcgaa cccccagga aaaccgactt    43200 ggctggaaag ctcgtgaggg gaggcctgga catcgccggg gcgaccgcct taatcctgga   43260
tccggagagg aagttggaac cggaagtcct cctacggggg tccttgcacc ccttgcatat   43320
cggttacagc ccaggagaac acagatcatt cacctccgca gataattccc aaacgtcatt   43380
agccaaaacc ccagccaggt gttgggactg gagcccgtg tccctctctt gtcttctctg     43440
tcccttctct cctggaagcc attcctctag ggtttcaaaa agatgggccg tgggaaggtg   43500
gaggccagaa cacaccagct cggttataca ggagtcctgt ggcgccttgt gggcagaaat   43560
gaggtcttat ttcctggggg tgcttgctgg gtggagagga tctgcccttc cccgctcagc   43620
cttagttcta gggaagtata tttcgaaact ttctacccat ttccccgctg gggagatgga   43680
ggcttcagtg atggagggaa gggagtgtgg atggccagag gggcctctgt gccgtgcgcg   43740
ctgggactgc tgagctgaca gcccacaggt ctcttactgt aagggtggt cttcccaatc    43800 taccgctcag ataactgagc tggagccagg gaggggagga ggtgaatggg acaggctagg   43860
cttcggattc tccttctttc tctctgagat ccttggggtg agccctgggg ggccctttcc   43920
ctccgccctc ccttctccac tccgctcctg cccaccaatc cctggagcct gctggcacca   43980
caccctctca gtgccctgac cacactctgc tgccatcact gggaagggc ggggagcacg    44040 gcccctaatt cccttttctc ctctcccaca accccagagt ccttctcctc taaggtttcg   44100
tttgtccctt tgtcccctcc ctcagcccca agaattcgtg ggcagccagc agcagttgtg   44160
atgactctaa ttcctgcagt gccccagcg ctggtctcat ggatggtggg aggggctact    44220
ggactggagg acagagctgg gctcaggagc cctctgtggc aggcctctgg ggctgggaaa   44280
```

```
aaagtggggg agggtggttc agggaggagg cagaattagt gattccatta gtggtcaaga    44340
ggccagctgt agattcaagt ttgaatccca tttctgccac ttttttcgctg tgtaacacag   44400 gctatgtgac ttcgctcatg ggcctcagtt tcctctcctg taaagtgggg agattagtag   44460
cacctatttc attgaacagc tgccaagatg aaataagatc atgctcactt aaggagtttt   44520
ctagtatcag caatggtaat ctcctttctg tctggaacac tctgctcttt taaacttcac   44580
agcccagact taaggaacca gaaatgacca gttggagttc ctgcccttca accatcgtga   44640
cggccggtca tatttatctt tcagaccaca gctcctccct ggtcagggtc ttttaaagca   44700
ccaggagtga aaaggccaaa ggattttttca ggctctgcgg tccagccatt cctgatagtt   44760
ggtgcacata agatggaggc ggtgcgttgt gttttgcaga ggggtagctg cgcccaggct   44820
cagccccacc tcagcgcttt cagcagcagc gccttcacct ctcttgctgc tgctgctgct   44880
gcaaagtcgc ttcagtcgtg tccgactctg tgtgaccccca tagacggagc ccaccaggct   44940
cccccgtccc tgagattctc caggcaagaa caatggagtg ggttgccatt tccttctcca   45000
atgcctgaaa gtgaaaagtg aaagtgaagt cgctcagtcg tgtctgactc ttagcgaccc   45060
catggactgc agcctaccag gctcctccat ccatgggatt ttccaggcac gagtactgga   45120
gtggggtgcc attgccttct cttcccttgc ttctctgtaa actcatgact gtcctgtggt   45180
ggagggttta tgtcatcgct ttacaggcag ggaaatggac gccccttgcc tacagcacac   45240
tttgagcaag aggtcaggat gaccctcaaa tacgggctc ctggctccca ggcctggtat    45300
gtttgtccca gcgtccagag cgcgcagggg cctcagagac agggcccgg ggtctggcca    45360 cagcgcctcc tgcctgttcc tcctccccccc accgcctgcc tccaggcggt gaggtctggg   45420
ccccagcacc tgtcgaagga gccagccgga gcgcaccagc tgatccgggt aatccggggc   45480
tttgtgattg gcagggagga gccctggagg cgggaggggtg gggaggaggg gaggatgaag   45540
gagaatgcgg gagacaagca cttgttgagc aaccctggat gcccgagacg aaaggagaga   45600
ctgataacca agggcgcttg actcagtgcc tggcacatag taggtgctta gtaaatgatg   45660
atggttattc tatttctatc gcctcctagt cttactagat gtctgccaac ttacctaaac   45720
ccctccatct gaggatgtca tgccgtaacg ttcaccctct ctcacctacc ccaccagggg   45780
tccttccctc cttgggacca gtggccgcac tcccgcttg cctggagccc ggtccagagc    45840
gcacagctgc ggccaggctg tgaacacttc tggagtcaac ctctccgccc agagcccagg   45900 ggtgggggt aggggtggag gtgggagtgg ggtcggggtg gggtgggggt gggagagcg     45960 gccttgaccg aggagcgaag gacgaaaaag cagtgcagcc ttaagtcttc agggacgcta   46020
tggcgagtgc tggcaggtcg ccccaggccg gagggaattg acttggaaaa cgaaaaaaag   46080
gcaactgata aagaaacaa ccaaatctac tccccccctcc aggcttgagc agccgccaga    46140
ggccagaggc gaggcccag gaacccgccc gcggacatcc ttaggaggtg gcgttttgc     46200 tgcatttatt cggtgtcaat tcagggcccc tcgcacctct gctgatccgc gcaacatccc   46260
tcccgccata gccctcaccc aggggctgcg aggctgaagg ggacacggcc gaacacccg    46320 ggaaagggca accggccgg agtcggcgct ggaacgaact ttgactggag agccgggccc    46380
tgcgttctca ggcctccgcg cctttacgcg ctggggcctt ggacacccag gttcttgcct   46440
cagcctcttc tccccagatg ccttgccatc ctcgggagcg cggaaacgcc tagctgcttt   46500
ctccaagtag aattcgtttc caggtcgtag tggaattttt caacgggtag ttgagaacgg   46560
tcagcttctg gaggcaggca tctgggcgct agccctgatc cgggctggtg caagcttggg   46620
cgatccattc tcctccctgt gcttcagtgt gcttatctgt gaaatggcag tgactcttct   46680
```

```
catctcctgg gaaagctgtg gggagcagag atcacctggg taggtgctcc cttaactcca   46740
gttgttaatc ttttggggga tagttgcaga tcttggggga cttggaggaa cactcagttc   46800
ttgtggccac cccgacctcc tgtccagttc agatcacccc tcgccaggat tccaggattc   46860
tgggattcct gagtgcttca cccgggacca tgtgactagc tctttgatgg cccatagagt   46920
cctttcgtgg tgggtcttct ttaaaaaaaa tttcactggt cttgccctca cccttgccaa   46980
gctaactgga ctcactttca gtttcttggg gatgaaggta gcagacaaaa tgagcattgc   47040
caaatagcaa tcgatgcatt ttttctttt cctgtcttaa ggtgaaatcc acataactta    47100
aaattaacca tttaaggctt ccctggtggc tcagacagta aaagaatatg cctgcaatgc   47160
aagagaccca aattcaatcc ctgggttggg aagatcccct ggagaagaga gtagctatgc   47220
gctctagtga tcttgtctgg agaatcccat agatagagga gcctggcagg tccatgaggt   47280
cacacagtca gacacgactg agcgactaac atataaccat ctaaaagtga gcgattcagt   47340
ggcatttagc acatttgcag tgttgtacaa ccactgtctc tgtctagctc caaaacattt   47400
ccatcacccc aaaaggacct attttttcttt ttcaacactt tctccagaac tgagctgtgt  47460
gctggcggag agcgagaggt cagcacttca tgccctttca acttatcttt tcaatgcctt   47520
taacaggagc tctgtttaca aatgacttgc aaagttgagc tcaggaaacc agggagcccc   47580
ggagatggga gtagggtgtt tattcagaat ccatgggggg accagtgtgt gtctgagagt   47640
gtgggctggg cccagggaat tattggacag ggagctggag aaccaggtcc agagagaggg   47700
tctttaatgg ccctgcccat ctaaaagcta tagataaaat tctcatcctg caggagtgag   47760
gactctatttt cacagacatt ttaaatcaca ggctctcagt ctctttagga aagctacttc   47820
tttgatcatc cgatgaaagc tgaggaccct cttcttggac agatgcagcg aaatgctgcc   47880
ttagtttcca agggtttgta acaaatgact gcacacttgg tggtttgcaa gaacagacat   47940
ttattctgtc tcagctctgg aggccagaag tctgaaatca aggcgtcccg gggccaagtt   48000
cataggaggg gacttgcttg cgattcccag ctttctggtgg ctccaggctt tccccttggc   48060
ttcacttttc ccatcactac cttcatcttc atgaacttct gtcttctgct ctcccgcctc   48120
ttataaagac gctcatcatc agaattagag actacctgct ggagagccca agatcaggtc   48180
ttcttgaggt cctttactta attaaactgt aaatatcctt tctgtagggc ttcccaggtg   48240
gttcagtggt aaagagccct cctgccaatg caagagacac aggagacccg gctttgatgc   48300
ctgggtcagg aagatcccct ggagaaggaa atggcaaccc actccagtat tcttgcctgg   48360
agagtcccat ggcaggctaa agagtcaaac atgactgtgt gactgagcac acatcttttc   48420
tgtaaataag ctcggtctca caggtactgt ggagaaggca gtggcacccc actccagtac   48480
tcttgcctgc aaaaccccat ggacagagga gcctggtggg ctgcagtcca tggggtcgct   48540
aagagtcaga cacgactgag caacttcact ttcacttttc actttcaggc attggagaag   48600
gaaatggcaa cccactccag tgttcttgcc tggagaatcc cagggacggg ggagcctggt   48660
gggctgccgt ctatggggtc gcacagagtc ggacacgact gaggcgactt ggcagcagca   48720
gcagcacggg cactgtggcc actgtcttgg gggactaccc tttaacctca gtacaggtgc   48780
atacagccag cttcatactc aacctcaggg gctctcaggc tcctgtcaag tcagaaatgt   48840
ctgattgaat gtcacaaagc gaagtgaagt cgctcagtcg tgtccgattc tttgcgaccc   48900
catggactgt agcctactac gctcctccgt ccatgggatt ttccaggcaa gagtactgga   48960
gtggggtgcc atttccttct ccaggggatc ttcctgaccc agggactgaa cccaggtctc   49020
ccgcccctgta ggcaggcgct ttactgtcta gccaccgggc aagtccagga acgtcacaaa   49080
```

```
ggaatcctta actgccacct tcagaaaggt tggagagagt agaaaccacc cttctcttta    49140
aggaaggaca tttcccacttg cggttaaaag gagaaaatga acccaccatc ctgcctcggt    49200
gataccatct gccctcttga ggaaggacat tccagaacat tctagaggca gaaaccagtt    49260
gccttttttac aaagaagccc ttgaaaaatg caagcatcag ccagaatctc aatttgtgaa    49320
aatggaccga caggaaattt cttcaccctg tcagacaaac ttcataaagg ctctgtaggg    49380
gccctaccac tccgagaagc cttttaagaa aattgcaact tttagtcaga ccctgaggga    49440
agtctcacaa aggtcttcac accccttttgg ctcctctttg tggggtggtg agggaagagc    49500
aaggtttttt tttccagggg aggagagagg tgagggatca gggctgggga gaggctgctc    49560
tgaggcagcg aacaggatgg ctccacagat agaggtgaca gtttcctcaa ctgagtcccc    49620
gggtcgccac ctgtgtcctt cctgcagatt ggatttatag agtgtaacat tttaataaaa    49680
aacacacaca ccttcccatt ttggtgcatt aagagatttc taacaaaaca ctgtaatgtt    49740
gctataaatt tttctcccag caccctcaca agtaataact cagccccgga attttgcatt    49800
taatgtttat tttgatggct acattccagt cagagtgggg gctcagggtg gggagggaga    49860
aagcaaaaaa aaaaaaaaa aaaggctcct ctttcctagc cattaactgt gtgttttaa     49920
taaaaaaaaa aaaaaggtc cccacaaatt ggggagccaa cacttggaaa ggaaggaggg    49980
aaatcatgac accctatgag gaagcgccag tggcctcagc tctaggaagt tgacagggtg    50040
agccctggcc gggtcctgcc aaggtgggtc tccagagggt ttctggaatg tcgcctttgc    50100
ccatgccatg cattcagcct gagatgcctt tttctcttcc ctcagagctt ctgagcctca    50160
gaagtctcat cttctggaat tttccccaca tcctttctcc acgagagtta tgggcccttc    50220
ccctgaacag tattcattct attcactcaa cacttgtagt ggaatctgtg gctggaacgg    50280
gctcagatga aagcgtattg agtgaatgaa caagtgaact gagtaggttg gagaattcta    50340
ttttattcca tctgaattgc ttccgcgaag gcagctattt tggaatggtt aatgattttc    50400
tccctaaaaa agaatctaaa tagttcaaaa tcatgtggag atcagatcac aaccccttt     50460
ccttcaaaag tgctatattt tagttgtctt atccccagc gtcagaaggg aagcttctag    50520
tttattcttt tgcctccagg tagaaacaaa agatgggatg ctggtccaga ctgtcacaga    50580
tgggtggaga ccacttcctg gaggctgagg ctgaagagtc ccactgcctg atagctgatt    50640
aatgctcatc ttccctgtgc cttggctgtg gggctgatac ccttctcaca acccctctc     50700
cttctaagaa catcacattc ccccagcatg tcttcccatg gggccactga tcaaagcctg    50760
ggttctgggg ttgccctgtt cccgaggcag gggataacac tcaaattgtc ggtggggata    50820
atgaatagag aaaaatgctt gtaaactatg gagtgcctgg aacacagagg gtggccccta    50880
acagcgtgta tgtctcagtg actgtgaggc acgtaagtgg ggggatcaga ccccaaagtc    50940
agatgatttg cgcttattgg tgtaagacct cagttttctc atctgtaagc tggggacaac    51000
ttcagcagtt ggatcctggg aagtgggaga agggaggat tatttgagaa agttgttcat    51060
ggcatgtgcc tgactcactg ttcaggttgg gaggggacct ggccctaccc ctgccactca    51120
ctgacctatg gcaccgtca gctggctggg ttggagcccc tcgctttcct tacctccacc    51180
gcacagcctt ccccagaaag gaaggacagc ctgttccaag ctgctttact ttgccttctc    51240
catggcgaaa aactgttttt tcatgaaggg tttcaaatcc tgcctcttcc acttatttgc    51300
tggttgacct cggatcaatt gcttaacctc tctgggcctc ttatttgctt atctgataaa    51360
tgaggatgat aatgctggcc ttggtgcatt gccctgagga ttgaagacga taaggaagcc    51420
tggtacacag caggcacttg ataaatgttc tcccttttccc taaggagatg agaagcagat    51480
```

-continued

```
actggatgtg atgctccggg tacctgtcct aggacctacg cacaaacagt gcctactaac    51540
tgctctggag gtatgggccg gcaggaagct gcattgccca taatgggag ctctcaggaa     51600 gaccccctca ctcatcatgc tctgtgagga caccatacat tcttcccttt tacaaactct    51660
cagcctggcc cattgcattt taaagctgaa taaatagttc cagggcaaag ccagggatca    51720
gggctgctct tggctctttc caaagtattt ctgagccttt cagcaggatc cgagtcccca    51780
ccctgcaacc cctctaactt taatgggtgc tgatcacttt acaccctgtg aaaccctcag    51840
caaatggtcc tgatctctga tgtgccgttc aggctggcag cagggcgctg cactcagac     51900 tctgcccgag gaaatgaaag cctgatgggg ctggaggggg aggtggcgaa ggagcttcca    51960
ggccatcatg gcagctggag gaagttttcc cctagctgag ccgtcctgca ccctgccatc    52020
tctcccttct caaacacggc agccaggcct gctccgtctg gggcctcaca aaggcccttc    52080
ctgagcaagc tgtgtagatg tctaccctac agaagtaata atcgacagga ccatttatcg    52140
agcgcctatt atgggtcaga cccaattctt gacttatccc atgaataccc tcttctgcgg    52200 cccctggcc accccgccag tcaaaattag ctccctcttc ggggactcac tgtccctcac    52260
ctgctttaat tcttcagaac catttgtcac tagctgtaat gatctggttc atttatctt    52320 ttcctttgtc tactatacat ctctcctatt acaatgacgg gaaccttgtc tgtctgttca    52380
tacaccatgg cccggagaag cgctcagtgc agaataggtg ttcggaaaat attttatttt    52440
tcatctgaat gaatcttcat tcatcttcag agtgatctta tgggagggga ctatgattat    52500
ccccatgttc cagataggaa aactgaggca gagaaggggc caggagtttt gacaaagggc    52560
acacaggaag ggcagagctg ggattctgac cctggaatgt ttcactgaaa tctgtgctgt    52620
tctgccccac acaacctaac cccacctacc tggcttccga tagagtgagt gctctgttgg    52680
aaatagaaga tcttgtcaga aatggaaact tgaggcccct gtgtctgaat aaatacttcc    52740
cgaatattta tactcatgat cctacaatat tttattttct gtagttttca cagaaaccca    52800
ttacattgtt atctttctat accattttat aacgaagaag tcaaaactca gagaggttgt    52860
gtgcttgcct aaagacacac agcgaggaag tggctgagtg gccttgggtc tggactggga    52920
tggaaaggct gtgctcatct cacttctcag atgcatggcc tcctggggaa tccgagtgac    52980
ccctctggac tcacacagtc gggaagtgac aaagcagata cagggccagg tcttgtgatg    53040
ctctgcccaa atctccccta tttcagtatt gcagcctgga aaccaggcac acagaaggaa    53100
ggcatgaggg tcctgaccga gggcatgatg tggttgcctt gagggctggg aattggcaag    53160
gaaactcaca aggtcatctg catgtgtgtg tgtgtgtaaa acacaaagat ctgaccctgc    53220
cctaccctac tgcgtggatc agtaactgtg gagggaagac aagggcaga gaagctggac     53280 aaactagcca gatttatatg ggaaaacctg cagagacata ggaagtagga gaacatcgag    53340
aaagggtgaa gctgcagcct atggaggaga gagggaggtt tgggggggtct ggagtcaaag    53400 aagggaggct tcgaggaag ctgccaggtc taggagttgg gggagcagag ggggagagag     53460
agtcctcaag gtattttcc acctgatacc ttgggaatat gatcttcctt ttctggtgag     53520
tctgccatca acatttaat agaatttaa gttacctgtg gatgctggct gacatttgt       53580 ggattgagac tccgtgtcga gagagaggca tgagccagcc tcgtttgcga gggttcatgt    53640
gtctatgggt ttctctacat gtgtgcacac gtctgcacat gtatgtattc acgtgggtgg    53700
gggcgtttgc tctaactgaa ggcctgtgtg catgtgtacg tgcgtgcctg gggtaccgat    53760
ggcctgtcca tcccccctgc cctgcccag attgtgaaca cagcccccac ccaggagtgg     53820
agtcagacga ctggtgtggg gagaggggg ttggagggtc tgaattggga ggagtgcccc     53880
```

```
acctccattg tgggaaagct ggcatttgtg ggggctaaaa cagggtgtgg ggggatgggg    53940
atgggcttgc aggggcacaa gacacagaat tcctccaggg ggatttagca gagagagggg    54000
aagagagcag agaggaggg gcccaggcaa ggggggggtg gtccttggcg ggggtggggg    54060
ggagtgggga cactctagag gcggtgaggg acatccagca agactgtccc catccctgcc    54120
tttccctgcc agtgatgctg gggcctctgt gaaccgatgg ccacgtgcag gggctcagca    54180
gccaaggaac cacgcacagg gggagctttt gaacttagac ccgagaaacc gggttctcag    54240
cctagctcag ctcatcccaa caggctgtgc aacctgggca gatcacctgg gctctctcat    54300
cctagcttcc tcactgtggc gccacctggg gggctgagg cctgcatggg cgggtgggtg    54360
ggacggggct gggtgggctc tggagtgccg gtgtgtgagg cctgggtttc ttactgggat    54420
cgccagtttt ggccctgccc tgggctccca agaatttctg gacctggtgt tcagcaagca    54480
gggtacctat tgggttgtct ccaaaaaaat gttctcagcc ttcattttgt tgtatttaat    54540
cttcttgaat gtgaccaaat cagtctgttt taggaggcgg gggccctcgt gcaggtccac    54600
ctgccccgtg atcaccctcc ccgtgccagg ggggtgactg atgactactc cctgcccttt    54660
ttggtgttaa ctttaaaagg tgttaactgc ccttggtatc ccttcagacc cagctctcgc    54720
ctctccagga gggatcacct gcctgggtga tcgctgaata cacagaagca gccttggcag    54780
ttggcatgag tgttgccact gactggccag ggaacccaga ttcttgaccc tcggcgagta    54840
agcactggag ccagcaggcc ggactcaagg ccttttgtct cctagcccgg tttggccaca    54900
gactgtaata ctatgttgat gacgaactta tttgtcaacc actttcctct ttgcaagtat    54960
cagtcatccc ccacatcgct gaatgtgttt gttaacactt ggttttctg gccgtgccga    55020 cggacacaca ctgttctgaa acgtgtcatg tgatggctac acctgagaca agccttgaac    55080
aaatggtttc tacgactgct gccttgcagg tgtgtgtata atggtaccct ccttgccctg    55140 atcccttct atttttttct acgctattcc ctcccctctc cgatcacact tttccttgag    55200
cctccctctc ccccacattc cctctgtacc ctcttgcaac ctggtctgcc cccgtcctct    55260
ctctctcccc cagccccgtc tctggagcca gagccttggc caggatgaaa gccactggcc    55320
aggcccataa atcagccggc ctgtgcccct taaccttccc cattaacctc tcacacgggc    55380
aggcattagg tgttacactt ggctcccgta aattacttgc caatgaattt atgagtgctc    55440 accccctcaga ggcctgcttc ctcatcctcc cccactttcc ctcagggttt ccagacatcg    55500
agccccagcc tagcagtcag tgcctggttc tggcccgcga ctccctgagt gatgctctgc    55560
acctgatccc cccaccccgt ttcacacatg gactagaaga ttgaagaggg gaaggggggg    55620
gcgggtgtgc gtgacagtca cccctggct ccgctgtcta gaatcccctt ccccagaggc    55680
caccccctgg agcttccaca cgtttacctt ggaaggtgag aggaccctgc ataagaaccg    55740
tcaccactgt ttattgtgtt tctgccacgt gtttctacca cgtgccagat gatcatgctc    55800
attgtttcta attctttgaa caattcttcg gaggtatgaa ttgttatccc gttttacaga    55860
tgaggaatca gaggtgcagg caagtgatgt gacttgggca ggaccgggca tcactggtgc    55920
tgagagttag tggatttcgt tgtatcctgc gtgcctgctc agtcgctcat tgtgtctgac    55980
tctgcggttc cttggactat agcccaccag gcttctcagt ccatgggctc tcccaggcaa    56040
ggttactaga gtaggtggcc attgccttct ccagggaaac ttcctgaccc aggggtcaaa    56100
cccaggtctc ctgtattcgc aggcagattc tcctaccaac tgagctccta ctctatacaa    56160
atccaaatct gcaaaacaa ggccacgtat ggaaaccgtg ataagcccgt gacccagaat    56220
ctctctgcct cactccctca tcttgctgca tgtcggttta caaggaaaaa tagtagtgac    56280
```

```
gatgttcatc acgagaatgg ctgaccccg tggatgttta ctaagcacct gttattatgc    56340
caagcgattt atgtgcagaa acttgcttaa ttatcatccc tgtgtaaggt tgatgctata    56400
gttatgcctg ttttacagaa gaggacatag gcaaaaagag gtcagttaat ttgttgacgg    56460
tcacccagtg aggaagggcc gggtccagcg gtcggacccc aagagtcagc ctgcagaacg    56520
cccaacactt caccatgagt agtgacacta atgacaaatg tgatgccacc acagatagag    56580
cgacagttgc gtaggcgccc caggggctca gtgctgttag ccccgcgtcc ctgcggggag    56640
cccctggaga gttctccgtg ggtgacccag gggcgcatct cacctggttt tccttctttc    56700
gcttttccca ggtgacagca ggggcggagc tacaaacttt ccccagatga gcccaggacc    56760
tctctgggtg cctgtccctg gctgctgctc cagctctgat ccctgatccc caaagctatg    56820
aggtctccac ctcagcttcc tgagtgtgat cctggggaga cgggagcaca tgtctgggat    56880
ggcagggagc agctggaggg ggatgaggag ggatgcgagg agagcacgct gtgttccggg    56940
gacctgcagg gacagcagac cgaagctgga cggcaggact ccaggaggat gtttctgggc    57000
cagctgtcac caagggccct cccctccctg tgcccccacc cccgaacttc ggcccatgt    57060
gaatgcctcc tgtgcaattc accaaggggc ctcctctccc tgtcccccc ctgaacttcg    57120
gcccatgtga atgcctcctg tgcagttcag tcaccactgc aaaggagggg cagacagctg    57180
cttgtgttcc tctgggttgt gtgtgaccct gacttagagg gaaaaggaaa ggtcagccag    57240
agggtgctgc cacaaaggca ggacgcgggc cctgttatac tgggagggca ggaaagcaag    57300
agccatacag acctggctca gtcccaggg gaacagggct gaataggggtc ccctcccaat    57360
tcacgcccac ctggaacttg tggatgtgat tttgttcgga caaaggtgta actgcaggtg    57420
ccgtgagtta agatgagatc aacctggatt agggcgggcc tggcatcctt gtaagaggtg    57480
ggaatctaga cacagacacg caggggcgaa ggccctgtga gatggaggca gagatggagt    57540
gtcagatcca caagccaaag aatctcagcg gttgccggcg ctccccagga gtgacaagag    57600
gcaaagaagg atcctttcct tagaagagag tatggccctg ctgacacctt gagtttggac    57660
tcctggcccc cagaactgga cgagagtaag cttctgttgt ttcaagccac tcagcgtgtg    57720
gtactttgtt atgcttctt gttaagaaag ctgacaagcg agctccaatc acttatgagc    57780
aggatggcct ggcatcagtc actggtctct ccaggccttg ctgagcatcc ttgtagtgag    57840
tgtgacacta gttcagaggg tgctgtgagg atgggatgga atgatgcctc caaggctaaa    57900
acggttcagt aaagacagtg gatttggctc tgggattcct gggtcaggca gatctgctgg    57960
agaagggata ggccgcccac tccagtattc ttgcgcttcc cttgtggctc agctggcaaa    58020
gaatccgcct gcaatgcagg agacctgggt tcgatccctg ggttgggaag accccttga    58080
aaagggaaag tctacccact cccgtgttcc ggcctggaga aattccatgg actgtatagt    58140
ccatgcgatc acaaagagtc agacaaaact gagtgacttt cactgtcatg tctaaataca    58200
gcgattcttc agagctgggc ttcctagttc cttctggaag gactgagagc cccgtgttat    58260
ttttttatgg ttaattttgg aaattccaag ttaacagtta gggtacaagg tgatcacatt    58320
tatgtaatct ttatcagaag tctcacaagt tgtatattca acattttgaa gaaaaaaaaa    58380
aagcaactct agttttttact ctgtacatcc agattacatg cttggaccaa ctgcacgaac    58440
agttagttta taccagatgc cagctgactg cctgatgcca actggaaata aagttatgtg    58500
cgtatgcaca ctcatataaa ctgatcgcta accttgtata caaaaccata tgtgtctatc    58560
tccctatgca tattggatgc ttacatattc ataacagatg cgtacatata tctgctcaag    58620
aaatccatcc agcaaatatt tattcagtgt tcaccttgtg cagggtgtgt gcgtacatgt    58680
```

```
gggtgtgcag atagagagga atacgtgttc atacataaat aatgtataca cgtagctgat   58740
tagaccagaa gccaaccaaa tatctagatg ccagtgtggg agcatggctg ttggaaagcc   58800
atatacttca aattccctgg ctgggaacag gccggagcct ggaggtgagc tgagccccca   58860
aatgagagag gggtcagcac agggcagaca gctggggcgg gaggaaggcc ttgggccccc   58920
tctaatgcca tcggggtgag gcttgggget cccagccect tctggtcagt tgtcccaag    58980
ctgtcactct ctctgtcttt gtggggactt ggaacgaaaa cccatttga gaagagtagc    59040
atctaggggc acggcgacct gttcctgcct tctcccactc tgagcatcct cagagtggga   59100
tgtatcctct ctggatacag gggcgctgga tgctttgctg gccccagcac cactttggag   59160
acctgctgtg tgcttctcaa tgccaccccc tccctgatgg cacttctctc cgtgaagggg   59220
ccaggccggg gaaggggtgc tctgctgtca cgcttccttt cgtaactgaa gtgatacaat   59280
ctccgcctgc cccgcctgct ggactccaag ggtgctgttg gacatggct gctcttcctc    59340
cacagcccag cccagagtct gcttcctagg aggcccttcg taaaatctgg ggcactcagg   59400
ggtttagcca ggtgaagggg tgtgtccagg gccgccaggc agtggaggga ggcttatgca   59460
aacacgccct gactcagcag actccctgct ccagaaatgc tgcagctcac cacccgcctt   59520
ggaccaggac ctccctgtgc cacggacctt gtctgaccct gccaaccgga gaggggaatg   59580
cctggggtgg cccttgtatg gcactttcat atctgaattt ccagtaacca gcatgccaac   59640
ctgcatacag taggcaatca gctggtgttt gctgaaagaa ttaatgactt caaggcctgg   59700
gtatacagct ctgggccctc gggactgtga gggctcagag gagcagtgtt tttgccctgg   59760
tagacggcga attctctgct aagaccctaa agccaatgtg gcgtcttagg ggagaggtgg   59820
gtgggcagtc agcatgggc aggaattggc tgctgggtta acagaaaatg aacgagattt    59880
gcctgtgtca gaggggctct ggtcaaggac acttcctgta ataagtaaac attcctgaaa   59940
gggtgagagc ttaaacacag taagtgatgc taaatggagg agagcagttc aaggagggag   60000
attctttcca ggtgaggctt ggaaggggag ggaaggaaac gatctttctt taagctcctg   60060
tgaagactga tgctagagac tgcacacatg ttcttcctgg aaaagcaggt cactggaacg   60120
atctctgttt aacagatgag gacactgagg ttcagagagg taaagcacct cgctcaaggt   60180
cacacagcca ggatgtggca acatcggtcc gactcaactc ctgtactggt ctggctgctg   60240
aatctaggta atagctatgt attgcctgct tgaccttccc ttttgttct ttttctgtga    60300
ggatttagtt attctctaga gcaaaagaa tatgttttgg gggtattcaa gctttgggga   60360
ttttttttc cgtcctctgg tatattgtta ggagggcttc cgtggtgact tggtggtaaa    60420
gaatctgctt gcaatgcagg agacttggat tcaatccttg ggtggggaag atcccctgga   60480
aaagaaatg gcaacctact ctagtattct tacctggaga atcccatgga tagaggagcc    60540
tggtgtgcta cagtccatgg ggtagcaaag agttagacat gactgagcga tcaaacaaca   60600
accgcaacaa ataccgtttg gaagggtatc agttctggcc tcttccaaag gctccatcaa   60660
agataacgtg ggaggctttc ctggtggctc agtggtaagg aatccttctg ctagtgcagg   60720
agacacgggt tcaatccctg atccaggaaa gtcctgtgag ccacgactat tgagtctgtg   60780
ctctagagcc ccggagctgc agctactgac tccgtgcact gcaggtattg aagtccacgc   60840
ccctcgagcc cgagctccac agcaggagaa gccatctcaa tgagaagcct gtacatggcg   60900
actagagagt agcccctgct cctcgcaact ggagaacaag ccctcgcagc aactaagacc   60960
cagcgaagga aaaataaata aataaatgaa attattaaaa aaaaaaaaga caacatgggc   61020
ttcctgcaag gtgcccctcc accataaacc tatccttcct gctccttcaa gagcgatccc   61080
```

```
tggatgctgt agtgagaagg atgtgtttt gagggggcct cttcccaggt ggtgctagag   61140
gtaaagaacc cacctgccaa tgcaggaggc ataagagacg ccagttcgat ccctgggccg   61200
ggaagatccc ctggaggagg gcatggccac ccactccagt attttgcct ggagaatccc   61260
gtggacagaa aagcctggtg ggctacacaa tccatgaggt cccaaagagc cagacacgac   61320
taaagcgact tagaacagca cagctcatcc ctgtcaactg gtataaaagc aaattgtttg   61380
caaacttaga tgctggagag atcaatgaaa gaactaaaag tgtttccgcg ctgatcccat   61440
aatcaacaca cgtctgggga ctgatccgac cgagcctgtg ctagtggcat gtgttcgact   61500
atccccagga cgaggcccct gcaggtcaca ccggtgtccc cttccccag aatcccaggt   61560
aagtggcaga gagccttggc agacaaacct ggtcgaaaac acttcctgta ataactaagc   61620
cagtctgttt atctagcttc ttggctacta acaggcatt gtgagggagg gggcccttcg   61680
tcactaaatc cccacgcccc tttgtagcga gtgatgtcct ttgtaagttg ctgggtgtcc   61740
ctgaacaagt tactccagcc ctctcttcct catctgttta aaggggatt atattaccac   61800
ctcctacgtg ctgtgaagtt ttagcccaag cacttagcac agagccgggc acctgggaag   61860
ctctgaatga acattagctg ttaggaccac agttagcatc atctgccggg cagggctgat   61920
ggaagagctg gtgagtggag gtgagtgtcc ctgtgtgagg gtgggagggt gtgtgtgacc   61980
cctgcctctg ctctggggac actgaggccc tagggcagac tctggaggga tatggataag   62040
tctcctgtct tgcttgggca gactctggag gcatacagat gagtctcccg tctttgctcc   62100
agcgaggagg aactttgtcc tcccgcacag gctgcctcct gcagactctg tcctctggac   62160
ccgctgcctg tcccttccct ggcgagggcg gggaggaggc ccagccacgg ggccctggcc   62220
cccggggccg ctggcccagc aggccaagga ctctgtgtcc tgggagggga gcagccctgc   62280
gccgcagctg ctcctcctgg gagggctgg ggcagcaatc tcatctctca gcagagacct   62340
ctcaacccag ggggcagtgc cccagaaagg gcacaacccc gagaccccgct cagagctgct   62400
tcctcctcct gttcatgtgt cccagaaacc tgagaaatg agccaagtcc tggggagagg   62460
gggctccagc tggggacccc ggtcctcctt gaccccact tactgccgct tggggtggg   62520
gagagcggtc gtccgccctc caccctccgg aggtcccctc cgcgtcccgc cctccctctc   62580
aggccacggg ccggttttcc agacttctcc ctttcccaca ctctttcccc gaagcctcct   62640
tcacacaccc agttcttctt aaaggggttc taagaagaac gaatttccta tgaacagaac   62700
aatgccctat taatcttacg agggatttga acttggccac atttcagctt ttgatttaaa   62760
tatcattttg gtaatggggg agaaaaaaaa gaaggctgac tcttggacag ccccgagttt   62820
ccaataccttt ctgagcatga gacgatttca aatataaaat taaatccaac tcccttctgc   62880
ctccccctcc ccccaccgt ccccttcccc cgctttcact cagacaaaaaa agctcacgtc   62940
ccacatactt catggggata tttcaagtta aagttttgtt tacctatag aaaagttaat   63000
tagttccttt tgatctcacg gggaaaacca cacaggaaat ttttcttcag aaagtgtaca   63060
cacgaaggca tgctttaccc tcataaccag agatattcat taaaacaatt cgtttcgatt   63120
tttaatttaa agaaaacatt ttacatttc ctgatttatt attaagagag tagttgtccc   63180
tggggcagag cgtgaagggg gtcggctgaa gtgtttttgc tgtgctggca gccagcattg   63240
ggcagtttgt tttgctactt tggataacaa gagacttctg cagagaggca aacctttcaaa   63300
cacgccagat ttcagtcgcc aaaatattaa aaatccaggg tttgggagat tgggactgta   63360
tggtttaaat aaagatattt aagttctgaa atataaatat tcgagatcct gaaaaaacat   63420
atcattgcat taaaatctga aacaggcaat gggtgaatcg agggagaaaa atgtttactt   63480
```

-continued

```
ttttgaggtt tatctaatga aatataataa atagtacatc atgctctttt ttttttttaa    63540
cccctagaga tatttaagca atacctggat ttgtacaata agctgcttag gaaaagtcta    63600
gaaagagaaa cggttggatt ttcgaaatgc gattttcaac cttaagcaca ttttccacat    63660
cttgtattgt tatgggatga gggatgcaga ggaccctgta aattgtggaa ctcatttcca    63720
gcccagacca attgaaaaaa gaaatagtat ggcttccccg aggttgaaag aacaaattaa    63780
aagatattgc tgatggagca gccaaaagct gtggtcccca ttactgcaag gaaaaaaatc    63840
ttaaatagat atggtatgga caaaaagcct gtggaagaga tgttttttact aaagcaaaac    63900
cgctaaagca aaacagctct aaagagtggt gttgacatca gtatacgatt ttgagggtat    63960
ttttgggtgc gtatcccttt cctgcccctg acacaaatat ttggagattg ggactgtcat    64020
tgttgataaa aattaaattg atgccgcata caaaagatat ataaaaacca tgttaacata    64080
tggggcgact ttgatgatgt tctgtacaca gcaaagtat aaaaatctga tgacatttta     64140
ttgtcaccaa tttgcttttt aatctgtccc aaccactgct tttaaaaaca gaactcttaa    64200
tatagatttc tttatcaaaa gtttgcacct gaagataaat tttctgattt aaatgtattc    64260
cactctccta tttttttattt ttgttttttg gtaaatggtg aaggtgtgtg acagtccgtt    64320
tgtgaagtta gggaagaatg catttatttt gaagagggat ttaaaaatgc tggctgtagg    64380
agcagattcc tacaaatgaa gccagttctt aaggcaagtt tccaaaatct ttctgttcaa    64440
atacagagtc tgaaaatctt tttaaaaaat tgtccttcta caacacaatt agttttattt    64500
cctgcctaag atacctttgt attttcttct gaagaaggat ttacctttt tttagagctg     64560
gaaatattcc cttttttctt cttttcctgg aggaaaatgg tttaatgtaa agtttaaggg    64620
agggagagag atgtatggaa atgaatggaa aacagaagct tcaaacggct acccaattcc    64680
ctctttggat ttgccaaata acaactcaaa aatcagatac ttcccataag accattgatg    64740
ggagaccttc ccaataaata tgcatctatt cctgttttca tcaaaacaaa taattttctc    64800
tgctgattag gggcccttcc ttctccagta cccatcattg ggaactttga gatttcacta    64860
aacatatata catatatata tatatatata tataatttc ctttccgtga                64920
atttctacga agttggcttt ctttctccag gaggctggag tagagtcggg accctgggta    64980
gacacttcat tggtctgaat gcaagaggga aaggggtgac actctaaagg gaaagccacg    65040
accccaaagg agaaagcacg gacagataaa aagaacaaga caagtaaata ttttcctagc    65100
gcgtttccaa gttaaaaccg atcaagctac ccggttaaag aaaggcaaaa acaaaattcg    65160
tccctacctt tgtcagatgc aaagtaatga gggttgttc ccagagtggt tatgacctac      65220
acagagcttc ttaccttaaa tctatacatt ttgaacaaaa acagcttgga gcaattctct    65280
ccaaacaacc ccaaatgtta accattccaa ctcaagatcg ggtttctcct tcagcctaga    65340
cggtgatatc agttgggttt tcttttcttt tctttctttc tttctttttt tttaaaatat    65400
gtattcttat gtttccaatc ctcaaacata cttttttcat ctttgttaag gctccttctg    65460
gctgctggat gggctgggag tcgcaggagt ccttctcttc gggacaatta gtctctcact    65520
tgatcacttg aaaacggaat gatttgtcgt ggtcactgag tggggctctc tccctctttc    65580
ctctaatatt gttgcagata cgtaaagttt actgcgtgct gtaaatatgt cagcttttgc    65640
cagggagttt gctaataaag aacctagagg tattattgat ggaaaagata atgttttcaa    65700
taagactggc ccgggctaaa gtctgagaca ttccacaccc agccaagcat aggcgtttga    65760
gacgccgacc cctggccga ggtgccgggc tggtttaccg gccacaggcc ggccgtgctg      65820
cctgcttctc cgtggtcccc gtgactgttt tattcagcgc agttttaaac gcccgactgg    65880
```

```
ttttaggagc tctgtccttt ctgaaaaaat ggccttcctg accgtcagga ataggtgaac  65940
ttatcagaga atcatgagat acgcttgccc agattgatct ctttggggat ttatcagctc  66000
acccatgctg agagcagagg aaaaaaaaga agtccaccct tttctgtttg atgctcactc  66060
acattttcat ttgtcgtgac aacttctgag tgtaaattgg attcatttt ttcctggat   66120
gttcgtttgt ggaggattgt ttggcttccc tctcttaaag gaaaaaaaa aaagaaatcg   66180
cagaaagctt ggcgtccgtc tgccccacgg ccctggtccc ctgatttcag tctcctggtc  66240
tcggtgtttt gtcacatcac ccacatgaca gtttcatctg gtgctaatgt ggccgtcaca  66300
tgggttggtc gtcagaattc catgctcatt taccattaat caaatgcatc attatgaatt  66360
gtgtatgcat tttagggcag acccaaaccc cggcttgata ggaaagtgtt tttgttttt   66420
tccacttaac gttcggcaac ggcagatgaa tggcaaggcc aaagtgacac tctttgtgtt  66480
tgcttagccc agaaatcaac aaccctaaat tacaggttgg taagctatgt ccaggtagca  66540
ttagcttctc tgggtgatta ttattactta agggcggcca cagtcagcgc cagcaaactg  66600
aagctggcca gagggagggc agacaaggcg agcagagagc agggtctcgg cttccaaggg  66660
gcccggtgcc tccttttgac tgggggggatt ttagtcttag attgcatttt cctgaaata   66720
gggactggcc cttctaattt ggaagaatgt gaggtatttg cagggcgagt tcggatgagt  66780
gggggtgggg acgggttacc actgatgct tttggcaatt tgtggactct acttccccag   66840
gactcacttg ccagcttggc tctgtgggga acattccaag ttctggaacc ttccttggaa  66900
ggcctgactc ctgttggttg gtggggacct ggcgtctcct gggcgtataa agacggtttt   66960
cattgggagt tttcagtgat taaagtcttt cctgaggacg ggggactgtg tttcaggtaa  67020
aaacccttc ctgagctgtc acaatagttc tgggagatgg ggggcctggt gcctgagacc   67080
ggagggcccc aacctgaccc ctctccccca gcgagccttg ggagacagat ctgacctggg  67140
cttagctccc attcgttgtc taactgccag ccgtcccagg ccagatcggg aacagggaag  67200
gaggttggtc ccgaaaagcg atcagagacg gggtacaggg gctgcggtgc tggcttattc  67260
gatggcgcaa ttttttttt ccttcccagc agacagctgg gcctggttgg tggcttggag   67320
gcctctccca gggaagcggc ggagcactct tgccccagg aatgtctctt atttgtgagg   67380
ctgtcctggg ctacttggga gctcaggatg ttaggaaagc ctgttaaaag ataaatacct  67440
tttcagaata agctgctcag gatccacctt agcctgcggt gggggaggct ccaggagagg  67500
cagagagtgc agtgctgggg ggccagggtc tctcatgagg cctcctgggc tggctttggg  67560
aatgttcctc ccttcaaagc cccacttcag cctggaaggg ctgagccgct tccccagagg  67620
gcagtccagg gccgcggcac acagacttca gcccttctcc cctcttctcc tggtcagcag  67680
ggagagatgg ggctcccgag agctgggtcg ggtggcagct gctggcagag gcctcagagg  67740
tgggccctat gcatagggct ggggccaggg gagtgtgtga gtgtgggtga aggggtgtgt  67800
gaggggcagg tgtgacctca ggaaggaggg ctactgggt cgcattgctt ctcctcccag   67860
cccgtgacct tcggggcctg gaaccaggca gtagcatcca gcctctgagc ccaggctctg  67920
agcccaggct ccgagcggct ttgaagaggc ctgtgggtca gcgctgaggg tgctgttttt  67980
tgaggcctta ggctccacta gccgggtctg tgtcttcatc ccagaatgag ctgtggcttc  68040
accaaggggc tcagaacggt tttccactca ttcaaggtca cctcaagccc agggcttttct  68100
catctgaatc ttgaacctag cctctgtgaa ggatgtcctg agctgtcacc ctgctgacaa  68160
aaatgctggg ccctgagacc ctgaaataga gcttctcaga caaagatttg agcaacagtc  68220
taactgaact ccttatgaaa atacagaggt ctggtgccag gccgagtggg cggccttggg  68280
```

```
agtttaagga aataggtctg gttccatgga cttttttttt ttaaattagg gtttgggtca   68340
ttttggtttg aagttcaaca aatcagcatg gcttgtctgg cttttatct gccacctggt    68400
ttggttcaag gacagagaaa cgtttctgtt tataaaacat gtgcagacgt ggctggccaa   68460
tgctggtgtc atttctcctg gcttctgctc cttttcaagg gagctggtaa agctgatctt   68520
ctccaccctg ggctggtcat ttagccgggc ccggctgagg cccctgtgta atggacaact   68580
gcagccggct ggtagaggtg atgggtgtgt gcgtgcgtac tcagttgtgc ccgactcttt   68640
gtgaccccct gcactgtagc ctgccaggcc cctctgtcca tggggttttc caggcaagaa   68700
tactcgagtg ggttgccagt cccttctcca ggggatcttc ctgacccagg gattgcaccc   68760
gtgctcctat gtctcctgca acggcagaca gattctttac cactgatcca cctggtagta   68820
tgtaagatag atattatttg atgtggagag atgttcactg caagcactaa tatagactca   68880
tttttgtaac tgcaaaaata acacataaat ctggtaagaa atgaaagctg tacagaagta   68940
tttttaaagt aaatgaaata ccttaatatt tgtacagtgc ttagaagaac agtacctggc   69000
atgtaataaa cactagacac acttaataaa taagagtata tggaactaga agtcattttt   69060
cctcccaatt tggatctgta gtctccctct ccagaagcaa ccaaattaat attttcttgc   69120
atattcttcc agaaatttta tgtgcttatg aaagcgtgtc agcacacata ataatttttac  69180
atcgtaaaga gaaagggta ggttaccaag tagcttttaaa gagcataatt ctattttttaa  69240
aacaaacaaa caaacatgca tagaaaataa tctggaatca gatatatcaa tcaggtaaaa   69300
ctatgattat cttcaaaagg tgggatcatg ggtggatttt ctttgtcttt ctgttcactc   69360
cttctataat tctaaaactt gattagagaa aaacgcatat gaagaaacac atgcatggat   69420
gggcacatgg accctggtcc tcttatataa acgtgtttaa gagggctgac atccatgcca   69480
ggccctggga tcccatcaca gaaccagcct ggacaacctc ccctttgctc cctggggcca   69540
gctgctctgt tgctgacact gaaccctgat ctgcgtttgg cttgcccag tggctccagg    69600
actctcctgg ggaccctgg actgatgatc gaatgaggat aagatttgag ggactgtcca    69660
acacatgcat cccccttaa ctgtttgttt tgctgcttct atatccctct gccagttgtg    69720
gggaagaccc cttcctccct ctgccagcct gggcctgggg gtggcatgcc tagttgaccc   69780
tgatctccca tcaaggaaca aaggtgagcc ccgtttgaac ttacatgtcc atcctgagcc   69840
cccgagtctc atggcctggg tcctttggac ctatcagaag cccctctga tgtgcctctg    69900
agatgcagac aggcaggccg gtgcagcact ccagcttccc cacctgactt cctagaagcc   69960
agtctggtcc ctgtaatgac cagtggagca ggggtctcgg cggtggtggt cctgagtagg   70020
cacagtggac tcctcttgac tctgtagaca agaatgggga atcaaacaga cctgggccat   70080
gaaccagctg ctgttgctgt aggacctggg gcagatcagt tcacctttct gagcctcagt   70140
ttcctcatct ccaaaatggg tgcactgagg gtaccttcct cctgggctc atatatcttc     70200
attctcaatt cattcctta acacagattt ttctgagagc cttgtgtgcc aagctcttta    70260
ctggactcac aaaggctcac atataagctt ctacataaga taccagagag aacaacagca    70320
acaaaaatgt tttccagagg taaaagcatg gggaagaag gagaggcttc ttgaaggatg    70380
cataggagtt ctgacacggt gagggttgca gttgggaaag aaagatgagg ggtttccaca   70440
gtccttgcat gtgtatgatt ttgcatattt ctcacaatac tcttagaatt tgaattttct   70500
gagggtaggc tgtcattgtt gctggttgct aagtcttatc tgattctttt gcgacctccg    70560
tggacctcca tggcccacca gcctcctctg tccgtgggac ttcctgagca agaatgcgaa    70620
tgctggagtg agttgccatt tccttctcca agagatcttc ctaacccagg gatcaaaccc    70680
```

```
atatctcctg tgttggcagg tggatccttt accatctgag ccacctagaa aacttagact    70740
ggattcagct agattgaatc gtaagcagag ggtaatgtgc tagacaaaac caaataatat    70800
cgaagagtcc aatctcctgt ctcctctgct ctcatcctgg ggaattggtt gcctcttcat    70860
ttttgagtca gggagaggtt tccccaggag acctatcttc catttttccta ttgctgttgt    70920 tctcagggct ggaaagaata aggtctttag acaggctggc ctccatccct gactctgtca    70980
catgtgggct ggaggtctcc agcaagcctc agtttcctca tcagcaaaat gggcacagtg    71040
gcaatgtcca ccttgccaaa ctgctgtgag acttcagatg gggcaaagca cccacttaat    71100
gctgggcaca tgccaggatg cctgagacag ggctgagtcc tctgccagca gggcccagtg    71160
tctggactca aggcatcctt ctctttatta caaagccaca cattgagtct gagctcatct    71220
ggggcccatg tgaccccggg ggagtccaga gatgtttcat ccctctgttt ggcttccatt    71280
ttccccaccc tggctgaatg cctccagcca cctgccacac ctccagatcc ccatcaggca    71340
gagaaattgg tgaccgtaa gagcagaggg agaaggaagc tgtgaggtag aaaccagaag    71400
agatgtgttt gcagatgtga gtcgcagggg tgattaggac cccaggcacc gtttctgcag    71460
gatgggacct tctgggcgac agagccgacc gtggaatcta ccctcctggt cccaacagtt    71520
cccaaatcga gaaggcaaag aaggattggc ttttcccct ccgcccctcc ctcctctcat    71580
ctgtaaaatt gagacattac agttccaaaa tgggctttga gcctgtagaa attaatctgg    71640
tctggcagga ggtctacaaa taaacatatt gtttcgattg tgttgacat ttgaattgtg    71700 agaaggtttg aaaatgtaac tgtagttggg attttccagc ccatctaagt ttttttccat    71760
ggaggggctc agtgaatgcc aactgggaac ccagcaactg ccctctttaa aaggacttgg    71820
gcgctgggcg aggctgcgga tgtcagggct cagagcctgt gctgaggcgg cagcccttt    71880 gttgggggt gggcaaggat ttcaggaggc ccagtgcctc tgggcatctg gggcaaccag    71940
ccactccagg agtgacctga aacgtttaga gcaactcctg tgtgcccgga accttgtatg    72000
tgaaacctca ctcaagtcct cacaccagtg ctctctgttg tccagttgct aaattgtgtc    72060
cgactctttg tgaccccata tactgtagca ccaggcttcc cagttcttca ccagcttctg    72120
gagtttgctc aaactcatgt ctattgagtc agtgatgcca cccaaccccc ttatcctctg    72180
tcgttccctt ctcctcctgc cctcaatctt tcccagcatc agggtctttt ccaatgagtc    72240
ggctggtctc atcagatagt caaaggattg gggcttcagc ttcagcatca gtcgttccaa    72300
tgaatattca gggttggttt tctttaggat cgactggttt ggtctccttg cagtccaaag    72360
gattctaaag agtcttctcc agcaccacag ttggaaagca ccagttttta gtggtcagcc    72420
ttctttgtgg cccaactctt acatctgtac atggctactg ggaaaaccat agctttgact    72480
atatggatct ttgtcagcaa agtgatgtct ttcttttta acacgctgtc taggcttatc    72540
atagctttcc ttccaagaag caagtgtctt ttaattgctc ttattatccc cattttacag    72600
actgaaacac tgaggaaaag agaggttaat ttgctaaaac cacataggag taaaatgcag    72660
acttagacac agccttctct ggctcttggt gtcctgccct atacaatcta ctttatgcca    72720
gaattttcca gaatgttgtc tcaccaagag aaaggctcat tgtcccagaa aaagactga    72780 gccttgactg aggtgatctg gttgttgaga acaccagctc cattctatgt ctggaaccct    72840
tgaggattta agccccaccc ccttatcttc ctgccaccaa ggaagggtc tgtccttctc    72900 cctccctccc cacctccacg ctctggatct catccttcag tggcctctga gtccccactg    72960
cctgcccatc ccacctggct ccagcctccc ccaccggcc ccacagggat gcagctagtt    73020
ccctgtggga ggggcagctc tgagacagcc ccctactcag gggtgaggtg cacatggctt    73080
```

```
tcaaccacga actcagagtg ctggccggtt agggcagaca cctcgttttg gggaaaggct   73140
tggtgatttc tgtacctggc aacttctgtg tgtgtcaggc atcatctcct ggcccctttag  73200 ctccagagat gcgaagatcc atcttcaggg tcttcagtca cctgctacca tctcccttct   73260
gcgcttccac acctaccccc acagagctga gcatggccgg aaacacaca tgggaactat    73320 gctgcctgct cccccttat cctcatcatt gggagcatct aaggggccca tctggagaag    73380
ccttacaaat agctgtgaaa agaagagaag tgaaaagcaa aggagaaaag gaaagataca   73440
agcatctgaa tgcagaattc caaagaatag caaggagaga taagaaagcc ttcctcagtg    73500
atcaatgcaa agaaatagag gaaaataaca gaatgggaaa gactagagat ctcttcaaga   73560
aaattagaga taccaaggga acttttcata caaagatggg ctcgataaag gacagaaatg    73620
gtatggacct aacagaagca gaagatatta agagaggtg gcaagaatac acagaagaac     73680
tgtaaaaaga tctccacgac caaataatc acaatggtgt gatcactcgc ctagagccag     73740
acatcctgga atgtgaagtc aagtgggcct ttgaaatcat ccctacgaac aaagctagtg    73800
gaggtgatgg aattccagtt gagctatttc aaatcctgaa agatgatgct gtgaaagtgc    73860
cgcactcaat gtgccagcaa atttggaaaa ctcagtagtg gtcacaggac tggaaaaggt    73920
cagttttcat tccaatccca aagaaaggca atgccaaaga atgctcaaac taccgcacaa    73980
ttgcactcat ctcacacact agtaaagtaa tgctcaaaat tctccaagcc aggcttcagc    74040
aatacgtgaa ctgtgaactt ccagatgttc aagctggttt tagaaaaggc agaggaacca   74100
gagatagaaa aggcagagga accagagatc aaattgccaa catccgctgg atcatggaaa   74160
aagcaagaga gttccagaaa aacgtctgtt tctgctttat tgactatgcc aaagcctttg   74220
actgtgtgga tcacaataaa ctgtggaaaa ttctttaaga gatgggaata ccagaccacc   74280
tgacctgcct cttgagaaac ctatatgcag gtcaggaagc aacagttaga actggacatg   74340
gaacaacaga ctggttccaa ataggaaaag gagtacgtca aggctgtata ttgtcaccct   74400
gcttatttaa cttatatgca gggtacatca cgagaaacgc tgggctggaa gaagcacaag    74460
ctggaatcaa gattgccggg agaaaatatca gtaacctcag atatgcagat gacatcatcc   74520
ttatggcaga aagtgaagag gaactcaaaa gcctcttgat gaaagtgaaa gaggagagtg   74580
aaaaagttgg cttaaagctc aacattcaga aaacgaagat catggcacct ggtcccatca   74640
cttcatggga aatagatggg gaaacagtgg aaacagtgtc agactttatt tattttttgg   74700
ctccaaaatc actgcagatg gtgattgcag acatgaaatt caaagatgct tactccatgg   74760
aaggaaagtt ataaccaacc tagacagcat attcaaaagc agagacatta ctttgccaac   74820
aaaggtccat ctagtcaagg ctatggtttt tccagtggtc atgtatggat gtgagagttg   74880
gactgtgaaa aaagctgagc gccaaagaac tgatgctttt gaactgtggt gttggagaag   74940
actcttgaga gtcccttgga ctgcaaggag atccaaccag tccattctaa aggagatcag   75000
ccctgggtgt tctttggaag gaatgatgct acagctgaaa ctccagtact ttggccacct   75060
catgcgaaga gttgactcat tggaaaagac tctgatgctg ggagggattg ggggcaggaa   75120
gagaagggga cgacagagga ggagatggct ggatggcatc accgactcaa tggacatgag    75180
tttgagtgaa ctcgggggc tggtgatgga ccagggaggc ctgacgtgct gtgattcatg    75240
gagtcacaaa gagtcggaca caactaagcg actgaaccga actgaactga cacttgctcc   75300
cccactgcct gagtcctgtc ctctcctatc tccccaacaa ctatttacgc aggggtccaa    75360
attaggccag atgcgggagg aaggagtcct caagggcagg acctctatgc cacctaggat   75420
gaaggctccc cacgcccata cctcccatcc ctttgatgcc tggagggaca ggaagcaggg   75480
```

-continued

```
tggcaagatg gtgcctctgg tctagtccac accccacacc cctggtttgg tggtgaggtg    75540
gccccatgcc tgaccaggaa gatgagtcct tggccacaga ctggcctcgc tgcatcctct    75600
gctccctacc tctcctcctg aggtccctgg gggtggggg aattggtggc ctcctaggaa    75660
agaacccact tcatctgtac tacagatacc accccgacc ctgagaccac gagaggcctt    75720
gtctttgcac cttaacacac ctcgtctttg ctcctctgtc tgccctgccc ccagcctcca    75780
ttggtttgac tcctcagtgc cttcctcctc atattcaaaa gctcgaaacc atgaccgaaa    75840
gtttggggac actgggtttg tcctgacaca tctgggagca catgttcagg cttggatccg    75900
tctgtctgga tgttttccgt tgttggctg gttttgcctg caagaggtgt gaacctctga    75960
ttggctttga ggttctggaa atcaggaagg tttgtgttca tttcaaagtt cagaaaaatc    76020
actgtggttt tgggtcacgg ttgggttttgc ctgcttgatg gcagcggtgg tctgggggt    76080
atctgagcta ggtctctgtg gggtccccat ggggtctgag tgtgagacgc tcaggggtg    76140
gccctctggg tggggctgat cctggactca gtgatgggt gagtggccaa gggcggaggc    76200
aggggtaggg cgctgtgctc gcttaatgag gtctggatgc tctggctttc cagctatggt    76260
ttaaaatcct cagtgccact gtcagcctag tggccttgga ttttggtctg taaatgccaa    76320
tattggcctt gacttactga cttcctcaac tttctgggca ctgacttaat cctcactgct    76380
gctgtggtat ggcatgatag cactgtcctc attttataga tgggaaaatg gaggctcaga    76440
gaggtcaata acctgcccaa gatcacacag cgtatagtgg cagagctggg acacaaagcc    76500
aggtctctgg ccccatggtg gactgtctgt tctgccccag acacagtgca cagattggaa    76560
cgagggagag ctggtgtcca gagctgctct cccttcaaac ttactaccag cacacctgga    76620
tgtgattttt cgtggacaca gagaggtgg ttgtggtcaa agcgtgatga gagggcgggg    76680
ctcagagtct gagggcccca gacacggtgg tgtgagcagg cagtcagggg tcttctctgg    76740
ggtctgccga tgacgggct gctcctcact tttctgaacc ccaggttcct cctgccgctt    76800
cctaaggcgg ttctgaggct gcatggggat aatgttgata gaaactcaca gaggaggtca    76860
gaacatatcc gatttcatga gctctgcaaa gacggctgtg cctcgttagt catgttcttc    76920
ccaagttagc gcaatgcttg gccctgcgct cgctcagtaa gccctcttga agccacgtgg    76980
ggtctggcct cacagtcacc gctgtcagtt ttagagataa gtctgtttcc ctgaccggca    77040
ctctgggttg gagtcccgga tggccccgac ttgttctgga aggagcccca ctgtctgggc    77100
acagcagtct tcctgcaaca gacacgagcc tttggttgcc tcccaggggt gtttcccctg    77160
cctgctaagg cctgtcacct cctgcctctg aactgactct atgcctttcc ttcttcccag    77220
ggctggagga gcctgacttc cctccctgt ccaaggagtt cccacagtct ttgggttttc    77280
aattggaaca atgtgctaga gcttgaggtg ccttgaaatt taaaacagct acagtttaaa    77340
atcctcagtg ccaaggtccc tgtgtcagcc tagtagcctt gaatttgggt ttgtaaatag    77400
caatattggc ctcaacttac tgacttaact ttctattcta ggctcctagt taatcctcac    77460
ggctgcctcg gtgggtggtg ttatagcatt gtccccattt tatagatgag tttgaagagg    77520
tccagagagg tcagtaatgt acccaaggtc acacagcttg ccatggcagg ctgggacac    77580
aaaaccggct ctctggccct gtggccagcc atctcttctg ccccaaacac agcacacaga    77640
tcggaataat gtgaagctgg tgtccagcgg acccctctgc ctctgacttg gtcggtgact    77700
cagagtctcc ccggatccct tccccatctg gaacagggaa ggcgaggaat gtgcccagcc    77760
ttgggagaca tgaatggctg gctgcttcgt cgggctgagt cgtcacagcc tgttcagaag    77820
gtgtgacagt catgaaaggt ggcctgttct aaacagcact gcccagggct gtggcggggg    77880
```

```
ctgccttccc cacactgcat gctgattagc tggtcatggc cccctcact cccaccccg    77940 cccagatctg ttctgccacc aaaaccacga gtctcaggtc ggcagcccca cccctgtcc    78000 cagccatcct ggccttcctc ctgcttccct ggggacgagc ggcccaggcc ccccgtcaat   78060
gctgcagtgt tccgggtggc attgcccacg tcaggattgc tttgccctct tcaaaaagga   78120
tcggctgcta ccccacggg ggccttaccg ggcttcgggg ttccctgggt gggagcacag    78180
aaggcctttt gtggctgatg tgaaaaggcg ctgccacctt ggaggataag aagcgacctc   78240
tgatgagaga gtcacgttgg cagacagaag gacacaattt aacttgtcga aaagatttt    78300 tgtttccctt caccccgtgg ggcgggagtg gaatgaggca ggaaggttct gtccccttc    78360 gcatgctctc ctagctttct tctccggcgt ctcccttcc ttttcttgt ccggcctccc     78420 tctttgctct gctgagatgt cccctgtgt gtaccgcctc tcaaaacgca ccctgtctg     78480 tctgcttcag gcccgtggat agcatctctc tctgagatgc gcctgctctg cgggcttcca   78540
ctcctgctct ccttggatcc tcacaggggc caggatgacc ttgaaaagca ccggtctgat   78600
tccattggcc tcaactacct cctgggtcgt ctcctcccct cttgcccttc agtttctgct   78660
ctggggttct ccaggcaggc ttcaggctca gaggctttgc acatgtggtt ccttctgcct   78720
ggaatgctct tcccccagt aaccgcgtgg ttccccttatc tcatctaggt tttcccgagg   78780
tcatcttctc agaccctgct ggtctacccc atttcaagtg gcagcccct ttgccaacac    78840 cactgatctc cctctgcccc caaccccttg cctttcttca tcacgtgacc actgtctggc   78900
tagaggtgga gtttctaaga agtcaatgat gcttaagctt cagagcccct catcagtagg   78960
ttccaaggcc cgacacctga attgatactg ataatttttc attctttttt cataaggaat   79020
ccactctccc caccaaactg tataagcttc aggtcccaca gaagcctgga tcgacctggt   79080
cctatgtctg acaacgcatc tgttttcatt ctactgtgtc tctccctcta ctgttaaaaa   79140
acaaactcca agagggcaga gggtttttta aaattattta ttcgattttt ggggttgtgc   79200
cgggtcttca ctgctgtgtc tgggcttct ctagttgtgg agagcggggg ctgttctcta    79260
gtttcagttc acgagcttct cgttgtggcg gcttctctcg tcgcggagca caggctctag   79320
ggcacgcggg ctcagttgtc gcaacatgcc agcttagctg cttcctgcca tgtggaatcg   79380
tcccagacca gggatcgaac gcatgtgccc ggcactggca ggtggattct tagccactct   79440
acctccaggg aagtctagaa ggtaggtgtt tttgtctttt tttgtaaaac tattttatct   79500
ccagggtcca gaacagtggc tatgcacagt aggagcttaa taaatgttgc tgtatgtacg   79560
tatatatgac aactccaggt tcatacttct ttcagggcgt cacatttctc ttaggataaa   79620
ggtcagcctc cttaacacac cccacaaggc cctgcccttc tgcctgctcc cagatgtgct   79680
aggattcaga ctcagggcct ttgcacatgc tccttcctct gtctgatgtt ctttctctcc   79740
cctgcctctg cctccatcag gtctctacag cgggcagtct gcatcagtgg gcactccaca   79800
tatgtgggct ccacagcctc agatatcgat ggctgacagt accacaccat cttagctgag   79860
cgacttgaac atccacggat ttcagtatct gcagaggtcc tggaaccaac ccctgtgga    79920 gactgaggga cgactggact tgaatgctgc ttctctgtct gtgcccagcc tggccctggg   79980
gatacgtgtt ctgggaggat cttggagctt ctgttgatag cacttgctgc caccctcacg   80040
tggtatccat gccattgctg ggttagtact tatttccctc caggactgtc agctccatca   80100
gggcaggacc gcctcttgtg tgctcctgta tccccagcgt aatgcctgac atgtgctcgt   80160
ttttactgac tcagtcaaga gctgctgagg agatgtgcaa gataataata ctttaaaaaa   80220 aaaaaaggg agggaaagac agaaatcagg cacagttaat atgaaaatac acaaaatcac   80280
```

```
agactctctg gggcttccct ggtggaacag acagtaaaga atctgcctgc agtgcagggg   80340
ccctggattt gatgcctggc tcaggaagat cccctggaga aggaaatggc aacccattcc   80400
agtattcttg cctggagaat cccatggaca gaggagcatg gtgggctgct gtccatgggg   80460
ttgcagagtc atacatgact gaacgactta gcagcagcag tagcatgtca agtcagagtc   80520
gggagggcat ttgtccacag cttgtagact gtggttcctg gtgccctggg gatgcgcctc   80580
tgggaattct gggaattcta tggagtggtc cctacagtcc actgctgtga acgtgcaagt   80640
gtgtgtgttc acatgtgcac atatgcgagt gtgtgttcac gtgtgtgtgc tcatgtacac   80700
gtatgcaagc gtgtgtgcac acacacaggt gttgtgactg ggggtcaggg aagtagaacg   80760
agctgcatac ggacagatct cagagcccca ttcccacttc agacagagca gttctgctttt   80820 tacctgttga ggtattgaac ttctgcttct gatgttgttt gaaagaaat aagctttcca   80880 tccaaaatca aatttggaaa tttctgatct gatttacgga gaaggcaatg gcaccccact   80940
ccagtactct tgcctggaaa atcccatgga aggaggagcc tggtaggctg cagtccatgg   81000
ggtcgccaga gtcggtcacg actgagtgac ttcactttca cttttcactt tcctgcattg   81060
gagaaggaaa tggcaaccca ctccagtgtt cttgcctgga gaatcccagg gacgggggaag   81120 cctggtgggc tgccgtctat ggggtcgcac agagttggac acgactgaag tgacttagca   81180
gatctgattt aacgcccct ttccatttta gggatgagta aactgagatc tagagatgga   81240
ggtccttgtc ctagatcaca gagtgaaagg agaacaggac tgggaccaac catcaacccc   81300
cctgccccac cccgaggccc tgcccacggc ctgttccctg atgccagcc ccctctttct   81360 ggttttggta cagcgctgcc gcctctcagc tgtgaccagg cggccgaaca cctggatgtc   81420
ctggagctga tggaaaagct ccagggatcc ccatgcttta atcccatcat gtaaatcagg   81480
aatcatttta cttgcagaag acatgacttc ctacatgtgt gctggaaaat tcacattgtc   81540
tggtacacct actcaggggg aaaatcccaa cacacaaaac taactttcct ttgagtcttt   81600
cagttgatat ccactggcta cctgttcatt tatattattg tctgaaagtg ctcctagcag   81660
acacccagca gcaagcactg aaggttaga aaaatctgtg ggagcaaaaa gcaaatgatt   81720
ccatccacta gtttcatggg gggtgggggg tgtaggtgtg aagatatgaa aaaaaattaa   81780
aaggatcatt tcccatatac tttgatgctg gaacaaatac ctctggccaa tgtataggg   81840 agagaaaaac cattattttt cattctttaa aaataagtct tcaattcatt ctctgattac   81900
aaaagtacat cataggtact tctggagaag tagaacttct agaaatgtac atgacttaga   81960
aagtaaatat cagtattatt cctagccccc tcccaccaac cacagctaat tccaatttgc   82020
tttcaaacct actaagtgtc aggttctatt ctaggcactg gaggggcaac agtgaacaaa   82080
catagatgac agttgtgccc tgatgggact cacagctgaa tggagaagag ggggaaatgg   82140
tcacacaatt gtaaaaagtc aactgtgttt tgctttgaaa agaagagata tgaaagcata   82200
aaatctgggg agaggacctt tcatgaggat ttctggcgaa gctttgtgag ggagtcaaga   82260
tagagttggg aatctcccac gtttgtgaag atgggaagaa agagaggtca agggagaaaa   82320
aaaacgtcca tgcaaaggcc tgtggcagga gggcaaagag cgacatgacc agaggaactg   82380
gttcaggcga agcggcagag gctcctgggg ttttgtgaag accacggtaa gattttggg   82440 tctttgttct aagagcaaag aaagctataa actgtttaaa gtaacggttg ctgtctagtc   82500
actaagtcgg gtccagtgct gttgcaatct tatgaaatac ggttctccag gctcctctgt   82560 ccgtgggggtt tccaggcta gaatactgga gtgggctgcc attctcttct ccagggatct   82620
tcccaaccca gggatggaac atgcacctcc tgtattggca ggtggattct ttactgctga   82680
```

```
gccaccaggg aagccccttaa aataaggatg cgtatgatta tatttgcatt tgatatatat   82740
tcattctgat ttttcttgat gcatacatgc atcagctaat gttgtagcag aatggcttaa   82800
gcagaagaga ttctgaactg gctcttgtgg ctgcagcttg atctggggtc tcaaacagtg   82860
tctccagttt ctctccaatt ttcatccttt tcatctgccc tcctgactct tccaagcccc   82920
atggagggcc tcctgtggca ccaggcgttc atacactatc tttcagcctg tacctcagtg   82980
aaaacgacta acctgcctcc gctggcatgg cagttctagc cctgctcatc ttcagccaac   83040
ccctaaacca atcactgtgt ttagaggaat gcgatgctct gattggctag gcctgagtca   83100
catgtttcac aaggggggcgt ggaataaact ctacccagag catatggcct ggtagaggga   83160
aaatccttat gatgaaatta cttgtagaat tagggctgag attgaccagg agagggcgca   83220
gggtgtgttc taggagggtt ggaaatgttc tatattcctg atctggggggt agttaggcag   83280 gtatgtgtgt gtgtatatgt gtgtgtgtgt ctgtgtgagt gtatgctaag tcacttcagt   83340
cgtgtccaac tctatgtgat tctatggagt ataggccacc aggttcctct gaccatggag   83400
ttctccaggc cagaatactg gagtgggcag cctttgcctt ctccagggga tcttcccaac   83460
ccacggatcg aactcaagtc tcttgaattg caggcgtatt cttaccatc tgagctacca   83520 gggaagccta agaatactgg agtgggtgat ctatcccttc tttaggggaa cttcctgacc   83580
caggaattga acccaggtct cctacattgc agacagattc tttaccagct gagctcccag   83640
ggaagcccat gtccagctat accaagattt taaaaaatac ctcactggag agtgggaaag   83700
aggaaaatcg ggatgttgtt accaagagga tggtgagtgg gtgttcatta taatacatta   83760
atatgctgtg tatatacatt tgctgtgtct atacacaggg tttcccagtt ggccctagtg   83820
gcagagaatc tgcctgccaa tgcaggagat gcaaagatg tgggttcgat tcctgagttg   83880
ggaagatccc cagagtagga aatggcaacc tccttgagta ttcttgcctg gaaaatacca   83940
tggacagagg agcctgttgt tgagtcgagt ctctgagtcc catggactgc agcacaccag   84000
gcttccctgt ccttcactat tttctggagt ttgctcaaac tcatgtctgt tgtgtcaatg   84060
atgccatctc accccataat ctcatcctct gtcgccccct tctcctcctg ccttcaatct   84120
ttcctagcat caggatcttt cccaatgagt tggctcttca cagcaggtgg ccaaaatatt   84180
ggagcttcag cttcagcatc agtccttcca aagagtattc agggttgatt tcctttagga   84240
tttgagggct acagtccatg gggctgcaga gagtcggaca tgactgagag attaagccct   84300
cacacacacg tatgtacgta cataatatat acatgtatgt tatgtatcag ttcagttcag   84360
tcgctcagtc gtgtccaact cttttgcgacc ccatggactg aagtatgcca ggcttccctg   84420
tccatcacca actcctggag tttactcaaa ctcatgtcca ttgggtcgat gatgccatcc   84480
agccatctca tcctctgtca tctgcttctc cttctgcctt caatctttcc cagcatcagg   84540
gtcttttcca atgagtcagt tcttcacatt aggtggccaa agtattggag tctcagcttc   84600
agcatcagtc cttccaatga atattcagga ctgattcctt taggatggac tggttggatc   84660
tccttgcagt ccaagggact ctctagagtc ttcaagaaca ccacagttca aaagcatcag   84720
ttctttggca ctcagctttc tttatagttc aactcttaca tccatacatg actactggaa   84780
aaaccatagc cttgactaga cggacctttg ttggcaaagt aatgtctctg cttttgaata   84840
tgctgtctag gttggtcata actttccttc caaggagtaa gcgtctttta attccatggc   84900
tgcaatcacc atctgcagtg attttggagc ccccaaaata aagtctgaca ctgtttctac   84960
tgtttcccat ctatttgtca tgaagtgatg ggaccagatg ccatgatctt agttttggtt   85020
ttcagcttta ctgaggtata attggcaaat aaaattataa tacaataagt ccctataca   85080
```

-continued

```
tgaatcttca agttgcagac tttcaaagat gcaaacgtgt gttccatcac cgtcaggtgt    85140
gagtgaaact gcggcttgcc cttcatctcc tattgttgac gatccttcag ctctactgtc    85200
tcccacctcc tctcccttct ccagtcagta actcttcttg actgttcact cagtgccagc    85260
ccctgtgtgc cagctgttgt actgtagtac tgtactttc aagattctgt actgtgagat     85320
ttaaaatgtt ttctttatgt ttgttttttt aaaatgtatt attgtgtga aaagtattat     85380 aaacctatta cagtacagta ctatatagct ggggcttccc aatgtctcaa tgggtaaaga    85440
atctgcctgc aatgcaggag acacaggaga ctgtgggttc aatctctggg tcgggaagat    85500
cccttggagg aggaaaatgg caacccagcc cagtattttt gcctggaaaa tcccatgggc    85560
agagaagccc agcaggctgt agtccaaagg gtcacaaaaa gtcagacaca atataactga    85620
ctgtgttagt tgggaaccta ggctaacttt tttggactta caaacaaact gaacatagga    85680
acacactctt ggaatggacc tcattcgtat gcagagaatg tccaacgtga tggtttgata    85740
tatggctgca ttatgaaagg attcccacta cccagttaat tagtgcatct gtaagctcac    85800
gtttcccttt tttgttttgt tttcggtgag aacactcaag ttctactctc ttagcaaatt    85860
ttggcgttac ggtacaggat tttcaactat ggacaccgta ttgtatgtag atagacattt    85920
ggtgagaagt gctgtagcac a                                              85941

<210> SEQ ID NO 3
<211> LENGTH: 1686
<212> TYPE: DNA
<213> ORGANISM: bovine

<400> SEQUENCE: 3
gtttaacgaa ttcgcccttc aggcaatttc cagggaagag ccaacacatg aacccagagc      60
tcttgatgtc cagagaagcc atggagtggg gaaggagaaa gcaagaagc agctactcag     120 ccaccagaga agatccaggt ggtctgtggc aactctaagc cctcccctta cggggtaaag    180
ctccacccac ctgggagcag gctgcccttc tccgcccagc ctctccagca ccaatccatt    240
aactgcagtg aaccaagcta ctagtctgtc tccccatccc gacctgaagg cagaggctgt    300
gtccagggcc tcacagaatc ccccaggagg ccaggaacag ggacaggcaa agtctggtga    360
ggagctggaa ttaggcattt cagtcccctt ctctgtgaaa actgggcatt tgggccagga    420
ggcgtctggc gtctcttcca acactgggcg ggacacccat cccgacacca ggacccatca    480
tgttggaggg ttgacttccg ggcctcaacc aaggtccccg acctggcagg tggtcagcct    540
cagaggagga aataagtcat gtggcctcag ctaacacccc ttgggctctc actgccgggt    600
ttccacacac ttaggaaaca aaaccccggg tcagggagcc cagcagagag caggagtccc    660
tgccccactg ggtcacattt ggggatgagt tcctgcaatc ccatcaggtg ctcttctgtt    720
gccctggcaa ccccaggagc tcccagtgga gcccatctca tttctgaagg aggggaaag    780 ggcaagcatc tgctgtgcat gagacacaga gtgtgtggcc aactgatgg attacagtga     840 aaggagacgg taggagaagg ggcacaggta ccccagctcc ttcttccttc tccaccctct    900
gcagtccttc cttccttccc actgacttgc ctgtggggtt ccattcccct ttaggcctca    960
gtttgttgtt gattagtggc taggtcgtgt ccgactcttg caaccctgtg gactgtagcc   1020
tgcctctgtc catgggattt tcccaggcaa gaatactgga gggggttgcc atttccttct   1080
ccatgggggt cttcctgacc cagggatcga gcccagccc gcgtctcctg catcagcggg   1140
tgggttcttt accactgagc caccagagaa gcccaggcct ccgtttgcca agacggtgct   1200
caggctggtt tctcttcctc agaactgagg aaatgctcaa gagctggagg tgggaggagg   1260
```

```
ccccactgcg gtcctcaagg gcaggacctc tatgccacct aggatgaagg ctccccacgc    1320
ccacacctcc catcccttg atgcctggag ggacaggaag cagggtggca agatggtgcc     1380
tctggtctag tccacacccc acacccctgg tttggtggtg aggtggcccc atgcctgacc    1440
aggaagatga ctccttggcc acagactggc ctcgctgcat cctctgctcc ctacctctcc    1500
tcctgaggtc cctggggtg gggggaattg gtggcctcct aggaaagaac ccacttcatc     1560
tgtactacag ataccacccc cgaccctgag accacgagag gccttgtctt tgcaccttaa    1620
cacacctcgt ctttgctcct ctgtctgccc tgccccagc ctccattggt ttgactcctc     1680
agtgcc                                                               1686

<210> SEQ ID NO 4
<211> LENGTH: 45693
<212> TYPE: DNA
<213> ORGANISM: bovine

<400> SEQUENCE: 4
gtgtgggtgg gctgggtgag agctctagga agcctctggg gcttgttcca ccccaagg       60 tcccagggag actctgcctc cccggggagc acaaccagc aaccgggaag gccacaggtc     120
atgaagcaca ggctcttagt caccgcctcc tcgcccaaga ctctggtggt tgcacagacc    180
acaagcatgg tccatccccc ggggagggg tcgcacagga tcccatgcag gttctcattc     240
tcacctgcac gctgctgact atactgggtg catccttgca agtgctaggg ggcacgcaag    300
gcttccatat aggcgtgcac atgaattggt acgcatgtat ggtccctgga atcccctgg     360 gacagacacc ctggtccagg acagatgagt gtgagccggg aacaccaccc cacagtcacg    420
cgggactcgg gctcacaccc actcccaggc ctccacccgc accagtaaag gtattgggat    480
gtgctcatag cttccttccg gacaaaagaa aagtgaggag ggtgaggagg accaggaaat    540
tgggtgggcg ggggagcggg gagagtccaa attggtacca gcacagtaac ccctagaggg    600
cctttggaaa ctgtccaaac tcccggtttc gtagaaataa aatccggatc cagaaggga    660 agggacccca aggccgtgcg gggagttaag aacagcgtgg tggagacccg ccaccatctc    720
aacctggacc ttagtgcctg ccccaaacct tccacagcct ctccatcttc tctgccatag    780
ccttgccctc ggacagcttg ggaaacctgc tgctctgccc cgacccggga ccccggcagt    840
ccatcttcga ggtgcttggg gctgatgccc aggttcctga accctagtt tggaaggaaa     900 tccgctctcc aggacaatct gctttaagaa tccgatgaaa tgcgcactga ctccctctct    960
ttctaaaacg cacagctgca acgcgcccac gcccagcagc cccaattctg tggttcccag   1020
gacacgacca accgaggtgc ggtcgtaggg aaagcagggt agttggcagg tggtggcacc   1080
tccgtcagtg accctccacg cgggagggct atgatatctc cccgtaaccc tcctctcaca   1140
cgccgtggtg accctgctag ctgcccccgg agctgaattc cgaaaccgcc cgctgcccag   1200
tccccagcct ttcgcagctc cgagcctcct cttttgcacgt ctctttccct ccccaccaag   1260
cctcagctcc ccttccgcgg ctccctctct tccttggagc tgccggttgg gggtgggacg   1320
gggcagagaa gagagtcttg gctacggcgg cagaatgttt cagggaggcg cggggtgcac   1380
ggccgctggt gtgtctgggg tctcgcgacc cctccgtgga cacactggag gctccggtcg   1440
cactcttgag tcagctttgc tggagagaac aacgtccagg cagcacggcg tcggctgccc   1500
gcggccaccc cagggaatgg aggtgggggt gttaccgtcc atctgtaggc gaaagaagag   1560
ggcacaggct gcacctctgg gtgggaggcc cctgggagac caccaggaac tcggatggct   1620
gagaagcacc agcttatggc tggaaggttt gttggccaga cagaagtgtt tctctaaaaa   1680
```

```
ggccctgttt tgaaggaagg ccctcttctc aactctctag tctggaccag ccgtctcggc    1740
cagtggtgtc cacagcccca gaccaagggg tggggagcgg ggttgggggg gggagggtgc    1800 cttttcactct aaattcgctg ggtggtatca tcccgcagct gagtacccc  ctgtctgggt    1860 tttcgaatct gatgacccgc cttgtgaccg taatacctcc tggggaaccg ggtagcgagc    1920
gggagcatgt ggccaggtgg cacctgggta agctgggtcc agatacagga ccaccctccc    1980
accgccagtg cctcagtcct tcggtttcct ggtggggagt ggagggtcct gggagctgag    2040
gacgcggagg ttgcctccag ccaggcattc tcccagatcc atcccaccaa ctccccttcc    2100
ccggccgcaa aaggcgcacc cgctgcagct cgggcttcgc gggtctccac cccaagccct    2160
cggagccgct ggggatcccg gcagttttcc tatcctttct cctgccgccg cttcgggcac    2220
cctggaccag aggtgaacgg aaaagtccaa gccctgaca  aacgccggga cccctccctc    2280
cctcccccca gcccccgtcg acgcgaaggt cgttatattt ccattttata tttcaatttg    2340
tcaccgaaac aaagccgcac gcagatttgc gggaagagag aaaagggctg ggaccaaggg    2400
ataaggtatg atcacggggc agcgtgcgcg caactgcttt ctgaaacgaa agttctcatg    2460
gagcatggcg acattttacg tttggtactg ttaacttgtt ttcctgttgt ggcccctctc    2520
tgcagcgcac caaactcggg gcttcagcga cttcgggaga gcctttggcg gcaaggtttc    2580
tggggcagcc ggcagttccc agcaagagtg aggactgcgc aaatgcccga caggcaaggt    2640
tattctctgg agaaacgcca ctatcgggag aggggcaggt tctctggctc ccccgaagcc    2700
tcttctgaaa tttccttgaa acaactgaaa aaaaatcccc caccctagtt ttcgtttagg    2760
gatacaatat gtaaatggtc tgtatctcca tccacgtgat agttatacct ggagcaagta    2820
attaacaatt cttccaacgt ttcattaacc gggtgcttca ctgtatataa attataataa    2880
agacacatcg actgttttaa aataatagga gacctttaat ccaggtctgt ttttctattt    2940
aagatgctat gtgtttaggc tgaactgttt cagcagactg agggctatag aaattaacaa    3000
agtaaaaaat taaaagcatc tttcttcttc tcctccccac ccgcaactga ctggggatcc    3060
tggacgtcac agctcctacg cttgagtttt cccttcatca tcccacaatc atccatgggt    3120
tcttaaggct aatgcgcgcc cctcagtttc tccctgtctt tgggggat  ccctcttaca    3180 caaagcacac cctggttctt tggcttaatt tgactatgac ccacgtggag tttacatatt    3240
tcgtggtgtg tggattgtgt cggtgctggt gggggaata  aatatctcta gcattcaatc    3300
actgcgtcta attcgacaaa tcaaggccag cccctcggtg gcgccccagg ggtctccggc    3360
cgggctcagg tctcccaaga cctctgcgcg gagagcactg ccttcacgcg ccgggatggg    3420
aaggtagcaa tcggctagca acgaaaacct gcgtgcacca aatagaaagc gaaagagaag    3480
gaagtagcaa gactgctttc ggaagcgtcc cggcgcgcct ggccgaggcc tggggtggcg    3540
agcgcggctt ggagagttgg ccccgttg cgagcgagat gccagggtcc cgactcctgc    3600
agggatgagg ctctttgagc agctgaaaaa cactgggtct ccaacctggc aggtctcctg    3660
gggtacaagc cgccaagtat gggccaggat gggcgggac tttggaaggg cgacgtgtgg    3720
ccccagggaa cctggtgggg ttgggattgc agaaggcagg atacgtggg gctcttgcat    3780 aaaatagtga atgtgtatgc ctgaagggaa ccgtgactcc acggttcggg acccttcag    3840 taccgacggg gaagcagtgg aggcgcagtt aggggcagga acttctgcag cctggattcg    3900
tgtctcccct ccaagttcca catctccaag cagcaacccc cccaactccc cacaggaggc    3960
tgcaggcggc ttcctgctcc aggctctcgg gctgcggccc cagtgcagcc cccggaccca    4020
cagctctccc gtcaaggagc gcttgtatcc aagcactggc tcccggcgga ggagacctca    4080
```

```
gaccctcact tttgctccga gcagttacac agatggagga actggcctct ggcccccgga   4140
ccaacggagc tggaaaggtg gttgccaggc cgaagcccca ctgggtggcg gcccgagcca   4200
cagtcagcct ggcaccaaag ctgagtctgc ctctgccttt cccaagctcc tgggaacctc   4260
cgaggctttt tccctcctac tcacttactt tcccccttt g gggtacacac tctcacgagt   4320
gtagggagag aaccatgtcg gtgtgtgtgt gcttcagagt ccctgcctgc tgccagctcc   4380
aaaggtcttc tgcgcaaccg cctctctggg cggcagaacc tcacctcttg gtgcctcggt   4440
tccctccttt tgggcctaat gtgcctttcc ccccaacccc cacctacaag agccagaaat   4500
ctcctcctgg ccagagagac agcagctgct gagagaagga aacgaataag cagagctgtc   4560
catagtttgc ggccgcaccc tgagcagtgc ctccatcttg gacagccggg gagggcagtc   4620
ctgttggtgt tttccaagct gccgtttgtc ccaacctgcg gctttgggat tttaccagcg   4680
cagggtcagc gcccgccctg tcctcacaag cgggtgctta caggttccca gtgcagcaca   4740
gaggccgacg gaagaaacgt ggaggggca ggctagactc ctctgtctct ctgggctggg   4800
ggccgtgggg gtgtgtgtgt gagacattta ctacccagtg aggcctgact gtcatctccc   4860
tgggatgcag gtgaggaaat ggggctttag agaagctcct cacacgcagg tcagcgggga   4920
gccccatggc cactgcccat cgagggtgca ttatggagac tggcagtggg ggcccagcag   4980
ggctcagagg tggtgctcag aggggtctca cactttcccc ctttccctcc aaagccgaaa   5040
acatttccaa atgagacatt gggagccacg tagaatctct ccttacctac tttctcagac   5100
gccttgctgg ggaatttctc taaaacatga aaaaccagtg cagagggagg gaaaactgtc   5160
cgtggggcgt tccgtctggg atatacccac acctaacgtt cccaaaggac aggaaccagg   5220
agaggcctgg cggggggagga agcctgagtc ccagggggca gggggggcgt gcaggcaggg   5280
gcacgtggac agggtgaaag cccctcgctg cctgagtgtg aagaagcat ctgtgcggag   5340
atgcggctgt gattcacgcc gcctgaactc attccaacag gaaggtggag aggcgaggta   5400
gaggaagtgg ggagagcccc ggagctctca gcctgctgtt ctctgggttt gagaggccac   5460
acgagtgtac taggcgtgtg tgtgagcctg ctgctcctaa ggaagaggtt gtgtgtgtgt   5520
gtgtgtgtct gtgtagaatc caagtgtaga caagagtacg accctgtgaa tgtttgtgcg   5580
tgtcaacaac cacttagtgg acccccttctg agcctgtggg gagccagctc caggcagagg   5640
gtaaaaaaaa aaaaaaaaaa agcatcggcc gaagttgttt cctaacgtta ttccagtcgc   5700
caaggcctcc accccgtctc acctctgtcc ccggggcccg gtgtctcatc ccgcctggat   5760
cagtgcagcc aaaccactgt actgtcagaa ccagctcgtt tccagggccc tttgtgaggg   5820
ccgtggccca agggggagcg tgtgaaccca gcgctcctag cccagagatt ctcccatccg   5880
tctcagtttc tctccctgcc agactggagc tcaccagtgc cgatcctgta gcagaaaagg   5940
ttctggccgc aggccttcct tgagaagccc tctcctcctc tttggtcgcg gcgctccggg   6000
gcccaggcct gtgtcccgtg gccgcgttca agggggcttg gaggtcattt aggcctcgag   6060
ttcccgttgg gcccaaatca ggacccagaa ccttccctct ggcccagcac cgcgccgcct   6120
ggagctctgt ggcttcctgt tttcccagcc gctcggtcct aaagcgtggt tcagaggccg   6180
gccgcctccc gggatcgccc aaggcgaagc gcttgggaac tccgattcgc tcgcctcgcc   6240
tgctgcgagc caccccgatt cgggtcatcc gcggcctcgg gcgtcttcga acccgcaccc   6300
agctggctcc cctgcgccac cgcatccccg gcgcgccccg ccggctgcgc ttcaggctcc   6360
cggccgggct ccgcacctgc gatgctccca cctgcagcgc cgcccgagga gccttctagc   6420
cggccaggag tcaggcctca gcggcccggg aacccggagc ccaagcgttg tgctgcaact   6480
```

```
gtttcccgcc gcacgccggg agccggtgct gcgaagcatc cgcttcgaag ccggcccggc    6540
aagcagcgca aagcaagcgg tttgcggaaa cggcgaaaag gaggagaaac ggactccggg    6600
ttgagtttta acagccaacg ctccgtgccc ttggccgaag atcccaagg gggctggacg    6660 gattccccg gtcccttcag agcggtcgat ccccattttc cgacccaaag tcacaaaccg    6720
ctcggcccca cgcctcccca gcccgccaac tctcgcctcc agcaagttga tcgcgtttcg    6780
aaggtcccgg agcccgggt ccaggggtcc ccagccccga gggattcgca catgcactca    6840
ccgtagcagg ggacctgcaa ggccgcgttg tggccgccgc cgccttcctg gagtttgagg    6900
ctgccgtccg ggggcgtctt gcaggcgcct cgttgcaagt agagatgcgg ctgcggcgcg    6960
ggcggctgcg gctgcggcgc gggcggctgg ggctggaact tgctgaagga gccccgcgcc    7020
ccggcgccgc tctccagagg tgctgccggg tcctgctgcc ccgcgccgta gcgggcccgg    7080
ctcttggcgt ccccgaatcc ctgccctttg gcggcggctg acaggaaagt tgtgctgaac    7140
ttatcaccgc cggggtatgc cctaaaaggc gacgagccct cccggctctg cgacaccggg    7200
ctgtagtagg cgtccatggc agcagccggc gactcgcagt aagagacgca agtctcagca    7260
ttcatgcctg gctcgcgcgg gcgacgggcg ggggcgcgag cgggagcgcg aggacgccac    7320
cgcgcgcctt ggccgggagt taggagaggc caggaggcgg tggctgtgcg ctgcgcgcgg    7380
gcctgctcgc tccccctcct ccctccacg cctctctctc tggctcctca ccccctcctt    7440
tctctccctt ctccctcccc acagctggcc aagggaaaga accgaggact gtaaaaagat    7500
tcagatgttt cggaaagttg accagatctc ccaaaccctc ttaaggtttt tgaaccggaa    7560
aaagagagtg cttttttttt ttttttcccc cgactctttc ttttttccctt ccgtctccct    7620 ctcctcctct ctgcctactc cccttctccc tcacccttac cccgtctccc ttcctttctt    7680
ttaaggaggt gctactaatt cggtcgccac tccgagggga ttttacgcgg agccgcccga    7740 aggcctttc aagtcaaggc ggggccaggg aggtctctgg actccccggg ctcccgaggc    7800
taggtgggtc caagcttcgg cctatgggag ggggcatgc acaactttag tgatggatta    7860
aaaaaacaaa aacgaaaaac aatccaaaaa atctgacagg gtttgacatt tggaggcaga    7920
ggggccgcta acttctgggt gcaggcaagt cgttggggca catccctgag aatttagcgc    7980
gcagctgcta cggtaaatgt agcgcgcaac tttcctgtct tcccaactgg tgccttttgc    8040
tctatttcca acccctttc cctattgtcg gttcctcctt gaaagtaaca cagtcacaca    8100
cacacacacc cgcgcgctgc agtcaccctg cgcacggcca ctttcttgtt aactgttttc    8160 ctcccttttaa gggcacgggc gagggttgcg gaggaatcca tgttcactca gacactggag    8220
aaccagcagg ctgctccagt ttctgaagct ttgcgcccag cccaggagat tttctggctg    8280
ggttaagggc gctttgagag tggggagttg agagacccgc acctcaccgc tgcgcagtca    8340
cctgctcact gctcaggtgg gggtgagaca gtctaatctc tggcctcaca gtccccacta    8400
gaaaagtaat ggcctggatt tgacggggttg tgtgcgcctc agggccctgg aaccggccac    8460
agcaagggaa caggacttca ctacagtgag ccgcgtccct tctacacggc taatcactga    8520
ttgcgcctca cagcaaccgt gcttggtgga aatcggggtc cccaaatttt ccgatgagca    8580
aaccgaggct cagagaggta tgagcccttg actgaggtca cacagctggg aagcagcagc    8640
gcctgccttg aaacccacgc tgaggctcgt ccctccgccg atctgggatg acgttgctga    8700
cagcgaaaac gaaaccacgc agaacggagg aaacggagct ctgactgtag gatgactcgg    8760
gtttggagga gcccattaag agcagtcctg gataaactgc agagaaaagg atagaagaca    8820
tatctcaagg gaggctggga gtggggtgaa aggtgaaggg gcaaagtaaa atgagagagg    8880
```

```
gcctgagcgc cctgaaccca ggaatgtagg tcagaagtca atcttctgca cctaaaaggt   8940
ctccctaaga agaaatatcg ggggggggggg ggcgtcatgc ttctaccccc aaccttatcc   9000
tagctaatcc tcaccccac ccctctccct tggtatctct gctccttgct ctgccgccga   9060
ctgcgcgatc ccacatctgg tttccatcgc ggcttacctt gaagtgctcg ttaataaaga   9120
tattctgcaa accgtggcca ggggtgcgca ggcctgaacc cctcccccac tgcccatagg   9180
gacccgcacc tctctggctc acggcccaag ccaagtgagg atctcatata tactgagtcc   9240
ttgttgtgcc agaagccatc cacaggttgt ctcttgggc taccccagca atctggggat   9300
gctggtcgtc tcctcatacc cattttccag atgggtagac tgaaactcaa agacaccaac   9360
taatttccca acctcagtta gccaaaagtg agtgagcctg catcatccca aattctcctg   9420
ttcagcccta gtttctttta gttcttagac tctgccaagt tctggaattc ccgtctcatc   9480
cctgtgcttt ttgtcttgct aataacttgg tattcagcaa agagtgtctc ctccaggaag   9540
tcttcccatc tttcccagtc gaagtgcatc tctgttttgg acttcaggtt tgtctggttg   9600
ccggttcagt gttcatctcc atcgcactag tctgaggttg caagagggca gcttctgcgc   9660
tgcctggcgc cccacaaata tttacagaat aaaatattag agcctgggtt ccttccactg   9720
ctcagcgagg cagttcccag cgtatttggt ttcctctagc caaggacgac cggctgctcg   9780
ccctcccct cttcatgaat caagcgacaa aattaagagt acgctggcct ctccctggcc   9840
gcacaagaac agtgagttct ctcagagaag gggccaggcc tgtcttgttc actgcagggc   9900
ttggcacatc ctaggtgctc ataaaatgcg cattgaatga atgaatgaaa acactgagcg   9960
atccagtctg agatcttaaa ggtgcatttt cgctaaggtg ttccaagctg agaaggctac  10020
tccggtcccc tgtgccccaa aactggctac tagaacccag atgatgtctg cgatccttct  10080
acttctctcc cctcattttc caattccagg agtagacaca agggggaaac taagagaagt  10140
gagctatatg gggtggggaa tggtgactag acaggtagaa tggcaatcac catattctct  10200
agtaacttct gagctgctct ggctgtcaat gcaaaaagac aaaaccaaaa aacaaccctg  10260
ctgcgatcca gaaagctttc tttgcattgg tggtatagtg gttagcatag ctgccttcca  10320
gaaagctgtc tttgagtgct gcctcctgcc acctacccac cccacgatct tatcaccagt  10380
ttcatcacta ctccattatt taacctttc ctggccaccc cccacccctc accctcacc  10440
cagggaggaa tttcagcctc ccagccctcc aggcacagac tctggcgtcc tcagtcagaa  10500
gccctcctgg tgcactgagg tcatggttct tggaaccagc aggggggcct tctacctttc  10560
aaggtacctt agaggtgaac tcagaaagag tgagcatctg cctgggcctg gaatgtgcat  10620
gtgggtttgc ctgtgaccag tgagaacatt ctgggcatgt tgttttcccc atgaaaacct  10680
ccacagaccc cctgcccaag tcccttcaaa cacgtctttt ctaggagaat gagaagcata  10740
gctggttatt tctgtgtgcg ttaagtcatt tgcaggttga tcagcccatg cctccctatc  10800
tccctttatc tctccctcca tctctccatc catcaatcta tccatccatc cctctgccat  10860
agctgaaagc caaggctctc ccacccagtt ctcctgcaag ggtgcggggc atctttccag  10920
ccagaagtga ggtggatgac tctgaagcct ggttctggtc tttgctctcc ccttgcatta  10980
tttcttcctc ggctaaggct cctccggctt gctgattgtc cctccatcac tgatgtgtct  11040
ggcagtatct ctacttct gatcacttta atgtgccagg aatagtgggt gcagccagtc  11100
cctctgcttc aagtcctgat tcctgtcccc agccctggca gacacacccc ttggccatcc  11160
cttctctctc ccagtggcac tgtcccactt caccctcttg gaagcggctt cccccttcga  11220
tgggctccgc acacagcctg ggaaggggga gtggtgacaa agtctttgtc aaggccaagt  11280
```

-continued

```
gctcagtgtc acctcctctt ggaggccttc cttcaccacc ctagcatctg cctggttatt    11340
tccttgatcg tctctattct gacctgacat tttctcccac atttatcaac ctacttgttt    11400
tattgtctgt cttcctacca gaacgtgagc ccatagctac actcgcccca ggaggaaaat    11460
acagggcttg gcacatagca ccactcagca ctcgataaat atctattgag cgagtgacta    11520
aatgagtgaa tgaaccagta agttgaatga acagatgaag aatactggag gagaaatgca    11580
gtaactgccc agtccctatg gctcagggcg ggagctcttg aggctggggt gtagaactga    11640
gttggagaac ggggaggcat ggactggaag ttctttcttt taaaggggag gacggattcg    11700
gagccacccc ctttggtctg agctccctcc actccatccg gcgctgcagt ctccacctcc    11760
tacagacagt ggagctgggg aggggagcag ccctgcttat ctgctacttg acttctcctg    11820
acagtgcccc aagtcttggc ccccagtgtg ggtaaaaccg ggaccataca cacctcagcg    11880
agtcacgtac tacttggctt gcacttgcca ctttgtaaat gccaggaggc agcaaagatt    11940
gctcgaaagg ttggggctgc tgaatagaca ttttggacat ctgcagaggg gcaggaagag    12000
tcaggatatg aaggggaagg gccagggatc ttacaaatct tgggcagaaa tgcttctgct    12060
ctgcagaccc gggcacacag acctcacatt cccagcaaga cataaattag caactgtgtt    12120
ttggacaact gttaaaagtc agctcttgca cacagatctt agcagtcctt gaaacggccc    12180
ggtgatggta ctattatcct cgttttacaa tgattaaaaa aatatatatc gaagcacaga    12240
gaagtgaagc gactgcttac agtcacacag caaagcagac gacttgggat tcgaattcaa    12300
gtgacttgat ctcagaaccc acgctcttaa ccactcgcg ttctctgaga tctctgcggc    12360
gacgcgggtg gaaaggttcc cgagtcctct cggcctaccg ggcgctcaga gaagctcccc    12420
cttcgccagt gccgcgggca taggggcaag gggctggggg cgctcgccag cctcggccgc    12480
acgcgcggac cctggtcctg tggcggagga ccaggctatc gccccgaggt ctgtgccagc    12540
gttcgccacc ggcgtccagc cttcagcgt ctgcccgatc tcccaggaat gcagacacct    12600
agtcaccttc ctgcattcgg ctccagcccc cgcgcagccc ccgggacagc cgcgcctgct    12660
gtgggatgga gcccgggagg gaggcactcc ccaccaacat tctccgaaga ctccaaggcc    12720
acgcggcgtg ggcgggcgca ccccccggcag tccgcaccct agtgcgctag gctgcccggg    12780
gcaagaagcg agggtctctt aggcgttttg agccgaggga ggacctcgcg aggggccacc    12840
acgctccgag agccgcgggt cgcctgcgct tcctcctggt ccacggcccc tatctctcac    12900
ccggaccggt actccccgtt taggtgttta gcgttcgcgg agtctggccc ctggtcggct    12960
ccctggtggc gcacgatagg ggattcagcg cggggagagg cccagaagg acctcctctt    13020 ccccattctc cgcttctaa ggccggggag cgagggtcca aaaggaggtc tgcgttcagg    13080
gacgtatctt cattcacatg ggaaaaacac taactcccga aatgcgggta aacgggcgt    13140 tctcgtgggt tctagacgct tgcacaactg ttcggtcggg agggtcaatg aaatacaaag    13200
ctggagggat gaaggttttt aaaatgacca ggcgcgacgc cccgacccgc aggaacgcat    13260
ccctccaccg cccttccccg cccccacggt gcgtttctgg gacctgcctt cccagtcgcc    13320
ctggtacttt tcagcgtggg actgggctc ctgtctgaac gcgcggtcca ggcgcacgac    13380
agaacctggt tccctgctcc ccacttatcc gcaggggcag agcaaagagc tcagggcagg    13440
gagagagaac tgagagggcc acagctgcg aaactgcagt ctggcgaacc ccccaggaaa    13500
accgacttgg ctgaaaagct cgtgagggga ggcctggaca tcgccggggc gaccgcctta    13560
atcctggatc cggagaggaa gttggaaccg gaagtcctcc tacggggtc cttgcaccccc   13620 ttgcatatcg gttacagccc aggagaacac agatcattca cctccgcaga taattcccaa    13680
```

-continued

```
acgtcattag ccaaaacccc agccaggtgt tgggactgga gccccgtgtc ccctctttgt   13740
cttctctgtc ccttctctcc tggaagccat tcctctaggg tttcaaaaag atgggccgtg   13800
ggaaggtgga ggccagaaca caccagctcg gttatacagg agtcctgtgg cgccttgtgg   13860
gcagaaatga ggtcttattt cctggggtg cttgctgggt ggagaggatc tgcccttccc   13920
cgctcagcct tagttctagg gaagtatatt tcgaaacttt ctacccattt cccgctggg    13980 gagatggagg cttcagtgat ggagggaagg gagtgtggat ggccagaggg gcctctgtgc   14040
cgtgcgcgct gggactgctg agctgacagc ccacaggtct cttactgtaa ggggtggtct   14100
tcccaatcta ccgctcagat aactgagctg agccaggga gggggagagg tgaatgggac    14160
aggctaggct tcggattctc cttctttctc tctgagatcc ttggggtgag ccctgggggg   14220
ccctttccct ccgccctccc ttctccactc cgctcctgcc caccaatccc tggagcctgc   14280
tggcaccaca ccctctcagt gccctgacca cactctgctg ccatcactgg aaggggcgg    14340 ggagcacggc ccctaattcc cttttctcct ctcccacaac cccagagtcc ttctcctcta   14400
aggtttcgtt tgtccctttg tccctccct cagccccaag aattcgtggg cagccagcag    14460
cagttgtgat gactctaatt cctgcagtgc ccccagcgct ggtctcatgg atggtgggag   14520
gggctactgg actggaggac agagctgggc tcaggagccc tctgtggcag gcctctgggg   14580 ctggaaaaa agtgggggag ggtggttcag ggaggaggca gaattagtga ttccattagt    14640
ggtcaagagg ccagctgtag attcaagttt gaatcccatt tctgccactt tttcgctgtg   14700
taacacaggc tatgtgactt cgctcatggg cctcagtttc ctctcctgta aagtggggag   14760
attagtagca cctatttcat tgaacagctg ccaagatgaa ataagatcat gctcacttaa   14820
ggagttttct agtatcagca atggtaatct cctttctgtc tggaacactc tgctctttta   14880
aacttcacag cccagactta aggaaccaga aatgaccagt tggagttcct gcccttcaac   14940
catcgtgacg gccggtcata tttatctttc agaccacagc tcctccctgg tcagggtctt   15000
ttaaagcacc aggagtgaaa aggccaaagg atttttcagg ctctgcggtc cagccattcc   15060
tgatagttgg tgcacataag atggaggcgg tgcgttgtgt tttgcagagg ggtagctgcg   15120
cccaggctca gccccacctc agcgctttca gcagcagcgc cttcacctct cttgctgctg   15180
ctgctgctgc aaagtcgctt cagtcgtgtc cgactctgtg tgaccccata gacggagccc   15240
accaggctcc cccgtccctg agattctcca ggcaagaaca atggagtggg ttgccatttc   15300
cttctccaat gcctgaaagt gaaaagtgaa agtgaagtcg ctcagtcgtg tctgactctt   15360
agcgacccca tggactgcag cctaccaggc tcctccatcc atgggatttt ccaggcacga   15420
gtactggagt ggggtgccat tgccttctct tcccttgctt ctctgtaaac tcatgactgt   15480
cctgtggtgg agggtttatg tcatcgcttt acaggcaggg aaatgacgc cccttgccta    15540 cagcacactt tgagcaagag gtcaggatga ccctcaaata cggggctcct ggctcccagg   15600
cctggtatgt ttgtcccagc gtccagacgc gcaggggcc tcagagacag gccccgggg    15660 tctggccaca gcgcctcctg cctgttcctc ctccccccac cgcctgcctc caggcggtga   15720
ggtctgggcc ccagcacctg tcgaaggagc agccggagc gcaccagctg atccgggtaa   15780
tccggggctt tgtgattggc agggaggagc cctggaggcg ggagggtggg gaggaggga   15840 ggatgaagga gaatgcggga gacaagcact tgttgagcaa ccctggatgc ccgagacgaa   15900
aggagagact gataaccaag ggcgcttgac tcagtgcctg gcacatagta ggtgcttagt   15960
aaatgatgat ggttattcta tttctatcgc ctcctagtct tactagatgt ctgccaactt   16020
acctaaaccc ctccatctga ggatgtcatg ccgtaacgtt caccctctct cacctacccc   16080
```

```
accagggaggtc cttccctcct tgggaccagt ggccgcactc ccgcttgcc tggagcccgg   16140 tccagagcgc acagctgcgg ccaggctgtg aacacttctg gagtcaacct ctccgcccag   16200
agcccagggg tgggggggtag gggtggaggt gggagtgggg tcggggtggg gtggggggtgg  16260 ggagagcggc cttgaccgag gagcgaagga cggaaaagca gtgcagcctt aagtcttcag   16320
ggacgctatg gcgagtgctg gcaggtcgcc ccaggccgga gggaattgac ttggaaaacg   16380 aaaaaaggc aactgataaa agaaacaacc aaatctactc cccctccag gcttgagcag     16440 ccgccagagg ccagaggcga ggccccagga acccgcccgc ggacatcctt aggaggtggc   16500 gttttttgctg catttattcg gtgtcaattc agggcccctc gcacctctgc tgatccgcgc  16560
aacatccctc ccgccatagc cctcacccag gggctgcgag gctgaagggg acacggccga   16620
acaccccggg aaagggcaac ccggccgag tcggcgctgg aacgaacttt gactggagag     16680
ccgggccctg cgttctcagg cctccgcgcc tttacgcgct gggggcttgg acacccaggt   16740
tcttgcctca gcctcttctc cccagatgcc ttgccatcct cgggagcgcg gaaacgccta   16800
gctgctttct ccaagtagaa ttcgtttcca ggtcgtagtg gaattttttca acgggtagtt  16860 gagaacggtc agcttctgga ggcaggcatc tgggcgctag ccctgatccg ggctggtgca   16920
agcttgggcg atccattctc ctccctgtgc ttcagtgtgc ttatctgtga aatggcagtg   16980
actcttctca tctcctggga aagctgtggg gagcagagat cacctgggta ggtgctccct   17040
taactccagt tgttaatctt ttgggggata gttgcagatc ttgggggact tggaggaaca   17100
ctcagttctt gtggccaccc cgacctcctg tccagttcag atcacccctc gccaggattc    17160
caggattctg ggattcctga gtgcttcacc cgggaccatg tgactagctc tttgatggcc    17220
catagagtcc tttcgtggtg ggtcttcttt aaaaaaaatt tcactggtct tgccctcacc   17280
cttgccaagc taactggact cactttcagt ttcttgggga tgaaggtagc agacaaaatg   17340
agcattgcca aatagcaatc gatgcatttt tttcttttcc tgtcttaagg tgaaatccac   17400
ataacttaaa attaaccatt taaggcttcc ctggtggctc agacagtaaa agaatatgcc   17460
tgcaatgcaa gagacccaaa ttcaatccct gggttgggaa gatcccctgg agaagagagt   17520
agctatgcgc tctagtgatc ttgtctggag aatcccatag atagaggagc ctggcaggtc   17580
catgaggtca cacagtcaga cacgactgag cgactaacat ataaccatct aaaagtgagc   17640
gattcagtgg catttagcac atttgcagtg ttgtacaacc actgtctctg tctagctcca   17700
aaacatttcc atcaccccaa aaggacctat ttttctttttt caacactttc tccagaactg    17760
agctgtgtgc tggcggagag cgagaggtca gcacttcatg ccctttcaac ttatcttttc    17820
aatgccttta acaggagctc tgtttacaaa tgacttgcaa agttgagctc aggaaaccag    17880
ggagccccgg agatgggagt agggtgttta ttcagaatcc atgggggac cagtgtgtgt    17940 ctgagagtgt gggctgggcc cagggaatta ttggacaggg agctggagaa ccaggtccag    18000
agagagggtc tttaatggcc ctgcccatct aaaagctata gataaaattc tcatcctgca    18060
ggagtgagga ctctatttca cagacatttt aaatcacagg ctctcagtct ctttaggaaa    18120
gctacttctt tgatcatccg atgaaagctg aggaccctct tcttggacag atgcagcgaa    18180
atgctgcctt agtttccaag ggtttgtaac aaatgactgc acacttggtg gtttgcaaga   18240
acagacattt attctgtctc agctctggag gccagaagtc tgaaatcaag gcgtcccggg    18300
gccaagttca taggagggga cttgcttgcg attcccagct tctggtggct ccaggctttc    18360
cccttggctt cacttttccc atcactacct tcatcttcat gaacttctgt cttctgctct    18420
cccgcctctt ataaagacgc tcatcatcag aattagagac tacctgctgg agagcccaag    18480
```

```
atcaggtctt cttgaggtcc tttacttaat taaactgtaa atatcctttc tgtagggctt    18540
cccaggtggt tcagtggtaa agagccctcc tgccaatgca agagacacag gagacccggc    18600
tttgatgcct gggtcaggaa gatccctgg agaaggaaat ggcaacccac tccagtattc    18660
ttgcctggag agtcccatgg caggctaaag agtcaaacat gactgtgtga ctgagcacac    18720
atctttctg taaataagct cggtctcaca ggtactgtgg agaaggcagt ggcaccccac    18780
tccagtactc ttgcctggaa aaccccatgg acagaggagc ctggtgggct gcagtccatg    18840
gggtcgctaa gagtcagaca cgactgagca acttcactttt cacttttcac tttcaggcat    18900
tggagaagga aatggcaacc cactccagtg ttcttgcctg gagaatccca gggacggggg    18960
agcctggtgg gctgccgtct atggggtcgc acagagtcgg acacgactga ggcgacttgg    19020
cagcagcagc agcacgggca ctgtggccac tgtcttgggg gactacccctt taacctcagt    19080
acaggtgcat acagccagct tcatactcaa cctcaggggc tctcaggctc ctgtcaagtc    19140
agaaatgtct gattgaatgt cacaaagcga agtgaagtcg ctcagtcgtg tccgattctt    19200
tgcgaccca tggactgtag cctactacgc tcctccgtcc atgggatttt ccaggcaaga    19260
gtactgagt ggggtgccat ttccttctcc aggggatctt cctgacccag ggactgaacc    19320
caggtctccc gccctgtagg caggcgcttt actgtctagc caccgggcaa gtccaggaac    19380
gtcacaaagg aatccttaac tgccaccttc agaaaggttg gagagagtag aaaccaccct    19440
tctcttaag gaaggacatt cccacttgcg gttaaaagga gaaaatgaac ccaccatcct    19500
gcctcggtga taccatctgc cctcttgagg aaggacattc cagaacattc tagaggcaga    19560
aaccagttgc cttttacaa agaagccctt gaaaaatgca agcatcagcc agaatctcaa    19620
tttgtgaaaa tggaccgaca ggaaatttct tcaccctgtc agacaaactt cataaaggct    19680
ctgtagggc cctaccactc cgagaagcct tttaagaaaa ttgcaacttt tagtcagacc    19740
ctgagggaag tctcacaaag gtcttcacac cccctttggct cctctttgtg gggtggtgag    19800
ggaagagcaa ggttttttt tccaggggag gagagaggtg agggatcagg gctggggaga    19860
ggctgctctg aggcagcgaa caggatggct ccacagatag aggtgacagt ttcctcaact    19920
gagtccccgg gtcgccacct gtgtccttcc tgcagattgg atttatagag tgtaacatt    19980
taataaaaaa cacacacacc ttcccatttt ggtgcattaa gagattcta acaaaacact    20040
gtaatgttgc tataaatttt tctcccagca ccctcacaag taataactca gccccggaat    20100
tttgcattta atgtttattt tgatggctac attccagtca gagtgggggc tcagggtggg    20160
gagggagaaa gcaaaaaaaa aaaaaaaaa aggctcctct ttcctagcca ttaactgtgt    20220
gttttaata aaaaaaaaaa aaaaggtccc cacaaattgg ggagccaaca cttggaaagg    20280
aaggagggaa atcatgacac cctatgagga agcgccagtg gcctcagctc taggaagttg    20340
acagggtgag ccctggccgg gtcctgccaa ggtgggtctc cagagggttt ctggaatgtc    20400
gcctttgccc atgccatgca ttcagcctga atgcctttt tctcttccct cagagcttct    20460
gagcctcaga agtctcatct tctggaattt tccccacatc ctttctccac gagagttatg    20520
ggcccttccc ctgaacagta ttcattctat tcactcaaca cttgtagtgg aatctgtggc    20580
tggaacgggc tcagatgaaa gcgtattgag tgaatgaaca agtgaactga gtaggttgga    20640
gaattctatt ttattccatc tgaattgctt ccgcgaaggc agctatttg gaatggttaa    20700
tgattttctc cctaaaaaag aatctaaata gttcaaaatc atgtggagat cagatcacaa    20760
ccccttttcc ttcaaaagtg ctatatttta gttgtcttat cccccagcgt cagaagggaa    20820
gcttctagtt tattctttg cctccaggta gaaacaaaag atgggatgct ggtccagact    20880
```

```
gtcacagatg ggtggagacc acttcctgga ggctgaggct gaagagtccc actgcctgat   20940
agctgattaa tgctcatctt ccctgtgcct tggctgtggg gctgatacccc ttctcacaac   21000 accctctcct tctaagaaca tcacattccc ccagcatgtc ttcccatggg gccactgatc   21060
aaagcctggg ttctggggtt gccctgttcc cgaggcaggg gataacactc aaattgtcgg   21120
tggggataat gaatagagaa aaatgcttgt aaactatgga gtgcctggaa cacagagggt   21180
ggcccctaac agcgtgtatg tctcagtgac tgtgaggcac gtaagtgggg ggatcagacc   21240
ccaaagtcag atgatttgcg cttattggtg taagacctca gttttctcat ctgtaagctg   21300
gggacaactt cagcagttgg atcctgggag gtgggagaag gggaggatta tttgagaaag   21360
ttgttcatgg catgtgcctg actcactgtt caggttggga ggggacctgg ccctacccct   21420
gccactcact gacctatggg caccgtcagc tggctgggtt ggagcccctc gctttcctta   21480
cctccaccgc acagccttcc ccagaaagga aggacagcct gttccaagct gctttacttt   21540
gccttctcca tggcgaaaaa ctgttttttc atgaagggtt tcaaatcctg cctcttccac   21600
ttatttgctg gttgacctcg gatcaattgc ttaacctctc tgggcctctt atttgcttat   21660
ctgataaatg aggatgataa tgctggcctt ggtgcattgc cctgaggatt gaagacgata   21720
aggaagcctg gtacacagca ggcacttgat aaatgttctc cctttcccta aggagatgag   21780
aagcagatac tggatgtgat gctccgggta cctgtcctag gacctacgca caaacagtgc   21840
ctactaactg ctctggaggt atgggccggc aggaagctgc attgcccata atggggagct   21900
ctcaggaaga cccccctcact catcatgctc tgtgaggaca ccatacattc ttcccttttta   21960 caaactctca gcctggccca ttgcatttta aagctgaata aatagttcca gggcaaagcc   22020
agggatcagg gctgctcttg gctcttttcca aagtatttct gagcctttca gcaggatccg   22080
agtccccacc ctgcaacccc tctaacttta atgggtgctg atcactttac acctgtgaa   22140 accctcagca aatggtcctg atctctgatg tgccgttcag gctggcagca gggcgctggc   22200
actcagactc tgcccgagga aatgaaagcc tgatggggct ggagggggag gtggcgaagg   22260
agcttccagg ccatcatggc agctggagga agttttcccc tagctgagcc gtcctgcacc   22320
ctgccatctc tcccttctca aacacggcag ccaggcctgc tccgtctggg gcctcacaaa   22380
ggcccttcct gagcaagctg tgtagatgtc taccctacag aagtaataat cgacaggacc   22440
atttatcgag cgcctattat gggtcagacc caattcttga cttatcccat gaatacctc   22500 ttctgcggcc ccctggccac cccgccagtc aaaattagct ccctcttcgg ggactcactg   22560
tccctcacct gctttaattc ttcagaacca tttgtcacta gctgtaatga tctggttcat   22620
ttatcttttt cctttgtcta ctatacatct ctcctattac aatgacggga accttgtctg   22680
tctgttcata caccatggcc cggagaagcg ctcagtgcag aataggtgtt cggaaaatat   22740 tttattttc atctgaatga atcttcattc atcttcagag tgatcttatg ggaggggact   22800
atgattatcc ccatgttcca gataggaaaa ctgaggcaga aaggggcca ggagtttttga   22860 caaagggcac acaggaaggg cagagctggg attctgaccc tggaatgttt cactgaaatc   22920
tgtgctgttc tgccccacac aacctaaccc cacctacctg gcttccgata gagtgagtgc   22980
tctgttggaa atagaagatc ttgtcagaaa tggaaacttg aggcccctgt gtctgaataa   23040
atacttcccg aatatttata tcatgatcc tacaatattt tattttctgt agttttcaca   23100
gaaacccatt acattgttat ctttctatac cattttataa cgaagaagtc aaaactcaga   23160
gaggttgtgt gcttgcctaa agacacacag cgaggaagtg gctgagtggc cttgggtctg   23220
gactgggatg gaaaggctgt gctcatctca cttctcagat gcatggcctc ctggggaatc   23280
```

```
cgagtgaccc ctctggactc acacagtcgg gaagtgacaa agcagataca gggccaggtc    23340
ttgtgatgct ctgcccaaat ctccccctatt tcagtattgc agcctggaaa ccaggcacac    23400
agaaggaagg catgagggtc ctgaccgagg gcatgatgtg gttgccttga gggctgggaa    23460
ttggcaagga aactcacaag gtcatctgca tgtgtgtgtg tgtgtaaaac acaaagatct    23520
gaccctgccc taccctactg cgtggatcag taactgtgga gggaagacaa ggggcagaga    23580
agctggacaa actagccaga tttatatggg aaaacctgca gagacatagg aagtaggaga    23640
acatcgagaa agggtgaagc tgcagcctat ggaggagaga gggaggtttg ggggggtctgg    23700 agtcaaagaa gggaggcttc ggaggaagct gccaggtcta ggagttgggg gagcagaggg    23760
ggagagagag tcctcaaggt attttttccac ctgatacctt gggaatatga tcttcctttt    23820
ctggtgagtc tgccatcaac attttaatag aattttaagt tacctgtgga tgctggctga    23880
cattttgtgg attgagactc cgtgtcgaga gagaggcatg agccagcctc gtttgcgagg    23940
gttcatgtgt ctatggggtt ctctacatgt gtgcacacgt ctgcacatgt atgtattcac    24000
gtgggtgggg gcgtttgctc taactgaagg cctgtgtgca tgtgtacgtg cgtgcctggg    24060
gtaccgatgg cctgtccatc cccctgccc tgccccagat tgtgaacaca gcccccaccc    24120
aggagtggag tcagacgact ggtgtgggga gaggggggtt ggagggtctg aattgggagg    24180
agtgccccac ctccattgtg ggaaagctgg catttgtggg ggctaaaaca gggtgtgggg    24240
ggatggggat gggcttgcag gggcacaaga cacagaattc ctccagggg g atttagcaga    24300 gagaggggaa gagagcagag agggagggc ccaggcaagg gggggtggt ccttggcggg    24360 ggtgggggg agtggggaca ctctagaggc ggtgagggac atccagcaag actgtcccca    24420
tccctgcctt tccctgccag tgatgctggg gcctctgtga accgatggcc acgtgcaggg    24480
gctcagcagc caaggaacca cgcacagggg gagcttttga acttagaccc gagaaaccgg    24540
gttctcagcc tagctcagct catcccaaca ggctgtgcaa cctgggcaga tcacctgggc    24600
tctctcatcc tagcttcctc actgtggcgc cacctggggg gctggaggcc tgcatgggcg    24660
ggtgggtggg acgggctgg gtgggctctg gagtgccggt gtgtgaggcc tgggtttctt    24720
actgggatcg ccagtttttgg ccctgccctg ggctcccaag aatttctgga cctggtgttc    24780
agcaagcagg gtacctattg ggttgtctcc aaaaaaatgt tctcagcctt cattttgttg    24840
tatttaatct tcttgaatgt gaccaaatca gtctgtttta ggaggcgggg gccctcgtgc    24900
aggtccacct gccccgtgat caccctcccc gtgccagggg ggtgactgat gactactccc    24960 tgccctttttt ggtgttaact ttaaaaggtg ttaactgccc ttggtatccc ttcagaccca    25020
gctctcgcct ctccaggagg gatcacctgc ctgggtgatc gctgaataca cagaagcagc    25080
cttggcagtt ggcatgagtg ttgccactga ctggccaggg aacccagatt cttgaccctc    25140
ggcgagtaag cactggagcc agcaggccgg actcaaggcc ttttgtctcc tagcccggtt    25200
tggccacaga ctgtaatact atgttgatga cgaacttatt tgtcaaccac tttcctcttt    25260
gcaagtatca gtcatccccc acatcgctga atgtgtttgt taacacttgg ttttttctggc    25320 cgtgccgacg gacacacact gttctgaaac gtgtcatgtg atggctacac ctgagacaag    25380
ccttgaacaa atggtttcta cgactgctgc cttgcaggtg tgtgtataat ggtaccctcc    25440
ttgccctgat ccctttctat tttttttctac gctattccct cccctctccg atcacacttt    25500
tccttgagcc tccctctccc ccacattccc tctgtaccct cttgcaacct ggtctgcccc    25560
cgtcctctct ctctccccca gccccgtctc tggagccaga gccttggcca ggatgaaagc    25620
cactggccag gcccataaat cagccggcct gtgcccctta accttcccca ttaacctctc    25680
```

```
acacgggcag gcattaggtg ttacacttgg ctcccgtaaa ttacttgcca atgaatttat   25740
gagtgctcac ccctcagagg cctgcttcct catcctcccc cactttccct cagggtttcc   25800
agacatcgag ccccagccta gcagtcagtg cctggttctg gcccgcgact ccctgagtga   25860
tgctctgcac ctgatccccc cacccgtttc acacatggac tagaagatt gaagagggga    25920 aggggggggc gggtgtgcgt gacagtcacc ccttggctcc gctgtctaga atcccctttcc  25980 ccagaggcca ccccctggag cttccacacg tttaccttgg aaggtgagag gaccctgcat   26040
aagaaccgtc accactgttt attgtgtttc tgccacgtgt ttctaccacg tgccagatga   26100
tcatgctcat tgtttctaat tctttgaaca attcttcgga ggtatgaatt gttatcccgt   26160
tttacagatg aggaatcaga ggtgcaggca agtgatgtga cttgggcagg accgggcatc   26220
actggtgctg agagttagtg gatttcgttg tatcctgcgt gcctgctcag tcgctcattg   26280
tgtctgactc tgcggttcct tggactatag cccaccaggc ttctcagtcc atgggctctc   26340
ccaggcaagg ttactagagt aggtggccat tgccttctcc agggaaactt cctgacccag   26400
gggtcaaacc caggtctcct gtattcgcag gcagattctc ctaccaactg agctcctact   26460
ctatacaaat ccaaatctgc aaaaacaagg ccacgtatgg aaaccgtgat aagcccgtga   26520
cccagaatct ctctgcctca ctccctcatc ttgctgcatg tcggtttaca aggaaaaata   26580
gtagtgacga tgttcatcac gagaatggct gaccccgtg gatgtttact aagcacctgt    26640
tattatgcca agcgatttat gtgcagaaac ttgcttaatt atcatccctg tgtaaggttg   26700
atgctatagt tatgcctgtt ttacagaaga ggacataggc aaaagaggt cagttaattt     26760 gttgacggtc acccagtgag aagggccgg gtccagcggt cggaccccaa gagtcagcct    26820
gcagaacgcc caacacttca ccatgagtag tgacactaat gacaaatgtg atgccaccac   26880
agatagagcg acagttgcgt aggcgcccca ggggctcagt gctgttagcc ccgcgtccct   26940
gcggggagcc cctggagagt tctccgtggg tgacccaggg gcgcatctca cctggttttc   27000
cttctttcgc ttttcccagg tgacagcagg ggcggagcta caaactttcc ccagatgagc   27060
ccaggacctc tctgggtgcc tgtccctggc tgctgctcca gctctgatcc ctgatcccca   27120
aagctatgag gtctccacct cagcttcctg agtgtgatcc tggggagacg ggagcacatg   27180
tctgggatgg cagggagcag ctggagggg atgaggaggg atgcgaggag agcacgctgt    27240
gttccgggga cctgcaggga cagcagaccg aagctggacg gcaggactcc aggaggatgt   27300
ttctgggcca gctgtcacca agggccctcc cctccctgtg ccccacccc cgaacttcg     27360 gcccatgtga atgcctcctg tgcaattcac caagggccct cctctccctg tccccccct    27420 gaacttcggc ccatgtgaat gcctcctgtg cagttcagtc accactgcaa aggaggggca   27480
gacagctgct tgtgttcctc tggggttgtgt gtgaccctga cttagaggga aaaggaaagg  27540
tcagccagag ggtgctgcca caaaggcagg acgcgggccc tgttatactg ggagggcagg   27600
aaagcaagag ccatacagac ctggctcaag tcccagggga acagggctga ataggggtccc 27660 ctcccaattc acgcccacct ggaacttgtg gatgtgattt tgttcggaca aaggtgtaac   27720
tgcaggtgcc gtgagttaag atgagatcaa cctggattag ggcgggcctg gcatccttgt   27780
aagaggtggg aatctagaca cagacacgca ggggcgaagg ccctgtgaga tggaggcaga   27840
gatggagtgt cagatccaca agccaaagaa tctcagcggt tgccggcgct ccccaggagt   27900
gacaagaggc aaagaaggat cctttcctta gaagagagta tggccctgct gacaccttga   27960
gtttggactc ctggccccca gaactggacg agagtaagct tctgttgttt caagccactc   28020
agcgtgtggt actttgttat ggcttcttgt taagaaagct gacaagcgag ctccaatcac   28080
```

```
ttatgagcag gatggcctgg catcagtcac tggtctctcc aggccttgct gagcatcctt   28140
gtagtgagtg tgacactagt tcagagggtg ctgtgaggat gggatggaat gatgcctcca   28200
aggctaaaac ggttcagtaa agacagtgga tttggctctg ggattcctgg gtcaggcaga   28260
tctgctggaa aagggatagg ccgcccactc cagtattctt gcgcttccct tgtggctcag   28320
ctggcaaaga atccgcctgc aatgcaggag acctgggttc gatccctggg ttgggaagac   28380
ccccttgaaa agggaaagtc tacccactcc cgtgttccgg cctggagaaa ttccatggac   28440
tgtatagtcc atgcgatcac aaagagtcag acaaaactga gtgactttca ctgtcatgtc   28500
taaatacagc gattcttcag agctgggctt cctagttcct tctggaagga ctgagagccc   28560
cgtgttattt tttatggtt aattttggaa attccaagtt aacagttagg gtacaaggtg    28620
atcacattta tgtaatcttt atcagaagtc tcacaagttg tatattcaac attttgaaga   28680
aaaaaaaaaa gcaactctag tttttactct gtacatccag attacatgct tggaccaact   28740
gcacgaacag ttagtttata ccagatgcca gctgactgcc tgatgccaac tggaaataaa   28800
gttatgtgcg tatgcacact catataaact gatcgctaac cttgtataca aaccatatg    28860 tgtctatctc cctatgcata ttggatgctt acatattcat aacagatgcg tacatatatc   28920
tgctcaagaa atccatccag caaatattta ttcagtgttc accttgtgca gggtgtgtgc   28980
gtacatgtgg gtgtgcagat agagaggaat acgtgttcat acataaataa tgtatacacg   29040
tagctgatta gaccagaagc caaccaaata tctagatgcc agtgtgggag catggctgtt   29100
ggaaagccat atacttcaaa ttccctggct gggaacaggc cggagcctgg aggtgagctg   29160
agcccccaaa tgagagaggg gtcagcacag ggcagacagc tggggcggga ggaaggcctt   29220
gggccccctc taatgccatc ggggtgaggc ttggggctcc cagcccctcc tggtcagttg   29280
tccccaagct gtcactctct ctgtctttgt ggggacttgg aacggaaacc cattttgaga   29340
agagtagcat ctaggggcac ggcgaccgtg tcctgccttc tcccactctg agcatcctca   29400
gagtgggatg tatcctctct ggatacaggg gcgctggatg ctttgctggc cccagcacca   29460
ctttggagac ctgctgtgtg cttctcaatg ccaccccctc cctgatggca cttctctccg   29520
tgaaggggcc aggccgggga agggctgctc tgctgtcacg cttcctttcg taactgaagt   29580
gatacaatct ccgcctgccc cgcctgctgg actccaaggg tgctgttggg acatggctgc   29640
tcttcctcca cagcccagcc cagagtctgc ttcctaggag gcccttcgta aaatctgggg   29700
cactcagggg tttagccagg tgaaggggtg tgtccagggc cgccaggcag tgagggagg   29760 cttatgcaaa cacgccctga ctcagcagac tccctgctcc agaaatgctg cagctcacca   29820
cccgccttgg accaggacct ccctgtgcca cggaccttgt ctgaccctgc caaccggaga   29880
ggggaatgcc tggggtggcc cttgtatggc actttcatat ctgaatttcc agtaaccagc   29940
atgccaacct gcatacagta ggcaatcagc tggtgtttgc tgaaagaatt aatgacttca   30000
aggcctgggt atacagctct gggccctcgg gactgtgagg gctcagagga gcagtgtttt   30060
tgccctggta gacggcgaat tctctgctaa gaccctaaag ccaatgtggc gtcttagggg   30120
agaggtgggt gggcagtcag catggggcag gaattggctg ctgggttaac agaaaatgaa   30180
cgagatttgc ctgtgtcaga ggggctctgg tcaaggacac ttcctgtaat aagtaaacat   30240
tcctgaaagg gtgagagctt aaacacagta agtgatgcta aatggaggag agcagttcaa   30300
ggagggagat tctttccagg tgaggcttgg aaggggaggg aaggaaacga tctttctta    30360 agctcctgtg aagactgatg ctagagactg cacacatgtt cttcctggaa aagcaggtca   30420
ctggaacgat ctctgtttaa cagatgagga cactgaggtt cagagaggta aagcacctcg   30480
```

```
ctcaaggtca cacagccagg atgtggcaac atcggtccga ctcaactcct gtactggtct    30540
ggctgctgaa tctaggtaat agctatgtat tgcctgcttg accttccctt tttgttcttt    30600
ttctgtgagg atttagttat tctctagagc aaaaagaata tgttttgggg gtattcaagc    30660
tttgggaatt tttttttccg tcctctggta tattgttagg agggcttccg tggtgacttg    30720
gtggtaaaga atctgcttgc aatgcaggag acttggattc aatccttggg tggggaagat    30780
cccctggaaa aagaaatggc aacctactct agtattctta cctggagaat cccatggata    30840
gaggagcctg gtgtgctaca gtccatgggg tagcaaagag ttagacatga ctgagcgatc    30900
aaacaacaac cgcaacaaat accgtttgga agggtatcag ttctggcctc ttccaaaggc    30960
tccatcaaag ataacgtggg aggctttcct ggtggctcag tggtaaggaa tccttctgct    31020
agtgcaggag acacgggttc aatccctgat ccaggaaagt cctgtgagcc acgactattg    31080
agtctgtgct ctagagcccc ggagctgcag ctactgactc cgtgcactgc aggtattgaa    31140
gtccacgccc ctcgagcccg agctccacag caggagaagc catctcaatg agaagcctgt    31200
acatggcgac tagagagtag cccctgctcc tcgcaactgg agaacaagcc ctcgcagcaa    31260
ctaagaccca gcgaaggaaa aataaataaa taaatgaaat tattaaaaaa aaaaaagaca    31320
acatgggctt cctgcaaggt gcccctccac cataaaccta tccttcctgc tccttcaaga    31380
gcgatccctg gatgctgtag tgagaaggat gtgtttttga gggggcctct tcccaggtgg    31440
tgctagaggt aaagaaccca cctgccaatg caggaggcat aagagacgcc agttcgatcc    31500
ctgggccggg aagatcccct ggaggagggc atggccaccc actccagtat ttttgcctgg    31560
agaatcccgt ggacagagaa gcctggtggg ctacacaatc catgaggtcc caaagagcca    31620
gacacgacta aagcgactta gaacagcaca gctcatccct gtcaactggt ataaaagcaa    31680
attgtttgca aacttagatg ctggagagat caatgaaaga actaaaagtg tttccgcgct    31740
gatcccataa tcaacacacg tctggggact gatccgaccg agcctgtgct agtggcatgt    31800
gttcgactat ccccaggacg aggcccctgc aggtcacacc ggtgtcccct tcccccagaa    31860
tcccaggtaa gtggcagaga gccttggcag acaaacctgg tcgaaaacac ttcctgtaat    31920
aactaagcca gtctgtttat ctagcttctt ggctactaaa caggcattgt gagggagggg    31980
gcccttcgtc actaaatccc cacgccccct tgtagcgagt gatgtccttt gtaagttgct    32040
gggtgtccct gaacaagtta ctccagcccc tcttcctca tctgtttaaa aggggattat    32100
attaccacct cctacgtgct gtgaagtttt agcccaagca cttagcacag agccgggcac    32160
ctgggaagct ctgaatgaac attagctgtt aggaccacag ttagcatcat ctgccgggca    32220
gggctgatgg aagagctggt gagtggaggt gagtgtccct gtgtgagggt gggagggtgt    32280
gtgtgacccc tgcctctgct ctggggacac tgaggcccta gggcagactc tggagggata    32340
tggataagtc tcctgtcttg cttgggcaga ctctggaggc atacagatga gtctcccgtc    32400
tttgctccag cgaggaggaa cttttgtcctc ccgcacaggc tgcctcctgc agactctgtc    32460
ctctggaccc gctgcctgtc ccttccctgg cgagggcggg gaggaggccc agccacgggg    32520
ccctggcccc cggggccgct ggcccagcag gccaaggact ctgtgtcctg ggaggggagc    32580
agccctgcgc cgcagctgct cctcctggga ggggctgggg cagcaatctc atctctcagc    32640
agagacctct caacccaggg ggcagtgccc cagaaagggc acaaccccga gacccgctca    32700
gagctgcttc ctcctcctgt tcatgtgtcc cagaaacctg agaaaatgag ccaagtcctg    32760
gggagagggg gctccagctg ggggaccccgg tcctccttga cccccactta ctgccgcttg    32820
ggggtgggga gagcggtcgt ccgccctcca ccctccggag gtccctccg cgtcccgccc    32880
```

```
tccctctcag gccacgggcc ggttttccag acttctccct ttcccacact ctttccccga    32940
agcctccttc acacacccag ttcttcttaa aggggttcta agaagaacga atttcctatg    33000
aacagaacaa tgccctatta atcttacgag ggatttgaac ttggccacat ttcagctttt    33060
gatttaaata tcattttggt aatgggggag aaaaaaaaga aggctgactc ttggacagcc    33120
ccgagtttcc aataccttct gagcatgaga cgatttcaaa tataaaatta aatccaactc    33180
ccttctgcct cccccctccc cccaccgtcc ccttccccccg ctttcactca gacaaaaaag    33240
ctcacgtccc acatacttca tggggatatt tcaagttaaa gttttgttta ccttatagaa    33300
aagttaatta gttccttttg atctcacggg gaaaaccaca caggaaattt ttcttcagaa    33360
agtgtacaca cgaaggcatg ctttaccctc ataaccagag atattcatta aaacaattcg    33420
tttcgatttt taatttaaag aaaacatttt acattttcct gatttattat taagagagta    33480
gttgtccctg gggcagagcg tgaaggggt cggctgaagt gttttttgctg tgctggcagc    33540
cagcattggg cagtttgttt tgctactttg gataacaaga gacttctgca gagaggcaaa    33600
ccttcaaaca cgccagattt cagtcgccaa aatattaaaa atccagggtt tgggagattg    33660
ggactgtatg gttaaataa agatatttaa gttctgaaat ataaatattc gagatcctga    33720
aaaaacatat cattgcatta aaatctgaaa caggcaatgg gtgaatcgag gggagaaaat    33780
gtttactttt ttgaggttta tctaatgaaa tataataaat agtacatcat gctcttttt    33840
tttttttaacc cctagagata tttaagcaat acctggattt gtacaataag ctgcttagga    33900
aaagtctaga aagagaaacg gttggatttt cgaaatgcga ttttcaacct taagcacatt    33960
ttccacatct tgtattgtta tgggatgagg gatgcagagg accctgtaaa ttgtggaact    34020
catttccagc ccagaccaat tgaaaaaaga aatagtatgg cttccccgag gttgaaagaa    34080
caaattaaaa gatattgctg atggagcagc caaaagctgt ggtccccatt actgcaagga    34140
aaaaatcttt aaatagatat ggtatggaca aaaagcctgt ggaagagatg tttttactaa    34200
agcaaaaccg ctaaagcaaa acagctctaa agagtggtgt tgacatcagt atacgatttt    34260
gagggtattt ttgggtgcgt atccctttcc tgccctgac acaaatattt ggagattggg    34320
actgtcattg ttgataaaaa ttaaattgat gccgcataca aaagatatat aaaaaccatg    34380
ttaacatatg gggcgacttt gatgatgttc tgtacacagc aaaagtataa aaatctgatg    34440
acattttatt gtcaccaatt tgctttttaa tctgtcccaa ccactgcttt taaaaacaga    34500
actcttaata tagatttctt tatcaaaagt ttgcacctga agataaattt tctgatttaa    34560
atgtattcca ctctcctatt ttttattttt gttttttggt aaatggtgaa ggtgtgtgac    34620
agtccgtttg tgaagttagg gaagaatgca tttattttga agagggattt aaaaatgctg    34680
gctgtaggag cagattccta caaatgaagc cagttcttaa ggcaagtttc caaaatcttt    34740
ctgttcaaat acagagtctg aaaatctttt taaaaaattg tccttctaca acacaattag    34800
ttttatttcc tgcctaagat accttttgtat tttcttctga agaaggattt accttttttt    34860
tagagctgga aatattccct tttttcttct tttcctggag gaaaatggtt taatgtaaag    34920
tttaagggag ggagagagat gtatggaaat gaatggaaaa cagaagcttc aaacggctac    34980
ccaattccct ctttggattt gccaaataac aactcaaaaa tcagatactt cccataagac    35040
cattgatggg agaccttccc aataaatatg catctattcc tgttttcatc aaaacaaata    35100
attttctctg ctgattaggg gcccttcctt ctccagtacc catcattggg aactttgaga    35160
tttcactaaa catatataca tatatatata tatatatata tatatatata taattttcct    35220
ttccgtgaat ttctacgaag ttggctttct ttctccagga ggctggagta gagtcgggac    35280
```

```
cctgggtaga cacttcattg gtctgaatgc aagagggaaa ggggtgacac tctaaaggga    35340
aagccacgac cccaaaggag aaagcacgga cagataaaaa gaacaagaca agtaaatatt    35400
ttcctagcgc gtttccaagt taaaaccgat caagctaccc ggttaaagaa aggcaaaaac    35460
aaaattcgtc cctacctttg tcagatgcaa agtaatgagg ggttgttccc agagtggtta    35520
tgacctacac agagcttctt accttaaatc tatacatttt gaacaaaaac agcttggagc    35580
aattctctcc aaacaacccc aaatgttaac cattccaact caagatcggg tttctccttc    35640
agcctagacg gtgatatcag ttgggttttc ttttcttttc tttctttctt tctttttttt    35700
taaaatatgt attcttatgt ttccaatcct caaacatact tttttcatct ttgttaaggc    35760
tccttctggc tgctggatgg gctgggagtc gcaggagtcc ttctcttcgg acaattagt     35820 ctctcacttg atcacttgaa aacggaatga tttgtcgtgg tcactgagtg gggctctctc    35880
cctctttcct ctaatattgt tgcagatacg taaagtttac tgcgtgctgt aaatatgtca    35940
gcttttgcca gggagtttgc taataaagaa cctagaggta ttattgatgg aaaagataat    36000
gttttcaata agactggccc gggctaaagt ctgagacatt ccacacccag ccaagcatag    36060
gcgtttgaga cgccgacccc ctggccgagg tgccgggctg gtttaccggc cacaggccgg    36120
ccgtgctgcc tgcttctccg tggtccccgt gactgtttta ttcagcgcag ttttaaacgc    36180
ccgactggtt ttaggagctc tgtccttttct gaaaaaatgg ccttcctgac cgtcaggaat   36240
aggtgaactt atcagagaat catgagatac gcttgcccag attgatctct ttggggattt    36300
atcagctcac ccatgctgag agcagaggaa aaaaagaag tccacccttt tctgtttgat     36360
gctcactcac attttcattt gtcgtgacaa cttctgagtg taaattggat tcatttttt     36420 tcctggatgt tcgtttgtgg aggattgttt ggcttccctc tcttaaagga aaaaaaaaa     36480 agaaatcgca gaaagcttgg cgtccgtctg ccccacggcc ctggtcccct gatttcagtc    36540
tcctggtctc ggtgttttgt cacatcaccc acatgacagt ttcatctggt gctaatgtgg    36600
ccgtcacatg ggttggtcgt cagaattcca tgctcattta ccattaatca aatgcatcat    36660
tatgaattgt gtatgcattt tagggcagac ccaaaccccg gcttgatagg aaagtgtttt    36720 tgttttttc cacttaacgt tcggcaacgg cagatgaatg gcaaggccaa agtgacactc     36780
tttgtgtttg cttagcccag aaatcaacaa ccctaaatta caggttggta agctatgtcc    36840
aggtagcatt agcttctctg ggtgattatt attacttaag gcggccaca gtcagcgcca     36900 gcaaactgaa gctggccaga gggagggcag acaaggcgag cagagagcag ggtctcggct    36960
tccaaggggc ccggtgcctc cttttgactg gggggatttt agtcttagat tgcatttttcc   37020 tggaaatagg gactggcct tctaatttgg aagaatgtga ggtatttgca gggcgagttc     37080
ggatgagtgg ggtgggac gggttaccac tggatgcttt tggcaatttg tggactctac      37140
ttccccagga ctcacttgcc agcttggcct ctgtgggaac attccaagtt ctggaacctt    37200
ccttggaagg cctgactcct gttggttggt ggggacctgg cgtctcctgg gcgtataaag    37260
acggttttca ttgggagttt tcagtgatta aagtctttcc tgaggacggg ggactgtgtt    37320
tcaggtaaaa acccttttcct gagctgtcac aatagttctg ggagatgggg ggcctggtgc    37380
ctgagaccgg agggccccaa cctgaccccct ctccccagc gagccttggg agacagatct    37440
gacctgggct tagctcccat tcgttgtcta actgccagcc gtcccaggcc agatcgggaa    37500
cagggaagga ggttggtccc gaaaagcgat cagagacggg gtacaggggc tgcggtgctg    37560 gcttattga tggcgcaatt ttttttttcc ttcccagcag acagctgggc ctggttggtg      37620
gcttggaggc ctctcccagg gaagcggcgg agcactcttg ccccaggaa tgtctcttat     37680
```

```
ttgtgaggct gtcctgggct acttgggagc tcaggatgtt aggaaagcct gttaaaagat    37740
aaataccttt tcagaataag ctgctcagga tccaccttag cctgcggtgg gggaggctcc    37800
aggagaggca gagagtgcag tgctgggggg ccagggtctc tcatgaggcc tcctgggctg    37860
gctttgggaa tgttcctccc ttcaaagccc cacttcagcc tggaagggct gagccgcttc    37920
cccagagggc agtccagggc cgcggcacac agacttcagc ccttctcccc tcttctcctg    37980
gtcagcaggg agagatgggg ctcccgagag ctgggtcggg tggcagctgc tggcagaggc    38040
ctcagaggtg ggccctatgc atagggctgg ggccagggga gtgtgtgagt gtgggtgaag    38100
gggtgtgtga ggggcaggtg tgacctcagg aaggagggct actggggtcg cattgcttct    38160
cctcccagcc cgtgaccttc ggggcctgga accaggcagt agcatccagc ctctgagccc    38220
aggctctgag cccaggctcc gagcggcttt gaagaggcct gtgggtcagc gctgagggtg    38280
ctgttttttg aggccttagg ctccactagc cgggtctgtg tcttcatccc agaatgagct    38340
gtggcttcac caaggggctc agaacggttt tccactcatt caaggtcacc tcaagcccag    38400
ggctttctca tctgaatctt gaacctagcc tctgtgaagg atgtcctgag ctgtcaccct    38460
gctgacaaaa atgctgggcc ctgagaccct gaaatagagc ttctcagaca aagatttgag    38520
caacagtcta actgaactcc ttatgaaaat acagaggtct ggtgccaggc cgagtgggcg    38580
gccttgggag tttaaggaaa taggtctggt tccatgggact tttttttttt aaattagggt    38640
ttgggtcatt ttggtttgaa gttcaacaaa tcagcatggc ttgtctggct ttttatctgc    38700
cacctggttt ggttcaagga cagagaaacg tttctgttta taaacatgt gcagacgtgg    38760 ctggccaatg ctggtgtcat ttctcctggc ttctgctcct tttcaaggga gctggtaaag    38820
ctgatcttct ccaccctggg ctggtcattt agccgggccc ggctgaggcc cctgtgtaat    38880
ggacaactgc agccggctgg tagaggtgat gggtgtgtgc gtgcgtactc agttgtgccc    38940
gactctttgt gaccccctgc actgtagcct gccaggcccc tctgtccatg gggttttcca    39000
ggcaagaata ctcgagtggg ttgccagtcc cttctccagg ggatcttcct gacccaggga    39060
ttgcacccgt gctcctatgt ctcctgcaac ggcagacaga ttcttttacca ctgatccacc    39120 tggtagtatg taagatagat attatttgat gtggagagat gttcactgca agcactaata    39180
tagactcatt tttgtaactg caaaaataac acataaatct ggtaagaaat gaaagctgta    39240
cagaagtatt tttaaagtaa atgaaatacc ttaatatttg tacagtgctt agaagaacag    39300
tacctggcat gtaataaaca ctagacacac ttaataaata agagtatatg gaactagaag    39360 tcattttttcc tcccaatttg gatctgtagt ctccctctcc agaagcaacc aaattaatat    39420
tttcttgcat attcttccag aaattttatg tgcttatgaa agcgtgtcag cacacataat    39480
aattttacat cgtaaagaga aagggtagg ttaccaagta gctttaaaga gcataattct    39540 attttttaaaa caaacaaaca aacatgcata gaaaataatc tggaatcaga tatatcaatc    39600
aggtaaaact atgattatct tcaaaaggtg ggatcatggg tggattttct ttgtctttct    39660
gttcactcct tctataattc taaaacttga ttagagaaaa acgcatatga agaaacacat    39720
gcatggatgg gcacatggac cctggtcctc ttatataaac gtgtttaaga gggctgacat    39780
ccatgccagg ccctgggatc ccatcacaga accagcctgg acaacctccc ctttgctccc    39840
tggggccagc tgctctgttg ctgacactga accctgatct gcgtttggct ttgcccagtg    39900
gctccaggac tctcctgggg acccctggac tgatgatcga atgaggataa gatttgaggg    39960
actgtccaac acatgcatcc cccttttaact gtttgttttg ctgcttctat atccctctgc    40020
cagttgtggg gaagacccct tcctccctct gccagcctgg gcctgggggt ggcatgccta    40080
```

```
gttgaccctg atctcccatc aaggaacaaa ggtgagcccc gtttgaactt acatgtccat   40140
cctgagcccc cgagtctcat ggcctgggtc ctttggacct atcagaagcc ccctctgatg   40200
tgcctctgag atgcagacag gcaggccggt gcagcactcc agcttcccca cctgacttcc   40260
tagaagccag tctggtccct gtaatgacca gtggagcagg ggtctcggcg gtggtggtcc   40320
tgagtaggca cagtggactc ctcttgactc tgtagacaag aatggggaat caaacagacc   40380
tgggccatga accagctgct gttgctgtag gacctgggggc agatcagttc acctttctga   40440
gcctcagttt cctcatctcc aaaatggggtg cactgagggt accttcctcc tggggctcat   40500
atatcttcat tctcaattca ttcctttaac acagatttt ctgagagcct tgtgtgccaa   40560
gctctttact ggactcacaa aggctcacat ataagcttct acataagata ccagagagaa   40620
caacagcaac aaaaatgttt tccagaggta aaagcatggg gaagaagga gaggcttctt   40680 gaaggatgca taggagttct gacacggtga gggttgcagt tgggaaagaa agatgagggg   40740
tttccacagt ccttgcatgt gtatgatttt gcatatttct cacaatactc ttagaatttg   40800
aattttctga gggtaggctg tcattgttgc tggttgctaa gtcttatctg attcttttgc   40860
gacctccgtg gacctccatg gcccaccagc ctcctctgtc cgtgggactt cctgagcaag   40920
aatgcgaatg ctggagtgag ttgccatttc cttctccaag agatcttcct aacccaggga   40980
tcaaacccat atctcctgtg ttggcaggtg gatcctttac catctgagcc acctagaaaa   41040
cttagactgg attcagctag attgaatcgt aagcagaggg taatgtgcta gacaaaacca   41100
aataatatcg aagagtccaa tctcctgtct cctctgctct catcctgggg aattggttgc   41160
ctcttcattt ttgagtcagg gagaggtttc cccaggagac ctatcttcca ttttcctatt   41220
gctgttgttc tcagggctgg aaagaataag gtctttagac aggctggcct ccatccctga   41280
ctctgtcaca tgtgggctgg aggtctccag caagcctcag tttcctcatc agcaaaatgg   41340
gcacagtggc aatgtccacc ttgccaaact gctgtgagac ttcagatggg gcaaagcacc   41400
cacttaatgc tgggcacatg ccaggatgcc tgagacaggg ctgagtcctc tgccagcagg   41460
gcccagtgtc tggactcaag gcatccttct ctttattaca aagccacaca ttgagtctga   41520
gctcatctgg ggcccatgtg gaccccgggg agtccagaga tgtttcatcc ctctgtttgg   41580
cttccatttt ccccacccctg gctgaatgcc tccagccacc tgccacacct ccagatcccc   41640
atcaggcaga gaaattggtg acccgtaaga gcagagggag aaggaagctg tgaggtagaa   41700
accagaagag atgtgtttgc agatgtgagt cgcagggtg attaggaccc caggcaccgt   41760
ttctgcagga tgggaccttc tgggcgacag agccgaccgt ggaatctacc ctcctggtcc   41820
caacagttcc caaatcgaga aggcaaagaa ggattggctt ttccccctcc gcccctccct   41880
cctctcatct gtaaaattga gacattacag ttccaaaatg ggctttgagc ctgtagaaat   41940
taatctggtc tggcaggagg tctacaaata aacatattgt ttcgattggt gttgacattt   42000
gaattgtgag aaggtttgaa aatgtaactg tagttgggat tttccagccc atctaagttt   42060
ttttccatgg aggggctcag tgaatgccaa ctgggaaccc agcaactgcc ctctttaaaa   42120
ggacttgggc gctgggcgag gctgcggatg tcagggctca gagcctgtgc tgaggcggca   42180 gccctttttgt tggggggtgg gcaaggattt caggaggccc agtgcctctg ggcatctggg   42240
gcaaccagcc actccaggag tgacctgaaa cgtttagagc aactcctgtg tgcccggaac   42300
cttgtatgtg aaacctcact caagtcctca caccagtgct ctctgttgtc cagttgctaa   42360
attgtgtccg actctttgtg acccccatata ctgtagcacc aggcttccca gttcttcacc   42420
agcttctgga gtttgctcaa actcatgtct attgagtcag tgatgccacc caaccccctt   42480
```

```
atcctctgtc gttcccttct cctcctgccc tcaatctttc ccagcatcag ggtcttttcc    42540
aatgagtcgg ctggtctcat cagatagtca aaggattggg gcttcagctt cagcatcagt    42600
cgttccaatg aatattcagg gttggttttc tttaggatcg actggtttgg tctccttgca    42660
gtccaaagga ttctaaagag tcttctccag caccacagtt ggaaagcacc agtttttagt    42720
ggtcagcctt ctttgtggcc caactcttac atctgtacat ggctactggg aaaaccatag    42780
ctttgactat atggatcttt gtcagcaaag tgatgtcttt ctttttttaac acgctgtcta    42840
ggcttatcat agctttcctt ccaagaagca agtgtctttt aattgctctt attatcccca    42900
ttttacagac tggaacactg aggaaaagag aggttaattt gctaaaacca cataggagta    42960
aaatgcagac ttagacacag ccttctctgg ctcttggtgt cctgccctat acaatctact    43020
ttatgccaga attttccaga atgttgtctc accaagagaa aggctcattg tcccagaaaa    43080
aagactgagc cttgactgag gtgatctggt tgttgagaac accagctcca ttctatgtct    43140
ggaacccttg aggatttaag ccccaccccc ttatcttcct gccaccaagg aagggggtctg   43200
tccttctccc tccctcccca cctccacgct ctggatctca tccttcagtg gcctctgagt    43260
ccccactgcc tgcccatccc acctggctcc agcctccccc caccggcccc acagggatgc    43320
agctagttcc ctgtgggagg ggcagctctg agacagcccc ctactcaggg gtgaggtgca    43380
catggctttc aaccacgaac tcagagtgct ggccggttag ggcagacacc tcgttttggg    43440
gaaaggcttg gtgatttctg tacctggcaa cttctgtgtg tgtcaggcat catctcctgg    43500
cccccttagct ccagagatgc gaagatccat cttcagggtc ttcagtcacc tgctaccatc   43560
tcccttctgc gcttccacac ctaccccccac agagctgagc atggccggga aacacacatg   43620
ggaactatgc tgcctgctcc cccttttatcc tcatcattgg gagcatctaa ggggcccatc   43680
tggagaagcc ttacaaatag ctgtgaaaag aagagaagtg aaaagcaaag gagaaaagga    43740
aagatacaag catctgaatg cagaattcca aagaatagca aggagagata agaaagcctt    43800
cctcagtgat caatgcaaag aaatagagga aaataacaga atgggaaaga ctagagatct    43860
cttcaagaaa attagagata ccaagggaac ttttcataca aagatgggct cgataaagga    43920
cagaaatggt atggacctaa cagaagcaga agatattaag aagaggtggc aagaatacac    43980
agaagaactg taaaaagatc tccacgacca aaataatcac aatggtgtga tcactcgcct    44040
agagccagac atcctggaat gtgaagtcaa gtgggccttt gaaatcatcc ctacgaacaa    44100
agctagtgga ggtgatggaa ttccagttga gctatttcaa atcctgaaag atgatgctgt    44160
gaaagtgccg cactcaatgt gccagcaaat ttggaaaact cagtagtggt cacaggactg    44220
gaaaaggtca gttttcattc caatcccaaa gaaaggcaat gccaaagaat gctcaaacta    44280
ccgcacaatt gcactcatct cacacactag taaagtaatg ctcaaaattc tccaagccag    44340
gcttcagcaa tacgtgaact gtgaacttcc agatgttcaa gctggtttta gaaaaggcag    44400
aggaaccaga gatagaaaag gcagaggaac cagagatcaa attgccaaca tccgctggat    44460
catggaaaaa gcaagagagt tccagaaaaa cgtctgtttc tgctttattg actatgccaa    44520
agcctttgac tgtgtggatc acaataaact gtggaaaatt cttaagaga tgggaatacc     44580
agaccacctg acctgcctct tgagaaacct atatgcaggt caggaagcaa cagttagaac    44640
tggacatgga acaacagact ggttccaaat aggaaaagga gtacgtcaag gctgtatatt    44700
gtcaccctgc ttatttaact tatatgcagg gtacatcacg agaaacgctg gctggaagaa    44760
agcacaagct ggaatcaaga ttgccgggag aaatatcagt aacctcagat atgcagatga    44820
catcatcctt atggcagaaa gtgaagagga actcaaaagc ctcttgatga aagtgaaaga    44880
```

-continued

```
ggagagtgaa aaagttggct taaagctcaa cattcagaaa acgaagatca tggcacctgg    44940
tcccatcact tcatgggaaa tagatgggga aacagtggaa acagtgtcag actttattta    45000 tttttttggct ccaaaatcac tgcagatggt gattgcagac atgaaattca aagatgctta    45060
ctccatggaa ggaaagttat aaccaaccta gacagcatat tcaaaagcag agacattact    45120
ttgccaacaa aggtccatct agtcaaggct atggtttttc cagtggtcat gtatggatgt    45180
gagagttgga ctgtgaagaa agctgagcgc caaagaactg atgcttttga actgtggtgt    45240
tggagaagac tcttgagagt cccttggact gcaaggagat ccaaccagtc cattctaaag    45300
gagatcagcc ctgggtgttc tttggaagga atgatgctac agctgaaact ccagtacttt    45360
ggccacctca tgcgaagagt tgactcattg gaaaagactc tgatgctggg agggattggg    45420
ggcaggaaga gaagggggacg acagaggagg agatggctgg atggcatcac cgactcaatg    45480
gacatgagtt tgagtgaact cgggggggctg gtgatggacc agggaggcct gacgtgctgt    45540
gattcatgga gtcacaaaga gtcggacaca actaagcgac tgaaccgaac tgaactgaca    45600
cttgctcccc cactgcctga gtcctgtcct ctcctatctc cccaacaact atttacgcag    45660
gggtccaaat taggccagat gcgggaggaa gga                                 45693

<210> SEQ ID NO 5
<211> LENGTH: 22
<212> TYPE: DNA
<213> ORGANISM: bovine

<400> SEQUENCE: 5
tgctcaggct ggtttctctt cc                                             22

<210> SEQ ID NO 6
<211> LENGTH: 22
<212> TYPE: DNA
<213> ORGANISM: bovine

<400> SEQUENCE: 6
gtgcaaagac aaggcctctc gt                                             22

<210> SEQ ID NO 7
<211> LENGTH: 22
<212> TYPE: DNA
<213> ORGANISM: bovine

<400> SEQUENCE: 7
cacccagtat agtcagcagc gt                                             22

<210> SEQ ID NO 8
<211> LENGTH: 20
<212> TYPE: DNA
<213> ORGANISM: bovine

<400> SEQUENCE: 8
atattggcca ggtcttgatg                                                20

<210> SEQ ID NO 9
<211> LENGTH: 20
<212> TYPE: DNA
<213> ORGANISM: bovine

<400> SEQUENCE: 9
aagctacaga ctgagggttg                                                20

<210> SEQ ID NO 10
```

```
<211> LENGTH: 20
<212> TYPE: DNA
<213> ORGANISM: bovine

<400> SEQUENCE: 10
agtagaacga gctttgccac                                            20

<210> SEQ ID NO 11
<211> LENGTH: 20
<212> TYPE: DNA
<213> ORGANISM: bovine

<400> SEQUENCE: 11
actgggaatt gctggcatag                                            20

<210> SEQ ID NO 12
<211> LENGTH: 20
<212> TYPE: DNA
<213> ORGANISM: bovine

<400> SEQUENCE: 12
atggacagtg gagcctgaaa                                            20

<210> SEQ ID NO 13
<211> LENGTH: 20
<212> TYPE: DNA
<213> ORGANISM: bovine

<400> SEQUENCE: 13
ttcagattac tgccaagccc                                            20

<210> SEQ ID NO 14
<211> LENGTH: 20
<212> TYPE: DNA
<213> ORGANISM: bovine

<400> SEQUENCE: 14
tgatcctggt gatggttaca                                            20

<210> SEQ ID NO 15
<211> LENGTH: 20
<212> TYPE: DNA
<213> ORGANISM: bovine

<400> SEQUENCE: 15
ctttgtcatg gaccagcatc                                            20

<210> SEQ ID NO 16
<211> LENGTH: 20
<212> TYPE: DNA
<213> ORGANISM: bovine

<400> SEQUENCE: 16
gggaatctag cctcaactca                                            20

<210> SEQ ID NO 17
<211> LENGTH: 327
<212> TYPE: DNA
<213> ORGANISM: bovine

<400> SEQUENCE: 17
tgtggcccag gagatggccg cgctgtgctc cttggccttc atgcggaggg ccgcgatgct      60
cgaagtcttg cggtccggct ccccgttgag ctcatagccg ttgaggcccg ggctgaggcc     120
```

```
cgcagctcca aacaggctgc ccatgtgcgt ctggcccacg tggctgccag ccccccgagac    180 gctcaggaag tcggtgacgc cgctggcccc ggagccgggg gggtgggcgt gaggggacat    240
gcaggcgggc accgggtcac agggcaccac acaggccggc acgggcgagg cggccccatt    300
gttgccgatc caggacgggt tctgaat                                         327

<210> SEQ ID NO 18
<211> LENGTH: 20
<212> TYPE: DNA
<213> ORGANISM: bovine

<400> SEQUENCE: 18
ttcctgagtg tttacctggg                                                  20

<210> SEQ ID NO 19
<211> LENGTH: 20
<212> TYPE: DNA
<213> ORGANISM: bovine

<400> SEQUENCE: 19
cctggccttc agcattcctc                                                  20

<210> SEQ ID NO 20
<211> LENGTH: 129
<212> TYPE: DNA
<213> ORGANISM: bovine

<400> SEQUENCE: 20
ctgggcatag ttttccgctc gggtgaggag gggcagctcg taggctgtgg agaagtgggt     60
ccgaacctgc tgcatttgcc cgaagcgttc cctcttcctc cacttggccc tccggttctg    120
gaaccagac                                                             129

<210> SEQ ID NO 21
<211> LENGTH: 20
<212> TYPE: DNA
<213> ORGANISM: bovine

<400> SEQUENCE: 21
agagcagttg tcgccagggt                                                  20

<210> SEQ ID NO 22
<211> LENGTH: 20
<212> TYPE: DNA
<213> ORGANISM: Bovine

<400> SEQUENCE: 22
gcaggatggg aacgtgaaca                                                  20

<210> SEQ ID NO 23
<211> LENGTH: 20
<212> TYPE: DNA
<213> ORGANISM: Bovine

<400> SEQUENCE: 23
ttgctctccg agtcggcctt                                                  20

<210> SEQ ID NO 24
<211> LENGTH: 20
<212> TYPE: DNA
<213> ORGANISM: Bovine

<400> SEQUENCE: 24
```

```
ccagcttcct tcacactgag                                          20

<210> SEQ ID NO 25
<211> LENGTH: 311
<212> TYPE: DNA
<213> ORGANISM: Bovine

<400> SEQUENCE: 25
ctgcacgcgg gcctcggtga ggtcggtcct catggccagc tgctcccgcg cgtacacatc    60
ggggtagtgg gtcttctgga agaccttctc cagctcctcc aactggtagc tggtgaaggt   120
ggttctgttc cgccgcttct tgccttgtt gctctccgag tcggccttct ccattgggct    180
ggggaggtcg gcgctggccc ggtcctgggg ccccttcacc ccagcttcct tcacactgag   240
gtagctgctg tccatcccca ccgtgtcaga gtcgggtggc aactctggct cacccaggga   300
gctctctttg g                                                       311

<210> SEQ ID NO 26
<211> LENGTH: 20
<212> TYPE: DNA
<213> ORGANISM: Bovine

<400> SEQUENCE: 26
gaagcatggg atgcaaggtc                                          20

<210> SEQ ID NO 27
<211> LENGTH: 21
<212> TYPE: DNA
<213> ORGANISM: Bovine

<400> SEQUENCE: 27
tgggtgggtc tggacatgag t                                        21

<210> SEQ ID NO 28
<211> LENGTH: 22
<212> TYPE: DNA
<213> ORGANISM: Bovine

<400> SEQUENCE: 28
cgtatggagc gtctgtctaa gg                                       22

<210> SEQ ID NO 29
<211> LENGTH: 20
<212> TYPE: DNA
<213> ORGANISM: Bovine

<400> SEQUENCE: 29
gctagaatcc tgaatggtgc                                          20

<210> SEQ ID NO 30
<211> LENGTH: 20
<212> TYPE: DNA
<213> ORGANISM: Bovine

<400> SEQUENCE: 30
gagacagtgt ctaagacgca                                          20

<210> SEQ ID NO 31
<211> LENGTH: 20
<212> TYPE: DNA
<213> ORGANISM: Bovine

<400> SEQUENCE: 31
```

-continued gctctgtgca tacgatgaag                                           20

<210> SEQ ID NO 32
<211> LENGTH: 20
<212> TYPE: DNA
<213> ORGANISM: Bovine

<400> SEQUENCE: 32
acattccaca gacctccgtc                                           20

<210> SEQ ID NO 33
<211> LENGTH: 20
<212> TYPE: DNA
<213> ORGANISM: Bovine

<400> SEQUENCE: 33
ggcatgaaag gaggactcta                                           20

<210> SEQ ID NO 34
<211> LENGTH: 20
<212> TYPE: DNA
<213> ORGANISM: Bovine

<400> SEQUENCE: 34
cgagtctgtt accacttcct                                           20

<210> SEQ ID NO 35
<211> LENGTH: 20
<212> TYPE: DNA
<213> ORGANISM: Bovine

<400> SEQUENCE: 35
aaagcattgc caagtgtgga                                           20

<210> SEQ ID NO 36
<211> LENGTH: 20
<212> TYPE: DNA
<213> ORGANISM: Bovine

<400> SEQUENCE: 36
atcaattgtg aggttgccag                                           20

<210> SEQ ID NO 37
<211> LENGTH: 20
<212> TYPE: DNA
<213> ORGANISM: Bovine

<400> SEQUENCE: 37
agcacagtgc ttgtcaggaa                                           20

<210> SEQ ID NO 38
<211> LENGTH: 20
<212> TYPE: DNA
<213> ORGANISM: Bovine

<400> SEQUENCE: 38
ctgtctgtca aagtttccgg                                           20

<210> SEQ ID NO 39
<211> LENGTH: 20
<212> TYPE: DNA
<213> ORGANISM: Bovine

<400> SEQUENCE: 39
cattagaagc tgcgcctgtt                               20

<210> SEQ ID NO 40
<211> LENGTH: 20
<212> TYPE: DNA
<213> ORGANISM: Bovine

<400> SEQUENCE: 40
atcttcagga cattcacggg                               20

<210> SEQ ID NO 41
<211> LENGTH: 20
<212> TYPE: DNA
<213> ORGANISM: Bovine

<400> SEQUENCE: 41
ggagttgagc aggatgactt                               20

<210> SEQ ID NO 42
<211> LENGTH: 20
<212> TYPE: DNA
<213> ORGANISM: Bovine

<400> SEQUENCE: 42
aagaggctgc actaagtctg                               20

<210> SEQ ID NO 43
<211> LENGTH: 20
<212> TYPE: DNA
<213> ORGANISM: Bovine

<400> SEQUENCE: 43
taagtcccag tccattcgca                               20

<210> SEQ ID NO 44
<211> LENGTH: 20
<212> TYPE: DNA
<213> ORGANISM: Bovine

<400> SEQUENCE: 44
agcgtcatca gaagaaccag                               20

<210> SEQ ID NO 45
<211> LENGTH: 20
<212> TYPE: DNA
<213> ORGANISM: Bovine

<400> SEQUENCE: 45
atcagaggtt ctggcacgat                               20

<210> SEQ ID NO 46
<211> LENGTH: 20
<212> TYPE: DNA
<213> ORGANISM: Bovine

<400> SEQUENCE: 46
tatcagggag gcccacaaac                               20

<210> SEQ ID NO 47
<211> LENGTH: 20
<212> TYPE: DNA
<213> ORGANISM: Bovine

<400> SEQUENCE: 47

| | |
|---|---|
| caggcaattt ccagggaaga | 20 |

<210> SEQ ID NO 48
<211> LENGTH: 20
<212> TYPE: DNA
<213> ORGANISM: Bovine

<400> SEQUENCE: 48

| | |
|---|---|
| tgaggagctg gaattaggca | 20 |

<210> SEQ ID NO 49
<211> LENGTH: 20
<212> TYPE: DNA
<213> ORGANISM: Bovine

<400> SEQUENCE: 49

| | |
|---|---|
| gagttcctgc aatcccatca | 20 |

<210> SEQ ID NO 50
<211> LENGTH: 22
<212> TYPE: DNA
<213> ORGANISM: Bovine

<400> SEQUENCE: 50

| | |
|---|---|
| tgctcaggct ggtttctctt cc | 22 |

<210> SEQ ID NO 51
<211> LENGTH: 20
<212> TYPE: DNA
<213> ORGANISM: Bovine

<400> SEQUENCE: 51

| | |
|---|---|
| aagactctgg tggttgcaca | 20 |

<210> SEQ ID NO 52
<211> LENGTH: 22
<212> TYPE: DNA
<213> ORGANISM: Bovine

<400> SEQUENCE: 52

| | |
|---|---|
| acgctgctga ctatactggg tg | 22 |

<210> SEQ ID NO 53
<211> LENGTH: 22
<212> TYPE: DNA
<213> ORGANISM: Bovine

<400> SEQUENCE: 53

| | |
|---|---|
| agatgagtgt gagccgggaa ca | 22 |

<210> SEQ ID NO 54
<211> LENGTH: 20
<212> TYPE: DNA
<213> ORGANISM: Bovine

<400> SEQUENCE: 54

| | |
|---|---|
| tcatagcttc cttccggaca | 20 |

<210> SEQ ID NO 55
<211> LENGTH: 20
<212> TYPE: DNA
<213> ORGANISM: Bovine

<400> SEQUENCE: 55

| | |
|---|---|
| atgaaatgcg cactgactcc | 20 |

<210> SEQ ID NO 56
<211> LENGTH: 20
<212> TYPE: DNA
<213> ORGANISM: Bovine

<400> SEQUENCE: 56

| | |
|---|---|
| tacggcggca gaatgtttca | 20 |

<210> SEQ ID NO 57
<211> LENGTH: 20
<212> TYPE: DNA
<213> ORGANISM: Bovine

<400> SEQUENCE: 57

| | |
|---|---|
| actctaaatt cgctgggtgg | 20 |

<210> SEQ ID NO 58
<211> LENGTH: 20
<212> TYPE: DNA
<213> ORGANISM: Bovine

<400> SEQUENCE: 58

| | |
|---|---|
| aggcattctc ccagatccat | 20 |

<210> SEQ ID NO 59
<211> LENGTH: 20
<212> TYPE: DNA
<213> ORGANISM: Bovine

<400> SEQUENCE: 59

| | |
|---|---|
| acaaagccgc acgcagattt | 20 |

<210> SEQ ID NO 60
<211> LENGTH: 20
<212> TYPE: DNA
<213> ORGANISM: Bovine

<400> SEQUENCE: 60

| | |
|---|---|
| ggtctgtatc tccatccacg | 20 |

<210> SEQ ID NO 61
<211> LENGTH: 20
<212> TYPE: DNA
<213> ORGANISM: Bovine

<400> SEQUENCE: 61

| | |
|---|---|
| ggttcttaag gctaatgcgc | 20 |

<210> SEQ ID NO 62
<211> LENGTH: 20
<212> TYPE: DNA
<213> ORGANISM: Bovine

<400> SEQUENCE: 62

| | |
|---|---|
| cacagaggcc gacggaagaa | 20 |

<210> SEQ ID NO 63
<211> LENGTH: 20
<212> TYPE: DNA
<213> ORGANISM: Bovine

<400> SEQUENCE: 63
tcagaggtgg tgctcagagg                                              20

<210> SEQ ID NO 64
<211> LENGTH: 22
<212> TYPE: DNA
<213> ORGANISM: Bovine

<400> SEQUENCE: 64
tttaacagcc aacgctccgt gc                                           22

<210> SEQ ID NO 65
<211> LENGTH: 22
<212> TYPE: DNA
<213> ORGANISM: Bovine

<400> SEQUENCE: 65
cgacccaaag tcacaaaccg ct                                           22

<210> SEQ ID NO 66
<211> LENGTH: 19
<212> TYPE: DNA
<213> ORGANISM: Bovine

<400> SEQUENCE: 66
acctgcaagg ccgcgttgt                                               19

<210> SEQ ID NO 67
<211> LENGTH: 20
<212> TYPE: DNA
<213> ORGANISM: Bovine

<400> SEQUENCE: 67
ctggagtttg aggctgccgt                                              20

<210> SEQ ID NO 68
<211> LENGTH: 20
<212> TYPE: DNA
<213> ORGANISM: Bovine

<400> SEQUENCE: 68
cgcctcgttg caagtagaga                                              20

<210> SEQ ID NO 69
<211> LENGTH: 22
<212> TYPE: DNA
<213> ORGANISM: Bovine

<400> SEQUENCE: 69
gctgacagga aagttgtgct ga                                           22

<210> SEQ ID NO 70
<211> LENGTH: 421
<212> TYPE: DNA
<213> ORGANISM: Bovine

<400> SEQUENCE: 70
cgtagcaggg gacctgcaag gccgcgttgt ggccgccgcc gccttcctgg agtttgaggc    60
tgccgtccgg gggcgtcttg caggcgcctc gttgcaagta gagatgcggc tgcggcgcgg   120
gcggctgcgg ctgcggcgcg ggcggctggg gctggaactt gctgaaggag ccccgcgccc   180
cggcgccgct ctccagaggt gctgccgggt cctgctgccc cgcgccgtag cgggcccggc   240
tcttggcgtc cccgaatccc tgcccttttgg cggcggctga caggaaagtt gtgctgaact   300

| | |
|---|---|
| tatcaccgcc ggggtatgcc ctaaaaggcg acgagccctc ccggctctgc gacaccgggc | 360 |
| tgtagtaggc gtccatggca gcagccggcg actcgcagta agagacgcaa gtctcagcat | 420 |
| t | 421 |

<210> SEQ ID NO 71
<211> LENGTH: 24
<212> TYPE: DNA
<213> ORGANISM: Bovine

<400> SEQUENCE: 71

| | |
|---|---|
| agttgaccag atctcccaaa ccct | 24 |

<210> SEQ ID NO 72
<211> LENGTH: 27
<212> TYPE: DNA
<213> ORGANISM: Bovine

<400> SEQUENCE: 72

| | |
|---|---|
| agttgaccag atctcccaaa ccctctt | 27 |

<210> SEQ ID NO 73
<211> LENGTH: 17
<212> TYPE: DNA
<213> ORGANISM: Bovine

<400> SEQUENCE: 73

| | |
|---|---|
| aattcggtcg ccactcc | 17 |

<210> SEQ ID NO 74
<211> LENGTH: 20
<212> TYPE: DNA
<213> ORGANISM: Bovine

<400> SEQUENCE: 74

| | |
|---|---|
| ggagttgaga gacccgcacc | 20 |

<210> SEQ ID NO 75
<211> LENGTH: 20
<212> TYPE: DNA
<213> ORGANISM: Bovine

<400> SEQUENCE: 75

| | |
|---|---|
| ggaacaggac ttcactacag | 20 |

<210> SEQ ID NO 76
<211> LENGTH: 20
<212> TYPE: DNA
<213> ORGANISM: Bovine

<400> SEQUENCE: 76

| | |
|---|---|
| ccttctacac ggctaatcac | 20 |

<210> SEQ ID NO 77
<211> LENGTH: 20
<212> TYPE: DNA
<213> ORGANISM: Bovine

<400> SEQUENCE: 77

| | |
|---|---|
| catcgcacta gtctgaggtt | 20 |

<210> SEQ ID NO 78
<211> LENGTH: 20
<212> TYPE: DNA

<213> ORGANISM: Bovine

<400> SEQUENCE: 78
ggaatgcaga cacctagtca                                              20

<210> SEQ ID NO 79
<211> LENGTH: 20
<212> TYPE: DNA
<213> ORGANISM: Bovine

<400> SEQUENCE: 79
gttctagacg cttgcacaac                                              20

<210> SEQ ID NO 80
<211> LENGTH: 20
<212> TYPE: DNA
<213> ORGANISM: Bovine

<400> SEQUENCE: 80
agctctagga agttgacagg                                              20

<210> SEQ ID NO 81
<211> LENGTH: 20
<212> TYPE: DNA
<213> ORGANISM: Bovine

<400> SEQUENCE: 81
ggtccagact gtcacagatg                                              20

<210> SEQ ID NO 82
<211> LENGTH: 20
<212> TYPE: DNA
<213> ORGANISM: Bovine

<400> SEQUENCE: 82
cctaaggaga tgagaagcag                                              20

<210> SEQ ID NO 83
<211> LENGTH: 20
<212> TYPE: DNA
<213> ORGANISM: Bovine

<400> SEQUENCE: 83
gtcctgatct ctgatgtgcc                                              20

<210> SEQ ID NO 84
<211> LENGTH: 20
<212> TYPE: DNA
<213> ORGANISM: Bovine

<400> SEQUENCE: 84
ttggctccgc tgtctagaat                                              20

<210> SEQ ID NO 85
<211> LENGTH: 20
<212> TYPE: DNA
<213> ORGANISM: Bovine

<400> SEQUENCE: 85
tcatcttgct gcatgtcggt                                              20

<210> SEQ ID NO 86
<211> LENGTH: 20
<212> TYPE: DNA

```
<213> ORGANISM: Bovine

<400> SEQUENCE: 86
cagcttcctg agtgtgatcc                                        20

<210> SEQ ID NO 87
<211> LENGTH: 20
<212> TYPE: DNA
<213> ORGANISM: Bovine

<400> SEQUENCE: 87
catacagacc tggctcaagt                                        20

<210> SEQ ID NO 88
<211> LENGTH: 20
<212> TYPE: DNA
<213> ORGANISM: Bovine

<400> SEQUENCE: 88
acgctctgga tctcatcctt                                        20

<210> SEQ ID NO 89
<211> LENGTH: 20
<212> TYPE: DNA
<213> ORGANISM: Bovine

<400> SEQUENCE: 89
cttagctcca gagatgcgaa                                        20

<210> SEQ ID NO 90
<211> LENGTH: 20
<212> TYPE: DNA
<213> ORGANISM: Bovine

<400> SEQUENCE: 90
agtcacctgc taccatctcc                                        20

<210> SEQ ID NO 91
<211> LENGTH: 22
<212> TYPE: DNA
<213> ORGANISM: Bovine

<400> SEQUENCE: 91
ccgaactgaa ctgacacttg ct                                     22

<210> SEQ ID NO 92
<211> LENGTH: 20
<212> TYPE: DNA
<213> ORGANISM: Bovine

<400> SEQUENCE: 92
acctctatgc cacctaggat                                        20

<210> SEQ ID NO 93
<211> LENGTH: 20
<212> TYPE: DNA
<213> ORGANISM: Bovine

<400> SEQUENCE: 93
aagatgagtc cttggccaca                                        20

<210> SEQ ID NO 94
<211> LENGTH: 22
<212> TYPE: DNA
```

<213> ORGANISM: Bovine

<400> SEQUENCE: 94
acgagaggcc ttgtctttgc ac                                    22

<210> SEQ ID NO 95
<211> LENGTH: 20
<212> TYPE: DNA
<213> ORGANISM: Bovine

<400> SEQUENCE: 95
tcagtgcctt cctcctcata                                       20

<210> SEQ ID NO 96
<211> LENGTH: 20
<212> TYPE: DNA
<213> ORGANISM: Bovine

<400> SEQUENCE: 96
tgatcctgga ctcagtgatg                                       20

<210> SEQ ID NO 97
<211> LENGTH: 20
<212> TYPE: DNA
<213> ORGANISM: Bovine

<400> SEQUENCE: 97
acagattgga acgagggaga                                       20

<210> SEQ ID NO 98
<211> LENGTH: 20
<212> TYPE: DNA
<213> ORGANISM: Bovine

<400> SEQUENCE: 98
agtaagccct cttgaagcca                                       20

<210> SEQ ID NO 99
<211> LENGTH: 20
<212> TYPE: DNA
<213> ORGANISM: Bovine

<400> SEQUENCE: 99
tagagcttga ggtgccttga                                       20

<210> SEQ ID NO 100
<211> LENGTH: 20
<212> TYPE: DNA
<213> ORGANISM: Bovine

<400> SEQUENCE: 100
aacacagcac acagatcgga                                       20

<210> SEQ ID NO 101
<211> LENGTH: 20
<212> TYPE: DNA
<213> ORGANISM: Bovine

<400> SEQUENCE: 101
ctgcatgctg attagctggt                                       20

<210> SEQ ID NO 102
<211> LENGTH: 20
<212> TYPE: DNA

```
<213> ORGANISM: Bovine

<400> SEQUENCE: 102
ttctgaactg gctcttgtgg                                                    20

<210> SEQ ID NO 103
<211> LENGTH: 20
<212> TYPE: DNA
<213> ORGANISM: Bovine

<400> SEQUENCE: 103
ttcagcctgt acctcagtga                                                    20
```

SCREENING FOR THE GENETIC DEFECT CAUSING TIBIAL HEMIMELIA IN BOVINES

STATEMENT REGARDING FEDERALLY SPONSORED RESEARCH OR DEVELOPMENT

This invention was at least in part made with government support under AG 2004-34480-14417 and 58-5438-2-313 awarded by the USDA. The government has certain rights in the invention.

REFERENCE TO A SEQUENCE LISTING

A sequence listing containing SEQ ID NOs:1-103 is submitted as a text file with filename: 163-06 replacement seqlist.txt, created Oct. 18, 2011, 398841 bytes in size, and is specifically incorporated by reference.

BACKGROUND OF THE INVENTION

Tibial Hemimelia (TH) is a lethal congenital disorder in cattle characterized by severe and lethal deformities in newborn calves, including multiple skeletal deformities such as twisted rear legs with fused joints, large abdominal hernias and/or skull deformities. Often, such a calf is born dead, or if it survives birth cannot stand to nurse and must be destroyed, resulting in economic loss for owners.

TH was first described in Galloway cattle in the 1960's and in Shorthorn cattle in 2000. Since that time there have been hundreds of calves identified with TH. Extensive breeding and pedigree studies (see Marron et al. 2005; Ojo et al., 1974; Lapointe et al. 2000) have revealed that TH has an autosomal recessive mode of inheritance. For the TH phenotype to be expressed, a calf must have inherited the defective gene from both parents. A calf that expresses the phenotype is "homozygous" for the mutant TH gene, and the parents of such a calf are "heterozygous carriers" for the mutant TH gene. It is virtually impossible in the absence of planned breeding studies or test matings to classify whether a normal appearing individual is a heterozygous carrier of the mutant TH gene or is homozygous for the normal allele. Genetic screening is beneficial in avoiding loss of genetic resources due to culling based only on pedigree.

Because heterozygous individuals appear normal, carriers of the trait cannot be identified by eye, and instead exhaustive and time-consuming familial analysis must be done in order to identify potential carrier individuals. There is a need in the art for screens that can identify heterozygous carriers of TH by genetic testing to facilitate a breeding program that eliminates the genetic defect from the population. Such a screen requires an understanding of the genetic basis of the defect, including identification of the causative mutation within the DNA sequence. The present invention discloses a mutation associated with TH and provides a genetic test to determine whether apparently normal individuals carry a defective gene associated with TH. The present invention enables testing of individuals to determine whether an individual is a carrier. Individuals that are carriers can be removed from the breeding population, thereby facilitating removal of this genetic defect from the population.

While dramatic culling of suspected carriers would reduce the frequency of the mutation responsible for TH, such culling is long, expensive and can result in unnecessary reduction of beneficial genetic traits, as many of the culled animals would not be carriers of the mutation. Accordingly, there is a need in the art for a diagnostic or genetic screening test to determine whether or not an animal is a carrier of the mutation responsible for TH. The present invention provides materials and methods for screening animals to determine whether an animal is a heterozygous carrier of the mutant allele responsible for TH.

SUMMARY OF THE INVENTION

The invention features screens, methods, kits and associated probes, primers and DNA sequences for diagnosing in an animal, the genetic defect responsible for TH. The methods of the present invention are used to diagnose whether a phenotypically "normal" animal is a recessive carrier of a mutated gene which is associated with TH. In an embodiment, the method is for detecting a genetic defect in bovine genome that affects the ALX4 gene and, more particularly, a genetic defect that comprises a deletion mutation. The methods described herein are useful in detecting a deletion mutation greater than about 10,000 base pairs in length in the bovine genome that results in loss of ALX4 gene function. The specifically disclosed deletion is within SEQ ID NO:2, wherein about 45,693 base pairs are deleted, as reflected in SEQ ID NO:2 (wildtype gene), SEQ ID NO:3 (mutant TH gene) and SEQ ID NO:4 (deleted portion).

The methods of the invention rely on the finding that the mutation associated with TH is a deletion mutation. The deleted portion of the DNA corresponds to a "middle region" of the DNA sequence. The adjacent sequence portions upstream and downstream of this middle region correspond to an "upstream region" and "downstream region", respectively. A normal TH genome (e.g., "non-mutant" or "wildtype") has upstream, middle and downstream regions in a contiguous configuration. A mutant TH genome has at least one allele comprising the corresponding upstream and downstream regions in a contiguous configuration (e.g., the middle region is absent). In accordance with the present invention, each strand of a wildtype DNA molecule to be tested or screened comprises three regions: (i) an upstream region; (ii) a downstream region, and (iii) a sequence between the upstream and downstream regions. In a mutant DNA molecule associated with TH, the sequence between the upstream and downstream regions is deleted.

Accordingly, diagnostic assays and DNA tests of the present invention determine whether or not a deletion mutation within the region of the genome that encodes ALX4 is present. In an embodiment, the bovine genome comprises the bovine DNA sequence of SEQ ID NO:2 (wildtype) and/or SEQ ID NO:3 (mutant TH—found in TH-expressing phenotype and heterozygous TH carriers), wherein the middle portion corresponds to bases 29,693 to 75,385 of SEQ ID NO:2; also provided in SEQ ID NO:4.

An example of an upstream region DNA sequence is at least portion of the sequence upstream of, and contiguous to, base 29,693 of SEQ ID NO:2, or bases 1 to 29,692 of SEQ ID NO:2, or upstream, including and contiguous to base 1270 of SEQ ID NO:3, or bases 1-1270 of SEQ ID NO:3.

An example of a downstream region DNA sequence is at least portion of the sequence downstream of, and contiguous to, base 75,385 of SEQ ID NO:2, or bases 75,386 to 85,941 of SEQ ID NO:2, or downstream, including and contiguous to base 1271 of SEQ ID NO:3, or bases 1271 to 1686 of SEQ ID NO:4.

The DNA analysis optionally comprises PCR to amplify specific DNA sequences, thereby providing for accurate and reliable diagnostic and screening methods of the present invention. Primers are selected that flank regions of interest, including potential breakpoints or portions of the DNA sequence corresponding to the middle region. In an embodiment, a forward primer is selected that is capable of specific binding to the upstream region and a reverse primer is selected that is capable of specific binding to the downstream region. Such a primer pair cannot amplify DNA if the middle about 46 kb portion of DNA is present (e.g., wildtype), because the primers are sufficiently separated that amplification cannot efficiently occur. In the presence of the specifically exemplified deletion mutation, however, the two primers are close enough, for example less than about 5,000 base pairs, or less than 1,000 base pairs, or less than about 500 base pairs, for efficient amplification. The amplified DNA product is detected by any means known in the art, including with a probe (radioactive, fluorescent, luminescent or colored, for example), by a DNA sequencer, or by running the sample on an electrophoretic gel and detecting the DNA of an expected size.

Forward and reverse primers (as well as probes) useful in the present invention are shown in Table 3 in bold and in bold and underline. The probes and primers of the present invention comprise those having sequences corresponding to, or a reverse complement of, the bold or the bold and underlined sequences outlined in Table 3. Reverse primers correspond to reverse complementary sequences of the DNA sequences in bold or in bold underline. The invention includes the reverse complement sequences to obtain primer and probe sequences that specifically bind to targets of SEQ ID NOs:2-4, including specific targets within the upstream, middle, downstream, or potential breakpoint regions. A reverse primer is paired with a forward primer having a sequence with a region identical to at least a portion of the DNA sequences of any of SEQ ID NOs:2-4, including a region identical to at least a portion of the upstream region DNA sequence. Each of the indicated primers are capable of specific binding in that they do not span a DNA repeating sequence and do not have significant homology with any other DNA sequence of similar length. For example, the probes or primers may have up to seven adjacent nucleotides in common and have approximately 70% homology, including 70% and greater, with the corresponding target sequence given by a portion of any of SEQ ID NOs:2-4, or reverse complement thereof. Accordingly, the probes and primers are not limited to those explicitly exemplified, but encompass other probes and primers that one of ordinary skill in the art identifies as capable of specific binding. In addition, probes and primers specific to the breakpoint regions, (shown by the triangle in Table 4 and corresponding to between bases 1270 and 1271 of SEQ ID NO:4; upstream breakpoint between bases 29,692 and 29,693 of SEQ ID NO:2; downstream breakpoint between bases 75,385 and 75,386 of SEQ ID NO:2) are particularly useful in DNA-based analysis for determining TH deletion mutation status.

The two primer system that distinguishes between a (deleted) mutant gene and a normal gene relies simply on the presence or absence of an amplified DNA product, for example. If the primer pair flanks the potential deletion region, an amplified DNA product only occurs for the mutant and the animal is classified as "normal" if there is no amplified DNA product. Similarly, if the primer pair spans the breakpoint region (e.g., one primer specifically binds only if upstream and middle (or middle and downstream) is contiguous, absence of amplified product indicates the animal has a mutant allele. Accordingly, for quality control, addition of a third primer to the forward and reverse primers is desirable so that two distinguishable DNA products are generated which can then be distinguished by, for example, size or differentially-labeled probes. Preferably, the third primer is capable of specific binding to the middle region (or at least one end of the primer specifically binds to the upstream region and the other end specifically binds to the middle region, or alternatively one end of the primer binds to the downstream region and the other primer end binds to the middle region) so that a DNA product corresponding to the third primer and the forward primer is amplified. In this manner, every sample processed will have an amplified DNA product, which can be differentially detected and which serves as an internal control on PCR. Such a three-or-more primer system addresses a concern about whether lack of signal can be attributed to deficient PCR processing of an individual sample instead of whether or not there is a TH mutation.

In a particular embodiment, the DNA analysis further comprises providing one or more of a forward primer having the sequence of SEQ ID NO:5 (to specifically hybridize to the complementary strand corresponding to bases 29,619 to 29,640 of SEQ ID NO:2 or to bases 1,197 to 1,218 of SEQ ID NO:3), a reverse primer having the sequence of SEQ ID NO:6 (to specifically hybridize to bases 75,709 to 75,730 of SEQ ID NO:2 or to bases 1594 to 1615 of SEQ ID NO:3) and a third primer having the sequence of SEQ ID NO:7 (to specifically hybridize to bases 29,941 to 26,962 of SEQ ID NO:2; bases 249 to 270 of SEQ ID NO:4).

The DNA can be analyzed directly by providing a DNA probe that is capable of specific binding to a region that identifies the DNA as normal (e.g., the middle region, or the contiguous ends of the middle and upstream or middle and downstream regions) or is capable of binding to a region that identifies the DNA as a mutant (e.g., the breakpoint region). Alternatively, the DNA can be analyzed by DNA sequencing and comparing the sequences to those provided herein to determine whether there is a mutation. These techniques are optionally combined with PCR to generate an improved signal or additional information.

The oligonucleotide probes or primers of the present invention can be used with any of the methods disclosed herein. Probe or primer sequences are designed based on the DNA sequences provided herein, and specifically hybridize or bind to DNA regions so as to provide information about whether or not a deletion mutation in the ALX4 gene is present. In an embodiment, the probes or primers comprise a purified oligonucleotide having a length of about 15 to about 50 nucleotides. Particular specific binding sites include those encompassing bases 1270 and 1271 of SEQ ID NO:3, by the middle region defined by SEQ ID NO:4, and the middle region of bases 29,693 to 75,385 of SEQ ID NO:2 and contiguously associated upstream and downstream flanking regions.

The methods and materials provided herein can be used on any animal, and is preferably used in bovine to detect the presence or absence of a TH mutation, and is particularly useful in testing animals having any Shorthorn ancestry, for example Shorthorn and their composites. The tests and materials can be used with the DNA obtained from any animal tissue or fluid. Convenient samples are obtained from hair, blood or semen.

The invention encompasses an isolated and purified nucleic acid molecule of any of the sequences disclosed herein (e.g., those of Tables 3 and 4, and any of the SEQ ID NOs), or including at least a functional fragment thereof. Useful primers and probes include those that specifically bind a target sequence that resides in at least a portion of a particular DNA region such as an upstream region, downstream region or a middle region. Other useful oligonucleotide primers or probes include those that specifically bind a breakpoint or those that specifically bind two adjacent regions, such as an isolated and purified nucleic acid molecule comprising at least a functional fragment of a deletion breakpoint that is the causative agent of TH. The probes or primers can be of any length and homology, so long as the length and homology is sufficient to result in specific binding to a specified target region. In an embodiment, the probe or primer is an oligonucleotide or a DNA sequence that ranges in size from about 15 to 80 bases, or about 18 to 60 bases, or about 20 to 25 bases. Desirably, at least 12, at least 15, or preferably at least 20 bases are homologous to the target sequence. In an embodiment, all the primer or probe base are homologous (e.g., complementary) to the target sequence. Exemplary probe or primer sequences are provided in Table 3 in bold, and also in bold and underline.

Kits comprising any of the oligonucleotide probes or primers of the present invention are within the scope of the invention. The kits can further comprise instructions for appropriate DNA processing, hybridization and/or PCR conditions, and for visualizing or detecting amplified DNA products.

For quality control, the kit optionally comprises DNA test samples that are a positive control (e.g., a mutant DNA sample comprising the breakpoint indicated in Table 4; corresponding to between bases 1270 and 1271 of SEQ ID NO:3) and/or test samples that are a negative control comprising the middle region and associated flanking upstream and downstream regions, as summarized for SEQ ID NO:2. These controls can comprise DNA sequences corresponding to expected DNA-amplified products from the primers of the kit, or can be isolated and purified DNA sequences corresponding to wildtype or to normal that can be used by the probes or primers of the kit.

DETAILED DESCRIPTION OF THE INVENTION

Figure 1A:
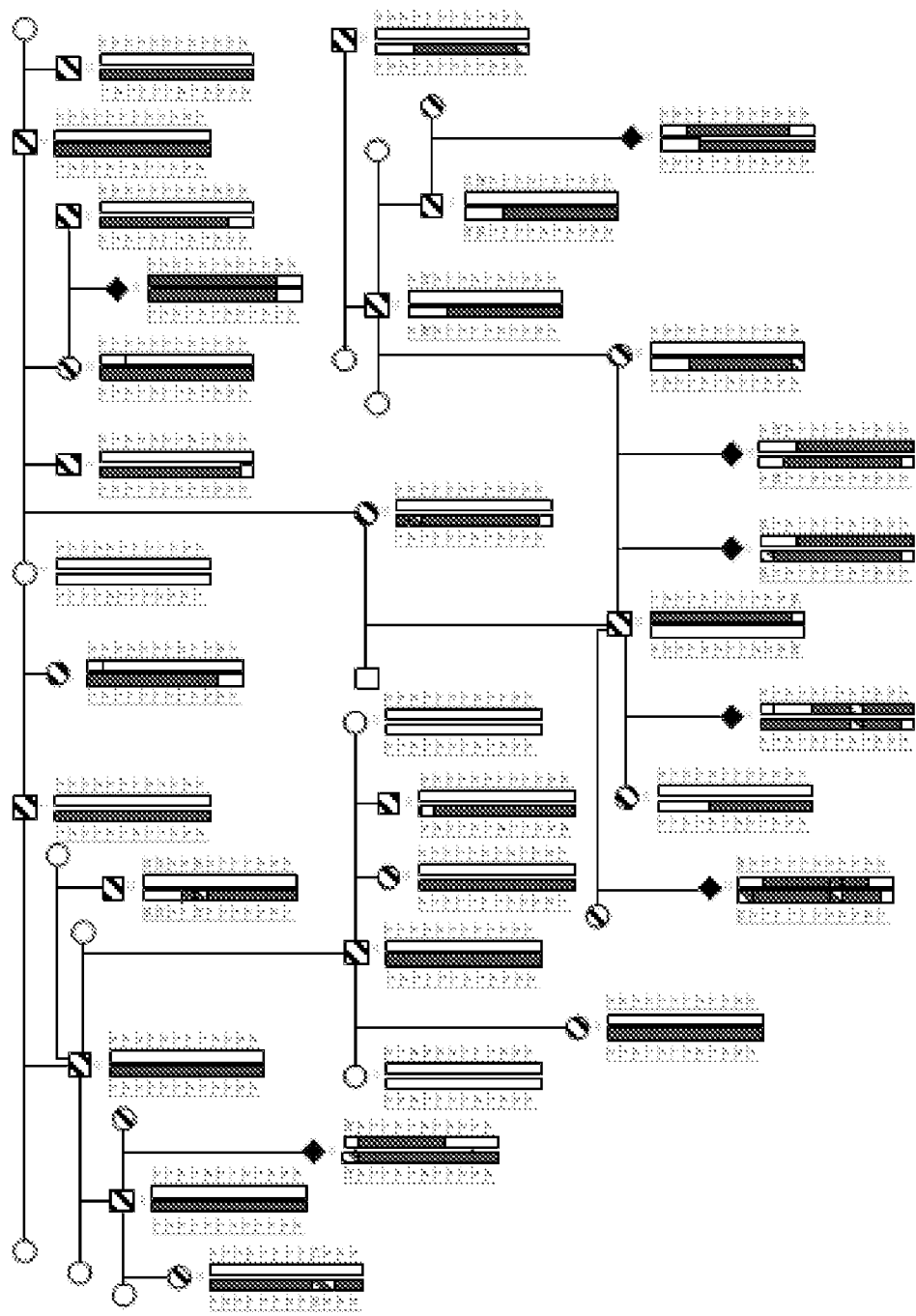
FIG. 1 shows two pedigrees (A and B) representing a panel of 61 animals used for mapping the TH locus. Bulls are represented by squares and cows are represented by circles. Hatched circles or squares refer to carrier animals and filled diamonds refer to affected calves (e.g., TH phenotype expressed). Haplotypes are located beneath each animal on the panel. Filled chromosomes represent the TH haplotype. Hatched alleles and those in parenthesis are inferred.

TH is observed in Shorthorn cattle and Shorthorn influence cattle, including but not limited to non-purebred registered Maine-Anjou, Chianina, Santa Gertrudis and Simmental and any crossbreds. In particular, any animal that can be traced back to a particular Shorthorn bull imported to the US in the 1970's is potentially a carrier of the defective gene responsible for TH. Analysis of lineage lines indicates that TH is an autosomal recessive disease. Accordingly, many animals in the breeding population are potential "heterozygous carriers", e.g., animals that have one copy of the gene responsible for TH. This number is estimated to be as high as 10% in certain Shorthorn breeds. The methods and compositions of matter presented and claimed herein are particularly useful for diagnosing whether or not an animal is a recessive carrier of the defective gene responsible for TH. These animals can be removed from the breeding population so as to breed out the gene responsible for TH.

As used herein, "DNA sample" includes the part of the bovine genome that is a locus for TH. In particular, it is that part of the genome associated with expression of ALX4. The invention, accordingly, is useful for detecting whether or not there is a deletion mutation that when inherited from both parents results in phenotypic expression of TH. An animal that is a heterozygous carrier of this deletion mutation is said to have a mutation that is associated with TH.

"Obtaining" is used broadly to refer to any method of obtaining a biological sample that contains DNA, and specifically a sample that contains at least a portion of the genome spanning a region associated with the mutation that is a causative agent of TH. The sample can be from any tissue, so long as the sample contains DNA that is not significantly degraded, and can be fresh, frozen or otherwise preserved. For example, blood, semen or hair are relatively easily obtained and can be processed for immediate analysis or stored for later transport, processing and analysis.

As used herein, "analyzing" broadly refers to any technique that reveals genetic information, particularly whether or not a DNA sample contains an allele comprising a mutation associated with TH. In a preferred embodiment, the technique comprises PCR processing to amplify selected DNA sequences to yield information about the status of the sample. Other techniques, including DNA hybridization with probes, DNA sequencing, DNA separation by gel electrophoresis and others known in the art can be optionally combined with PCR to generate improved signals.

The portion of the bovine genome that is involved with TH, including those portions useful for determining whether an animal is normal or a heterozygous carrier of TH, can be divided into three regions: (i) an upstream region; (ii) a downstream region; and (iii) a middle region, wherein the middle region forms a contiguous configuration with the upstream region at one end and the downstream region at the other end. "Contiguous configuration" refers to two or more DNA sequences forming a continuous DNA strand, wherein there are no additional DNA sequences between adjacent strands. The invention is based on the discovery that the TH mutation is associated with deletion of the middle region, such that the upstream region and downstream region form a contiguous configuration. DNA analysis of known TH mutant genes reveals that the mutant gene has a deletion, whose size and location tends to be conserved among different animals. With this information, methods and related compositions of matter are presented herein that are useful in determining whether or not an animal is a recessive carrier of a TH mutant gene by determining the presence or absence of this middle region.

Polymerase Chain Reaction ("PCR") is a technique in which cycles of denaturation, annealing with primer, and extension with DNA polymerase are repeatedly used to amplify the number of copies of a DNA segment, up to and greater than $10^6$ times. PCR and associated PCR conditions are known in the art and are described more fully in U.S. Pat. Nos. 4,683,195 and 4,683,292, which are herein incorporated by reference. A "primer" is a single stranded oligonucleotide or DNA fragment which hybridizes to a DNA strand. In PCR, primers are generally paired, with a 5' forward primer that hybridizes with the 5' end of the DNA sequence to be amplified, and a 3' reverse primer which hybridizes with the complement of the 3' end of the sequence to be amplified. The amplified DNA sequence encompasses the target sequence hybridized by both primes, as well as the intervening sequence between both primer target sequences. Any portion of the DNA sequences provided herein can be used as a probe or primer, so long as the probe or primer sequence specifically binds one target. Such specific binding improves the reliability of DNA-based screens useful for identifying carriers of the TH mutation.

The oligonucleotide primers and probes are generally selected for their ability to specifically bind to at least a portion of the upstream, downstream or middle DNA region. "At least a portion" refers to the embodiment where the target DNA sequence spans adjacent regions, including upstream-downstream (e.g., TH mutant), upstream-middle (e.g., no TH mutant) or middle-downstream regions (e.g., no TH mutant).

As used herein, "Shorthorn composite" refers to any bovine animal with any Shorthorn ancestry.

Analyzing DNA encompasses any means known in the art: cleavage, where cleavage is dependent on whether or not there is a deletion mutation; hybridizing of probes, where probe binding is dependent on whether or not there is a deletion mutation; PCR amplification, where the presence of amplification products, or the size of the amplification products, depend on whether the deletion mutation is present; DNA sequencing; etc. The invention can be practiced with any DNA detection methods known in the art, including any future-arising detection methods. Analysis methods rely on the discovery of a deletion mutation that is associated with TH, as reflected in the difference between the wildtype genetic sequence (SEQ ID NO:2) and the TH mutant genetic sequence (SEQ ID NO:3), and more specifically, the recognition that a large deletion mutation that is located within a defined location in the genome is associated with the disease (SEQ ID NO:4, corresponding to breakpoint between bases 1270 and 1271 of SEQ ID NO:3). Some examples of methodology that can be useful in detecting whether or not a large deletion is present include U.S. Pat. Nos. 4,683,202 (Process for Amplifying Nucleic Acid Sequences), 6,013,444, 6,225,093 US Pat. Pub No. 2006/0063191 (Detecting Nucleic Acid Deletion Sequences).

The typical DNA deletion of the TH gene is greater than about 40 kb (e.g., the difference between SEQ ID NO:2 and SEQ ID NO:3 is a 45,693 length deletion of SEQ ID NO:4). Accordingly, if this sequence is present (e.g., the genome is from wildtype), under typical PCR conditions (e.g., "short PCR conditions"), a primer pair located on either side of this deletion sequence will not generate any amplified product. If, however, the mutation is present and this sequence is in fact deleted from the DNA sample, the primer pair is then sufficiently close to result in generation of an amplified DNA product that is then detected.

In the use of the oligonucleotides or polynucleotides as probes, the particular probe is labeled with any suitable label known to those skilled in the art, including radioactive and non-radioactive labels. Typical radioactive labels include $^{32}$P, $^{35}$S, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in International Application No. WO 93/16094.

Various degrees of stringency of hybridization can be employed. The present invention contemplates nucleic acid sequences which hybridize under low, moderate or high stringency hybridization conditions to the exemplified nucleic acid sequences set forth herein. Duplex formation and stability depend on substantial complementarity between the two strands of a hybrid, and a certain degree of mismatch can be tolerated. The more stringent the hybridization conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example in Keller, G. H., M. M. Manak (1987) *DNA Probes*, Stockton Press, New York, N.Y., pp. 169-170, hereby incorporated by reference. For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5 times Denhardt's solution, sonicated salmon sperm DNA (50 μg/ml), 0.1% sodium dodecylsulfate (SDS), and 10% dextran sulfate at 4° C., with washes at 42° C. in 0.2×SSC and 0.1% SDS.

An example of high stringency conditions is hybridizing at 68° C. in 5×SSC/5×Denhardt's solution/0.1% SDS, and washing in 0.2×SSC/0.1% SDS at room temperature. An example of conditions of moderate stringency is hybridizing at 68° C. in 5×SSC/5×Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) supra or Ausubel et al. (1995) *Current Protocols in Molecular Biology*, John Wiley & Sons, NY, N.Y., for further guidance on hybridization conditions.

In general, salt and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

"Complement" or "complementary sequence" means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'. This invention encompasses complementary sequences to any of the nucleotide sequences claimed in this invention.

A "functional fragment" of a nucleic acid is a partial sequence of the nucleic acid molecule such that the functional fragment has utility as a probe, primer or a target sequence for specific binding to a complementary probe or primer in the present invention, for example. A functional fragment that is a probe or a primer is useful for diagnosis, sequencing or cloning of the portion of the DNA genome that is associated with TH, including the portion of the genome that encodes ALX4, and that portion of the genome that comprises a deletion mutation associated with TH.

In accordance with the present invention, there is provided a purified and isolated nucleic acid molecule which regulates and encodes for ALX4 protein. Desirably, the nucleic acid molecule is a DNA isolated from Shorthorn or Shorthorn composites. Further encompassed are nucleotide sequences for probes and primers to various portions of the genome associated with the ALX4 gene, and in particular probes and primers that bind specifically to an upstream region, downstream region, or a middle region, wherein the middle region corresponds to a mutation deletion associated with TH. Given a particular sequence, the generation of primers to that sequence is well known in the art. Sequencing and diagnostic primers are typically 20 to 28 base pairs, more preferably 22 base pairs in length, and generally match the sequence of interest between approximately 90% to 100%, most preferably approximately 100%. Primers are typically approximately 20 to 34 base pairs in length, more preferably 21 to 24 base pairs in length, with annealing temperatures in the 50 to 70° C. range. Gene probes are preferably approximately 1 kb in length comprising the gene of interest to be probed.

Particular probe or primer sequences are selected for their ability to bind a single specific region of the DNA sequence in one or more of SEQ ID NOs:2-4, (e.g., "specific binding"), but not to other genomic loci. As used herein, "specific binding" or "binds specifically" refers to an oligonucleotide (e.g., a primer or probe) that is sufficiently selective in hybridizing the target sequence so as to result in DNA analysis that is reliable and accurate in identifying DNA having a TH mutant allele. A probe or primer that is capable of specific binding to a DNA target sequence does not hybridize in significant amounts (e.g., measurable) amounts to a non-target sequence. To ensure specific binding, a number of different considerations are employed. For example, none of the target sequences should be located in DNA repetitive elements. In addition, potential target sequences can be analyzed against the remainder of the sequence to determine whether there are other regions with significant homology. "Homology" or "sequence identity" means the proportion of base matches between two nucleic acid sequences. When sequence homology is expressed as a percentage, e.g., 50%, the percentage denotes the fraction of matches over the length of sequence that is compared to some other sequence. Gaps (in either of the two sequences) are permitted to maximize matching. When using oligonucleotides as probes, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%). A primer or probe sequence of the present invention is considered capable of specific binding if there is less than 80% homology, less than 70%, and preferably less than 50% homology (corresponding, to a 20 base pair probe or primer having less than 16, less than 14, or less than 10 identically aligned bases) to other "non-target" sequences.

Hybridizing the probes or primers with the DNA sample under stringent conditions also reduces the likelihood of binding to regions other than the target region. In general, probes or primers having higher homology to other sequences besides the target sequence can be hybridized under more stringent conditions than probes or primers having lower homology.

For regular PCR conditions, the location of primer pairs are preferably separated by less than about 4,000 base pairs, less than about 2,000 base pairs, or less than about 500 base pairs, thereby ensuring efficient amplification. The invention is not, however, limited to a specific primer separation distance; the constraint is the ability of the primers to generate amplified DNA.

As used herein, the terms "isolated and/or purified" refer to in vitro isolation of a DNA molecule from its natural cellular environment and from association with other components of the cell, such as nucleic acid, so that it can be sequenced, replicated, amplified and/or expressed. An "isolated and purified nucleic acid molecule" is a nucleic acid the structure of which is not identical to that of any naturally occurring nucleic acid. This term covers, for example, DNA which has part of the sequence of a naturally occurring genomic DNA, but does not have the flanking portions of DNA found in the naturally occurring genome. The term also includes, for example, a nucleic acid incorporated in a vector or into the genome of a cell such that the resulting molecule is not identical to any naturally occurring vector or genomic DNA.

All references cited throughout this application, for example patent documents including issued or granted patents or equivalents; patent application publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated.

Whenever a range is given in the specification, for example, a temperature range, a size range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art. All tables attached hereto (e.g., Tables 1-6) are part of the specification.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that starting materials, materials, reagents, synthetic methods, purification methods, analytical methods, assay methods, and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLE 1

Mapping of the Locus Causing TH in Shorthorn Cattle

Tibial Hemimelia is a congenital abnormality present in Shorthorn cattle that is characterized by severe and lethal deformities in newborn calves. These deformities include malformed tibias, abdominal hernias, and meningoceles. Pedigree analysis indicates an autosomal recessive mode of inheritance with a single proband sire. DNA samples from 17 affected calves along with their sires and most dams are collected as well as samples from putative homozygous normal individuals, not related to the proband. A total of 264 microsatellite markers distributed evenly across bovine autosomes are selected for genotyping and linkage analysis. Genotypic data is analyzed for all chromosomes having candidate genes corresponding to human and mouse disease loci with similar phenotypes. This analysis revealed significant linkage between BTA15 and the disease locus. Results of this study provide a foundation for the discovery of the causative mutation of TH and the development of a DNA-based diagnostic test.

The tibial hemimelia (TH) genetic defect was first recognized in Shorthorn cattle in 2000 (Lapointe et al., 2000), but may have been recognized in Galloway cattle in the early 70's (Ojo et al., 1974). The defect is characterized by multiple skeletal deformities, most notably shortened or absent tibia. The tibial deformity can range from bilateral shortening or malformation of the tibia with joint fusion to a completely absent tibia. Other characteristics of the disease may include abdominal hernia, due to incomplete fusion of the pelvic symphysis, presence of meningocele, and a long, shaggy coat. Calves are born dead, or fail to thrive and die shortly after birth (Lapointe et al., 2000).

Pedigree analysis of the affected calves indicates a single common index sire within 6-7 generations. The defect appears in equal frequency between sexes and all parent individuals are normal, indicating an autosomal recessive mode of inheritance. Evidence from prior breeding studies in Galloway cattle suggests the involvement of only a single gene (Leipold et al., 1978).

Prior to the present invention, the frequency of the TH locus is unknown. The prevalent use of asymptomatic carrier animals in breeding populations has resulted in an increase of TH in Shorthorn populations. Currently, progeny testing is the only available testing method used to determine TH status of breeding animals. Therefore, a DNA-based test for the causal mutation is of great importance to identify carrier animals without the need to perform breeding trials. The first step towards this DNA-based test is the identification of the chromosomal location of the TH locus.

Possible candidate genes are selected based on similar phenotypes in humans and mice. Bovine chromosome segments corresponding to human and mouse regions containing these candidate genes are identified based on comparative mapping data (Everts-Van der Wind et al., 2004). Chromosome screening is prioritized based on the number of candidates located on each chromosome. A panel of 61 animals with known TH genotypes is used for mapping the TH locus. These animals are contained within 2 pedigrees and include 17 affected calves, 4 normal, and 40 carrier animals. Over 260 microsatellites from the USDA-MARC map, approximately 10-15 cM apart are selected for genotyping this panel. PCR is carried out in 10 µl reactions containing 1×PCR buffer, 200 µM each dNTP, 0.5 µM each primer, 0.25 U of HotstarTaq polymerase (Qiagen), 5 µCi of [α-32P] dCTP, and 30 ng of genomic DNA. Reactions are incubated at 95° C. for 15 minutes followed by 35 cycles of 94° C. for 30 seconds, 50-65° C. for 45 seconds, and 72° C. for 45 seconds, with a final incubation at 72° C. for 10 minutes. PCR products are analyzed on 7% acrylamide gels. Upon completion of each chromosome, linkage analysis is performed using CRI-MAP v. 2.4.

Figure 1B:
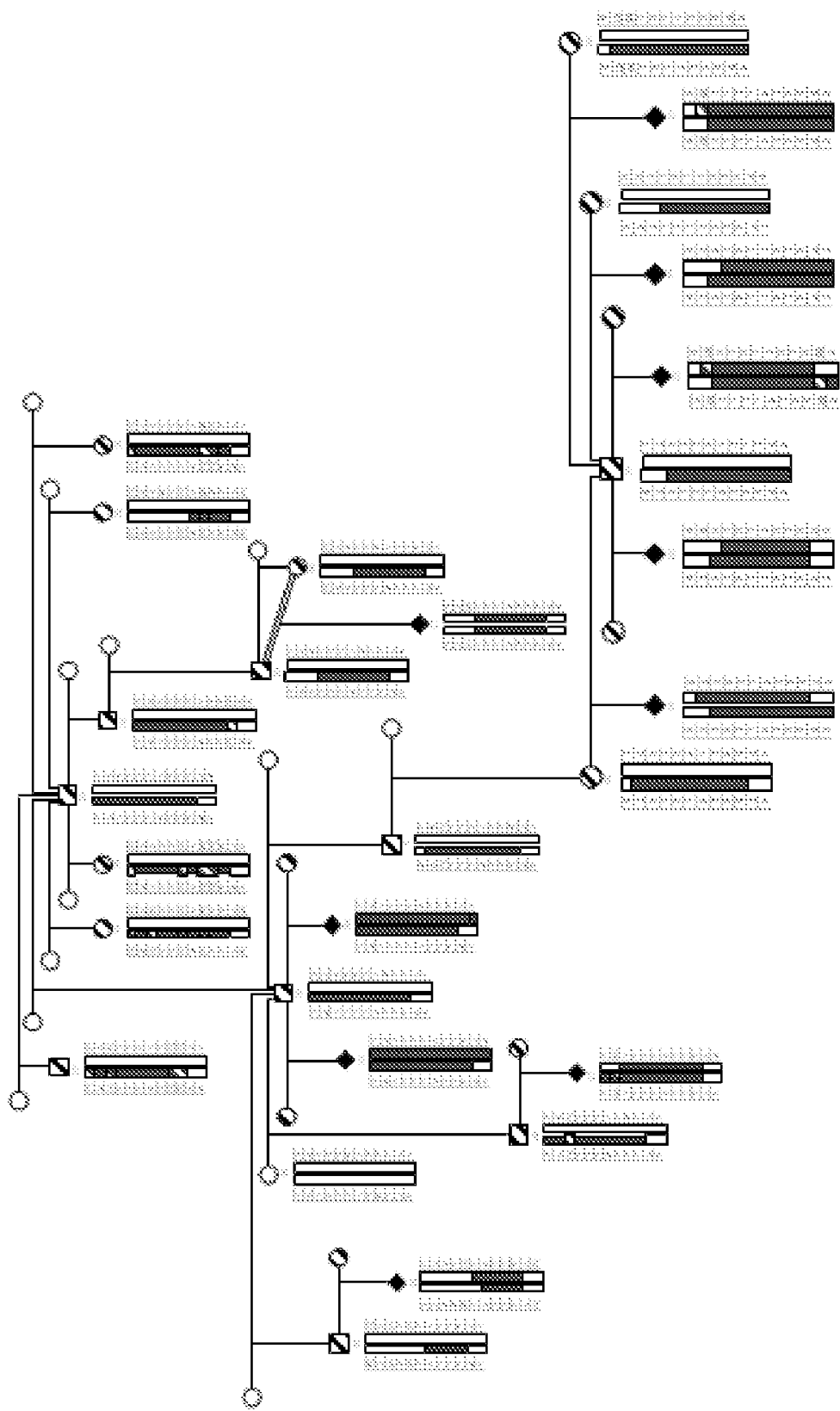

A total of 39 candidate genes are identified on 16 human chromosomes corresponding to 19 different bovine chromosomes. Among these, 2 chromosomes containing three or four candidate genes, 6 with two candidate genes, 9 with one candidate gene, and 10 with no candidate genes are identified. Genotyping is completed for 179 markers corresponding to chromosomes 1-8, 10, 14-16, 21 and 25. Following two-point linkage analysis, one chromosome (BTA15) exhibited strong linkage to the TH locus (FIG. 1). Additional markers are used to genotype the panel in order to fine map the region. The most significant LOD scores are exhibited between TH and BL1095 (5.85), DIK2382 (4.82), BMS820 (8.73), and IDVGA23 (8.73) (Table 1). Using information from affected calves, recombination events between the TH haplotype found in the proband sire and the normal haplotype are used to construct a critical region in this area of BTA15. The haplotype analysis suggests that the TH locus lies between markers 6 and 7 (BL1095 and BMS820) (Table 2).

A comparative genomics approach is used to map the TH locus. This approach is invaluable for both the identification of possible candidate genes as well as prioritization of data collection. Upon examination of homologous conditions in humans and mice, a list of candidate genes responsible for the TH phenotype is assembled. Using the human-bovine comparative map (Everts-Van der Wind, et al. 2004), cattle chromosomes of interest i.e. those containing candidate genes, are identified and analyzed quickly. The strong linkage between two markers on BTA15 and TH prompted genotyping of additional markers in that region. LOD scores for these markers revealed significant linkage to a region between BL1095 and IDVGA23, between 94.7 and 99.9 cM, or approximately a 5 cM region. In order to decrease this region, recombination events between affected calves and the proband sire are analyzed. The haplotype analysis revealed a critical region between BL1095 and BMS820 surrounding the marker DIK2382, corresponding to roughly 95-98 cM. Bovine microsatellite sequences surrounding the critical region are compared to the human genome by BLAST analysis. The microsatellites were homologous to the human sequence between 42.3 Mb-45.2 Mb on HSA 11. One candidate gene identified in the beginning of the study is located in this region of HSA11. The candidate gene in this region is Aristaless-like4, or ALX4 gene. This gene is picked as a candidate due to its strong role in limb formation. Previous studies have linked mutations in this gene to such deformities as parietal foramina (Wu et al., 2000 and Wuyts et al., 2000) and polydactyly (Qu et al., 1998 and 1997).

EXAMPLE 2

Location and Sequence of a Deletion Mutation Responsible for TH

The general location on the bovine genome of the mutation associated with TH allows focused examination of DNA sequences in that location so as to identify the genetic mutation. Table 3 (see SEQ ID NOs: 1-2) provides the sequence for bovine EXT2 and ALX 4 genes from a bovine (Hereford used to generate the CHORI-240 library for the bovine genome sequencing project). The sequence in Table 3 corresponds to the bovine DNA sequence that encompasses the exostoses (multiple) 2 (EXT2) and aristaless-like homeobox 4 (ALX4) genes. Exons corresponding to the protein coding sequence of ALX4 are highlighted and labeled as ALX4_EXON1, ALX4_EXON2, ALX4_EXON3 and ALX4_EXON4. Investigation of normal and mutant alleles reveal that a mutation associated with TH comprises a deletion of the sequence highlighted in gray, running from BREAKPOINT A to BREAKPOINT B. Exon 1 of the ALX4 gene is within this deleted segment region along with associated regulatory sequences. SEQ ID NO:4 contains the sequence of this mutation deletion region. Various probes and/or primers useful in defining the precise breakpoint region as well as for diagnostic tests and screens are in bold or in bold underline.

The portion of the sequence in Table 3 with repeating "N" indicates a sequence gap that is less than about 2 kb. SEQ ID NO:1 corresponds to the sequence upstream of the gap. SEQ ID NO:2 is the sequence contained downstream of this gap, and includes the upstream, middle and downstream regions of the portion of the genome that regulates a protein (ALX4) that is associated with TH. The middle region comprises bases 29,693 to 75,385 of SEQ ID NO:2 and is provided in SEQ ID NO:4. The upstream region is at least a portion of the SEQ ID NO:2 that end with base 29,692. The downstream region is at least a portion of SEQ ID NO:2 wherein the sequence begins at base 75,386. The upstream and downstream regions of the presently claimed invention can be of any length, so long as it is possible for a probe or primer to specifically bind the region in a manner required to carry out the claimed invention.

The deletion breakpoint is determined by PCR amplification across the deletion breakpoint for DNA obtained from TH calves or cattle known to be heterozygous carriers of the TH mutation. Table 4 (corresponding to SEQ ID NO:3) is a sequence obtained from such PCR studies and an arrow highlighted in grey ("▲") (corresponding to between bases 1270 and 1271 of SEQ ID NO:3) indicates the position of the deletion breakpoint. Referring to SEQ ID NO:3, this breakpoint deletion mutation is located between bases 1270 and 1271, such that an upstream region comprises a DNA segment ending at base 1270, and a downstream region comprising a DNA segment beginning at base 1271, wherein the upstream and downstream regions are in a contiguous configuration. As summarized by the shaded portion of Table 3 (corresponding to SEQ ID NO:4), the deleted portion encompasses the 5' regulatory region and exon 1 of the ALX4 gene that controls early events in limb bud (e.g., hind legs) formation. This mutation results in complete loss-of-function of ALX4, thus producing the disease phenotype when an animal is homozygous for the deletion-containing chromosome. Corresponding gene "knock-out" models in mice result in similar pathologies.

BLAST analysis (Table 5) shows the alignment between the sequence of Table 3 (wildtype) and Table 4 (mutant), indicating that the mutant sequence comprises flanking sequences (e.g., upstream region and downstream region) of Table 3 with a middle region of 45,693 deleted.

SEQ ID NO:4 is the sequence of the entire middle region of the bovine genome, wherein the absence of this region is associated with a mutation responsible for TH.

Those of ordinary skill in the art will recognize that any number of DNA-based diagnostic tests can be developed that detect the presence or absence of a deletion on the order of greater than about 30,000 base pairs, or greater than about 45,000 base pairs, or about 45,693 base pairs. Given the length of the DNA sequence of SEQ ID NOs:2 and 4, the invention tolerates variation in both the precise breakpoint location and breakpoint sequence. For example, primers and probes can be designed so that the breakpoints (e.g., between bases 29,692-29,693 and bases 75,385-75,386) can vary, for example by plus or minus 20 base pairs, or plus or minus 10 base pairs, or plus or minus 5 base pairs or less, without affecting the ability of the probe or primer to specifically bind the target sequence and generate an output signal that can be used to determine the presence or absence of a deletion. One example of such designing is to ensure the probe/primer sequence is of adequate length, and also to target sequences that are greater than 5, greater than 10 or greater than 20 base pairs away from the potential breakpoint location.

EXAMPLE 3

DNA-Based Test for Tibial Hemimelia

Any DNA test that detects the breakpoint of the sequence that is associated with TH (e.g., between about bases 29,693 to 75,385 deleted from SEQ ID. NO:2, corresponding to the breakpoint between base G1270 and G1271 of SEQ ID NO:3) can be used as the basis of an assay for testing whether a subject is a carrier of the TH gene. Such tests include but are not limited to DNA sequencing, hybridization and allele-specific extension. For example, PCR can be used to amplify appropriate DNA portions, and the amplified DNA run on a gel that separates DNA by size. In this example, such a PCR test uses three different primer sequences, a first (forward) primer that binds upstream of the breakpoint, a second (reverse) primer that binds downstream of the breakpoint, and a third primer that specifically binds to the middle region, corresponding to the deleted portion of DNA associated with the mutation responsible for TH. The actual location of the target sequence to which the primer specifically binds is not critical, although under "normal" PCR conditions (e.g., not long range PCR conditions, see U.S. Pat. No. 6,225,093) it is preferable if the target sequence is within about 5 kb, or within 1 kb, or within about 500 bases of a potential breakpoint site and the other end of the to-be-amplified DNA sequence. In one embodiment, the primers used are as follows:

```
First (forward) primer (SEQ ID NO: 5):
TH_BIGBREAK_F (5'-TGCTCAGGCTGGTTTCTCTTCC-3')
(corresponding to bases 29,619 to 29,640 of SEQ
ID NO: 2; bases 1,197 to 1,218 of SEQ ID NO: 3)

Second (reverse) primer (SEQ ID NO: 6):
TH_BIGBREAK_R (5'-GTGCAAAGACAAGGCCTCTCGT-3')
(reverse complement of bases 75,709 to 75,730 of
SEQ ID NO: 2 or of bases 1594 to 1615 of SEQ ID
NO: 3).
```

```
                    -continued
Third (binding to middle region) primer (SEQ ID
NO: 7) TH_BIG_344C (5'-CACCCAGTATAGTCAGCAGCGT-3')
(reverse complement of bases 29,941 to 26,962 of
SEQ ID NO: 2, or of bases 249 to 270 of SEQ ID NO:
4; primer does not specifically bind to SEQ ID NO:
3).
```

Figure 2:
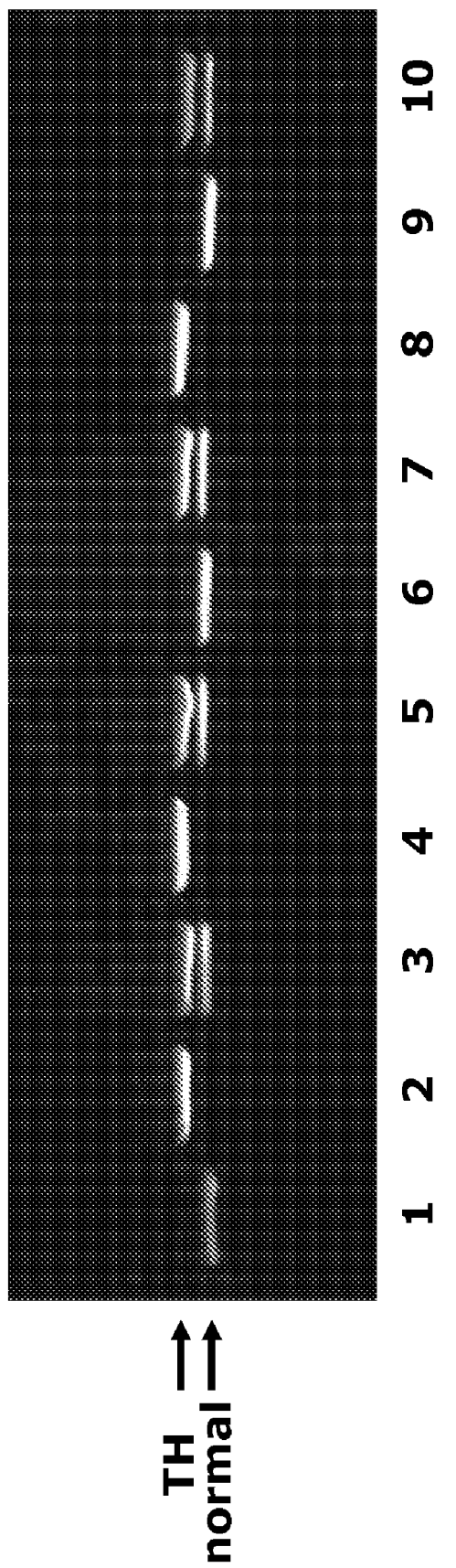
FIG. 2 is an image of the results of a DNA-based test for tibial hemimelia (TH). PCR amplification using primers capable of simultaneous amplification of a normal chromosome segment and a mutated chromosomal segment is used to determine TH status in each of ten DNA samples from different animals. Animals in lanes 1, 6 and 9 are homozygous normal due to the presence of only the DNA segment representing the normal chromosome. Animals in lanes 2, 4 and 8 are homozygous for the chromosome with the deletion mutation causing TH, indicating that the samples were taken from affected calves. Animals in lanes 3, 5, 7 and 10 possess both DNA segments, indicating they are heterozygous and carriers of the mutation associated with TH.

The names of the primers correspond to those provided in Table 3. This combination of primers is used under standard PCR conditions to generate the test results as depicted in FIG. 2. The first and second primers are each located on a separate side of the breakpoint. Accordingly, in a normal allele there is no amplification product attributed to the first and second primers as the intervening about 45 kb sequence between the first and second primers prevent generation of PCR-amplified DNA product. If there is, however, an allele for the TH disease (e.g., the intervening about 45 kb sequence is deleted), a first DNA product is amplified, wherein the DNA corresponds to the region encompassed by the first and second primers. The resultant length of this first DNA product is $L_{12}$. The first and third primers generate a DNA amplified fragment corresponding to the normal chromosome having length $L_{13}$. The third primer resides in the deleted portion, and so a DNA product is not amplified for a TH mutant chromosome. DNA of length $L_{13}$ is generated only if the DNA sequence is wildtype. By selecting precise target sequences, the size of the amplification products generated by primers 1 and 3 ($L_{13}$) can be different than the size generated by primers 1 and 2 ($L_{12}$). The amplified DNA can be run on a gel to separate DNA by size, with the observed pattern dependent on whether or not the DNA from the subject to be tested is a carrier of a TH gene, as summarized in Table 6. FIG. 2 shows that two bands in a lane indicates a chromosome having one allele that has the mutation and another allele that is normal (lanes 3, 5, 7 and 10), thereby identifying the subject as a heterozygous carrier of the TH gene. If only one band is observed, the subject is either normal (lanes 1, 6 and 9) or the sample is from an individual that expresses the TH phenotype (e.g., both alleles have the TH mutation (lanes 2, 4, and 8)), and can be distinguished by size.

As summarized in Table 6, the third primer is not required in order to distinguish a normal animal from a heterozygous TH carrier. For quality control reasons, however, the third primer is optionally present and ensures that the DNA has been appropriately amplified and detected. As known in the art, the DNA need not be run on a gel, rather probes specific to each of the amplification products can be used, including radiolabeled, fluorescently labeled or any other detection substances and associated means for detecting the substance. Size separation and DNA labeling with, for example ethidium bromide is, however, a low-cost and easily performed assay for detecting TH heterozygous carriers.

In an aspect, the amplified DNA products are detected, thereby identifying heterozygous carriers of a gene that is associated with TH. In an embodiment the DNA product is detected by running the DNA on a size-separation gel, wherein the expected sizes of each DNA product is known. Isolated and purified DNA sequences of the present invention corresponding to (1) normal, and (2) mutant can be used to ensure PCR conditions and DNA analysis is functioning appropriately.

A unique, DNA-based diagnostic test that accurately determines the (TH) genotype status within Shorthorn cattle populations through analysis of DNA containing samples i.e. blood, semen or hair follicles is important for eliminating this genetic defect from the population. Such a test eliminates the need for parental validation. FIG. 2 is an example of one such test where PCR amplification of the DNA from each individual is used to determine TH status. This diagnostic assay is supported by three independent validation experiments, including blind analysis of 48 samples of known genotype status based on progeny analysis, analysis of phenotypically normal individuals of suspect pedigree, and analysis of unrelated cattle breeds for the presence of the mutation. Results of the blind sample analysis were 100% concordant with the known genotypic status of the individuals. Among all phenotypically normal individuals of suspect pedigree, as expected no individual was genotyped as homozygous for the deletion mutation. This is further support that that those animals that express the TH phenotype are homozygous for the deletion mutation. Ongoing experiments of bovine animals indicate the deletion mutation is present within Shorthorn and Shorthorn composite animals.

As understood in the art, genomic DNA comprises a sense strand and an antisense strand that is complementary to the sense strand. The sequences listed herein, are to the sense strand, running 5' to 3'. Accordingly, the invention comprises the corresponding antisense sequences that are complementary to the listed sequences, and further include the reverse complementary sequences of all the primers and probes disclosed herein.

SEQ ID NO:1—DNA sequence upstream of gap region

SEQ ID NO:2—Wildtype DNA sequence comprising upstream, middle and downstream regions SEQ ID NO:3—Mutant DNA sequence comprising upstream and downstream regions in contiguous configuration SEQ ID NO:4—DNA sequence of middle region that is deleted in TH genes SEQ ID NO:5—oligonucleotide sequence useful as a forward primer for PCR SEQ ID NO:6—oligonucleotide sequence useful as a reverse primer for PCR SEQ ID NO:7—oligonucleotide sequence useful as a third primer (reverse) for PCR References U.S. Pat. Nos. 6,759,192, 5,498,521, 6,013,444, 4,683, 202, 6,225,093, 6,306,591

U.S. Pub. Nos. 2006/0063191; 20030203372

WO0246465, GB012566; GB0103156; GB0030076; AU0220920

Everts-Van der Wind et al., (2004)

Lapointe, J.-M., Lachance, S., and Steffen D. J. (2000). "Tibial Hemimelia, Menengocele, and Abdominal Hernia in Shorthorn Cattle." Vet Pathol 37:508-511.

Leipold, H. W., Saperstein, G., Swanson, R., Guffy, M. M., and Shalles, R. (1978). "Inheritance of Tibial Hemimelia in Galloway Cattle." Z Tierzuchtung Zuchtungbil 94:291-295.

Marron, B. M. et al. (January 2005) Mapping of the locus causing tibial hemimelia (TH) in shorthorn cattle. Plant & Animal Genomes XIII Conference. San Diego, Calif.

Ojo, S. A., Guffy, M. M., Saperstein, G., Leipold, H. W. (1974). "Tibial Hemimelia in Galloway Calves." J Am Vet Med Assoc 165:548-550.

TABLE 1

Linkage analysis results generated by CRI-MAP. The number informative meioses for each marker is provided on the diagonal (italics). Two-point LOD scores are provided above the diagonal (bold), with those above 3 highlighted in shading.
The recombination frequencies between pairs of loci are provided below the diagonal (plain text).

|    | 1  | 2    | 3    | 4    | 5    | 6    | th   | 7    | 8    | 9    | 10   | 11   |
|----|----|------|------|------|------|------|------|------|------|------|------|------|
| 1  | *38* | 1.13 | -    | -    | -    | -    | -    | -    | -    | -    | -    | -    |
| 2  | 0.24 | *50* | 4.01 | 3.40 | 3.14 | 4.53 | 2.43 | 1.75 | -    | 2.50 | -    | 1.18 |
| 3  | -    | 0.07 | *39* | 4.21 | 2.05 | 1.76 | 1.04 | 1.52 | 1.40 | 2.44 | -    | -    |
| 4  | -    | 0.05 | 0.00 | *30* | 2.08 | 5.42 | 2.28 | 2.52 | 2.31 | 3.37 | -    | -    |
| 5  | -    | 0.06 | 0.07 | 0.08 | *20* | 3.61 | 3.19 | -    | 2.05 | 2.32 | -    | 2.15 |
| 6  | -    | 0.06 | 0.11 | 0.00 | 0.00 | *46* | 5.85 | 2.48 | 4.81 | 4.01 | -    | -    |
| th | -    | 0.19 | 0.25 | 0.14 | 0.06 | 0.05 | *60* | 4.82 | 8.73 | 8.73 | -    | 3.37 |
| 7  | -    | 0.11 | 0.08 | 0.05 | -    | 0.09 | 0.00 | *25* | 4.82 | 4.52 | -    | -    |
| 8  | -    | -    | 0.16 | 0.12 | 0.07 | 0.06 | 0.00 | 0.00 | *39* | 7.53 | -    | 2.52 |
| 9  | -    | 0.12 | 0.09 | 0.05 | 0.07 | 0.07 | 0.00 | 0.00 | 0.00 | *41* | -    | 2.78 |
| 10 | -    | -    | -    | -    | -    | -    | -    | -    | -    | -    | *21* | 2.71 |
| 11 | -    | 0.26 | -    | -    | 0.12 | -    | 0.14 | -    | 0.09 | 0.09 | 0.00 | *39* |

TABLE 2

Recombination events between th (dark) and normal haplotypes (white) of affected calves. The frequency of each haplotype is provided on the vertical axis, and ordered markers are provided along the horizontal axis. This graph suggests that the th locus lies between markers 6 and 7.

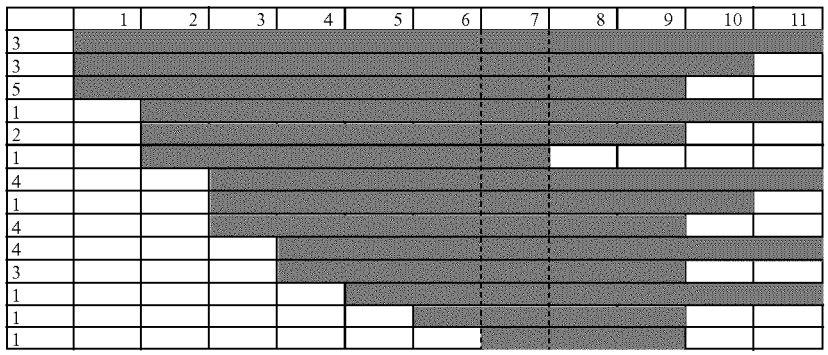

TABLE 3A

SEQ ID NOs: 1-2, BOVINE EXT2 AND ALX4 GENES

```
ATGAAATCCTTGCTGGGTACAATAATCTGGGCGGTAGGTTATTTTCTTCCATCATTTTAAGTATGTCTTG
CCATTCCCTCCTGGCTTGAAGAGTTTCTATTGAAAGATCAGCTGTTATCCTTATGGGAATTCCCTTGCGT
GTTATTTGTTGTTTTTCCCTTGCTGCTTTTAATATTTGTTCTTTGTGTTTGATCTTTGTTAATTTGATTA
ATATGTGTCTTGGGGTGTTTTGCCTTGGGTTTATCCTGTTTGGGATTCTCTGGGTTTCTTGGACTTGGGT
GATTATTTCCTTCCCCAGTTTAGGGAAGTTTTCAACTATTATCTCCTCAAGTATTTTCTCATGGTCTTTC
TTTTTGTCTTCTTCTTCTGGAACCCCTATGATTCGAATGTTGTAGCGTTTAATATTGTCCTGGAGGTCTC
TGAGATTGTCCTCATTTCTTTTAATTCGTTTTTCTTTTATCCTCTCTGATTCATTTATTTCTACCATTCT
ATCTTCTAATTCACTAATCCTATCTTCTGCCTCTGTTATTCTACTATTTGTTGCCTCCAGAGTGTTTTTA
ATTTCATTTATTGCATTATTCATTATATATTGACTCTTTTTTATTTCTTCTAGGTCCTTGTTAAACCTTT
CTTGCATCTTCTCAATCCTTGTCTCCAAGCTATTTATCTGTGATTCCATTTTAATTTCAAGATTTTGGAT
CAATTTCACTATCATTATTCGGAATTCTTTATCAGGTAGATTCCCTATCTCTTCCTCTTTTGTTTGGTTT
GGTGGGCATTTATCCTGTTCCTTTATCTGCTGGCTATTCCTCTGTCTCTTCATCTTGTTTAAATTGCTGA
GTTTGGGGTGTCCTTTCTGTATTCTGGCAGTTTGTGGAGTTCTCTTTATTGTGGCTTTTCCTCGCTGTGT
GTGGGTTTGTACAGGTGGCTTGTCAAGGTTTCCTGGTTAGGGAAGCTTGTGTCGGTGTTCTGATGGGTGG
AGCTGTATTTCTTCTCTTTGTTCAGTCGCGCTGTGGGAGGGAGGGAGGGATGCTGCAAACAAATAACAC
TGGCGTGTGCTCGCAGTGCCTCAGCCACACTGGGTCTGCCCCCGCTCACGGCGCGTGTAGCCTCCCTGCC
CACACTGCTCGGGCTCTAGGTTGTTCCGCCGGGAACAATCCGAGGCTGGCCCTGGGTTGCATGTACCTCC
CAGGTCCAAGCCGCTCAGGTTCAGGCACTCGGGTAGTCCTCAGAGGCGCAGACTCAGTTGGGCCTCAGTT
TTGTGCTCTTCCCAGGTCCGAGCAGCTCAAGTGATGAGGTGTTTGGCGAGCGCCAATGCTGCGACTTATC
GCCTCCCCGCCACTCGGTTATCTGGGTGTAAAACCGGCGCATCTTCTCAGGCAGATGTTAACCGTCCAGA
```

TABLE 3A-continued

SEQ ID NOs: 1-2, BOVINE EXT2 AND ALX4 GENES

```
CCCCCAAGAAGTTTTAGTTAGCAAAGAAGCCTGCTTACAGTTTTATAGATAATGTCTCTCTGGGGCTGCG
ATTGCCCCCTTCCGGCTCTGGCTGCCTGTCACCGGAGGGGAAGGTCTGCAGCCGGCTATCTCCGTTCAG
TCCTTTGTTCCGTGCGCGGGCCTGGCGGTGTCTTAGGTTGGGGCTGGCTTTTCGCGTGGTAGATATCCCA
CAGTCTGGTTTGCTAGCCCAAATTATTTCGCTCAGATAGTGCTCAGGGTATTCAGGCCAGATTCTTACTC
TAAGCGATGCAGCCCGCGCCGCGCCTCCCTGCCCAGCCCCCGCTTGCTAATGGCGCGTGCAGGCGTCTGC
GCTGCTTCTCCGCTGAGGGAGTTACCGTAGGGCTCGCAATCTTCGAGTTTTAATTGTTTATTTATTTTTT
CTTCCTGTTAGTTTGCCCTCTGTGCTTCCAAAGCTTGGCACAGATTCGGCAGTGAGAAGGTTTCCTGGTG
TTTGGAAACTTCTCTCTTTTTAAGACTCCCTTCCCGGGACGGAACTCCGTCCCTCCCTCTTTTTGTCTCTT
TTTTTGTCTTTTATATTTTTTCCTACCTCCTTTCGAAGAGTTGGATTGCTTTTCTGGGTGCCTGACGTCC
TCTGCCGGCATTCAGAAGTTGTTTTGTGGAATTTACTCAACGTTTAAATGCTCTTTTGATGAATTTGTGG

GGGAGAAAGTGTTCTCCCCGTCCTACTCCTACGCCATCTTGGCTCCTCCCAAATGTCAATTTCTTTAGTC
TTTTTCTCTTTTAAAAATTTAGCTTTACAGATCCTGTTTGGTTTTTAATTTGTGTTTTTTTTAATTACT
TAATTACTTCTATGTTTGAATTTATTTTGTTGTGATAATATCTTTTTTTATGATATGTAACTCATTAAAA
TTTGTAAAGCTCATATTTGGATACAGCTTTTGTTCCCTTAGCCCCAGTTTTGTTTATACATGAAAACAGTA
TGTTTTCACACTGTGGGTAATAGACAATTGGGTGGTATAATCATTGTAGTAGGTTATGGCCAGTATTTTA
AAAAACGGTGATAGGATAATACAAGAATACAGTGTTCATCACATATTCTATGGCAAATACTGTGTACTAA
GGTTAAATAAGCGTCGTTTTGTGAAACTTATTTCAAATGCATCTGTGTCTATGTTAGATCACAATACAGA
ATGTTGTTTTATTATAGGTTTTAGTAAAAAAAAAAAAAAAGAGCTTAAACCACTGTATTAAAAGGCAGTTT
GTCTAACATTTAGTAAAGATTTCAAACCTGGCTGCCTAAAATAAACATGTGAGGGGCTTGCTATTTTGAC
ACATTCTCTTTTTTTTTTGACACATTCTGTGACCTTATTTTAGGCCTGCTGATACAGCCCTCCAGTGCTG

GGACCAAGGACTCTGTTTTAACAAACTCTACCTGTGTGATTCTTACAGTTCGGGTTTTTGAGAACCACTG
ATTCAGGATATAGATAGACCTTGAGAGCCTGTTGGGCTGTTGTGACACGGGGCTTGTGGAGAGTACGGCT
CCTTGCATGCATCTGTCCCAAGGCCGCCTCTTTTCTAGCTCCGGGGGGACATGGGGAAGGAAGGAAAGC
GATCAGATGGGTCCGGTGGTAGTAGGGGTCGGGGACCGCCTGTAAACATCTTGTTCGTTGTTAGGATGAC
AGAAAACATGAAATAGCTCTAATGCCTGCATTTCTGTCATGGAATCGATTAGTGTATATTGAATGGCTAA
TGTATATACCCCAAAGATGATTATCTTTAAGCTTAAAATGTATAAACTTTCATACACTAGTCCATGACAA
TCATGTTTTTTTGATACATCCCAGACCATGGTCTCAGATACAGCAGATACAAGTTGAAATCATTAATGAT
CATTCAGCACATTTTACCCCCAAAGCTGATAATGATTGCAACATTCAGGGCTTGACAGGACCCTACTAAG
CTAGGCAGGAAGCAGTTTTACCATGTAGGCATGATTGGAGAGAACTCCATTTAGCAAAGTGAAAATGGTT

CATAAACCCTAAGATGGTCTATGAGCTTTTCAATTGTTTTCCTTTATATTAACGTGTGCTCGGTCACTCA
GTTGTGTCTGACTCTGCAACCCCATTGACTGTAGCCCACCAGGCTCCTCTGTACATGGAATTTCCCAGGC
AAGAATACTGGAGTGGGTTGCCATTTCCTACTCCAGGGGATCTTCCCAACCCAGGGATCAAACTCGTGTT
GCTTGCATCTCCTGCATTGGCAGGTGGATTCTTTACCACTAGCGCCACCTGGGGTTTGAATAACTTTTCT
GAAAGATCAGAGACTAGAATGAGACCATTTTGAAGATTGGAATCTTGACACAAGGAATGCCGAAGTCACT
TGTTGCAGTGACGTGTCTGTGATAGATGAAGGAATCACGCTCAGGTGTGGGTAGGCATCAGGTGTTGGGG
GGCTTGTTTGGTAAGGATCTTAATTTGTGGTCTACAGGGGCACTTTGCATTTTCAGCTGAGGGCTAAAGA
TTTCTTTTTATGTCTCTGTCCATGACGCATTGGCTGTTTCACTTTTTTCTTGCTATGTAGCAAACCACCA

CAAACCTTACAAACAGCAGCAACAATCGTGTGCTCGCTCAGGATTCTGCCGTCTCTGCAGGGCTCGTTGG
GGATGGTTCCTCTTGGCTCCACGTAGTCTCTGCAGTCTTCCTGAGCTTCCTCACAGTGTGGCCCCTGGCC
AATGGCTACAGGGTCTTTTAAAGCCTGGTCTCAAACCCCCCAGAATCTTCCCTTTGCCACTTTCTCTTGG
TCAAAGCAAGTCCCAAGTCTAGCCCGGATTCGGGTGGAAGGGAAAGAGATTCCACGCCGTGAATGGACAA
GGGGCATGCACATTCATCAGTGGGAAGAATGTTTAGCGTCTGTCTTTAGAGACAGATCTACCTCGCTGGC
CTTGCTTTTCCTCCATCTCTCCTTTCCTCCTTCCCTGTTTCTTTCTTCATTTCTCCCTTCCATCAAAATG
TGCCAACTATCCCCTTATTATAAAACATCAATATATCTTTATTTAAAGATTAGTCTTTTTTTCTCTAATA
CCCTTTTCCCCTTTCTTGATATTTTCCTAGTGGTATTTTACATTATACATTTTGTTATAGTTTTGGGTA

TCTTATTAGTATCTAAATTCCTCTAAGGTAGATCTTTGCTTTCTTCTTTAGGTTCTCTATGAGGTTTGAA
TGAATGAATGAATGAAAACTTTAGTATATCAAACAAAAGGCCAGTTTGTCCAGATGAAGCATCAGTTTTT
GTTAGGCAAGTATTTAAAAAACAAAATGAAACTGTCCTTTGGCTGTTCCACTTCTAATTTTCCTTGCTTG
GTCAGCGCTCTTCTTCTTAGGCCTGATATTAACCAGCTTATGCTTTCAGAGAATTTGTATTTATAGAATA
TATTCTATAGTAAATATATAGCATATTTTCACATGTACAAATATTTGTTTACTTTATCAGTTCAGTTCAG
TCATTCAGTTGTGTCCAACTCTTTGTGACCCCATGGACTACAGCACACCAGGCTTCCCTGTCCATCACCA
ATTCCCAGAGCTTACTCAAACTCATGTCCATCGAATCAGTGATGCCATCCAACCATCTCATCCTCTGTCA
TTCCCATCTCCTCCCACCTTCAACCTTTCCCAGCATCAGGGACTTTTCAAATGAGTCAGTTCTTCGCAGG
GTCAAATGTACTGGTCCTTTCGGGGGTCATCTGTCACCCTGAAGGCTTCATTTTCCTCTCTTCTCCGCTG
GTAACCAGGAGTGTGAGGAGGAGGCTGTCGGGGTCATTATGTGCGCGTCGGTCAAGTACAACATCCGGGG

TCCCGCCCTCATCCCGAGAATGAAGACCAAGCACCGCATCTACTACATCACCCTCTTCTCCATCGTCCTG
CTGGGTCTGATCGCCACGGGCATGTTTCAGTTCTGGCCGCACTCCATCGAGTCCTCCGGCGACTGGAGCG
TGGAGAAGCGCAGCGTCCGAGACGTGCCGCTGGTCAGGCTGCCGGCCGACAGCCCGGTGCCCGAGCGCGG
CGACCTCAGCTGCAGGATGCACACGTGTTTCGACGTCTACCGCTGCCTTCAACCCCAAGAACAAGATC
AAGGTGTACATCTACCCGCTGAAGAAGTACGTGGGCGAGGCGGGTGTCCCGGTGAGCAGCACCATCTCCC
GGGAGTACAACGAGCTGCTCACGGCCATCTCAGACAGCGACTACTACACCGACGACGTCACCCGCGCCTG
CCTGTTCGTCCGTCCATCGACCTGCTCAACCAGAACTCGCTCCGCGTGAAGGAGACGGCGCAGGCGCTG
GCCCAGCTCTCCAGGTATCCGCAGGTCTCCCAGAAACTAGGGGCAGGGGAGGGCAGAGCCGGTTTCCAGC
CGGCGGCTCATCTCCTGTCTCAGGTGGGCACGTGGGTGAGCCGCTGACTTGGAGGAGGACCCGCGCTGCG

GGCAGGCAGCCGGTCTCTGCACCACCCTCTTGGGCCACTGCTGTGGGTTCCCAACTTCTTCTTCTTCTTT
TTTTTTTTTAATTTTATTTTATTTTTAAACTTTACAAAATTGTATTAGTTTTGCCAAATATCGAAATGA
ATCCGCCACAGGTTCCCAACTTCTTAACATTTAGAAGCTAAGGAGGGCTCATCTTCCCAATCCTTCCTTT
TAAATGTAAATGCCTTTCCCCACCTCCCCTCTTTATTACTCACATATACATATTCACTATAAAAGCTTG
AAAATACAGTTAAGCAAAAAGAAGAAAGTTAGAGTCATCCCATAAGCCTGCTTTTGACATAACCATTAAT
ATTTTGATGTTGCTTCTCAGTCGTTTCTGTATAAAACATGTACAGGGGCACGCATAGATGCATTTTAGTA
TGTATATGCACATGTATATACACATATCGGAGAAGGCAATGGCACCCCACTCCAGTACTCTTGCCTGGAA
AATCCCATGGATGGAGGAGCCTGGTGGGCTGCAGTCCATGGGGTCTCGAAGGGTCGGACACGACTGAGCA
ACTTCACTTTCACTTTTCACTTTCATGCCCTGGAGAAGGAAATGGCAGCCCACTCCAGTGTTCTTGCCTG
```

TABLE 3A-continued

SEQ ID NOs: 1-2, BOVINE EXT2 AND ALX4 GENES

GAGAATCCCAGGGACGGGGGAGCCTGGTGGGCTGCCGTCTCTGGGGTCGCACAGAGTCAGACACGACTGA
CGCACTTTAGAAGTAGTATATACACATGTGTAGTTCCCTGGTGGCTCAGACAGCAAAGCATCTGCCTACA
ATGTGGGAGACCTGAGTTCAATCCCTGGATAGGGAAGATCTCCTGGAAAAGGAAATGGCAACCCACTCCA
GTATTCTTGCCTGGAAAGTCCCATGGACAGAGAAGCCTGGTGGGCTACAGTCCATGAAGTCGCAAAAGT
CGGACACGACTGAACGACTTCACTTTCACTTTCATACACATATGTGTATGTATAACATTTTGCTCACACA
GCAAAGCGTATTCATTTTGCTGCCTTTTCCCCTTCATTTACCATGCATGTGTTTCCAAATAATTTCATCT
TTGTATGTCAGTGCTGTATGACATATACACAGAATGTATATGTATTCGTTTTTACAGTTCTGTATGGGAC
TCCATTTTGCACACATTCCCTAATGTCCTTAATTAGCCTTCTGTGTTTCTTTGTGTTTTTGTAACCAAAT
GGTGAACACTGCAGTAGCGTTCAGATTTTCATCAGCGTAAGCAGTTCTGCAGTGCACCAGCTTGGAGGAC

ACATGCCCTGGCTTTCCTTTGGAGGAGCCAAGCCAGTGCCCGGAGCGCTGTTGCGATCTCCAGGCATGCA
GTTTGCCTTCCTGAGAAGTGACCCTGTTACAGGTCAGGGATGCTTGCTACTTGTTGTCCAGCTTCCTTTG
TGGCTCATATGGTGAAGAAGCTGCCTAATGCAGGAGGCCTGGGTTTGATCCCTGAGTCTGGAAGATCCCC
TGCAGAAGAGAATGGCAACCCACTCCAGTATTCTTGCCTGGAGAATCCCCATGGCCAGAGGAGCCTGGTG
GGCTGCAGTCCGTGGGGTCGCACAGAGTCAGACATGGCTGAGCAACTAACACTTTGACTTGTCATCCAGA
AACTGACTTGCCTGTTTCTTCACAGTTGATGCGTGAATTCTACATGTTTACTCTCTTATTAGGTGGGATA
GAGGTACCAATCACCTCCTGTTCAACATGTTGCCTGGAGGCCCTCCAGATTATAACACGGCCCTGGATGT
CCCCAGAGACAGGTAGGTGTATTTGGGGTTGTCCACCTGATGGGTTTCTGAGGATTAAGTCAATGTAGGA
CCCTTTTGTTCATGTGAAATCATATTTCTAAGCCCACTAAGACATAACTTTGTAATCAGAATTGTTTGTT

CAAGTGTAAAATTGTCCTCGGTCTTTTCCTCCCTGAGACCTGGAAGCATTGAAACCTGCCAGAATCTGTC
CCGGGAAACTAATGGAGGGTTAGGTTCCAGTGGAGCATCTTAGAGGTCTGTCTTGTCTTCTTTAGTCCGGG
TTATGTGCTCCTGAGCACACGGTCTTTCCCCTAAAAGGCCTGGTTCATATCACTGGCTTGTGTCAGCTCT
CTCTACATTTGGGAGCATTAAGTAGAGTCTCAGCTCCTGAGGGGAGCAGGCGTGGCCGTGTCATTGGAGC
CTGTAACGTCCGGGAAGTGAGGCACTCTAAGTACCGCTTACTCTCTTCTTTCCTTCCTTCCTAATGAAAC
TTCCAAACAGGCAGAAGTGGCATGGGGTGGCCACGATGGCGTTCAAGTTCAGGTGCTGTGCATTTGGCC
CTGTTGTACCAACTGCGTGGCTTCCTGGAAACCTCAGAAGGGAGGTGCCCCTAAGGTTCCTCTCCTAGTG
CTTGGCCTGAGGCTCCGAAGAGCGGGAAGTGTGGGCCCAGCATGAGGGTCCTGGGCAGCAGCCACGGG
AGGGGATTACTGCAAGTTCAGATATGAACTCATTTATACCCAGCTTGTGCAGTTGATGTTTAATTCTT
GAAATCATTGTTACTGAAAGAGGTGAGAACAGCCTTAGGCCCGCTGTGGTCTCTGCTTACTTGAGGCCAA

CATCGTCATTTGTGAAAATCTACACTTAGTACTGCTTTTCCCCAGAAGATTAAGTCTAAGCCCTCTTTGC
TTTTAAGTGTTTATCTAGAGTCAGTATTGAGTTTCTATCTGGAAAGATGATCATCACTAGAAAAGACCCT
AGCGCCATCCCTCAGCTTTGGTGTAGAAACCATTTTGGACGGTAGAGGGCAGTCAGGCCACACAAGTTCT
GTAGAAACCCGCTGAACACAAGGCGGTCTCTGGTTTGGCTCTTCGCCCAGCGCTCCGAGTGCGTTACTG
TCTATGCGTTTGCTTGTTCTGGGAAAGTGAAATGTGTTAGGGGACAGAAAAGGGAAGGCAGAGAGGTGCT
GGGAATGCAGTGTCTTCACCTGCTGCTCTGGGTTTAGTTTGAGGAGGGTTCGTTTCTGTTTGGGACATGT
CGGTTCTTGCTGACGCTTTGGTATTTGTATCTGACTGGGAGAAAGATTTCATTTTTATCGAGTGCACATG
TTACAAGGAGTTTCATTTCTCTGCAGGAAAGTGTCAAGTAATCAGAGGAGAGTTGAAGTTCTTGCTGGTG
CTTAGGTGTTAAGGATCAGGAAGGGTAAATCATTTTCCCTGTGCGTGTATTTTTGGAAGTGATTATAGGC
AGTCCTGTAGCAAGTAATGAATCATCAAATAGTCCTCCTTTATCTTTCCACGTGGGAAATTTCATTTTGA
AGCCGAGGTGGTCTTCGACTGGTTGGAGTAAGGAATAGTAGATTTGTTTGTTAATTTTTCTGACCCTTTG

TCCTTGCTCCTGGATTCAGAGGAGGTAAGAACCATGCGTGTAGGATGGTTTTAGCAGAAGCTGCATATCT
GGTTATTCAGAAATTAGAAAACAGGCTAGATTTAGACCGTTTCTAAGATGCCCCTGAAATCTAAAGTCAT
AAGTGTGATTTTTTTTTTTTTTTTAAGAATTATCTGACTCAGAAAAATGCAAGGACCAGGACTAAAGCA
GATGTCAGCTCAGCAAATACATCTTTCATGCTGTGTGAATCTGTGTTTCTCTTTCAGTTTTTGAAAATCC
TATGTGTGGTACACATATACCTTCTGGGTACAAGATTGAAACAGTGTGCAAGTATACAAAGAGTAAAGTG
TAAAAATATGTTTTCAAATTTTCCTCTGGTTTTACTCTTTTACTGAGAGGTAATCATTGTTCTCAAATAC
TGTGTGTTTTTGAGTCTTTGATGGATTTCTAGTCAAACACCCACATATATTCACCTATCCATTTTAAGT
CAAATGATAGCAAATTATACCTCTTCAATGCCTGACTTTACTGATCTTTGTTTTCTCAGCTATATTCTGT
AATTTTATTACTACTTTAGATTTTTATTATCCTTTCTTTGCAAGTATCTCTCTCAAATTTCTACTTTTGT

ATAGGTGTATATTTATTTAAACTTCTTAGGGAAAATTTTAAAACCTGTATAAAAGAAGTGAGCCCCACAC
AACCACTGTCCAGCTTTGTTAATTGTCAACTTGATTCATCTATGCTCCTACCTTCTTCCCACCAGATTAT
CTAGAAACAAATCTCAGATGTTGTATCATTATGTCCGTAAATATTTCCATTTGAGACTGCAGAAGAAGTT
TTTGTGTGTAACTCAGTGGCTCAGTCGGTAAAGAATCTGCCTGCAATGAAGGAGACCCCTGGTTCTATCC
CTGGGTTGGAAAGATCCCCTGGAGAAGGGAATGGCTACCCACTCCAGTATTCTTGCCTGGAAAATCCCAT
GGACAGAGGATCTTGGCGGGCTGTAGTCCATGGGGTCACAAGGAGTTGGACACAATTGAGTGACTGATAC
TTTCAACTTTTTTCAAGGGCTTTTTAAAAAATATAACTACAGCACTAATATCATACCTACAGCAATTAAC
ACTTAGTTCTTTAACATCACTAGATATTCACCAAATATCTAGCCGTTGCTCAGATATATATGTCTCATTT
TCTTTTTTTACAGTTTGAATCTGTAAACAAATGAGGATAGCCAGTAGAGTTGGTCAGTTTTTTTTTTTTT
GCAAAACCTAAAACTTGAATCTTTGTATTTGAGGGATTCGCAGGCCTGATTAAAAGGAAGCAAAAGATAC
ACTTGCAGACAAACCGTGTTTAGCTCTGTGGATACTCAGATGGGAGGAGGCGAGCTGTGAGGGCATCTGG

GGCAGACCCAGCGTAGGGACGAGGGTCCACAAGACAGGGAGGAAGAGGGCTCAGTGATGTCCCTGGGTCT
TCGAGTCCCGGGAAGTGCTGAAGATGCTGGCGGACACTCCCAGCGACGGAGCCACTGGCCTGGGGTGAGT
CGTGGTGCTCACAGCTATGCTTTCTTAGGTGCACCGTTCCCGTTCAGTCTCTCTCAGCTTTGGAACAGAT
CTCCGATTTGGGAAAACAGAACGCGCTTCTCAGCAATTCACTTTTCAGTCAATGTAAAACATGTGCTG
TAAAGCAAGGGAGGCTTACACTATTTTCTCCTTGGTAATGTTCAGGAAAGCTTGGCAGAAGAAGATGCGG
TGATTTGGAGTGGAGGTCTTGTCAGCAGCAGGGCCGGTGTGAGGCGTTGTTGACTAATTGCAGCGGTGGC
TCCTCCTGAGAGCTCCAGCGAGATTCATGTGCGTGATCTGTGACATGAGGCATGCTTCCGGTTACCTGC
TTGCCTCCTCCCAGGGCTTAACCCCCTCCCTCAGCCCCGGGGCTCCAGGGAGAGTAACAGTGAAAGTT
GGTGTCATGTACACCTGCTTCCTCACCACAGATGCTCGCCCCTTCCTCTGGGCGTGGGTGTAATTACAT

CACCCACCACGCCGCTTACCTGGGCCGCCTGATGCTGGTATATTGGATCTGTGTTTCCTCCTCTGCACAT
CGATCGTGGGGGCCCCTGCAGTCTGCTTGCCATCATGTCATGGAACCCACCCAAATTCATGTTGGACAG
AGTCACTGCCGAATGCTAATCAGGAAAAATGAGACCGTATGTTGGTACTACGGCTAGTCATTAAGTTTTA
CAGAGCGGACTGGCAGCTGGAGAGGTGTTCCAGCCTGCACATTACCTCCCTAACCAGTTCTTGGTTTCAT
AAAGCTTAAACAAACAGATTGGGATTTCCAGGGGTGGTTTGGAAATCTTTGAACTTAAACTGGTCATGTA
AGAAGGGAATGTAGGCTGTCATCAGGGCAGGGAGGGGATTGGTTGACTCAAGATTGCAAAAAATGTGGC
TTTGCAGTTCATACATTTTGGCTCAGACTGTGCCGCGCATGGACCTGGCAGCACTCTGCCCCAGTAAGTG
ATTTGATGGGCTCGGGGGCCCCCGGGACACAATAACCATAAACGTTGGTGTGATGTACACCTGCTTCCT
TTCTAATGAAGTGTCACTGTATTACTTGCTGGATCCAGTTAAAGCAGCGTGTTCATGGTTTTCTAATTAA
GGAGAATAAAAGCTCGTGTGGGTGGACTTGCAGGAGAAGCACTCGAGGTCAAGTTCTGGATTCTGCTTCC

TABLE 3A-continued

SEQ ID NOs: 1-2, BOVINE EXT2 AND ALX4 GENES

```
TGTGGAAGCATGGGGTTGATAAGACTGAGTAGCTGGAATGGGTGGTGAGAGCTGGTAGAGGCTACACAGT
GCACACGAAGCTTTGGGACGACAGTGAAAAGAACTGATCTTGTGGGAACTGGAGCGGGCTGGGGCGCAGG
CAGCGTGAGATGGGGTACTTTGCCGTCACCGTGGCTTTTTTTTTTTAGCTCATTGTCCCCTGAGCTTC
CGTCAGTGGGACGGTAAGTGACTGCCCCAGCCAGTCCTGTTGTTATTCGTATTACTGTAAATGTGTTTAA
GAGTCAGGGCCTCCTCGGTGGCTCAGATGGTAAAGATTCTACCCGCAATGCGGGAGACCCTGGTTTGATC
GCTAGGTTGGGAAGATCCCCTGGAGAAGGGAATGGTAACCCACTTCAGCGTCCTTGCCTGGACAACTCCG
TGGACAGAGGAGCCTTGAGGGCTACAGCTCATGGGGTTGCAAAGAGTTGGACGTGACGGAGCGACTAACA
CTACCACGTTCACCGTCTGTGACTTCTCGGAGAGGTGAATGGGATCCAAACAAGGTAGCAGAGGGGCCGT
TCGCAGGCTGTCCTCCTGGCTGTGCTGTATTTTAAAATAGGGAAAGTAAGGACAGACTGCTTAGGACCCC

AGAGGAAGGCGGGTGACTCAGGACGAGGATGCAGCGAGTGCCCCTGAGATGCTGTACAACGTTTAGCACT
GTGTCTTTCTAGAAAAGTGACTTGGTAAACATCAGCTGTGGCTGATACTGTTATGAACATCCAGCTGCCC
CTTTCCACAGAGCTTATCAGAACGAAGACTGTCTTTCTTTCTCCAGCGTTTGACAAAACCCTTTGTTTTTC
AGGGCTCTGTTGGCTGGTGGTGGCTTCTCTACGTGGACTTATCGGCAAGGCTACGATGTCAGCATTCCTG
TCTATAGTCCGCTGTCAGCCGAGGTGGACCTTCCGGAGAAGGGGCCCGGGTAAGGCGCCTCGGGCACAGC
CAGCGGTGCTGAGAGATGCCAGTGAGGGCCCGGGGGGCGGGTTGCACTGCAGTCGAACCATCAGTGACAG
GCCGGGGTCCTTGAGGGTCCGTCATTCCTGTCCCACACCAACCTTATTTATCCTTCAGTTCTCTCTCTGT
CTGTCTCTCTCAGTCAGTTTCAAGCGCTGTCTACCAAGCTCCCAAATCAGAAATCTAGTTGCTGTCC
ATAAGTCTTTCCTCTCCCTTACTTCCTGTGCGGAATTGCAGGCTTCCAGAAGGAAAGCAGGTGTTCAGCA

TCAGTTCAGTTCAGTTCAGTCACTCACTCGTGTCCGACTCTTTGTGACCCCATGAATCGCAGCACGCCAG
ACCTCCCTGTCCATCACCAACTCCCGGAGTTCACTCAGACTCACGGCCATAGAGTCAGTGATGCCATCCA
GCCATCTCATCCTCTGTCGTCCCCTTCTCCTCCTGCCCCCAATCCCTCCAGCATCAGAGTCTTTTCCAT
TGAGTCAACTCTTCGCATGAGGTGGCCAAAGTACTGGAGTTTCAGCTTTAGCATCATTCCTTCCAAAGAA
ATCCCAGGGCTGATCTCCTTCAGAATGGACTGGTTGGATCTCCTTGCAGTCCAAGGGACTCTCAAGAGTC
TTCTCCAACACCACAGTTCAAAAGCATCAATTCTTCGGTGCTCAGCCTTCTTAACGGTCCAACTCTCACA
TCCATACATAACCACAGGAAAAACCATAGCCTTGACTAGATGAACCTTTGTTGGCAAAGTAATGTCTCTG
CTTTTGAATATACTATCTAGGTTGGTCATAACTTTCCTTCCAAGGAGTAAGCGTCTTTTAATTTCATGGC
TGCAGTCACCATCTGCAGTGATTTTGGAGCCCCCAAAAATAAAGTCTGACACTATTTCCACTGTTTCCCC
ATCTATTTCCCATGAAGTGATGAGACCAGATGCCATGATCTTCGTTTTCTGAATGTTGAGCTTTAAGCCA

ACTTTTTCACTCTGCTCTTTCACTTTCATCAAGAGGCTTTTGAGTTCCTCTTCACTTTCTGCCATAAGGG
TGGTGTTATCTGAATATCTGAGGTTATTGATATTTCTCCCAGCAATCTTGATTCCAGCTTGTGTTTCTTC
CAGTCCAGCGTTTCTCACGATGTACTCTGCATAGAAGTTAAATAAGCAGGGTGACAATATACAGCATTCA
TAAATCCTGTCATTTGTACTGTTTTCCCCTGAAATCGAAGTTCCCATGCACCAGCCAAGGGCCAGCCTTT
CAAAGAAGAGAGCCGCCAGGCCCACTGAGTTAAGTCTGTTCTGCACGGGGCACTGTGGGCAGCTAACAGG
CGGAGGTTGGTGATGCCCTAAACTTCTGCCATGCCCAGGGCGGCCCCTCACCACAAAGCATCATTGGGTC
CAAATGTCAGCAGTGCTGTGGCTGGAGAAAGCCTGGGGGACACAGGGTGAGCAGTCTTAAGATGGCTCAG
ACTAAACTCTCTTTATCATCTACTCTCCCGAGTGTAATCTAGGTCTCTAATGTTGGTTGAGGACTGGCAC
GTCCCTTAAGATTTAATCCAGGGAAGAAAACAGGCTGAAAGGAAAAGACTGAGAGAGATTGAAACGAAGG

AGAGCAAACCACTCTGAACAGTACAAATTACCTTCAAATAAGTTTCCAAGAATTACAAGCTTGTTCTGTT
GGTGGTATTTTCTTGGTAACTTGATCTCTAATTTTATGTGTAACTAGACTGAAATGACTATCCTTAGAT
GGTTTAAGGTTGCTGTTGATCTTTAGAGTCCTGAGACTCTAGAAACTAGAGAATCTTAAGCAGTCTGTCT
TCCAGAGCAGCAGCAGGATGCTCAAGACACAAGGGGATGGTCCTCCCCGTGGTGGACAAGCGGTGGATTT
CTGTGGCCCGATGCGGACCCACCCCACTCCGTTTCCCCTCCAGGGTTTGCAGTTGGGCCCTGTATGTGTG
CTGTTTCCTTTACAAATAACACTCCTCTGCCTCAGGAGGAGAAAAAGAAAGCAAAGACAGGCTCTAGGC
TCATCACACTTTTCCAGGGATCTGGGAGGAGGCAGTCTGGGTGACCTCACGGCAGCATTTGGAATCTGTTG
CTCTTTGTGAGAGTTGATTTTAAGGGAATTCCCACATCTCTTGAGGGCTGCGTAGAGTAGCAAGGGCTT
TGTTTTTATTTTTATTTTAAATGTCTCTCAATATTGTCCAATGGGAAGCTGAGGATTGTTGCTATTGATA
GCTTCTTCTCACAGATGTGTTGGCCTCAGCTGGAATTCTCGTCATTTCTCTCTAAAAGGAACTAAATT

GGGAGTTTACAACGGTTACTATGGAGGGAAACTTGGAGTTCTCAGCATGATTTTGCTGAACCTTCGATAT
CAGCTCTGCTGGGAAGAAACATGAAAGTCATAGCTGGTCATTTTAGCTCCTCGAAAGAAAAACAAATCCAC
CTTAAGATTCTGTTTGCTTAAAACTAAAATGGGCCTACTCCACCAGCCCACCATCTGCCAGGTCAGAGCG
AGCCAGCATGCAGGCAGGGGAACATTTTTAGACTCTTGTTCACATCTGCACATTTATGTAGAAAATGGT
GGTGTTGGGTGGGGACCCACTGAGCGTGGTGACTAAGTGTCTACAATAGAACTGTGTTTCGTAACAGCAA
AATCAGCCCAGAGTCTTTCTTTACTCCAGAGTTTCTTTGAGCACCACGTGTTAGCATCTGTACTTGTTTC
TCCGTCTTACGTAGATGCTCCCTCTCTCTGTCTATGTGTATTGAAAACCATGCCTTCCCGTCGCTCT
CTCCTATTCCATCCAGTGCTGCAGGGGATTCTGGCTCTCTCTTTCCGTAGCTGTAATTTCCTTCTCGG
ACAGTGAGGAGTCTAGCTCCCGTTATCCCCTGTATCTTGCTTGATCAACCCTGTCGTGCGTGACAGAGC
CCTGTGGTAGCCTCTGCCCCTCACCGCGCAGGTGTCTATGCGCCCCACTTGGGCTCTGACCCCCTGTGCC

GAGCTCCTGCTTCCCGTCGTCACCCCGGGGCAGGCCCCTCCTCACATATCCTGGGCTCTGACCCCCCA
CACTGGAGGGGTGCCGCCCGTGCCATCACCCTCCCCGTGCGCCTTCAGCCTGGGCTGCCCTCCTGCCCTG
ACTTGGCCTCCGCATCGCAGGTGGGGAGGCCATGACTCCCTCTGTCCCGTCCCCGCTCCCTCTTTCAGGG
ATCTCACAGTCTGGGCCAGGCCACCTCCCTGCTCTTCCCCCAAGAAGTTCTCCCCCAGATGAGGACTAGA
GCACTCCCAGTGGGCCAGCCCCACCGCACGGAAACGCTGCCTCCCCTCCAGGACGCCAGCACTGCACACC
CGCCTGCAGGGACCCCCTCGGACACCAGCGTGGCCGCTCCTGTTCGAGGCAGCCTGGAGTGCCAGTTTTG
TGTTAGCGGCTCTACTTAAATAGGAAGTCTCCAGGGACCCAGCAAGTCCCAGCGCTCTGTGGCAGCTGCC
GTAGAGCCAGCGTCTTGGGGACTGGAAAGGTCTTTAGAGGCCGTTTAGCTCTCACTTTGGAGAAGGAAAT

GGCAACCCACTCCAGTATTCTTGCCTGGAAAATCCCACAGATGGAGAAGCCTGGAGGGCTACGGTCCATG
GGGTTGCAAAGAGTCTGACACGACTGAGCAACTAACACTAGTTCTGACTTAATGTATACCTTGTTACTGT
GATTTCTTCCTGAAAAGTTTTCTGATTTGTGGTGAAAAAGACTCACCACCTCACAAGACAGCTCATCTTC
AAATGGCCTGAGTTGTTGAGGTGGTTTCCGTGCTTGCGTTGAGAGTTTGACTGTCCATCTTCCTCCTGTT
CTAAGCAGACGAGCTTGATCACAGAAGTCCTCCCTTTGGGATGCCTGAAGAAGACTCCCTATATGTGATC
TTCCCATCATACCTCTCCCCTCTGAAAACTGATGATTTTACGAAAGAAAAAATGATTGAGGCTGAGGCT
GGGGGTAGAATTCAAGAGTCTGTTTCAGTGGCTAGCAGGTATGGGGTCACACACAGTCGGACACGACTGA
AGTGACTTAGCAGCAGCAGCAACAGCAGCAGCCAATGTATTGTTCAGCAAAATGCAATTGAAGGAGA
AGTTGTCCAGGATGAGAGAAGCCAGTCTGTACGGCTGATCCAAACTGTCTCCCGACGGGCTGCTGTTCGG
TGTCTTTTTTACGTCTGCTCGCCTTTGCCCTGGGCTCCGGGTCTGCACTGCTGTCTGGGGCAGCTCTCTC
```

TABLE 3A-continued

SEQ ID NOs: 1-2, BOVINE EXT2 AND ALX4 GENES

```
AAGCAGGACTTTCAGTGAGGAAATGATCTGTGTTTAGTGGGGTGCCGACTTCCACGTATAGCTGTTGAGC
CCTTGAAATGGGGCTAAGGTGACCGAGGAACTGGATTTTAAAACTTTAATAGATTTAAGTGGTCTCACGT
GGCTAATTGCTATTGAACAGTGACGTTCTAGGGGGTCTGCTTGTCCCTGTCTTCCCTGCCTGCCTTTGCT
TTCAGTTCGACTGTAGAGAGAAATGACCGGAAGAGATGGTTCCGGGGACTTGAGGGCCATCAGCTGTGGT
GTGCGCTGCTCCATTTGCTGGAGTCGAGCTGATCTGCAGCTGGGAGAGTGTTCATTTCCTCACTCCCTGC
TTGCTCTGTGTCTTTTGGGCGTGACGCTTAAAGCTTGGGAAAGATAACACTCTCTCAGAGAGTGATTTCT
TTTTGGCCACGGGTAGATGTGTAAGGTGTTCTCCAGCTGGACCCTCCAATTAAGCCTGAGAAACGAAAGG
AAAATAAAGCAATTTCCCTTTCTTTCTCTCCAAAGCAAGAAGAAAAGAAGGTATGGGGTTGGGTTCAGAC
TAGAGGGTTTGAGTCCTTTCTTTCTCACTGCTTCTTGTTAGCTCCCCTGGTGGCCTTGCCTAGAGATGGC
TGTCTTGGGTGTTATCCTTGGTCTGTACAGTTTGAGGAAGATTTGAGTCCTGCTTCTGGGTTTGATGGGG

GTTTCATTTCTTCTGGAGCCTGCTTTCTATCATTCCTTTCTTCTTCAGTGATCCCTGCTGGTTCCTTTGC
TGAGGTCGTGTTTATTGCCCCTGTAACCTCTCTGCCTTGTGGGAATCTTGCCTTCTCGGAGAGAATTACT
TACCTTCTGGTCTCCCCAGTGAGTTCACATTTTGTTTCTCGTGGAGATCTGAATGGTGCTAGACCCTTGG
AAATCCTTTCTTCAGTCTGTTCTCTCTCACGCATCCTTGCTATCCGATGTTAAGACTGGTTCCATCCATT
GACAAAGCCAGTTTTTTCCACTTGTTCTCCACGACCAAGTTTGGTCTTCCTGAATCCATCTGGCCTTGAG
GATGGGGGCTGCCTTTCCCTGGAGCTCCCCCATAGCATAGGGTGCCCGTCAGCAGCCGGAAGTAGGCTGC
TTTCACGGTCAGTGCTGTCTGTTAAGACCCCTTGTTTTCCTCTTTGAAGGTTGCAGCCTGCTCTCAGCTG
CTTTTCAGAGCAGAGAACTCAGATCGAACTAATGCTAACGTTGGATGTTCTTCCAAATAATCAACCAGTC
AGTCAGTTTCTCTCTTTACACACACACACACACACACACACACATACACACTCACACTCTTAAAGCATGC
TCCCTAAGCTTGGCCTATTATAAGCATTTCCTCAAAACGTTAAGAACTTTTCCTAAATGAACCCTTTAAC

AACAGCATGATGCTTCAGCATGTGAATGAGTCATTGCTTGCCTTCTCAGCATGTATAATAGTTTAAATAT
TCAGCAGTGCTGAGTGTAGTTTCCCCAGAAGTCAAGGACGTGAGTGAAGATGGGTGAGAAAGCACTCGTA
GCCCTAAGCTCTAGACCCGAAGTTGGCCTCACCGTGACTCATGCAGCGGCGGCCAGGGTCCCAGTGCCCC
CCGTTTTCTGCTTCGCAGGCCGCGGCGGTACTTCCTGCTGTCGTCCCAGGTGGCCCTGCATCCAGAGTAC
AGAGAGGACCTGGCCGCCCTCCAGGCCAGACACGGCGAGGCGGTGCTGGTGCTGGACAAGTGCAGCAACC
TCTCCGAGGGCGTCCCTGCCGCCCGGAGGCGCTGCCACCAGCAGCAGGCCTTTGACTACCCGCAGGTGCT
GCAGGTGAGTGCTCCGCCCGCCCCTCTCAGGGCCCGGGCTGGGGCTGAGCCCAGCCGACAGGCGCTCCGC
TCCAAGCTGCACTCGTCAAGCTCCCTGAGCGGAGAGCAAAACCGGACTGCTCTCCACTGCTGCCCCGTGG
ACTTCTGGGAGCTTCAGGGTCTGCGTGCCGTTAGTGCAAAGCCGCTTGGCCCCTGAGCGTTCCGGCTCCT

TCCACGAAGCTCATCTTACTGCAAAAAGACACACCCCGTAGATGTACAGAGGAGCCGTGTAGTCAAAGCA
GGCACGTGTATTTTGCTTTTATTCCTGTATTCCTTATCCAGCCCAGAGGAGCTTGCTTCTTTAAGCTGCA
GCTTGTATCCTCCAACTGAGCCAGCTCGCCACGGCCACAGTTAGTTCTTCCTGGGAGTGGGAGGTCTTTA
TTTTTTGTTACCGTTTTTTCTCTTGGTGTTTTGCCTCCCTACATGTGTCCTCCTGGTGTCGTGGGAGTG
CCAGCACTTCGTAACTGCAGGCAGAGTAGTCCTGTATTATACTTCTGTATTATAAGCAGGCTGTTTGATA
CTCCAAGAGCCAGGGGGCTGGGAAAGCAGAAATTGAGTTTTGTTCACTCTGCTGTTGTCCAGTCACTCAG
TCGTATCTGACTGTCTGTGATCCCATGGACTGCAGCACGCAAGGCTTCCCTGTCCTTCATCATCTCCTAG
AGTTTACTCAAACTCATTGCTATCCAACCATCTCATCCTCTGTCGTCCCCTTCTCCTCCCACCTTCAATC
TTTCCCAACATCAGGGACTTTTCAAATGAGTCAGTTCTTCATATCAGGTGGCCAAAGTATTGGAGCTTCA
GCTTCTGCATCAGCCCTTCCAATGAATATTCAAGACTGGTTTCCTTTAGGATTGACTGGTTTGATCTCTT

TGCAGTCCAAGGGACTCTCGAGAGCCCCAACAGTTCAAAAGCATCAGGTCTTTGGCACTCAGCTTTCCTT
ATATTTTAAATCTTTTGTTCGCTTAAGTATTTAAAACACAAATAGTTCAGTTCAAGGAGAGATCTTAAGG
AGCTGGTGTGATTGTGTGATTTTTATTTTTTCAAAGTCTCCGAAGAGAACCGGCCTGTGCTGGGATTG
TTAAAATACCTTCAAAAAGTGCTGCATCTCCTCTGGAATGTCTGACTGATAACAGTGGTGAGCTGAGCAG
GAGTATTTATAGTAACCTTTGTCTAGACAGGAAAAATGGTTATCAGCACACATGCCCACATCTGGACGCC
GACTCTTCGGGGCCGGCTGAGCGTCCACCTGCCCCTCTGGGCGCCATGACCGGTGCCCCTTCTCCACCCC
CTGCCCTTTCTCATCGCTTTCTCCTTTATCCCCAGAGGAATTTGGCGTATTGAGTTACTTCATATTTCTT
CTGAACTCTCCTTTTCTCTAGCTTTAAAGATTAAGTATTTTTGCTTTAAAATTTTTTTTCTGTTTTTCT
CCTGGAGAGGCAAAAACTGGAAGAAACTTGAGTATTAGAGACGGGAGCTTTCCTTATTTTTTTCGGTTGA
CCTATTACAACCACCTTTTTTTCTTGTGCATCTCTCCTTTTCCCAAACAGGCCCACATCCAGTGGGTTCG

AGGGAGTGAATGAGGAAGACCTTTAGTGAGGTCTTGCTTTTTGTTCAGTTGTATCTAAATAGAGCCTATC
TGCCTTAATGTGTTTTCGAAGGCATAGCATTCATGAGATGAATGTCTTTCTGTATACAAGCACACTGCTG
GATGCTGTGGGGGTAGGAAGATGAAAGGAGATTTGATGCTTTCTGTGTAGGGGGTCCTCTCAAGAGCCCG
ATATGCCCAGTCCAAATAATTCTAGTACAAGGCAGGCAGAAGTAAGTATTCTGAGCCCTGGGAAGCCACG
GTGGATATACACAGCACCGCAGGGCTGAAAGAATCCAGTCCGTGGGAAGTCATGCTGTTGAGTTTCCAGA
GGAAGACCTGGAGGTGGGTTGTGAACATTTTCAGAATCCAAGCAGCGGAGGCATTGCAGTGACACTCAAG
AGTGGAAATCCAGAGCATTGCAACCTCTTCAGCTTTTCAGTCTCACCCGGGTGAGCTGTTATCTTTTAGC
ATTTTCTGTGTTGCCTGGCTTCAGCCCTTGAGAGAACTTTGTGGTCTGCCAGGATCAGAGTAAGTGGATC
AGCGGAACCGGTTTGTAATCCCCTCCTCTGCCTGTGTTCTGCAGGAGGCTACTTTCTGCATGGTCCTTCG
TGGAGCTCGGCTGGGCCAGGCGGTACTGAGTGATGTGTTACGGGCCGGCTGCGTCCCAGTGATCATCGCA

GACTCCTACGTTTTGCCTTTCTCTGAAGTCCTTGACTGGAAGAGGTGAGTGTTACCTTCTGATGAACCTT
TATCCCAGGGTTCCTGCATGGATTATTTTAAAGTCCCCCAGCAGTTGTAATGCATAGCTAGGTCTGAGA
ACTGCTCCTTCAGATTTTTTTTGCTCCATTTTCCATCAGGAGAGTTCGTCCATGAACCTGCAGCAGAGGT
TGGTCACCCGAGGCCTTTGGGCCGCATGTGGCATGCTGCCAGTGTCTGTAAATAAAGTGTTATTGCATCA
CAGCACACCCATTCATTGACACATAATCTTTGGCGGTTTTTGAGCTCCAGTGGCAGTTGAGTCCTGCAGT
TTAAAATGACAGAGATTGTGTGGCCTTGCATGTAGTAGGGCCTCCATAAATACATGCTAAATAAATGAAT
GGATTGGGGAATACAGCCGAAGGAGAAGTCATTGTTAATTTAGAGTGGACAGTGATGAGTGAAGACGAGT
GTACCTGGCAGGCAGAACTGGACACACAGAGGCCCTGTGGTCGGGCAGATGTGGTGTATTCAGGAGGCT
GAGAGGGTACCTGTGTGGCTGGAGCACAGTGGGGAGTGGACGGAGGACAGGAGAGGCATGGAGTGGTGAC

GGGGAGGTGAGAGATGGAGCTCGGGGAGCTCCTTTGCGCTGGTCGGTCCCAAGGAAGGGAGAGGAAAGA
GGGACTGCTCACTGCGAGGACCGTGGGGCTGAGGGAGGCGCGGGGCATTGTTGCTTCTGCTCGTGAGACC
CGAGCGGGACACACATGCAGCCGTGCTTTGTATGCAGGGCTGTCCATACATCCGCTGTCTCCCTCTCGTC
TCTAGAGCATCTGTAGTTGTGCCAGAAGAAAAGATGTCAGATGTCTACAGTATTCTGCAGAGCATCCCCC
GAAGACAGATTGAAGAAATGCAGAGACAGGTAAGGGGCAGGAGCCCTGCGGGGAGGGGGCGAGGGGG
AGGTGAAAGGTGGCCTTGACTGCTTGGACGCAGAGCAGTATCCATGCCGCTGAGAGCGGGCATGGGATTG
ATATCCTCCACTGAGTCGGTCAGCCAGACTTAAAAGAGGAAAACAGCGTTAGGGAGTTGCATCAGAGAGG
CTTGGAATAATAACTGTCAAAGATTCAGAAACGCTCCTGAAGCAAGCCTGCTGTGACAGTAATGTCACAC
CTCTGCTATGTGTTCAGGATGCAGAGCTGCCCATCTCTGGAAGGCCGTTTACACAGCAGGTGAGGGCTCT
```

TABLE 3A-continued

SEQ ID NOs: 1-2, BOVINE EXT2 AND ALX4 GENES

GGTGACTGAGACGGACATGGAAGCTGGTGTGTTTCAGGGTGATGCTTCTCAGGAGCTTTGACCTTGAGTG
TTGTGTATCAGCTAGCCAGGGTCCCCACAGAGTACTGAGCAGAGTTTCCTGTGCTATGCAGTAGGGCCTT
ATTAATTGTCTATTTTATGTATAGTAGTGTGTATACATCAGTCCCAATCTCCCAGTTTATTCCTCTCTCC
CTTCCACCCTGGTAACCCTGAGTTTGTCTTCTACATCTGTGACTCTGCTTCTGTTTTGTAAATAGGTTCA
TTTGTACTATCATTTTAGATTCCACATATAAGCAACATCATCTGGTATTTGTCTTTCTCTGTCTGACCTC
ACTCACCTCTAGGTCTGTCACGGTGCTGCCAATGGCACTGTTTCATTTGTGTGGCTAAAACCCCATCGTA
TATGTGTACGGCGTCTTCTTTACCCGTTCCTCTGTCCGTGGGCATTTAGGTTGCTTCCTTGTCTTGGCTG
ATGTAAACAGGGCTACTGCGAACATTGAGGCGGTGCCTGCGTCCTTTCAGATCATGGTTTTCTCCAGTTC
TTTTTCTTCTTTTAATGGGTTTTTACAAGTTTTTATTCTCATCAAAATTATCTGTGTAGGTGATGAGCCG
GAGAAGAGGTTTGGAGGGTTAGGGTTAGGCTGTAGCCGCCTCCACACACCCCTGTGTCTAACTTGGTCGC

AGGAATGAGCCTCAGGTCTCTGGGAGAGGGCAGGGCCGTCACCCGGTGGTGTGGAAGTGGGGAGGGACTC
TGGCTTCTGACGGCTGCTTACACACGTTGTCCGTCTGTCCTCCTGCCCCGAGCTCCGCCTCTCCCCCCGA
GTGTGCGCAGCGGAACGCGGGGGTTTCTCGGCTCCTCTCGGGTGCTGTCTTGGGCCTGTCGCGTCAGCCA
CCACCTGCTTTCCTGCTTCCACACTTTGGTGGTGTTAGCTCCTTCCCCGTCCTCTTTATCTTTGGTTATG
CCTTCATTTTAGGGTTTTAGGAGGGAGTTAGTGGATGTGTTCAGTCCACCTCTTTATTTTGGACCCAGCT
CCTTAGACCAAACAGATGGTACATCACACAGTGGTTGAGTCTGAGGTTCCGACCCTAGACTGCCTGTGG
CGAATGCCGCCTTGGCCGGTTACTGACTCTGTGCCCTTGGCCAAGGCTCTGCCTTCTGTGGATCCCCATG
ACCTCATCTGTCAAGCATTTTGACATTCCGATTTGAAAACAAATCACATGTTAAGTTTAGCCTCCCCGTA
GTCTATTTCCTAGCACACCCATGTTCAGGTTTCTGGGCTTCCCCATTTGTTGCTTAACTGCTGACCTCAT
TTGAGTTGTAGTGAATTAGAAAATCAGCCTAGAGATCTCTATAGTCTTGATCTGAACTTGGGGTTCTTAC

AACTCATGGGAAGAAAAAGTACTCCTTGAAGGGACCTGGTGTTTATGCTCTTTGTGTTTCATTTTATGGC
ATCTTGATTTGTTAACATAGTAAATAGGGAATCATCTGCTAAATCAGGTATCATCTTTTATAGATTTATA
AAAGGCTAAGAAAACACCAGGGAGGTGAAAAGGAGCAAATTCTGCCCAGTTATCTTCCCCACTACCTTCC
TGTTGGGAAGAGAATCACTTAGTTTTTAGAGCAGAGCACCCAGGGCCAGCTCACAGAATGTACTTTTTCC
CTGGGAACTTGGCTTAGGAACCACAGATCTGAAGACGAGCCTTGCAGTACTTTCTTCCCTCCCCTAAATCCCCCTT
CTGGGAACTTGGCTTAGGAACCACAGATCTGAAGACGAGCCTTGCAGTCTTTTCAAATGACAGGTTCAGA
ATCAGAACCATTGAAGCAGAGTGACTAAGGGTTACTTAAAACAGTGTACTTTTAGGTTATTTGGGCTCTG
AGAGACACATGTGGGGTCTTTAAAAGACTCTGGCTTGAGCCCTGTGTCAGTCTCTGTTAATTGTGTGACT
GTGACACATCTGTGACCAAAGCTCCTCAGACTTCCTCATTTATGGAATCAAGGGTGGGCTGGATCAGCTT
TCATGTTCCATTCAGCTGTTAAAAAACACTGTGAAACTCCTGTCCTTGACAGCTTTAATAACTGAGTGAT
CATCTCTTTCCCATGACCACCTCCTGTCATGAGGGCCTGTTACTGTCTCGGTGGTGAATAACCTGTATT

ATGTCCACTGGCAGAATAAAGGGGATCTCAGTACTTTCCTGGGCTTCCCTGGTGGCTTAGATGGCAAAGA
ATCCGCCTGCCATGCAGGAGACCCGGGTTCGATCCATTAGTTGAGAAGATCTCCCAGAGAAGGGACTAGC
AACCCACTCCAGTGTTCTTGCCTGGAGAATTCCACGGACACACGAGCCTGGTGGGCTACAGTCCATGGGG
TCGCAAAGAGTCGGATACGACTGAGCGACTCGCACTTGCAGTACTTTCTTCCCTCCCCTAAATCCCCCTT
CTGCTTGATGGTGCTCTTCTCTCTGCTACTTTCAGATGTTCTGAGATGCTTCGCTGCCGTGGCCCATTTA
GTCCTGCTCCCTTTCTCTGAATAGTCTGCATCCCCAAAATGACCTCTTTTCTTCTCCCAATGTCAGATTT
CTAGACTGAACTGATCTCAGCCAGAGGTGAGATTATCCGGTTGAAGCACTTCCCAGAGAGTTCGAAAGGA
TGACTAGGTTCCACTCCCAGATTCCAGTGGCACACCTGACTCCCAGATTGTGACACCTTGAAACGGCTGC
ACATGTTGCCAGATGCCTCCCAAGGCGGCAGAAGTGCTGTGCTTGGGAGCCGCCTTCCTGTTGATACCGT
GGCCGTCTCTCTAAGATTAGAGACAGCTCTTTTGTTCTTTGCAGAATGTGCTTGTCCTTTATCTCCTGTA

TCCCCTCCATTGATTCAGTCAGACCTTGGCAGGAGTGACTGAAAAAATAGCACACGCTTGGTTCTTGGAA
GTTATTACACCTCAGTGAATTCTCTTTAGGGAGGTCCAATTTGAAGTACAGCCCGCATCTGTGTTATCTAC
TAGGGAAAACCTGTTAACATCAGTAGTTGATACCTTAGAACCCTGGGTTGCTTATGTTAGAATGAGCTG
AGACTGAGGAGCAGAGGGTCAGATTTTCTTGCTCGGCAACTCAGGACCGGCCCGAGGGGCTGCACGCACA
GTTGTAACCAGCAGAGGGCTCCATCCACTTTGAAGTGACTCATTTTCCTTCTGAGTAGCCGTGTCCAAGG
AGTCCTGAGTGCCATGAGCTATGCTGACACCGTTCCTCAGAGCCGCTCTCTAGAGAGACCCGCTTCTTCC
TGTGCTTTTTAGCACAGGATTCTGCTCTCCTGTGATGGATCAGACCCAGACTTTCTGAATTTGACCCCTG
AGATACGGGTGGGATCTTGGTGAGGACGGTGATGCAGCTTCGAGTTCAGGGGCTATAATCTGATCGATGG
ATACGTGGTGACAGCCCTTAACATGACCCAGGAGTTAGGACGCACCCAGAGAGGAGGGTGTTCTGCCTGA

CAAGGAAGCGTAACTTTTCCTCCTCACCTGAGATGCGACAGTGAAGCAGCCGTTAAAGTCATATGCAGGG
CTAGAACCTGAAGTAAGAGCTGGATGTAAGCTAAGACTTTTGAAGTACAGCCCGCATCTGTGTTATCTAC
CCCTGAAGACCAATAGCTGGCTGTGTTGGCGTAGGTGGCATTGGAAGGCTGGGGTGGCCTATAGGGCTT
TCTGTGGTTTAGTTAGAAATCAGTTCCTTTCATTAATAGAAATTAATAGTTGCTTTTGTTGTTGTCCAGT
CGGTAAGTCATGTCCGACTCTTTGCAACCCCTTAGACTGTAGCACGCCAGGCTTCCCTGTCCTTCAGTGT
CTCCCAGAGTCTGCTCAAACTCCTGTCCATTGAGTCAGTGATGCCGTCCAACCATCTCATCCTCTGCTGC
CTCCTTCTCCTGCCCTCAATCTTTCCCAGCATCAGGGTCTTTTCCAATGAGTCTGCTCTTTGCATCAGGT
GGCCAAAGTGTTGGAGCTTCAGCTTCAGCATCAGTCAGAATATTCATAATATTCAGGGTTGATTTCCTTC
AGGATTGACTGGTTTGATTTTCTTGCTATCCAAGGGACTCTCAAGAATCTTCTCCAACATTACTGTTCAG

AAACACCAATTCTTCGGTGCTCAGCCTTCTTTATGGTCCACCTCTCACATGTGTACATGACTACTGTGAC
CCCTACCCACACATGCCTAATAGCCATCCTGGGGATATGTAGGTATAAGCCAAAGAAAGCTGAGAAGAT
GGTACAGATTTTCCAAAGCATGTTAGTGGTCTGAAATGGGAGGAAGTCTGGGTTAAAGCTGTTAGGGACA
GATTTATTGGGAGGTAGTACTTGATGGCAGCCTTAAAGATGGAGGGTTCCATCCACTATCTTTCTCGTG
TTGGAAGCCAGGAAGAAGTATGCAACTAAGTATTTTCCTATAGTCTCATGGAACATTCACGTCCCCAGTC
TCCTTTGGAATCACAATGAAAAGAGGGCAACCCAGGATATTGAAGATGCCGTCCAACCATCTGGACTGTAT
GGTTGGCAGTGTTTGTGTGGATAGGGAGGAAGGTGTAAATGGATCCTCAGTTTATCTGTTGAGTGGAGTT
TCCAAACATTCTTTTATTGGTCAGTGGCTCCGCCAGCAGTGACCTCTAACCTCAGCCACACTAGGAGGTG
GAAGTCAGGAGCCTGCCTTGCCTTTGAACTCTTCTTTGTACTCATTTGACTGGGAACCTTTGAGGTGGCA

GAAACATTCAGCATCTTCTTTGCTCTCTCTCCTTGAATGCTTGGCCAACTTAAAATACCAGTTTCTTTTC
TATTACTGACCCATCTCAGCCTGCCTTCATATTTTCCCTATTATACTAAGCATACCAATTATTTGTTCTC
CGGAGGAGGACGTGAAGATATAATGGGCTGATTAGGAAAAAGAACATGTCTGTCGAAGAATATGTGGTCC
CCTCTCCTGGCAGGACTGTTGTCAGGCCTGGCTGTGGTCGAGCAGAGAGCAGAGAGACCACAGAACAGG
AAGTGTGTGTGTCCACCAGTTCATGCACTTTATTCAGGGCAGAGACCCCACAGGAGGCTGCTCTTTTATC
TTGCATGTGATTTCAGCACATCCAACTGTTTGCTTTCCATAGACGTGGTAGTTTCGAAGTTACATCTTTG
AAGGACAGAAAGACTGTAAGTGAGGGGCTGTGACATGGGGCATCTGCCAGTCAGGCATGAATAGAGAAGA
CAGAAAGGCTGTTTTAAAAATAGAACTTGGATGGAATGCTCTGTGAATAATAAATCCTGGAGAGGGTGTG
GAGAGAAGGGAATCCTCCTGCACTGTTGGTGGGAATGTAAATCGGTATAGCCGTTATGAGAACAGTATGG
GGGTTCCTTAAAAAATTAAAGATAGAGCTGCAATATGACCTGGCAGTCCCACTCCTGAGCATATATTTGG

TABLE 3A-continued

SEQ ID NOs: 1-2, BOVINE EXT2 AND ALX4 GENES

```
AGGGAAACATGATCCAAAAGGATACATGTGCCCCAGTGTTCACTGCAGCACTGTTTACAATAGCCAAGAC
AACCTAAATGTCTGTCGACAGAGGAGTGGATAAAGGTGTACAGATATACAATGGAATATTACTCAACCGT
TACAAAGAATGAAATAATGCCATCTGCAGCAACGTGGATTGACCTAGAGATTGTCATACTGAGTGACATA
AGTCAGAGAAGGAGAAGTATCGTATGATATCCCTTATATATGGAATCTAAAGAGAACTGGTACCAATGAA
CTTATGAAACAGAAAAGGACCCGCAGACTCGGAGGGTAAACCTAGGGTTGCCAAGATGAGAGATGCGGGA
AAGAATAGCTGGAGAGTTTGGGATGGACCTGTACACGCTGCTGTGATTAGAATGGTTAGCCAAGGATGGC
CAGCGAGGACCTACTGTATCGCAGGAACTCTGCTCAGTGTTGTGTGGTGGCCTGGATGGGAGGGGAGTTT
AACGGAGAATGGATGCGTGTGTATGTATGGCCGGGTCCCTGTGCTGTTCACCTGAAACTGCCCTAACATT
GTGTGTTGATTGGCTATACCCCAACACAAGATAAAAGGTTAAAAAAAAATAGAACTTGGGGCTTCTTGGC

ACTCCAGTGGTTAGCACTTCACCTTCCAGTACAGGCTGTGTGGGTTTGATCCTCTGACTGAGGAACTAAG
GTCTCGCATGCGTCATGGCCAAAAATCCAGAACATAAACAACAGAAGCACCATTGTAACAAATTCAGTAA
AGACTTTTAAAAAATGGTCCACATCAAAAAAAACACAAAACTTAAAAAATGAAAACAGAACTCTCAGCAC
TCTGGATACATGGCAGACGGCAGAACGTGCTTCTCGATATCCTGGGTGTGTCCTCGTAAGACGGTAGAAT
TCCTTGGTTCAAAGAAATATGTACGTGTTTGTTTTGCATATTTTGGGTTTCTGGCATCCAAATGAGTCCT
ACCATCACTTTGATTGTTGAATATAGTTTCTGTTTTGTCGCCTTGAAGCTGTTTCTGACGGAGCATCTTA
AAATCGTGGAAATACAGAGATGGCTGTCCTGAGAACGCCCTGCAGTCTTTTCAGGGAAGGTTTACGTTTC
GCGTATATAAACGTGTTTTTAAAATACTGGCTTTCGCGTAAAGTATTTTCGAAAGTTTTCTATCTAAAAT
AATTTGCTTTTATTTTTTTAAAAGTGTTTTGTGATCCGCTAAAGGCGTCGGCCCTCGGATGTCTAGGAC

CCCCAGGAACCTGGATGGATGTGTTCTCTGAGGGTCCCCTGCGCTTGGCTGTTGTGTCCGTTGACGGCTA
GGTAGCAGTCTGTGTCCATTTCTCCCTCCCTCCCTGCCCCAAACACACACAATTTACAAAGCAAACTTG
TTAAACAGAGCAGTGAGACTAGGCAGTGAGAGGAGCGATCTGAATTTTTTTTAACGTGAGGAAACGGAAG
AAGAGCCGTGAAGCGATGCTCCGGTGATCGCACGACCTGAGAGGGACAGACGGGGAACATACTGTTTTGC
TGCCCACAGCTTGATTCAAATCCTAGAGCTCTGTGGCCTGGATTGAGGTTAAACGTCAGGATGAGCTTCC
CAGCAATTCAGGTTAGCTGCTTATTGGATCGTCTCTCCTAAAAAGTGGTTGCCTGAGACCCTGGAGACTG
GACACGTCTCTGGAAATATGAAGAACGTGGAAAAGACTTCACTTCTGATTTCCAAGATTTGACATTGTAA
CGTCTGTCACTCTTTCCCACTGCCCGCCCCCCCATACTGTGGAAATTGAAAAAAACTTTAATATGCATAA
ACTGAATTCTCAGGGCTTTGAAAAAAAATGCCAAGTATTCCCTTCCTCCCCCTGCTCTCTAGTCCCAGCAT

GCCACTCCAAGCTCTGTTTGCCGATCTCTGCTTTCATACTCGCCCTTAAAAAAGCTACTGGATCACTTAC
CCGTCTACGAAACACGTTGACCTTGATCCTTGGCGTTCTCCTGGTGAAACAGACAACCGTGGTTCTGATA
CAAAGCCAGGCTCTTTGGCCAGTGGGAGAGCCTTGGGGAAGAGTGTGATTATGGGATATTTTGAGTTTCA
TAATTTTATTTCAATTTTGTTACTCTGTTGGAGTTTTCCTGAATGTATAAATCCATATTGTGAAGGAGAT
CAGTCAACTTATGTTTAAAGCAGGATAAAATAAGGGCTCATTTAATTGGAACTCTTAAGGAAGAGCATTT
TTATGTGTTTAACTTTTTTTTTTTTTTCAAGTTTAGCATTAAGAACCTTATTGGAAAAAGACTTTTGCCAAG
TATCTGATGGGAAGCCAAGAAAAGCATTTTAATAGAACGGTCTCAAATTTATAGTACACCAGGGCCTGTA
AATAAATTTCCCTGTCTTTAAGGTTGGGGCTGATTTGCAGTTATTTTGTATAGCTTCTGAGATTTAAATC
CTCACAGTCCAGATGGGGAGACCATAAAGCTGCTTTCTTTGGCAACCCTGGCATACATTGTCCACGGCGA

GCTCTGTCTGTAAATGCTCACTTACCGTATTGTGATGCCAGTTTGAATTGGTTTAGCGACTTTTCCTAGA
GCAGCTCCCCCCACCCCAAATGTTCTCAAAATCTTGGAGAATTAAGAGTCCTTGATTTCATAATGCAGAC
TAGTCAAATAAGTATGTTTTAAGTACCGGCTTTTTTGCTAGAATTGTATAGGTATATTAAAGGAGATTTT
TACAAAGGGGGAGGGGAGGAACACAGATCCTGTCCTCAGGGTGCTAGGGAGAGCACTTTCAGCAATAGTG
AACGAAGAGGGCGGAAGTGCTGGCCCTCAGTCGTGCTGCGGAATGGATCAGGAGGCGAGAGCAGGCTTCG
TGACCGGGTGGCCTCGAATAGGGTGAGAGGATGCTCTGAGAGGTGCCGAGCTCCGCCCAGAGGTTGGCTT
CTGTGGGAAGGACTCGGTAGGTGAGGTGGAACAGCCTACCAGCCTGAGGGGGAACTTGAAATACCAGCAA
GAGAGAACTTTCTAGGAAGCTGGAAGGACGGGAAAGTCAGTGACAAGTGGAGAGTAATGAAAAAATGCGC
GAGGAAAGGGGAAAGCAGTATCAATTAAGGAGACAGGGGTAAAAAAAAAAAATCAAAGAGCTGGAAGGA
ACCTTAGAAATTATTCAGCCCTTTCTTCATATTTTGTAAATGAGGTGGAAGCCCTAGCGTTCAAGTGATC

TTGAGGATGAATTGTTAGGGCCTGAGCCTCGCCTCGCCTGGAACCCAGGTCTGCTGACTCCAGCTGATGG
ATTCTGGGTGGAAGGGGGACCTTGTGTACTACAGTATTTTTCAATTTAGGGAGTCTTGAGTGGCATTTTA
TTTTTTAAAAAATGAAGGATAATAGGAAGGCATCAGAGTATTACCTAGCAAGGGTAAATCTTTCCTGAAC
TCTTTTTTTTGATATGTATATGTGCAGTGTCATTATTTAATGTATTTGTATGTTTCTTGGTGTGGGCCCC
AGTCCAGAAAGTTTGAGGGATGTTGATAGTGAGTGGCAAGCACACAGGCTTTTGAGTTGAGGAGACCTGA
ATTTGCATCCCAGGCTGTGCCTTCTGTCTGCCAGCTTTGTGAGCATGGGCAAGTCACTTTGCCAAGCATC
AATTTTCTTATCTTAGACCTGGGGATAATAGTCCGACTCTTTGTGAGCCCACGGACTAGAACCTGCCAGG
CTCCTCTGTTCATGGAATTCTCCAGGCAATAATACTGGAGTGGGTTGCCATTCCCTTCTGGGGATCTTCC
TGACCCAGGGATCGAACCCAGGTCTCCTGCACTGCAAGCAGATTCTTTACCATCTGAGCTACAGGGACGC
CCCCAATAATACAATAGAGCAGTTGTGTTGTTTAAATGAAATCCTTGACTTAAAGCATCTAGAGGCCGGT

CTGCCTGCTCTGTGTTGGCTGTCGTCGGGAGTGCTCCGCCTGGGTCTAGGTTTGAACACTGGCAGGAGC
CTCCTGGTTTGGAGCTTGGACTTCAGGAACCACAGTAAGTTACCAACGCGGATGTATTATGCATTTGCTT
CTGGGCTTGGAAACTTGAAACAGAACTTATTCCTGTGGGCCTGGTGTCCTTTCTACATCTTGGAATAAAG
GGAGGTTCCCCTCTCTGGTTTTCAGAATGGCTTATGAAAATCAGTGGTTCTTTAGCTGGCCTTAAAAAAA
ATTCATTGGCACGTTTGAGTGCCAGAATTCATAAAGCAACGTTTGGGTCAAGTACTATTACTTTTTCCCC
TTTCCAGTGAGAACGATTTTCATACTGAGTCTTTTTACCCCGTCTTTTAATGTATCCTCTGCTGGATCTT
GATTTTACTCATTTTTTTTGAGCCAGAAGATTAAAAAATAAGCATAAAGAGAAAAGTCAAAATCAGAATT
GACATTTGGGTGGTGAACACTTGGAGAGTTGGCATTTTACTAGGTATGTACTAAAAATAAAGCAACTTTT
TATGTGAATTTAAGAGGGCTGGTGAGATACCTCTTAGGAATAGCTGTTGTTCGCCTCCTACTGAAAGGGT
AATGAGTTGTATCATCTGGTTTTCCTGGTTCTCTGCTGTTCCCCTAACCCCTGCTGCCCTTCCCCCCACC
CCTGCTGCCCTTCCCCCACCCCTGTCCAGCCAGCTCCATCCCCATGTTTGAAATCCCGCTGGAGAGCAGT

GGAGCGCTTCATCCCTAGATGATTTGGGCCAGGGGCTAAAACACTGCCATAAATCTGCAGCTCATTTTAA
TGCCACGTTAAAACAGTGTGAGCGGCTGGTTTCCGTGGCCCCTGCCCTCTTTCTTTATGGGCTTCTTTGG
CTCCTTCTTTATAAAGAGGCCCTGTGGAGTCATTTTAAAGTTCTTATCAGTTTGCTGACAGCTATATGGGC
CTTTCTGCTGAGTCCAGGAGCTCAGGCAGGCGTGTGAAACTTCTGATATTAAAATTGAAGAAAAATGCCA
GGCAGAAGGGATTGGGGAGCGCAGCGGTGATTTGGAGGTGAAGACTAGCGAGGTAATTAACCTCTGCAG
GTCCGGAACTGCGCCCTTGGCTGGATAAGTTGCTCCTGGTTGGTGGGGGCAGGGCAGCAAGGGTTAGGCC
AGGGAGGGCTTTCCAAGGGCTTTTATTTTTATCCCCGATGAGAAATGCCGTTCAGCTGGCAGCCTGTGCT
TTCAGGCTTCAGCAAGTGCGTTGGGCAGTCCTGAAAGGCTAAGGGAGCCAGGTTTACAATGCAGTTTTTT
TTTCTTTTTCCTAAAGGCCGTCTGACTGGCTAGACCTCGGCTTGTGAGTCTCTGGCAGCTCCAGCTCACT
```

TABLE 3A-continued

SEQ ID NOs: 1-2, BOVINE EXT2 AND ALX4 GENES

GTCTCTGTCCACAGCATCGCTGTTATCGAATTTAAAGGGGCTTTCATCAGTCTGCTCCGCAGCCCCTTTT
AGACCAGCTTGCTAACTCCCAGTGATCCTCGCAGAGTGCTTCGTGGAAGCGCCAGGCCCTCTATAAATGT
CAGCCTGCAGCTTAGCCCTTCTTACCCTCTCAGTTACGGAGAGGTAGCCTGGAAGCCGCTCCTCCCTCTC
CTCCACCGCTTTTCCTTTCTCTCTTTGCTGGAAAACTCTAGCAGCAGACAGCTGAGGGGAAGGAAAAACC
ATTACCTGGATCAAGGCCAGGGGCTTGATGGAGCCTCAAAATCTCTGGCATCTCCTGACCAGAGTGTTTT
TCCAGGCATTTCAAAAAGTACACCCTCACCCTCCGCCAGCTTTCAGCTTTCCAGCCTTGATTCCAGGTGG
GCTGGCTTGGGGGCATCATGCCCTCAGAATCTGTATCTGTCTGCTCCTCTTCTCCTAACTAAAGCGTTTA
GGAAAAGGATAGTAGAGATAAGCAAAATCCAGTGGACATGTATTTTTAACTGCCTTGCACCCTTTTGGCG
CAAACACATTATTTTTCCTTTTTCAAATAGTTTTGGACATGAGTACTTTTGCAAGTGTATTCAATTTAAA

ATAGTCATTTAACTTGAGGTTGAAGCAAAAGCAAAGAATTTTTGTAGTTAGTCAAATTATATAGCTGTTG
ATCTAGGATCAATGATTTTCATTGAGCAAACAATAAAAAATACCGGTTCGTTTTACTACTTGTGTGGAAG
TAGCTCCTGTGGGGGGAGTAATTAGGTATGAAAACTGACCAAGCTATAAATCAAAATAAAATACCCCAAC
CTCCAAAGCAATCAAGCTACTTTTTTGAACATTTCTGACAATATCAATAGATATTTTGGTATTCTGAACA
ATATCAGTAGAATAAATTGATATTCTATAATTAGTTAAGTTTACTGAATCAGAAGTTTTTGCTTGTGGTA
TAATTTTAATAAATTTACTAAAAATATTTTACAAATAATGTACTGAAAGTTCTCAGTAAGTATATGATTA
TGAGCAGTCTTCATTGTACAGCCTTTGCAAGGGGTGTGGTTATATCATATGACCAGTTTCCTCTTTGGGC
ATTGGTTGCAGAGCTGGCTCTAGAGTTAGCCATGGGTTAATCCCTTGTAACAAGTCCCCAATATGGGGCA
TTGCTTTAGGAAATGGCCTCTCTAATAAAAGTGTTAAACATTAATTTGCAGCCTATATAAGGATTGTCTG

ACTCTTTGGGGCTGGTTTCCTACAGAGTGGAACTATTTGTGAAGCATTTCTGAGAAATAATTGCTCATTA
CAGGAAGTGTAGTGCAGGCTTTGTGAATTCATTATATATCTACTTAGAAAAATATCTAGGTTTGTTTACA
AAAGAATAACTTATAAATTACCAAGTGTCGATACAAGCATTTGGTAAAGAATTCACTATTGTCAGGTCTT
CAGTAAGAGTCAGACTGATCCATTAGATTTCTGTCTATATTTATGATTATTTTGTATTTGAATGTATTTT
TCTGTCTCCCTCAGCATTGAAGAGGCTGAGAGAGTTTGGAGTTGCCTGACTACTTTGTAATAACACCATC
TTGTAATTCCATGCTACTGTTCTTGGGAATGTAAGCAACAATTGTGTATTTATTTCATTTTATTTGACT
AGATGACTTTAATACTGAATCAGACCAGAATTGGTACAGAAATAGCTTCATAAAGTCATTTCTGGCAAT
GTAGTTCTCTCTCTCTCCCCTTATAGTTTAAAGGTTAATTTGTATTTAAATGTGCACTTATTTCCCATTT
TGATAAGATTTCAGTAGTAAGCAAGCAGGTCATTTGTTATCTTTCAGAATTCAGTACTTTTTATTAAAAG

GAGCAAGCGGTTTGTCTTCAAGTGTTTGAAGCCCATATATGTATATATATATATATTGAAGTGTTCTGAATT
CTCTGAATATATATATTGGCCAGGTCTTGATGATTTTATATATATATATATATATATATATATAAAATTT     TH_MICRO243
GTATTTTAGAGAGATCTTTGAGTTTTTTGTTTGAAGCTACAGACTGAGGGTTGAATTCTCTCAACTCTCTT     TH_MICRO348C
GCTCTCACTCAGATTCTTAGATGCTTTCTGGAGTGGGGAATGGGGACATAAATTTCTCTTGAGAATCCTC
GCCGTGATGAACCTCTGCTATGCTTACTCATAGGTAAGAAAGGGCGCGGGGTAAAGATGAGAACCACTCA
CAGAGCAAGCATAGCTCTTTCAAACTTCTCCCTCTGTTCAGAGTCCCAATTTAGGGAACGCACATTGGGG
TTTCCACTCAGATCAACAGGAGAGCGTGTCTTAATACCTGCCACGTGATCAGACCAAGGACATTCCCAGC
TGCAAGCGGCTTAGGGAGGGCTCCCGTGGCTCCGGTCAGCTGGAACCGGCATTGGACCCACACTATTCTC

AACTTCTCTGTTTCTGGGAATGTGTGGGGACAGTGGAGAGGGCTCCCATGCGACCTGACTGCGTCTGTAT
AATATCCACAGCCAGAAAAATAAATAAATAAATAAATAACCTGCTAAAGAATAGCTCCCCAGCCTTCTTT
AGAATTGTTACTACCTGGGAAGCAGATGGAGGGGGGAACATGGCCCTGATGTGGCAGGATGTGGGATGAA
ACGAGCCCTCAAGTTCTGTCCTCGGTCCCTTCACACGTGCTATCTGCGTGTGTGTCTTAATTAAAAGGGG
TCGGCCTTTCAAGTGTGCCCGCTGCAGTGAGACTTGTTTTATATTTACCTTTTCTGATCAAACAAGCATA
CAGCTCTCTCCCTGTTTTGGTATAGCAAACATGGGGAATCTCACCCCAGGCGGATTCCTTTACAACGAAC
TGACCCAAGTTGTGCTCTTATTTATTTATTTTTGATGACAGATCCTGATTAAAGGTTTCCAGTCCAAACC
TTTTAGCTGGTCCATGAACCCAGCCAGGAGAGAGGGCTGGTCAGCTGCTGCTGATTGCCAAAGAAGCTCCCCG
ACCTGACCGAGGGAACAGTGTAATTCAGAGGTGTGGGTAACTGGGGAACCGGGCACAGCAGAAATGAATC
TCTCGTCTCTTTGCTGAGAAGGTTTGACCAAACACAGTTTTATTGGTCAGTGGCTCCTGCTTTAGTAACC
TTTCACCCCCATGGCTCTTGGAGGTGTAAGCCACTGGCCGGCCTTGCCTTTGAACTCCTCATGGCTCCTG

CCACCTCAAAGACTCACAGTCGGAGCTTGTGTTTTGCTTGGGATCTCTCCTCACAGCAGGGCATCAGCAG
TTGGGAAAACTGATCCACCCTTAGAGCCCTTGACATATTTGAAGGTGATACCCCTGAGACTTGAAACCTAT
GGCTTTCTATTTCAGGAGCTGCCTGTCACATGTCAAGAAACACGACACAGGCTGCCCACTTTGCTCCTCT
GTCCCTCCTGGCTTCCCATAGGACGGGAGATAGTAACATCTGAGCACACCCTGCAAGTATTCACCGAGTC
CTCCCCTCATCTTCAAGCTCTTTTACCCATTTTTCTTCTGACTTGTCCCAAGTAGAGTCTATTTTGAAAT
AAGTTTTTCTTTTAAATAAGGCTAAAACGTGCAAATCTAGCCCTCTTTGGTGTCTGGGAACTTGATGCAGG
TGAAGATGATGCAGTGAAAGTGTCACAGGGCTTACATTGACACGTTCAGTCCCAGTGCGTCCAGGTCAGA
TGAGCCCTACTTTTAAGATGGCCCAGCTTCCTTTTAAGATGGGACACTCTCCCCTGTCTTCTTGAGTCAT
TCTACGTTCTGGAAAAACTAGATCTTGCAAGAAGAGATAGAAATAGCATGGATTGCTCTCCCACATCTGC
TTGGCTTCCAGCCTACGGAACAAGAGTGAGAGCTTTAGTGTTGAGAGGCGAATCCAGGGACCCATGGTTA
TTGGGTGACTTCAGTAAAGCTTCTTTGGCAAGAAATCAAACCTCATATTCAAAGAATATTGAGTTGAAAA
ATGCCTTCTACTTATGATGCCGTTAGCTTAGCAAAGGAGTAAATGATCTCCATTGAGTTCCTCTGCTTTC

CTAGAATTCAGGTAGAACATTACTGATAATCCTTAGCAGAAAGAATACTCTGGCAGGGTCTTTTTCTGCT
TCAGAGTAAAGGTTGAGTTTTTAGCAGGTACCCAGGTGTCAGAAATGGTAGCCCACTCCAGTATTCTTAC
CTGGAAAATCCCATGGACGGCAGAGCCTGGTAGGCTACCGTCCATGGGGTCGCAAAGAGTCAGACACGAC
TGAGGGACTTCACTTTTCTCTTCAGGTGTCAGAAGAGGCAGGCCTGGTTTTTCTGCTGTCTTATTCTGTG
GTCGTGAGTGTGGTCATGAGCTTGAGCTCGACAAAGGGAAGGTTGACAAAGGGATGAGAAGTAGCATTTA
TGTTAACTCCCATGTCTGATAACTGACCTCATGAAAATCTGATGAGGCAGTTGTAGTTCTTCTCATTTTT
ACAAAGAGGGAAGGTGAACTTAGAGGCTAATGGCTGGTCTGTAGTTACAAAACTTTAGTGGCAGGCTTGG
GACTGGGAAGAATTTGTAGCACATGATTAAAAAGTTCACTTTTCTCACCTTTCCTCTGGGGGCATTTGCC
TTTTACACTGAGGTAAGTATGTCTTTGAGATGAGTATAAACCATCATCAATACATTAATTGCTGTATTGA

TGATGGTTTATAGGTTGCTTCTCCTTGCCACTATTTTCTGTTTTTTTCCACCTACTGGGAAATTTAGTTC
TCCCATTTCTAAATCCTATTGCATGACTTAGAGGAAGGAATTTGAAATCCCCTTTCTTCACTTGCCTCTC
TTTGTCCCATGTTCCAGTTCTTTCTCTGTATCCTTGCCCTGATGATAACTCAGATTTTTCAACTCTTTAT
GGGAATCAGCCGTGTTATATGATGTTATATGATGCCATGTAAGCTGATAAGGAACCTGTACATATTTGAT
TAGCCTTTGGGAAAAAAACCCACGTCGTCTAATTAAACACTGTGCACTTAACTGAGCACACCGCCTTGCT
GTCAGAAAGTATTGCTCTGGGCCTCATCCTCCTGACCTCTTCCTTACATTTTGTCATTCTTCTTCTAAA
AACATGTTTACTTCTCTATCTGGCTTTGCTGGGCCTTGGTTGCAGCACGTGGGCTCTCCTAGTTGAGGCA
TCTGAGCTCGCAGTCATGCCTTGTGGGATCCAGTTCCATTTGAACATGGGCCCCTTCACGGGGAGCCAC
TGGACCACCAGGGAAGTCCCTCGTGATTCTTAACAAATATATGCTGGAACCGTTTTCTCTGGTAACTATA
GGCGGAACTAACTGCATGTCCATTCTTTAATCACTCCCCATAAATATAAATATGGAGGCTGGAGATGAAC

TABLE 3A-continued

SEQ ID NOs: 1-2, BOVINE EXT2 AND ALX4 GENES

```
AGAAGGACATCTTTGGTTCTAAATGGATGACATGCGCTTACATATAGGCATTTTTGGAATTTTCTATGCA
ACTCTGTATCAAAATAGGATTTGAATGCTGGTCCACATACTTGCTTGTTTTCTAACCTTTGAATGACTCA
GGGTTTTATGTGTAAGAGCAAGGTCTAGAACTCCTAGAAATAAGCACAAGTGGGTGTGCTCAGCTCTTCC
TACGAGGCTTGGGCTGCGGCTGGTGTTGAGAAGCCTTTAGCGGTTGGTGGGAGCAGGCTAGGGGGGAGCT
TGGCCTGGAAGACTGTGTAAAGACCTCTTCCTCTCAGCACCAGGAAAAGGGGATTACATTGAGGGAAGTT
AGGGGATGGTTAACAAAAATGGTACGCGGGGAGAGAGAGAAAACTAGATTTAAAGGCTGAGTACTCTGCA
GCCAGCCAAGGGGAAAGGCTGTGAGCAAGTTCTCAGAGTCTTCACCAAAGGGTGAGAAGGGAAGAAAGG
GCGCCTTTTGCATGGCAGAGGTTCATAACCATTTGTCATTGTTTATTTGCTAAGTCGTGTATGACTCTTG
CGACTCCATGGACTGTAGCCCGCTAGGCTCCTCTGTCTATGGGTTTTCCCAGGCAGGAGTACGGGCAGGA
AGGGATTGCCATTTGCTTCTCCAGGGGATCTCCCCAGTCCAGGGATTGAACCCATATCTCCTGCTTTGAC

AGGTAGATTCTTTACCCACTGAGCTACCAGGGAAGCGTTCATAATGATAGTCGCTATTATTAAGGTGATTT
TATGTTTCTCTTCACTACCTATGTGCCAACTGGGTAGAGATTATTTTAAACAAGACACAACTACAACAAA
CCTACTGTGGATTCTGAATTCTGATATGTTTTTAGAAGGCTGGGAATGCGGAAGAATGTAAAAATAAAAA
TAAAATAGAGATTAAATCCTAGGAGAGATTAAAGTCCTAACAAGAATCATCAGGTTCTATATGAGATCCG
AGGAGAAGAGCAAAAATGTGTTCATTAGGTGTGATACATTAGATCTCGCACTGGGTAGTGGCTGCATTTC
ACATTTAATATGGTTCTCAGCTGTTCCCCTGCAATGACACAGCTGAAAATAGAGGCCTTGCTGGTTAAGC
CAAGTCTAGTCAGTCCTGCTTGCTGCTGCTGCAGGGGAAAATGAGACATTGAGAATGGCGCTCAGTCCCC
TTAGTCTGCTCCAGTTTCTCGACACTCGGGCATGACTCTAGAGGAACTGTAGGATACCAGCGTAAAGAAG
CCACGAGAACCCGCGGAAACCTACTGCCCCAACTCTGTAGTACTTATGGGCCAAGTTTTCAAATCCTTGT

CCTTGAGTGGGGCCCAGCAGATTTTGGTTTTTACTGAGGGCCACCAGAGAGTTTTCAGTCTAACTAGGAA
GATAAGTATTTTCACCCCATGAGATAACAGTAGGGCAGAGAATAGATGCTGACTCTTGTGTAGAAATTGT
CAGATGAATTGGAAAAGGGCCTCAGTATGCTTTCAAGGAGATAAAACTTGAAGCCCAGGTAGGATTTTTT
GTTTTTTAATTACTAAATTTTAAAAAGGTATTTATTTAATTTATTTAGTTGCCCCTCGTCTTGGCTGCAG
CTCGTGGAATCTTTAGTTGTAACTCAGATCGTAATGCAAGCTCGGTTCGCGTTCTAAGAGTCGCAGCGT
GTGAGCTCTTAGTTTCAGCACGTGGGATCTAGTTCACTGGCCAGGGATCGAACCCAGGCGCCCTGCACTG
GGAGCTCGGAGGCTTAGCCACTGGACCACCAGGGAAGGCCCTTAATCACTAAGTTTTATTTTTCAGAGCA
GTTTTAGGTTCACAGCAAAATCGAGCAGGAGGTAGGGAGAGTTTCCCATACACCCTGTGTCCCCACAGACG
CATAGCCTCCCACACTAACAGTGAGCCACAGTGGTTCATTGTTAGAGTGGAGCCTACACTGACACAGCCT
TCTCTCTCAGAGTCTGTAGTCCTTGTTAGGGTTTGCTCTTGGGGTTGTCTATTCTGTGGGTTTTTAACAA

ACGTATAATGTTTCCTCCATGTCACTATTTCTAATTTAATTCCATTGCGGTCTGGGAGCAGACATCATAT
GACTTCTTTTCATGGTTGTTCAAGTATGCTTTATGGCCCAGAATGTAGTCTGTCTCGGTGAATGTTACAT
GTGAGCTTGAGAAGAATGTGTCCAATCTGCCGCTGTTGGATGAAATAGTCTACAGATGTCAATTATTTGG
TGCTGTGAATACATTCAACTATGTCCCTTACTGATTTTCTGCCTTCTGGATCTGTGTGCTTCTGACAGAG
GGCAGCTCTGGGAGAGGATTCATCTGTTTCTCCTTGAATTTCTACCAGTTCTTGCCTCATGTGTTTTGAT
GTTCTTTTGTCGGTTGCCTTGAGGAGTGTTATGTTTTCTTGGAGTATTGACCTCTTTATTATTGTGTATG
CTACTGTTTATGTGTTGTAATTTTCCTCGTTCTGAAGTCTTCTTTGTCTGAAATTAACATAGCTACCTAT
ACTGTCTTCAGATTAGTGTTAGCATGCTCTATCTTTCTCCGTCTCGTTTAATTTATGTGTATCTGTTTAT
TTAAAGTGGGTTTCTCATAGACAAGATATAGTTGGGTCTTGTTTTTTCATCCACCCTGACAAGCTTTTAA
TTGTAGTATTTAAGCCATTAGCATTTAAAGTAATGATTGAGATACTTGAATTGACATTGACCATATTTGT

CACTGTTTTCTATTTGTTGGCTTTGTTCTTTTTTCCTGTTAATATTTTTGTCTTCTACACATTTTATGTC
TTTTGTGGTTTTAATTAGTAGTTTATATGATTTTATTCTCTGGTTGACATACCAATTACACTCCTTTTTT
AAATACTTTTTTTAGTGGTTGCCCTAGAGTTTGCACTTTACATCTATATCAAATCCAAATCCATTTTCAA
ATATTCCTGCTTCAGTGATAGTGCAAGTACCTTCCTTATGTTAACACAGTAATCCTGGTTCTCTTGTCCC
TTGTATCGTTGCTGTCACTCATTTCACATATACATATATATATATAATACACACACACATAATCAAATT
TGTTGCTTTTATAGATTATTATATGTTAGATCAATTAAGAATAAGGAAAATGACGATTTTAATTTTACCT
TCACTTAGTCCCTCTCTGATGCTTTTCCTTTCTTTATGTACATCTGTTTCTGACTACATCATTTTCCTTC
TCTCTGAAGAACTTCTTTTAACATTTCCTGTAAGCAGAAATACTGGCAACAAATTTTCTCGATTTTTGCT
TGAGAAATTATTTATTTCTCCTTTACTTCTGAAGGGTTTTCCAGGGTGTAAAATTCTGTGTTGGTGCGTT

TTTTCTCTTAACCCTTTATAGCTGTCATTCCACTTTCTTCTTTGCTTTCTGTGGTTTCTGAGAAGTCAGATG
TAATTGTTACCTTTGCTCCTCTATAGCTAAGGTGTTTTTTTCCCCCCTGTGGCTTCTTTCAGAAAATTTT
TAAATATTTGCTTTTCTAAAGTTTCACTATGATATGCACAGGTGTAGTGTTTTTGGTATGTATCCTACCC
AGTGTTCTCTGAGCTTCCTGGATCTGTGGTTTGGTGTTTGGTATTAATTTGAGGAAATTCTCAGTCATTA
AGTTTCCTCTCCCATTGTATTCTTTTCTTTTGGTGTTTGTATTACGTGTATGTTACCCCTTTTATAGTAG
TCCCATGGCCCTTGGGTATTTTGTTCTTTCCCTGCCTTTTCTCTCTTTGCAATTTTGGAAGTTTCTGTTG
CAATATTGCCAAGCTCAGATTTTATCTTTTTAGTTATGAAAACTCACAAATCCAGGGACTGCACGCAAAC
TGTGTCACATAGTGTCCGTTGTCACATAGCCTCCATTGCTACAAGAGGCTGGGTAATATAGTATTTTAAG
TTGATTTTGTTAGTAAAGATGAACGAGATACCAGATACTGGGGAGGCAGCTTAATGTCTGTCTGGAGGAC
TAAGAATAATCTGGATGTGAGAAGTTAGGGTAGTGAGATGAGCTTTGTCTTTTTTTGATTGTGCTGGGTC

TTCCTTGCTTTGCGAGGGTTTTCTCTAGTGGCAGTGAGTCCGGGCTACTCTTAGGATGCAGGAGCTCCTC
ACTGTGACGGCTTCTCTTGCTGCAGAGCACGGGCTCTAGGCACATGGGCTTCAGTAATTGCAGTGCTTGA
GCTCAGTAGTTGTGGCTCGTGGACCCTAGAGCACACGGCTCCAGGGATTTGGGGCACAAGGCATGGGGAT
CTTGCCCAACCAGGGATCGAACCCACGTCCCCTGCATTGGCAGGGGGATTCTTTTCCACTGTACGACCAG
GGAAGTCAGTAGAACGAGCTTTGCCACTAACTCTGTGTGTGTGTGTGTGTGTGTGTGTGTGTG      EXT2_840C
TGTGTGTGTATTTGTGTGTAAAATCTCACTGGGAATTGCTGGCATAGAAGAGTCTTGTTTTTGTTTTAT  EXT2_744
TTATTTTACAAATTATTTTGTAGCTGGCCACTTTATTAAACTTCCTTATTAGCTTTGATGGATTTTTAGT
TGATTTTCTAGGATTTTCTTAATAGAAAATCAATGGAAAGCTCTTGGATTTCTTTTCAAATACTCTTCCT
TTGTCTGTTTTCTTATTAATTACTGCTACTAGATTCCTTAGGTTTTTTTCCTTTCTTTCCCAAATTATC
AGATTGGGGTGCTTACTTTATTTTTGGATGATAATTCTGTGTATATATCAGAGTAAAATTAAAGTATGAG
ATTAGAAGCAGTTGAAATTTAGAAATATTTGTGGTCTCAGTAGATTTCATCTCTAAGATTTTTAGTAAAA

ACTGGCTACATGCTTTTCTCTTTTCAGTAGCTAGGATATGTTATCAGGCTTCAACTTAACATTTAAGGCA
TATGTCAGATTTTTTTGTTAGTGGAATTATTCAAGAAAGAAAATGTTTTATACTTCCCTAAGCCACAAA
TACCTAGAGGCTTAAGGATTTAATAGAATCCTGTTCTGTATATACGTAGACTAGCTGTGTGTGTGTGTA
TGCACACGTGCGTGCACGCTACTCAGTGAATGGAATTTCATAGTTTTTAATTCTTTTAAACAACACTAAA
AACAGTATGCTATTTCTCTGATACTACCTCCTCCGGGATGTAAAGCTTAATTATCTTCTCTTTGAATATG
GTCTGAACATAGTGACTTGGTTCTAATGCATAGGCTATGAGATGGGGATGGTAACTTTACCATGGAGAA
CCTGGAAGACCTCACCTTTAACTAGGTGATTAAGGTGAACCTCCCCTGTAATAAGTCACGTTGATCCCA
CCATGTGTCCCAGTTACGAAGGAAAGAGAAAGGCACGTCATCTGTGTAGTATTCTCCAAAATCCATAACC
TCAGTCTTAACAGTTAAAGAACCTCAGACCAACCAGACAGAGGGACATTCTACAAAATTCCTGACCACAT
```

TABLE 3A-continued

SEQ ID NOs: 1-2, BOVINE EXT2 AND ALX4 GENES

TTGGCAAGGTGTTAAGGTCATGAACTATAGGGAAAGATTGAAACTAAGGAGCCATGACAGCCAGAAGCAA
TGCAGTGTCCTGGATAAGGTGCCGGATCAGAAAAATGACCTTAGAAGAAAACTAGGAAAATCCAAAAGA
AAACAAAAGTCTTTAGCTGAGTTAATAGAATTAACCTAACATTAACATCTTAGTTTTGATCATTGCACCA
TGGAGATGAAAGAGACTAACATTAGGAGAACTAGTGAGGGTATTCAGAGCTCTCTGTTCTACTGTTGCAA
CTATTCTCTAAGTCAAAAACTGTTTCAAAATGAAAAGTTCAAAAGAAAGCGATTACAAGTCGGCCTGGTA
AATAAAAACATTTTTTATATTTATCAAAAATTGTAAAGTGAAGTCTGCTACTGTTACCAGAACAGATGTC
TGTGGCTTTGTGGAAGGGTCAGTGAATGGTGGGTGTGGGCGCCTCAGGTGCCAGGATCAAGTAATTGAGA
TAACGGGACTGGGAAGACCGTGGTAGGTGCCGGAGAAGTGCTTCCGGGGGCACCAGGGACAGGTCCTGGT
GCAGGATGCTGGTGTGGCGAGGGCGAGTGAAGTCACTTTGTGAGTACAGAAGTGAAGAAAAGCACTCTCA

TGTTTTACGGAGGAAGGCATTTCAGTTCAGTTCAGTCACTCAATTATGTCCGACTCTTTGTAACCCCATG
AACCGCAGTACGCCAGGCCTCCCTGTCCATCACCAACTCCCGGAGTTTACTCAAACTTACCTCCATCGAG
TTGGTGATGCCATCCAACCATCTCATCCTCTGTCGTCCCCTTCTCCTCCAGCCTTCAGTCTTTCCCAGGA
TCAGGGTCTTTGCTAATGAGTCAGTTCTTCACATCAGGTGGCCAAAGTATTGCAACTTCAGCTTCAACAT
CACTCCTTCCAATGAACACCCAGGACTGATCTCCTTTAGGATGGACTGGTTGGATCTCCTTGCAGTCCAA
GGGACTTTCAAGAGTCTTCTCCAACACCACAGTTCAAAAGCATCAATTCTTTGGTGCTCAGCTTTCCTTA
TAGTCCAACTCTCACATTCAAACATGACCACTGGAAAAATCATAGCCTTGACAAGATGGACCTTTGTTGA
CAACGTAATGTCTCTGCTTTTTAATATGCTGTCTAGGTTGGTCATAACTTTCCTTCCAAGGAGTAAGTGT
CTTTTAATTTCATGGCTGCAGTCACTATCTGCAGTGATTTTGGAGCCCCAAAAATAAAGTCAGCCACTG

TTTCCCCATCTATTTGCCATGAAGTGATGGGACCGGATGCCATGAGCTTAGTTTTCTGAATGTTGAGCTT
TAAGCCAACTTTTTCACTCTCTTCTTTCACCTTCATCAAGAGGCTTTTGAGTTCCTCTTCACTTTCTGTC
ATAAGGGTGGTGTCATCTGCATATCTGAGGTTATTGATATTTTTCCCGGCAATCTTGATTCCAGCTTGTG
CTTCTTCCAGCCCAGCGTTTCTGATGATGTACTCTGCACAGAAGTTAAATAAGCAGGGTGACAATATACA
GCCTTGACGTACTCCTTTTCCTATTTGGAACCAGTCTGTTGTTCCATGTCCAGTTCTAACTGTTGCTTCC
TGACCTGCATAGAGATTTCTCAAGAGGTAGGTCAGGTGGTCTGGTATTCCCATCTCTTAAAGAATTTTCC
ACAGTTTATTGTGATCCACACAGTCAAAGGCTTTGGCATAGTCAATAAAGCAGAAATAGATGTTTTTCTG
GAACTCTCTTGCTTTTTGATGATCCAGCAGCACTTAAATTTAATTAAATTAACAAATGATTTAAGTAAAG
AAAAAAATGGTGTGCTGATAAATCCTCGATATGTTGACCTCTTTTGCTTCAGAAATCTCTTATTTTAAAG
CAGATAAACCCTATTTATGATTGTTCGTTGGACCACTGAGTAAAAGTATCAAATGTCAGTGAGCTTCTCC

TTTAGAAAAGCTGACAGCCTGGGGCTAGTACATTTTTATAAAACCTTCAGTCCTTGAGGATTGCCCCGAG
GGGATGTTGTTGATTTTTGTTTTTTTTCCTCTCCCTGTTTCTGTTGTCAGTTAACCCTCTGGTTTATAAA
AATGGAGTCAGCGAAAGAATAAACAAGAAGCCAGTCTTGCAGTAATGCTCCACTGGGAATCAGGACACCC
TGATTATCCCTCGACCTCACCATTGTGTGTGTTTTCAGCTGCCAGGCGGAGGCTGTCCATGCCTGTCTCC
ATTGCCTCCAGGCTGGCCATGGGGTTAGCCACACCCCGGAAGTGAGGTCAGCAAGAAGGGCACTCGGCTC
CCTGCTCGGGCCCTGTCACCTGCCCAGGAAGGTGGCGGGGAAGAGAGCCCGTGTGACCCTGCAGAGCTTG
CCGTGTAGGAGGCTCAGGGGCCGTCACAGGCATGCTCACTGGCTCCATTTGTCACAGGCAAAGAAACGAAA
AGGAGCTCGTCTGCCGGTGGTACGTTAAGTGCTTGGAAAGCCTCGGAATCCCTTTGGAAGTTTTCAGATT
CACCTTCAGACACAGCTTTGAAAAATTAATCCATGAGGCGTGGAAATATTTTCCAGCCCTTCACCTGAGA

TAAATGTTCTGTCAGTGCAGTGAGCTGAGAGAAAATCTCCTGGCCTCAGATCCCCCGGAATCTCCCAGGT
TGCTGCTCAGAGGCAGAAGGGCTTCTGCGGCTCGAACGGTGCAGCTGTTTCTCAAACTTCCTGAGGGAGA
AGGCAAATGCTTTATTTAATCTCCCTTGGTTCTCTGTGCTTATTCAGTCCGTTTTATTGTTTTTCATTAA
TTTGGGAAAACTCTTAGCCACTATTTCTCTAAATGTATCTGTTGCCTTGTTTCCTTGTTTCTGAACCCCCTCTCTGGA
ACTCTGGCTCCAGGTACTGTTAGGACATTTCCATGTGGTTCTACAGTTCTTGGACGCTCTATTTTCTTGT
ACTCTTTTTCTCTTTGCATTTCGGTTTGGATCATTTCTTTTTTATTTCCAAGTTTACTACCGTTTTTCTT
TCCTCTGCTCTATTGTGATAAGCACACTTGAAGAAATTCTATGATGGTATGCTTTTTATTTCTAGCATTT
TCATTTGGCTCTTTGTTTACAGATAGTTTTCATCTGTCTACTGAATAAGCCCATCTGTTCATGCAGGTTG
TCCACTTTTTCACTAGATTCTTTCACATGTTAATTATAGTTATTTTGAAGTCTCCATCTGGTAGTTCCAA

ACATCTTGGTCATCTTTCAGCCTAGTTCTTTTGACGGGTTTATGTTATGACAGTGGATTGTTTCTCTCG
TATTTTGTTTCTGATAAACTTTGACTGAGTGATGGACTGTGTTAGAAAAACAGGAGACCTAAAGTAAATG
TCGTGTCCAGCAGTGGGCAGACCTTCTGTGAGCCATTCGCATGGGAGGTTGACTCAACCTAGCATGTAAC
TGGGATGGGTCTGAGTTTTTCTGTCGCTGGACTTACCTTCAGCACCGCTGACTCCAGATGCTGCCAGTGG
TCTCCTCGTTCTTGTGTGGGGCACAGGGTACTGGGGCTTTTCTCAGAGTTCCAGCTCCGCCCTCCGCTTC
CAGCAGGCCCTGCCCCCTGCACTACACAGGGAGCCGTGCTCCCGTCGGCGGGTAGGTAGACTTCTGTTG
CTTGTATGGTGCCAGACCTGTGGTGGGCCAGGAGGGTTCCATTCCCCTGGTCCAGCCTCAGTCTTGCA
GGCTTGTTTGCTGGGGCCGTGAAGGGGTGCTTTCTCAGTGTTTCCTGGGGCAGCTGGAGTCTGCCCTTTG
TCTGTGGGGGTCTGGGGTTGGAGGGAGTCTCCTACCCCTCCCTTGGGAGCAGAGGCTTTTGCTTCGACCC

CAGCCACAGCTGAGCCTTCTAGGAGCTGGAAGGGTTCCTGCCCTCCGAGTGCGGGGCAGGCTGCCTGTCT
CCCCCTCTCCCAGAAGCCGAGGATCTGCATCCGCCTTTGGGGGTGAGGGCTTTTCCTGCTAACCCCCAAG
CAGGTAGAGATTTGGCTTTGGATGAAAAAAAAAAGATTTGAGAAAGGGACAGGGCTTTCTCCCTGTGTGC
CATTGAAGGGAATGTCTCTGGTTTCTTCTCCTGCCCTCCTCTTTCTCCAGAACATCCAGCAGAAAAGGGC
TCGAAAGTGAGTGCAGATTCTGCTTGTGTCCAGAACTCCCAAACTGCCCTACTGAGCCCACACTCAGTTTG
AAGAATTTGTTAAAATGTTAGCTGGTTTTGGTGACTGCCTTTATAGCAGCCACCCCCGCCTTCTCTGCTC
TTCCCGAGCTGGATTTGAGTGTCCCATGGCTCCTGGATGGCGCTCTTAGAAATGGGTGTCCCTGATTGC
CTTCTGACCGCAGCTCTCCCACGCGTCCAGGGCAAGTTACAGTGTTGGTGGTGTATCTGGTGGCTTTTTC
TCATGGTTACTGTAGATTCCATGTTTCTTTGCGACTTTCTACATCCCAAGCAGAGGCAGATCTTTTATTC

TGTGGCCAACCAGTGGGTGGGGGTGGGAAGTAGAGTAATATTGGGGTACCTACTGATCCACCGTTACGT
GTTTGGACAGCATTGCCTGATGAGGTTTGACACAGAGGCATCACCGGCTGGTATATTTTTTATTTTGTG
GGTTTTCATTAGAAATGTCCTTTTAATATATTAAAACGAAGTCTGTTGGCATGGGTCACATTCAGGAGATT
CTGTTGGAAAGGGCAGTGCGCAGTTGGTTGCCGATGAAAGGGTGTTGGAGACTCGTCACTGTGCTTGGGA
TGCAGTCGCCCTTGGACTACTTTGGGGTCCTGGGGTTCTTCTGTGTAATTTCTTCATGGTTAGATATCCT
GGACACTTCCAGGTCAGACTTGCAAGGCATAGTTCTAACCACTGATTCTCTCTCGTGGTCTATACACACA
CAATATAAGGGACACCCATGGTCCCATTTCTGCCTTGCCATTTCACCTAGAAACACGTTTTCCTTTTTTT
TCCCCCCTCAAATCCACTCCCTGCCCCATCTTTTCCCTTTTAAAATTCTGCATGCACGAGGTGATCCTTT
TTATGAACTGACGGTTTTCCTCCTTTAAGGTCATGGGCTGGTGCTTAGAAGATCGGAGAGTTCTGTGAG
ATGCCTGTGGTGCCTGTGAGGGAGATGGATTTGTTCTTTCAACAAACATTCGACTGTCCAGTCCTTGACA

TABLE 3A-continued

SEQ ID NOs: 1-2, BOVINE EXT2 AND ALX4 GENES

```
GGCGCTGTGCTAGGGGCTGCAAGACCAGTGATGAGCAAAACCAGATGCGTCCCCACTCTCACGGTCTGCA
GAGAAGTGCTGGCCTCTGCCTTGGAAGCTTAGAGATTCAGGTAGAAGAGACATGTTAGTGGGTGAGATAT
TTTCCAGTATTAAGGTCTGTCATCCTTGTATTTATTTTTATTATACCTACCTCCCTTCTCTGACCAGTTG
GATTCTTTTCCTGGCTTCAAGAATTGAAATGAATGGAGTGTAACCTTAGAATCCCTTCTGTCTCTCCTCT
TCCCCTGTCTCCCTCCCCGCCCCCAAATCACGCAGAATGTAGTATATACTGTAAGTGACCTCGAGGGGCA
GGATGGGTGCAGGTGTGGAGGAGATGTTCTGATTATCTGCTCTGCACAGGGCGAGGAGCTTTACAAACCT
CATCTCACGGAACCTGCAGCTCCAAGAGAAAGGTGGTGTGGTGTCCATCCCCTAGATTCAAAAAATAGAG
AGGGTTAAGCTGCTTAACAGAGAAGGCAATGGCACCCCACTCCAGTACTCTTGCCTGGAAAATCTCATGG
ACGGAAGAGCCTGGTGGGCTGCAGTCCATGGGGTCGATAGAGTCGGACATGACTGAGCAGCTTCACTTTC
ACTTTTCACTTTCATGCGTTGGAGAAGGAAATGGCAACCCACTCCAGCGTTCTTGCCTGGAGAATCCCAG

GGACGGAAGGGCCTGGTGGGCTGCCGTCTATGGGGTTGCACAGAGTCGGACATGACTGAAGCGACTTAGC
AGCAGCAGCAGTAAGCTGCTTAAAATCGTGCAAGACACTCATCACCATGACTCTTTCTCCCATATTGTAC
TTGCTTCCTTTAAACACTTGTTATTGCTAGTCCTGTTGGCTTTATGTTACTGAAAATCAAAGAAATTAAA
CCACAGTAGCAGTTTTAGTTTGAAGTTTGTGTTTGCTTGAGATAGTTTTAAGTTGGCCCAATCCTTGCT
TTTGCTTCATGATTCTAATGTTTGAAAGTGTCATAGGAACTTTAGTTCCTGTGCTTTGAAATCTGCTTTT
ACAAAATTACTGTGGTATCAGTTTCATGAAGAAAAGTTAAATGCTTTGTCGGAGGTTGTTGGTATGACCT
TTTCATATATGACTTAGCTTTCAGCTGTGTAGATGCATAGAATAGAGCGTGTGGGGAATCTGCAGGTTTG
TGGAAGAATCCCTCATTTCAAATTTTCAGATAGAGATAAGTGTGGCCCATGTTGATGGGGGAAAAATCT
CAAAACAAAATAAGTGTTTGCATTTAGCTCACTGGATGGGAATGGTGGTGCTTTCATGTATATCACAACA
GAGCTGAAAACTCCTTCCTCTCTGCCAAAAAGTGGCCTATGCTGAGTCCTGGGGGGCTGTAAATTATGC

CTTCTAAATGCTGCAAGGTGTTAAAGAGGTCCTGCAGAAATAATTAAGCCTGTGAAGTTCACTTATCCTC
AGGCGGAGACACTTGAGCTGTGATTATTGGCAAGGCTTGCTTCCTTTCCAGGAGAACTGCAATTTGGTGG
ACAGGATGAGATGATTTGAGACATCTTAAATCAGAGTCTCTGTCCTACACTTGTGCCTCTGGCTGGTATT
CTAGGTGGATTTGTTCCCAGTCATTGTTTCATGTAAATCCCAAACGCTGCTGTCTCCACTGTGATTAAAT
GTGAATGCAAAGCTTTGGAATGCTCGAGTTTGAGTGTGGTGTGATTTGAAATTAAAACAAACAAACAAAC
ATATGACGATGAACCCATTTGCGTAGAAAAGGAGGTAAATATTTAAGCTGTGTTTATGTGTGGGCTCATG
CATCTTGGTGCCTTGGTAGAGGACCATTTCCTTACTCTGTGCTGTGACTTCTTCATATTCTAGAAGGAGGT
AGAAGGTCTGACTTTAGAGTTAGTATTCACGGGTTGGATTGGTGACTTTGCCACTTAATAGCTCAGTTTC
TCACATATAAAATGAAATTTGTATCTGCCACCCGACCCCCAAAAGTTAACAAACTTGGTTATAAAGAGCA
GATGAGATCATGGGTACAGTAGTGCTTTGCAGCAGGCAAAACATTCTAACGTTTGTAAGGATACTAATGA

GGAAAAAAAAAATGCCAGTTTCCACAGCCAAGAAATTCACAGTGTAGCTGGAGAGAGAAAAGTGGTCATC
TGAAATGCCAGTAAAGCAGTGTTAGAACGGTGTATCAGAGAACTAAGCCATAAGGTAAAGGCTGTGAATG
CGGTGGGATGTCTTAGTAAGGGAAGATTGTTGATGTTGGGGGTGCTCAGTAAAGGTTTCACAGAAGAGGT
AGGTTCTCTTAGGCCTCATGAACTGTAGATGCTTTGGCTGGATGATGGGAGGGGAAGCAGCAGCATGGCT
GAGCAGGAAAGAGACTAGAGTGAGTAGAGTGTATCTACGAAGCAGCAGCAGGCAGCCAAGAGGCCCCCCC
TGGCTGTACCCAGATGGCAAACCGCAGGACGGCTCAAGTCAGATGCCCCTGGAAGCTAAATCTGTTTTTG
ATTTTCTCTGAATAGGAGAAATTCTCATTGTGATGCTTTGCCTTCTCCTTATTGTTAGTGGAAACAATAG
TCGTCATATAACTCAGAAGTTATCCAAGGCTTTAACTAATAGAGGACTTGTCCAGGAAACAGACCCAAAG
TCAGTAAGTCTAGACTAGAAAGTGTCTTTTTTTCCTCTCCCTATTTTGGTTATGCTTCCAGTTTCTCATG
CTAAACTTGGATATGTTTGGCCCCCTTGCATAAATGCAAACAGCCTCTGATTTTGAGTGGGATCGTAGGC

TGAATGAAGCTGGAGAGGTCATCGGCGTCAGCATCCTGCTTTCTTTAGGAACCGAGTTTAAACTCTGCTT
GGATAAGAAACTGTCTTCTTTCAGAAGACTCTGACAGAGTGGCTGGTTTGGGAGTAACCCTCCTGTCAAT
AAAAGAAAAAGAAGTACAGAAGCTCATTATAATAGATGAAACAACAGTTCAGAGAGCAGCCAGGACTTGA
GGGATAATTCCTGAGAGACAGGAGCACCCTGAGAATAGCTGCCTGTTCACTCTGATGCCATCCCCCGAGG
ACTTCTAATTCACAGTCATGGGTATGGGGACTTCACAGGGAAACAGCAGCCCCACAGGGCTGACAGGCTGG
GGTTAGGGGGTTCCCAGAGTATCTGGGATTTGAAGGACAAAAGTCTCAGGAGAAAAGGGAATCATGGGGAA
ATAAACAAAAAACGAGCATGCAGTCTTCCATTAAGGTCTTTGCCAACTCCTAAGGTGCACACGATCAGAG
CAAGACTCCTGGAGTCCCTGCAGAAAGAAGCGGCTGGGAGCCTAAGGAGCTGTGCAGCTATTTCAGTAAC
CATATATAGTGCTAATGAGACAAAGGTCCATGTTCAGGGCTGGCCAGGATGGAGGGGTCCTGGGAAATAC
CCCAGGCTTTAGTTGAAGGCCCAGAAGGCCACACCTTCAGACTATGGGCAAGCTGAAAAAAGTCCTGACA
AAAGTTGAAGCTGATAGGATTAAAGTGTTCTGACTGCATTCTCTGTGCCTGCAAGCAGAATGTGTTATAT

TCTTAAGAGAAAGATAATCTGGATTGTCCAGAATCTCTATAATTTTTAATGCAGAATATTGGTATCTAAT
AAAAAATTAAGATGCAAGTTAGAAATTGAAACCAAATGACCAAAATGAAGAATAAAAAGAGATGGCAGAA
AGAGACTTAAAGTTTATTCAGATATTGGAGTTATCAGTCAGGAACTAACAATACTCAATAATACAGAAGT
GAAGGAGGATTTCAACAAGATACAAAATCTTCTTAGCCAAGTGGAATTCTGGAAATGAAAAATATAAGAA
GTGAAATTAACAGTTCAATACATGGATTTAATAGCAGTTTATAGACTTACACACACAAAGGATAAAGGAT
TATTGGAAAAGGATAAAGGATTATTGGACCAGAAGGAATATTAGTAGAAAAATACACAGATTGAAGCACA
CAGAGAAAAATACAGAAAAGAGAATAAGAGACATACAGGACATGGTGAAAACATTTTACATACACGTGT
GTCTGGAGTTGTAGAAGAGGAGAGTGTGATAGAACCAACATTTTAAAAAATACTGACAGAGTTTTCTAGA
AGCATCAGAAGACATAAAGTCACAGATTAGAGAAGCTATACAGTTCTCAGTAGGATAAATACAAAGAGCT

ACACTGAGGTACATCTGTGGACCTCTGTGGACAAATAGAATGAGCAAACACTTAAACTCAACTGTATCAG
AAATTACATTAAGTATAAGTGGACTGTATGTACAACTGAAAGCCAAAGATTTTTAAATGGGATAAAATAT
TAAAATCCATTTATATCTTTTTATGAGAGATAATCTTTAGACAAACTTTAAGGGCAGAAATTTGAAAGTA
AAAATTTTGGAAATAAAACACACATACACGCGTGCATACAGGCAGAGAGCAATCAATAAAGGTATAGAATA
TTTAGATAGTACTAAATAATCAACTTACTCTGCTTGACAAGTGTAAAACATTACACTCATCAACAGCAAG
ATGCTCTTTTTAAAGTGCACGTAGATCATTGACAAAAATAAATAATGTGCCTGGCCATAAATCAAGTTTA
AATAAATTGCAAGGTTTTGAAATAACTTGTATGTTCCCTGACTACAGTGCAAAGTAGAAATCAGTAACAG
ATAAATATAAAATCTGAGAGTGTTTGGAAATTAAACAGTATACTTCTATTAATAAATGCCCTTTGGGCCA
AGAAAGTGTTACAATGGAAATTAATTTTTTTTACCTAAATTGTAATGAAAATGATATGTAAATGTGTGG
GATGCATTTAAAATAGTGCATAGAAATAAATTTACAGCTTTGTATTTAGGTATTAAGAAAGAAGAAAGAT
```

TABLE 3A-continued

SEQ ID NOs: 1-2, BOVINE EXT2 AND ALX4 GENES

```
TGAAATATCTAAACTTCAATCTCAAGAATCTAAATGCAGTATGGATTAAAGTCCCCCAAAACCCAAAGAAA
GTAAAAATAAGAGCAGAAAGGAGCAAAATAGAAAAAAAGTTAGGTGAAGAATTAAGTAAGTAAGATACCA
CATAGTTGCACTCATCTCACATGCCAGCAAAGCAGTGCTCAAAATTCTTCAAGCGGGGCTTCAACAGTAT
GTGAACTGAGAACTTACAGATATTCAAGCTGTATTTAGAAAAGGCAGAGGAACCAGAAATCAAATTGCCA
ACATCTGTTGCAGAGAGTTCCAGAAGAACATCTACTTCTGCTTCATTGACTATGCTAAGCCTTTGACTGT
GTGGATCACAGCAAACTGGAAAATTCTTAAAGAGATGGGAATACCAGACCACCTTGCCTGCCTCATGAGA
AATCTGTATGCAGGTCAAGAAGCAGCAGTTAGAACTGGACATGGAACAATGGACTGGTTCCAAATTGGGA
AAGGAGTACATCAACGCTGTATTTTGTCACCCTGCCTGTTTAACTTATATGCAGAGTACATCATGCAAAA
TGCCATACTGGATGAAGCACAAGCTGGAATCAAGATTGCCGGGAGAAATATCAATAACTTCAGATATGCA
GATGACACCACCCTTATGACAGAAAGCGAAGAGGAACTAAAGAGCCTCTTGATGAAGGTGAAAGAGGAGA

GTGAAAAAGCTGGCTCAAAACTTAACATTCAAAAAATTAAAATCATGCCATCTGGTCCCATCACTTCATG
GCAAATAGATGGGGAGACAATGGAAACAGTGACAGACTTTATTTTCTTGGGCTCCAAAATCACTTTAGAT
GGTAAATGCAGCCATGAAATTAAAAGATGTTTGCTCCTTGGAAGAAAAGCTGTGACAAACTTAGCATATT
AAAAAGTAGAGACATTACTTTGTCAACAAAGGTCCATCTAGTCAAGTCTGTGGTTTTTCCAGTGGTCATG
TATGGATGTGAGAGTTGGACCATGAAGAAAGCTGAGCGCCAAAGAATCAGTCCTGAATATTCATTGGAAAGACTGATA
GGAGAAGACTCTTGAGAGTTAGTCAGTCCTAAAGGAAATCAGTCCTGAATATTCATTGGAAAGACTGATA
CTGCAGCTGAAACTCCCATACTTTGTCCACCTGATGCGAAGAGCCAACTCATTAGAAAAGACCCTGATGC
TGGGAAAGATTGAAGGCAGGAGGAGAAGGGGACGACAGAGGATGAGATGATTGGATGACATGGCTGACTC
GATGGATGAGTTTGAGTAAGCTCTGGGAGTCAGTGATGCACAGGGATGCCTGCCTGCTGTAGTCCATGGC

GTCGCAAAGAGTCAGACACGACTGAGCGACTGAACTGAACTGAAGATGAAGAAAATCAACAAAATGAAAT
GGAAAAGATTAATAAAATTGATAAACATCAGTAAGACTGATCAAGTACAAAGGGAAAACACAGATGATCA
ATATCAGGAATGAAAAGAGAGATATTACTACAGATTTTATAGGCATTAAATAGACATACATTTAGTCCAA
ACATTTAACAGTTTAAAGTGAACATATTCGTTGAAAAATACCACCTACAAAACTGACATGAAAATATGCA
GAATCTTATGTCTGTGGAAGAAAATTCATGATTTAAAATCGTTACCCACCCCACCCTCCCAAAAAAAACA
CAAAACCTTAGATGGCTTTTTTGATGACTTCTCAGTCTTTCAAGGCAGAAATAATGCCAAACTTGGCTAA
CATTTGTCAAAGAATAGAACTTTTTCTACTCACTTTTCAACTCCTTTTATGAGGCCAGCATAACCTGACA
CTGAAATCCAATTTTAACATTACAGTGTTCAGCAAAAGAGGTCCGACACAAAAGAGTAAATACTGTTTGG

TTCCATTAATATGAAATTCCTTAGTGGGCTAACAGAAATCAGAGTAGGGATTACTCTTGGAGGGGTGAGA
TACTGGCTGGGTGCAGCAGAGAGGACTCTCCTGGGGTGCTGGAATGTTCTATATCTTTATCTGGATAGTG
ATTATAGGAGTACTGAATGTACTTTATGTGCACTTTAGTAGTAACATTAAAAAAAAAAGACTATAAACTT
GATACTTCATTCCCATGTAGTTTCTTTTCTGTCTAAATTGGGTTCCGTGTGCATTGCCTGCGCTCATGTC
CTGTTTGACTGCCTTGGATGAATGCCCATTCTGATGGAGTTGCCTTGCACAGCAGGCAGGCTTTTGCCTT
GGGCCTGCTCTTCTTTGAGAATAAGGAAATGACCCCGACGCAGAGGTGCCTGTGATGGAGCCTCTAGTTC
TTCCCTCACTGCTCATTTCACGCAGTGTGGTTTTCTTCACAGGCACGGTGGTTTTGGGAAGCATACTTCC
AGTCAATCAAGGCCATCGCCCTGGCCACCCTGCAGATCATCAATGATCGGATCTATCCATACGCTGCCAT
CTCCTATGAAGACTGGAACGACCCTCCTGCTGTGGTGAGTAAATGCTGGGGTGAGCCACGTCAGGTATAG
GCCAGAGGCCAGGACGATGGAACATGTACTGGATTTGTAAAGGTGATTTAAGTTTGAGCTTTCTAAGATA

TAAGAGTGTGCTAGAATATGTGGGACCCAATAGGACCAGTTTTGGTCTTCCCTGTTGGCTCAGATGGTAA
GGAATCTACCTGCAGTGCGGGAGACCTAGGTTCAATCCCTGGGTTGGGAGGATTCCCTGGAAGAGGGCAT
GGCCACCCACTCCAGTATTTTTGCCTGGAGAATCCCCATGGACAGAGGAGCCTGGCGGGCTACAGTCCAC
GGGGTAAGGAAAGAGTAGGACACGAATGAAGCGACTTAGCACACACACGCACGCAGGACCAGTTTAATTTTG
AAATGACCAAAGTAACAAATACTGAAGCAGCAGTTTGTTTTAAATGTGCTTAGGAAGGCAGTGTGTTTGT
TTATTGCAGAAATAAATTGGGAGGCCTGGGTCTTGTTGGAAATGGAAGCTTCCTGATGACTTTTGCAAT
GGTGGTGCTTTGAACTCTTGAAAAGATTCTCTAAGCAATTAGTGATGGCTTATATTTTGAGCCCTGCCTC
TTGTGCTTTATGCTAACTAAGTGCTTTGCATGGATGTCAATTAACATTCAGGCCCCTGCTAGGGACATC
ATCAGCAAAAATGATAGAGAGGCATTAGGGATTGCTCAGGGTGGCCAGACCCCTCGGTCCTTCCAGCAG
CAAGATGGGGTGGGCAGATGCTGCTCTCAGAGCTTCGTCCTTAATTGCAGGAGTCATGAGGTACCTGTGG

CCTGGGAGGGACAAGTACCTGAAGCTGTGGGGGGCACAGTCTCTGCTCTGGGGCACACCTGCTCTCTGGC
TCACAGACCCCGAGGCCTCTGCGTGAGAGAGCTAGACTCCTCTCCGCTGAATCATTGCTCTTCTCTTTGT
GGCCAGCCGTCCTTGTCTCCTGACTCTACCCGCTCTTAACAGTGCTGTATGCTGCCACCTGGTCGGTCTT
CTTTTTTCCCTCCCCATCTCCCTCCTGCCTTTCTTAAGGGCTTATTGTGTGCCAGTGCTCCACCAGGTGCT
TAGAAAGCAGAGGAAACCAGGCCCTGCCCTCAGAGGAACTCAGTGCTAACTTGGGAAGCCCGGAAGGAAG
GGTATTGTATGAGTTGCCCTGCAGTGGAGCTGAGGGTGGAATTCCCAGGGAGCCCCGGGCAAGGGCGGGC
AGTGCTCCTGAACCGGGAGTGCCCGAGAGGAAGTAAAACCGTCAAGGCAAGTGAAACAGTAGCAAACACC
TCCTTTCTGTTTTCCTTGAGGGAAGATTTCCTTCTGTCCATCTCTTCCCTTGACTTCCTTGCCAAAGGTA
ACCTTCCAGAATGTTTGTGTTCCTGTATAGACATACTGTGTAATTTTAGAATACAAATGGGGTCACACGA

TGCATATTATTCTCAACCTTGCCTTTTTACTTTAAAACTAGATCATGGGCTTACTTCCATTTCATTCTG
TATAGGGATACTTCAGTTTTAAGGACTGCTGTAATCATGTTTTGGCCTTTTGGCTAAGATCACGTTGG
ACTGCTGTATGTGATCCCATCGCTTAGGTCTATCTTACAGGCAAATCTGTTTTCAACAGTAATAGGGGGG
ATGCATATTATTGCATCCACACAGCCTTTCAGGTGTGTATGCACATAAATGTGTGAATGTATCTGTAGAA
TTAGTAATAGCAGAGAAATAACTAGAAGAATAGGCACACTTTAAGTGTTGATCAGTCAATCGTCAATCGTTC
AATTGCTCAGCCCCGTCTGACTCTTTTCAACCCCATCGACTTGAGTGTTGATAGATTTTAACAAATTGCT
CTTTCAAAAGACTACACCAGTTTATAATTCCACCAATAACATTTTGGTTATTCTGCTTCTTCATGCCTTC
AGTAACCCTGAGTACTTGAATTTTTGCTTACTTGGAAGGTTGATATCTCTCTGTTGCTCCCAGAATAC
AAATATAAATCCTATTTGAACTGTGATTGATAACCCTGACTTTTTAGATTGTTTTTGGCATGTATTCATT
CAGCGGGTATTTCCTGAGTGCCTATTTTGTTCCAGGCAGTGTTCTTGGTACTTGAGATATGTCAGTCAAC

AAAGCAGAGAAAAATCCACGCCACTGGGGAGTTTACAGTGCAGTAGGTCTTGCTATCTGGAAGCAAGGTT
TGTCTTTCTAGTAAAATTTTAAAGCTTTCTGTATACTGGTCCTTTACAAGTCTTGCAAAATTTTTCTTA
GGTGTTTTATCATTCTTACACTCCGATAAAGGAATTCATGCTTTCTGACATTTTAGTTCCTAACTGATTA
CTTTTGTATGAAGCATATTGTTGGCTTTTATGTATAAACTTGTAATACTCTGAGTTCTGTAATTGTTTG
ACTTTTTTCAAGTTGATTCTCTTGTGTCTTCTAGATGTACAGGTATCACGCAAATGCTAATTATTCTTT
TTTCCAACACTTGAACCTTTTGTTATCTTTTATCTAATTGCCTTGGCTGCTGCTTCCAGAACAATGTTAA
ATGACCATCATTTAATGTTGTTAAGTGTTAAAAGAGAAGGGCGGGTGTTGTGTGAGAAAGGGGAAGTTA
GATTTCCCCCTCCCACAGCTTACCTGGTTCTCTGGAGGACAGAGACTCAGGCAAGTGAGCGTTAGATACA
GGGAGGGGGTGGGCCAAGAATGATGAATTTTGGGGTTTCTGGTTCCATCCAGAAGGAGAAGCAAATTCAG
```

TABLE 3A-continued

SEQ ID NOs: 1-2, BOVINE EXT2 AND ALX4 GENES

GGGTCAGAGGGACAAGAGAACACGGCGGCTTCAGGAACTTTGAGGGGGTCAGTGTAGCAGGAGTGAAGGG
TTTGTGAGGGAGATGCAGAAGGTGGAGCCTTCTGAGGGCCCAGATTGCCAAACCCCTGGCATCTTAAGGG
AGGTGCTGGAATGTTTCCGGTGGGTGATGGGAGATCAGCAGGACACCTCCACAGAAGTCATGTGCTGAGA
TTGCATTTCGGGTCATTCTGACATCAGTGTGGAGGGTGCTTCTGTTGTAGGAGGACAGGGCCAAAGGCAG
GAGACTGTTTCAGGAACCAGGTGAGAATTAATGGAGGATAAATGTGAGTGATGGGCTTCCCTGGTGGCT
CAGTCGGTAAAGAATCTGCCTGCAATCCTGGAGACTGCCTGCAAGACAGGTGACCTGGGTTTGATCCCTG
GGTCAGGAAGTTCCCCTGGAGAAGGAAATGGCAACCCAGTCCAGTATTCTTGCCTGGAAAATCCCATGGA
CAGAGGAGCCTGGCAGAACAGTCCACAGGGTCGCAAAGAGTTGGACACAACTTAGCGACTAGACCACC
ACCCAAATGTGAGTGATACCAGGGACCACCTGCCGTGCTAACTGGGAAGGCGTTTAGGAAGAGTGAGGAG

GATGGTGTTGTCTATTGAGTGCGAGTACATGGGCATCGCGGGCCAGGTGGTGTTGGAGTCCAGGCATGGT
CTGGCAGCAGGGCCTTCCACCGTCCAGCGCCAGGCCTCCTTTCCAGCCTTATTTCCTTCTGTTCCCTTTT
GGGGAGCACTAGGTTTCTGGCTCCACAATGTTGTCCTTCCTGGTGTTTGCTCTCTGCTTTTCCTTCCTGTG
CCCTTGTGACCATTGCTTCTTTCCCTGGACGCCGTTCTTCACCATCACCTCTGGTCTTATGCATTTTATT
CAGGGGCCCTGGCCATGTACCCCTTTCTCCATGAGATTTTTCCTGGACCCCTTACAAAAAGTAATCTTTC
CTTCTTGTAAATCTTAAAGCGTATTATCTATTTCTTTCCTGTCATTTAACATACATAGAAGTACAATTTC
CTGTAAAATTTTAAGTTTCTTAAGGGAATTTCTGAGTTATCTTGGTATTCCTTATAATATTTAGAGCAAT
TTAATTCAGGTAGGAAGCCCTTTATACATAAAGAAGGAAGGAGGGATTGAGGAGGGTGGAATTTCCAGGA
CTTGAACCATCCAAAGCTCAGTCGCATGCTGACGTGACAGCCTTTATTTTATTTGACCTTCACCCTATTG
GGAAGGTGAGAAAAGTGAAAGATTCCCTCTCATGTCTAAAGCAGACCTAATGAGGCTCACAGAGCCTGAT

GACTCGTCCAAGGTCGCATAATGGGCAAGTTGTGTAAACAAGCAGGAACCCGGGTCTTCTACCCACAGAG
TGTCTTGACTGGCTTATGCAGTATTATGGGAGCCATTGAGCCTCCTCCAGGCTGAAACATTTCCACTCTT
CTGAGCATATGGTACAAGCTTGAGACAAAGAAGATCACATCTGTTGCTCTGCAGGAGAATTCATACAGGT
GGGATAATCATGACCCAGCTAGAGAATGTGGAGACAGTGGGCGCTTTCCTGTACTTTTATCTAAAGCTCC
AAGAAAAGTGTTTGAGGATAAATGGTTGGGATTCTGGTCTCTGTCTTTCATAAGAATACAGACTAGGAGA
AAATAGTATATGAAGTTTTATAGTTTTGAAATAGGCATATTTTAATTGAGGACAAAGCAGAATGCTGGAC
TCAATTTGGGAAAGAAGATGAGTATAAAAAGCATAGATCTGAATAAGCAACTGGAAACTATATTATTTAT
TTATTTATTTATTTTTCTTTCTTAAGGGGAATTTAGTGTTTAATTCTAGGAGCTCAGGTGATGAGAGCC
CTGATTTAAAGCTGTAGGTTGTACATTTCTGCTTCTTCAGTGAAAGCAACTGACAGAAAGCCTGAATAGC
ATTGATTTATTTATAGTTACCTCCCCCGCCCCCGCCCCTTCAGAAATACTTAACCTGTCCTAGATGTGG

TTACTATGAGCCCAGCCTGCAGGGGAGTCTCCCCTCTAGATTCCATCAAATTTACCATTTCAGGCACCCC
GAGGTGGGAGTTGGTGTGGATCTCAGTCAGTAAATCAAGGGTTGGCCTGGCTTTTTTCAAAGATCTGCAGT
CAGGGCCTCCAGCCATGGCTCTGAGCTTGCTCAGCTGGAGAGGAGGGCAGAGAGCGAGAGCCTTTTTT
GGCCAGATGCCACTGCCTGAGTTTAACGTTAAAAAAAAGAAGAGGCTTGTGTGGATGGTGAAAACAGG
GAGGGGTGGTGGCCGGCCGTGCAGAAACCCGGTGCCTGGGCCACCAGATGCTCTGCCGTCCTCATTTGTA
ACCGGAGCGGGGCTGATTGCATTATCCACCTTTTGCTACACTCTCAAGATGGTGAAAGCGTGTGAGTAGG
TCATTCTGGAGCACAACTTTAAAGTGGCACAGTGGTCCAGTCTGGAGGATGGGCCCTTTGTCTTGAATC
TTCTCTTTGGAAGGAATTTCTCACCAAATGGAAGTTTCTTTGTGAGAGATGACACATTTGTTCTTAATCA
TTAAATTTTTAGCTCCTCTTGTCAAGGATGCCTGCATTTTACGGTCTCTTGAGGTTTTCATTTCTCCCC
CCCCCCCCTTTTTTTTTTTGCAAGTCTCAGCAAAACTTTACCATCTCCCCAAACACTCCCCGCCTGTGT

CGCTTCTCAGGCGTGTGCCATTTCTGGTCTCCCCCTTGGCGGGCCTGGTGCCTGGATCTGGGCCTGGCCT
GGGTGGCTGGGGGTCTCTTCAGACAGCCTCCCCCAGCTTACCTCTGGTCGCCTGCAGGGCACGAGCTTGT
CGGGAGGACACAGACTGAGGCCCGGGAGCATTGAGAATGCGAATATGGAGCGGGCCAAGAGCCGTGAGGT
TTTGGATTCTGGCCTGTGCCAACAAAGCCATATCCTCTCGGTAAAATCACGTAGAGTGGAGTATTTTCC
CATATTATTTTGTACAGCGTGATTAGAAGGATTATCTCCACCTTATCGTGTGCTAACGTGATTGAGTAG
TGGTGGTAGTGTCAGTCGCTCAGTCGTGTCCGTCTCTGTGGACTGCAGCCCGCCAGGCTCTTCCATCCGT
GGAATTCTCCAGGAAAGAATACTGGAGTGGGTTGCCATGCCCTTCTCCAGGGGATCTTCTCAACCCGGGG
ATCAAACCCAGGTCTCCTGCATTTAAGGTGGAGTCTTTACCATTTGAGCTACCCAAGAAGTAAACTTTAT
TTACCTAGTTCCTTCTGGCAGTGTTTTTCAGATTTTGTTGTCATAGATAACCTAGTATAGATAACCCAGG
TTTTTTTTTTTTTTAACACTGACTATACTGGACCTAGAACAACAGAAAAGGGAGACAGCAGGGGTCCCAT

AGCTATTGACAAAAAACCTGACAAACTGACGAGGAAAGTGGGGAAGTGACTTAAAACGGATTGTTGCGCC
CAGCATAAGAATAAGGCTGACAGCAAAAACTTGTTCCTATGAAATCTAGCCCTTGTGGCAGCTTCGCTGC
AAGCCAGGCCTCAGGTGCGGGTTATATGCACTCACCTAGGCATCCTGTGGAGAAGGCAATGGCACCCCGC
TCCAGTACTCTTGCCTGGAATATCCCACAGATGGAGGAGCCTGGTGGGCTACAGTCCATGGGGTTGCTAA
GAGTTGGACACGACTGAGCAACTTCACTTTCACTTTTCACTTTCATGCATTGGAGAAGGAAATGGCAACC
TGCTCCAGTGTTCTTGCCTGGAGAATCCCAGGGACGGGGAAGCCTTGTGCGCTCCCGTCTCAGGGTCGC
ATAGAGTCGGACACGACTGAAGCCACTTAGCAGCAGCAGCAGCAGGCATCCTGTAAGCCTGAGTCCAGCT
TTTGAAGATAGAGGGGGAAGGCTCAGCAGGTGGGAGGCCTGTAAGAGCACTTGCTTGCATGGCAGTCC
TCACCCACGAGGGGCAGGGTCAGAGCTGTGGACTCGGTCGCAGCAGAGCCTGCTGCTGTCCCTAGTTCTTG
GGGAAGCGGTTCTCCAATGTCAGGAGGTTCTCCAATGTCAGGACGTGTCAGAAGCTCCTGAAAGGCTCGT

GAAAATGCAGATTGCTGCCACTCCACCCCTAGTCTCAGATGGTGTTGGTCTGGGTGAGGTCCTCGGATTT
GCATTTCTAGCAAGTTCCCAAGTAGTGTCGATGCAGCTAGTCCAGGGGCTGTGCTTTGATGTGGGATTGG
TTCACTGTGTGTCCTGACTCACTGCCTGGAGAAGGCACTCCCTCTCCCCCATCCAGTGCCTCTTCTG
CATCCCTGGAACTTGATTAGAAGCTTCCAGAGCCTGGGCTAAGCCCACATCTGTCTCAGCTACAAGAAGA
ACTCAGGGCTACCGGTACTTAGATGTCCAGACGGCAGCCCTCCTCATTCACAGAGGTTGTGGTTGTATAA
GCTGCTGAAAATATCACTCAGCTGTAAATACTAACAAGCTATAAATCACTCTGCAGGCCGAAGGAGCGCC
AGCTCAGATGCCTGGAGCAGAACCCCGAGTCTGTTTAACTCCACTCCCTGCCCTTTAACATCCAGGTTGT
GGAATGTGTCTCTGGAATTTGAACACCTCCCCTGCTCACCCCCTCCCCCAGGAGGCCTTTTTGGCTTATT
TTCTCCCCTTTTTCCTCCCACTGCCCAGATATGGCTGAAGTATGTATGGAATTCAGAAATTTTAGCTTGA
ATTTTAAGTAAGTTTAAGCGTTTTGGAGTCTTTTGTTTTTTAGAGGTGCCACATTTACAGGGTCACAGTTG

CACAGAAGGTCCGCCTTCCTGCCCCCAATGCCAGGCCTTTCCTTGAGTTGCCTTCGCCATTGAACTGTTT
CGTAGCTGTACTTGCTTCTGTGGAAACAAGCCGGACAGTCTCAGGTCATGGAGTAAAGAAAGCCGAGTTG
GGTCTGTGGAGCGAGAGACGCAGGAAGATCCCAGGAGCTTGACCCGGGGCCCCATGCCAAGAATTCTGAT
GGTCAGATAGTAACGTGGGAAAGATGAGGTCGCAGGTCAGATCCAGGTGGGGAGGATAAGTAAAGCACAG
GAAGGGCCACAGACTCGGGGGTGCTGCGGAGGGGGTCCTGTCAATCAGAGCATCCTTCCTGGAGAGGGAGA
TCGTGTACCCGGGTTGCCATGTGTGCATGGCGACTCCAGTGGTGGCGGAGGTCGAGCCGCACGTGCAGTT
TCTCTGGATGCAGACCTTCCTCACCCACCCGGGCTTTTGTAGAGTTCACTTTTATGACTCTGGCATTTAT
GAGTCAACCCCTGTCTGCTTCCTTACGTCCCAGAGAGGAGGGCAGCGAGTGGAGTAGGTCCTCGGGGTCC
ATGGAGCTTGGTCTGGCAGCAGATGAATTGAGGACACCTTGGGTATTTTGGCAAAGCCATCCTTCACACA

TABLE 3A-continued

SEQ ID NOs: 1-2, BOVINE EXT2 AND ALX4 GENES

CCAGCTGTCACTCACCGGCACATCCAATTCCCTTTCCCCTTGCTTCAGGGCCCACTTTCTTTCTCCCTCG
AGTCAGTTTAAGAGGTTCAGTAGCAGAGGTTACTGGGAAAATGAGTTGTCGGGTATCCCAACATCAGGGG
TAATGAATTCTATTTCTCGTATCCTATACTGTTTACATAGACATATCATTAATATTTGAGTGTAATTTT
TCTAATGAGAGGGTCATTACAGCTGCAGAGTAGAAAAATTTCCACATTGCTCCAGCTGGAGTTTGAGTCT
TGATTTTTGGTTCTGTCTTATCTTTCAGCTATATTTCTTAATTTCATGTTTAAGAAAAAAATAGAATGGC
TTAACACATGAATGGTTTAAAAAGTAAAATCATAAAATAACGCCTGTAAATTAAGGCCCATTCCCGAGGG
GCAGCTGCTCTCAGCTCTCCTCTGATATTTATTTTCCTACCTTCTCATAAAATGCTGATAGTGCTGTTTT
TTTTTAATTTCTCTATCTCAGACATTCTCTCTTTACTTCCATAGAGTTAGTGCTTTGTTTCCTGTTCCTG

CCTCTTCCTCTGCACGTTTCTCTTCCCTCTCATCTTACCAGTGGGGCAGTGTCATCATTTTTCATTAGAG
CAATGTTTATTGTTGCGTCATTAGGACTATATAAATGTTGGTGTCAGTGGGACCAAGTAATAAAACATGG
TTATGTTTCCTTTCTTGCATAACTTTTTTTATTTTCCAGGGAGTAAATGCATAGCTGTCTTAAAAACAAA
ACAAAACAAAAACACTCTCTTAGCTTTCCATGTTCCTATCACTGCTTTTTACTAACTTCTCCAACGAAGA
GTGAAATGGTCAAGCGCAAGTGAACTATGGGCTGTCCCCCGCCTTCGCTCTCTTTCCCTCCCTCCCACCC
TTCTCGTACATAGCCCGCACCTGCAGCTCCAGTGTGGATTGACTGCTCTCTAGGTCTCCTGTACAGAGGT
CAGCCTCAATTCTCTGTTCACCATGATTCTTGCAATTCTCTTCTTTTCTCTTCTTTGTTGGATTTTTGTT
TTCAAGTTCTAACATCCTCTTTCTTTTTGGGTTTTTTTTTTTTTTAATCACAGTAGCTTCCCCAGAAAAG
GGACTGTTGGGGGGTAAATTTGCTGTCACCTTGTGTCTCTGAAAATGCATCTATTCTCTTTCACCTTGAT

GAATAGCTGTGTGCAGTGCTGTGCTTGGGCTGGTATAAAATTCTGGTCCACGTGGCTTTTCTTCAAAATT
TCAAAGGCATTGCTTCATTGTCTGCTGATCTTCCTGTTTTAATCTCAAGAGATGTCATTCTAATTCCTGA
TCCTTTTGTGTGAAACTTTTAATCTTCCTGAAAAATCCTGTGTTCTGAAACTAATGATGATACACCCTGG
TATGAGTGTTTTTTTTGTTCACTGGATACTGATTTGGGCCCTTTATAAGGGAATTTTCACATTTTCTATCT
CCCCCGCCCCGCCTCGTTTGCTCTCTTTTTCGCTTGGTGGAACTTGGGTTACCTTGATGATGAATGTGCT
AGACTGACCCTTATTTTTCTTATCTTTTCTTTCTGTCTTAATGGACTCTTTGTTTTAATTTCTTAGATAT
TTTCTCAATTTTATCTTCTAATTTTTCATTTTAAAATTTTTGTTCACTTTTAATTTCTAAGAGTTTTTTC
TTGTCTTCTACCTAATCTTTTTTATAGCTTCCTATTCTTGTTTTAAGGATACAGTACTTTCTCTCTCTGA
AGATATTTGTGGTTTTGTTTTTATTTTTTATTGTTTTTATATAAATTTATTTTAATTGGAGGCTAATTAC

TTTACAATATTGTATTGGTTTTGCCATACAGAAACATGAATCCGCCACGGGTGTACATGTGTTCCCCATC
CTGAACCCCCCTCCCACCTCCCTCCCTGTACCATCCCTCTGGGTCATCCCAGTGCACCAGCCCCAAGCAT
CCTGTATCCTGCATCAAACCTGGACTGGTGATTCGTTTCATATATGATATTATACATGTTTCAATGCCAT
TCTCCCAAATCATCCCACCCTCGCCCTCTCCCACAGAGTCCAAAAGACTGTTCTATACATCTGTGTCTCT
TTTGCTGTCTCGCATACAGGGTTATCGTTACCCTCTTTCTAAATTCCATATATATGCATTAGTATACTGT
ATTGGTGTTTTCTTTCTGTTTTTATTTGTCTTAAGCTCCGTGTATTGTTTGTTTCCTTTGAATTCCATC
ATCAGGGCTTTATTTTCTGTCTTTCACATTGGAAACTTTCTTCAAATACCTGATGTTTTTCAGCAGTCTA
TTCTTATTTGGGTGAGGCACTGAAAACTGATGGGAAGCCCTGTGTGCATGGTTTGGCTTGTCAACTTTTG
GGCTTTACTGAGGTTTATGGATGGGGACTCAACTGTTTACCCCGTTGTTGGTACTCTTCAGTTCAGTTCA

GTCGCTCAGTCGTGTCCGATTCTTTGCGACCCCATGAACTGCAGCACGCCAGGCCTCCCTGTTCATCACC
ATCTCCCGGAGTTCACTCAAACTCACGTCCATCGAGTCAGTGATGCCATCCAGCCATCTCATCCTCTGTC
GTCCCCTTCTCCTCCTGCCCCAATCACTCCCAGCATCAGAGTCTTTTCCAATGAGTCAACTCTTCGCAT
GAGGTGGCCAAAAGTACTTTTAGGTTATTTCTGTTGGATTGGTTCACTGACCCAAAGGATAATCTTTCTG
CCCTTGGGAGTAGGGCGAGGATGGATAGTAAGTCTGGGCTGCAAGTCTTTGGGGAGGAGAACGGGGGAAG
GAGACTGGTTCTTATCCTTCATACAGTAGATGATCACTGAATCTGCCGTATTTGGTGTGGCGCCTCATCC
TGCTGGCCGTCCGTTGTGTCTCTGGAGTGTGGGGTCTCTCTAGTTCATTTTCTCCAGAGAATAAACCTCC
TGCTAAGATGCAGTGGGTGGAGAGGACAGGGAGGGCATTGACCTGCCTGCTGCACGTAGGTTTAAGGGATC
TCAGAACCAACTTTTCTTATTCCTGTTTTCAGAGTCCGTCCTCCCTAGACACCTAGGCCTTCCCATTTCT

CAGTCTGCTAACCATCATCCTTGGAAGGATTAGCTTCCCATGCTTTGCTAGGCAGTTTATGTTCCTTTAT
CTGCCTTTTGTTTGTTTGCTTAAACAGACCTACAATTCTGTATATTTTTTAATTTTCTATTTTGACATAA
TTTTAGACTTAAATTTCCAAAACCAGTGCATCGTTTCTGCACACCCTTCACTCATAGTCATCAAACACTA
ATATTTTGCCACCTTTCTTTTATTCTTTTCTGTGTGTGTAAGCACACACAAACATATACATTCATATT
TATGTATTTTTTCCTGAACCATTTGCAAGTTACAGATATGAGGCACCTTTACTCCTGAGATCTTTCTCAG
AAAATCACCCAAATGATCGCTAGTGGTAAAGAACCCACTTGCCAGTTTAGGAGACATAAGGGATGCAGGT
TCAATCTCTAGGTCGGGAAGATGCCCTGGAGGAGGGCATGGCAACCCATTCCAGTATTCTTGCCTGGAGG
ATCCCCATGGACAGAGGAGTCTGGCCGGCTACAGTCCATGGGGTCACAAAGAGCTGGACACCGCTGAAGC
CGCTGAGCGCACACATACAGACCTTATTTAGATTTTGTCAGTTATCTTCATTATGTCCATTACAGCAGAA
GATTGCAGGCAGTCATTGTGTTCAGTTGTCATGTCTCTGTAGCTTCTACTAGAACAGTTTCTCGGGTCCT

TCTTTGTCTGGCATGACAGTGGCCTTTTTGAAGAGAACATGTCAGTTATTTTGGAAGGTATCCTTTGATT
TGGATTTGTCTGGTGCTTTTGTGTTAAATTATGCATTCCATTTCAAATTATTGAAATTCAGGTTAAGTAT
TTTTGGCAGGAATGTCACAAAAGTAATGTTGGTTCTTGGTGTATCACGCTGGAGGACACGTGATGTTGGT
CTGTCCCATTGGTCGTGACGATAACTTCACTCAGAGCTTTCTCCAGTGGGAGGTTACTTCCTTCTTTTAG
TGTGTCTTGTTCGGACGTACTTTGAGACTGTGTAAATATCCTGTTACTCCTCAAACCTTTACTAGGGTTA
GCATCCACCAATGATTTCTTGTCTGAATCAATTGTTATAATGGTTGCCAAATGGTAATTTTAATTCCCAT
GCTCTATCTGCTTTTGAGAGTGATTTTTATTCTTTAACCTGAGGGTTCATGTCTTTTAATCAGTGTTGGA
ATATTCTGCGTCATTTTCTTGTTGAATATTATGTATCTGTCATTCTCACTGATCTTGGAATCCTATTAAA
TGCATGTTAGACCTCTTTAATTCTGTTGTTGTGTCTCTCAAGTTTGTTTTTTTTTCCCCTTATGTTTT
ACACATTTTTAACTCTTTGTGCTGCATGTTGGAAAATTTTTTCTCATCTATTTTGCTCTTTCCTTTGGCC

ATGTCCAATGTGTTTTTACCCATCCAGTGGGATTAAAATTTCAGTAGTTATTTCTAGAAGCTCTGACTAT
TTTTCAAATCTGTCTGCCTGATCTTTTTTCATAGTATCTTTTTTTCCCTATGTATTTTCACTTCCCTCTT
TTGTGTGTTAATTATTTGAGATACTCACTTTATATTTCTCCAGTAATTTCACTAAATTTCTCATAGCT
TCTAACCCTGTCGTTTGCCTCCTGCCTGTTGCTCTTGTTGCATTATTTCCTTATATGTTTTGCAATCTTG
GAATGTGAGTTTCATCTCTGGTGAGGTTTTCTGTGGAAATCTTCGCCACCTGAGTGTAAGAAGGTATTTC
TCCAGAGAGTTTGTTCTTGTTTTGTGGCTTCTGCCAGATGTTCCAGGAGGTATTGCAGAGATAAATCACT
TTTTAACATTAGTTTCTCGGTCAGAGTTTCCATACTGCACAGGGAGGGTCCATTTAAACCCCACACCAG
TGCGAGGGCTAGCCTCTGTTGAAGCATCCCCCGTCCAAACTCAGGTTGAAAAGGACAGATGATTTTCTG
TATGTCCATGTTCTAGGAGTGACTTTCGGGACCACCTTTTTACTGATTGTACAGGCCTTCAAGGGGTTCAG
GCTTGGTATGTAAGTCCCACCGCCTGCCCCCTCTGCCCCCGTGCCCAAAGCTGTGCTCCTCGTCCAAAGT
GGGTGTGAGTGTCCACGCCCTGCGCCGCTGGGCCCAGTGACAGCCTCCCCGCGGCGCCTTCAGTTCTTTG

TABLE 3A-continued

SEQ ID NOs: 1-2, BOVINE EXT2 AND ALX4 GENES

```
CAGTTTGCTCATCGATTTGGGTTCCTGGCAACTTTCCATTTCCTGAATATTTTTTTTAATTTTGTTATA
TTTTATCCTACGTTTCTGTCTGTTGTCCAGCAAGAGACGCTGTCTTTTTCGCCTCCCCAGATACGTTGAG
CTCCTGTCCACTGTTGTTTCCTTGCCTGTTCTTTGTGCCCTGTGGGTTTATGCTCCCCCTCTTCTCCCCC
CAGGAGGAAGCAGGGCTAAAACACAGTAGACAAAACATACACCTTATTGGAATTCCGGAGAAGTTAAGAA
ATGATTGCATTTTAGAGGTTGTTCTTTCCACTTTGTATTGACCTTAATACTCCTGTCAGCTCAAAACTGT
ACAAAAGCTTTGATTTTCTTGGTCATAACTGTGTAGGTATTTTGAGCTTGGAGGCCACAAGCTATAACTT
AATCTTTCCCAAGAGTGTCTGTTTACCAAGCTAGTGATGTCTTCCTTCATACCATAGCTGACCTCTGAAA
TATAGTCAGCGGGCCGCCAGCAAACATTTTTATGCCCAGGCCAAAGAAGGAGCCTGTCTTTCGAACTGAG
TATTTCAGGTGTGGGATAGCCAGATGAAACTATAAATTTGTTTCACCTCTCATGAGAAGTAGTGCTTTGA

GCCACCATTAGCATTCTTGAACACTTTGGATTATAGATCAGCCTGTTTGCTTGAATCAGAGAAATTACTA
GCTTTTTCACTGAAGTTTTTTTTTGTTGTTTTTTTTTTAAAGTGTTTTCAGTATACTTTTTAAGTAACA
GATCCAGGGATGAGGATGGTGAATTTGAAGACTGTGTCTTAAGAATAATCCACATTTTTTACTATCAAAC
GACTGAACTGTTATTTTTAACATACAAAGTTAAGAACCAGTAAAATCAACAACATGTTGTATGTGCTCCT
ACTTTATTGTATTCACCCATTTAATTGATTAGACAGTATCTTAAACCATTTTACCACAGATGTATTTAGT
GAAATTTATTACTTGCAGACTGATATAACTCATGAATTATTAAAAGCATCAGCATATGGAACCTTCTCTT
TCTCATCTAGATTCTTTGAATACGGCTTAGGTTGAGCCATTTAACTGGCTTCTGTCCATCCCACTGATGG
AAGCCACAGTCAGATGAGGGTTCTTATAAATGATTGGCTTCCTTTCCGACAAGAAGAGGATAAAATGTC
AGCTTTTTCCTCTACTACCTGAAAAGCAATCAGGAGCAGCCCTCCCACTCTTCTTGACAGTAGTTTGGCT

TTATAGAAGAAGGGCAGGCATTGAGCCAAATGTGAATGTCAGTGCTATATAAAGAAAAAAGTTAAGTAGC
TAAAACTCCGATAGTAACTGGAATTTTTAGAGCAGTATTCAGATGGGTTTACCCTGTAAGCTTTCAGAAA
GCTAACAATAACTCAGCCTGAACTGCAAGGTTTAATCCCTTCTTTCCTGGTGATGATCCCAGTAAATTGA
AGTTACTTACCGAATGTCTCTTCACAGCGATTTGCTCATGTGTAGGACTGGGTTTAGGGGGTAATAATAG
TTTCAGAAGAATAGGGTAGTGGTTAGTGACTGATTACCAATTACTAATCAAAGCCATTGAAAAGGACATT
TTGGAATCAACCGGAGTTCCAGACCATTTAGGAGCCTGACATTGTGCTTTCTTATCTCTTTAAAATTTGT
TATCCTTACCTGTAAAATGAACTATTACTTATTTCATAGGATTATTATGAGACAGTAGTGAAGTAATGTA
TGTAGGAGCATTTTGTAAGTGGTATTGATAAGGCTGCTAGTGTAACGTTCTATCACATGGAAACATACAC
TCTAGAATTGGGTGGGACTCTGGAGAACAAAACTGAAATTTACAGAGGGCACAGTTTTATACCCAGATAG

GCTCTGTTGTGTATTTTCTGTTGTTGAATCCTTGCATCCCCAAAGTAGCATTCTGCTAGCTCCATTCCTA
CAGATGAAGAAGGGGAGTCTTGTTTATTTTTAAGATCTGCGTCTCCATCATCCCATTTCATACATGAGGA
AATGGAGGTCTGCAGAAGTGTGGTGACTTGTCTGACGCAGAGATTCTCAGTCCATCATTCCATCTGTTAT
AATAGGTTATGATGTTGTCGCAGTAATTGTTTTTGTATTGCACACAGACTTGGCCCTGAAATTAATCAGG
AAATACAATAGCACCTAATTCAATTATTAGCGTAAATATAGAAAAGACTTGTGTCACTGGCTTCTTGGTGG
ATTAGGTATGCTAAATGACCTTCCCAACTGAACAACAAAAATATTGAATGAAGTATGATAAAGCCTGTTG
CTAAGTTGAGTGAAAAGTAAGATACTTGTTGACCCTAAACAAAGTGAAGCCAGGTGTCCTGGGAGGTGCT
TTCACTGCAGACATTTGCAGAGTTCGGTGGCGTAGAGCCTCAGCCTGGTTGACTGTCTGAAGCAGGGAGC
AGGGGAGCGGGAGAGAAAGTGTGTGGCCTGAGCAAGTTGGAGAATCTATCGGGAGCTTCCTGGGTGAAGC

CAGGGAGCTAAAAGAGCCTCTTGAGTGAAGGGGTGAAGAAGCGCAAGTCTGTATTGACCCTGCTGTTGAG
CACTGCATTCATAAGCCAGCTTCCACATGGTTTGTGGTCCATGTTCGTACTACAGGTATAGTCCAAACAAA
CCGTAAGAGGAGAATTTCCTCGGAGGTGGCCATGAGTTGGTAGGGGCCAGCAGAAGTGGACACGGACCCT
CTCTGTAGGGGTTCGTTTTCAGTCCAGCTCTCAAATGATGAACGTGTCTGTGGAAAATGAGCAGCTCACT
GTAAAAAACAAAACAAAAACCCCACGATCAGAAATAAGGCAAACCCTATCAAGAAATAAGGCAGTATCAC
GAGCGAGAACCAGCAGAAACACAGCTGCAAGGCTTGGGCAAGCTCCAGAAGATAGTGGAGGACAGCGAGG
CCTGGCATGCTGCAGTCCGTGGGGTTGCAAAGAGTTAGACGTGACATAGAGACTGAATGACACTTTAGAT
GATTAAATTCAAAGAAATGGTTTGGAATGCAGCCCAAAGAGACAGAAAATATTAACGAATTGAAGTTACG
TGGAGAGCAGAGGGACAAGGTCCAACATATGTCTAGTCAGAGTTCCAGGACGAAGAGAGACAATGGAGAA

GAGGCCCATTTTTGAAAGAATAATAGCTGACAGTTTTCCAGAGCTGTTGAATGATAGTAGATCTCAGAGC
TAGGAAGACCAGCAAACCGCAAGCAGGACAGTCGTAGTGAAACTGCAGTGCACGGAAGAAAAAGGAGCTT
TTAAACACATCTAGATGTTCAAGCTCGTTTTAGAAAAGGCAGAGGAACCAGAGATCAAATTGCCAACATC
CGCTGGGTCATGGAAAAGCAAGCGAGTTCCAGAAAAACATCTATTTCTGCTTTATTGACTATGCCAAAG
CCTTTGACTGTGTGGATCACAATAAACTGTGGAAAATTCTTCAAGAGATGGAAATACCAGACCACCTGAC
CTGCCTCTTAAGAAACCTGTATGCAGGTCAGGAAGCAACATTAGAATTGGACATGGAACAACAGACTGGT
TCCAAATAGGAAAGGAATACATCAAAGATGTATATTGTCACCCTGCTTATTTAACTTATATGCATAGTA
CATCATGAGAAATGCTGGGCTGGAAGAAGCCCAAGCTGGAATCAAGATTGCCGGGAGAAATATCAATAAC
CTCAGATATGCAGATGATACCACCCTTATGGCGGAAAGTGAAGAGGAACTAAAGCGCCTTTTGATGAAAG
TGAAAGAGGAAAGTGAAAAAGTTGGCTTGAAGCTCAACATTCAGAAAACTAAGATCATAGCATCTGGTCC

CATCACTTCATGGCAAATAGATGGAGAAACAGTGGAAACAGTGTCAGACTTTATTTTTTTTGGTTCCAGA
ATCACTGCAGATGGTGATTGCAGCCATGAAATTAAAAGACGGTTACTCCTTGGAAGGAAAGTTATGACCA
ACCTAGATAGCATATTCAAAGTAGAGACATTACTTTGTCAACAAAGGTCCATCTAGTCAAGGCTATGGT
TTTTCCGGTGGTCATGTATGGATGTCAGAGTTGGACTGTGAAGAAAGCTGAGTGCCGAAAAATTGATGCT
TTTGAACTGTGGTGTTGGAGAAGACTCTGGAGTCCCTTGGACTGAAAGGAGATCCAACCAGTCCATCCTA
AAGGAGATCAGTCCTGGGTGTTCATTGGAAGGACTGATTTTGAAGCTGAAACTCCAATACTTTGGCCACC
TGATGCAAAGAGCTGACTTATTTGAAAAGACCCTGATGCTGGGAAAGATTGAAGGCTGGAGGAGAAGGGG
ATGACAGAGGATGAGATGGTTGGATGGCATCACCAACTCGATGACATGGGTTTGGGTGGACTCCAGGAG
TTGGTGATGGACAGGGAGGCCTGGTGTGCTACAGTTCATGGGGTTGCAGAGTTGGACACAACTGAGCGGC
TGAACTGAACTGAAACACATCTAGAGGAAAAAGAGGCTAACAGTGAAAAGGTCTGGCTTGCTCCTGTGAC
CCTCAGTTAGTCTCAGTGGCTCAGTTTCTTTGGATATTAAAGAGTCACAGTACCAGTTTACTCCAGTCCA
CCCAGATGTGGTTAGACCCCTTCCAAGACCAACATACAGAAAACTGATTTGTGAGGACATTACTGTAAGT

AAATTGTAGGAATTCTAAGTTGATAATTTAACTATCTTAGTTTTGTCTACAGCACTGAAAGGGATTCTG
GCCTTCGATTTTCATCTCTCATGTGTCTGTTTAATGTCAAGTCAGGGAGATTTAGCCATCAGCATTCTCC
TTATTTTTCAGAGCGGTCAGGTATTTTTTAATGGGTGGGATGAGGCAAAGACGCAGTGTAACAAATAGAC
TTCAGGCTTGTCCCTGAATCTTTTCCCTCTCAATGTTAAGAGAGCCCGCTGGCACACATTCTTTAGGTCT
CTCATCCTCCAGCTTCCCAAGTCAGCGCACACCCAGGGCAGTGCTGTGCTGCAGAGAGAAGCTGCAGAGG
GTTAATGATTAAGGCAACGTGGGCCGCGTTACTGATTGCCCCTTTCAGATCTTCCAGCACCCATTAACAT
AAATATCATCTCACCATTTGGACAGGGGACACCACCCTTATGCACGTTAGTAATGCGATGCTAATGCTT
AACCCTTTCATTGCCCTCTCTGCTTCAAAGGCCTTGCCCTATGTCCATTGATAGGGAGGCTGTTTGAACC
TCAAGGCAAAAATGAAAGGGTTAACTCCTTTTGGTTTTGCCCTTTGACCACTTCAGGATGAGAGGCATGA
```

TABLE 3A-continued

SEQ ID NOs: 1-2, BOVINE EXT2 AND ALX4 GENES

```
TGAAATACTTTTCAAAGTCTTCAGTGGAAACACATCATGCATAATTGGAGCAAAAAGAATAAATCAAAG
CTTCCCCCCCCCCCTTTTAGTCTGGTAATTCATAATTGAAACCACATTGAGGTAAGGGTTGATAACTTCA
AAACAACCATGAAAACTGCCCTTTCGATCAAGGTAGGGATAGGTAAGGCTGCTCATAACCAGGGGCTTGA
AAGCTTCTGTATAACAAGCCTGTCCTCTCCTTTTCCTTTCTCCTCTGACTTCTCACTTTTCTGTTCTGGC
AAAATACCTTCATTTAAATCAAATGTGGGTTGACTCAAATATCTGCTTAATTCTCTTCTTGTCACAGGAC
GTTATACATAGTGACATAAAAAAAAAAAAACCTCTGCTATAATAGGTGTTAAATTTTGGATCATCCTGCT
TTGAATGTGATTCCTTCTGTGTGGGTTTTGCCTAGTGTAGGTTGAGAGAGTCCTTTCGTTGATATTAGAA
TGTGTATTTTATAATCCTCCTGTAGTTCCAGCAAGACCCTTTCAGAATGGCTCTAGCAGTTTGCCCACCA
GCTTCCTCCACTTTCTGTAGGTAGGTAACTTTGGCCAGGATGGTTTTGGTTAAGGCTCGCGTAGGACTCC
CATGACCTTTCAACCAAGGAAGTAAAACAGGATTGCAGGAAGGGCCCAGACAACTTCCCTGTGTGTGAGC

CTGCCCAAGGCACACCAGTTAGTTGAGTTGGAATCCCCTGCTTGAAGGAGAAGACCCCTTTGAACTGGTG
GTGGGCTTTAAGCCTGATCTCCCAAGGCTTCTCTTTCAAGAGATCCTGCCACCCGAACCCACAAGTCCGT
CTCGCTGGCTGGTCTGTTCGCTGTTAATTCATTCACCAGGGCGCTCCAGGATAAGAGATGCGGTAGAACT
TCTCGAAAGTGGGCGTGGTGATGTGACAGTTGTCATGGCTGTCGTGGATTAAGTTAACAGTCTGAGTTTC
TCAGCTTCCTGAAGAATGTTTGTTCTGAGTGAGGAGTGCAGTGGGGGAGGGTGAGTGGTGGAGGAAGG
AGGTATTTGGCCTCAACGCGCCGTGCACACACTCCTCCTCTGGTATCACCTCCCATCTTGGAGTGAAGAG
TTTCACCGAGCATACCGGAAAGTTCCTTGAGAGCCAGGGTTCCGGGCTGCAGCTGCGGTAGCAGGGCTCA
GCCTTCTCCTCTGGCCCCTCTTTTGCTGGGTGCCTGGTTTCGTGCCCCATCGTGCCATGATTGAGATTTA
ATCAGGCCGCCGAGTTAATTGCCAGTGCTGTTTGCCTTTTCCCTGGCAGAAGTCAGAGTCTTGAGTAAAT

TATGGAGGTTTAAATTTGCTTGATTTCCTGCAGAAAGTGGGGTCAGGAGGTCCCAGACTGTAGACACTCT
CTTTGGTCAGCCAGCAGGGGTCAGTCCTTAACGGTATTTCAGAGGTGACTAAACGCTGTTTTTGAAATG
TCCTTCTCCAGTAAGTTTTTTTTTCCTCTGGGGGTTGGTCTGTTGACCTTACCCTGGCGGAGTGGAGTGT
CTGTATGAAGGCACACACCCCGTTAAAGCTGCCTTTCTCCTCCCCATCACCGGGCTCCAAAGGCAAATGG
AATCATGTTTGCGGACGGAGAGGCACCCAGCACAGAAGCCCAGCTGCAGATCAGCATTTCCTGTTTCTGA
CCTTTTGAGACACAATGTGAAGGTAGCCGTGTTAATTTATCAGTAAAACAATACTCTGGACAAGAAAGCT
TCAAAACAAATCAACAGAAAACCAATCATGAGACTTAAAAAGAAACTTCTGTCGAATGGGCTTTTCATGA
TGTGGCTTTAGTCTTGAGTCTGAGGTCCGTTGTCTGTGCTCCCCTCCCTCCCTCCTCCCGACCTTGGCCC
TGGCAGAGTCTGCCCCTAGCCAGCGAGGAAGCAGGTCTCAGCACTTGCCCACTCAGCTTGCCCTGCGGCTG

TTTGATTAGCTCCGTCCCCTCCTCACCTCCTCCAGGAAGATGGAGGTGATTCTGTGGATCTTCTGGGCCC
ACGGGACTTGAGGACCTTGTTGTTTGCGTTATAATTTGTCTTTTTACCTAGCTGTCTTCCCTACCAGATT
CTGAACTGTTTGAGGAGAAGGAATTTGTCTTTGCGTCTTTAACCCTATTCTTGGCTTATAGTTTATGCTC
AGGAAATGTTGACTGAATGAATGAGCACCAAAAATCATACTGATGGAAAGATTGCTGAGCTGCTAATACT
GTTGTTTTGGCAGATGAGAATATGAATTGGAGCGAGCTAGTTTTTTTGTGTTTACTTACAACTACCATTCC
TAGTTTCCCTGATAGCTCAGTTCATTCAGGGCTTCTTGGATAGCTCAGTTGGTAGAATCCGCCTGCAATG
CAGGAGACCTTGGTTCAATTCCTGGGTCAGGAAGATTCCCTGGAGAAGGGACAGGCTGCCCACTCCAGTA
TTCTTGGGCTTCCCTTGTGGCTCAGCTGGTAAAGAATCTGCCCGCAATGCGGGAGACCTGAGTTCGATCC
CTGGGTTGGGAAGATCCCCTGGAGCATGGAAAGGCTACCCACTCCAGTGTTCTGGCCTGGAGAGTTCCGT

GGACTGTATAGTCCACAGGGTCGCAGAGTCAGACACGACTGAGCGCCTTTGACTGTCACTTCACTTTCTG
CATCCCTGGAGCTCTGTGTTGAGCCCTGGGCTGAGGGCGCACGTGCATCATCTGGAGGGAGGTGCTGTCA
GGCTCTCCATTTTACAGGTGAGGAAGCTGAGAGTCACAGAGGAGGTTTTCCACACCACAGTAAATGTCAG
CATCCAGGGTCACACTGTTTATTAAATATCCTAATACACTTCTTCAGAATACTTAGCACGATAAGATTGT
GGATGCGTATTTTAAAATGAATGAACTAAGTTGGAAACCATTTCAGAGCTTTGATGTCACTCATTTGAAT
GTACATTAGCTGTTCACACCCATGCACAGAGAACAGAAAGAACACAATTTAGGCTTCATCATTTTTAACA
AGTTTTTGTTGAGTCGCACCAAGCACTGTGCTAGGCGCTGAGTGTTAATAGCGGTTATGACTCTGGTTTT
CATGACGCTTTCAGGATAGCTAAAATATAATGAATAGGACAGAAAAGAGAAAAACTTTGAAAATAAAAAG
TGTATTTGGAGAGGAAGAAGAATCCAGGAGAATCCAGGTAAACCAGGACCCCAGAGCATGGTGAGGTGAA
GGTAGAGAGGAAGAAGGGATTCATTTAAGATCCTAGTGGCTGGAAGATAGCTCATGATCACTTAGCCACC

TCCCACCTGCTTTTGAGACCTGCGGAAAGTGAATCCCAGGGAAATTGCTGTTCCCATAAGACCATCTGTT
GGCTTCCTTTATCGAGTGTTGCTATGTGTCAGGCACTTTACATTTATTAGCTTGTTACTGTTATTAACAG
CATCTAGATTGTTAAGAAATAATAAGTAAGACATGTTAATAATTTAGTTATTGTGTTAAGTAACACTACC
TAGAAAAGAGCCTCCCTCATAGCTCAGTGGTAAAGAATCTGCCTGCAGGGCAGAAGACCCGGGTTCGATT
CCTGGGTCGGGAATAGCCCCTAGAGAAGGGAATGGCTACCCACTCCAGTATTCGTGCCTGGGAAATCCCA
TGGACAGAGGGAGCCTGGTGCCCATGGTGTCACAAAGAGTATGACACAACTGAGCGACTAGCACTTGTACT
TGTGCCTAGATAAGTTGTAGTTTTAACGTGATCTTATAGATTCAGAAACTGAGGTGCAAGAGAGGTTAAG
CGCTTTGCCCAGGCCACACAGCTGGTAAGTGAAGATCCTGGGTTCTGATTAAGGACATGTGATTCTAAAA
CTGACCTCCAATGTGCTGGCTCACTTTTTGAAGGCATGTCCTACAGTAAAGCGTCAGGCTCATAACACGG
TAGACCCATGCTCAGCGGTTTCTGTGTCGCCTCCATGTTCATCTCAGCGCCTGTGTTTTATGGGAAAGCG
TTGGCAAGATTTCAGAGCTTGTTGCGCTTCTTTACGTGCCCTGTCTCCCCCAGTATGCTGCCGTTTCTGC

TTCTCCAGTCTTCAAGCCCTGTTGGCACACAAGTGAGCGGTGTGGAAAAATTGAGAGCCAAGACAAGTTA
CTGTCCGTTTCCCACCCATCCTTCATCTCCTCCCACATCCCATAACCATCCGCTTCCCGAAGGGAGCTGG
CATACCAGATGAGACAGGATCTGCTGTCTTGCCAGAGACTTCGTTTCTTCTCCTGGCAGTGCTGTGAAAC
CAGAGCTGTGATGCCTTTCGGGGGGTTTAAATTCCAAGGGATTCATTTTCTGAAACCAAGCTTTGCATCT
CTCAGGGAATTTTCCCCCTCTTTTGAATGTCATAGAGGCATGCGAGTGTACTGGCGTTCCCCACTTCTCC
CGAAGAACAGACCTCATTTTGTTGGAGGTTTAATAGTTTTTCCTCCTGTGTTAGAGGTGTATTTACCTTT
TTAAATTTATGTGCTCCCTTTGTGTCAGTGTTATGTATTTGGTGTGTTTTTATTCCATGTACCCTGTGAA
ATCATAGTGTTTAGGTGGGCTCTTACTTATTGGCCCAGATTTGATCATCAAGAATCAAGAAAACCTTCAG
CATTTCTCTTCTCTTCTCTTCTCAGAAAAGAGCTACAAGTAATAAGCTCTGGAGTTTCCCACAGTTCCAG

AGTCTGTAAATGGTGATGCTTACCTCAAACTGGGGAAGGACCATGAAACACCACATCCTGGTGTTCTGGA
GTCAGACAGCCTGGGCGCTTTCCTGCTCTGTCATGTATAGGTTATATGACCATGAACATCATTCACTATT
TCTTCTTTCCTTTCTGGACTGGTAAAGCAAATGAATAGACATCATTCACTATTTGTAATCCCACAGTTTC
ATCATCTGTAAAATGAGAGTGGTAGCCATCTATTTTGGGGTTGTCATGAGGCTCAAATGAGATAATATAT
GTACAGCACAGTGCCTCACAGTAAAGTCATTCAGTCTTTACTGAACTCTTTGGAACCCCATGGACTATAC
AGTCCATGGAATTCTCCAGGCCAGGATACTGGAGCAAGCAGGGATTGAACCAGGTCTCCCACATTTCAG
GCGGATTCTTTACCAGCTGAGCCAGAAGGGAAGCCCAAGAATACTGGAGTGGGTAGCCTATCCCTTCTCC
ATCAGATCTTCCTGACCCAGGAATCGAACTGGTGTCTCCTGCATTGCAAGCAGATTCTTTACCAACTGAG
CTGTCAGGGAAACCAAAGTACTTAGTAAATCTTGACTATTTTGATATCACATATTAAATTATTTTACATA
```

TABLE 3A-continued

SEQ ID NOs: 1-2, BOVINE EXT2 AND ALX4 GENES

```
CTTCTTTAAAAACTTTTTTTGCTTTTCCATTTAAAATGGTGATTTTCAAGCACACAAGTTTTGTGTTGGG
AGGGGTTGATGAGTGGGCTGGGTTGGTGAGGGCAGAGAGACCACGAACCTTAGTGATTAACTGTGACTTA
GTAGCACAGGGCTACTTCCGTTTCCATACAAGTCAGGAAACTGATGAGTAAGATAGGAGTAGAAAATGAA
AAGGTGTTCCTGCAAAGGTGATCGGATGCAGGGTGGAAACACGAAGATCCAGGCCCCGTCCTAAAACCAC
AGCTTAATGCCCAAGAGTGATATTGTGGAAACAAAAAGTCAGCCTTAGGAGGATACTCTTTCCTGTGGTG
TCTCTTGGTTGTGAAATCTTAATTATGGCCTGTTGTGGACATTTTGGCGTTATTATCCTGATGACATTAG
GACTCCAGGAATCCCATTCGGTCTCCTGGAGTTCCCATCCATGTGCATTCCATGTGCGTGTGTGCATTTC
CTGCCCCACACTGTCACATCTGGCAAACAGCTGCTGTCATATACCGTGGTGATGGCTGTCCGTCAGTGATA
TGGATGGGGGTGATGGGGGAAACCTTGGAGATCCCAGAGTATGAAAAGACTAAGGAGCGTGAGCAGCCAG
AATAACAGGCCATTTCATATTCAGCCTCCTCCTGGTGAAGCTGAAGTTAGGTCCTAAAGTTAGGCTTTTC

ATGTAAAAGCACGTGAATGTAAATGTAACTCATGCCACTGAAATGTACACTTGAGTTTGAAATGGCAGGT
TTTGTGTTATATTTTACCAGTTTTTAAAATTTAGCAGTGTAATATACCAAAGCCATTGCATACCTTAAAT
AGATGCATTGTTTAGTACATAAATTATTGGGCTTCCCCTGTGGCTCAGCTGGTAAAGAATCTGCCTGCAA
TGCGGAAGACCTGGTTCAGTCCCTGGGTTGGGAAGATCCCCTGGAGAAGGGATAGCTTACCCAATCCAGT
ATCCTGGCCTGGAGAATTCCATGGACTGTACAGTCCATGGGGTCGCAAAGAGTCGGACGCAGCTGAGCAA
CTAAACCACCACCCCTCGGCTTCTTCTATTGTCTCTGTTTTCTCTGACTTCTTGTGTTTCTTTCTGTTCA
TTTGTTTTCTATTGTTCATGCTGAAGATGTTCTTGAAATGTCTTCAGAAGCATGTTGCTGCTGCTCATCAGC
AAGCTGATCAAAAGCTTTTTGTTTAAGAGAAGCTTGTTACCTGGAGGGCTTTGCTGTGAGGTGATGGGGC
CTCGCTGTAAGGTGATGCGGCCTCCCTGTGAGGTGGTGGGGCCTCGCTGTAAGGTGATGCGGGCTCCCTG
TAAGGTGGTGGAGTGGCAAGTAAACCACATGGCTGCTAGTGTTTGGGTTGCTAGAAGGGGAGGAAGCTGT

AGAGCTCATCATTCAAAATTTAGGCTCTAACTGCATTTTCCTCTCTTCAGTACCTATGTTTCCATGTCTA
GAGCTTTAGGTTTTTCAGAGAATCAACCTCCCTTCTGTAGCGTGGGTAAGGAAGAAGCGTAGTTTTCTGG
CTGAGTGGGCAGGTGGTGGGAACGCTTGTGCCCTGAGCCTGTCGCTGCTCCTTGCACGTATTTCAGCTGT
TCCTCCTGTGTTCGCCCTCCTCCTCTTACCTCGTGAGGCCCGCCGAGCACAGCCCCTGGGCCGTTGTGGG
GCTGGCAGTGGGACTTGGCTGCCTTGTTGTCTCGCCACCGCCTTTGTAGCACTTGGGTTGCAGCTCTCAG
CCTTCTGCTCCGTCACCACTTCTCCAGCCCCTTTCAGTCTTTCAGAAGCATGTTGCTGCTGCTGCTCATCAGC
TGCTGTCTCTGTTCCCATTTCATTGTCTGGGTAGATTTATATTTTTTATCTATTAATTGCCATTTTAGTG
GGTTTGGGGAGGGAATGGAGATAAACGCATGTGTTTAATCTGCCATGTTTAACTAGACATCTCCTCTTAG
CTGCAAAGATTCTCTGATTCTTTTTTTAAGGGTATCAGAGCCAAACTCAGTTAAACAGCATCAGTACAGA

TTTTGAGGTGGGGAAGACTTTGAACAGTTGCTTGCCTCTTGGATTGGTCATGGTAGAAACTACATCGAGT
CTCCCGTGTTCCGGTTTATTGGTCATGCTGAGAAAGAGACCAGCACCATTGTTACTAGATCCTTCTCTGA
CCCATATTAATCTGTTCTCTTGCAGAAGTGGGGCAGTGTGAGCAACCCTCTCTTCCTTCCCCTCATCCCC
CCACAATCTCAAGGTTTCACGGCCATCGTCCTCACCTACGACCGAGTGGAGAGCCTCTTCCGGGTCATCA
CCGAAGTGTCCAAGGTGCCCAGCCTATCCAAGCTGCTGGTCGTCTGGAACAATCAGAATAAAAACCCTCC
TGAAGGTAAGACGAGCGGAGAGACGGTGTGTCCAGGAAAGGCCCGGTTTGGACGTTTTGTGTTCGTCTCA
ATGGGATCGAGTTTTTTTGATGGACAAATGATTTGCAGCCTTTGTCTTAAATGAACTTTCCTGCTTTGTC
AACAGTAATGCCATTCCTGAGGCAGCATGACCCTGGTTTTCTCAGTCATCTTGTTCTTGTTCTAGGGTGG
CCGGTTTAACTCTTAGCCCATGGCATGCTCTGTAGCCACAAGTGTTTGAGGGCTTAGGAGTCAATAGGAT

CAAAGGCCATCAGCCTTGGGAAAACAGATCTCAGCTTCCCTCAACCCTCTCAGCTGATTTGTTTACATGA
AAAGTCAGTTTAAAAGGCATTAGTTTTCTCCTTCCTTATCTCGGCTCTGATACTGTGCTCTTCTTCAAAA
AGGACGGCCTCACCTCTGATGGGCAGAGTCAGCAAAGTGCGCCTCCCAGGCTTGAATCAGCTCCTTAAA
GTGACCCCTCACTGGAAGTTCCCACCAGCTCATCCGTAATCACTCTGTCCCTTGCCTTGGCCACCCCTGT
AATCTGCTGACTGGCAGCTCGGGCTGAGCCTGTTTGATTCATTGGATTTGTTTTTAATTCAGGACGCATA
ATGTACGTTCCACCTGCATTTCGTTTCTCATTCAGTCCGTCTATTATGGATCCTAATCCCAGGGACTTCA
AAGCCCCTGCCCTTTATAGCCTATTAAAGCCAGGAAGTTTCTGATGGATTAGAGCAAGGAATGAGTTTGA
AGTTTGTAATGTGCACCACTATCACCGATAAGGTCTAGTTTATTGCCTGACAGTAGTATCTGCACTTTTT
ATGGCTGTTCCCGTTTAATTGGTTATCCTGAAGTCGGGATAGTCAACCTTGGAAAACCCAGTAGTAGATC
CCTAGTCTAGGCTGGGAGAAGAATGTACTTCTGTCTGTGAGGCAATCAGGATTTAAATGCCCTCTTTGAG
ACTTTAAAATTTTTCCTTGGTGGGACTTTTGTTCTCTGCATCAGTACTTGCTTTTTAGATTCAGGGGGC

CACAGTTTAGTAAACAAAGTAGCTCTTTTATGTGAAGGCCCATAGTACTCCCTGAGGCACACGGCGTTTA
TTATCGTTGTTGCTATTCTCATCTTTTGTGCCGGGTTGTTTTCCTCCCAGCATTCTTGGATTTTTTTTG
TTTGTTTGACTCTCAATAAAGGGGACAGAAAAGGGTAGAAGAAAAAGAGGATGTTGGCACCTTCTCAGAG
GGAGAGAGGATGAAACTGACGGGAAGGGGGAGGAGGAGGAGGCAGAACAGAACGGGACAGCAGGGA
GGCTCTTCAGAGCCCCGGGTCCACCCAGAGTGAGTGGATCGGAGGCACTGCATTGCTCATCTGAGTCTTC
ATTCATAAAGGATGGGTTGTGTTTCAGAAGGAAGGCTGTGTGTCCCTTGTTGGAGCTGGAACAGCTGTGT
GTCGTATCTGCAGTCACCCTGCTGCATGCCGAGGCCACCAGCTTCCAGGGCGGGAGCACCCCAGCTGCAC
CCCACCCTCCTGCCCAGACAGGCAGTGCTGCTGCTAAATGCAGAAGAGACGTCTCCTTAGAAACCCGGGT
TAGCCACTTTGGGCATAAGGTGACTTATTTAATGTGACTTTGAGTCACTTCTTTAGAGCAAGTATCACTG

CAAACTGTGAGGAAAGAGAACTAGTTTTCTTCCTTCTTGGTCTAAGGTCCTGCCTACATTGCTGTCACTA
AAAGCAAGAGCACAAACCTAGGTTCTGGAGTTGGGTGTTTAGTTTTAATTTTTGGTACACCCTACCAAAG
TGTAGTGGTGAATGTCATGACCAAGAGTGTAGTTTATTTTTGAAATATTTTGGCTCTAGAGAGGAAAGAG
CCCTCAACTGATGAGGCCCAAATTTTGACACATTCAGGGGCTGGACCAGCTTTTTTTCTAACAGTGGTTT
TTAGGTCAGGGCTCTGGTTCTGGCGTTGTGGTTGTTTGGGGAGAACATGAACTGTGTTTAATCTTCTGTG
GGGTGTTTGTTCAGTTGTAAATGGGGCTGTCAGCTCTGGCCCTCGTGCCAGCAAAGGCATCTGATTTTT
CATGTACGGCATTAGTAACATATATATTTTTAAAAGACAAGTCCAAGGCTTTGAAATATTAGAGGCAAA
AGTGATGTTTTCACTTTCTCTACATTTACTAAAATAAATATTGTGGTTAACATGTCTGCTGGGAGG
ATTAGTGTAGGCAGAAATCCCTCCCCTCTACTTTTTTTTTTTTCACTCTCCAACCCAACCAAATAGTAT

TTTCTTTTTGGTTACATTTAAGTCTAAATTGCTGGGTTTGAAGTTTAAGTAAATACTTAGACTAGGCAAT
AGAAATTTCCAGCGAGCTTTCGTCACGTTGGTTTTGAGCTCTGTCAGACGAAACAGGCGAGCCACTGCCC
TCCTCCGACCTCAGCTTTTCAGTTTCCCGGCTTGATGGATATAGAGGTTGTTAGGCTTGGCCCCTGGCCT
CAGCCTGAAGGAAGCTGTTACATCGTACATTTCAGATAGATTTAACTCAGCCTTCTGTTTTAACTGATTT
CAGTTTTTAAATTTGAATTGATCTCAGGGAACTCCCCTATGGCCACCCCAGCTTCGGGTTGCTACTTCCA
CAGTTCTTAATAGGCAGGATGGGATTGGCTGAGCGTTTCAGGGCGGTCTGTCGGGATGGAGGCCATCGAG
AAGCAGAAGCAGGAGTGCCCTTCCTTCCAGCTGAATTCAGGGACCGTGGGGAGTGAGGCTCTGGGGACCC
GCTGTTCACCAGGCAGGTTGAGGACTTCTGGAGGGAGCTCAAGATTTGTACAGAGATAACCTGATGGTTG
ATTTTGTGAATCTGTGGTTGTGTTTGACAGTGATCCCCAGGATGGACTTGGGGTCATCGTCGGACAACCT
```

TABLE 3A-continued

SEQ ID NOs: 1-2, BOVINE EXT2 AND ALX4 GENES

GAACATTTCGTAGTACCTTTGCCAAGTTGGAGAATTCTCCTAGCTCACATGGCTCCTGGCATCCAACTTG
GAGAAAACTGTTAATCAATACATGTTTTTAAAAAAATCCTTAACACAAGGAGTTCTTTTTCTCCTTCAAG
TTGGACTAAAGCTCAGAACTGTAAAGTTATCAGGTCAGTTGGCTCAGCTGTTTGTTTTTCATAAATTTGG
CAATGTTTTTGAGAAATCTTATTTTTCAGACTACTTTGTGTGAATGGAAGGTGACATTTCTGTTTTGCCA
GCTATAGATTCGCAGGATGAGACACAAGCTACAATTCATGCAGTTCCATTTAGAGGTTAAAAGAATAAGG
AAAAGACCCCACCTGGGCCAAGCAGTGGTGGAAGAACCCGAGGTTTCTAGCTGTGACACTGTTTCCTTCT
GCGTGCTAAGGAGTCACCACCTGTTCTTCTGTCTACACCGCTTCAAAATGTCAGAGGCAAAGTGAAGTTT
GTAAGACCTTACAAGAATCCATTTGTGAAGATGCCTGGGTAAGGAAGATCTCCTGGAGGAAGAAAATAGC
AGCCTATTCCCGTATTCTTTCCTGAAAAATCTCATGGACAGAGGAGCCTGGCGGGCGACAGTCCAAAGGA

CTGCAAAGAGTCAGACATGACTGAACCACTACGCACATCTGTGAAAATGAGAATGATACAGTGTTGTTAC
AACATGTATCGTGTACCTTTTATATCCAAGGAATGGGAACTGTGCTGAGTGCTTTACACGTATTGTCTCT
ACTGCTTATAACAAAACTGAAAGAAGCTGATATTATCCCCATTTACAAAAGTGAAACTCAGATTAACTGA
GTAATTTGCCCTAGGGCTCCCCTGGTGGCTCTAACAGTAAAGAATTCGCCGGCAGTGCAAAGACCCGGGT
TCAATCCCTGGGTTCGGAAGATCCACTGGAGAAGTGCATGGCAGCCCACTCCAGTATTGTTGCCTGGAGC
ATTCCATGGACAGAGGAGCCTGGTGGGCTACAGCCCATAGCATCACACAGAGCCGGACACGACTCAACAA
CTAACACACACACGTCAGAGGTCTGCAGAAATGAACACAAGTCTCTCTGGATCCAAGCTCATGCTCTGTG
CCCCGAGCCCCACTGTGTCTATTCAGATTGCTGTTTAGCAGCAAGGAGATCATGCTTTGTCAGGTCTCTG
ATTTGGGATTATGCAGATCAACCAGGTTCTTATCAGGGGCTCGAAGAGAGGCAGAAAAATAAATCTTATT

CTTTTGGAAGTACTAACGGAAAGAAAAATACAAGTCTTCTGTTCTTTCTCACTTACGTTTTTCTTTCCTA
CCTTGTATTCCTGTCCTTTTTTTTTTTTTTCCCAAACTGTATCAAAATCCTATATCAGAATTACCTTC
TTTAAGGCAGGGAGTAATTATACTGCTTCTTTGGCTAGCCACTTTCTTGTTCCCGTGTTCCACAGAAGGG
ATACAAAAGCCCAAGGAAGTTGGATCCCCTCCTTAGAGCCCTGTTCTATTTGAAGCTGTGAAAACAAGCA
ACTGGGAGTTCTACTTGGAGTCCTTCCTTGTGGTCACAGTGGTTCATAGGGAGCTGGACCGTTGAGCTGG
AGACTTCTTTTACCAAAGCTGCCTTTGGCTCTCCAGGCCCAACTCAGGACAGGAAAAGGTAATCACCTTT
CCAAGAAAGCCACGATTCATTCTACATTTCCATCTGTACCCATTTAGCTTTCCTCACTTGCTAAAACTTC
CCTATCAAAGACCTTATCAAGGAAGGTTGTTTTTAGACATTGTCTTGAGTAATTTTCTGGCTACACATAG
GAAAAGAATGTGGAAAACTCTCTGTTGAAGATGTTGTGCACACTCCCTGGGTGAGAGGGACTCTCATCCA
GGGTCGAGAACATTGACACATCATGCAAGCAGCTCACCTGTTTTCTAGCCTCTTTCTGTATTGCAGAAAG

AGAGGCTGTTTGTTGCCTTGTGAAATTTCCTTGGCAAGAGTTCCATGTTCTTGCCAACGGAACTGTTGG
CAAGTTAGGTTTTTTCAGTTCTAGAGGATTAATGGCAGGGTTTCCGCTAGTCTCAAAGTGAACTTTGAAG
ATAAAAGCTGAGGACATGCCACTAGACTGTTGGAGTGATGTACGAGATCTAACGTGTGCCTCTTTGCCAC
CACTACCTAGGGTTCATCCTTTGGTCTGTAAATAGGCACAGACTTGCAAGGGAAAGCACAGCCAACGTTT
GGTGGACGTTCTGCCACGTGCTGGGCACTGAGCTGCTAAAAGCATTCCTGTTCCTCCTCACGCCTTGCCA
CAGGTGGAGATGGTGTCACTATCCCATCTTCATAGTCAAAGAAACAGGTACAGAATCACGGACTTGTTCA
AGATCACATAGCTGATAAGGAATACAAACACCTGAGATTTGAAGCTCTTTCCAAAGACTGTTCTCTCTGT
GAAACGTGACTGGCCATACAGTCCTCAGAGGTGTCTTGTTTGGTCCCTGAAGTTGGTACATTTCACGTGG
AAGAGCACATAGCGTTGCTGAAGGCATTTCGTTCCATCAGAACATTCTTACCGACTTTGAGCCTGAATCG
GTTTCCCTGTAACTTTCACCCAGGCGTTGGTCACGCTTCTAGCTTCAGAAGCCATAGAGAAGCCATTCAG
AAGCCTTTCATCTGGGAACCCTTCTGATAGCCCTAGTGTGTTAGTCAAGGTCCAGGTGGGAGACAGAAAC
CACACAGCAACTTGACCAGGAAAAGTTCAAGTTTTAACTAGGAATTGTTAAGGAGGACTAGGAGATTGGT

GGCTAAAGGGTGAAGAGAGCTCCCGGGATATAGGAAATCAGCTTGGGGATTGAGAGCGCTTCCCCAAGCT
CGGTCTGAGATTCAGACCCACTGCATGGTGAAGCTGCTCAGGTGCCACAGGCTGAGTCTGGCAAACAGGA
AACCAGCAGCCCCTTTGGATACCCATGGAATTCAATGGGAAGCCATCCGGGGGGTGTTATTGGACTCAGA
GGGGTACTGGCGAGGGCTTCAGTTCCTGAGGAACCACCTGAGGGCAGAACCTCAGCTGAGTTGCTGCTGA
AGGTATCACAGAACTTGCCAGGAAACTGCCTGCAGAGGAGCTGCCAGACTCCTTCGGGAGCCTGTTGGGG
TGTCTGTAGAACCTGCTGGGAGCCTCCCTTGGGGGTGCCGTCTACATGCTGGAGAGGGGTGCTGCTGC
CTACCTGCTGGCCAAGTACCGAAGGAGCAAGTGAAAAAGGCACACCAGAACCAGGAAGCAAAGCCCTCAC
CTCCCAGCGTCCCTCCAGCACCTGCTGCTGACGTGTTAACATCAAGTCAGTGGGCAAAGGGGAAATGGTG
ATGGGGCTGGCTGCCAGTATCACCCCCAGGGCAGTGAAGGGTGAATTTGGAGCTGAGAGGCAGTGCATGG

CATATTCAGTTTAAAGAGATCCTGGATCCGAGGACCTGTACTGTCCTCATCAACTCCGCCTATCTCCCAG
TTTGTTGGTTCTTCTGTAAGTGTTTGTGTGCTGGTCGCTCAGTCATGTCTGACTCTTTGCGCCCCCACGG
CCTGTAGTCCTCCAGGCTCCTCTGCCAATGGAATTCCCCAGGCAAGGATTCTGGAGTGGGTTGCCATTCC
CTTCTCCAGGGAATCTTCCCGACCCAGGGATTGAACCCTGGTCTCCGACATTGCAGGCAGATTCTTTATC
GTCTGAGCCATGCTGGGCAGCTCTATTGCAGTACCCAAATCTAAATACAAGGTCTCATACAGAGGTTCTC
AAAGTGCAGTCCGGGGACTGCTGAGCATCCCTGAGGTCCTTTCACAGGGTTGGTGAGGTTGAAATTCTTT
CTCTGAGAATGCTGAGTCACCCTGCGTTCCCACGCTTATATTTTTTACGTGTGCATAGTGGGGTTTTCCA
GGGACTGCCCAACATGGGATGACATCACCACTCTACTGGCTGATGGAGGGTATGCTCGTGTGTCCTGGGT
TTTAAAGTTTCCTTGGTTTTCATTCAGAATATAATAAATTGTGTGTGTGTGTCCTACATAAATAAAACCT

CTTTGGGGATCTCAACAGTTTTTAAAAGCACGAAGGAATCCTGACACCATTTGAGAACCACTGATCTAAA
GATAACCACTGATCTAGTTAGAGCTATAACTTCCTTCACTTTTAGATATTACAATTTATTCATGTTTTCT
AAGGATTTGGATTTATGACAGGGATTTCTTTTACTTAACTGGAAGAGGGAATGGGAAGCAGAGAAGAATA
AGGATGATTGTTTTGTTCCAGATCCAGAGAAACATGACATTTTCAAGCTGCAGTAAACGGTGCAGGTCC
TATTTGGTCTTTGATGCTAAACAGACTTAGATTCAAATGCTAGCTGTATCATTTAGCCCTAACCCCAGCC
AATGTACTTAACCTCTCTGAGCCTTGTGAATCCTACTCTGTAAATAATTTCGTCTCTATAGACTTGTCAG
GAGGATGAATGACAGTGCACCTGTAAAGTATCTGGCATATACTGGTGCTTAATGAAGGTTCCCTTCTCT
CTCTCCACTTATTCTTACCCTGAGAATAAGGGACCTGCCTAAGAACCCCATGGGAAATGCAGAACTCAGG
TCTCCAGTCTCTTAGTCCTGTGCCTATCCATTTATTCTGAAGACAGTTTTTGATTATGTCATTCTGGACC
AGGTTAAGTATTGATTAAAAGGGACTGACCCATTGGATCATTTCTTTGGTCTCCAGTCCTTTCTCAAACA

TGCTTTTTTTGGAGTTGAACACATTTTTAGACCCTAAGCTTTTTCAGGCTGTGAAAGTGTTAGTCGCTC
AGTTGTGTCTGACTTTTTGTGACCCCATGGCTATAGCCTGTCAGGCTCCTGTCCTCTGTCCATGGAATTCTCCA
GGCAAGAATACTGGAATGGGTAGCCATTCCCTTCTCCAGGGGATCTTTCTGACCCAGGGATCGAACCTAG
GTCTCCTGCATTGCAGGAAAACTCTTTACAATCTGTGTCACCAGGCACTTTAGGCCCTAGGCTTATTTAG
AACTTAAGGACTATCTTCTCCATATATATATATATATATATATATATGTATGTATGTATGTATAGGAATATC
TTCTTTAATTACAGGGCCTCGCACTTTCACAGGCCTCTTCCAGAACCTAGGAGCACCTTACCTGGACAC
ATTGTAAATTATGCAGAAGTAAGATATTTTATATGATGTCTGTTAGAGCAACCTTTTTCCTCCTGATTT
TCCCTCAGTCATACTTATCCTTCGGTATGATAACTTCGGAGTGGCCACAGGCATTTTGGGGCTTCAAGAC
TCACAAAACTAGACCCATCCCACAATTATGTGTTGGGTTTCTGGAAGCAATATGACACCTTTCCGTGCTCA
TCTGACAAATGTTGTGTGAAGAACAAACTGCCCTCTGTAAAGAACCCTGAGGTCTATGGACATAGGTCCT

TABLE 3A-continued

SEQ ID NOs: 1-2, BOVINE EXT2 AND ALX4 GENES

```
GTACCAAAGAAGTGTTAATTTTATTCTGTGCTAAATGCATCACTTTAAAATGAGGAACCTGAGGTTGAAT
TGCTTCAAAGTAGAATGGGAAAAATGTAAGGCGAGTCACAAGTTCGTGGGTCTTCAGTATACCAGAAAAT
CCCATGTAATCGGACCTAGAAATTTGATATTTACTCTGTAAATTGGTCATGATGAGAACCCAAACCCAGT
GAGTCAGGAGAGAGCGGCTGTTGAGCGGTGAGGTGCTGAGTTAGGAAAGCTGAACTCATTCAGGGCAACG
GTTTTGTGAGGGTGGCTTCGGCGGCCTTGGGAGCCGTTGGTGGTGGAAGTGGGCACTCTCATCTTCTTTC
AGCAAATGTTTCCCAGAGGGGCTGCAGGCAAGTTTGGGGCTGGGTGTACACACCCGGAAGGATTATGCAG
AGGTGGCCAGGTGGTCGAGTCCTGGTGTTCAAACCATGGGCCTGAGAATGAGGCAGACAGGGCCCATGCC
TGCTCCTGCCCTGTCCCTGTGACCTTCATCAAGTCGTTCGGCACCCCCCACCCCCACCCCCGGCCTCTCA
GTTGTGCCTTGGAGCCTGTTTGTGGATTCTGGTTAAGACAGCATTGAGCAGCAGCAGTGTTGTAAGGATG

TAGAGAGAAGAGAAGTATTTATGATATATTATAAAAATTCATCTTTAAGAATGTCCTCCTGTAGTTGTGC
ATGCGGTTATTGTTTTTTCCCCATATTCTTATTTATTTTTGGCTGTGCTGGGTCTTCGTTGCTGTACGGC
CTTTTTCTCCAGTTATGGAGAGTGGGGGCTGCTCTCTAGTTGCAGTGCGAGGGCCCCTCCTTCCAGTGGC
TTCCCTTGTTTCCTAGCGTGGGCTCCAGGGTGCACGGGACTTCAGTAGTTGGGGCTCCCGGGCTCTAGAG
CAGCGGCTCAGTAGTTGTGGCACACGGGTCAGTTGCTCTGTGGCATGTGGGATCTTCCTGGATCAGGGAT
TGAACCCACATCTCGTGTATCGGCAGGCTGATTCTTTACCACTGAGCCACCGGGGAAGCCCTGCGCCTGT
GGATTTCATGAGAGTCACAGCTTTGAGTTGCTTCTTCTGTCTTATTTGTGAGACATGGCTTTTACCAGTT
TATCTTTTCAAAGAAGTTAGAAGAGTCATAAATACCTTGGTTTTTTTTTTTTTTTCTTTTTCCAGATT
CTCTGTGGCCCAAAATCCGGGTTCCATTAAAAGTTGTGAGAACAGCTGAAAACAAGTTGAGTAACCGCTT

CTTCCCTTACGATGAAATCGAGACAGAGGCCGTCCTGGCTATTGATGATGATATCATCATGCTGACCTCT
GATGAACTGCAGTTCGGTTATGAGGTAAGGAGGTCTCAAACAGTGCGTTTTCATATTTAATATTTATTGC
CCATTATTGCTTGTCTTGCCTAATACAGAGGGTTATATTTCATTCTCTGAAGTTGTGATTTGTAATAGCA
CCCAAAAACCGTGTTTGGGAGCGTGGGTCACGAAGCTGTTCTTTAGAGCTTCGTGGAACCCCTATTCCAA
AATGACAATTGTGCTGGCTGCCAGTTTGGGGAGCTCCCAAGGAGGGTCCCAGGGGACATCTTCAAAAGAG
CATCTATGAGATTTAACAAGCGCTTTACTGATGTCTCCATGAAGAGCACTGCCCAGACTCAGGCAGCTGG
GCATGGCCACAATAAAAACATCAGTAAGTGAAGAAGCTGGCGACACTGCACAAACAGAAAGCAGACCCGCT
GCTGGCTTGCCTTCTGAGTTTGAAGTGCAGAGGCTGGCTGCCTGTCTTTGGGGAGGAGCATTCTCTATCA
CCGTTCATTCAGGGAGGCTGATGGATTAGGCCGGGTTCAAGGGTTAAGTATGGAGACCAGGAAAGGTCTC
CCCAGGGGAAAGTGCCAGAGCCGAGGCCTGGTGAAAAGCACTAGGAGCCATTGGAACATAGCCAGGGA
CATAAAACAAGGTGCAAAAATCTCATGGTCTAAAGGTATTGAAATCATAGAGTCTGTTCTCTTACCACTG

TGGAATTATGTTAGAAATCATATTTTTAAAGTTATGAAAATAATTCACCTATTTTCCACTGCAGCATGAC
ATTTACCAAGAGATATCTTTGATTTAGCCATTAAAAGCCTCAATAAAGTTAGAAGACTGAAAAACAATAC
AGTTATTGCAGAGAAGAAAGCATTTAAATAAGAACTTAATATCAAAGATACTTTAGAAAACCTCATGTAT
TTGGAAATTCAATGTCCACTGAAAGTGGATTTTAAAGGGAAGAAATAGGAATCCCCCCTGTGACCACCAG
CACCAAAAATTAGAAGCTTATATTCCCCCAGGTGTAATCCCATGGACCGTAGCTTACCAGGCTCCTACGT
CCATGGAATTTTCCAGGCAAGAGTACTGGAATGGATTGCCATTTCCATCTCCAGGGGATTTTCCCGACCG
AGGGATTGAACCCAGGTCTTCCACATTGCAGGCAAACGCTTTACCCTCTGAGCCACCAGCGAAGTCCTTT
TTATATATAGACATAAATAATTTAACATATATGGAAATATATATAAATAATTATATATAATGCATATTAT
ATATAAATAACTATATATCAGTTCAGCGCTCAGTCGTGTCTGACTCTTTGTGACCCCATGGATTGCAACA

TGCCAGGCCTCCCTGTCCATCACCAACTCCTGGAGCTTACTCAAACTCATTTCCATTGAGTTGGTGATGC
CATCCAACCATCTCATCCTCTGTCATCACCTCCTCCTCCCACCCTCAGTCTTCCCAGCATCAGAGTCTTT
TCAAAGGAGTCAGCTCTTCACATCAGGTGGCCAAAGTATTGGAGTTTCAGCTTCAAAATCAGTCCTTCCA
ATGAACACCCAGGACTGATCTCCTTTAGGATAGACTGGTTGGATCTCCTTGCAGTCCAAGGGACTCTCAA
GAGTCTTCTCCAACACCACAGTTCAAAAGCATCAATTCTTCAGCACTCAGGTTTCTTTGTAGTCCAACTC
TCACATCCACACATGACTACTGGAAAAATCATAGCTTTGACTAGACGGACCTTTGTTGGCAAAGTAGTAT
CTCTGCTTTTTAATATGCTATCTAGGTTAGTCTTAACTTTTTTTTTCAAGAAGCAAGCGTCTTATAATTTC
ATGGCAGCAATCACCATCTGCAGTGATTTTGGAGCCCAAAACCATAAAGTCTGCCACTGTTTCCACTGTT
TCTCCATCTATTTGCCATGAATTGATGGGACCAGATGCCATGATCTTTGTTTTCGGAATGTTGAGCTTTA

AGCTCAACATTTTATAATTATACATAATGTATATTATATATTAAAATATATTTATATATCCATTGAGTAT
AAAAGAAATTGTTGTGAAACAGGCTGGTATGTGAATACCCTGGTCTGCACATCATTACTGGCCAGTGAAAGG
CATGAATGTAGCTAGTACATAGACTCACCTTCCTGGGTTTATTTCCATTCATAGAGATGTGTTTCCTATC
ATCACACCTAAGGTGTTGGGGATTTTTCATACACTATCTTTCCCTTTTTTTAAAAAAAGCAAATTACTTA
TTTCTATAGCCAACTCTAGGCAAACAGACCTGGTTTTTTCTTGCCAATGTTTTCTCTCTCCATTATATA
TAATGGCTTCAAACTATATCCTTGTGTTTGTTTTTGTGGTAAAAGGAAGGTGGGAAGTAGGAACATTTCA
ATGAGGAAAGGTAGCCAAGATGGACAGAGTGCTGCCTCTTTGCTATTTGCAGTCGGTCTAAATGAAGTCT
GATAAAAGAAAGGTACCCTGGAAGAATTCCTTTCAACCATGGCTTAAAATCTTGGGATCTCAGGAATATT
GCAGCCTGAAATCTCTTTCAACCTTGAGTTCATTTAGAGCGACAAAAAGTGTATTGATGAGAGGAAGTGC

AAAACCCAGAGGGACTGAGCTTAAATCTTCATCTCTTCCCTCTGAGGCCCTGTGTTTACTCCACGTGACC
TCTGAAGCAGTCAACTGTGGATCAAGAGGTAGGGGCAGGGACACCCTTCATCTCTAGTAATGGGGTCTT
CTCCAGATGCTAAGACAGGAGTAACTTCCCTAACCACCATCTATGTGCTGCTTACTGTGTTGCTACCGGT
TTGCTGGCTGTTTACATACACCAGTGGAGACCAGTCCTGGGTGTTCACTGGAAGGACTGATGCTGAAGCC
GAAACTCCAATACTTTGGCCACCTGATGAGAATAGCTGACTCATTTGAAAAGACCCTGATGCTGGGAAAG
ATTGAGGGCAGGAGGAGAAGGGGACGACAGAGGATGAAGCGGTTGGTTAGCATTACTGACTCAGTGGCCA
TGAGTTTGGGTAAAACTCCGGGAGTTGGTGATGGTCGGGGACGCCTGGCGTGCTGTGGTTCATGGGGTTGC
AAAGAGTCAGACATGACCGAGCGACTGAACTGAACTGAACGATCTTTTCCCAAACCTCCTAGGCAGTTAT
TGGGTTTTGTTGGGTTTTGGTTTTTGTTTTGTTTTCCCCTTTCTTTACTGAGACTAAGCAAGATTAGAT
GACTTCCCTACAGTCACACAGCTAAATAAGTGGGAGAGTTGAGATCTGAATCCAAGTTTGGGTGACACTA
```

TABLE 3A-continued

SEQ ID NOs: 1-2, BOVINE EXT2 AND ALX4 GENES

```
TATTGTCTTCCTTGAGGATTTTACCATGTCAGAGACTACTGGTCCTCAAAAGTAGTCCTCAGAACCATCT
TCTATCACTTGTCCATCACTAAATTACCTTGGTACTAAAGAAAACAAATTTATTTCTCAGGCATCCCTAC
CACTGGTGCTCTAGGGTGCTGTTGTAAAGTTACCTCTTGCATAATAATTAATACTATGAAAAAAGTTAGT
GCTGGACCCAAGTTTCTGTTCTGTCACCGTGGACGACTTATGTAATCTCTCTGGGTTTGTAGTTTATTCTT
GGACAGAATGGTGCTGACAGTGTCTGCTTCGCTGGGTTCTCATGTGCATTAGATAAGATTGTGTAGCGGA
GAAGGCAATGGCACCCCACTCCAGTACTCTTGCCTGGAAAATCCCATGGATGGAGGAGCCTAGTGGGCTG
CAGTCCATGGGGTCGCTAAGAGTCGGACACGACTGAGCAACTTCACTTTCACTTTTCACTTTTCATGCATT
GGAGAAGGAAATGGCAACCCACTCCAGTGTTCTCGCCTGGAGAATCCCAGAGACGGGGGAGCCTGGTAGG
CTGCCGTCTCTGGGGTAGCACAGAGTCGGACACGACTGAAGCGACTTAGCAGCAGCAGCAGCGCCAGTGC
ACGGGCAGCGATTAGAAAGTGCATGTTCTGGCTGGTGGGTGCGTGCTCTGCTCTTTATGAGATGCTTCA

TCAGCTGCTCTACCATGACTGCTGCCGTCCTTCTCGTGATCCAGTGATTCATGGGGAGGGTTTGTGGTTG
TTTTCATCATTCAGAAGGGATAGTGCTCTTCTGGGGAGGGTACCCAGTTTTGTGTTAAAATCAGAAGACA
GAAGAGGATGGTACTCCTAAATCCTGTTTTTTTTATGCCAAAGCCTGGGATTATTTTCATGTAGACTTGA
TGGATTAAGAGAATAAACAAATCAGTTAATAAAAATTTATGTCCTAGGGGGGTTATGTTGGAGCCCAGAA
CTACTTCTTTGTCACAGTTACCACTGTGTGTTAGGATTATATCTATCTGTTGTTGACTGTTTTTCGTCCTTC
AGCACTCAGATCAAAGAAGCTTTCACAAAGTCTCCAGACTGGAGCACTCAACCTCTTTGTAAGCAAATA
ATTGTGAAGTGTGTTGTTTAGTGTCTGCTTTTCTTCTAGAATGGAAGCCCCATAGGGACAGAAATATGGC
CATCTTATTCATTGCTGTATCCTCTGTGCCTAACCCAGCTCAGTCCAGTTCAGCAGTTAGTAATATTTGAT
AAATGAACAAATTTTCATTACCAGCATGCACATGAAAGATAGGAGACAGATGATTCTGGCCCGCATGCCT
TTCCACTTTACTGGGATCCATAACCTAGATGCAACCGTTTCAGCAAACAGTTTGGTGTTTAAAATGTTGA
CTGTAAATCTACAGTGTGACCCCACCGTTCTTCCCACAGAGATTTACCCTAGAGAAATGAGAGCATATGT

ATACATAAATAGTTGTACGCTAATGTAAGTTTTAGTGTTTGTATTTGACAGTGTTTATTTGTAAAAGCAAA
AAACTGGAGGAAAAAAATCTTATCAGAAGTTGAATGAATGAACTAATTGTAGTGTCTCCATACAGTAGAG
CACTACTTAGTAATAAGTAGATGAGCTATTGATATGTACAATATAGACGTATTTAAACATGATTATGCTG
AGTGAATGAAGCAAGGTGAAAAAGAGAACATATTTTATGATTTCATTTATAGGAAACACAAACTAAATCT
TCAGTGATTGAAAGGTCAGTGGCTGCCTGGAGAAGGGTAGGGCAAGTCAGCTTGAAAACTTTAGTAAAAC
GTGTGCCCCATCGGTTCAATGAAAACTAGGAAACATTGCTCAAAGAAATTGAACAGCTTCATAAATGGAA
AGACGTATCATACATTTGAATCCGAAGGTTCACAATTATTAAGGGGTAAGTTCTCCCCAAACTGATTTAT
AGATTCAAAGCACGCACAGTCAAAATCCCAGAAGGCTTTTTTAAAAAGTTGAAGTTGACAGCAGTTCTAA
TTGAAATGGAAACACAACGGACCTGAAAAAGCCACAAGCCAAAGTTTTAAGAAAGAAGGACAAAATTATA
AGACGGCCTTATGTTAAGACAGATAAAGCTAACGTAATCAAGACTCTGGTATTGGTGTAAACTTAGACGT

GTAGATCAATGAAACAGAATATAAAGATTCTAGAAATAGGCTACATGTGTGGTCAGTCAGTTTTCTGCAA
AAGACCCGAGTCAATTCAGTAGAGGTGGAATAGGCTTTTCACTACATAGTGCTGGAGCAATTTGATATCC
ATATGTCAGTTCAGAATAGATCTTGTCCTAAATACAAGAACTAAAACTATAAAACTTCTTCAAGGTAAC
AGTGAAAAAAGTTCTAGTGTGCCTGAGCTAAGCAATGATTTTTTTTTTAAAGTAGGAGACAAATAACATA
ATTTATAAAAGAAATCATTGCTGCTGCTAAGTCGCTTCAATCGTGTCCGACTCTGTGCGACCCCATCGAC
AGCAGCCCACCAGGCTCCGTGTCCCGGGATTCTCCAGGCAAGAACAATGGAGCGGGTTGCCATTTCCTT
TTCCAGTGCGTGAGAGTGAAAGGTGAAAGTGAAGTCGCTCAGTCGTGTCCAACTCTTCGAGATCCCATGG
ACTGCAGCCTACCAGGCTCCTCCGTCCATGGGATTTTCCAAGCAAGCATACTGGAGTGGGGTGCCATTGC
CTTCTCTGAAAAGAAATCACTGGATTTCATCAGAATTAGCAACACTTAAAAAGACACTTCTAAGAAAATA
AAAAGGCAATTTATAGACTGGGAAAAATATTTTCAGTATATATAAAGAACTATTCACACCTCTCTAATGA

GAAAACAAGTCAATTAAAGATTTGAGCAGTTACTTCATAAAATAAAATATACAGGTATAGACTAACATAT
GGAAAAACTCTCCACCTCATCGTCATTGGGGCAGTTCTACAGTAAAAGCACAGAGGGTCATCACCATACA
CCCACTGCTGTGACTAAAGAAAACTGCAAATGCTGACAGTGCTGCATGCTGGGGGGATGTGGAGCAGCTT
AGAACTCTCGTACGTTGTTGGTAAAAATGAGAAGTGGTACAGCCAGTTTGGGAAAATGTTTAGCAGATTC
TCATAACGTTTAAGAAAAAAAAGTTTCACTTTTCTATGACCCAGATTCCAAAAGAAATTCATAGCGTCAC
TCATAATATAGAAAACCTAGATGAATCAACTTGCAAATAGAGAAACAGTATGGAATACCTGTGCTGTGAA
ATATCATTCAGCAATAAAAGAAATAAACTCCTGATATATCCAGCAACCTGGATAAATCTCAGAATTGTT
ATACTGAGAGAATGAAGCCGTGTGCAAAAGACCACTTACTGACATGTTCTGTGCATAAAATTCTAGGAGA
AACTGTGTTGCCACGGGCGAGGGCAGACCTGAGAACAAAAGAGCAGAAGGAAACTTTTCACAGGATGGAAA
TGTTCTGCTCTGATTGGGATGGTGGTTATAGGACTGTGTACTTTTATCAACACAGACTTTGAACTGGTGA

TTTTTATTGTAAGTAAATTATTTTCCCAACCTGAAGAAAAATTGTGGAAAGCAGTTCTTAGGGGAAATTT
ATAACAAGTAAACGCATATAATAGGAGAGAAGAAAAGGTTAAATGCAGTCACCTAAACTTTGTTCTATTT
TAAGGAGCTAAAAAGAAGAGTAAGTTAAACTCAGAGCAAGTAGAAGGAAAGAATAAAGATAAATGCTAA
TAAAATCTAGGAAACAGAACAGAAATTAATAGACCCCAAATCTGACTTTTTGAAAAAATTAACAAAATT
GATAAATCCCTAGCCAAACCACTCAAAACAAAGGAACACAACTTATCATCATTAGGAATGAAAAGGAATT
AAGGAAAGGTTGTCATAGATCCTACAGGCATTTAAAGAGTATTATAACAAAGAAGGGCTTCCCTGGTGGC
TCAGATGGTTAAGAATCTGCCTACAACACAGGAGACCTGGGTTCAATCCCTGAGTGGAAAAATCCCCTA
GAGAAGGAAATGGCTACCCACTCCAGTATTCTTGCCTGGAGAATTCTGAAAGATGACTGCCAGAAAAGTA
GAGCTCATCAATGAATTTGGTAAAGTTGCAGGATACAAAATTAATGCACAGAAATCTCTTGAATTCCTAT
GCACTAACAACAGAAGATCAGAAAGAGAAATTAAGGAAACAATCCCGTTTACCATCACATCAAAAAGAAT

AAAATGCCTCAGAATAAACCCACCAAAGGAGGCGAAAGACCTGTACTTAGAAAACAGTAAGACACACTTG
AAAGAAGTCAAAGGTGACACCAACAGATGGAGAGAGAGACCATGTTCTTGGATTGGAAGAATATTGTGAA
AATGACTGTACTACTGAAAGCAGTCAACAGAGTCAGTGCGATTCCTATCAAATTGCCAGTAGTATTTTC
ACAGAATTAGAACAAAAATTCTTACATTTGTATGGAGACAAAAGATCCCAAATAGCCAACGCAATCT
TAAGGAAGAAGAATGGAGCTGGAGAATCGAGCTCCCTGACTTCAGACTATACCACAAAGAGATGGTCAT
CACAACAATATGGTACTGGCACAAAAACAAATATGGATCAGTTGAACAGAACAGAAAGTCCAGAGATGAT
CCAGGTACCCTATGGTCACCTGATCTATGACAAAGAAGGCAAAATATACCGTGGAGGAAAGACAAGCTCTT
CAGTAAGTGGAGCTCGAAAACTGGCCTGCTTCATGTAAAAGACTGAAATTAGAACATTCCCTAACACCA
TACACAAAAATAAGCTCAAAAGGATTAAAGACCTAAATTTAAGGCTGGATACTACAAAGCTCTTAGAGGA

AGACATAGGCAGAACTCTCTCTGACATAAATCACTGCAAGATCTTTTTCAATCTACTGCCTCGAGTAATG
AAAATAAAAATAAACAAATTGGACTTAATTAAATTTAAAAGCTTTTGCACAGCAAAGGAAACCATAAACA
AAACAAAAAGACAATCCACAGAATGAGAGAAAATATTTGCAAACCAAGTGACCAACAAGGGATTAATCTC
CAGAATATACAAACAGCTCATGCACTTCGATGTCAGAAAAACAAACAACTCAATCAAAAAGTGGGCAGA
AGATACTAATCAGACATTTCTCAGAGAAGATGTACAGATGATCGAGAGGCACATAAAAACATGCTCAACA
TAACTAAGTAATCCAAACATCACTAGAAAAATCAAATCAAAATACGATGAGCTATCACTTCACATTGG
TCAGAATGGCCATCATGAAAAAATTCAGCAAACAGTAAGTGCTGGGGAAGATGTGGAGAAAAGGAAACCT
CCTGCACTGTTGGTGGGAATGTAAATTGGTACAACCATTATGGAGAACAGTATAGAGGTTCCTTAAAAAA
CTAAAAATAGAGCTACCCATGATCCAGCAGTCCGACTCCTGGGCATGTATCTGGAGAAAAACATGATCTG
```

TABLE 3A-continued

SEQ ID NOs: 1-2, BOVINE EXT2 AND ALX4 GENES

AAAGGATCGCACCCCAGCATTCATTGCTGCACTGTTTACAGTAGCCAAGACATGGAAGCAACCTAAATGC
CTATTGTCGGAGGAGTGGATAAAGATGTGGAGAGATATATATACACACACACATATATATTTTTTTCCC
ACATATTTATGTGGAGGCAGAGGACGGGATGGTTAAATAGCATCACAGACTCAATGGACATAAGTTTGAG
CAAACTCTGGGAGATAGTGGAGGACAGAGGAGCCTGGCCTGCTACAGTCCCTGGGGTCTCCAAGAGTTGG
ACACAACACAGTGATTAAACAGCAAAGTATCACTGAGTTAGTGAGTCACACCAATAAGGACATGTAGTTC
GTATCAGTGCAGTTTTCCCCATACCAGGCCAGCTGTAAAGATCATGTAGTTCGTATCAGTGCAGTTTTCC
CCATACCAGGCCAGCTGTAAAGATCATGTAGTTCGTATCAGGGCAGTTTTCCCCATACCAGGCCAGCTGT
AAAGATCATGTAGTTCGTATCAGTGCAGTTTTCCCCATACCAGGCCAGCTGTAAAGATCATGTAATTCGT
ATCAGTGCAGTTTTCCCCATACCAGGCCAGCTGTAAAGATCATGTAATTCGTATCAGTGCAGTTTTCCCC

ATACCAGGCCAGCTGTAAAGATTTCATTGTGTAACTATTCCATTTTTGCCTCTGTGCCACTCAAACCCAT
TTGTTCAGAACCTCTTTTTGGTGAAGGTAAAAACACCTGAACATTTTGTTTCATATTTTAATATTCACAA
ATAATCCATATAGTCAGGAAAACAGAATCTATACTAATGGTTTCAATAGAATGGATTTAATGTATGAAAA
TTTCTAATACATGGTATTAGAGAGTTGAGAGGGCAAAAAGCGAATACTGAAAATACAAAGAGTTAACAAT
TCCAGAGTGTACCCACCACCCCTAGGATGGGAGAAGCAAAGGAAGAGAAGGAAGAGGTTGGGGTTGTTAG
AACCTGGAAGCATGGAGGAGACGCCCCATCCCACTCCCTTCCTGCCAGAGCTGGGCCTTAGACCTCTGAG
GGGGTGGGCCACTGGCTGCCATTGCTGGTAATTCCACGGGGTCAAGATGAAGTTGGTTCTGCCAGAAGAG
GTTAGAACCACCTGCCGACATGGGTGAAATGCCACGCTGTCGGGGGAAAGCAGGCAAAACAGAAGTAGTT
TCCTTCTCCTTTGCTCCAGTTTTCTAACTTCTATCTGGTGCCCCTGTTGACAGAACCTAACAGGAAGTCA
CCTAGCAAAGGTGAGATGTTTGCTGAGTCTCAGCCCCCACATCACAAGGCAGAATCTAGGGTCTACGAGC

TGCAAGCCCACCACCCCTTTGGCTACTCCACAGCCCCATGCACACCTTTCTCCGCATGTCGCTACTTCCA
CGCAGCAGCAACTTTGTTCTTCCACTGAGAAGATGTAACTATCCTTTATGCAGAGAGAGGCCTCACGTTC
CCCCCCAGAAGGGGAGAAACAAAGTCCCGATGGTCATAATTATCAACGTCTGTGTAATTCCTTCAATGAA
AAGTCTATGAATTCCTTCTGTAATTTAGTCACAGGTCTCCTTAACATTTTATAACTTAATTAATACATTC
CAGGCTTCCAATTCTGGACATGATTGAGCAAGCACATCCCACCCTGTTTCTGGAAAAGAAAGACAGACTG
GTTAGGGTCCTCAGGACTTAAGAGATGTTCCAGCAGTTCCCTTGGATTTTTTTTTTCCCTTCCTTTCTTC
CTCCATTTGTCCCTGCCTCTCATATACCTCAGCCTCAGAGCTAGAGATGGCTATGGCACAGGGACAGGTA
ACATGCTAAACAAACATACAGACAACCATCCTCCACTTTCTCTTGTAAGGGCTGGGAAGAACCCAGAGAT
GCAGATGGAACCCTTCTGACCATACCCGCTTGACGCCAGGCAAACGCCACCAAAGAAGCCAAATGTACCC
CTGCCAGCTAGAGGCTGTGGTTATGGAGATTGTCTACAGAGCCCTGCCATCCATCCCCATCCTGCACTAA

CCGGAGACAGGAGCAGAGACGGTGCTCCTGGCCTGCCTCTGTCCACTCTGGGGACTGTGAATGGAGCCCA
CCTGACCATCCATGTCCTCCATGAAGCGAATGTCAGTGAAGAGGCAGCTGCAGAGACTGTTGCGGGGTGG
GGAGGGAAATCCAGCCTGCACCAGACAAGCAGGCAGCAAGAGGCAGCATCGCATCCCCTCCCAGCTAGAG
TGGAGGGAAGGTCGCGTTAGGGAGGGGTTCTTTAAATCTGTGTGTGAAGTTCCGAGCACACTGGTGCTCC
TCTCCCTTCAAAGCAGCCCTGCATGAAACTGACTCGAACCAACACAAGAAAAGCTATGAGAACTAAACT
GTGGTGTAGAATACTGCCCAGGCTCCAGAGTGGCCGCTGGGTGGCATACAAGCTGGGTAGACCAGAATAG
CCCCAATATAGTCTTTGGAAATTAAATTGATATTCAGCCCACAGCCCACAGAAGTGGATCAGGACATGCA
TTCTGAACCTAAACTCTGTGCTAAAATTGAACACATGCAAGGCAGCAGCATTGCATAGTAACACTCAACA
TGTTCAGGAAAAAATCCAACATTACTCTTCATACCAAGAACCAGGGAAATTGCAACCTTACTGAGAAAAG
ATAATCAATAGTTGCCAACACCAAGATGACACAGATGTTGGAATTCTTGACCAGGATATTAAAACCGCTA

TTTAAAAAAGAATCCTCTAATAAGCAATTATGAGCACTGTTAAGTGGAAAAATAGAAAGTTTCCACTTTC
AGCAAAGAAACAGAAGATATAAAGAAAAACCAGATGGTAATTTCAGTACTGAAAATTTCAGTAACCAAAA
TTTAAAACTTGATGGGCTCAATCAGTGAATGAAAGTAACAGGAAAGAATTGGTGAACTTGAGGATGAAAC
AATAGGAAGTATCCAGTCTAAATAGCACAGAGAAAATAGATTGGGAAAAAAAAAAAAAGTGAACAGACACT
CAGGGACTGTTGGGACAGTCACAAAGGATATGACATTCATGTCATCAGAGTTGCAGGAGAGGAGAAAAAA
TGTGGGGCAGAAAAAATATTTGGTGAAATAATGGCTGAAAGCTTGCAAAATTTGTCTGTAAGGTCATTAA
ACTTATAGACTCAAGAAGCTGAGGAAACCACAAATATCCAAAGAATAAGTTGTATAAAGTATGTACCTTG
TATGTACCGAGTAAATCCTGGCAGTAATTCTTGTATCAAATAGTCATCGGAAGAGAAAAGGAGACAAATA
AATTGGGATGTATATGCATAAGGAAAGAAGAAAGGTTCATGGCTGCTACTTTCTTGCTTCTGCAGCTTGG
TCCTGAGCAGCTACCCATCTCTCCCTTTGTTCTCAGCCAGCACTCTAGCAGGTGCTGGAAACTGGGTTTA

CAGACCCAGTTTCTTCAATGGCTCTGGTACTATTCAGACTCTCCATTTCTTCTTGTGTTAGTTTTTTTGA
TAAGTTGTGTTTTCCAAGGACTCCGTTCATTTCATCTAAATTGTAAATGCATTGCTATAAAATCATCCA
TAACATTATCTTGTTATTGTTATAAATTCTATAGATTTTGAAATGATGTGTTCTTTTTCATTCTTGATA
ATTTTCATTTTCTCTCCTTTTCTTGATCAGCCGTGGTGAAGGAATGTCAATGTCATATTCTTTGCAAAGA
ATCAACTTTTGATTTTGTTATACACTTTTCTTTAGTGTTGCTTGTTTTATATTTAGTAACTATTCTTTT
CTTGATTAATCTCTTCCTCAGTTTCAGGAGTTTAAGTTGCTGTTACTTTTCTAACTTTTTGACTTGATAG
TTTAGTGATCTCAATATTCAGTTTTCTAATATATGCATTTCAAGCTGTAAATTTCTCCTTAATTAGGGCT
TTAGGTACCGTTCCAGGTTTTGACTTGTTCTATTTTTATTATCAAGTTTAAAATATTTTCTAATTTCTGT
TGTAATATCTTCTTTGACCCATAAAAGCATTAATATATTGCATACTTTTGTCAGTTTTTAAAATTATGTT
CTTATTGATTTCTGATTTGGTTCCACTGTGGTCAGAAAATGTACTGCATATGATTTCATTGTTTTGAAAT

TTATTGAGTCTCTATGGCTCAGTAAAAGGTCTATTTTGGTAAGTGTTCCGTAGGCCCCTGAAAAGAGTAG
ACATTCTGCAGCTGAAGATTTAATGACCTTAGTAGGTCAGTTAGGTAAGGTTAGGTACATTGGCACCTTG
AATATAATCAAAATTTTTTATTTGATTATTTTTATTCTTCTCTAGAATAGGCAACTTCGTTTCTTCTGAT
TTGGTTTGTTTGTGTGTGTGTGTGTGTGTGTGTAGCTTTTGTCATTTCTGTAGTAGTTACAATCAC
AATCTTCTTTTAAATGAAAAATGGTTTAAACAGTACTGAATATGTGGGAATCAAAGGGGAACCATGCGGC
AGACCTTTCTTACTGTGACTCCAGAGACAGAGGCGCCTCCCACTTGGGAATTTTTCCGAAAGGGGCAGCC
AGCGGCCCTCCAGCATCCAAGGTGGTTTTACTAGTCCTGCCTGGGACCGAAAAATAGGCCAGATGACTTC
CCCCAATCCCTCAGCTGTAATGAATCTAAGAGATCAGAAGTCAGGCAGATGTGTAAGGTGGGGTTTCATG
TGAAATAGTATCCAATGCTATGCGTAGGAAGTGTCAGACTCCCTCTGAGGACCCAGGGGTATTTGGAGGT

GGTGCCAGCAGCACGTTAGGAGTGGAAGGGAGAACTGGCCGCTGCCTTAGCGGAGGAGAGTGTGGTGACC
GGGGCCTGTTTGGATCATGGTTCTGCTGTCCCTCTTGAGACCTAACACGCAGGCTCAGGCCCCAGAGTCT
CTCACAAACCACAGGGCAATCTCACAAACAAGCATGTCTCTCACCAACCGGAGGGCATTTTAAAGCAGAG
CTGCTATTGGAGGGTTGGAAGCATCACTCCACAGAGTGGTTTTAAAGCACCAGGCTCCACGGGTTGCTTA
AGGGGCTTGGAGCAGAGGCTGAAGGCAGCTCTGTGATGGCACACTCCCTGCCTGAGCTGTGAGAAAGAAA
GGCGGCCCCATGCAGGGATGAAAGAGCAGTGATGGGGAAGATCTCTGCTACCTGGGCTGTTAGCTTGAA
ACCGGTCAGGACCTCTGGAATCCCTTGGCAGTTGTTGGAGCCACAGCAGTGCTCAGCCAGCCTCTGTGAA
ACCGTAGCTCACGAAGGGAATGTTGAGGCTGTCCCAGGATCCGCCAACAAGGCTGCTGCACTGACCTGGT

TABLE 3A-continued

SEQ ID NOs: 1-2, BOVINE EXT2 AND ALX4 GENES

```
TCAGAGGGGATCCGAACCTCTGTGCGGCGGGCTCCATTCATAGCGCCCCAGGCAGAAAGCTCTCTGTCTT
GGTATCAGAATGGGAAGGGAACCTTGGAGACCATTCAGTTACTTCATGCTTTATTGCTGAGAAAACTGAG
ATGTGAAGAGGTTAAGTTACTTCTCTAAGGTGTTAAAAGTACGTTGAATATAACCCTTTAAGGGACACCC
TAGCACGTTCTTGGGACTGAAAGGCCAGATCCTGTAAGAAAAGGCTTTTTTTTTTTTCCTTCCAGTGTCTG
TGACTTGAGTACACAGACATTTGGATTAGGCAATGGCACCCCACTCCAGTACTCTTGCCTGGAAAATCCC
ATGGGCGGAGGAGCCTGTTGGGCCGCAGTCCATGGGGTCGCTAAGAGTTGGACATGACTGAGCTACTTCA
CTTTTCACTTTTCACTTTCCTGCATTGGAGAAGGAAATAGCAACCCACTCCAGTGTTCTTGCCTGGAGAAT
CCCAGGGACAGGGGAGCCTGGCGGGTTGCCGTCTATGGGGTCTCACAGAGTCGGACACAACTGAAGTGAC
TTAGCAGCAGCAGCAGCAGCAGCCTGGGTATCATTATTCATTTAATTGGAAGAAAACACAGGGGTCATTT
GCCTGTTTAAATGGGTCGTATTCCCTGTTGGAAGGCAAAGAGCTTTGGGAAATGTCACATTCTCTAGCCA

GCCCCGAAATCAGAAGCAAAGAGTGATCTTCTCTGGCCCTGCATGTTTCTGACTTGTTTGACAAGCTCT
AGTGAGCTACCAGATGTGGAAATTCTTTTCAGCCTGGGATAATTTATTTATCTGTTTATGTATTTTACCA
GGAAAGTATCTATTGAGTATCTTGATACTCATTTGCAAGGAGCTCCTGGGGGAACAGTAGCAGTGTATAG
TGTTACTCGAATGTTTGATTCCCCCCACCCCCGCCACGTCCGTCTGCTTTTATTTCAAACCTAAAGAGC
TGAGAAATAAAATGCAACTTGTTCCTCCTCCCCTCCCCCGCCTTTCAGAGAGGCCGTTTAAAACATGTGG
CAGAAAATGAGCCATGCAGACTTGGCTGGCTGTATGAACCCGGGAATTTATTTTTCCTTTCGTACTTTGA
TCCTCATTTCCAACCATAAAAATTATTAGTAGCACTTAAGTGTTGAACATTTTTCACCTGAGAGATGTGA
AACACTCCTGGCCAATAACACTGGTTATAAAGTCAGTCGTTCACGTGGGGCTGAGAATTGACTATGAGCA
GCCATGTACTGTTTTGTGCACAAAGTGCTGATCCCTTCCTCTGCTCCTCTGCATCCCATAGGTGGCAGCC
TCTGGGTAAACAGCTTGGGCGCTAATAAATTATGAGAATTTATCTGTGTTATTTTGTCCACAACTCCACA

AGGTGATGGCAAGTAAAGAATCAGGAGAAGATAGCAAAATAGTGTGGAAGGCCCCACTTTTTTTTTTTCT
TGAGGACACGAAACCATCCCGAGTGGGTTTTCCTGCTGTAGAAGCACCAAGAGGGAAAGCACCTAAGTTA
GAACACGCTGGGTGAGTGTGGGCGCATGGGGGACTCCAACGTCGATTGACGTGGTGGGGACGGAGCTTGC
GTTTGGGTTGACGTCGGAAGCTGGGTTGGTTCACCCACGTAGGGCCAGGTGATGGACAGGCTAAGAGGTC
AGCTGAAAAGTCGAAGGCAGTAAAGAGGTGTTGTAGGTTTGCAAAGAGGTATCTGGTCCAGGCAGTGAGA
TCACAGGATGAATTAGAGGTGACAGGTTGAGACAGGAAACGCCAGTTGATAATGGTCGTGGTAGCTTAA
TGTTCATCTGGGTTGAAGAACGAAGGGAGAAGGGAAAGACGGGCGCCGCCAGGGCTCGAATTTGATTGCT
GATGAGGGAGCTTGGCTAGTTGGAGAATTCCAGAGCTGAGCCTCTAGTATCTAACAGTTACATTTTAAAT
AGAATCAGTTAACTTTAAAGGTCTCTATATATTCATCCAGGGAAAGATGGTATATTCTGGGATTCTAAGT
AAACTATCCCACTTTTTCTCTTCTCACTAGAAGAACAGAAAGATGGAAACAACCTATCATAGACTTCATA

ATAACCTTTCTAAAAAGCTGGTGGGTAACTTTTAAAGAGGAAGAAAGTGTCACTGTCCTCCTGTGTGCCC
CCGCTGAGCCGCCTGCAGCGTCAAGACCGCAGACACCGCGTCTTGGGCTGGGTCTCACAGACCTGTGGCT
GTGGTCCTTCCGACGGAATTAACTGCTGTCCTTGCTAGACTTCAGCCCTAGAGTCCTAAATCTGAAACTG
TGCTCAAGAGTTGTTGGGAATCCAAGGAGGGTTTTCTTTACGGTACTTGGAGCCACCTGTCTCATCCTGC
CGTGGGCCCTACAGCAGGCCCCACCACACCCTGTGGTCTCACCTAGGGCACCAAGAAGCTGGGTTCTTAC
AGCCCGCACGGATGAAAACAAGGCCTCCCTGAAGGAGAGCCCAGATGCAGATAACAGCACGCAGTGGGAG
CCTGCGCCACGGGTTCCCATCCCTTGGCACATGGTCTGACCCAGTGGCTGCCTGGAAGGACTGGGGGCCC
GGGTGTTCCTTCTCCTCTCCGGATGATGGGCTGCAGCGGCAGCGCCCCGTGGAGCCCGTGCAGGAGTCGG
TCCACACGGCTGCTCAGGCGTCCCAGCGAGCCAGGCCTGTCCCTGTCTGGGACATGGGCAAAATCGAACC
TTGCTAGAGCGGTTCTGGATCAGCATTCATTTGTACTGGGTCTACACTAAAGCTTTACAATAGCTAGATC

CATTTTGCCAAAACTGAGCTTTTTTTTGGAATGTAATTGCTCTACAGTGTTGTGATACTTTACAGTGTT
GTGTTAGTTTCTGCTATACCACAACATGAACCAGCCATACACACACACACACACACACACACACACCCTC
CTAAGAGCCTCCCTCCTACCCACCCCGTCCCACCCCTCTGGGTCCTCATGGAGCAAGAAGCTGAGCTCCC
TGTGCTATTCAGCAGCTTCCTGCAGAAAGCTGAGCTTTTTGAAAACGAGAAGCTGTCTGGGACTTGCAGT
GACTTCTCTATTTAGGGTCTGAAGAAGCTGGTGACTGGAAGCTGTCTGTGAGCCTTGTGTGTTACATCCG
AGTGGGGACAGTTCTCCCCGGAGTGCCTTTCTTGGGCCTGGCCGCCCTGCAGGTCAATAGAATGCGGAC
TGTTGAAAGGACATCTGTCTGTCCTTTTCCTTTCCTTTTCACGTGAAGCGTTGCCTTTATAGAGACT
GTTGTCTCGAGACAAGAGAACGGGGTGGAATGGAAGGACCCACTGGTGAGGGAGTGACTCGTTCTGTGAG
GGTCCCTGCCCACCAGGTTCAGTCAGGAGACCCGAGGAAGACTGGGGTTGGAGGGAGTCGTCCTCCCTAG

AGCATGACCTCCTTGGGGTCCTCGCCACATCGCTTCAGGCTCCTGGTCTCCAGCCTGTAGGAGCCCTGAA
TCCTCTGTTAGGCCTATGCTGTCTCCAGCCTGCACTGATTTGCACCCGGACTCTCGGGGCCTGGAGAGAG
GCTAGTTCTCAAGTGCTGCGCTGTGCACGAGCTGCTGAAAGCAGACCCCAAGCAGACCCCGGGCCCAC
GGAGGTGCTGAGAGAAGCTGCCATGAGGGTTTGACCTCTTGGAGCTTTCCTAAAGCACCCAGTCCCCATCG
GAGAGTAAGTCAAACAAATATTAAGGGAAGGAAATCGAATATGTCTGCTGAACTTTGAAATAACATCTGA
TGGTTTAAAAAAAAAAAAAAGCACCCAATTGGGAATTACAATAGAGTGACACTTTTTCCTTCCCCACTGA
GCAGAGTAAAACAGCAGGCCCAGAATTTGTTTGCCTAGCCGTTAATGAAACAGTAAATGGAGGACTCGGG
CCCCTTATCCCGAAGAGGAGGGCGGTGCTGCCCACTGGCACGTCCAACCACCGAAGGGCGTCTCCTCGCA
GTCTCCCATCCCAGAGAGGTGATTTCGCGGTTGTCCGTGGAGCTCTGTGCCGGTGAGGGAAGAGCTCGCT

GACCTGCCCACTCCCTGCCCTCTGTGCCCCCGCGCGCCCCCCCCCAACCCCCACCTCACCATCTTTTC
TGTCCGCAGCACTGGCAGGCCCACCTGGCTCTGCAGTTCTTCTGCCTCAAAAACGAATGCTTGTAATGTGG
AATCGTTATTTTAAAGAGGTGTTGGTCCACTTGATGGTTTAAAGAATCCTTTCCCTCCCCCTGTTCTAAA
GGAGATAACTGTCATGATATTCCAGCCCTGAGAGGATCCATATGTTTGCGGGTTATTGTTCCAAAACCTG
CCTGTTGTTTCTTTGGGATTGATTACAGACCTTGGCTGCCCCAGGAATCCAGAGCTTCAGAATTTGGTTT
ATGATTTGGGGATAGGGGGAATTTGTCTTGCATGGGCTGCTTCTCTGCCTTGATTTTGATGGAGATGCTT
AGAGGAGGTGTGTGGGCAGGACTTGGCATGGGACCAGGGGAAATGAAACCCACCACAGCTCTCTCAGGAG
GGCAGTGCCCGCAGCCTCCGAGCAGGATTCTGTGGTGTGGTTCCTGAGTGTGAAGCTACACCATTCATCG
CCAGTTATAAAGCTGCTTGCAAAGTCAGGACTTGGAAACAGTGGTTGGTGGGTGTCATTGCATTAGACAG

AGCAATTCCTGGTTTTGAAAGAATAGAAAGAAAGAAAACTTTAAAGGAATGGAATACTCCCCTAATCTTA
AACATGTCACACCTGGGAGAAGGAATCTCAAGAAAGCAAGGTGGCCAGTGGGTGTGGATATATACAATTCA
CTTCTCAGATCAGATTTATTCTCGGTGCTCCAGAATTGGTGTGTACGGTTCACGTACGGTTCACACACG
TATAATCGTGATTATAACTGCTACTGTCTGTTGGCTGCTTTAGAGTAAGAGTTGGCAGCCTTTAAAGTA
AGATTTCTAGGATCCCATCTAGACCTTTGGGTTGGGCTGTAGATTTGAGAGGTGGGGCAGAGGTCCTGAT
CACATGTGACACTACCCCTAGAGAAGGAAGGAAGGGGCTAACTTCTTATAACCAAGGTCACTAATTACA
TCCACGATATAGATCTGGGCTAGACTGACAAATTTCCCTTGAGCACGGCCCGACCACACAGGCCTGTCCG
CCTGCTTTGCTGGTGTCTGCCTAGAGCTTGACACATAGCGGGTGCTCAGGAAATACTTATTGACCGAGTG
GACTTAATGTGATTGGACATTGAATTTTCTTTTATATAGTTTCTGTGAGTGAAATTATAAGGTGTTTTTC
AAAGTTAAGTGATTCCATATTTTGTATTCAGGGGGAGATATCTGGTCTTCTCTGTGTTAACCTGCTAAAT
```

TABLE 3A-continued

SEQ ID NOs: 1-2, BOVINE EXT2 AND ALX4 GENES

AGCAAAGAGTAAAACTTTGTACTAATTATTTATCTGATTGAGGGAAGTGGAGATCTCAGCTGAACTTTGT
AATTTAATAACTTTCTTTTCCTTTCTCCCCTTAAAATTCATGAAGCTTTTTCCTTCTTCCCGCTTTACCA
CCCCCGACTTAACTCTTTTTTTGTTGTTTTTTGTACTTTTTCCTGCATGCTTACCTTATTTCATCTTCA
GTTTTTTAATGTATATGTCATTAGTTTTTCTAAATAGTAAGCTCCTTAGTAGCAAGATATATGTGTTATT
TTTGTATTCACTCTTTGAAGTGTAATTCAGTCCCTAAAAATAGTTGGGGGCAGCTGATTTTTGCCCAAAG
GTGCAAATGCAATTTGGTGGAAGAAAGACAGCTCTGTTACATGATGCTGGACAAACTAGTCATCCGTAGG
TAAGACTTTAACCTTGACCTAAGCCTCACATGAAATTAAAAGACGCTTACTCCTCGGAACGAAAGTTATG
ACCAACCTAGATAGCATATTCAAAAGCAGAGACATTACTTTGCCAACAAAGGTCCATCTAGTCAAGGCTA
TGGTTTTTCCAGTAGTCATGTATGGATGTGAGAGTTGGACTATGAAGAAAGCTAAGCACCAAAGAATTGA

TGCCTTTGAACTGTGGTGTTGGAGAAGACTCCGGAGAGTCCCTTGGACTGCAAGGAGATCCAACCAGTCC
ATTCTAAAGGAGATCAGTCCTGGGTGTTCTTTGGAAGAAATGATGCTAAAGCTGAAACTCCAGTACTTTC
TTTGGCTACCTCATGCAAAGAGTTGACTCATTGGAAAAGACCCTGATGCTGGGAGGGATTGGGGGCAGGA
GGAGAAGGGGATGATAGAGGATGAGATGGCTGGATGGCATCATTGACTGGATGGACGTGAGTCTGAGTGA
ACTCCGGTAGATGGTGATGGACAGGGAGGCCTGGTGTGCTGCGATTCATGGGGTCGCAAAGAGTCGGACA
TGATTGAGCGACTGAACTGAAGCCTCACACCTTATAGAAAAATTAACTGGAAGTGAATCATGGACTTAAA
TGTAAAACATAAAATTGTGTAACGTTTGGGAAAAAAGTTGAGAAAAATCTTTAGGATCTAGGACTAAACA
AAGAGAAACATGATTCATAAAAGGAAGAGTTGGTAAATTAGACCTCATCAGATTTTAAAACTTTTGGGCT
ATGAAAGGCTTGTGAAGAGGATTAAAAGAGAAGCTGCAGATTGAGACAAAATATTTGCAAACGATATAT
CTAACAAAAGACTAAGCATCTAGGATATATAACTCTCAAAATTCGGTAGAAGAATTCAGTAGATTAACAG

TAGAAGACGAACAGTCCAGGTGGAAAATGGACAAAGGACAGGAGCAGTGATTTCACTGAAGAGGATATGC
AGATAGCAAATAAGCCCATGAAAAGAGGTTTGGCATCCTTAACCATTAAGGAAATGCAGATTAAAATGAG
AATTATGTAACACCTGTCAGAATGGCTAAAATTTTGTTTTAAATAGTGACTACAGATAAAGATGCAGAGA
AACCTATTGAAGACGCTGAGAAACTGGATCTCTCGTACATTACTGGTATGAATGTAAATGGTACAGCCA
CTGGAAAAATAATTTGTTCCACTTCTTATAAAACCAAGCATGCAACTACCATACGACTCTGCAGTTGCAC
TCTTGGGCATTTATCCCAGAGGCAGTAAAATTTATGCCTACAGAGTGGGCACAATGAATCTTCATAATAA
CTTCATTTGTAGTGCCAAAAAATGAATCAGCCCAGGTATCTTTCGTGAATGAATGGTAAACCAACTGTGG
TACACCCACACCGTGGCATACCACTCACCAGTGAGAAGGCACAAACCGCTGACATGGTACATCCACACCG
TGGCATACCACTCACCAGTGAAAAGGCACAAACCGCTGACATGGTACATCCACACCGTGGCATACCACTC
ACCAGTGAAAAGGCACAAACCGCTGACATGGTACATCCACACCGTGGCATACCACTCACCGATGAAAAGG

CACAAACTGCTGACATGGTACACCCACACCGTGGCATACCACTCACCAGTGAAAAGGCACAAACCGCTGA
CACACAGCCACTTAATCCCAAAAGGGCATATGCTGTGTGGTTCCACTGATACACAGCCTTCTTGAAATTA
TGAAATTGTAGAGACAGAGAACAGATTAGCAATTGTCAGAGGGAATCTGGATGGGGAGGATCTATAAAAG
GTCAATAGGAGGGACCCTCGGTGATGGCAGTGCTCTGTATCCTGACTGTATCAGTGTCAATATCATGTGG
TTAAGTCACACTGATGTTTTGCAAGATGTTACCATTGGGGGAAACTAGGGAAAGATCCAGAGAAGGCAAT
GGCACCCCACTCCAGTACTCTTGCCTGGAAAATCCCATGGGCAGAGGAGCCTGGTAGGCTGCAGTCCATG
GGGTCGATAAGAGTCAGACACAACTGAGCGACTTCACCTCCACTTTTCACTTTCATGCATTGGAGAAGGA
AATGGCAACCCACTCCAGTGTTCTTGCCTGGAGAATCCCAGGGACGGGGGAGCCTGATGGGCTGCCGTCT
ATGGGGTCACACAGAGTCAGACACGACTGAAGCAACTTAGCAGCAGCAGCAGGGAAAGATCATACAG

GATCTCTCTGCATTATTTCTTACAGCTACTTTTGAATCTACAATTATCTCAAAGCAAAATGTTGAATTAA
AAAATCGTGAAAACTCAGTAAGTATCCAAGGGTTAAATGTGTAAATGAATTAATAAATAGGAACACTCAA
ATTTCTTCATCCCTATACTATGACTTGACTTTGCTGTGGGATTGCCTTTCTAGCACTTCATAGCAGGATT
AATATCTCCAAGATGGGTGGAATACCATCTTACAATTCTTGAATTTTTAAAGAAAAGCTGTTGAGGGCAT
CATCTGTTTTGATGGTTTGGACTTTATTCTAGTTTTTGCCTTTTGTAGTAAACTGTCCCAAATCATTTTT
GGGGATGTAGATGGGGTCGAAATAAATAAGGAATTTAAAAGAGTTCTTCGGCTTCTTGATTCTCCACCAA
GATATTACGGAGTTTAGGCACATAAGGAGGGGACTATGGTGGATTAAAGAATCAGTTCAGAACCACATTT
ATATTTCAGAGTCAGCCAGGATTATAGTTTGTGGTCAATGCCGTTTCCTTCCTTTGCACAAGAAGAAGAC
AACAAGCCTGGCCAGTTCCACCGTGTCTTCTGTGACAGGAGAGTGATCTGAGTCCCCAGGGCAGTGGCTT

GAAGTCACGAGAGTTTCTCTTGCTGGATGGAGCTGGTGTCTTTAGTCCCCAGTCAGTCAAAGCAAGCCTC
ACCAAGATCAACTTGAAATTTTGAAGGCTGGGTAATGGTTATTTACATTAGAAATAGAAGCTGGAGTGTC
TGTTTATACCTCTTGCAGGATTTAAAGAGAATAGCCATTTGGCTTATGATCATTGTTCTCCTTTTAGCTT
CATTCAGTAATCCCTGGGACTAGACTTAGAAACAGTATGACCCCCACTGGAGTTGAGGTTATGGAAATA
AAAATGATTTCACGTTTAGTAGATCTTAAGGAGCGCAAAATTTGAAAACCCATGACCCAACGCTGACCCG
TGTCTTCCTCCTCCCATCCCCTCAAACTCACATCACATCTCCCCTGCCTTTCTGTATTCTTTCTCAAGAG
ATTCATTGCCTCATGAAAAATACGCATTAAGTTTAATCTTCCGTTCAGCTGCTCTTTGCTTGTCCTTCCC
TCCCGGCCCCAGAGTCTCTGGGTCCCAGGGTTCCAGTAGGTGCTCAGGGGTCCTGCGTGGCATCTCACTC
ACTTGCTCTGCAGGCTCATGCGAGTTCCTTCTCTCAGTGGGTGAGCCTCTGGCTTTCTCTGCTGAATGGA
AACCGCGTTTGCGACGAGCCTCAGGCTATCAGAAGACAGCGCTGAGGGGAGCAGAAGGTCTTGTTGTTTT

CCCCGCCACCTCTCTCTCCCTGTTCTGTTCCCTCCCTGCTCATTCCGCCTGCATGTGGGACCCGTGACCA
TCTCTGCCCCCAGCTGAGCACATTGACACTGGTGTGACCTCAGACGCCGTCACCTGGCTTCCTTGACAAG
TGAGGGTCTGAGCTGGGGAAGAGGAGGTGCTTTTTAGAACCACGAGAGCAGGCGACCACAAGACTTTAAG
AGCAGAGGCCGGACGGGAAGTTAGGCGGGACCATGTGGTGTGACCTCGGGACCGCCGCCTCCTCTCCAGC
CCTCATTTCCCATCTGTCCAGGGAGGGGATACCGGACCAAGTGACCTCTGCCGTCCTGGTGACCCGCGAG
TTAGTGTGGACGGGGCTCCACAGCTCAGACTGCTGGAGCGTGAGTCTCTCCTTAGCATCCACCAAAGGCC
TGTGGGCCTCCGTCCGGGGAGAGAGTGACTGTTGGAGCCCCCTCCTCAGTGTGTATGCATGAGACTCAC
TCAGTCACGTCTGACTCTTTGCAACCCTGTGAACCGTGTGTGTGTGTGTGTGTGTGTGTATCACTC
AGTCGTGTCCGACTCTTTGCGACGCTATGGACTGTAGCCCACCAGGCTCCTCTGTCCATGGGATTCTCCA

GGCAATGATACTGGAGTGGGTTGCTGTTTCCTCCTCTGCCTCTCCAATGATGCCCTCCTAACAGTGGTAG
TGGTGAAAGGTTTACTGGCACACAGTCCTCTTACCAGCTGTGGCCAGCCCTGGTCTGTCTCCTTAGCTTC
GCCACTGCCCCAGGCCTGATGGAAGGGCTTGAGAGGAATGGTGATCATGTACCCCAGCGCCAGAGCACTG
CGTCCAGCCAGACTGGGGTGAATAGGGCTGCTGCCAAAACCCAGAAGCCTCATGGTGCTGCTCTTGCTTT
GGCTTATTTTAAGCAGAACCCCACCTTGGGTTGGAAAGGTCTCTGGGGCAGACTGAAGTGATCTGTCTAA
TAACAGGTAAAGCTTAATACACAACGCAGCATGTACATGAGTTTGTCAAAACCCATCAGCATTAGGGCAC
TCCAGATGACAGCTTCAGGGCTCACCGGCTCTAGGTGCCCAGCATGAACATTTAATGGTGTTGGTGATGG
ACAGGGAGGCCTGGCGTGCTGTGATTCATGGGGTCGCAAAGAGTCGGACACAACTGAGCAACTGAACTGA
ACCGAATAACCACCCTTGACGAAAAGTACCATCCGCCATTGTAATTAAAAGCATGAACTGAAAACAAGGC

TABLE 3A-continued

SEQ ID NOs: 1-2, BOVINE EXT2 AND ALX4 GENES

```
CAGTCAGTCCCTCCATTCCACTTCATCTCAGGAAATTCCAAATATAAAAGGTGAGCTTTGTTCCCAGAGG
GCCGAGAGTGAGTCCAATAACCAGCTCCTCTGTGGAAACCAGCTAGAAATTGGAACCCCGGCAGCCTCCC
CCTCTCCCATCTGGGGAGCACGCAAGACAAGCCCGACGGGAAGGATGGCCACTAACTCCGAGGTGTTCGC
ACGTCGGGTTCCTCGCAGCGCTGCCCTGACTCGCCTGCGCACGTGGCCGCAGGGTGTGGGCTGGGTCATA
GCGTTCTGTTCCGCTTTGCTGGTCAGGGACTGACACAATCAAGGGGATGTGTGCAAGGAGAGGAATGAAT
CCTAGCCCCGCTTGGGGTACCTTGGGCCCACCGTCCCCGTTTCCCTCACCACTTCTTAGTCCGTCTCTT
GGTTCACGAGTCCCAGTACACGTGGCGTTCTTCTCACGCAGTGGCAGTATCCCTGTGGAGCTCTGCCTTT
GAAAGTGTGATGACTGCAGCGGCCACTTCAGAGAGTCCCTTTCCCCCTGGAGCTAACCCGTGAGCTCCTC
AGCAGACATCCCAGATGGGTGCCACCTGTTGTTATACCTTCCCCACCCCCCCACCTCCCGACCCCTGGGC

TGTTTCCTGAATCTGACTGTGGTTAGCACACACCCTGAGTTTAAAATGCACTCGCTTAGCTGGCTTAGAA
TATAGTGCATTATCCTCTTTTCAGGAACATTTGTTGGGTACCTGTATGTGTATGGCATTTTAAAAACAAA
GTTAAATAATGCAGACCAGCAACTGATCACTGTTGCTGAATTAGTTTCCTTGGAAATAGGTTAGTGGGGA
AGAAGATATAAGAATTTAGGCCTGAAAGTGCATTAGAGGTCATTTAATCCAACCCCTCATTTTGCAGAGG
GCAGAAAGAAATCAGGGCAACTTGAATAGGTCTGGGGCACAACTCATCCATGGCAGAACTGTTCCTAGGT
ATACACTAACCATGTCCTGCGGTGCGTTTTCTATAGGCGGTAGTCAGGGCTGCCTCCTTTGCCTTTTCAA
AAAAGGTAGAACATCTTAGTTTTATCCTCTAGGAGTGGGAAGCCACAAAAGACCTCAGGAAGCTTACAAA
AGAAAAAATATATAAGTAGGTAACTCTGAAAACAGACACATGAGCACAGCTGGACAGTCCAGAGAGGAG
AGGAGATTTCCATAATCCAGGTAAGAAGTGGTTGGGACCAAGATTATAAAAATTAGAACGGAAGGACATA
GGATGGCAGTCTGTTGTTACCATCTTTGTTGGAATAGTGATATTGTAAGTAAAAAGTGAAAGTGAAGTCG

CTCAGTCGTGTCTGACTCTTTGCAACCCCATGGACTGCAGCCTACCAGGCTCCTCTGTCCATGGGATTTT
CCAGGCAAGAGTACTGGAGTGGGTTGCCATTGCCTTCTCCAGGAGATCTCTCCAACCCAGGGATTGAACC
CGGGTCTCCCGCATTGTAGGCAGACACTTTACTGTCTGAGCCACCAGGGAAGCCCTCTTTGTTGGAAGAG
CGATATGGAATAGGCTTCAAATGTAAGGACTGTTTGGATTTCCCTAGTGGCTCAGATGGTAAAGAATCTG
TCTGCAGTGCACAAGACCCAGGTTCAATCCCTAGGTCGGAAAGATCCCCTGGAGAAGGAAATGGCAACCC
ACTCCAGTATTCTTGCCTGGGGAATCCCATGGACAGTGGAGCCTGAAAGACTGCAGTCTGTGAGTCGCAA    TH_MICRO470C
AGAGTAGGACACGACTGAGCAACACACAGACACAGACACACACACACACACACACACACGCATGCACGCACA
AGGACTGTTCAGATTACTGCCAAGCCCCTGATCGAGGTGTGGGGTTTGTTTTAACAGACATGCGCCTCTG   TH_MICRO332
TCTTCAAAGATGTGTGCAATTTAAAATAGATGACACTTTATACAAAAGATGTTGATAGGACAGGCAGGCA

GTTGAATGATGGCTTTGTGACTTGAACATATTAATAGCTCTGGGAGCACTATTACTCCAGCTATCGGGAT
GTAATGTGAAGTTTCAAATGCCTGCACTACAATATATAAAGGCATCTGTTAGTAATGACAAAAGGCTGAC
CCCAGAGCATTTCCCCGAAGTAAAAAGAAAAAAAGTGGAATTAGGGCGGGAGGTGGGGAGCGATGAGGGA
AAGGGGGTTGAAGTCGGGTTCCCGCTCTCTGGCTGGGAAAATGCTTTACTGTATACCTAATCGGGCTTCG
TACTACACCCGGGCTCTGGGAGAGAGGGCCCGTCCCCTTCCGTTCCGCTCCGTTTTGATCCTGCAGTCAG
CTGCAGAGTTATAGATGAAGTGACAAGGATGGTATCTTGATTGCATCCAGCTGCCTGGAGTAAGTCAAGG
GCAGAGAGGCCCCGCCTGAGGAGCCGCGCTTGCCGAAGCTCCAAAGGCGTCTGGGAGCCAGGACACCGT
GGGGCTTTCAGAGCGGCGACATTCAGCGTTCTGTGACCCAGTGTCACCAAATTAAGTGTCCCCAGAGAGA
AGCCTGGTAAGTGGCTTAGCTCACAGGAAGAGGACTGAAATCAAAACAGCCTTCGACCCTAAAACTGAG
CCTGTGTTGTTATCATTGCTGTCAACTAGGGGCTTGAAAAGAAGAACCCCTTGGGAAGGTGATTTCACCT

TCCTTCACATGGATTAGAGAGCTGTGCTGTGCTGTGCTTAATCGCTCAGTCGTGTCCAATTCTTGCGACC
CCATGGACTGTAGCCTGCCAGCCTCCTCTCTCCATGGGGATTCTCCAGGCAAGAATGCTGGAGTGGGTAG
CCTTTCCCTTCTCCAGGGGATCTTCCCAACCCAAGGATCAAACCCAGGTCTCCTGAATTGCAGGCTGATT
CTTTTACCATCCAAGCCACCAGGGAAGCCCAGGAATACCAGAGTGGGTAGCCTGTCCCTTCCCCAGGAGGT
CTTCCCAACCCAGGAATTGAACCGGGGTCTCCTGCATTGCAGTTGGATTCTTTACCAACTGAGCTACCAG
AAAGCCCCAGATTAGAGAGTTGACTCAAATACATGTGGGTGGGGGGAGATGGGATTCAGCTTCTATCCAG
CAGAGGTGCCAACTGAATGGATGCCCCCCACCCTGCCCCTTCTCCTCTACCTTGCCTGTTGCTGGTGCTG
AGTGCAGTTGCTTGTGCTCGTAGCCCTCCAGAAACCTCTTTCATCCCATTGAGACGAATTGATGATGGTG
GTTGTGATGTGGCTTGAACAGGCAGGTGGTTAGTGCCAAGCAGAGAAACCTGGCTGTGCACTTTGGTGGG
GTCTACCCCAGTCTGCAGGCCAGATAGAAGTTAGGACCCACAGCCTGTGTTGTGGCTCCATAATAGTATT
ATATTAATCTGCTGAAATACAAACCCCAGAGTAGAGAGAACACAGCCGCAGCATTATACATCTGAGGAAA

TGTTTGACACTGATTCATTTGTCTGCAGCTATTATGATGACGCCTGTGGCCGATTAGCTCAGTTGATTAC
AACATGGTGTTCATGAGGCCAAGGCTGTGGGTTGGAGGCCTGTTAGGTGAGCTGGTTCCACACAAAGGAA
ACCTCTTTCCGCCATTCCAGACCACGTTCAAGATCCCAGTCAGTCAGACATCCATGAAAGCAGATAGACGATC
ACAAAGACTGGGCAAGAGAGTGTAATGACTCAGCAAATGTCCCTTACCTGCTCCTGGAAAAGCGATTTAA
AACACGTGCTTTAGCGATGGTGAGTTGTTACTGTGGTCTTCTCACACAAAGGCTATCACATTATTACGAA
CGATGACTGGTGATCAGTACTGTTGCAGGCCTCCTTTCTGAATGAAGAAGTGTACTAGCTCTGGCTGTGA
AGAAAACAGGAAGGGGCTTTGGTCCCCTTCTTTCCTGCTCAGCTTTTTCCTGCTGAGGTTTTGCCTGTCC
GTCTGTGCCTTCAGCAGGTGTGCGTGAAGGCTGTCATGTGCTCTGTACTTGGAATGCCACCGTGAACCT
CTGTCCTCATGGAGTTTAAACTCTGCAGGAGGAAAAGAGATAATAAAAAAAATAGATGATAAATAACCAG

TGCAGTTTCATGAAATGGAAGTTTGATGCAGAAGAGCATGGAGTGAGGGGTCTAATGAAGAATGGCTGGT
CAGGGATGGCGTTTACCTTGGATGGAGGGTCTGGAAAGGCCTGTCAGAGTAGGTGATAGTTAACTAGAG
ACGTGACTGATGGGCAGGAACCAGCCTTTTGAAGAGCTAGGGGAACAGCCCACCTGAGAAATAGCAGGTG
CAGAGGCCTTAAGGTCTAGTCACGGTTGAAGGACAGGGAAGCCCCTGACTCGTCGAGAACGTGGTAAGAG
AGAGGCTGGAGGGAGGAAGGCTGTTTAGAACATGCGTAGGAGTTAGCGTATTATTCTTAAGAGGAAGCCA
TCTTTTGTTTTGTTTTATGGGTGGAGCATTTTTTAACGCTCTTGTTAAAGCAGCCCTGTGCTCAGTTGAACA
TGCCTAAAAAAGGTATTCCCTTTTTTACCTTTCACCAAAAGTCTTCCCTGGTGGCTCAGACAGTAAAGCA
TCTGCCTCCACTGTGGGAGACCCAGGTTCAATCCCTGGGTGGGAAGATCCTCTGGAGAAAACAGTGGCA
CCCCACTCCAGTACTCTTGCCTGGAAAACCCCATGGACGGAGGAGCCTGGTAGGCTGCAGTCCAGGGGGT

CGCTAAGAGTTGGACATGACTGAGCAACTTCACTTCTTCACTTCAAAAAGCTGAAATCCTAATCCTTAGT
AACCTTACTGGAAATAGGGTCTTTTCAGAGGTAATCAAGTTAAAGTGAGATTGTTAGGGTGGGCCCTAAT
CCAGTTTATCTGGAATCCTTATAAAAGGAGAAATTCGGACACAGAGGCACACACTCAGAGAAGAAGTCC
CTGTGAAGACAGAGGTTTGGAGTGGTGCGTCTACAAGCCAAGGAATGCCGGAGATTGACAGCCACCCACC
AGGAGCCGGGGGAGGCAGGCAGGATCCTTTCCCCGGGTGAGATGGCCCACCAGCACTTTGACTTCTGA
TTTCTAGATTTCTGTTGTTTTAAGCACCCACTTTATGTTTTAAAGCAGCCCTGTGCTCGGTTGCTCAGT
CATGTCTGACTCTTTGCGACCCCAAGGACTGTAGCCCACCAGGCTCCTCTGTCCATGGATTTTTCCAGGC
AAGAATACTGGAGTGGGTTGCCATTTCCTACTTCAGGGGATCTTCCTGACTCAGGAATCAAACCTGCATC
TCTTGCGTCTCCTGCATTGGCAGGTGGATTCTTTACCACTGTACCACCTGAAAGGTGTGGGCAGGCGGGG
GGTCCTAGCATGCTGACTTTGGGAAAGCAGTGACGCATCCTCCCTGGTGGGGCAAGCCTCTGGGTGATGT
```

TABLE 3A-continued

SEQ ID NOs: 1-2, BOVINE EXT2 AND ALX4 GENES

```
AGCATGCATGACCATAAGACTTAGATACATGTGGGTAGATAGATAATGAATATATATAAATTAATAGG
ATGGCACCCGCTGGTTGAATTACCCTGTAAAGCATACCCTACTCTTCTTTTAGAAATAGTCCTTTTGGGG
ATGCTCTGTAAATGATGGTTTGGAAGGGCAGGGGTGGAAGCACACAGATTGGAAGCCTGCTGCAGTAACC
CGGGAATCCACAGTGACCTGGTAATGACGGTGGTTTGAGCTGGGGACAGTGTAGCAGAAGCAGTAGGAGG
GCGTCAGAAGTAGAGTCAGCAGCAGCTGCTAGAGGACTGGGTGTGGAGAGAGGAAGAAGGAGGAAAG
GCTGGCCCAGATAGTTTACTGAGGCAGGAAATACTGAGAGGATGGCTTTTCCCAGGCTGTGGAATCAAGA
GTCATGCTTCGGACATATTAAGTCTGAGGTGCCTGTTGTTAATCCAGCTGAAGGTATTAAGTAAGTAGTT
GGTTGTATCAGAAACATTCAGGGCCAGACCTGCATTTAGAGGTCTTCAGAGTCTAGATGGTATTTAAAAA
GACTGAAGCTAGATGTTGCTTGTGGGGAGAGTTTAAGAGGGTATAGCTCTCCGGGACTAGGCCCTCAGGA

ACTCCACTGTGTAGAGGTCTGGGCGAGGATGAGGACTCCGTGGTGCTGAGCAGAGGCTCCAGGACAGCTG
GTAAATTGTCAGTATTCACTAATGGTTAGTAGTTTAAAGGCTAAGGAAATTGTATGGAAATACATGGAGG
AAAGTACTGGATGTACCCCACCCTTGTATACCAATTCTGTTTAACAAAACTATATCTCAGAGCCTTTCCA
AATGTGGAAATAAAATTTTTGTTTTCAGTAAAATCAGGCAACATCTCTATGCCTAAGGCTTCCAAAAGAT
CGTAAAAAATGTCTTTGTGCTCCAGATAGGTTTTTTTTCTTTTTCAGAAGCAGAGACTTTGTAAGTTTCC
ACAATCATCAAAATTTACCATAAATCATGGTTTCATTTATACTTCATTTGTGCGTTCATTAAGAGTGGAA
CCTATTTCACTAATCGCCTGTTGAGAGATTACATACCTTGGCGCAATTCAAGAAACTGTTAGTCTACATT
ACTTGAAATTTCCAAATACAAACCCGAAAGTTTTAGAGGAAATTAGAATCAACATTTATCTTTGAATGTT
GGCAGAAGAACTAGCACCTGTTGGATCGAATTTCTTCAGAAGCCCATTCTGCTCTTAGTTTGTGAAGATT

TGAATGCAGGGATTCTGTCATTTAAAGAGCTGAGCACTGTACTTGCTTATTGTCTGAACTGGGGATTGAT
TGCTGATGTGTTTCTGTCCTCAGGTCTGGCGAGAATTTCCTGACCGGTTGGTGGGTTACCCGGGTCGCCT
GCATCTCTGGGACCATGAGATGAATAAGTGGAAGTATGAGTCTGAGTGGACCAATGAGGTGTCCATGGTG
CTCACGGGGGCAGCCTTTTACCACAAGGTAAGGTGGGGACGAGCCTGAAGCAAGTGGGGCCGAGCTGACG
AACACGAGAGCGTGATACTCGTTTTGTTTCGCCGAAACTAAATTTCGCCAAGTTTAGGGAAAATGTTCCG
TTCAGAGAGCTTAGGAAGGCCATGCTGTGTGATTTAAAAAAAAAAAATAAAGTTATTTTTCTAATTATTAA
AGTATTACATGCTCAAATATGGAACAAATTTATTGTATAAGAAAATACTTAAAGTTCTATCATAGGAT
TGCTGCTGCTACTGCTGCTAAGTCGCTTCAGTCGTGTCCAACTCTGTGCCACCCCATGGACAGCAGCCCA
CCAGACTCCCCTGTCCCTGGGATTCTCCAGGCAAGAACACTGGAGTGGGTTGCCATTTCCTTCTCCAATG
CATGAAAGGAAAAGTGAAAGTTGCCATTTCCTTCTCCAATGCATGAAAGGAAAAGTGAAAGTGAAGTCGC

TCAGTCGTGTCCGACTCTTAGCGACCCCATGGACTGCAGCCTACCAGGCTCCTCTATCCATGGGATTTTC
CAGGCAAGAGTACTGGAGTGGGGTGCCATTGCCTTCTTGATCATAGAACTAATGGTAGAGAAACTACTGG
GTTGGCCAAAAAGTCCATTCATATTTTTCTGTAAATCTTATGGAAAATAATGAATGAACTTTTTGGCCAA
CATAGTATTATTATTTAGGTGTTTTTTCCAATTTGTCTTTTTTATTTATTGATTCACACATACAGTCATA
AATATTCTCATTAGCTTTTTTGCATGTATTATGAGTTTTTTCCTTATGTCATTAACATTTCTTTATAAAC
AACCTCTACTTAACATAATTGCTAATATACCATTATATTAATATTCCATAGATCATATACAGCTGTTTCT
CTGTTATTGGATATTTCAGTTCAGTTCAGTCGCTCAGTTGTGTCTGACTCTTTGTGACTCCATGAATCAC
AGCATGCCAGGCCTCCCTGTCCATCACCAACTCCCAGATATTTAGGTTATATCTAATTTTTTTTGCTAG
ATAATGCTTTGTATCAAATCCTTAAATAATGATCAGTATCCATTTTCATAACTGCCTATACTTATGATCT
TTATGATAGATTCCTAGAAGAATTATAAACATTTTGGGGAGGCTTTGTTGTATATATTTGTAGGTTCTCA
GTATCGTTTGTGCCAGTTTACATTCTCACCATACTCTTTCTTGCATGAAATACATTTTTAAAAAAAATCA

AACTTAGCTATTTTGCTAAGTGAAAATTGATTTTATTGATTTCACTTTGATCACGTGGGGTTTGCGATTC
CTTTTGTGTATTTAGCCTTTTGTATTCCTTCTGAGAATTGTTGCTTTATGTTTTTGACTCTTTTTATTA
AAGGGAGAGATTGAAGGGTATACATTGGGCTTTAGAATATTATGTTTGGTGGTGGAGTGCTCCCTGGGAG
TGTGTGGCTTAATTGAACAGTAATGTTCAGTTGTCAGCAGTGGCATAAGGAATTGATGTCAGGAGAAGA
TGGGTTCAGCCCAGTGCAGTTAAGTTGACTTCACTGTCAGTTGTCAGCAGTGGCATAAGGAATTGATGTC
AGGAGAAAGATGGGTTCAGCCCAGTGCAGTTAAGTTGACTTCACTGTATTTATATCGGCTGCGTGTTGTG
ATCTCAGCACTGCTGCCCTCATATTTTTCAGGGCTCTCGATCCAGAAATGAGTTTTTTTTCCTTAGCAAA
GCATAAATAAATATATAAGGTTTATAATTCTTGGGGCTATGATAGACTGATAAATGCCTTTTTGGCAGAT
GTATTTCTGTATTATACCACAAATTTCTGTATTATTTCATACATGTAGGTTATGGTAGTTTTGGAATTGC

CTCATTTTTGTTGTACTTTAACAAAGAACATGTCTGCAATGTCAGTCCACCATCAATATATCTCTGTTGC
TATCTGCAGTCCATGGGAAGAAGATAAAAAACGGCGGAGCACTGTGACTCAGAGGGAAGGATTCAGTAAA
GCTCAGTATGTAGTGTGTCTCTGAACTATGTTTATTAAACACATCTGTTAATCAGTCCAAAGGGCCTGCA
TCTTACAGGGACTTCATACTGTACCGTATGTTCCTCTGCTTACAATAGGTGATTTTTTAAAGAATGACAG
TGTTAAAGACAGTTGGTCACCTGACCAAAAGCATTCTAATACTTCCCTTGGCCTTTGTATTGATCCAACA
TTGTGACTCATCTTATGAGGGAAAGCTTGTCCCCCTGTCATGGCTCAGTTGCTCTTTGTGTATCAGCCAT
AGGGAACTGCTATTTGAATATGTCTCCTCTTTTGTCTCACCTGGCAGTATTTTAATTACCTGTATACCTA
CAAGATGCCTGGGGACATCAAGAACTGGGTGGATGCTCATATGAACTGTGAAGACATTGCCATGAATTTC
CTGGTGGCTAACGTCACAGGGAAAGCTGTCATCAAGGTAGGAGGCATCTATGGCCAGCTCTGGGGCACAT

CTTGGGCACCTTTCTGAGTCTCCAAAGTGTTCATAGCTATAAATGAAACTTGGAATAGATGAACTTTCAG
CTGCCTTTTAGCTTTAATATTCTATGATGGATATTTCACATTGTGAAATTGAAGCTCAACGTATTTTCTT
TTGTTATATAAAAATTGCTTTAGTTATAGTTTTTTAAGTACCAGGGATCAGAAAGTAAGTCTATAATGGTTA
ATCTACAAATTGTGTTTGTTTCAAAAATGTAATTTTTATTCTCAACACTGATTTGGAATCTAGTTCTTGTA
AAGAATGCAATTATGTCTTTCTTAAGGTAGCTGATTTTTTTAAAATAAATGTTGAAAAGATAGTATACTT
TGTCCAATTATACTGGTAGTTGTCCTAAACACTGTTTTAAGACAGTGATTATCAATTTTTAAAAGAACCT
TTCCCATAGCATATTAAAAGCAGAGAGTATGTAAAGATCATGTGGGGATCTTTGTTTCTATAATAGATGT
CTATTCCTAAAATGTAGGTCTTGCCCAAATCAGGGCCCTATAAATGTAGAAAAAGTATACTTCTTTATAT
CAGTGGAGTCATCTTGACCTTTTTTCTTCTGGATTAGATTCCACATGTAAAAATGGCCAATGCTTCTA
GGCCAGAATCCTATACTGGAAGCTTATATTGGAAACGTGGTATGACATTCCAGAATGATTGCTCATGCTA

TTAATATTAATCGATGAGAGAAGCCAGATTAAAGCAGTGACTGAGAACAGAGGAAAAGTCACTGTCCAGA
CTTGATCCAGTCTTTACACTATCCCTCGGCTCTCTAAATAGCTCAGTGAACAGCTCACTGCAGGGACAAT
TAAAGAATGTAAATTGCAAGACGAGTTTTAAAAGAACTCCTCTTATCTCCAAATTCATTTTTTGACATTC
TTCAAGACATTCTTTAGCTGTGCCTTTACTCTGGACAGTAATTCCTCGAGTCTGTATACTTCTTAGCCGA
GTCTCAGCTTAGCCGGGTCTTAGCTTTCTTCCCCACCCACCCTCTACTGTTTACTTATCTTCGCTGGGTT
ACGATAGCAGCCTTCCCTGAGTTTGCTAGAAAAATATTCGAAGTTTGAGGTGTGGGGAAGGTGGTGGGGA
GAGTCAGAGAAAAGGGATTCAGAGGGCAAAGGACCCCTGGATTTTTTCCTGACTTAAAGGGGTTGCAAAA
TAACCTGACATCTTCAAGAGCATGGTGCCGCCCGTAGCTTTTGCCATTAGCTGGAAGGAGAAAGAGCGCC
TGTTGGAACTAAGGTTACGGTGAAAGTTATGGGAAGCTGTATTTCATCGCCCTTATGGCTGCAAGAACAA
ATGGTGTTTATACAAGGACCTTGGCAGTGAGAAAACAGTCATTAAACAGGAATTAAGGAGCTTGTCATCA
```

TABLE 3A-continued

SEQ ID NOs: 1-2, BOVINE EXT2 AND ALX4 GENES

CCACTTCTTTCCAGTTACAGAAGGCAAAAGCCCTCCAAGCCTCTTTTATTGGGCCCTTGTGAGTTCTGCC
TTGGCCGAGCCAGACAGAATTGAACGGAGGAGCGGTGAGGGGTGTGTGTGTGCGCGTGGAGAGGGAGCAG
GCATCTCAGCTTACAGAACAGAAGCATGCAGAGTGGCATCACAAGCATGGTTTTATTGTCCTTAGCACTG
ACCGCCGGGTATATTTTTGTGCTCCTCTGGCAGGTAACACCACGAAAGAAATTCAAGTGTCCTGAATGCA
CAGCCATTGATGGGCTTTCGCTCGACCAGACGCACATGGTGGAGAGGTGAGTGGGCCTCTAGACAAAAGT
CTGCCCTGGCCTCTGATCCCCATTTCCTGCTTTGGGCCTGTTTATGGGACTTTGTTGCAGATATAAGGAC
AGCAGCTGGTAGCCATAGTCACCTCCTTTTGCACATGGGAATTGGGTTAGTTCAAGCCCAGGTCACCCAA
AGAATTAATTTGGAATGCTATTCACTCAATATGTAATGGCTGGAAGGGTCTTAAAAATATAGCTGGCCTT
AAGCTCCAGAAGCCAGATTCTCCATGTGGACTAAGCAGTTAACCATCCACAGTCACTCAACTGGAAGTGA

GCTAATTCCAAGGAAATCCTGGGTTGTTTTTCAGGGTAGTATCTCTGTGTTACAGTAAAAGTTCGATTAG
AGAGAATTATTAAACCAAACCCACCAGAGGCCAGATTACCTTTGTGGACACACTAAAACACCTACCAAGA
ACAGAATTGAAAGCACAGCTCTTTACATTTCAGAGAGCGAAGCAGGGCCGCTCTGAAATACCTGCTTTAT
ATTGATTCGGTCACTTAGCCAATGAGCACCCATTTCTGTGGATGTAATACAGGGCCTTGTAGGTGAGCAT
GAAGGAAGTGGGAGATGTCTGTCTGCCCTCAAGACCGTCTCACTTGTGTCCCAAAGGCCCCAAGCTTCAA
ATCTCCTGAATCAAACCTAATTCTTCCAAAAGGCAGCCTCTTACATAAGACAGCGAGCTCTGGCAACCAA
TGGCATTTTTGTCAAGGGACCAGAATGCATTCAGAGAATGTTGTGATAGCTGTCAGAGTGAGATATCTAG
TTCGGGTCTCCCTGGGTCTCATGCGTCTGCGTGCAGCACTCATTTCTGAACCCTACCAGCTGCATCAGGG
TCCTTCAAGCCTGGAGGACGTTGTACAGGGGGCTGTTTCAGTTGGCCTGGACCCTTCTATAATGCTTTAC

TCCTTCTTACGCATTCTCTCTAAATAATCTCTTTCATATGTAAATATCTTACCCAAATGACTTGACTTTT
ACCAACTGTCAATATGAAATTATAGACATTATCGATATTATTATATATCACAATATATATTATATATATT
ATCACAATATATATAATTATATATCACAATAATATTGATACAATTGTATTTGTGACTTTGAA
ATATCTGTCACTGGTATCAAGTAATCACCTAGTCAAGGACAGTGACATTCCTGACACAGCTCATTTGGAA
GAGACCCCAATTATAGTTCTGTGGCTGCTGCTGCTAAGTCGCTTCAGTTGTGTCCGACTCTATGCAACCC
CATAGACAGCAGCCCACCAGGCTCCCCCGTCCCTGGGATTCTCCAGGCAAGAACACTGGAGTGGGTTGCC
ATTTCCTCCTCCAATGCGTGAAAGTGAAGTCGCTCAGTCGTGTCCGACTCTTCGCGACCCCATGGACTGC
AGCCTACCAGGCTTCTCTGTCCATGGGATTTTCCAGGCAAGAGTGCTGGAGTGGGGTGCCATGTTAGAGC
ACATGAAATTGTTACTTAAACCTACCCCCATTCTGTGTTGAGAATTTCATAGCATTAAGCAATTAGTTTG
ATTGGGCTGAGTTACATGGTGGGGTTTTATGGTCTAAGAAGAATTGTATTTAGAAAATTTCACCCAATAC
TGGCCTTAAAGTTCATGCTAAAGCTGAAAAACTGAGATAACAAATGCAATGAGAAAGATTTAAGTTAGGT

ATAATTATTATTTAACACTGAAGTAAGTAACTAAGGGAAGTGTGGAAGCTTCCTCTCGGGAAAAGGGTTT
TGAAAATAGACTAGGCACTGCCCAGATGTTGGTAGGCTTGATTTTATCAGATTTTTATAATTAACAACAG
TAGATAACACACATGTGTATGTGTGTATCGAACCTAATCCGAAGCTATATGTGATAAGTCAAAGGAAGGC
TCAGAATGTTGTAACTGGTCAGAGGAAAGAAAAGTGACTTCTTACTAGGTTAGTCATTATGAATGATTTT
GTAAGAGGTGGCACTTGAAGTGAGCCTTCCAAGATTGCTAGGATTCCAGCTCCAGGCAGGAAGAGGAGAT
CCTCGGCAGGGGAAACCGGATGGTCCAAGGTGCATTTGGCAAGCAGTCAAGATAGCCAGTTTTGTTAGAG
CAGAACATCCTGGCCTGTCAGTGCCAAAGGGCTTTTTTCTCTAGGTAAGCCGTGGAAGGTTTTTGAATAG
GGAAGTAGTTTGATTAGAGTATTGTTTTAAGATTGATTTGGAAGGAGTACATAGAATGAAATAAGGGTGA
GATTGAAGAAAGAAGAACAGTTAGAAGGCTTGAACTAAGTTGAGTGTGGAGAGGAAGGGTTGAAGTAAAT
TACACGGTTTTTTCCTTTTTTCTCCCAAAGGAGACTGTGCTAGCATTTGATGTCCAGCTGAATGGTGTGG

GGAGGTCTTGGAGGAGTTGACTGAGATAGGAAGAATGGTAGTACCTTTAACGGTGGAAATAATATGATTA
GGAGGGATGCTAAGTAGGGAGGGGAGGACATGGATGTTGTAGCTTTCACAGTGTAATTAATGAGGCCAG
GAGATTTTAATGGTGTGTCAAGTTGGAGAGCAATAAGGCAGGTGCGTTTGCGCTCTTACCCTCTGTATAT
GCAGATATAGATATAGAGCAAGCAGTTGGAAATATAGAACGAGCTTAAGAAAAAGATTAAAACAAAGA
TGGAGATTTGGAAGGCATCCGTCCAGAGATGACAACTGATTGAAGAAAAGCTATGGGTAGAATCTTGAGA
AATTCAGACAGTTAGGAGACAGAGTAATTGAAAAGAGAGAAGCAGGCACTAGAGAGAGGCCAGGAGAGAA
CCAGGGTCTCCAGTGCCAGCAGCATTGGAGACTTTGGAAAAAGTAATGCGTAGGGTGAGGGCTGAAGGG
CGGTAGCGTGGGAGCTGACAGTGAGGACGCAGGGTCAGTGACAGCAGGCTCCCCTTTGGAGAAATGCGAT
GGAGAACAGAAGGAAATCGGTCTTGAATTAATTGGAAACTGCGAGCAAAACTATTTGGATTAAGGTTAAA

TGACTGAATTATTAAATAAGACACTTAGGTTGGGTGGGAGGGGGTATGATTTAAGCCCTACTGGATAGG
CCAAGAGATGGAGTTACAACTGCAGAATTGTTCACTTGTTTCGAAATAGTTCCCTTTGCGGAATCTGCAT
TTTTTGCACAAAACGGTGAGAAGAGTTAACCGCTCTGTACGTTCTGATCTTGTGTTGAGTTGTGTGCTTCA
GTAAGCTTATTTATTCTTATGTTTGGGGTCTGGGATCAGAAATCTCAGCTGTGGAGGAGAGTACTTTAAC
TGCCCTTCCTCCATTTCCAGGTCCTGCTATTAGTTAATTTAAGAAAAAGAAGATTTTGTAACTTCTTTTT
GCCCAGTAGCTTTACCCACGTCGAGACAATATGGCAGACAAACAATGCCGATTTAAGAAACAAACGTTGT
ATTTTGATTCAGGTCAGTCTTTGTTCAAATTATGAATTAGCCATTTATTAGCTGTCTGACTTAAGGAAAT
TGACTTACCTTATCCTGAACTTCCAATCATTTCATCTCTGAAAATAGATATATTAACTGTCATATTACTG
TATCCATTCAGGAATTCAACAAATATTTATTGAGCATTTTTGTATCAGTGCTAGGAAAGTCTGTACCCTG

GGGCCTGGCAAGGTTAGTTCACTTCCCAGTTTCCCCAGCACTGACCCTCAAGCTCCTTGTTACTTTAGGT
AATAGTATGAGTTTGAAAGGAAAACAGAAAGCCATTAGTCTTTTCTCCCCAGCCCTTGCAGCACTTCAGA
GATAGACATTGCTGTTCTTAGCCTATCTGTTGGTTAGAAAACCAAGCTAGGGGAACAGTTACTGACATA
GTAGCTGGACCCCCAAGAGAACAACTCAGATAGACCCACCAGCAACCAGCCTGACTCATAATCTACCCTA
ACTTGTTCCCCACCCCAGGTCCCCTGCATGAAATGACGGTAGGAGACACTGTCGGTACCTGGCAGTCGAG
GACTTGTACCATTCAGCATGGCAGTCGCTTCTCCAGGGTGGGCTGCTGGAGAGAAAGGAGGACTCAGTA
GCCTGGGTCAGCCAGGGGCAGCTGTCAGCAAGCCGAGCTGGCCTGAGCCCCAGCGGCCTCTCGCCTGTGG
CCCGGCCCGGCCGGCCGGTCTAGTTACAGAGGAGATGTTGTCCTGGGCTCCCCAGGAGCCCTGGAGACAC
CACCAGCCCCTGCCAGGAGCCGTGAGTCTTCTTTCATCCATCCTCGCTGGCACCCTATGCTGGACACGGC

TGGGCTTTGCTGGCCGGAGTCCACAAGCAGAATCACTGGAAACTACAAGAATCTGTCCGTGTTTATAGGC
AGAACAACTGTCAAAGTGAGACCTTGGGGAGATTTGACTTAGTCTGCCGCTGTCTTGACCCCGTAATTTA
AGGTGAGAAGAGCTGTTGGCCAGTGCTTGCTTCCTATCATTTTATTAAAACCTCTCTCAGTCTTTTCCCC
AGTCTCCTGTCATTTTGGAACCTGAGACTGCGACCTCCTGGGTCTCGAAAGACTGCCAACAGGAGGGGAG
CTCAGTGATCTGTGGGCCATTGTAGAATGTGATAGAAAGACCCAGGCCTCTCTTAGCAACGCAAGCCTGG
GTTTGAACCCAGCTCCACCACCTTCCGGCTCAGGGTCCTTGGGAAAGTCCCTTAGCCTCTCTCAGCCCAA
ATCTCTCAAATCACACAAACCTTCGGGCTTATGGAGGGGATACTTAAAGGAATCACTGGGTCGTGGATG
TAAATTAGCTGGCACTTAATAGGAAATGGCAACCCATTCCAGTACTCTTGCCTGGAGAATTCCAAGTTCA
GAGGAGCCAGAAGCCTGAAGGGCTACAGTCCATGGGATTGCAAAGAGTCGGATACGACTGTGCGACCAGC

TABLE 3A-continued

SEQ ID NOs: 1-2, BOVINE EXT2 AND ALX4 GENES

TTTCACTTTTTCAGTAGGTGCTTAACAGTTGTTAATTTCCAGCTTCTCTCTTTGGACCCTAGAATAATGA
TAATAAATAAATGTGTCTCCTCTCATAGTGAAGACTTCAGCCTCAGCAACCAGAGTGCCTGGATTTGGCT
CTGCTCTTTCCGGTTATTTGGCTTTGGTCCTGTCTCTGAGTCTCCCTGTGGTGTGCCTCTGTCTCCCCAG
TATGCCGTGGGAAGGATAGGAGGCCTGCCTCGTGAGCTTGTTGTGAGGGGAGACGTGAGTGACTAGTGCA
CGCCAAGCACTTTTAACACAGCCCGGAACATAGCGTAAATGGTAGGTGCCGCTGCTCTGTGGCTGTGGGC
ACAGTGATGTTATTAGCTGGAAGAGCTCACAGTGAGATAGGTAACACCTTCTGAGCAGCAGAATAAGTGCA
AGAAAAGAATTGACAATAACTGGCTTCTTTATTAATTGGTTTCTTGCTGAAGCTCAAAGGACTCAAATAA
AAGCTGTGGACTGAAATAGCTTGAAGCAAGGCTTACAGTCTTTCCGAGGACAGAAGAGCCTTGCAGTCTG
TGTCTTGAAATTCGGCCCTTCCCCGGGAACCGGTTCTCAGGTGGCATGGGCCTGACTGAGGAGAGAGAAT
ACTGACCTCGCTGAAATCCATCCTTGAGGTCCCCTTAACTTCAAAAGCGGTCTTTGCGGGCTCGTTTTCC

CCCTTTGGTCTGATGCCGAAATGTCCTCATCACCCGCTGTCACACTCAGTTGGCCTGATTGACCAGAGCC
CTTTCCTGCCCGTGTGTCTGAGCCGCTCCCCTCTGAGGGGGCTGCTCACGAGGTGGGGGTGAGGGGCTGC
ACCCTCCCCTCACCCTGCGGTGCTAAGTTGCTTGTTGCTGTTGATTCTAACACGAGAACAGCTACAATTA
TGAAAGCTGTCCAGTGTGAACTTCAGCTCTCACAGAGGAGCTTATGGAAGTGGACTGATAATTCCCAGAG
ATTGCCACTCACAGCCCTCGATAGATGTTGGTTGAATGCCTGAAGTGTTTGAAATTGAGGTTCACGGCCC
CCGTTGTCTCCTCTGCCTTCCATCGCCCCACATGTAAGAGCCTTCCTTCTCCCTTTTAAGCTCAAGCGAG
CTGAAGCCAAGATCCAACCCTTTGCCTCCTCCCTTTGCCTTCTCTTCAGCTGGCAGGGATGGGGTTAAGG
CTTGTTGGCAACTAATCCACCTAGGTTAGAGGCCTGCTTGTAAGGACGTGGAGGAATGACTGGAATTTGA
GGGGGAGGGGAACGATACTCTGACCTCTGCAGGCCCATGGCCTTCGAACAGCTCAAACAGCATCCCTGGT
TCCCTTTCTCCCTCTGAACTAATAGAGTACCCCCGATCACTTTGTTCCTCCACAGCCTCCCAGCCGTGGG
AAGAACCCGGGAGCATGCTGGGGAACCTTGCGTTTCTCTGGCCAGTGTTGAATACGATATATTTTGCTC

TCAGCTCTCAGCCTCTTGAACGTTTTCTTTGTTCCCCACCCCTGTCCCTCTCATCTGCCCCACTGCCCTC
CCCAATTCCCCAGGTCCGAGTGCATCAACAAGTTTGCTTCCCTCTTTGGGACAATGCCTCTTAAGGTGGT
GGAGCACCGAGCCGACCCTGTCCTATACAAGGACGACTTCCCTGAGAAACTGAAGAGCTTCCCCAACATC
GGCAGCTTATGAAGCAGGCCGCTGGTGGAGGTCTCAACACGAATGCCGGACAGAGGAAGAGAACTCGGCC
CCCCAGCCCTCTGACCCCCGGATTTCAGAGTGGAAGACTGGCACCTCCTCGCCTGAAGAGCAGAGGCCCC
AGGAGGACATCTGAGCACCTCTGGCATCCTCTGATGCTCTCAATGGGTTTTCTGAAAACTCTAGGTGGAA
GCCTGTGGCAGGCTCCAGGGGAAGGCCAGATCAGGCTTTCTTTGTCTCCAGCTCCAGTACAGTGATCTGA
GAGGAACTGTCCCTGGCTCTAAGACTGCTGAGAAGCCTCCAGCAGATCTGTGATATCATGGAAGAGCTAC
CGGACTCACTTTTTGTTATTTCACATCAGTGGGTTCTTCAGAGGAAGAGCCACACCCAGAATTTGGTGCA
CGATCCAAGCATCTTAGTGGCGTTTGATGCCTTGGGAGCACCAGCTGCTGAGTTGGGACCCGTAAATTCC

ATGAAACTCTGGTTTGGCTTTTGGATATGATTAAACTTATTTTTATTCCGTTTCATACTACATCTTAAA
TATTGACTGTGGAACTTTGTGCGTATGTAACTTGCATCTTCTGACCTCAACTCCAGCCTCCTTCCCAGGT
CTGGGAAGACAGTCGGCCGGGAGGCGTGTCTGGTGCCATGTGTATCCAGCTGTGCAGTTTTAAAAGAATCAATCCAACTAC
AAATATTCTTAGCGTCCCCAGACCTACAAAGGAGTCTCTGTGCTTGCTGATTAGATCTAGATATCCTTGG
GGGAAAGCAGAGGGCCTCTCACAGCCATACGCTGAGTCGCTCTGCTGGTACCACATTGTAAAATTGAGCG
AGTTGTGACCCTCGTCCCAAGGGGATGCCAAAATTTCCCTCATTCTTTTGGTATAAACCTAACGTTAGCC
AGGGAGGCTCTGGCTAATGTTAAATGCTGCTATAACAACTGCTTTGCAATAGTTGCCGGTATATTTAAAT
CGTTACATTTCAGCATTTAGTAATACTGCACATGTGTGAATTATACCTCTTTAAGCTCAGTTGATGAACA
AATCTACTCTGGCAAATGTTAGATGTTAAGGATTCGAAACAGATTTATCTGACTCTAATATTAAGATTAG
CCACAGTTTGGGCTTTAGCCATAACATATGTCCCCAGAACACAAAATACATAACAATTTGCTTGGAATAT

GGATATAATTACTGAAACTTAGTTGTGTGCCCGGTCCAAGTCACTAAACCACCACTCATTGTTCTGTTGA
GTGACACGGAGGTGAGCTGGTCTCATGCTGGTGTTTTCAGACTTGCAGTTTTAAAAGAATCACTTCAAAT
GTGTTCCCATGGACTTTGAGAGGCCAAAGAAAATTTTCAGAAGTAGCACAATTGAAAGTGGAAATCTTGA
GTCTGATCTTTCATATTTAGGCCTGGTGGGATGGCAGGCTGTTCTTGGCAGAAGGGATAAGATAACATCT
CCAGGTCATTCATTTTGCAGTTGCAGACACTGGAGCAGTGATTTATTCATGTGTTGCTGCTGTGAACACT
GGTGCTTAATCAATACTTTTGATTTGAATAATTATATCCTAGCCAGCAGGGGAGATGGGAAGGCATTTTG
GCCTCATAGTACTGGGGGTGATACGGTAGAAACCAAGAGAAAGGGGTTTTCTCTTGTCACCCAGATACCA
GTAGCTGACACGGCGAGTAGGAACCTCTGATCTTTCCAGGGGTTCCCTTGCTTGTTCTCCAAGGTTTGGG
GCAAGTGGAAGGGGAGGAGGACCTCACAGTTAAATTCTAGCTAAAATCTAAGAACTGTGCTGACATTGTC

TACTGTGTGACGTGCGTTGACGCACACCCTCGGCATGTATTAGTAGCGCTCTGCTCCTTTCAGATGACCA
GCTGCACTGCATTAGTGGCTGCTTTCTAAGCCACCTCCCCCTCTCAAAAGGGCCACCTTTCCTCCTCCTC
CTTCCTGCCCTCCTTCTCCCCTCTCTATTATTCCTTTGATTCTGGAAGAGAAATGCTTCAGTAGCAGGT
CATTGGGGGCCCAAGGGGACAGAGCCAGTGGACCTTTATCACCTTCTCAGAAGACATTGGTCTTCTAAGG
GCATTAAAACTCCATTTCGAGTACCTAACTACCCCCAGAAATATTGGGGGTTGATTTTGCACCATAGTG
TACAATTTTCTTTTATTATTATTATAGAATAAAATATTACATCCTAGGCACTGAAAGCAAACCTCAAAGCT
TCTGTCCTAGGGAAAGAGAGAGGGTACAGGTCACAGGGAAAAATTCAGGACAGGAGTATAGCAAGTGCTC
TGATTCATGGGTTCAGAGGGGACTAGGAGCTCCACCCTGTCCTGTGTGGGTGTATTTCTGAGCTGCTCAC
CAGCAAGCCTCACTCATAAGCTTGGGCCAGGATCATCTGCCCTTGGGATGCCATAGGTTCTGGTTTCAGA
AGCGGAACAATAATGCTAATTAAAATGTCATATTCTGGCCTACAACAGACAACAGCTGGTTTTAGATTAA

GAAATCTTTTTAAGGAATTGCATCGTACTGGCCTGCACCGACGATGAACCTGAGCTGGCCCTGGCCTTG
CCACACATGTATGTACTAAGTCGCTAGCCTTTGCCCTCAGGGACCTAACTGGGATGGGCCGGGCTGCGTG
GAATGCCAGTGTTGACTGGTGCGTGCTCAGTTGTGTCCGACTCCATGACCCATGGACTGTGGCTCACTA
GGCTCCTCTGTCCGTGGGATTATCCAGTGGGTTGCCATTTCCTTCTCCAAATGCCAAGGTTGGAAACCCT
TTTTTGCTAGTTAAGTTTAGGTAGCTATACATATTCTTATCTGATGTATTTTAGCAAGGCTCACACATGT
TTAGGCAAAACCCTCCTTTTCTGGGAAAATTAAGGAGGAAAATATCCACTTTTGTCCTCAGACTCTCTAG
TTCCTTCCTGCAAGTGATGCTATCCTGTCTCTTCTTACTCGGCATCGTGAAGGTCAGAACTCTGGCTTCT
CTGCTGAACCTTCTATGCTTCCAGCTTGTGGGTTTTAGGAGTTTCTCTGCTGCCTCTGGAGAGAGTGGCC
ATCATCCTGGCCTGTGCTGACCAGGACCGGGAGCTGGAAGAGGCCACCAGCCTCTGTGCTCTCACTTGCC

AAAGGGTGGCTGGTAGCTCTGTGATCCGGCTTCCTCCTGGGACAGTCCCTGAGGATCCTTGCCACTGAAG
GGCCGCAGGCTCCTGGCCACGAATTCTCAAGGTGTGATTGCTGACTCAAGTCCAAGACCCCTTGGTGGT
AGAATTAAGAAGTCAATGAAGCAGAGTCCGGGTCAGGAAGTGGTTCACTCCTGGGGGGACTCTTCCTGAC
TCTACAGTCACAGAACCCGGCCAAGAGGGTGGAGGTCTCGAAGGTTCCCCATTGTCTAGCTTCCCTGAGC
CTGGTGGGTTTCCTCTGCTCTCCCAGTGGCGGCTCCGGGGTAAGCTGTTTTCTCCAGTTCTGTTGGTCAT
CTTCTGCTGCAGCAGCTGAAGCCGCAGTACGCCATTCCCCGAGGAGCCCTGGCTCGGGGAGGCAGAGGGA
GAAAACACCCAAGTGGCCCCACGCCACTTCCTGAGGAGCCATCCTGGTGGAAGTGCCAACCGGATTGGCA
GGCAGCGGCCGTCGAGGGAGGCTCTGAAGAGACTTGAGCTTTCCACTGAGGGCCCGGAGGCGTGTGAAC
CCTGGAGGCTGGCTGCTCACCTCACCCCAGAGCTCTGTCCCAAGCCCCAGGGCTCCTGTGCTAGGCAGT
GTTTGCTTCTAAATGAAACGGGGGCAGCTTTTGGCCCCACTCTGCCAGCCAGGCCCGGTGAGATGATCTG

TABLE 3A-continued

SEQ ID NOs: 1-2, BOVINE EXT2 AND ALX4 GENES

AACCGGTTTCACTGAGCTGCTCCTGACAGGACAGTGAGGCAGGCCAGATTCTGCTCTCACTTGTGAGGTT
TTCCTCTCTCCTAAGCTAAGGGGTTCCCTGGTGGCTCAGTGGTAAAGAATCCACCTGCAGTGAAGGAGGT
CCAGGTTCAATCCTTGGGTCAGGAAGATCCCCTGGAGAAGGGAATTCCAACCCACTCCAGTATTCTTGCC
TGGAGAATTGCATGGACAGAGGAGCCTGGCGAGCTACAGTCCGTGGGGTCGCAGAGTCGGACATGACTTA
GCAACTAAACAACAGTGACATCATCTAAACGAAGCTCACAGCCTCTCTCCCACCTCCATTAAATAGACT
GTCAGGGCTCCCCAGCCTCAGGCTTTGTGATGTCCAGCCTCTCTCCCACCTCCGTTAAATAGACTGTCAG
GGCTCCCCAGCCTCAGGCTTTGTGATGTCCAGGTTCTCTCCCACCTCCATTAAATAGACTGTCAGGCCTC
CCCAGCCTCAGGCTTTGTGATGTCCAGGTTCTCTCCCACCTCCATTAAATAGACTGTCGGAGCTCCCCAG
CCTCAGACTTTGTGATGTCCAGGTTCCCTCCCACCTCCATTAAATAGACTCTCAGGCCTCCCCAGCCTCA

GGCTTTGTGATGTCCAGGTTCTCTCCCACCTCCATTAAATAGACTGTCGGAGCTCCCCAGCCTCAGACTT
TGTGATGTCCAGGTTCCCTCCCACCTCCATTAAATAGACTCTCAGGCCTCCCCAGCCTCAGGCTTTGTGA
TGTCCAGGTTCCCTGGGACAGGGTGTGGGCTGTCTAGGCAACATTGTGCTACAGCTTTTTCATGTCCAGC
TCACCACTGCTTCAACACAAGGCAGGTGACGGGGCAGCTTGCCCCCTCTCCCAGCTTTGCAGGCATCTT
TCCTTTTCAAGAAATTGTTGAGTCACCCACCTCTGTGTCTGGCATCTCAAATTTAACAGCCTTTGTAGGG
TAGAGTTTTTCCTTCTTCTGCTCCCAACTGGTTGGGCCCATGGTTACACTTCTTTGCAGCCTCCCTGA
AGGGCAGAGCTGTCAGGCGGAGACGAGGAAAGGGAAGGATGTCTGGGTGCCACTCGAGAGGTACTAGGCA
GCTATGTCTGATAAGAGGTTTTCCCAGCAAAGCACCTGCTCACCCACAGCATCTTGGGAGCTGCCTGTGG
AGACAGCTGCCAACGGAGCTGGGACTGGAATCTGCGTGTCTTGGACCCAAGCCTCCAGCCACTCCATCCA

CCCTTCAGAGCCTTCCCTTCACAGAGTATCAATGTGAGCTCTTATTTATAGCTGCCAACTTCTATCATTA
ACTACTATGCCCAAAGAATGTCTGGTTTTCTGGTAATCACAGTCTGAAGAACAACCAACTCGTTACTGACC
AAGATGAGGGAATAATTCAGTCATTCGGTTTTCTAATTGTTCATTCACTCATTAAAATGTACTCTTTGCT
AGAACCTGTGCTGCGTCTGAGACAGAGTGGAATAAAACACAGTCTTGACCTCCAGGAACTTGGGTTCCCG
TGAGAGTTCTTGGCTCTGTAAGATGGTGTGAGTCCCTCAGAGGCCTAGGGCTCCACACAGTACGTTTGA
GTCCTGACTGCGCAGGAAGAGTCCATTACGTGAACACCACCTTCGCTGGTGCCCAGAGGACGCAAGCATT
GTTTGTTTCCCGTTCTCATAGCGCCTTCCTTTGAGTTGAGCCCTGGGCCTTCCTCGGCCTTGAGGGATTC
CACTCCCTTGCCTTACTTTCCTCAACCAGAAATTGAAGATGGCAAGAGTGTTTCGACCCGGGTGGCTGAG
AGGCAGTGATGTATCAGATCTCTCCCCTCTCTACCCAGAGCCCTGGCCAGATTGTACCTGGTGGTGCTGG

CAGCCGGCCCTCTTCCGGCCCCTATTTCTGCTCACCCTGTTACCAGAGAGCCTGGGGGTCTGGATCCTAT
CCGGCCCCGTCAGGGTAGATTACAGATGAGTGGCTCTTTTGCCCCAGTGCCTTTCCTGTGCTATAAATA
AGCCCCGTGTTTATTTTCTAATGTTATTGAAATGAGCACTTGGGATTGGGGCCTCTTGACTAGTCCGGAG
AGCGTCCACCCGGTGCCTGGTGAGGGCCCTGTGTGGCTGGCTGCTGTCTGAAGCTATTTGGAGTCCTCCC
CCTGTGTTGTGGATGTGGCTTCATTTCAATAGTAAGGGCTGTATGCAGCCCTGTATCTGCTGATTTTCAG
GTTTCAGCTTTCTGCCAGCCTCACTGCCTGCTTAGAAGTAAAGCTGTGTTTCTCATTAAGGGGATAACAG
CCACAATTGAGATAATTAACGAAATTGTATATTGGTGGCAGCAGGTCCTATAGGATTTCCAATAGTCTA
CCTAGTAGATCCTGAGGGGCTTTACCTTCATCTCCTCCCTTCTGCCTACCCTGTGCCCAATCTCTGTTCT
TGTTTTCTGGGTATAGTCCCAGTAATTTCTCTCCATACAGCCTTGTTCTTGTCAGCAGTTTGGTTTGATG

TACTGACAACTTGACCCAATGAAGATTTCGTCAACTGCCTCTTCTCCAAGGCACAGAAGATGCAAGGATT
TCCCCCCACCACCACCACCTTCGCAAAGTATCTCCCATTTGCTGGTTGTACCTTGGATATAAGATGAATA
TCCATTAATAACAGATAGACGTTCCCTTTAGTACTATGGCTGCACCATCTCAGTGGGACAGTGCTGAGAC
AGAATGGAAACGTAACAGCCCAGTGCAATGTCTTATATGCTATGTGGTTGTCTAGGAACTAGGAAGTGTT
CCGAATTAGGATTTCCTCAGGAGTGGTTTCGGAGAAGGCAATGGCACCCCACTCCAGTACTCTTGCCTGG
AGAATCCCAGGGGCAGGGGAGCCTGGTGGGCTGCCGTCTGTGGGGTCGCACAGAGTCGAACACGACTGAA
GCGACTTAGCAGCAGCAGGAGTGGTTTCTAGCTCCATCAGGCTTTGATGATGCATCAGACATATCCAGTG
AGACTGAGCAGGACACAGCATTGTCTATCAGAACTTGAGCTAAAGATCGTTATCTACTGCTCAGGAGGGA
TTATTCTGATAAGTCACTCGGTAGAGAAATGTTTGCATGAACAAACCAGAACCTATAGCCTATTCATGAG

CAGTTACATCTAACAACCAGATTTAATTCACTTTCAGACATGGAACCAGAAGAAAGTGAATTTTTACTCA
TGTGTTTTTAGTCTATTGACTCCTAAAGATCCTTTTCTCTTAAAAAGTAAAAAGTCTTTTGTGATGGATT
CATATTTATTGAGCGCTTATTATGTGCCAGATACTGTTCACAATTATGAAGACGCTGCATTGAACAAAGT
GCCTGCTCCTGCTAAGTGTACATTCTAAGAAGGAAGACAACCAAAAAAAGTAAATGAATACAATTTCAAA
TGGTAAAAAAATGCTATGAAAAGAACAAAGCAGAATAAGGGGAGATGGTTAGTGACTTGAGCATGCTGCT
GCTGCTGCTGCTAAGTCGCTTCAGTCGTGTCTGACTCTGTGCAACTCCATAGACGGCAGCCCACCAGGCT
CCACCGTCCCTGGGATCCTCCAGGCAAGAACACTGGAGTGGGTTGCCATTTCCTTCTCCAATGCGTGGAA
GTGAAAGTGAAAGTGAAGTCGCTCAGTCGTGTCCGACTAGTAGTGACCCTGTGGACTGCAGCCTACCAG
GCTCCTCCGTCCATGAGATTTTCTAGGCAAGAGTACTGGAGTGGCTTGGCATTGCCTTCTCCATGAGGAG
ATATTTAAGATGAGTTGGTCAGAAGTGGCATTTAAACACAGATCTCAGTGTTGAGGAGTGGAGACAGGGG

GATGAGCTAGTATAAAGTCCCTCAGATAGGAAAAACCTCAGCTTGTTTTAAGAACAGCAGGAACCCCTGT
GTGGCTGCAGTGTATTGGGTATGGAGCGCAGGGTAGAGATGATGCCAGGAAAAGTAAGTTAAGGCCAAAT
TGTGTTGGGATCATGCAGGACAGAAGGGTCCTGGATTTTTATTGTGAGTGAGATGGGAAGACACTGGAAG
GTTTTAAGCAGGGGATTGGCATCCGAATGGGATTTTTGTTTAAAGAGTCATTTCAGCTGTTATGTGAAGA
ACAAGAATGGAAGAAAGGAAATAGAGAGGCTGCGTTACAGAGAGATGGCAGAGGCTTAACTAGACTAG
GATGGTAGCAACAGAGAAAGTGAGGAGTTCCATTGGGAACAGAATCTGTTGGACTTACTCACGATTTGGT
TATAGGAGATGAAAATAGGATTCACAGCTAAGTACTAGGTTTTGTTGTAACCGAGTGACACAGTTCAGT
GAAGTAGAGCCGACTGGGCAGGGTAAGGACAGAGAAATGTGAAGGGAGATATCAAGAGCTCCACTTTGAA
TGGGTTAAGTTTGAGATGTCTTTTGGTCATCTAGTGGTACTGCTATTTAAGCAGTTAGATATCTAGAGCT
TAAGGGGAAAGTTAAAACTGAATATATAGGTGGGATGTAAAACCACAGGATAGATGAGACTACCCAGAGA

GTCAGAATATGTAGAGACAAAGAGGACTGTGGCCTCATTTACGGGGAGAGAAGAAAAGAGGAACCAGAAA
AGGAGATTGAGGCATTGCCAGTGAGTTAGGAAGAAAACCAGGAAGAGATCTGCATGACAGACTGTGATGA
ATTAGAGATACACATTGTAAACCCTGAAGCAATGGCTAAAAACAGTTTAAAGGAAGCACAGCTAATAAG
ACAATATTGGAGATAGAGTATGATAAAAATATTCAGTCAGAAAGAATGGATTGAAGAAAAAGTAAACT
AAGAATAGACGGGACACAAAAAGTAGGAGACTAGACTTAAACTCTAACATGTTAATAATGACATTAAAT
GTAAATGATCTAAATGTTATAATTAAAGGAAAGAGACTTTCATTCTGAATTAAACATCAAGGGCAATCAT
ATGCTATCTCTGAGTAAAGCACTATAAAATACAGTTGAAGTAAAAGAGTAGAAGAAATTATACTAGACAA
ATATGAATCACAAGGAACTGGAAGTGATTTTATCAGTAAAGGACAAAATAAACTTCAACACAGGAACATT
TCCAGGGAGAAAGAGGAATAATTCATAATGTTAAAGGTGTCAGTTCATTAAGAAGACATAACAGGTAATT
CTAAGTAAGGTAGGCACTAAATAACAACACTTAAAAATATATACAGCAAATTGACAACTGAAAATAAAA
TAGAAAAATCCACAGTTATATTTGGATGTCTCAGCACTCCCCTCTTAGTAATTGATAGAACAAGTGGATG

TABLE 3A-continued

SEQ ID NOs: 1-2, BOVINE EXT2 AND ALX4 GENES

```
GAAAAATCAGAAAGAGAGAGATGACTGGATAATGCTGTCAACCGCTTTGGCCTAGTTGACAGCTCTGGAA
CACTTCACCCACCAATAACTAAGCAGATATTCTTCTCAGGTACACAGACAATATTCAGCACCTGTGTGTG
GCACCATAAAAAGTCTCCGTTTTAGAGGAAATGAAAATACAAGTATGTTCTCTGATCACAATGGAATTAA
ATCAATAACTGATATCTGGGGGAAATCCCTAATAGAAATTAAATAACATATTTCTAAATGCCTGGGTTAA
TAAAGACACAAAGCAAATTAGAATGTAACTTTAGGTGAATGAAAATGTGTCTAAATGTGTCAGGTGGAGT
GCTCAGAGATCTGTTCTTGAAGGGCTAGTGTTAGAAAAGCAGAAAAAACTAAAACTAATTATGTAAGCTG
CTACTATAAAAAAATTGAAAACAGCAAATTAAATACAAAGTAAGTGGAAGGAAGAATAAAGACAAGCTTG
GAAATAAACAGAAGATGGACAAACAATGGAGAAGAATCAACTAAACAAAACCTGGTTCTTTGAAAAGACC
AACAAATACTTTAGACTGTTCCAGGGGGAAAAAAAGAGTATATAAATTTACCAGTATCATAAATCAAAC
GGGGAGCTTTGGTACAGATTCTAAAAATATTAGAAGTGAAATACATGAGAAAACTTTATACTGATAAAAT

CTACAACATAGATGAAGTAGTTGCAAACTTTGAAAGACACAAAGTGATAAAAACTACCTCAAGAAGAAAT
AGAAAAATCTAAATAGCCATATCCACTAAAGCAGTCAAATTTGTAATTTAAAACTTCACACAAAGAAAAA
CCTAAGTCCACATAGTCTACTGACATATCAAATAATTAAGAAACGACACCAATCTTACACAAACTCTTTT
CAGAAAATAGAAGACAAAGAGATGGGTCCCAGCTCATTTTATGTGGCCATTATTACCCTGTTATCAAAAC
CAGACAAAAATCTTACAAGAAAAGAAAACTGCAGACTTAAAGCCCTGCTGAGCATAGACACAAAGGTCTT
TTTAAAAATTAGCAAGCCAAATCAACATACAAAAAAGATAATACATGACTAAAGAATATGGAAGGAAAGT
TATGACCAACCTAGATAGTATGTATATTCAAAAGCAGAGACATTACTTTGCCAACAAAGGTCCGTCTAGT
CAAGGCTATGGTTTTTCCTGTGGTCATGTATGGATGTGAGGGTTGGACTGTGAAGAAGGCTGAGTGCCAA
AGAATTGGTGCTTTTGAACTGTGGTGTTGGAGAAGACTCTTGAGAGTCCCTTGGACTGCAAGGAGATCCA
ACCAGTCCATTCTGAAGGACATCAGCCCTGGGATTTCTTTGAAGGAATGATGCTGAAGCTGAAACTCCA

GTACTTTGGCCACCTCATGCGAAGAGTTGACTCATTGGAAAAGACTCTGATGCTGGGAGGGATTGGGGGC
AGGAGGAGAAGGGGACGACAGAGGATGAGATGGCTGGATGGCATCACTGACTCAATGGACGTGAGTCTCA
GTGAACTCCGGGAGTTGGTGATGGACAGGGAGGCCTGGCATGCTGCGATTCATGGGGTCGCAAAGAGTCG
GACACGACTGAGTGACTGATCTGATCTGATCTGATCTGAAAGAATATGAAGTTTGAAAATGTATTTTATA
TTTGAAAATGTAATTCACAATAGCAATAGAATAAAGGAGAATAGTCATATGATTATCTCAGTAGTTTTTA
AAAAAAAAAAAAAAACAGAAAACATACATCCACACGAAGACTTGTATACAGATGCTCTCGGCAGGTTTG
TTCATGATAGCCAAACCTGGAAAAAACTCAAAGGTTAAACAGCAGATGAGTGCATAGATAAATTGTGGT
ATATCCATACAATGGAATACATCTAGGCAATAAAGATAATAAACTACTGAGACACACACAAGGATGTGTT
TCCAAAATAGGTGAGCAAATAAGCCGGACGTGAAAGAGTGCATACTTCACATACATAGCTTCTATACATA

CAGGGATTCCCTGGTGGTCCAGGGAAAGGTGAGGTTCACCCTCAACTGTTCAGTCTTACGCAGTAGACAG
GACCCTTAATGGCTTCTCTCCTGTATTAGTTTGCCTGGGATGAGGTCAAGGGAACTTTTGGGAGTGAGG
AGAAGGTTTTATATTTTGATCCTGGTGATGGTTACATATATATATATATATATATATATATATATATATA    TH_MICRO772C
TATATTTGTCTAAACTCATCCAACTCTACATGTAAAGTTGGTGCGTTCTTATCTAAGTAATACCTCAATA
AAGATGATTATTTTTTCAGTGATAGTTAAAAACTGTCATCTTTCACAGTTCCTTTGCTTTGTCATGGACC    TH_MICRO573
AGCATCCCTTTTCCCTCCTTTACCTGGAGGTTTGCTTAGGGCCTCAGGGTCCAAGCTGCCTCCAGTTCTG
TTTAGTGTTTTCTATCGTGTTTTGACATGGAATGCAGATTTGCCAGCCATCCAGCTGATATTTATCAAGT
GCTTGCTGTAATACTCTACCAAATATTGCAGATAAACAATGAAGCCGTTTCTGCCTTATAATCAAACTAA
CACAGGAGATAAGTCCCTAATAGCCCTGTCTACTCTGTAAGACTGAACAGTGGAGGGTGAATGCACGCAT
TCCCTGCTGTGGAAGGAGCATGTGATCGCTTCTGACTTGGTGAAGGGGTGAGACTTGAGGTGTACTTTGG
AGAATTCATTGGTAGAGACAGGCACTGTGTGGATAGGGGTGTGCTGGGAGGTTGGGCAGTCACTTTGACC
TGAGGGGGGTGAAAGGAAACAAGAAGATGAGGAAGTGTACTGATACCCTAGATTTGTAGGAGCACTAACT

CGAGGTTGGGACTTTACAAATTATAGAGCTGGATAGGGGTTTAGGGCTAGACAAAAGAGCTAAAATGTTT
GTGGGCAGTGTGAAGGCTTTGCAGATGATTGTTCTGGTTGGGAGCGTGATTGCCTAGTCTTAGGCACT
CCCACTTTGGCATCAGCACAGATGAGCGGGTGGAGCAGAGAGGGACCAGGAATGGGACGTGACCACTTAG
CAGTAGCCTAGGTGATAAGTGACAAGGAACCGAGCCCAGTGGCTGCTGGACTCATGTGGGAGCTTGCTGG
ACCTGTTGAGATGCTTTGGGATATGAAGTTGAGAAGAGCAGTCACTTCACCCATTTAACACATACCAGCC
AGTCTTCTTGTTACAGACTAAATTATATCCTCCGTAAAACTCATATATAGAAGCCCCAACCCCCAGTGTG
ACGGGATGAGGAGATAGGGCCTATGTAGAGGTAGTCAAGTTTAAGTGAGATCATAAGGGTGAGGTCTTAA
TTCATTAGGACTGATATCCTCAGAAGAAAAGGAAGAAATAGCAGAGCTCTGTCTCTGCATGAGCAAAGAC
CACGTAAGGACACAGTGGGAAGGTGGCCGTCTACAAGCTAGGGAGAGAGGCCTCACCAGAAACCAGATCT
GCAGACACACTGGTCGGAGCTTCTAGCTTCCTGCAGCTGTGAGACAATAAATATCTGTAATTTAAGCCAC
CCAGTGTGTGCTCTTCTGTTACAACAGCCCAGACAGACCAATGCACTGCTCACCACCAGATTCCTCACCA
CCCGCCTTCCCAATTCCCATAAATAGAATATTGAGGGTTCCTGGTGCTTTATATTCTGATGACATACTTT

TGTGAAACAGTACCCCAATCTCTGGCTTCCTTCTCTTAGCCGTTCGGGTACAAGTCAACCCTGCTGGCCC
TTCCCAACCGTCAGCGTGTGTAATTCCTCCTGTCTCTACAGCTCTTAATTATTTCCAAGTATTTTAACTC
GTTTGGATTTCATAACCACTTGTCTCACTTCCTATGACATAAGCAGGCAAGAGTTGGTTTGACCCCATTT
TACAGATGAAGAAATTGAAAATCGGGATTTTCGTGGCTTGTCTAAGATAACCAGGAGGAGTTGCAAAGTC
AGCCCATTAAATCCAGCTCTCTCACTTCACCACACAGCTTCCTGGCCTGTGCTTTTCTATGACTTTGTCT
GGAGAGAGCTTTCTGTTCAAACCTGTCTTGGAGTGGAGATGTGGGCTGCCTTTGGGCTTCCTTCTTCCCT
TCCTTCCTTTGTCCTCCCAGCATGCACACACACACACACACACACACACATAAACACACACATTTATTTTCG
TTCTCTCTCCATAGTGTAGCTTGGCCTTAATGTCATAGGAACAAGGAGCTCCTCCTTTTCCCGCAGAGCC

TAAACATGACAGATCCCCTGTGGGTAGAGGACAAAGAAGGGATGGGCAAGGGGCTTACGATGCAACCAAA
AGAGAAACCTCGGAAGGCGTAGCAAGAACACTGTAGCCCCTGGGCTGTCTGAACCGCATCCTGGCCAGGG
CTCTGGGGGGCATCTCCTGCGGGCCCCACAGTGGGTTTGCTCCCAGCTAACAGTTAAGGCAGCACCTTAA
CACATGGTATGCACATGGTCATAAACCGAAGCTCCTTTCGGAAGTTTGCCCTTCCTCAAGGCTGTTGGTC
TGTGTTGGGCTAAAAAAAGAAAATCTGTTTGGAATCACAGAATTCCTGGGAAATGTCAACTCTCACACC
CCATTGTCTTTGGAGCTGGCATGCATCTTCTCACTTCTGAGCCCTGTTTGAGGGGCGGGCGTGTTTGCG

GAGGGCCTATTGTTCCTGAGCAGCTGAGCATGCAAGTCTGGGCCTGTGTGTGTGTGGAGAAAGACCAC
CACTACCGTATCACCCCCCACCAGCCGAATCAAGGATTTCTGCTGAATCACAGAGCAGCCCGCTTGTGGC
GCCCTGAGGTTGGCAACTGTTCTTGTAGCAAGACCTGGGACAATGGGATTGGTGAGAAAGATTCACTGGT
GGTTGAGGCAGAGCAGAGGTGGGAAGGAAGGTTTAGAGCATGAGGGTTGTCGAGGGATGACATGGGGAA
AAGCAGGCTTTGAGCCCAAGGATAAATGGGAAAACCTCTGAGATGAGCACTCTCAGATTACAACACCTAG
CCATCTCGAGGAGCTGGCCTCATGCCACCCAAACCCCAAGAACACTAAAGAGGTTAGGCTTCCTGTCCTG
ACCTTGGCTCATTGGGGATGCATATGACCCCTGAAGGAACAGGATGGACAGAGTCCACAGACAAGCGGAG
GCTGTGAGTTCACACCAGGCTCATCTCTAGCCTTCCTCTTCCTATCCTGAACCAAAAACAGAGCCTCTCC
GCATTCCTACCTTCCCATTCATTCTCCCAGTGAATTGCAGTTACTCAGTGTACTAATTTTCTGAAGGATT
CATTCAGAAACAGAATTGGCCTGTCTTTTCTTGGCACTTGGAAGGCAGCTGGGGCAGTCAGACAGATACA
TAAGATACTATTATAAACAGTTCTGTGGGAGCATGGAGCCGCAACCACTGGCCTGGGGGTGGAAGTTGGG
ACGGGGCATAGAGTTAAGGAAGAACTTCACGTAGCACATTCTTATTAGGAGGAAGCCACAGAGGATGACC
```

TABLE 3A-continued

SEQ ID NOs: 1-2, BOVINE EXT2 AND ALX4 GENES

```
AGGAGTCCTCCTGGTAGAGTGGGCTGGTGACAGGGCGCAGGCATTCTAAGGAAACAGATGGCAAGTCTAC
CACTGTAGCCAAGTGAAAGGCCCCAGATGGTTTGGGGAAGCAATGAGTGGTCCTGGCACCCAGACAGGGA
AGGGCTGAGCCACAGCTGATGTTCAAGGAAGCCCTGCTGACAGGGGAGTGTCCTCCCCAGCGATGCTCCT
TGGAGGCACACATCCCAGGAATGGGTTACTTGAGTCCCCAGGGAGACAGATGACCCGGCAGCCATCCT
GCCCTTTGGTGGGAGCACTCATCTGGACTCCAGATACTGTTGGGGTTGCTAAGCAAGGATTTCAGGCAGG
CGGCTTCCCATGCACAAGAAATTTCTCCCTCTGCTTCCATTCCCACCTTGGGACTTGGCAGCGACTTGGT
GTGGAGAGTCCAAGAGCTGCCATGACCCTGTCAGATGGCAAGGGTCACTTTTAAAAACAAGTTCCTAGTT
AAAGTCAACCTAAAGCCATCTGGGTCTATAGTGAATGAAAACTTACCCTAGAGGTACGGTTGCAGAAAAG
GGGACCCCTTCCAGGGCCCAAGAGTGGGCTCTTGTCTAACACTCGGAAATGAACTGTCCAAGGAGACACA
TGTGCTACCAAAGCAAGAGACTTGGGACGGGGCACCCAGGTGGAGAATGGCAGGGTAAGGGAACCCAGGA
GAACGGCTCTGCCATGCAGCTCAGTCTCGGGTTTTATGGTGACGGGGTTAGTTTCCAGGTTGTCTTTGGC
CAATCGTTCTGACTCAGGTCCTTCCTGGTGGCACCTGCATTGCTCAGCCAAGCTGGATGCCAGCGAGAAG

GACTCTGGGCGGTGGCGGGACAGGTGGCAGCTCCTTTTGGCCTTTCCAGAACTCTTGCAGTTGGTGATGG
CTTGTTAGTTCCATGTTCCTTACTAGGACCTCCTGTCGTAACGTAACTCTCACAGATGATTCCTAGCCAG
GATGGGTGGTTTCAGTCAGAGTGCTTCCCTAACGGAACCAAATCTGAGATGTGGCTCCAGGAAAGCAGC
ATTTACATAGTCAGAGAAGATGAAAAAGAGTTTCATGTCGGACTCAGAGCTGGTAGCCGGAGGGTGATGT
CTTTCTCCCGGGAATAATCATAGCCCTTCATGTATTGCCACATCAGCTTACAAAGCCCAGGCATAGGCCA
TCTCACGCATACCTCCCCATGAACTGGGAAACTGGGCAGAGACAGGCTTCTTCCCCTCCTTCAGATGTGA
GAGTTGATGGTCAGGCAAACAAGGATGCCTCCCCTTCAGCTTACATAGGGGTCCCTGGGAGACTAACTGC
TTGAGTCACCTTTAGGCTGGAAAGCAAGGAAGCACCTCTTGCATAGCAAAATCCAGGCCTCCAGCTTGGC
TTTATAATTAGTATATTAGTGCTTTGCTTTAAAAAATCCCCAGGCCTTACCTCCTGCAAGCTGTCTCAGC
CACTAAGCGTTAGAGCTGGGACAGAGACCTGCCTCTCCTGGAAGCCTATCCTGCACCATTTGTCCCAAGC

AGCCAGGTCTCCCTACCCTGACCTCCAGGCCCTAGCTGGCCCCTCGCTTTCAGAACAGACCCCGGAAACC
CAGATGGTACCAGTGATATCGAGGGGCCGTGATGAGCGCGCTGGAGACGCAGGGGCGGCCCCTGATTTCC
CTCCACTGCTTGTCTGCCGTGAGGCAGGTCCTTTGGGATGACTGGGGGGGGGGTGCTCCAGCCCCTCGC
AGGCCATGCGCCCCTCTTTGTGCAGGAGCCCTGGCCGGCCACCTGTTGTTAATCTAGCCCTGGTAATCCA
TTCTGTACTGTGTCAGCAGTTCAAAAGGGCATTGTTAGTATTTTTTGCCGACTTCAATTAACGTGAGATT
TCAGAGGCCCCTCTGATCACATTTCATCTGTCACAAGTTAGGAACAAAACAGACAGGTTCCAGTTGAGGG
GAGGAAGGAGAAGGAGTTTATTGCAAACAACAACCAAGCGGACAGTGTGGGCCGTGCCCAGACAAGGGCG
CTCTGCGAACGCGCAGCGGCGCCCACGCTCCACGCGGCCCCACGCCTGGACCCCGACGCCCCCTCCTCAT
CAACAGTCCAGCAGTCCTCCCCTCCCCCCAAAGATGTACGTGCAATAACTTACTTTAAAAGGCAAGAACT
TTTTTTTTTAATATTTTGCTATAATGTAGTTACATGGTGGTATAGGCAGTAAAACTTTATGGAACCGACT

TCCTTTTTTTTATACATTTTTTTTCTGAATTTTTAATGTCTTTTTCATATATACTTTTAATATTCCACCCC
AGGCCATTAAGCTAAAGGAAAAGTTGCATTTATACAGGGTTACAATATCTTACAAGGAGAACAGTCATTA
TTGATTGAGGTTCATGTTCCTTCCAGCACTCAGCTCTCTTTTCAACCCACTGCACACCAAACAGACTATT
AGACATTGAAAACTGTCCTTCAAAATCAGTAGTATAAAGGCCTAGCTCTGTGTGTGTAAGTGCAGGGGAA
GAAGGGACAGGGCAGGGCAGGTTAATGTTTGGTTGACTGGGACACCTTTCCTCCCCCCCAGCATCTTTAC
AGACATCACGTGGGCTCCCGGGAACTTGAGGAGTGGAGTTTTCCTTGTCTTCCCAGTTTTCTCTTTTGTG
GTCATGGATTATTATCCTGGGGGCCCGTTTGCCCAGCCATCCTCAGTCCTCCCACCAGGCCGTCAAGCAGAC
CGGAAGCCCCAGAACTGTCCAGCCCAGGGGGAGAAAAGCCGCAGAAGCAGGATTCATGCTGCGTTTGCATG

GAGGAGTTCCTCTCGTCGACCCAGCCGAAAGACGGCAGAGGGGACACTGGCGCTGGGCCCGATGTGGCCG
CGGCCACGTGTACTAGGGACCCACCTCACGCTTGCTACCGCCACCCCCTGGCAGTGTCTTTGAACCAACC
TGGCCGCCATGCTTCCCCACGTCGGGGGCATGGTAGTGAGAGCCGAGAATCAAGTATAGTGGAAAGAATT
CAAGGAAAGTTCCAAAGCCCGTGTCCTCCAAGTGCCGTCGAAGACTCGGGGACAAGCCTCTCCGTGCGTC
CCCGGAGCCCCCTCTCCCCACGCTGCCCTGGGAGCAGCGACGGCATCTGAGGGTGGTAGCAGCACCGTAG
TGTCAAGCCTTGGCCGCCGAGACTGGTTCCCAGCAGGATTCGGGGGCTGGCAGCGTGAGGAGGCTGCCC
GGGGGCCTGCCAGCCACCCATTATTTCCGGTTTTGTGTGGCCATCTCTGTTGAGATTTTAGGCAAAGAGC
AAAGGAAACCCCACCTCTTTTAGCTTATTGGCTTAACAGTGACCACCGGAGCCATCCACTCTCCCCTGTA
CCTGCCTTCATGAGACCGCGCTCCTGAGGATGCCGCCAGCCCAGAGAGTCACACCCAAGCTTGCTTTAGT

CATCACAGGAGAGGCTGCGGGATACCTCCCACCCCAGCAGCTGAGAAGGCAGAAGGCCTAGGCCCAGCCC
CCCACCCTGGGGAGCTCCACGCAGCATCAGTCATCAGAGCCCCTCTTAGCTCTGCCTCAAGTGAAATG
TGGCTCAGGATGATGACCTTCCCCACTGGGGACTGGGTCATCTCCGTTGTGAAGGGATTGGGCAGGCTA
GAAGTTTTCTGATCCCTTCCCGCTCAGCGATTCTGTGATTGTTGGAGTGTCAGGCAGGCCCTAGGGTCTG
GGACAGGCCAAGGGCAGGCCTAGGGGCAGGCAGCTGCCCGAAGGGAGATGCAGAGGTGTTTCAGGCCGAC
ATTTTAATCCTAAATACTTAGCTGCGTTGGTGGGACGGGCGGTCAGCGCCAAAGAGCCTTCTTCTATCGG

AAGATTTTTCTTCTCAAGGTTTGGGGTGGAATTTGCCTGACTGAGGTCTGGCCCAGGTGGAAAGCAGACA
CACAGCGGAACTGATCGCCAGAAGTCCCTTCCAGAAGGTTCCACTTAAGAGCCGTGTCTCTCCCTTCCCT
CCCCCTCGGTGTCTATCCTGGTTCTCTCTCTGTCTGATTCTCACCCAGGTGAGAACATACCTCCCAGG
TCTTTCCAGCCATGATGGCATTTAAGGAGGAACTGGGGGGACTGTCTCCATCCTGAAGCCATTTCTTCCT
TCCTTTTCCTAGATTTTGGGAGTCTTGAGTTGTTTCAGCCAAGCTTAGAACTAGAAAAGCCTTCCTAAGA
GTTATTCCCAGATCCTCAAACATAGAAAACACTTAAAGCTAAGTCTCCAAGACATTCAATTCAGTGTCC
AAGATGCTTTTCACTTTGAGAAGATCAACTTTAGAGCTACGATTCCCAAAGAGGGTCTGACTCTTACTAGG
GGGAGGTTGAGGCCAGCTCCTTCCATAGTCCTGTTTCTGGAGCACATGAGGACTTGAGACACAGCTGGAG
ATGGCCACGTCCCCAAAAACCTAAGCAGGTCAAAGGGGGAGGGTCTCACCCCTCCCCACCCACCCAAGAG

GCTGTGCTGAGTCCAGTCCCCTGGGCCTGGTAGACCTAGCTCTCCTCACTGACAGGATTGGGGTAGAAGG
GATAAAAAGCAGACCCTTCTCCTCGGGGATACCTGCAAGGGGGCCTCCAGCGCTCAAAAGGCCGGCCTT
GGAGGATGGCTACCCCATGCCCCGAGCTTAGCTGACCCCTGGGCCCTGGAGCTGAAACTCAAGCTGCAGG
CTGCATGTCAGACGGAAATGCAGCCCCCTGAGAAGGAGGCCCCTTCCTGCAGGCAGGGAGATTGGCTTC
CAGAAAGCACTGTGTCCAGAACAGAGCAAGCGACCCCAAGGAGCTCAGCCCCACATGAGCCCTCTGGAGG
CCAGAACAAGGGACCGGGGTCACCCATGCCACAGGGCAGAATTGCCAGGGCAGGCGCTCTCTGCCCTACG
CCCAGAGGACTGCACAGAAGGCTCTGGGCAGGTGTGATGCAGGAGGCCGCTAACCGGGAAGGCTGTCTGA
GGCCGCGTGGGGCCGACCTGGTGCCCGGAGGCCGGGTGAGTGTGCCCTCGTCGTCTGCCAGACCCCACA
ACCCGCTCTGGACCCTCTGGCACCGTGCCCCCAGGCCCTAGCGGCTGTGTCAAGGTGCGAGTCCTTCTGC
ATCAGGACACTGGCCCAACAGCTCCAGCAAGTGACCAGGATCTTCAGATTCCACCTGGAGGGGCCAGACT
```

TABLE 3A-continued

SEQ ID NOs: 1-2, BOVINE EXT2 AND ALX4 GENES

| | |
|---|---|
| GGACAGGGTACAAAGCTACCCAGACCTGCCCCCTGCCACCATCATCCTGCCTGAGGTGGGGCGTCAAGGT<br>GGCCGGAGAGCCGACGTGTGTGCACGAGCCCTGCCTCCCCAGGACGCCTCCCTGCAGCCCTCTCGGCTC<br>CTAGAAGCGTGCTTCCAGCACCGTGGGGCCGTGGGCAGCGGGTCTCCTTCCCTGCACTGTTCACCCAGAT<br>CCGGAGCCTCAGGGTCCAAGGGGGCCAGTGTGGCTGGGTGACGGCGGGCTCCTTCGGCTCCAGCTCCTCT<br>CTCTCTGCCCTGTCCCTCCGGGTGCGTCCAGCACAGGGGACAGTCAGCAGGACGGGGGCTCCTCACGTCC<br>AGGGTAAAGGCGAGGTGGGTGCCTTGGATCTAGGAGGTTGGAGTCCATGGGCTTTGAGGGAGAGCACAGG<br>AGATGGGATGGCAGAGGCTGACTGGGCAGGGCATCTGTTCTCCAGACACGGTCACCGGGCTGGTGATCGG<br>GGACCACACAGCAGAGGGAAGGACGGACTTTGACGGAACCGTAGCCACAGCTGGTCCAGGTGGGAATCTA<br>GCCTCAACTCAATGGTCAAACCGGGCAGGGCGGAGGAGCAGGAGTGGGGAGAAAGGGTCTTCAGCTTATA<br>ATGGATGCAAAGCTGCAAAACTCGTGCCACCTGGCTGCCTCCACTGCCTCTGGCCGGGAGCGGGGGCACC | BALX4_4R |
| TGGCCTCGGTGCCCGCTGCCCCCTTCCCTCCCCACAGTCCCCGGGGGCCTCAGACTTGGGGCGGCTGAAA<br>GTGCTGAGGGTCAGGCTCCTGGGCCCAGGCCAGGTGCCTAAGAGGGGAGTTGAGTGGGGGGCCCGGGGGC<br>CTGGGGAGCATGGGCATGGCCAGTGCCACAGGGCAGGGGAGGGCGCAGGGATGGGGCGGGGTGGCCCTGT<br>CATGTGGCCCAGGAGATGGCCGCGCTGTGCTCCTTGGCCTTCATGCGGAGGGCCGCGATGCTCGAAGTCT<br>TGCGGTCCGGCTCCCCGTTGAGCTCATAGCCGTTGAGGCCCGGGCTGAGGCCCGCAGCTCCAAACAGGCT<br>GCCCATGTGCGTCTGGCCCACGTGGCTGCCAGCCCCGAGACGCTCAGGAAGTCGGTGACGCCGCTGGCC<br>CCGGAGCCGGGGGGGTGGGCGTGAGGGGACATGCAGGCGGGCACCGGGTCACAGGGCACCACACAGGCCG<br>GCACGGGCGAGGCGGCCCCATTGTTGCCGATCCAGGACGGGTTCTGAATCTGGGGAGAGGGGAGGGAGAC<br>GCGTCACAGGCTGGCTGGACACAGGGGTGCTTTCCTGTCCCACACGGGGGACCTCTCTTCACTTACAAAC | TCA STOP CODON<br><br>ALX4_EXON4 |
| CCATCCTGATGATAAAACCATTCCTGAGTGTTTACCTGGGAGGCTTTCCAAACCTGCCTGGCCACCTAGC<br>CCCCTAGGAGCCTCGGGGTTTTATGCTCTGGTTCCTCCGTTCCCAGGTCCAGGAGAGCAGTGGACAGAA<br>CTCCGTTTTAAGGACTGAACTCCGAATTCCATCAAGAGTCCAGTGAAAGGGTCGTCCTGGGGCACAGGTC<br>ACCAGCTGAGGGCAGCCCCTGATTCTGTTTATTTATTTGACCACACCACTTGCAGATCTTAGTTCCCTGA<br>CCAGGGATCGAACCTGTGCCCCTGCGGTCAGAGTCCTCTTCATTGGACCGCCAGGGAATTCCTGGCAGC<br>CCCGGATTTTAGACACAGAGGCAGACTCTGTCTCTCCATCCATGGACCCATTTAGGGTCAGCACCTGGGC<br>CTCACCCTGCTCCGGCTCCTCCCCAGGCCCAGCACGCCCTCGTGACTTGATCCATGGGAGGGGACACGAG<br>CTCAGAGAGCTCTGGCATGGCAACGTGGGCTCCGAGGCTGTCCACTCTGAGAGTGGACGTCGGGGGGGCC<br>TCAATTCTCTCAGAAGCCAAGGTCAGTAGTGGAGGTCCTAGGGGCCGGTGCCCTTGAGGCTTCAGAAGTA<br>ACTCAGGGTCTGAAAGGGCTGCCTTGAGAGGTGGTAAGTGGACAGATAGAGCCAGGCGGGATGCCCACAG | BALX4_4F |
| GCTCTAGGCTGGGGCAGAGACAGGTGGAGGAGGTGGAAGGTGCTCGGGCAGCGGGTGAAGGGTTGAACTG<br>GACACTTTGTCTTGTATCTGCACGGCTAAAATCCTTTCCCCCTCCCAGCTTCCAGCTCTAGACCCCACT<br>TTGCCCCAGCATTTATGTGGAGGCAGAACTGGGGACTCAGCCAGAAATGCATCTCTCCTGGGTGATGGGA<br>GGCAGGGGGGTTGGTGGGCAGGATGGGCTGTGAGGAGATGGTGCACCTCTCGGCCACGTGAAAGGGCTTC<br>TCAGTGGTCCTGGAGCAGCATCTGCCGGCCTGCCCCCTGCCCCCAGCCGTTTGGAGTACATTCAGAGAAGT<br>CTGTAATAAAAGGAGTGACAAGGCGGCCATGCCCCCAGATGCCATGGTGACTGCAGTGACAACAAGAACT<br>GCTTGCAGGTTCGGGTGATGGGGACCCCCTCTCTCGAAAGGCCTAGGGGATGTGGTGTGGTGCTGCAT<br>GGAAAAAATGAGCATGAGCCCCTCTGGTGTGTGAGCTCGGGCAGCAGAGGTCAAGGCCAGGGAGTCCGGG<br>CTGGAGGTCCATCCTCCCAGGGACAGAGGGAGGCTGGCTGGGGGGACGGAGAGAGGAGAGAAAGATATGG<br>GCGGGCCCAGGCTTGGAGCAGAAGGCGGAGGCCACAGCACAAGGAGGCCTGAGAGGAAGGAACCGGCTGC | |
| CTTTGCAGGGCAGGTTGAGGGGCGTCAGGATGGTACTCAGCCCCAAATGCACCTCTCCAAGGGTCCTGGC<br>TGCCTGACTTCACCTACATCGCTTCCCGTCCCTTGACATCCCACTGAGGACCCAAGTGGCACCAGGAAGG<br>GGACTGAAGGACAGCCGTAGAAGAAGATGCTCTGGAAGGGATGGGAAGAAATGGGCCAGATGCCTGGGAG<br>AGCCACAGACATACGAAGCAACCTTCCTAAAACCATGTAATTCACAAAGCACTTTTGCACAATCTAACGT<br>AGACCTTCCAACAACCTTGTGAAAGAGCTGAGGCAGGTGTTTTTTTGGCCACATCGTGTGGGATGTGGG<br>ATCTTAGTTCCCCGACTAGGGGTTGAACCTGAGGCCCCCCGCCCATGGAAACACAGATCTTAACCACTG<br>GCCAGGGAAGTCCTGAGGCAGGTTCTTTTAAAAGACCCAATTCCTAGGTGAAGAAACTTGAGGCTCAGAC<br>ATGTGACTTGCCTGAAGGGAGAAAGCTCTGGAGCTGGGATGACAGCCTAAATCCTGGGTCTGAGAATCCC<br>ACGTTCATTCCAGCCTTGCCTCACTCACGTCCTGAACTTCAGGAACCCCTTCTTCTAGGAAACACTCTG | |
| GGTGGCTCCCGGTGGCCTGGAGGGCCCCTGGCCTTCAGCATTCCTCGGTTCCGATGCCCGTCACCGAAGT<br>GGCCGAAGGAAAAGTCATTCTCAAGCTTCTCCCCCAGTCTCCCCTTCCCTAAAGTCCAGCCAAGCCTGGG<br>TCAACGCTTATGGGGGCAGAGAGAATTCTGGGCCTCCCACATCCTGGAGACACAAGTGCACTCCTGGAA<br>CGGGCCTGAAGCGGGGACTTAGAGCCCCGAGCTCTCTCTCCAGGGAAGGTGTTCCTCCTAAGGGCCCCAG<br>AGCAGGCAGCTGGGGGCAGGGACTCACCTGGGCATAGTTTTCCGCTCGGGTGAGGAGGGGCAGCTCGTAG<br>GCTGTGGAGAAGTGGGTCCGAACCTGCTGCATTTGCCCGAAGCGTTCCCTCTTCCTCCACTTGGCCCTCC<br>GGTTCTGGAACCAGACCTGCAGGACAGAGCAGTTGTCGCCAGGGTCAGGCCCGGAGCTGGGCCCCCGTG<br>TTCGAGGCAGCGCCAACCTTGCCCTCGAGCCCCTCTGGCTGTAGTTATAAGGTCAAGACTGTGGGCTAC<br>AGATTACACATCTGCCTTGGTCTCCGTGCTCAAGAGCTGATAATCTGGAAGGATCGACGCTGAGAGCCGG | BALX4_3R<br><br><br><br><br>ALX4_EXON3, BALX4_3F |
| GGAGGCAGTTCACACCCCAGTCGTAGGCGTGACTTCGGGCCAATAGGTTCCTTTTTCTGAACTTCAGAAC<br>CCAGAGCAGGCAAGTGTCACAAGCACACGGAACACGTCACCAGTCATCTCAGCGGTCAAATAACCAGCCC<br>TGACATGGGCGGCCCAGTCCTCTGGGGCCACAGACTACGGCAGAATCTGATGACAGCCGTGAAAGCTTC<br>ACCAGAGAGTCATTCTCCTGGGTGGCCAAGTGGTAAAGAACCCGCCCGCCAATGCAGGAGATATAATAAG<br>ATGCCAGTTCCATCCCTGGCCCAGGAAGATCCCCTGGAGGAGTGCATGGCAACCCACTCCAATGCTCTTG<br>CCTGGAGAGTCCCATGGACAGAGGAGCCTGGTGGGCTACAGTCCACGGGGTCACAGAGAGTCGGACAAGA<br>CTGAGCGACTAAGCACACACAGAGGATCACACACGTGTGGTTTTTCCATTGTTTTCCACTTCCTGAATCC<br>CCCATGCAGCCTTTTGTGGAAAGAGTCTGGACCCCCTGGGTTACAGCTTCTCTGGGAGACAGGGCTTTAG | |
| CCAGGCTGTTGGAGGACAGTCAGGGACAGCTTTGTGGAGGGAAGGTGGGGGCTGGAGGGACAGAAGTCCA<br>GGCTGAGTTTAGAAACGGCCCGGCCACGCCACCAGCTGGGAGAGTGATGGGAGGGGAAGGATGGTGGAAT<br>CAGATGGTAGGGGCCCTCAAATGCCAGGTGGGAGGGTCACCTTGGTGTTGTGAAGAAGCTGCTGCAAT<br>CTCAGGCCCCAAGAGCAGCGTGATGCCAGGGAGGAGGGGAGGCCCAGCTGTCACTCAGCACGGGGGTGG<br>CACATTGGCTTGACCAGGGTGCTCTAGGGGAGTGTGGTCTCTGAGTCAGGTGTGTATGAGCCAGGGTCTT<br>GTTTCATACTTAGGAAAAAAATTGAGAACCTTCCAACAAAAGCTATTGGGCTTAATGGAAGCTTCCTTTG<br>CAAAGAGCGTTTCTGGCAGGCTGAGAACNNNNNNNNNNNNNNNNNNNNNNNNNNNNNNNNNNNNNNNNNN<br>NNNNNNNNNNNNNNNNNNNNNNNNNNNNACTCCTTCCTCAGCCTCCCAGGGTTTTCTGGGCAGGAGGGA<br>GGCCAGGGCGATAAAGAGAAGCCCACTGGAAGCATCTAGATATACGACTGGACTGCTTTCTTCAGGGCTG | SEQUENCE GAP OF <2 KB |

TABLE 3A-continued

SEQ ID NOs: 1-2, BOVINE EXT2 AND ALX4 GENES

```
AGGAGAAGCCTAGAAAAAAGTGAGGTTGCCACTGTGGTGGGGGCCGCCCCCTTGAGTCTCTGTGGACTCA
GGTCCTACAGTGGGAGACACACAGGGCTGGCAAAGGGGGCCTGGGGGTGAGGGCAGGAGCAGAGCAGGGG
TGGTGGGAAAGGGGGCGGGGGACAGGAGATGGAATGCCGGCGGGCGGGGCGGAGCGGGGTAGAGGGGCG
ACCTGGGTTATCTGGGAAGACAGATGAGCTGGGGGAGAGGCAGCTGAGAGCGCTCGGCCTTTGGGAAGGG
AGTGAAGAGGGTCAGGCAGAGGGGTTTCTTTGCAGGTTAAGATGGAGATCGTGGGAGGCGGCACGGCTGT
GGGGAGCAGGCTGGGGGGAACAGAACTGCCCACCTCCAGCCCCTTCCTCCCTGGGGCCTCACCCTGCAGA
TGAGGCTGGAGCTTTTCTGCCCAGATAAGGCTTAAGCTCCATTAGCTTCCTGGTCTTCACTCTCATCATG
CATAAACTTGGGTGGTGGCAGGGGTATCCTCCCGGGCCCCATCTGTGCTCACATTCATGGGCCCCCAAGG
CTTAGAGCATCCTCCCATTTCTGACCCTTGGAGCCTGGGGTGCTGACAGCTGCGCCCCTAGATGCCCTGG

GCCTCAGGCTCTGCAGCCCATAGGCTTGACTCCACTGGGCAACCTTGGGCAGGAGAAGGGACCCAGAGGC
CCCAGCCTTCCCTTCAGTGCGTCACAGCAGCCCAGGACCACCCCGCTCCTGGCCCACCCTGGCCTGGACC
CGCTCAGCACGGGCCTCTCCCAAGGAACCAACTGTCTTGGCGGAGGCCCCTGCTAACCGCAGCCCATCT
GGGGCCAGGGCGGGGTGGCTCAGGGCGGGGAGGCCTCTGCCTTATTGTCTTCAGACACAGCTGCGTAGAT
GGAATCCCAGACAGCACAGAAGAGGCCCCTGCAGCCCCCTGGAGCGGCTCCAAACTCCGGGTTTCTTCC
CAGGAAAGGTCCATCTCGGGGGCGGGGGGCCCGTCCCTGTCCCCACCGTCACTCTGTGCCAGGCACCTG
GCTTCCCATCAGCTGAGTATGGGCCCCCAACAAACTCATCAGAGGCAAGCAGGGGGTTCCATCCCCACCT
CCCCCCATCTCCAGGGCACTGCCAAGCGCAACCCAGAGGTCTGACGCACCTGCCAATCCCACCAACCCTG
CTGCCTTTATACAAAGTAAAGTCTCAGAACAATTAGGCACGTGTTCCTGGTGAGGCAAACTACAGGAAAA
GCACTGGAAAGGGCTGGAACTCAGGGTCCCTCATTCTATTCTCAGCACGGCCACCCCATCACCTTTCCTG

AGTCACCTGGTCACAGGTGATGGTTTCCTGCCTCTGGGTCTCTTCCTCCTCGATAGCGAATGAGAGAACG
AGGTGGTCCTCTCCAGCACTAGCCTTCTAGAATTCTGCGGTCTCCCCTGAGATGATAAGACAGGCAGCA
CATCACAGTTCCCCTTTTTGCTTTGGCGGCTGGGAAGCTCAGCATTGAAATTTGCGCTCAGTGAAATCTA
GGATCCTTAGCTTAGCCTAGGTCTTTGACATAATTACCTTCCCATTTCATGGCACTGTTATTGTTCGAGG
ATGAAGATAAATCTTTTAAGTGTAAGCTGCCCCAGCTCCTTTTTGGAAGTAGGCATAAATGTGTGTGTGT
GTAGAGAGAACACTCCTGAGCTGTACTGTGGTGCCTGAAGAATGTTAAACATGCTCTGGCGTCATTTCGT
GTGTGGTACCAGAAGGATCATCCTATCAATGCTAAGCGAATTCTACTCCTGGGCACTTCTGTCCATTTGT
TAGGGACACACACACGTGTGTGCACACACGTGTACATGTGTATACCTCACAGAAAACGGACAGTTCATTT
TGCATCAACACAGCACCTACAGGAACATCCCATAGCCAGCTGCTCTCTCTCCACCGACTCCTTACGCTCC
TCTCAAATCCACTGGCTGAGCTGAGGCCAGAGGCTGGGGTTCCTGTCCAGAGTCTGGGGCACCAGAAGTC

TCAGGTGAGACAGTGGGTGTGAGAAGGTTTCTGGAACCACAGTGAGGCCTCAGCTGCCTGTCTTCCTTCC
CCAAACACTCACTGTGAGCTGGAGAGGAATAAGGTGGGAAGCTTGCTTTGGGGAATTTATGAATAAATGA
GCTGACCGTTCAGAGTTCCCTGGTGTTTCTGGATGGCTGTGTATTCACTGGCAACTACCAGTCTCTTTTA
CACTTTAGCCATTTTAGATGATCTAGTTTCTGGACCATGCTATTAATACAAATGTCTCTGCCTTGTTAAA
CAAAGACTGGTGAGCCTTTTATTGACACCGTAGGGGTTCCCTGGTGGCTCAGATGATAACAACTTGGCCT
GCAATGCTGAAGACTTGGGTTCGATCCCTGGGTTGGGAAGATCCCCTGGAGAAGGAAACTGACTACTCAC
TCCAGTATTCTTGCCTGGAAGAACCACGGACAGAGAAGCCTGGCAGTTCAAGGGGTCTCGAAG
AGTTGGACACAACTGAGAGATTTTTTCACTTTAGGAACACTCTACTTTCCTGGTAGCTTAGGTGGTAACG
AATCCTCCTGCAGTGTGGGAAACCTGGGTTTGATCCCTGGGTTGAAAAAATCCACTGGAGAAGGGAATGG
CTACCCACTCTAGAATTCTTGCCTGGAGAATTCCACCGACAGAGGATCCTGGCAGGCTACAGTCCATGGT
GTCACAAGAGTCAGGCGTAACTGAGCGACTTTCACTTCACTTCAAGATACTCTGCAGAAGATTCTTTAGT
GAAAAAAGGCGAGAAGGGGCACCCTTGGGGTCTGCTGAGTAACAGGGCTCTCAGTCCTGGCACCGAAAGG

ACCCCAGCTGAGCTTGCTGCTTTTTTAAAAAGACTCCTCTTTGCTCTTAAGCTGTTGATTTCTATAGCCC
ACGGGAGAGGGAAACACTGTTATCTGCAAACACTTGATTTGCTATTTCAACATGATTTGGGCTGGGAAGG
CAGGCCAAACGTGGCGTTCATTTAGTGTTACGCTGAAGCCTGAGCTTTATCTTGTCATCTATGGTTGGGG
TGCTTAGAGGACTTTGCATCCTCTCTGGTTTTTCCTTTGTTACAATTTCATGCAGGGAGGGGAGACATAC
CTCTCTGGACAAAGGAGGTCAGTTGGTCCACATATATTTATTTTTTGCCTTTTCTGATCTTAGTTCAGCC
TTCTCTAATTGGTGGGAATTATAGTGATGAAGAATCAGACCGTACCTGCCCTCATCATATTCTAGTGAGA
TGAGACAAACAGATGACATAATTTAAGCCAATCATAAATTCTAAGATAAAATAGCACAACTGGTAGAAGG
TGACCTGGTTTGTTTGTGTTGTATTAGGTTGAGTTGTGTTGGGTTGGGTTGAGCTGTATGGGGTTCCACT
GTGGTGCACTGAATTGTGTTGGGTTGTGCTGAGCTATGTCGGGTTAGGTTGCGGGGTGTTGTGTTGTGCT
GAGCTACGTTGGGTTAGGTTATGGTGTGTTGTGTTGTGCTGAGCTACGTTGGGTTAGGTTATGGTGTGTT

GTGTTGTGCTGAGCTATGTGGACTCTGCTGGCCTGTGCTGGGATTAGTGTTTTGGTGGTCGGGTGATGG
TAGGGGGCAGTAGTCATGGTGATTGGGAAGACTTCTCAGAGGAGGAGTTGGATTGTCTTGGTTTCTGCCCATGGGGTGCCA
TGGATGTCTTGTAAGTTCATCCTGTTTCCTTTCTAAGAGGTAGGCCTTCCAGAGCAGAGACCCCTCATCG
TCATCACCTCCTTCGCAAGAGAGCCTGGACTCACACACCACACAGAACTCAGAAGCATAGCTGACGGCT
GCCTGCCCCTTCCCTGGGAGCCCCGCCCTAGCCCCTGCCAACCAGAGCATGAAGCAGGATGGGAACGTGA   BALX4_2_1241C
ACAAAAGCAGACCTGCTCTGGTTACGGCAGGGGCGCGAGGGGCGAGCTCCTTGAGCTGAGGTGAAGAAAG
CCCTGGTGCGCTGGGGACGGGCAAGCGGCCCTGTCTCGGGCCACTGGCGGAAGGGGCCAGCCCCGCTCT

CCCCGCCTTCCCTGGCACCCTCACTGACCTGCACGCGGGCCTCGGTGAGGTCGGTCCTCATGGCCAGCTG
CTCCCGCGCGTACACATCGGGGTAGTGGGTCTTCTGGAAGACCTTCTCCAGCTCCTCCAACTGGTAGCTG
GTGAAGGTGGTTCTGTTCCGCCGCTTCTTGCCCTTGTTGCTCTCCGAGTCGGCCTTCTCCATTGGGCTGG   BALX4_2_889
GGAGGTCGGCGTGGCCCGGTCCTGGGGCCCCTTCACCCCAGCTTCCTTCACACTGAGGTAGCTGCTGTC   BALX4_2_836C
CATCCCCACCGTGTCAGAGTCGGGTGGCAACTCTGGCTCACCCAGGGAGCTCTCTTTGGCTGAAGGGGGA   ALX4_EXON2
GGAAACAAAGTCAAAAAAGCAATGGCTGAACCCAGCCCGAGAGGTAGGAGGGACGGGGGAGCCATTCCCT
GCTTTTCCCTTCTCGGGGAAGCATGGGATGCAAGGTCCGGAGGCCTGGGTTCTAAGGTCATTAATGTGCT   BALX4_2_627
TTGTGACCTTGGCTAAGTTTCTTTCCCTCTCTGAGCCTCTTCGCCGTTACGTCAGCATGGGCCCCTTTTA
GCACCGTGTCCTGTGACTCTGGGCCAGCCAATCTGACTTCTATAACATTTACCCTCCGCCCCCACTGACC
CAGGGCTCCTCCCTCTAGGACTCCCCTTGCCAGAACTTCTCCTTTGGGTGTTGAGGATGTTGTCTCAGTC

CTTCGGACTCAAAAGCTCAGCCAGCAGCCATGTCTGGCCCAACTGGCTTAGGGTGAGGAGGAGAGGCTC
CTCCCTTGCCTGGCCTGATTCTGTTTGGGGTTCAGCACCCTGCCCCCTCCAGGTGGGGGCTGTTTACTAAG
GAAATAGGGGGTCCTCCCCGTGACATGCCCAGGATGCTGAGCTGGGAGGCCCAGCAGATTTACACAAAGC
TCATGGCCCCGGGGCCCACAGCCACCGCTGTCTAGCAGAACGGGACTCTGCCGGCTGATTCCTGGACGCT
CAGAGCTGGCAAGGACCAGTTATCCAGTGCAGGTCAAGGTGAGGAGACAGGGGAGGGCAGGGAGGGCGA
GCTCATCCTTGTTCAGATAGCCCCATCAGTGCCCTGGGCAGACACACTCGCCCCAGGGCGGAGGTTAGGG
GACAGGCCCTGCAACTGGCCTCAGGGTGTGAGTCCCCCCCATGTCTGACTCCTGAGCTGTGTGCTTGGA
CCTTTCGCTGAGCCTCTCTGTGCCTCAGTTTCCCCCTCTATGAAATGAGGGCACAGATACTTGGATCTCC
CTCACAGGGACTTCCCTGGTGGCTCAGACGGTAAAGCGTCTGCCTACAATGTGGGAGACCTGGGTTCAAT
```

TABLE 3A-continued

SEQ ID NOs: 1-2, BOVINE EXT2 AND ALX4 GENES

```
CCCTGGGTCGGGAAGATCTCCTGGAGAAGGAAATGGCAACCCACTCCAGTATTCTTGCTTGGAGAATTCC
CATGGACGGAGGAGCCTGGTGGGCTACAGTCCATGGGGTCGCAAAGAGTCGGACACGACTGAGCGACTTC
ACTTTCTTTCTTTCCTTCTTTTCTTTCAAAGGGTAGCTGTGGGATTAAAATGTCTTACAGGTAAAGTTGC
TCCCTGTTCTGGTCTAGACTTGTGAGCAGCAGAAGAGTCTAGCCCTGGAAGAGTCCTCCCAGTGGGCAGG
CCCTCCCTGGAGTCCCCCAGCCCAGGAGTGGGTGCGGATGGGGTGCGAGTCCCTCTCTGAGCCAAATTCC
ACTGGGGACTCTGACTTTACTTATAGAGTGAAATAACATACGGGATAATAAGACATGTGTGGGGAGCATT
GGATAAAACTTTTCATGTGTGAAAGCTCTGATCATAACAAGCATTTGTGGTCTGTATGGGCTTCCACCAT
TCTGACTCTTGGTCTCCTCCTCTGGGAATAGATCTGAGCCCCAGGTGTTAGGTGTCAGGACGGTGCCTCT
AGCCCCGGTCCCTTGATCCTGACCAGATCCTGGGGCCGAAGCTTCGGATCCGCCCTCCTCCCTGGCACTC

TGTGTTTACTGGGGGCTCTCTTATTGCTGGGGAGCTGAGAGGGACAGGCTGCCCAAGGCGGTGAGGAAAG
GGAGTGGAGGTGAATGCTCAGAGTGGGCCTGGAAGCAGCTTCAGGAGGCTGTTCCTGAGGGCCACTGGCA
GCATGGGCGCCAGCAGGCTGGGGGGCCGGCCCTTGGGCACCACGGATGACACCCATGTGAGTCCAGGCAC
ACGCAGACCGCCACGGCTTTGGTGACAGCGTCATGCAAACTGCAGCTGGCAGCTGGGCTGGAGAGCTTTCA
GCAAAGATATTTATCTTCCTGGCAGACAAATACGTTTTGTGTTTTGGTTTTTTTTTTTTTTTAAAGAGAA
GAAATCCCACCCAGTCTCACCAAAAATAAACATCTCTGTTATGCAACCTCCTGGAGGCCAGACTCGGGGA
GCAGGCAGTGGCTGCAGCCCCTGCCCCTTGTGCCCAAGCCCTGCTGCCCAGACCCCATCCCATGACCCCA
AGGACCCTTCCCGTATCCTCTGGCATCCAGCCTGGGCTCAGGACCCACCCCACACAGCAAAAGGGGCTGGG
CCGAGCAGGGGAAACTCCATGTTATAAATATCAAGGGACGGTAGGGACTAAACTTCCTTGTGTTAATTCAG
GGGAAACAGAAGCCAGAGAGAGTAAGAAATGTGCCAATAGGGACAGGGTGCAGCCTCTCAGCTCTGGGTC

AGTCCTTCTCTTCTACCCCGTGGTCTTGGGGCCTTTCCCAGGGAGAGAGGGAAAACCAGAAGGATTCCCC
AGGGCCTCACGTAATCAAGAGGTATGGTCTGCACATCAAGGAGGCAGAGAACCAGTCCCGAGGATGAGA
GAGTGAGGATGTGGCCCCTGGGAGAAGCCCACCCCCGCTGAGCTGGTTCTAGGCTCACTGCGGGTGGAGC
TGGCTGAACACCCAGTCGTCCAAGTAGAGAAGCTTCCCCACCTCCATCCACCCACTGAAAGGGTAGGCAT
GGGGGGACAGCATGGTGTGGGGCGCAGCATGGGAGACCCCAGGCCCAAGGTGCGGAGATCTGCCTCGTCC
CAGCTCTCCCGAAATCTGCCTGTGACCTCAGAGGACGCCTTCCAAGTGCCAGAGCCTCCTGTGCCGATGG
GAGCAGGCAAGCCCTGTCCGCAGTGGGGAGTGCAGGCAGGAATGCATCTCGGCCCTGTGGGGCAGCCCT
CCCGCCTCAGTCTCCAGTGGGACCTTCCCCTTGGGACCTGGAGTGGGGAGAGGCTGGGGGCATATCTGTC
CAGGCAAACGTCAGCTAACTAGAAAGGCTTCAAGATTTCAAGACGGAAGGGATTCTGGCAAACCGAGGCC
TCTCTGGCCCTCGAAGAGGGACGAGACCTTCCAAATCTCAGGAGCTCTTGATTATTCTTGCTTTAGGTGGCT
AGGCGGTAAAGCGTCTGTCTGTAATGCAGGAGACCCAGGTTCGATCCCTGGGTTGGGAAGATCCCTTGGA

GAAGGAAATGGTAGCCCACTCTAGTACTCTTGCTTGGAAAATTTCATGGATAGAGCAGCCTGGTAGGCTA
TAGGCCATGGGGTTGCAAAGAGTCGGACACGACTGAGTGACTTCACTGACTTCACTTTAGGTTCTGAGGC
TTGGCCCCTAATTGAGACAGCAAAGGAAAATTCCCCAAGGTTCTGACCCAACCCATTAGAATGACAAGCC
AAGGTACTCATCCCTAAAGTGCCAGGCTTGGGGGCATCAGTTCCCACCTCCTGCCACCCTATAAGCATCT
GCACCCAGTGCTGTCACTCAAGCTTTGGTGACGGAGCTCATCGCCCCAGGACCACTGGACCGTCTGTCC
AAAGGTCCAGCCTGTGTCTGATTCCTGCGGTCTGGCTCATTGGCATGGGTTCCAAACCTCCATGGGCCTT
CCCCAAGGCAGCCCTGCGGACATCTGGAGATGGCTACCATGCCTCTGAGTGTCCCATCCTCCTGAATAAA
TATAGCTCTCACTGCTGTTCTGTAGGAGGCCCTGAGTTTAACAGGCCCGGTCTGGAGACAGGTGAATGCCAG
GGATGGGATGGGTGGTGGTGCTGGGCTCTGGGCAAAGCCAGCAGATCACTCTCCAACTAGAGGATCCAGA
GAGGCTGGGTAGAGACTTGGCACCATGGCCCGAGACCTGGGCCTGGTCAGGATCCAGCTTGCTCCGTAAG

GCCCTCCTCAACAAGACGGCCGCTGAAAACAGAGGGCCTGAGACTCAGGCTGACTCACTCCTGAACAAAG
GAAACCACTGAGCTCCTTGCTCTCCCTCACCTCCTCCTCTGTCCACCTGTCTGGAACGCCCCTCTTTTCC
AGCTGACCTCCAAGGTCCAGTCAAGCACCAGCTCCTCCAGGAAGCCTTCCCAAACTGCGGCAATCATACA
GACCCCCTCCATCTAGTTGCTGCCTACGTTTTAATCAAACCCTGAAGGTCCAGCTTCTCCTCAGGGAACC
AGTTCCCTGAGGGCTGGAACCTTGGGCCATTTGTCCCTGCTCAGCCCAGGATGGGGCAGGCAGGAGGTTA
CCGAGGAATCAATGGCCAATACAAACATTATCGAGCTCTCACCCTGTCCAGCTACCTCTGTGTACTCACT
GGCAGTACCTACAGGGTACGTGCAGAGACGTCTGCTGAACAAACACATCCTCGGAGACAATGGAGAAAGC
TGGTGAGGGTGCATGAAAGAGAGGCATGCAGTGGGTAGTGCCTCCATCAGAACTGACAGCTGAAACAGGA
GGAAGAGGTGAGATCACCGAACGACAAGAGGGGAAGAGGGCAGACCGAAAGGAGGCAGGAGGAGGAAGAA
CAGGCAGACACAGATGATGTCTCCACACAGTGAGCAAGGGGACACGCTGGGGGAGGCCACGCAGGAGCA
CCGAATGGGGGCTCTAGAATTGACGTTTCCAGAAACCCAGTCCAGGATCTGCCAGGAACCAGCTCTGCAT

TTACTGCACTGCCACACCAGGAGACAGGAAAGGCCCCAGCTAACCCCTTTGCCGGGCGCGCCTTCTTGAG
GCCACATGGCATCCGCTGCTGGCATGAAGCTGAACGACAGCCCTCACTAGGACCAGGCCACCTGCCTGCC
CGGCTGGCTTCCCCACATCCTCCCTGGAGCAGCCCCTCATGGTCTCTGGCCCCATCCAGAGCGGGAAGGG
ACCCCTGGGCGGGCTTTGTCCCAGGCTTTGGGGGCCAAGCAATGTCCTCGCGAGCTGCAGCCTTGCCCC
GGAATGTCTTGATCTGGAAATACATCCCAGACTACCCAGAGGAATCATGTATTGTGCACAGAACGTCGAG
AATCCAGAGTGCCTGCCCCCAGGGAGGGATGCACACCCTTCAGAGACTCCATGACCACTTCTGATGAGT
GGGCGGCGTTTGGTTCAAGGCTTACTGTTCATCAGGAGTCACAGACACCCTTGAGCCTCTGCCTGTTCTC
CTCCTGGGGAGGAGGCCTCGCCTCTTCTGAGGGCCAACTGGTCTGTGCCGGACAGCCTTGGCTGTTGGAT
TTTAAGAGCTACAAGAAACGGGGTACCTTTCTTCATTCTCTTGTGTGCATGCTTTGTCACTCAGTCATGT

CTGACTCTTTGCAACCGCATGGACTGTAGCCCACCAGAGTCCTCTGTCCATGGAATTCCCTAGGCAAGAA
TACTGGAGTGGGTTGCCATTCCCTCCTCCAGGGACCTTCCCGACCCAAGGATCTAACCCAAGTCTCCTGC
ATTTCTGGTGGATTCTTTACTGTCCGAGCCACCAGGGAAGCCCCTTAGCTTCTATCTACTCATCCTGGTT
GAATCCTAGGGTGTTGCTCCAACCTAGTCTAACTTTTTTTTTTTTTGACATGAAAGGCCTTGAAAGATTT
CCAAAGTTCACCTTAATTTTTTTTTTTTTTTCCATGACTGTGATTTCAAGAGAATTATTTCTGTGATTGT
GATTTAAGGAGAATGAGCTTCTGAAGCCATTTGGGGAGAGGCTGCTGGAGCCCTTTCTGCGTGTATCCCT
TTCTTGTGCACGGATGTGCGCCTTCGGGCATGTAGCACAAGCCTGCTGTTGTGAATGGGTGTGGGCAGCA
TATGTGTAGTTGCCTGCGGATAGGTCTGCGGAGCGTGCAGGCTTGTGTGGTCAAGGGCAGGCACACCAGT

GGGCGTGTGTGCCAGTGGATGTGTGCTGCTGTGTGTGTCTGTGAGTGAGCGTGAGCCTGCAGACAGCCA T ALX4_2F
GGGTGGGTCTGGACATGAGTTGTGTGTATGTGTGTGTGTGTGTGTGTAGCTGTGCACACACTCTGA
CGTATGGAGCGTCTGTCTAAGGGGCTGGAGTAATTTTATCCTCCATGGTTTTGATTATATCTATTTTTCC ALX4_2R
TCCAAACATCTGCTTTGTGGGGACACACCGCTCGCCCTGTTCTCGGGTGAGCCAGCCTCACACGCCCTG
TGGCAGTGTGCACAGCGCCAATGCAATCTCCTTAAAGAAAACAGGCGGCGTGAGGCCCTTTCCTGCTGT
TTAAAGGGCACCGAGTAAACCCATCGCTGTCCAAACAGTTGTGCGGGGGTGGGGGCAGAGGTTAAAGGTG
AGCCATCGATCACGTCCCCAGCCCACCTTATCTGCCACTGGGCTCTGTCCCGAGTTCAGCTTGGATGGCC
CGAGTTTAGGTCCAGGCCAATAAATACACCAACGGGGGAGCCCATGCTGGGGCACCTTTCAGCAGA
CACACGTGGAGCTTATCTGTGCGTACCGGGCCGAGATGGACTGTGTTCCTGTCCGGGAGGAACTGCCAGG
```

TABLE 3A-continued

SEQ ID NOs: 1-2, BOVINE EXT2 AND ALX4 GENES

```
CGGAAGAGGAGAGGTAAGCCAGGGACTCAGCCAGCCACCCACGAGGTGGGGTAGGCACTCCTGCCACCAA
CACACACCCACCCAAGGCCCAAACGTGCTTCTCCAAACAAGGCAAGTCTGAGAAACTGTCACACGTCACA
GGAGGCTGAGACATGGAGGACTAAATGTGATGTGGTTTCCCGGACAGGGTCCTGGAACAACAGTAAAAAG
CACATTAGCGGAAAACTAGTGAAATGGGAATAAAGCGTGGCACTTAGCAGGTAGATGGGTAAACTATTTG
AATGGACATTTCACCCAAGAAGATATACATCTGGTGGTTCAGATGGTGAAGAATCTGCCTGCAATGCAGG
GGACCCAGGTTCCATCCCTGGGTTGCAAAGATCCCCTGGAGAAGGGAATGGCTACCCCATTCCCTTGCCT
GGAGAATTTCATGGACAGAGGAGCCTGGGGGCTATCCTGAACTCACAGGATCCCAAAGAGTCAGACAAG
GCTGAGCAACTAACAAATATAATAACCAGCTCAATGTATTACCAATTAGAGATTATTTACTAGGGATATT
CATGAGATATGGCTACACACCAACAGCGATGGAAATAAAACTGGATGATACCCAGAGATATCAAGGAACT
GAAGGGCGTGAACTCGCTTCCATCAGTGGTGGGAAAACAGCGCAGCAGTGCCTTATACCATGAAACACAC

TCTCATGGCTCGAGCCAGACATCCCACTGCTAGGCATTCGCCCTCAAGAGACAAACACTTCTTTTCAGGG
CAAACCTGTATGCAAATATTTATAGTGGCTTTGTTCACAATCGCCTCAAACTGGAAACAGCCCAAATGTC
CTTTAAACCATGGAACAGCCATGCAATGGGATACTACTCAGAGATAAAAGGAGAAAACTAGTGATGTGAA
CTGTGGATGACTCTCAAAGACAGCATTACTGTCTGTAAAAGAAGCAGTCGTCCAGAGGTATATGGTGCCT
GGCTCCACTTGTTTATTGCATGCCATTCTGGGGAAGGTAACCGACTCAGTGGACGTGAATTTGAGCAAAC
TCCAGGAGACAGTGGAGGACCCAGGAGCCTGACGGGCTACAGTCCATGAGGTCACAAAGAGTTGGACACG
ACTTAGCAACTGAACAACAAACAAACAAACAGTCCCAGGACAGAGAGCAGATCGCTGGTGGCCTGGGGCT
GGGCTGGGGTGGTTTTAACCCCAAAGGGCTGGTGTATGGGACTATCCGATCCTGTATCCCAGCTGTGATT
GTGAGTACACGGATCTGTACAGGAACGTGTTCAAATTCATAAAATCACGCTCCTCAGTTTAAATTTTCAG
CATGCTATTTAAAAAATAAAAATATGCAAACTACAGGGCTTCCCTGGTGGCTCAGGGGTAAAGAATCTG

CCTGCCAGTGCAGGAGACACGGGTTCGATCCCTGGTCTGGGAAGATCCCACATGCTGTGGAGCAGCTAAG
CCCATCTGTCTGTCTGTCAGTTGCTCAGTCGTGTTCAACTCTGCAACCCCATAAACTGCAGCCGACCAGG
CTCCTCGGCCCATGGGGTTTTCCAGGCAGGACGTCGGAGTGGGTTGCCAAACTGCAACGTAACTATCGA
GCCTGCGCTCTTCGAGCCCGGGAACCTCAAACGCTGAGCCCACGTCCTGCAAGTACCGAATCCAAGGTGC
CCTTGAGCCTGGACTCCACAAACAGAGGAGCCACCACGGTGAGAAGCCCGCACACCGCAACAGAGAAAG
CTCGTGCAGTAAGGAAGATCCGGCACAGCCAAAAATAAATAAAAATATTAAAAAAATAAAAAATATATAA
AACTATAGAGAAAATACAAAATTGGGTTTAAATATAGTAAAGAAAAACTAAGCAGGTAAAATGTTTGTAT
GTCTTCACCCAAAAATCTCACCTCTAGGGATTTAAAGACAGAATTATGGATAGACACAAAGAATTAACTA
GAGAGAAAGTTCCTCGTGGCATTTTTATATGGGAAAATTGAAAATAAGCAAAATCTCTATTAATAGGAGA
TTGGTCAAATAAAGGATGATATTTCATAAGTGGAAGATCCTTCCTGGTTTTCTTTATTCTACACACTGT
TTCCTCTCTTGGTATTTAACACATATTATTTTGTATTTATTTGTTTTTTCCTTCATTTATTGTCTCTCTCT

CCCTTCCATAAAACAGGGAATATATCTGAATATATTTGTTTGGCTTAGCCTTTTGGTTTAATGCCTAGTA
TTGCGGCTGGTATGCAGAAGGGGTTCAATAAACACTGATGAAAAATGAAAGAAACTGATGTCCAAGAATA
GCATTTTATTACCTGAAAGTTGTTCATGTTACAGTAAGTAAAACTTATTTTGAAAAAAGGGGAGGTGAGG
ATGCGGTGTCTGTTCTTAGAAAATTCTAGCAGTTTCCAGAAGTAAAGAATATCAGTATCTGGGTTTAGTT
GCTTTTTTGTTTCTAGTCTGACTTAATTTTCTTATTTGTCCTACCATAAACAGGAATTTCTTTCATCATT
TTAAAATGCTATGTGAAAGCAGCAGCTAGAATCCTGAATGGTGCCGGCTCGGTAGGTTTGGGACTGGGCT      216232_R
GTGTGATGGGAGGCGGAGGGAAGCGCTGCAGGGAGCCAGAGGAGGATGGCAGTGATGCTTCAGAGAAAGG
CCCCTTCCGAGGTGGGACTAGCTACCGTCCTCACAAACTGGGCACCGCCCCCCACGGCTCTGAGGCCTCG
TGGGTGCTGGAGAGTCCCAGAGCTCTGGCTTACGTTCAGACCTCACCGGTTCCTCTGCCCTCAGATCACC
ACGCTCCACTACAACCGGAGACAGTGTCTAAGACGCACACTGCTGGTCTAGGGCCACCCTGTCTAACCCA      216232_F
GAGCTCTCCTTGTTGTTCAGTCGCTAAATCGCGCCCGACTCTTTGCAACTCCACGGACTGCAGCACACCA

GGCTTCCCTGTCCTTCACTAGCTCCCGGAGTTTGCTCAAACTCATGTCCATTGAGTCAGGGATGCCACGT
AACCATCTCATCTTCTGCCACCTCCTTTCCCTCCTGCCCTCAGTCTTTCCCAGTATCAGGGGCTTTTCCA
ATCAGGATGGTCAGATAGGGTACAGGGTGCTCAGTTAAATTAGAATTTCAGAGAAACAGGAGTCACTTTT
TAAGTAAAAGCATGTCCCAAATATTGCATGGGAAATACTTTATGCACTAAGTCCCCTACGAACAAACCTTC
AAGTTGCAGACTTTCAAAGATGCGAACGTGCATTCCCTCAGTGTCAGACCCGAGTGAAACTGCAGCTTGG
CCCCTACCATCTCCTATAGCTGACGATCCTTCCGCTCTACTGTCTCCCACCTCCTGTCCCTCCCTCCAGC
CAGCAACTCTTCTTGCCTGTGTGCTGGAGGCCAGCTCCTCTATGCCAGCTGTTACACTGTGCTACTGCAC
TTTTCAAGGTACTGTACTGGAAGATGAAAAATGTTTAATTTTTTCTGTTTGTTTTTATGTATTGATATTA
TTTGTGTGAAAAGTATGATAAACCTATTTCCGTACAGTACTACATAGCCGATTGTGCTCGCTGGGTTTCT

AGGCTAACTTGCTTGGACTTACGAACCAAGTGAAGTTACGAACTCGCTCTCGGAATGGAACTCGTTGTA
TGTAAGGGACACAATGTACTGAACATTATTCATTGTTTATTTGAACTTCAAATTAAATGCAGACATACTGG
TTTTGTTGTTAGATTTTTATTTTATGTATTTATTTTTTTTGCTAAAACCGCCAATGCTCGAGTCAGGCTG
ACTATGGCATTCAGGATTCCCAGGCAGGACCGGCCACTGTCCCCCTCACAGACTTACGTCTTGCCACAC
CCGCCCCTCCACCTCGCTTCCGGTCCCGCTGACCTGCCCGCACGCCCCAACACACTGCTCGAGCGGCTT
CAGGCTTCCCCACCCTTGCATCCTTCTCGCTGGGACGCCCTCTGCCCTTCGTGCACCTGGCTAACTCCTA
CTCTCCCTGGGTATCTTCCTCTGTAAGCTTCGTGGCTTTCCTCCCCACCCCCACTACATACAGTTATCTA
TGTTCTATATGAAGACAAGCCCAAAGAAGAAAACTATAATACATAAACAGAAAAGGGAAACATAATTTTT

TATAAAAGTCTTTTGTAAAACCTATCACTGCCCTGTACATCTTTCCATCCTGTTCTATATTCTTCTGCTA
ATACATCACTTTTAATGGCTGCATAGTATTCATCGTACAGACAAACTCTATTTCCTTTCCTCAGTCCTT
ACTGTTGGGTATACGGATTGTTGATTGTTTGAAATAGGAACAGGCCTGTGATGAATACCTTTATAGTTAA
GTCCCTTGACATTTTTGTGGCAGTTACCTTTGCAAAAGTTCCAAGAACTAGAAATACTGAGTTTGGTCAC
AGTCACACCTTAAGAGCTCTGATAAGTGTGTCTGCTAGAAATGTGCCCATTTTTTCAGCATGCCTGCCTG
CTTCAGGACAAGTACCAATCATTACACTGTTTATAAAAAGCTTTGCCAGTGTAATGGATAAAAGTGAAAT
CTCATTTGAATTTACATTTAAAAAAAAAAAAAACAAATTTGGGCTTCCCAGGAGGCTCCGGAGAAGGCAAT
GGCACCCCACTCCAGTACTCTTGCCTAGAAAATCCCATGGAAGGAGGAGCCTGGTAGGCTGCAGTCCATG

GGGTCGCTAGAGTCAGACATGACTGAGCGACTTCACTTTCACTTTTCACTTTCATGCATTGGAGAAGGAA
ATGGCAACCCAATCCAGTGTTCTTGCCTGGAGAATCCCAGGGATGGGGAAGCCTGGTGGGCTGCCATCTA
TGGGGTCGCATAGAGTCGGACACGACTGAAGCGACTTAGCAGCAGCAGCAGCAGGAGGCTCAGTGGTAAA
GAGTCCACCTGACAATGCATGTGACATGAGTTCGATCCCTGGGTTGGGAAGATCTCCTGGAGGACGAAAT
GGCAACCCACTCCAGTACTCTAGCTGAAAAAAGTCCCACGGACAGAGGAACCTGGCAGTCTAGAGTTCAT
GAGGCCACAAAGAGCCGGACGTGACTGAGGCCGAGCGTGCTCACACACACACAGGCACATATTACTAGTG
AAGTTAACCTTTAATGTGTTGCATTTCTTCTTTTGTGAATTGTTTCTACTGAGCTTCCAAGGTTCAGTGC
AAAGGTGACTCCTTCTTCCTCTCTGACCCCAGGGTCGGGCTTCTCTCTTAAAGGCTGAATTCCCCACTCT
GAAGCACGGCGGTGTGGTGTGGCCTCCCGTTCGACCGAGAGCTGTTGGGAATAGGGCTGCCCTGATGCAC
```

TABLE 3A-continued

SEQ ID NOs: 1-2, BOVINE EXT2 AND ALX4 GENES

TTCGGGGTCCTGAACTGGGCCCCGGCTCCTTCTGCCTTTGGTAGCACCAGGCAGCTCTGCGTGCCCTGCT
GAGGGCGACAAGGGCACCCAGAGGAAGGGGGCCCAGGACCATGAGGCTGGGCTCCAGAGCAGGGTGGGGG
GCTGCGATCCCCCAGCACACACTGCTGTGGGGTGGCTGTGGCATGGGGGTGGACCTTGGTCCTTGTGGGG
TGATGGGGCTCAGAGAAGCCGGCCACGGGGCAGGTCGTGTAGGACCAAGCCCCATGTAGCTCCAGACACT
GCTATGGCCTCAGGCAAGGGTTTTGGCTTTTCTGCTTCTTCACGTCAGCAAGCCCTGCCTGGTCTCCTGC
CAGGGGAGAGGAGAGGAGGGTTACAGAGGAGGTGCAGCCCTCCCCGGGAAGCCAAGACTGGGATGTTCTCC
TCACCCACAGGGCAGGTTTGTGCGGGCCCCTGTGTGAAGGCTCTAGGCACCCCCATCCTGCCAGTCAGGA
TCAAGGCTGCAGTAGCTCACACTGGCCACCAGGAGGCACTGCAGTCCCAAGTACCTTCCTCAGGGCCAGA
AGTGAGGCCCCAGGGCCCCGCCGCAGATGCTTCTCCCAGTTTGGTTAAAGACCCAGGCCCCCTCCCGGAG
GGTTGGCCAAACAAGTGGTGATTCAGCCCTACTATGTGTCTCTGATATCCCAGCCCTCCACACAGTGCTG
GGTGAGGAGGGTCCCTGCCCTTCTCCACAGAGCTCTTTCCTCCTCCGGCTCTGAGGGTATTCACGTTCTT

GACTTGTATCAGTCCCCGTCTTGAGCGTCCTCATTTTACAGATGGGCAAACTGAGGCTCAGAGAGAGGGA
ATCCACTAAACGTCACCAGCCACTGGGCAGCCGGCCTGACCCGAGTTGCTCTTATTCCCCCCAATCTCTT
CCCTTTGTGGAGACCTGAGGGGCATCGCTGGCCCTCCGGATACTGACAGGTAAGCCATGCCCAGGCTACC
CGACCCTGGTTTTGCCAAGTCGGCTGTCCAGGCAGCTCGTGGATTTGTTGCTGGCTCCTCTGTGGGCTCT
TCCCCAGGGAAGCTTCAGCAGTCTCGGGGACTGCAGGCTCTTCTTCCCATCACTCCACACTGAGGGGAGG
GGTTTCCTGTGAGCCAGAGGATCGAGGGGGCTCCCCAGAATCAGGAGGGAAAAGGACTCAACCCTGGGCT
CTCACTACACACCAGGAGCTTCATGGTTTACTAACATGCTCTCACTGCTGCTGTTTACAACAGCCATGTG
AAATATGCCCATTTTACAGCTGCAGAGACTGAGGCCAGAGGGCGTAAAGGACTTGTCTAAGAATGCACAG
CTGCTGAGAGGCAGGATTTGAACCCCAAGCCTGGGGCATCTTCCTCTGGGCCCTCCTGGAGTGGATACCC

AGTGTGGGGCTGGGACAGGGCAGCCAGGAGACAGAGTCAGGGAAGAAGGGGAAAAAAAAGTGGGAGCCAC
AGGAAAATTCCTCCTCTCTGATGCCTCTAAATCTGCCCAACATATCCAACCTTCAGTGCTGGCCCTGGTG
AAACTGTCCTGATAGAACTTCATAGAACATCTGGGACCTCCAGTGTGGACCAAGGCCTTTTCTCGGGACC
TTGCTTTCAGGGTCACTCCATCCCACAGTTTACATTCAACTAATTTTTTCTTTTCCTCTTCCTGACACTG
GGTCTGGATTTATATTCAATTCTCTGCTAAATACCGAAGTATTTAAAAGTAAAAAGGCTTATGTCTGCGA
CTTACCCCCAAACAGTTCTGAAAGAAATAATATGTATATGTGCATCTGAATATATATTAATATATACATA
CAGAAAGAACACAAAAGAGAGTGAGGGCAATAATGCAAATATGGTAAAACTTTAAGATATGGAGGATCGG
TGTCAAAGGGATCTGGGAATCCTTTGTATTCTACATTTAACTTTTCCTGGTGTCTGAAAACATGTCAAAT
GAAAAGCTTTTAAAAAGAACAAGAATGCAGACAAATGGGAAGAAACCACTTTATCCAGGAATCCAAGTTC

TGAAACCGGCATTTGTTACAGTTTGAAACAGGACCCAGACTAGAGTCTAGTAAGCAATCTCTCTGCCTCC
CTCTCACCAGCACCATCCACAACTTCTACAAACGGGCTTGCACGCTGAAATCAAATCACAAGGCAGATC
AACTCAAGGGACAAACGTATACTCCGTAGTCCTATGGAAACCCTCATTTCCATCCCCGGAAGCAACCGGA
GACCCCATTAAAACATGCGGTTCTTCTAAGGCCGTAGGAGGCAGTATTTTGTTAGCTGAGGTCGAGCTAT
CCTTGGGACTTAGAAGTACTTGGTACTGTTTGAGCCTATTCTAATTTCAGCTCCCTTACAGTTAGTCCAA
GCGGGTACGGCTTCCTTGCACCCAAAGAGAAGTGGTTAAAAAGGAAGCCCGCCGACAATAGCTGGCACAT
GCAAGTGACCGTGTTCATCGGTGATGAACCTCCACACAGAGGAGGATTATTCACCCTCAGAAAGGAGGGA
AATTCTGGCACCTGCTACAGCACGGATGAGCCTTGAGGACATCGTGGTGAATGAAACAAAGCAGTCACAA
AAAGGCAAATACTGCACGATTCCACGTACACGAGTCCCTGGAGCGGAGACAGAAAGTAGAACAATGGCTG

CCAGCGGCCGGGGCCCAGGAGGGTGCGGAGTTGGTGTTTCACGGGACAGGGTTTCGGTTTGACAAGATG
AAAAGAGTTATGCGGCTGGATGGTGGTGATGGTTGCACAACATTATGAATGCTCTTCATACCGCTGGACC
GTACACTTAAAAATGGTCATGATGGTAAATTTTATTTTTACTTGTATTTTAAAATTCTTTTAAAAATTGG
AGAGAAAGAAAAGAAAGTCCACTACTGGCTAGGGTCCCTGCGGGCCTTCATCCGGCCTTCCTTCAGTCCC
CACGGTCCTCTCCGTACCCCAGCTTAGGCCCCAGATTCTTTTCTCTTCTCTTCCCTGACACTGTGGCT
TGGGTTGCGTCTATTCATTGCACTCATTCGTTAGTTGACTTGTTTGTTCATTCACCAAGCACCTCCCCAG
GGCCTCCCTTTAGACATGGCCTCACCAAAGGGACAGACGACACCACGGCCTGACAGCAAGAGCCCTGTGA
CCTGGGCAAGGCAGGCTCTATGGGAGGAGTGGCCGGTGCTGGCTGAAAAGGTCAGGAGAGGCTTTAGCAA
GGATGTGAACTTGACCTGAGTACTGACATCTACAGAGGCCTTGGCAAGGCCCGGTAACCACATTTTATGG

CAAAACAGGACACCCAGCTTTCAGCTGAACTGGTCCTAAATTACTAAGTGAGAAGCCCCAGGGGCCCTCC
CCCAGGGCTGGTGACAACAATGAGACAATCATACAATTGCTTGCGTTGCAGCAGTTCTGACCCACTCACT
GTCTCATCTGATCTCCTCAGATCCCTAAGAGGTCCGTGATGAGGAAACTGAGGTCCAGAGAAGCTTGACT
TGCTCAAGATCACAAAGCGAGGAGGGGCAGAGCTGGGATTTGAACCCAGATGGTCCGACTCCAAGCCTGG
TGTCCCGTCCACGGCCTCTCACGTGTCTCCTGGACACAGGCAGGCAGTCTTGGGGGGTGGGCGGGCACT
GGCTGACTCGGTCTTGCTTTGAGTGACACAGTTGAGCCTGAGGAGAAATTTCCATCTCAGAGGAATAAC
CTCAACAGAGCTCTGGGGTCACCGCGTGCTGGTTTTGGTGGTGTAGTCACTCAGTCGTGTCCAACTCTTG
CGACCCCATGGACTGTAGCCTGCAGGGCTCCTCTGTCCCTGGGATTCTCCAGGCAAGAATACTGGAGTGG
GTTGCCATTTCCTTCTCCAGGGGATCTTCCCGACTCAGGAATCGAACCCAGATCTCCTGCACTGCAGGCA

GATTCTCTACTAACTGAGCTACAAGGGAAGTCCATGGGTCACCATGAGAAGCCCCATTTATGGTCTAACA
CTTGGACATCACCTGGTGCTGTTCTCTGGGGTGGGCTGGGGTCATGACCTCAGTCAGGGACTCTAACTAC
CCCTGTGAACAGCCCTCCTCATGGACACTGAGGTTTCCCAGCTCCCCGCTTCCTGGCCCAGCCCAGGTCT
CATCCCCAAGCCCTGCCTCACGAGGCTGGAGGGGATCCAGAGACCCAGCAGGGGAAGGGGCAGCGGCCCA
GGCTGGGTCTACTCCCAGAGAAACAGAAGGAACCTCCCCCATTCTCCCTTCAGCCCAAAAGAAGCCCCA
GAGCTCAGGGGCCACCCTGGGCCACCCCTCCTCTTTCAGGCAGGATACGGAGACCCCCGAGTGATCACAT
CGCCTGTCAGTGGAAGGACTGTCTTCTGATTTCAGATCAGCTCAGTGGTCTGCCTGCCCCTTGTCCCCCT
CTACCTTTACAGAACCATGTGGCCTTGGGCACGTCCTTATCTCCTTGATCCCTCAGAGCCTCCGTCTCTC
CTCTGCTTCAGAAAATCTGCATTCCCAAGCATCCCCTTGGGGACACTGGATAATCACCGTTGTATTCAAG
GGAGGCAAGATGGAGAAGCTCAGATCCTGCTCTAGGTGAAATGAATGAGGAGTCCTTGGAGCAGGACGGA
CTTGGGTTGACTCCTGAAACTGCCCCTGACTTGCTGCATGCATTCATTCAGCAGCATTTCTGGAGCGCTA

GTTATGTGCAGGGCAAAGCTCCAGGAGATGGAAACAAAGTCCAAGAAAGCATGGCCCCTCCCTTACAAAA
GCCCTGCTTCATGAAGGAGGCAGTGATTATGGCGGTGGAGGTGGATACGGCAGGGGCATCTCGGCCAGCC
TGGCGCGGGAAGCAGTGTTTCTGGGGCCTCTCCAGATCTCTAGGCAGCGATCTGGTTGGAGGGGTCTGTC
GAAGCTGTGTACAGCTAGCTCTGTGCATACGATGAAGAAATGTCAGCTCTCCCCATCAAAGAAATGGGGA NW_216232_R2
AATTTCTCAGGGAGATTGTTTAGGAGGCTTCCAAGCCACTCATGCCTTGGCAAAGTGACTTTGGCCTCTG
TGTGACTGGGTTTCCTCATCTGTAAAGTAAGGGGAGGGGACCCACCTCCCAGCATGTTTGTGGGCTCTC
AGTGAGGCCAAGGGCGAGAAGGCACACCTCTGCCTGACACCCAGCACGCTGTCTGTCAACGGGAATCCTC
CACGGGAGATTAACACACTTATTATTTGGAGGGAAGTTAGGCCAGGGCGGGAGGGAGACCGCAGAAGAGCC
CCTCAAGCTGCAGTGTCTCATCCTCCCCCTGCCCCCGCCCCCGCCCCAGGTATATGCTCTTCAGCTCAAG
TTTCCCCAGCTCCAGCTGCCCAGAACATTCCACAGACCTCCGTCCCAAGGAGCTCCCCCACCCCAGTCC NW_216232_F2
CCTTCCAATCAAGGCTCATTTCCACGTACATATAACAGAGAAATAAATGGGGTGAAACACTGAAACTATT

TABLE 3A-continued

SEQ ID NOs: 1-2, BOVINE EXT2 AND ALX4 GENES

```
TTGTTTGTCATTTGTTATAGATATTTAAAAGTGCTAGCTGATGTTCAAGAAAGCCCCTTCCATACATACA
TTTTGACCCAGGCTGCAACTTGTAGTAGAGGCATGAAAGGAGGACTCTAATTTTAAGCGCTGCATCGAAG    DEL5_699
ACAGTGTGGCTTATGCGCCAGTTGACAAAGGTCAGAGAGGCTGTGAGCTCCTTTCAAAAACCTCGCTCCT
GCTTAGACACTTGGTAACATCTGGACGACTCTCCTATGCAGGCACACCAATATTTAACGGCTCCAGAAGA
ATTTTCTCTGTGGGGGCCTTCGCTGTCCTCCACCCAGCATACCACCCAAAAGCTATCTGGGGGTGGGGAG
TGTCGAGAGGGATCGTTCCAGAAATGAACCGCCACTCCCACTGGCGCTGCTGTCTGCTGTCCTATAGAAA
CTAACCTTGGTGATTCGGGGCTATGTCAGGGCCCTTTCTGCCAGAGAAACCCAAATCACATTTCCAGGCC
CGAGTCTGTTACCACTTCCTCTTTGTAGATTTCCTGCCATGCCCTCCTCCAAACTCTCCTTCTTCTTCTG    DEL5_1109C
TGAAAGTCACTTAGTCGTGTCCAACTCTTTGTGACCCCATGGACTATACAGTCCATGGAATTCTCCAGGC

CAGAATACTGGAGTGGGTAGCCTTTCCCTTTTCCAGGAGATCTTCCCAACCCGGGGATCAAACCCAGGTC
TCCTGCACTGCAGGCAGATTCTTTACTAGCTCTTCACGAGCCACAAGGGAAGCCCCGAACTACTCCTAA
TAATTCGACTGCTTTTCACAAAGCATTGCCAAGTGTGGATGCATGGCACCCTCCACCATTAGACAGTGTC    DEL5_1389
TTCATCACAGGCAGGGAAAAAGTCTTGTCAAACTCTGGTCCGCACATCTGGCACTCAAAAAATACCTGCT
GAACAACCAACTCAACAGATACCTGAATTAAATGAATCTGGTTAAGTAACTAAATGTCTCAGTCTGTGGA
ACGACCACATCGGCCTAGAGAGAATGTTTTTCCCACCAAAATCAAGGGTTTTCTTCCTCCAGATGTGTTC
ATGGTAAACTAAACAATCATTTACAAGCCCCAAAAGCAAGAATATGTTTTCTCCCCTTGGACAAGAAGGG
AAAAATTATGGCTGGATCAATTGTGAGGTTGCCAGTTAAAGTTTTCTGAGGTTGATAAAGATGGATAAGA    DEL5_1754C
TTATTCAGGGTTTCCCAGGTGGTGGTAGTGGTAAAGAACCCACCTGCCAACACAGGAGACATAAGAGATG
CGGGTTCATTCCCTGGGTCGGGAAGATCCTCTGGAAGAGAGTATAGCAACGCACTCCAGTATTCTTGCCT

GGAGAATCCTATTGACAGAGCTGCCTGGCAGGCTACGGGTCCACAGAGTTGCAGAGTCAGACACGACTGA
AGAGACAGCACAGTGCTTGTCAGGAAAATGACTCATCCCATGAAACAGTGAGAATGCACCTTATGGAGCA    DEL5_2006
CAAAAGTGGCTTCCTGTAATCTTATCCGAGGGGCTGAGTCCTGGGTAGCTCATTAGGTAAACCTGGCCCT
GGATGTCCACTCAGGCAAGGCCTCTCCAAGGCAGCCCCTGATCCCTGGCACAGAACCAATGCCGAGCCAA
CGAGGAGGCCGTTCCAGGAGCGGTCATTTCTTGCGAGTTTAAGGGGAGCCTAAACTCCCCAGCAGAC
ATGGCTTGAGGGGTCTGAGGGGCCTAGGACTACCCTTCTCCCCTCCTTGATCCCTCCAGCCCCCATGCTG
GGCAGACAGCCAGCTTATACCCTTTTTTCATCACTCATCTGCATTTTAAATGCTTTGTCAACCACACAA
TATAGACTCAGCAATAATTTGTTGATTTTCAATTTTATGCATTCAAGTCAACCATAACTGTCTGTCAAA    DEL5_2497C
GTTTCCGGCCTCACCTACTCAAAGTTCCAGCAACATCCTATTATCAACAATAACAACATTTATTGA
GCACTTCTGCTGCCGTAAGCTCTTTACCTATATCACCCTCCTCAATCCTCACAACATTCCTTCATGGTAG

ATAGGATTCATATGCCCACTTTACAGACAAGGAAAATTGAGGCAAGGAGGCAAAGAGGTCAACTCATTTG
CCGAGGGGCACTCAGCTGGACAGGCCCAAATCTGTTTCCAGGTCCTGGCTATACTGGCCTCACTGAACCA
AAGGCACCTGAAGATGCAGGCAGCCGGTGCAGCCTGACTGTAGCATGAACACAGTTTCTATAAGATTCCA
AGGCATTAGAAGCTGCGCCTGTTACTTGCCTTTGGGCTTCCCCGAAGGCTCAGAGGATAAAGAATCGTCT    DEL5_2843
GCCACGCAAGAGACACAGGAGACATGGGAGATGCAAGTTCAATCGCTGGGCAGGGAAGATCCCCTGGAGG
AGGAAATGGCAACCCACTCCACCTGGCCGGGAGACCAGGCCTGTGTTTAACCAACTGGGCTGGGGGGTCC
CGAGGCAGGATACACTGGTCTCATGAGCGAGCCCCCTCTGGGGCTCTCACTGCTCCACTGGTAGCGCCAG
CCACCTGTCCGTTGCCCCCTGCCCCTCTGGTTACCCACCAGGGGCGCCGAATCCTACCTGGTCCCTGGCT

GAGCCACTCCCTGGGCAGAGCTTGGGATGACCAGGGTTGGGTACAGGGAGCAGCAGATGCCTCTGATGAG
GAGGAAGCAGAAATCTTCAGGACATTCACGGGCCCAGGAGTACAGAGCAGGGTGGGGTGCATGGACTTC    DEL5_3292C
CCTCCAGGGGCTCCTCCCAGCCCTGTGGGGAGAGGGCTCTGGGGTCATGTTATGGAAGGGAGTCCTCTCC
GATCTGGTCCTCTTAGGGGGTAGTGTGAGGACCCTAAGAGCACATCTACCCCAAGGCCATATCCTCATGG
GAGACTCAGCTGATGGACACGGGGGCTCCCAAGTATGGCCACAGGCCTAGTCAGAGGCCAGGGCTGGGGC
GTGGGCACCCTCGCCACTAGCTCTGCCCTCCCCCACTTCTCATCCGCTCTGGCTGCTGAAAAACAAATGT
GTCCCAGAGCCGAATCTCTTTGGCGGGTCAGTCGTTGGCCTGGAGGTGAGGAGGTGAGCAGGATGACTTA    DEL5_3659
ATGAAGTTCCTTATATTCTAGAACTCTGGACCTTCATCTCAGGAGGCCATGCCACACTGGGACATTGAC
TAGTGGTACAGAATAGAGAGCCCAGAAATAAATTCTCAAATACATGGCCAATGGATTTTTGACAAGGCAG

CCAAGACCATTCAATGGAGAAAGGGCAGTCTTTTCAACAAATGATACCGGGAAAAGTGGATATCCGCATA
TGAAAGAATAAAGATTGATCCTTATCCTATACCATCTACAAAAATTAACTCAGCGTGGTTCAAGACCTAA
ACTTAAGAGCTACAACTATAAAGCTCTTAGAAGAAGACATAAGGAAAATCTTCCTGCCACTGGAGTTAGC
AATGATTTCTTGGCTATGACAATGAAAACACAAGCAACCAAGGAAAAATTGATAAATTGGATTTTTCA
AAATTAAAAAATTTTGTGCATCAAAAGGACACTATCCGGAAAGTGAGAAGACAACAATAGAGAAAATGTT
TGCAAATCAGATATCTGACAAGGGATTATCATATATATATATATATATATATATATATATATATATATAG
GGCTCCCTGGTGGCTCAGATGGTAAAGAATCCACCTATAATCTAGGAGCCAGAGTTCGACCCCTAGGTC
AAAAAAAATGCCCTGGAGAAGAGAATGGCAACCCAGTCCAGTATTCATGCCTGGGAAATTCCATGAACACA
GGAGCCTGACGGGCTACAGTCCATGGGGTTGCAAAGAGTTAGACATGACTGAGCGACTAACACACATATA
TAGATATATCCAGAATATACATAAAACTCCTACAACTCAACAGCAAAAGCCAAGAATGCAATTCAAAAAT
GGGCAAATAGATATTTATTTATAAATATTTGCCCCAAAATGGGCAAATAAATCTTCTTTCTCCAAAGAAA

GAAGTTGTCAGAATAAAGGTCAAAGATAAATAAATAAAGATTGTCAAAGATAAAAAGGTCAACAATGGTTT
GACAAAATGGTCAAACACAGAAGGACAAATATTGTGTAATTCGACATCTATGAGGTGCCTGGGGTAGGAA
AATTCAGAGACAGAAGTAGAACAGAGGTTTCCAGGGAATGGGAGGAGAGGGAGATGGGGAATTATTGTT
TAATGGGCCCATTTGGGATGATGAAAGGGTTCTGGAAATAGTGGTGATGGTCACACAACACCACGAATGT
ACTTGATGCCAATGAATTGTTCATTTTAAATCCTTAAAATGGTAAATTTTAAGTTACGTATATGTTACCA
CGGGCTTCCCAGGTGGCACCAGAGGTAAAGAACCTGCCTGCAATGCAGGAGACGCAAGAGATGCGGGTT
TAATCCCTGGGTGGGAAGATCCCCTGGAGGAGGGCATGGCAACCCACTCCAGTACTCTTGCCTGGAGAA
TCCCATGACAGAGGAGTCTGACGGGCTATGGTCCACAGGGTTCCAAAGATCCAGACATGACTTAGCACA
GCACATATTTTACCACAATAAAAATTATCCCTAATTAAAATAAAGATTTGAATGTTGAAAGAGGCTGCAC    DEL5_5227C
TAAGTCTGGGGACGCAGCCTCTCACTGCACTGCTCAGAGGCTTCCAGGGGGCTTCCCAAAGTCTGAACCC

CTCGTCAGAAAGTGAATGGCCCCTCTGCTTTGCCCACGCCGTTCTTCAGGCTGATTCTTGCCTCTACCC
ATCATGCCCTCGCAAGTCACACACCTGCTCTTTCCCAGGCATTCCACGCACTTTCCTGACCTAGTTCTCT
CTGACTCTAGAGTCTGTTTCCAGCTCTTCCAGCTGGAGAACTCATCTACCCCAAGGCCCACTTCC
AAATGCCCCTACCCACTAAGTCCCAGTCCATTCGCACTTTTCCTGAGAACCGCGATGTTTGCACATTTAG    DEL5_5516
CTCCCCGTGGGCAGGAATCACCTGACTCGCTGCCCAGTGTTCCACACCCAACAACACAGGGCACAACCCG
GCAGCAGCATGTGTCAGATGTGAAGGGGGAGCCTTTGGCAGCACACCTCTCACAGCCCCGTCTATGCCCA
ACTCCTTCTCTACAGAGACGGGGGAGCCCTTCCATAGAGTCTCCTCCGCCTTTGTTGGCCGCCACCT
GTGAGAGCTGACTCCAACCCAGGCTCAGGTCTCAGTGTTTCTTCTCATCTGGGCTGTGAGCTCAGGACGG
CATATAGGCCCGAGCGGAGGGGGGCATCCCCTGGCGGGGGAATCTCAGAACCCTGGGGAGGGCAGGGC
TGAGTGGAGGGGGGAGGACCTAGGGAAGAGCGTCATCAGAAGAACCAGGGGCCCAAACTCACTGCAGGG    DEL5_5967C
AAGGGGGGAGCCCTGAGGAGAGGAGGGTGTGTATGGGTGGGTGAGGGGGAGACGGCCCAGGAGACTGCAG
```

TABLE 3A-continued

SEQ ID NOs: 1-2, BOVINE EXT2 AND ALX4 GENES

| Sequence | Label |
|---|---|
| CCACGGTGCTCCTCTAACTGCAGGAGCCTGAGAGGACACCAGGCCTGTGCAGAACAGAGCAACTCAAGGT CTCCTTCTACCACGCTTCAGAGGGGTCCCCGCAGGAAATATTTTTCGCCAGGGTAGAAGAGAACTAGAAG TCGGGTTCTCACCCATGCCCACGCCTCCTTCAAAAGGAGGAGGAAGGGAAGGAGGATGGGAAGGTTCCCT CCCTCCTCCCTGCCTCCCTCCCTTCCTCCCTACGTTCCCAAAATTCACTGAGCGCCTGCCTGTACAGCA AGCCCTGCTCTAGGCTCTGGGAAAACAGTTTGAAACAAAACCGTTTTGTAAGACAAAAGCCTCACAAGGT CTCACAAACTCCCCAGGAGGCAGGTATTTCCTCCTGTGGTCTTCAGCTCCACCCTGCCCTGATCAGAGGT TCTGGCACGATCCTGGAACCTCTGGGACTTAAGATGCAATCCCTCACAACAGTTATGAGGCACCGATGCC ACACCTGACCCCAACACAGCAGGACACTTGAACAGGGAAGAAACTAGGCTCCAACAGACCACAGGGTCAGGTC TAGACTCGGACCTACCGGGGCTCCAAGCCCATCCTTGACCTCCTCCCCAGCCACCGCCACCCCACCCGCC | DEL5_6496 |
| ACCACTGCACCTCCAGACAGGAGGATGGGAGGAGCTCTTTGGGGCCATGTTTGTAAACCCATGTCATCTG AGATAGGATGAGCTGTGTTTAGTCGCTCAGTCGTGTCCAACTCTTTGTGACCCCATAGACTTCAGCCTGC CAGGCTCCTCTGGCTCCTCTGTCCATGGGGATTCTCCAGACAAGAACACTGGAGTGGGGTAGCCTTTCCCT CCTCCAAGGGGATCTTCCCAACCCAGGGATCGAACCCAGGTCTCCTGCATTGAGGGCGAATTCTTCACCA TCTGAACCACCAGGGAAACCCCTGGATATCAGGGAGGCCCACAAACCCAGGAGGCCCCAGTGTTTCCTT TCTTACCCTGAAACCTGATCAGAATACCCCCCTGGCCCCCAACTGCCACCACCATTCAACATACCTTCAT CATCTGCAAGATGAAATGAGAAGGCAGCATCCCTTAGTCCAGACTTTGGCCACCTTGCAGGATAACCCTG | DEL5_7040C |
| CAGGCATATCAGCTCTCTGCATCCTCACATTTCCTCCCACAGAGGCGGGACTGCCCCACACAGCCCCCGT TTTGCAAACGAAGAAATAAACTAAAGAGATAAGCAGACCATTTCAAAAACACAGGCAATTTCCAGGGAAG AGCCAACACATGAACCCAGAGCTCTTGATGTCCAGAGAAGCCATGGAGTGGGGAAGGAGAAAGCAAAGAA GCAGCTACTCAGCCACCAGAGAAGATCCAGGTGGTCTGTGGCAACTCTAAGCCCTCCCCTTACGGGGTAA AGCTCCACCCACCTGGGAGCGGGCTGCCCTTCTCCGCCCAGCCTCTCCAGCACCAACCCATTAACTGCAG TGAACCAAGCTACTAGTCTGTCTCCCCATCCCGACCTGAAGGCAGAGGCTGTGTCCAGGGCCTCACAGAA TCCCCCAGGAGGCCGGGAACAGGGACAGGCAAAGTCTGGTGAGGAGCTGGAATTAGGCATTTCAGTCCCC TTCTCTGTGAAAACTGGGCATTTGGGCCAGGAGGCGTCTGGCGTCTCTTCCAACACTGGGCGGGACACCC ATCCCGACACCAGGACCCATCATGTTGGAGGGTTGACTTCCGGGCCTCAACCAAGGTCCCTGACCTGGCA GGTGGTCAGCCTCAGAGGAGGAAATAAGTCATGTGGCCTCAGCTAACACCCTTGGGCTCTCACTGCCGGG | DEL5_7326<br>DEL5_7683C |
| TTTTCCACACACTTAGGAAACAAAACCCGGGTCAGGGAGCCCAGCAGAGAGCAGGAGTCCCTGCCCCACTG GGTCACATTTGGGGATGAGTTCCTGCAATCCCATCAGGTGCTCTTCTGTTGCCCTGGCAACCCCAGGAGC TCCCAGTGGAGCCCATCTCATTTCTGAAGGAGGGGGAAAGGGCAAGCATCTGCTGTGCATGAGACACAGA GTGTGTGGCCAACTGGATGGATTACAGTGAAAGGAGACGGTAGGAGAAGGGGCACAGGTACCCCAGCTCC TTCTTCCTTCTCCACCCTCTGCAGTCCTTCCTTCCTTCCCACTGACTTGCCTGTGGGGTTCCATTCCCCT TTAGGCCTCAGTTTGTTGTTGATTAGTGGCTAGGTCGTGTCCGACTCTTGCAACCCTGTGGACTGTAGCC TGCCTCTGTCCATGGGATTTTCCCAGGCAAGAATACTGGAGGGGGTTGCCATTTCTTTCTCCATGGGGGT CTTCCTGACCCAGGGATCGAGCCCCAGCCCGCGTCTCCTGCATCAGCAGGTGGGTTCTTTACCACTGAGC | DEL5_7991 |
| CACCAGAGAAGCCCAGGCCTCCGTTTGCCAAGACGGTGCTCAGGCTGGTTTCTCTTCCTCAGAACTGAGG AAATGCTCAAGAGCTGGAGGTGGGAGGAGGCCCCACTGCGGTGTGGGTGGGCTGGGTGAGAGCTCTAGGA AGCCTCTGGGGCTTGTTCCACCCCCAAGGGTCCAGGGAGACTCTGCCTCCCGGGGAGCCACAACCAGC AACCGGGAAGGCCACAGGTCATGAAGCACAGGCTCTTAGTCACCGCCTCCTCGCCCAAGACTCTGGTGGT TGCACAGACCACAAGCATGGTCCATCCCCCGGGGAGGGGGTCGCACAGGATCCCATGCAGGTTCTCATTC TCACCTGCACGCTGCTGACTATACTGGGTGCATCCTTGCAAGTGCTAGGGGGCACGCAAGGCTTCCATAT AGGCGTGCACATGAATTGGTACGCATGTATGGTCCCTGGAATCACCCTGGGACAGACACCCTGGTCCAGG ACAGATGAGTGTGAGCCGGGAACACCACCCCACAGTCACGCGGGACTCGGGCTCACACCCACTCTCCCAGGC CTCCACCCGCACCAGTAAAGGTATTGGGATGCTCATAGCTTCCTTCCGGACAAAAGAAAAGTGAGGAG GGTGAGGAGGACCAGGAAATTGGGTGGCGGGGGAGCGGGGAGAGTCCAAATTGGTACCAGCACAGTAAC CCCTAGAGGGCCTTTGGAAACTGTCCAAACTCCCGGTTTCGTAGAAATAAAATCCGGATCCAGAAGGGGA AGGGGACCCAAGGCCGTGCGGGGAGTTAAGAACAGCGTGGTGGAGACCCGCCACCATCTCAACCTGGACC | TH_BIGBREAK_F<br>BREAKPOINT A<br>DEL5_8750C<br>TH_BIG_344C<br>TH_BIG_478C<br>DEL5_9059 |
| TTAGTGCCTGCCCCAAACCTTCCACAGCCTCTCCATCTTCTCTGCCATAGCCTTGCCCTCGGACAGCTTG GGAAACCTGCTGCTCTGCCCCGACCCGGGACCCCGGCAGTCCATCTTGCGAGGTGCTTGGGGCTGATGCCC AGGTTCCTGAACCCCTAGTTTGGAAGGAAATCCGCTCTCCAGGACAATCTGCTTTAAGAATCCATGAAA TGCGCACTGACTCCCTCTCTTTCTAAAACGCACAGCTGCAACGCGCCCACGCCCAGCAGCCCCAATTCTG TGGTTCCCAGGACACGACCAACCGAGGTGCGGTCGTAGGGAAAGCAGGGTAGTTGGCAGGTGGTGGCACC TCCGTCAGTGACCCTCCACGCGGAGGGCTATGATATCCCCGTAACCCTCCTCTCACAGCGCGTGGTG ACCCTGCTAGCTGCCCCGGAGCTGAATTCCGAAACCGCCCGCTGCCCAGTCCCCAGCCTTTGCAGCTC CGAGCCTCCTCTTTGCACGTCTCTTTCCCTCCCCACCAAGCCTCAGCTCCCCTTCCGCGGCTCCCTCTCT TCCTTGGAGCTGCCGGTTGGGGGTGGACGGGGCAGAGAAGAGAGTCTTGGCTACGGCGGGCAGAATGTTT CAGGGAGGCGCGGGGTGCACGGCCGCTGGTGTGTCTGGGGGTCTCGCGACCCCTCCGTGGACACACTGGAG | |
| GCTCCGGTCGCACTCTTGAGTCAGCTTTGCTGGAGAGAACAACGTCCAGGCAGCACGGCGTCGGCTGCCC GCGGCCACCCCAGGGAATGGAGGTGGGGGTGTTACCGTCCATCTGTAGGCGAAAGAAGAGGGCACAGGCT GCACCTCTGGGTGGGAGGCCCCTGGGAGACACCAGGAACTCGGATGGCTGAGAAGCACCAGCTTATGGC TGGAAGGTTTGTTGGCCAGACAGAAGTGTTTCTCTAAAAAGGCCCTGTTTTGAAGGAAGGCCCTCTTCTC AACTCTCTAGTCTGGACCAGCCGTCTCGGCCAGTGGTGTCCACAGCCCCAGACCAAGGGGTGGGGAGCGG GGTTGGGGGGGAGGGTGCCTTTCACTCTAAATTCGCTGGGTGGTATCATCCCGCAGCTGAGTACCCCC CTGTCTGGGTTTTCGAATCTGATGACCCGCCTTGTGACCGTAATACCTCCTGGGGAACCGGGTAGCGAGC GGGAGCATGTGGCCAGGTGGCACCTGGGTAAGCTGGGTCCAGATACAGGACCACCCTCCCACCGCCAGTG | DEL5_10399C |
| CCTCAGTCCTTCGGTTTCCTGGTGGGGAGTGGAGGGTCCTGGGAGCTGAGGACGCGGAGGTTGCCTCCAG CCAGGCATTCTCCCAGATCCATCCCACCAACTCCCCTTTCCCGGCCGCAAAAGGCGCACCCGCTGCAGCT CGGGCTTCGCGGGTCTCACCCCAAGCCCTCGGAGCCGCTCGGCAGTTCCCGCAGTTTTCCTATCCTTTCT CCTGCCGCCGCTTCGGGCACCCTGGACCAGAGGTGAACGGAAAAGTCCAAGCCCTCTGACAAACGCCGGGA CCCCTCCCTCCCTCCCCCAGCCCCCGTCGACGCGAAGGTCGTTATATTTCCATTTTATATTTCAATTTG TCACCGAAACAAAGCCGCACGCAGATTTGCAGGAAGAGAGAAAAAGGGCTGGGACCAAGGGATAAGGTATG ATCACGGGGCAGCGTGCGCGCAACTGCTTTCTGAAACGAAAGTTCTCATGGAGCATGGCGACATTTTACG TTTGGTACTGTTAACTTGTTTTCCTGTTGTGGCCCCTCTCTGCAGCGCACCAAACTCGGGGCTTCAGCGA CTTCGGGAGAGCCTTTGGCGGCAAGGTTTCTGGGGCAGCCGGCAGTTCCCAGCAAGAGTGAGGACTGCGC | DEL5_10637<br>DEL5_10942C |

TABLE 3A-continued

SEQ ID NOs: 1-2, BOVINE EXT2 AND ALX4 GENES

| Sequence | Label |
|---|---|
| AAATGCCCGACAGGCAAGGTTATTCTCTGGAGAAACGCCACTATCGGGAGAGGGGCAGGTTCTCTGGCTC<br>CCCCGAAGCCTCTTCTGAAATTTCCTTGAAACAACTGAAAAAAAATCCCCCACCCTAGTTTTCGTTTAGG<br>GATACAATATGTAAATGGTCTGTATCTCCATCCACGTGATAGTTATACCTGGAGCAAGTAATTAACAATT<br>CTTCCAACGTTTCATTAACCGGGTGCTTCACTGTATATAAATTATAATAAAGACACATCGACTGTTTTAA<br>AATAATAGGAGACCTTTAATCCAGGTCTGTTTTTCTATTTAAGATGCTATGTGTTTAGGCTGAACTGTTT<br>CAGCAGACTGAGGGCTATAGAAATTAACAAAGTAAAAAATTAAAAGCATCTTTCTTCTTCTCCTCCCCAC<br>CCGCAACTGACTGGGGATCCTGGACGTCACAGCTCCTACGCTTGAGTTTTCCCTTCATCATCCCACAATC<br>ATCCATGGGTTCTTAAGGCTAATGCGCGCCCCTCAGTTTCTCCCTGTCTTTTGGGGGGATCCCTCTTACA<br>CAAAGCACACCCTGGTTCTTTGGCTTAATTTGACTATGACCCACGTGGAGTTTACATATTTCGTGGTGTG | CTG45_R2<br><br><br><br><br><br>CTG45_F2 |
| TGGATTGTGTCGGTGCTGGTGGGGGGAATAAATATCTCTAGCATTCAATCACTGCGTCTAATTCGACAAA<br>TCAAGGCCAGCCCCTCGGTGGCGCCCCAGGGGTCTCCGGCCGGGCTCAGGTCTCCCAAGACCTCTGCGCG<br>GAGAGCACTGCCTTCACGCGCCGGGATGGGAAGGTAGCAATCGGCTAGCAACGAAAACCTGCGTGCACCA<br>AATAGAAAGCGAAAGAGAAGGAAGTAGCAAGACTGCTTTCGGAAGCGTCCCGGCGCGCCTGGCCGAGGCC<br>TGGGGTGGCGAGCGCGGCTTGGAGAGTTGGCCCCCGTTTGCGAGCGAGATGCCAGGGTCCCGACTCCTGC<br>AGGGGATGAGGCTCTTTGAGCAGCTGAAAAACACTGGGTCTCCAACCTGGCAGGTCTCCTGGGGTACAAGC<br>CGCCAAGTATGGGCCAGGATGGGCGGGGACTTTGGAAGGGCGACGTGTGGCCCCAGGGAACCTGGTGGGG<br>TTGGGATTGCAGAAGGCAGGATACGGTGGGGCTCTTGCATAAAATAGTGAATGTGTATGCTGAAGGGAA | |
| CCGTGACTCCACGGTTCGGGACCCTTTCAGTACCGACGGGGAAGCAGTGGAGGCGCAGTTAGGGGCAGGA<br>ACTTCTGCAGCCTGGATTCGTGTCTCCCCTCCAAGTTCCACATCTCCAAGCAGCAACCCCCCAACTCCC<br>CACAGGAGGCTGCAGGCGGCTTCCTGCTCCAGGCTCTCGGGCTGCGGCCCAGTGCAGCCCCGGACCCA<br>CAGCTCTCCCGTCAAGGAGCGCTTGTATCCAAGCACTGGCTCCCGGCGGAGGAGACCTCAGACCCTCACT<br>TTTGCTCCGAGCAGTTACACAGATGGAGGAACTGGCCTCTGGCCCCCGGACCAACGGAGCTGGAAAGGTG<br>GTTGCCAGGCCGAAGCCCACTGGGTGGCGGCCCGAGCCACAGTCAGCCTGGCACCAAAGCTGAGTCTGC<br>CTCTGCCTTTCCCAAGCTCCTGGGAACCTCCGAGGCTTTTTCCCTCCTACTCACTTACTTTCCCCCTTTG<br>GGGTACACACTCTCAGCAGTGTAGGGAGGAAACCATGTCGGTGTGTGTGTGCTTCAGAGTCCGTGCCTGC<br>TGCCAGCTCCAAAGGTCTTCTGCGCAACCGCCTCTCTGGGCGGCAGAACCTCACCTCTTGGTGCCTCGGT<br>TCCCTCCTTTTGGGCCTAATGTGCCTTTCCCCCAACCCCCACCTACAAGAGCCAGAAATCTCCTCCTGG | |
| CCAGAGAGACAGCAGCTGCTGAGAGAAGGAAACGAATAAGCAGAGCTGTCCATAGTTTGCGGCCGCACCC<br>TGAGCAGTGCCTCCATCTTGGACAGCCGGGGAGGGCAGTCCTGTTGGTGTTTTCCAAGCTGCCGTTTGTC<br>CCAACCTGCGGCTTTGGGATTTTACCAGCGCAGGGTCAGCGCCCCGCCCTGTCCTCACAAGCGGTGCTTA<br>CAGGTTCCCAGTGCAGCCACAGAGGCCGACGGAAGAAACGTGGAGGGGGCAGGCTAGACTCCTCTGTCTCT<br>CTGGGCTGGGGGCCGTGGGGTGTGTGTGAGACATTTACTACCCAGTGAGGCCTGACTGTCATCTCCC<br>TGGGATGCAGGTGAGGAAATGGGGCTTTAGAGAAGCTCCTCACACGCAGGTCAGCGGGGAGCCCCATGGC<br>CACTGCCCATCGAGGGTGCATTATGGAGACTCAGCAGGGCCCAGAGTGGGGGCCCAGCAGGGCTCAGAGGTGGTGCTCAG<br>AGGGGTCTCACACTTTCCCCCTTTCCCTCCAAAGCCGAAAACATTTCCAAATGAGACATTGGGAGCCACG<br>TAGAATCTCTCCTTACCTACTTTCTCAGACGCCTTGCTGGGGAATTTCTCTAAAACATGAAAAACCAGTG<br>CAGAGGGAGGGAAAACTGTCCGTGGGGCGTTCCGTCTGGGATATACCCACACCTAACGTTCCCAAAGGAC<br>AGGAACCCAGGAGAGGCCTGGCGGGGGAGGAAGCCTGAGTCCCAGGGGGGCAGGGGGGCGTGCAGGCAGGG | <br><br><br>CTG45_R1<br><br><br><br>CTG45_F1 |
| GCACGTGGACAGGGTGAAAGCCCCTCGCTGCCTGAGTGTGGAAGAAGCATCTGTGCGGAGATGCGGCTGT<br>GATTCACGCCGCCTGAACTCATTCCAACAGGAAGGTGGAGAGGCGAGGTAGAGGAAGTGGGGAGAGCCCC<br>GGAGCTCTCAGCCTGCTGTTCTCTGGGTTTGAGAGGCCACACGAGTGTACTAGGCGTGTGTGTGAGCCTG<br>CTGCTCCTAAGGAAGAGGTTGTGTGTGTGTGTGTGTCTGTGTAGAATCCAAGTGTAGACAAGAGTACG<br>ACCCTGTGAATGTTTGTGCGTGTCAACAACCACTTAGTGGACCCCTTCTGAGCCTGTGGGGAGCCAGCTC<br>CAGGCAGAGGGTAAAAAAAAAAAAAAAAAAAAGCATCGGCCGAAGTTGTTTCCTAACGTTATTCCAGTCGC<br>CAAGGCCTCCACCCCGTCTCACCTCTGTCCCCGGGGCCCGGTGTCTCATCCCGCCTGGATCAGTGCAGCC<br>AAACCACTGTACTGTCAGAACCAGCTCGTTTCCAGGGCCCTTTGTGAGGGCCGTGGCCCAAGGGGGAGCG<br>TGTGAACCCAGCGCTCCTAGCCCAGAGATTCTCCCATCCGTCTCAGTTTCTCTCCCTGCCAGACTGGAGC<br>TCACCAGTGCCGATCCTGTAGCAGAAAAGGTTCTGGCCGCAGGCCTTCCTTGAGAAGCCCTCTCCTCCTC<br>TTTGGTCGCGGCGCTCCGGGGCCCAGGCCTGTGTCCCGTGGCCGCGTTCAAGGGGGCTTGGAGGTCATTT<br>AGGCCTCGAGTTCCCGTTGGGCCCAAATCAGGACCCAGAACCTTCCCTCTGGCCCAGCACCGCGCCGCCT | |
| GGAGCTCTGTGGCTTCCTGTTTTCCCAGCCGCTCGGTCCTCTAAAGCGTGGTTCAGAGGCCGGCCGCCTCCC<br>GGGATCGCCCAAGGCGAAGCGCTTGGGAACTCCGATTCGCTCGCCTGCTGCGAGCCACCCCGATT<br>CGGGTCATCCGCGCCTCGGGCGTCTTGAACCCGCACCCAGCTGGCTCCCCTGCGCCACCGCATCCCCG<br>GCGCGCCCGCCGGCTGCGCTTCAGGCTCCCGGCCGGGCTCCGCACCTGCGATGCTCCCACCTGCAGCGC<br>CGCCCGAGGAGCCTTCTAGCCGGCCAGGAGTCAGGCCTCAGCGGCCCGGCTCTTGGCGTCCCCGAATCC<br>TGCTGCAACTGTTTCCCGCCGCACGCGGGAGCCGGTGCTGCGAAGCATCCGCTTCGAAGCGGCCCGGC<br>AAGCAGCGCAAAGCAAGCGGTTTGCGAAACGGCGAAAGGAGGAGAAACGGACTCCGGGTTGAGTTTA<br>ACAGCCAACGCTCCGTGCCCTTGGCCGAAGGATCCCAAGGGGGCTGGACGGATTCCCCCGGTCCCTTCAG<br>AGCCGTCGATCCCCATTTTCCGACCCAAAGTCACAAACCGCTCGGCCCCCACGCCTCCCCAGCCCGCCAAC | <br><br><br><br><br><br>BALX4_1_1162C<br><br>BALX4_1_1068C |
| TCTCGCCTCCAGCAAGTTGATCGCGTTTCGAAGGTCCCGGAGCCCGGGTCCAGGGGTCCCAGCCCGA<br>GGGATTCGCACATGCACTCACCGTAGCAGGGGACCTGCAAGGCCGCGTTGTGGCCGCCGCCGCCTTCCTG<br>GAGTTTGAGGCTGCCGTCGGGGGCGTCTTGCAGGCGCCTCGTTGCAAGTAGAGATGCGGCTGCGGCGCG<br>GGCGGCTGCGGCTGCGGCGCGGGCGGCTGGGGCTGGAACTTGCTGAAGGAGCCCCGCGCCCGGCGCCGC<br>TCTCCAGAGGTGCTGCCGGGTCCTGCTGCCCCCGCCGCGTAGCGGGCCCGGCTCTTGGCGTCCCCGAATCC<br>CTGCCCTTTGGCGGCGGCTGACAGGAAAGTTGTGCTGAACTTATCACCGCCGGGGTATGCCCTAAAAGGC<br>GACGAGCCCTCCCGGCTCTGCGACACCGGGCTGTAGTAGGCGTCCATGGCAGCAGCCGGCGACTCGCAGT<br>AAGAGACGCAAGTCTCAGCATTCATGCCTGGCTCGCGCGGGCGACGGGCGGGGGCGCGAGCGGGAGCGCG<br>AGGACGCCACCGCGCGCCTTGGCCGGGAGTTAGGAGAGGCCAGGAGGCGGTGGCTGTGCGCTGCGCGCGG | BALX4_1_1116C, BALX4_1_1061<br>BALX4_1_1042C<br><br><br><br>BALX4_1_851C/BALX4_1_830<br><br>ALX4_EXON1, ATC START CODON |
| GCCTGCTCGCTCCCCTCCCCTCCCACGCCTCTCTCTCTGGCCTCACCCCCCTCCTTTCTCTCCCTT<br>CTCCCTCCCCACAGCTGGCCAAGGGAAAGAACCGAGGACTGTAAAAAGATTCAGATGTTTCGGAAGTTG<br>ACCAGATCTCCCAAACCCTCTTAAGGTTTTTGAACCGGAAAAAGAGAGTGCTTTTTTTTTTTTTTCCCC<br>CGACTCTTTCTTTTTCCCTTCCGTCTCCCTCTCCTCCTCTGCCTACTCCCTTCTCCCTCACCCTTAC<br>CCCGTCTCCCTTCCCTTTCTTTTAAGGAGGTGCTACTAATTCGGTCGCCACTCCGAGGGGATTTTACGCGG<br>AGCCGCCCGAAGGCCTTTTCAAGTCAAGGCGGGGCCAGGGAGGGTCTCTGGACTCCCCGGGCTCCCGAGGC<br>TAGGTGGGTCCAAGCTTCGGCCTATGGGAGGGGGGCATGCACAACTTTAGTGATGGATTAAAAAAACAAA<br>AACGAAAAACAATCCAAAAAATCTGACAGGGTTTGACATTTGGAGGCAGAGGGGCCGCTAACTTCTGGGT<br>GCAGGCAAGTCGTTGGGGCACATCCCTGAGAATTTAGCGCGCAGCTGCTACGGTAAATGTAGCGCGCAAC | <br>BALX4_1_428, BALX4_1_426<br><br><br>BALX4_1_45 |

TABLE 3A-continued

SEQ ID NOs: 1-2, BOVINE EXT2 AND ALX4 GENES

| Sequence | Primer |
|---|---|
| TTTCCTGTCTTCCCAACTGGTGCCTTTTGCTCTATTTCCAACCCCTTTTCCCTATTGTCGGTTCCTCCTT<br>GAAAGTAACACAGTCACACACACACACACCCGCGCGCTGCAGTCACCCTGCGCACGGCCACTTTCTTGTT<br>AACTGTTTTCCTCCCTTTAAGGGCACGGGCGAGGGTTGCGGAGGAATCCATGTTCACTCAGACACTGGAG<br>AACCAGCAGGCTGCTCCAGTTTCTGAAGCTTTGCGCCCAGCCCAGGAGATTTTCTGGCTGGGTTAAGGGC<br>GCTTTGAGAGTGGGGAGTTGAGAGACCCGCACCTCACCGCTGCGCAGTCACCTGCTCACTGCTCAGGTGG<br>GGGTGAGACAGTCTAATCTCTGGCCTCACAGTCCCCACTAGAAAAGTAATGGCCTGGATTTGACGGGTTG<br>TGTGCGCCTCAGGGCCCTGGAACCGGCCACAGCAAGGGAACAGGACTTCACTACAGTGAGCCGCGTCCCT<br>TCTACACGGCTAATCACTGATTGCGCCTCACAGCAACCGTGCTTGGTGGAAATCGGGGTCCCCAAATTTT<br>CCGATGAGCAAACCGAGGCTCAGAGAGGTATGAGCCCTTGACTGAGGTCACACAGCTGGGAAGCAGCAGC | CTG60_F1<br><br><br>ALX4_68_249, CTG60_R1 |
| GCCTGCCTTGAAACCCACGCTGAGGCTCGTCCCTCCGCCGATCTGGGATGACGTTGCTGACAGCGAAAAC<br>GAAACCACGCAGAACGGAGGAAACGGAGCTCTGACTGTAGGATGACTCGGGTTTGGAGGAGCCCATTAAG<br>AGCAGTCCTGGATAAACTGCAGAGAAAAGGATAGAAGACATATCTCAAGGGAGGCTGGGAGTGGGGTGAA<br>AGGTGAAGGGGCAAAGTAAAATGAGAGAGGGCCTGAGCGCCCTGAACCCAGGAATGTAGGTCAGAAGTCA<br>ATCTTCTGCACCTAAAAGGTCTCCCTAAGAAGAAATATCGGGGGGGGGGGGCGTCATGCTTCTACCCCC<br>AACCTTATCCTAGCTAATCCTCACCCCCACCCCTCTCCCTTGGTCTCCTTGCTCTGCCGCCA<br>CTGCGCGATCCCACATCTGGTTTCCATCGCGGCTTACCTTGAAGTGCTCGTTAATAAAGATATTCTGCAA<br>ACCGTGGCCAGGGGTGCGCAGGCCTGAACCCCTCCCCCACTGCCCATAGGGACCCGCACCTCTCTGGCTC<br>ACGGCCCAAGCCAAGTGAGGATCTCATATATACTGAGTCCTTGTTGTGCAGAAGCATCCACAGGTTGT<br>CTCTTGGGCTACCCCAGCAATCTGGGGATGCTGGTCGTCTCCTCATACCCATTTTCCAGATGGGTAGAC<br>TGAAACTCAAAGACACCAACTAATTTTCCAACCTCAGTTAGCCAAAAGTGAGTGAGCCTGCATCATCCCA | |
| AATTCTCCTGTTCAGCCCTAGTTTCTTTTAGTTCTTAGACTCTGCCAAGTTCTGGAATTCCCGTCTCATC<br>CCTGTGCTTTTTGTCTTGCTAATAACTTGGTATTCAGCAAAGAGTGTCTCCTCCAGGAAGTCTTCCCATC<br>TTTCCCAGTCGAAGTGCATCTCTGTTTTGGACTTCAGGTTTGTCTGGTTGCCGGTTCAGTGTTCATCTCC<br>ATCGCACTAGTCTGAGGTTGCAAGAGGGCAGCTTCTGCGCTGCCTGGCGCCCCACAAATATTTACAGAAT<br>AAAATATTAGAGCCTGGGTTCCTTCCACTGCTCAGCGAGGCAGTTCCCAGCGTATTTGGTTTCCTCTAGC<br>CAAGGACGACCGGCTGCTCGCCCTCCCCCTCTTCATGAATCAAGCGACAAAATTAAGAGTACGCTGGCCT<br>CTCCCTGGCCGCACAAGAACAGTGAGTTCTCTCAGAGAAGGGGCCAGGCCTGTCTTGTTCACTGCAGGGC<br>TTGGCACATCCTAGGTGCTCATAAAATGCGCATTGAATGAATGAATGAAAACACTGAGCGATCCAGTCTG<br>AGATCTTAAAGGTGCATTTTCGCTAAGGTGTTCCAAGCTGAGAAGGCTACTCCGGTCCCCTGTGCCCCAA | ALX4_68_1421C |
| AACTGGCTACTAGAACCCAGATGATGTCTGCGATCCTTCTACTTCTCTCCCCTCATTTTCCAATTCCAGG<br>AGTAGACACAAGGGGGAAACTAAGAGAAGTGAGCTATATGGGTGGGAAGTGGTGACTAGACAGGTAGAA<br>TGGCAATCACCATATTCTCTAGTAACTTCTGAGCTGCTCTGGCTGTCAATGCAAAAAGACAAAACCAAAA<br>AACAACCCTGCTGCGATCCAGAAAGCTTTCTTTGCATTGGTGGTATAGTGGTTAGCATAGCTGCCTTCCA<br>GAAAGCTGTCTTTGAGTGCTGCCTCCTGCCACCTACCCACCCCACGATCTTATCACCAGTTTCATCACTA<br>CTCCATTATTTAACCTTTTCCTGGCCACCCCCCACCCCTCACCCCTCACCCAGGGAGGAATTTCAGCCTC<br>CCAGCCCTCCAGGCACAGACTCTGGCGTCCTCAGTCAGAAGCCCTCCTGGTGCACTGAGGTCATGGTTCT<br>TGGAACCAGCAGGGGGGCCTTCTACCTTTCAAGGTACCTTAGAGGTGAACTCAGAAAGAGTGAGCATCTG<br>CCTGGGCTGGAATGTGCATGTGGGTTTGCCTGTGACCAGTGAGAACATTCTGGGCATGTTGTTTTCCCC<br>ATGAAAACCTCCACAGACCCCCTGCCCAAGTCCCTTCAAACACGTCTTTTCTAGGAGAATGAGAAGCATA<br>GCTGGTTATTTCTGTGTGCGTTAAGTCATTTGCAGGTTGATCAGCCCATGCCTCCCTATCTCCCTTTATC | |
| TCTCCCTCCATCTCTCCATCCATCAATCTATCCATCCATCCCTCTGCCATAGCTGAAAGCCAAGGCTCTC<br>CCACCCAGTTCTCCTGCAAGGGTGCGGGCATCTTTCCAGCCAGAAGTGAGGTGGATGACTCTGAAGCCT<br>GGTTCTGGTCTTTGCTCTCCCCTTGCATTATTTCTTCCTCGGCTAAGGCTCCTCCGGCTTGCTGATTGTC<br>CCTCCATCACTGATGTGTCTGGCAGTATCTCTACACTTCTGATCACTTTAATGTGCCAGGAATAGTGGGT<br>GCAGCCAGTCCCTCTGCTTCAAGTCCTGATTCCTGTCCCCAGCCCTGGCAGACACACCCCTTGGCCATCC<br>CTTCTCTCTCCCAGTGGCACTGTCCCACTTCACCCTCTTGGAAGCGGCTTCCCCCTTCGATGGGCTCCGC<br>ACACAGCCTGGGAAGGGGGAGTGGTGACAAAGTCTTTGTCAAGGCCAAGTGCTCAGTGTCACCTCCTCTT<br>GGAGGCCTTCCTTCACCACCCTAGCATCTGCCTGGTTATTTCCTTGATCGTCTCTATTCTGACCTGACAT<br>TTTCTCCCACATTTATCAACCTACTTGTTTTATTGTCTGTCTTCCTACCAGAACGTGAGCCCATAGCTAC<br>ACTCGCCCCAGGAGGAAAATACAGGGCTTGGCACATAGCACCACTCAGCACTCGATAAATATCTATTGAG | |
| CGAGTGACTAAATGAGTGAATGAACCAGTAAGTTGAATGAACAGATGAAGAATACTGGAGGAGAAATGCA<br>GTAACTGCCCAGTCCCTATGGCTCAGGGCGGGAGCTCTTGAGGCTGGGGTGTAGAACTGAGTTGGAGAAC<br>GGGGAGGCATGGACTGGAAGTTCTTTCTTTTAAAGGGGAGGACGGATTCGGAGCCACCCCCTTTGGTCTG<br>AGCTCCCTCCACTCCATCCGGCGCTGCAGTCTCCACCTCCTACAGACAGTGGAGCTGGGGAGGGGAGCAG<br>CCCTGCTTATCTGCTACTTGACTTCTCCTGACAGTGCCCCAAGTCTTGCCCCCAGTGTGGGTAAAACCG<br>GGACCATACACACCTCAGCGAGTCACGTACTACTTGGCTTGACTTGCCACTTTGTAAATGCCAGGAGGC<br>AGCAAAGATTGCTCGAAAGGTTGGGGCTGCTGAATAGACATTTTGGACATCTGCAGAGGGGCAGGAAGAG<br>TCAGGATATGAAGGGGGAAGGCCAGGGATCTTACAAATCTTGGGCAGAAATGCTTCTGCTCTGCAGACCC<br>GGGCACACAGACCTCACATTCCCAGCAAGACATAAATTAGCAACTGTGTTTTGGACAACTGTTAAAAGTC<br>AGCTCTTGCACACAGATCTTAGCAGTCCTTGAAACGGCCCGGTGATGGTACTATTATCTCGTTTTACAA | |
| TGATTAAAAAAATATATATCGAAGCACAGAGAAGTGAAGCGACTGCTTACAGTCACACAGCAAAGCAGAC<br>GACTTGGGATTCGAATTCAAGTGACTTGATCTCAGAACCCACGCTCTTAACCACTGCGCGTTCTCTGAGA<br>TCTCTGCGGCGACGCGGGTGGAAAGGTTCCCGAGTCCTCTCGGCCTACCGGGCGCTCCCGACCCGCAGGA<br>CTTCGCCAGTGCCGCGGGCATAGGGGCAAGGGCTGGGGCGCTCGCCAGCCTCGGCCGCACGCGCGGAC<br>CCTGGTCCTGTGGCGGAGGACCAGGCTATCGCCCCGAGGTCTGTGCCAGCGTTCGCCACCGGCGTCCAGC<br>CTTCCAGCGTCTGCCCGATCTCCCAGGAATGCAGACACCTAGTCACCTTCCTGCATTCGGCTCCAGCCCC<br>CGCGCAGCCCCCGGGACAGCCGCCGCCTGCTGTGGGATGGAGCCCGGGAGGGAGGCACTCCCCACCAACAT<br>TCTCCGAAGACTCCAAGGCCACGCGGCTGGGCGGGCGCACCCCGGCAGTCCGCACCCTAGTGCGCTAG<br>GCTGCCCGGGGCAAGAAGCGAGGGTCTCTTAGGCGTTTTGAGCCGAGGGAGGACCTCGCGAGGGGCCACC<br>ACGCTCCGAGAGCGCCGGGTCGCCTGCGCTTCCTCCTGGTCCACGGCCCCTATCTCTCACCCGGACCGGT | 320933_F2 |
| ACTCCCCGTTTAGGTGTTTAGCGTTCGCGGAGTCTGGCCCCTGGTCGGCTCCCTGGTGGCGCACGATAGG<br>GGATTCAGCGCGGGGAGAGGCCCCAGAAGGACCTCCTCTTCCCCATTCTCCGCTTTCTAAGGCCGGGGAG<br>CGAGGGTCCAAAAGGAGGTCTGCGTTCAGGGACGTATCTTCATTCACATGGAAAAACACTAACTCCCGA<br>AATGCGGGTAAACGGGGCGTTCTCGTGGTTCTAGACGCTTGCACAACTGTTCGGTCGGGAGGGTCAATG<br>AATACAAAGCTGGAGGGATGAAGGTTTTTAAAATGACCAGGCGCACAGGCGCACGCCCGACCCGCAGGAACGCAT<br>CCCTCCACCGCCCTTCCCCGCCCCCACGGTGCGTTTCTGGGACCTGCCTTCCCAGTCGCCCTGGTACTTT<br>TCAGCGTGGGACTGGGGCTCCTGTCTGAACGCGCGGTCCAGGCGCACGACAGAACCTGGTTCCCTGCTCC<br>CCACTTATCCGCAGGGCAGAGCAAAGAGCTCAGGGCAGGGAGAGAACTGAGAGGGCCACAGCTGGCG<br>AAACTGCAGTCTGGCGAACCCCCCAGGAAAACCGACTTGGCTGGAAAGCTCGTGAGGGGAGGCCTGGACA | 320933_R2 |

TABLE 3A-continued

SEQ ID NOs: 1-2, BOVINE EXT2 AND ALX4 GENES

```
TCGCCGGGGCGACCGCCTTAATCCTGGATCCGGAGAGGAAGTTGGAACCGGAAGTCCTCCTACGGGGTC
CTTGCACCCCTTGCATATCGGTTACAGCCCAGGAGAACACAGATCATTCACCTCCGCAGATAATTCCCAA
ACGTCATTAGCCAAAACCCCAGCCAGGTGTTGGGACTGGAGCCCCGTGTCCCCTCTTTGTCTTCTCTGTC
CCTTCTCTCCTGGAAGCCATTCCTCTAGGGTTTCAAAAAGATGGACCGTGGGAAGGTGGAGGCCAGAACA
CACCAGCTCGGTTATACAGGAGTCCTGTGGCGCCTTGTGGGCAGAAATGAGGTCTTATTTCCTGGGGGTG
CTTGCTGGGTGGAGAGGATCTGCCCTTCCCCGCTCAGCCTTAGTTCTAGGGAAGTATATTTCGAAACTTT
CTACCCATTTCCCCGCTGGGGAGATGGAGGCTTCAGTGATGGAGGGAAGGGAGTGTGGATGGCCAGAGGG
GCCTCTGTGCCGTGCGCGCTGGGACTGCTGAGCTGACAGCCCACAGGTCTCTTACTGTAAGGGGTGGTCT
TCCCAATCTACCGCTCAGATAACTGAGCTGGAGCCAGGGAGGGGGAGAGGTGAATGGGACAGGCTAGGCT

TCGGATTCTCCTTCTTTCTCTCTGAGATCCTTGGGGTGAGCCCTGGGGGGCCCTTTCCCTCCGCCCTCCC
TTCTCCACTCCGCTCCTGCCCACCAATCCCTGGAGCCTGCTGGCACCACACCCTCTCAGTGCCCTGACCA
CACTCTGCTGCCATCACTGGGAAGGGGCGGGGAGCACGGCCCCTAATTCCCTTTTCTCCTCTCCCACAAC
CCCAGAGTCCTTCTCCTCTAAGGTTTCGTTTGTCCCTTTGTCCCCTCCCTCAGCCCCAAGAATTCGTGGG
CAGCCAGCAGCAGTTGTGATGACTCTAATTCCTGCAGTGCCCCCAGCGCTGGTCTCAGCGGTGGTGGGAG
GGGCTACTGGACTGGAGGACAGAGCTGGGCTCAGGAGCCCTCTGTGGCAGGCCTCTGGGGCTGGGAAAAA
AGTGGGGAGGGTGGTTCAGGGAGGAGGCAGAATTAGTGATTCCATTAGTGGTCAAGAGGCCAGCTGTAG
ATTCAAGTTTGAATCCCATTTCTGCCACTTTTTCGCTGTGTAACACAGGCTATGTGACTTCGCTCATGGG
CCTCAGTTTCCTCTCCTGTAAAGTGGGGAGATTAGTAGCACCTATTTCATTGAACAGCTGCCAAGATGAA

ATAAGATCATGCTCACTTAAGGAGTTTTCTAGTATCAGCAATGGTAATCTCCTTTCTGTCTGGAACACTC
TGCTCTTTTAAACTTCACAGCCCAGACTTAAGGAACCAGAAATGACCAGTTGGAGTTCCTGCCCTTCAAC
CATCGTGACGGCCGGTCATATTTATCTTTCAGACCACAGCTCCTCCCTGGTCAGGGTCTTTTAAAGCACC
AGGAGTGAAAAGGCCAAAGGATTTTTCAGGCTCTGCGGTCCAGCCATTCCTGATAGTTGGTGCACATAAG
ATGGAGGCGGTGCGTTGTGTTTTGCAGAGGGGTAGCTGCGCCCAGCTCAGCCCCACCTCAGCGCTTTCA
GCAGCAGCGCCTTCACCTCTCTTGCTGCTGCTGCTGCTGCAAAGTCGCTTCAGTCGTGTCCGACTCTGTG
TGACCCCATAGACGGAGCCCACCAGGCTCCCCGTCCCTGAGATTCTCCAGGCAAGAACAATGGAGTGGG
TTGCCATTTCCTTCTCCAATGCCTGAAAGTGAAAAGTGAAAGTGAAGTCGCTCAGTCGTGTCTGACTCTT
AGCGACCCCATGGACTGCAGCCTACCAGGCTCCTCCATCATGGGATTTTCCAGGCACGAGTACTGGAGT
GGGGTGCCATTGCCTTCTCTTCCCTTGCTTCTCTGTAAACTCATGACTGTCCTGTGGTGGAGGGTTTATG

TCATCGCTTTACAGGCAGGGAAATGGACGCCCCTTGCCTACAGCACACTTTGAGCAAGAGGTCAGGATGA
CCCTCAAATACGGGGCTCCTGGCTCCCAGGCCTGGTATGTTTGTCCCAGCGTCCAGAGCGCGCAGGGGCC
TCAGAGACAGGGCCCCGGGGTCTGGCCACAGCGCCTCCTGCCTGTTCCTCCTCCCCCACCGCCTGCCTC
CAGGCGGTGAGGTCTGGGCCCAGCACCTGTCGAAGGAGCCAGCCGGGAGGCGCACCAGCTCAGCTCGGGTAA
TCCGGGGCTTTGTGATTGGCAGGGAGGAGCCCTGGAGGCGGGAGGGTGGGAGGAGGGGAGGATGAAGGA
GAATGCGGGAGACAAGCACTTGTTGAGCAACCCTGGATGCCCGAGACGAAAGGAGAGACTGATAACCAAG
GGCGCTTGACTCAGTGCCTGGCACATAGTAGGTGCTTAGTAAATGATGATGGTTATTCTATTTCTATCGC
CTCCTAGTCTTACTAGATGTCTGCCAACTTACCTAAACCCCTCCATCTGAGGATGTCATGCCGTAACGTT
CACCCTCTCTCACCTACCCCACCAGGGGTCCTTCCCTCCTTGGGACCAGTGGCCGCACTCCCCGCTTGCC

TGGAGCCCGGTCCAGAGCGCACAGCTGCGGCCAGGCTGTGAACACTTCTGGAGTCAACCTCTCCGCCCAG
AGCCCAGGGGTGGGGGTAGGGTGGAGGTGGGAGTGGGGTCGGGTGGGTGGGGTGGGAGAGCGGC
CTTGACCGAGGAGCGAAGGACGGAAAAGCAGTGCAGCCTTAAGTCTTCAGGGACGCTATGGCGAGTGCTG
GCAGGTCGCCCCAGGCCGGAGGGAATTGACTTGGAAAACGAAAAAAAGGCAACTGATAAAGAAACAACC
AAATCTACTCCCCCCTCCAGGCTTGAGCAGCCGCCAGAGGCCAGAGGCGAGGCCCCAGGAACCCGCCCGC
GGACATCCTTAGGAGGTGGCGTTTTTGCTGCATTTATTCGGTGTCAATTCAGGGCCCCTCGCACCTCTGC
TGATCCGCGCAACATCCCTCCCGCCATAGCCCTCACCCAGGGGCTGCGAGGCTGAAGGGGACACGGCCGA
ACACCCCGGGAAAGGGCAACCCGGCCGGAGTCGGCGCTGGAACGAACTTTGACTGGAGAGCCGGGCCCTG
CGTTCTCAGGCCTCCGCGCCTTTACGCGCTGGGGGCTTGGACACCCAGGTTCTTGCCTCAGCCTCTTCTC

CCCAGATGCCTTGCCATCCTCGGGAGCGCGAAACGCCTAGCTGCTTTCTCCAAGTAGAATTCGTTTCCA
GGTCGTAGTGGAATTTTTCAACGGGTAGTTGAGAACGGTCAGCTTCTGGAGGCAGGCATCTGGGCGCTAG
CCCTGATCCGGGCTGGTGCAAGCTTGGGCGATCCATTCTCCTCCCTGTGCTTCAGTGTGCTTATCTGTGA
AATGGCAGTGACTCTTCTCATCTCCTGGGAAAGCTGTGGGGAGCAGAGATCACCTGGGTAGGTGCTCCCT
TAACTCCAGTTGTTAATCTTTTGGGGATAGTTGCAGATCTTGGGGGACTTGGAGGAACACTCAGTTCTT
GTGGCCACCCCGACCTCCTGTCCAGTTCAGATCACCCCTCGCCAGGATTCCAGGATTCTGGGATTCCTGA
GTGCTTCACCCGGGACCATGTGACTAGCTCTTTGATGCCCATAGAGTCCTTTCGTGGTGGGTCTTCTTT
AAAAAAAATTTCACTGGTCTTGCCCTCACCCTTGCCAAGCTAACTGGACTCACTTTCAGTTTCTTGGGGA

TGAAGGTAGCAGACAAAATGAGCATTGCCAAATAGCAATCGATGCATTTTTTTCTTTTCCTGTCTTAAGG
TGAAATCCACATAACTTAAAATTAACCATTTAAGGCTTCCCTGGTGGCTCAGACAGTAAAAGAATATGCC
TGCAATGCAAGAGACCCAAATTCAATCCCTGGGTTGGAAGATCCCCTGGAGAAGAGAGTAGCTATGCGC
TCTAGTGATCTTGTCTGGAGAATCCCATAGATAGGGAGCCTGGCAGGTCCATGAGGTCACACAGTCAGA
CACGACTGAGCGACTAACATATAACCATCTAAAAGTGAGCGATTCAGTGGCATTTAGCACATTTGCAGTG
TTGTACAACCACTGTCTCTGTCTAGCTCCAAAACATTTCATCACCCCAAAAGGACCTATTTTTCTTTTT
CAACACTTTCTCCAGAACTGAGCTGTGTGCTGGCGGAGAGCGAGAGGTCAGCACTTCATGCCCTTTCAAC
TTATCTTTTCAATGCCTTTAACAGGAGCTCTGTTTACAAATGACTTGCAAAGTTGAGCTCAGGAAACCAG
GGAGCCCCGGAGATGGGAGTAGGGTGTTTATTCAGAATCCATGGGGGACCAGTGTGTGTCTGAGAGTGT

GGGCTGGGCCCAGGGAATTATTGGACAGGGAGCTGGAGAACCAGGTCCAGAGAGGGTCTTTAATGGCC
CTGCCCATCTAAAAGCTATAGATAAAATTCTCATCCTGCAGGAGTGAGGACTCTATTTCACAGACATTTT
AAATCACAGGCTCTCAGTCTCTTTAGGAAAGCTACTTCTTTGATCATCCGATGAAAGCTGAGGACCCTCT
TCTTGGACAGATGCAGCGAAATGCTGCCTTAGTTTCCAAGGGTTTGTAACAAATGACTGCACACTTGGTG
GTTTGCAAGAACAGACATTTATTCTGTCTCAGCTCTGGAGGCCAGAAGTCTGAAATCAAGGCGTCCGGG
GCCAAGTTCATAGGAGGGGACTTGCTTGCGATTCCCAGCTTCTGGTGGCTCCAGGCTTTCCCCTTGGCTT
CACTTTTCCCATCACTACCTTCATCTTCATGAACTTCTGTCTTCTGCTCTCCCGCCTTCTTATAAAGACGC
TCATCATCAGAATTAGAGACTACCTGCTGGAGAGCCCAAGATCAGGTCTTCTTGAGGTCCTTTACTTAAT
TAAACTGTAAATATCCTTTCTGTAGGGCTTCCCAGGTGGTTCAGTGGTAAAGAGCCCTCCTGCCAATGCA
AGAGACACAGGAGACCCGGCTTTGATGCCTGGGTCAGGAAGATCCCCTGGAAGGGAAATGGCAACCCAC
TCCAGTATTCTTGCCTGGAGAGTCCCATGGCAGGCTAAAGAGTCAAACATGACTGTGTGACTGAGCACAC
```

TABLE 3A-continued

SEQ ID NOs: 1-2, BOVINE EXT2 AND ALX4 GENES

| | |
|---|---|
| ATCTTTTCTGTAAATAAGCTCGGTCTCACAGGTACTGTGGAGAAGGCAGTGGCACCCCACTCCAGTACTC<br>TTGCCTGGAAAACCCCATGGACAGAGGAGCCTGGTGGGCTGCAGTCCATGGGGTCGCTAAGAGTCAGACA<br>CGACTGAGCAACTTCACTTTCACTTTTCACTTTCAGGCATTGGAGAAGGAAATGGCAACCCACTCCAGTG<br>TTCTTGCCTGGAGAATCCCAGGGACGGGGGAGCCTGGTGGGCTGCCGTCTATGGGGTCGCACAGAGTCGG<br>ACACGACTGAGGCGACTTGGCAGCAGCAGCAGCACGGGCACTGTGGCCACTGTCTTGGGGGACTACCCTT<br>TAACCTCAGTACAGGTGCATACAGCCAGCTTCATACTCAACCTCAGGGGCTCTCAGGCTCCTGTCAAGTC<br>AGAAATGTCTGATTGAATGTCACAAAGCGAAGTGAAGTCGCTCAGTCGTGTCCGATTCTTTGCGACCCCA<br>TGGACTGTAGCCTACTACGCTCCTCCGTCCATGGGATTTTCCAGGCAAGAGTACTGGAGTGGGGTGCCAT<br>TTCCTTCTCCAGGGGATCTTCCTGACCCAGGGACTGAACCCAGGTCTCCCGCCCTGTAGGCAGGCGCTTT<br>ACTGTCTAGCCACCGGGCAAGTCCAGGAACGTCACAAAGGAATCCTTAACTGCCACCTTCAGAAAGGTTG | |
| GAGAGAGTAGAAACCACCCTTCTCTTTAAGGAAGGACATTCCCACTTGCGGTTAAAAGGAGAAAATGAAC<br>CCACCATCCTGCCTCGGTGATACCATCTGCCCTCTTGAGGAAGGACATTCCAGAACATTCTAGAGGCAGA<br>AACCAGTTGCCTTTTTACAAAGAAGCCCTTGAAAAATGCAACCTCAGCCAGATATCTCAATTTGTGAAAA<br>TGGACCGACAGGAAATTTCTTCACCCTGTCAGACAAACTTCATAAAGGCTCTGTAGGGGCCCTACCACTC<br>CGAGAAGCCTTTTAAGAAAATTGCAACTTTTAGTCAGACCCTGAGGGAAGTCTCACAAAGGTCTTCACAC<br>CCCTTTGGCTCCTCTTTGTGGGGTGGTGAGGGAAGAGCAAGGTTTTTTTTTCCAGGGGAGGAGAGAGGTG<br>AGGGATCAGGGCTGGGGAGAGGCTGCTCTGAGGCAGCGAACAGGATGGCTCCACAGATAGAGGTGACAGT<br>TTCCTCAACTGAGTCCCCGGGTCGCCACCTGTGTCCTTCCTGCAGATTGGATTTATAGAGTGTAACATTT<br>TAATAAAAAACACACACACCTTCCCATTTTGGTGCATTAAGAGATTTCTAACAAAACACTGTAATGTTGC<br>TATAAATTTTTCTCCCAGCACCCTCACAAGTAATAACTCAGCCCCGGAATTTTGCATTTAATGTTTATTT<br>TGATGGCTACATTCCAGTCAGAGTGGGGCTCAGGGTGGGAGGGAGAAAGCAAAAAAAAAAAAAAAAAA | |
| AGGCTCCTCTTTCCTAGCCATTAACTGTGTGTTTTAATAAAAAAAAAAAAAAAGGTCCCCACAAATTGG<br>GGAGCCAACACTTGGAAAGGAAGGAGGGAAATCATGACACCCTATGAGGAAGCGCCAGTGGCCTCAGCTC<br>TAGGAAGTTGACAGGGTGAGCCCTGGCCGGGTCCTGCCAAGGTGGGTCTCCAGAGGGTTTCTGGAATGTC<br>GCCTTTGCCCATGCCATGCATTCAGCCTGAGATGCCTTTTTCTTCCCTCAGAGCTTCTGAGCCTCAGA<br>AGTCTCATCTTCTGGAATTTTCCCCACATCCTTTCTCCACGAGAGTTATGGGCCCTTCCCCTGAACAGTA<br>TTCATTCTATTCACTCAACACTTGTAGTGGAATCTGTGGCTGGAACGGGCTCAGATGAAAGCGTATTGAG<br>TGAATGAACAAGTGAACTGAGTAGGTTGGAGAATTCTATTTTATTCCATCTGAATTGCTTCCGCGAAGGC<br>AGCTATTTTGGAATGGTTAATGATTTTCTCCCTAAAAAAGAATCTAAATAGTTCAAAATCATGTGGAGAT<br>CAGATCACAACCCCTTTTCCTTCAAAAGTGCTATATTTTAGTTGTCTTATCCCCAGCGTCAGAAGGGAA<br>GCTTCTAGTTTATTCTTTTGCCTCCAGGTAGAAACAAAAGATGGGATGCTGGTCCAGACTGTCACAGATG<br>GGTGGAGACCACTTCCTGGAGGCTGAGGCTGAAGAGTCCATGCCTGATAGCTGATTAATGCTCATCTT | ALX4_33_144<br><br><br><br><br><br><br><br><br><br>ALX4_33_708C |
| CCCTGTGCCTTGGCTGTGGGGCTGATACCCTTCTCACAACACCCTCTCCTTCTAAGAACATCACATTCCC<br>CCAGCATGTCTTCCCATGGGGCCACTGATCAAAGCCTGGGTTCTGGGGTTGCCCTGTTCCCGAGGCAGGG<br>GATAACACTCAAATTGTCGGTGGGGATAATGAATAGAGAAAAATGCTTGTAAACATATGGAGTGCCTGGAA<br>CACAGAGGGTGGCCCCTAACAGCGTGTATGTCTCAGTGACTGTGGAGCACGTAAGTGGGGGGATCAGACC<br>CCAAAGTCAGATGATTTGCGCTTATTGGTGTAAGACCTCAGTTTTCTCATCTGTAAGCTGGGGACAACTT<br>CAGCAGTTGGATCCTGGGAGGTGGGAGAAGGGGAGGATTATTTGAGAAAGTTGTTCATGGCATGTGCCTG<br>ACTCACTGTTCAGGTTGGGAGGGGACCTGGCCCTACCCCTGCCACTCACTGACCTATGGGCACCGTCAGC<br>TGGCTGGGTTGGAGCCCCTCGCTTTCCTTACCTCCACCGCACAGCCCTTCCCCAGAAAGGAAGGACAGCCT<br>GTTCCAAGCTGCTTTACTTTGCCTTCTCCATGGCGAAAAACTGTTTTTTCATGAAGGGTTTCAAATCCTG | |
| CCTCTTCCACTTATTTGCTGGTTGACCTCGGATCAATTGCTTAACCTCTCTGGGCCTCTTATTTGCTTAT<br>CTGATAAATGAGGATGATAATGCTGGCCTTGGTGCATTGCCCTGAGGATTGAAGACGATAAGGAAGCCTG<br>GTACACAGCAGGCACTTGATAAATGTTCTCCCTTTCCCTAAGGAGATGAGAAGCAGATACTGGATGTGAT<br>GCTCCGGGTACCTGTCCTAGGACTACGCACAAACAGTGCCTACTAACTGCTCTGGAGTATGGGCCGGC<br>AGGAAGCTGCATTGCCCATAATGGGGAGCTCTCAGGAAGACCCCCTCACTCATCATGCTCTGTGAGGACA<br>CCATACATTCTTCCCTTTTACAAACTCTCAGCCTGGCCATTGCATTTTAAAGCTGAATAAATAGTTCCA<br>GGGCAAAGCCAGGGATCAGGGCTGCTCTTGGCTCTTTCCAAAGTATTTCTGAGCCTTTCAGCAGGATCCG<br>AGTCCCCACCCTGCAACCCCTCTAACTTTAATGGGTGCTGATCACTTTACACCCTGTGAAACCCTCAGCA<br>AATGGTCCTGATCTCTGATGTGCCGTTCAGGCTGGCAGCAGGGCGCTGGCACTCAGACTCTGCCCGAGGA<br>AATGAAAGCCTGATGGGCTGGAGGGGGAGGTGGCGAAGGAGCTTCCAGGCCATCATGGCAGCTGGAGGA | <br><br>320933_R1<br><br><br><br><br><br>320933_F1 |
| AGTTTTCCCCTAGCTGAGCCGTCCTGCACCCTGCCATCTCTCCCTTCTCAAACACGGCAGCCAGGCCTGC<br>TCCGTCTGGGGCCTCACAAAGGCCCTTCCTGAGCAAGCTGTGTAGATGTCTACCCTACAGAAGTAATAAT<br>CGACAGGACCATTTATCGAGCGCCTATTATGGGTCAGACCCAATTCTTGACTTATCCATGAATACCCTC<br>TTCTGCGGCCCCCTGGCCACCCCGCCAGTCAAAATTAGCTCCCTCTTCGGGGACTCACTGTCCCTCACCT<br>GCTTTAATTCTTCAGAACCATTTGTCACTAGCTGTAATGATCTGGTTCATTTATCTTTTCCTTTGTCTA<br>CTATACATCTCTCCTATTACAATGACGGGAACCTTGTCTGTCTGTTCATACACCATGGCCCGGAGAAGCG<br>CTCAGTGCAGAATAGGTGTTCGGAAAATATTTTATTTTTCATCTGAATGAATCTTCATTCATCTTCAGAG<br>TGATCTTATGGGAGGGGACTATGATTATCCCCATGTTCCAGATAGGAAAACTGAGGCAGAGAAGGGGCCA<br>GGAGTTTTGACAAAGGGCACACAGGAAGGGCAGAGCTGGGATTCTGACCCTGGAATGTTTCACTGAAATC | |
| TGTGCTGTTCTGCCCCACACAACCTAACCCCACCTACCTGGCTTCCGATAGAGTGAGTGCTCTGTTGGAA<br>ATAGAAGATCTTGTCAGAAATGGAAACTTGAGGCCCCTGTGTCTGAACTAAATACTTCCCGAATATTTATA<br>CTCATGATCCTACAATATTTTATTTTCTGTAGTTTTCACAGAAACCCATTACATTGTTATCTTTCTATAC<br>CATTTTATAACGAAGAAGTCAAAACTCAGAGAGGTTGTGTGCTTGCCTAAAGACACACAGCGAGGAAGTG<br>GCTGAGTGGCCTTGGGTCTGGACTGGGATGGAAAGGCTGTGCTCATCTCACTTTCAGATGCATGGCCTC<br>CTGGGGAATCCGAGTGACCCCTCTGGACTCACACAGTCGGGAAGTGACAAAGCAGATACAGGGCCAGGTC<br>TTGTGATGCTCTGCCCAAATCTCCCCTATTTCAGTATTGCAGCCTGGAAACCAGGCACACAGAAGGAAGG<br>CATGAGGGTCCTGACCGAGGGCATGATGTGGTTGCCTTGAGGGCTGGGAATTGGCAAGGAAACTCACAAG<br>GTCATCTGCATGTGTGTGTGTGTAAAAACAAAAGATCTGACCCTGCCCTACCCTACTGCGTGGATCAG | |
| TAACTGTGGAGGGAAGACAAGGGGCAGAGGGATGGACAAACTAGCCAGATTTATATGGGAAAACCTGCA<br>GAGACATAGGAAGTAGGAGAACATCGAGAAAGGGTGAAGCTGCAGCCTATGGAGGAGAGAGGGAGGTTTG<br>GGGGGTCTGGAGTCAAAGAAGGGAGGCTTCGGAGGAAGCTGCCAGGTCTAGGAGTTGGGGGAGCAGAGGG<br>GGAGAGAGAGTCCTCAAGGTATTTTTCCACCTGATACCTTGGGAATATGATCTTCCTTTTCTGGTGAGTC<br>TGCCATCAACATTTTAATAGAATTTTAAGTTACCTGTGGATGCTGGCTGACATTTTGTGGATTGAGACTC<br>CGTGTCAGAGAGAGGCATGAGCCAGCCTCGTTTGCGAGGGTTCATGTGTCTATGGGTTCTCTACATGT<br>GTGCACACGTCTGCACATGTATGTATTCACGTGGGTGGGGCGTTTGCTCTAACTGAAGGCCTGTGTGCA<br>TGTGTACGTGCGTGCCTGGGGTACCGATGGCCTGTCCATCCCCCTGCCCTGCCCCAGATTGTGAACACA<br>GCCCCCCACCCAGGAGTGGAGTCAGACGACTGGTGTGGGGGAGAGGGGGGTTGGAGGGTCTGAATTGGGAGG | |

TABLE 3A-continued

SEQ ID NOs: 1-2, BOVINE EXT2 AND ALX4 GENES

```
AGTGCCCCACCTCCATTGTGGGAAAGCTGGCATTTGTGGGGGCTAAAACAGGGTGTGGGGGGATGGGGAT
GGGCTTGCAGGGGCACAAGACACAGAATTCCTCCAGGGGGATTTAGCAGAGAGAGGGGAAGAGAGCAGAG
AGGGAGGGGCCCAGGCAAGGGGGGGTGGTCCTTGGCGGGGGTGGGGGGAGTGGGGACACTCTAGAGGC
GGTGAGGGACATCCAGCAAGACTGTCCCCATCCCTGCCTTTCCCTGCCAGTGATGCTGGGGCCTCTGTGA
ACCGATGGCCACGTGCAGGGGCTCAGCAGCCAAGGAACCACGCACAGGGGGAGCTTTTGAACTTAGACCC
GAGAAACCGGGTTCTCAGCCTAGCTCAGCTCATCCCAACAGGCTGTGCAACCTGGGCAGATCACCTGGGC
TCTCTCATCCTAGCTTCCTCACTGTGGCGCCACCTGGGGGGCTGGAGGCCTGCATGGGCGGGTGGGTGGG
ACGGGGCTGGGTGGGCTCTGGAGTGCCGGTGTGTGAGGCCTGGGTTTCTTACTGGGATCGCCAGTTTTGG
CCCTGCCCTGGGCTCCCAAGAATTTCTGGACCTGGTGTTCAGCAAGCAGGGTACCTATTGGGTTGTCTCC
AAAAAAATGTTCTCAGCCTTCATTTTGTTGTATTTAATCTTCTTGAATGTGACCAAATCAGTCTGTTTTA

GGAGGCGGGGGCCCTCGTGCAGGTCCACCTGCCCCGTGATCACCCTCCCCGTGCCAGGGGGTGACTGAT
GACTACTCCCTGCCCTTTTTGGTGTTAACTTTAAAAGGTGTTAACTGCCCTTGGTATCCCTTCAGACCCA
GCTCTCGCCTCTCCAGGAGGGATCACCTGCCTGGGTGATCGCTGAATACACAGAAGCAGCCTTGGCAGTT
GGCATGAGTGTTGCCACTGACTGGCCAGGGAACCCAGATTCTTGACCCTCGGCGAGTAAGCACTGGAGCC
AGCAGGCCGGACTCAAGGCCTTTTGTCTCCTAGCCCGGTTTGGCCACAGACTGTAATACTATGTTGATGA
CGAACTTATTTGTCAACCACTTTCCTCTTTGCAAGTATCAGTCATCCCCACATCGCTGAATGTGTTTGT
TAACACTTGGTTTTTCTGGCCGTGCAACACACACTGTTCTGAAACGTGTCATGTGATGGCTACAC
CTGAGACAAGCCTTGAACAAATGGTTTCTACGACTGCTGCCTTGCAGGTGTGTGTATAATGGTACCCTCC
TTGCCCTGATCCCTTTCTATTTTTTTCTACGCTATTCCCTCCCCTCTCCGATCACACTTTTCCTTGAGCC

TCCCTCTCCCCCACATTCCCTCTGTACCCTCTTGCAACCTGGTCTGCCCCCGTCCTCTCTCTCTCCCCCA
GCCCCGTCTCTGGAGCCAGAGCCTTGGCCAGGATGAAAGCCACTGGCCAGGCCCATAAATCAGCCGGCCT
GTGCCCCTTAACCTTCCCCATTAACCTCTCACACGGGCAGGCATTAGGTGTTACACTTGGCTCCCGTAAA
TTACTTGCCAATGAATTTATGAGTGCTCACCCCTCAGAGGCCTGCTTCCTCATCCTCCCCCACTTTCCCT
CAGGGTTTCCAGACATCGAGCCCCAGCCTAGCAGTCAGTGCCTGGTTCTGGCCCGCGACTCCCTGAGTGA
TGCTCTGCACCTGATCCCCCACCCCGTTTCACACATGGACTAGAAGATTGAAGAGGGGAAGGGGGGGGC
GGGTGTGCGTGACAGTCACCCCTTGGCTCCGCTGTCTAGAATCCCCTTCCCCAGAGGCCACCCCCTGGAG    NW_419640_R1
CTTCCACACGTTTACCTTGGAAGGTGAGAGGACCCTGCATAAGAACGTCACCACTGTTTATTGTGTTTC
TGCCACGTGTTTCTACCACGTGCCAGATGATCATGCTCATTGTTTCTAATTCTTTGAACAATTCTTCGGA

GGTATGAATTGTTATCCCGTTTTACAGATGAGGAATCAGAGGTGCAGGCAAGTGATGTGACTTGGGCAGG
ACCGGGCATCACTGGTGCTGAGAGTTAGTGGATTTCGTTGTATCCTGCGTGCCTGCTCAGTCGCTCATTG
TGTCTGACTCTGCGGTTCCTTGGACTATAGCCCACCAGGCTTCTGGACCCAGGGGTCAAACCCAGGTCTCCT
TTACTAGAGTAGGTGGCCATTGCCTTCTCCAGGGAAACTTCCTGACCCAGGGGTCAAACCCAGGTCTCCT
GTATTCGCAGGCAGATTCTCCTACCAACTGAGCTCCTACTCTATACAAATCCAAATCTGCAAAAACAAGG
CCACGTATGGAAACCGTGATAAGCCCGTGACCCAGAATCTCTCTGCCTCACTCCCTCATCTTGCTGCATG   NW_419640_F1
TCGGTTTACAAGGAAAAAATAGTAGTGACGATGTTCATCACGAGAATGGCTGACCCCCGTGGATGTTTACT
AAGCACCTGTTATTATGCCAAGCGATTTATGTGCAGAAACTTGCTTAATTATCATCCCTGTGTAAGGTTG
ATGCTATAGTTATGCCTGTTTTACAGAAGAGGACATAGGCAAAAAGAGGTCAGTTAATTTGTTGACGGTC

ACCCAGTGAGGAAGGGCCGGGTCCAGCGGTCGGACCCCAAGAGTCAGCCTGCAGAACGCCCAACACTTCA
CCATGAGTAGTGACACTAATGACAAATGTGATGCCACCACAGATAGAGCGACAGTTGCGTAGGCGCCCCA
GGGGCTCAGTGCTGTTAGCCCCGCGTCCCTGCGGGGAGCCCCTGGAGATTCTCCGTGGGTGACCCAGGG
GCGCATCTCACCTGGTTTTCCTTCTTTCGCTTTTCCCAGGTGACAGCAGGGGCGGAGCTACAAACTTTCC
CCAGATGAGCCCAGGACCTCTCTGGGTGCCTGTCCCTGGCTGCTGCTCCAGCTCTGATCCCTGATCCCCA
AAGCTATGAGGTCTCCACCTCAGCTTCCTGAGTGTGATCCTGGGGAGACGGGAGCACATGTCTGGGATGG   NW_250796_R2
CAGGGAGCAGCTGGAGGGGGATGAGGAGGGATGCGAGGAGAGCACGCTGTGTTCCGGGGACCTGCAGGGA
CAGCAGACCGAAGCTGAACGGCAGGACTCCAGGAGGATGTTTCTGGGCCAGCTGTCACCAAGGGCCCTCC

CCTCCCTGTGCCCCACCCCCGAACTTCGGCCCATGTGAATGCCTCCTGTGCAATTCACCAAGGGCCCT
CCTCTCCCTGTCCCCCCCCTGAACTTCGGCCCATGTGAATGCCTCCTGTGCAGTTCAGTCACCACTGCAA
AGGAGGGGCAGACAGCTGCTTGTGTTCCTCTGGGTTGTGTGTGACCCTGACTTAGAGGGAAAAGGAAAGG
TCAGCCAGAGGGTGCTGCCACAAGGCAGGACGCGGGCCTGTTATACTGGGAGGGCAGGAAAAGCAAGAG
CCATACAGACCTGGCTCAAGTCCCAGGGGAACAGGGCTGAATAGGGTCCCCTCCCAATTCACGCCCACCT   NW_250796_F2
GGAACTTGTGGATGTGATTTTGTTCGGACAAAGGTGTAACTGCAGGTGCCGTGAGTTAAGATGAGATCAA
CCTGGATTAGGGCGGGCCTGGCATCCTTGTAAGAGGTGGGAATCTAGACACAGACACGCAGGGGCGAAGG
CCCTGTGAGATGGAGGCAGAGATGGAGTGTCAGATCCACAAGCCAAAGAATCTCAGCGGTTGCCGGCGCT
CCCCAGGAGTGACAAGAGGCAAAGAAGGATCCTTTCCTTAGAAGAGAGTATGGCCCTGCTGACACCTTGA
GTTTGGACTCCTGGCCCCCAGAACTGGACGAGAGTAAGCTTCTGTTGTTTCAAGCCACTCAGCGTGTGGT
ACTTTGTTATGGCTTCTTGTTAAGAAAGCTGACAAGCGAGCTCCAATCACTTATGAGCAGGATGGCCTGG
CATCAGTCACTGGTCTCTCCAGGCCTTGCTGAGCATCCTTGTAGTGAGTGTGACACTAGTTCAGAGGGTG

CTGTGAGGATGGGATGGAATGATGCCTCCAAGGCTAAAACGGTTCAGTAAAGACAGTGGATTTGGCTCTG
GGATTCCTGGGTCAGGCAGATCTGCTGGAGAAGGGATAGGCCGCCACTCCAGTATTCTTGCGCTTCCCT
TGTGGCTCAGCTGGCAAAGAATCCGCCTGCAATGCAGGAGACCTGGGTTCGATCCCTGGGTTGGGAAGAC
CCCCTTGAAAAGGGAAAGTCTACCCACTCCCGTGTTCCGGCCTGGAGAATTCCATGGACTGTATAGTCC
ATGCGATCACAAAGAGTCAGACAAAACTGAGTGACTTTCACTGTCATGTCTAAATACAGCGATTCTTCAG
AGCTGGGCTTCCTAGTTCCTTCTGGAAGGACTGAGAGCCCCGTGTTATTTTTTATGGTTAATTTTGGAA
ATTCCAAGTTAACAGTTAGGGTACAAGGTGATCACATTTATGTAATCTTTATCAGAAGTCTCACAAGTTG
TATATTCAACATTTTGAAGAAAAAAAAAAGCAACTCTAGTTTTTACTCTGTACATCCAGATTACATGCT
TGGACCAACTGCACGAACAGTTAGTTTATACCAGATGCCAGCTGACTGCCTGATGCCAACTGGAAATAAA

GTTATGTGCGTATGCACACTCATATAAACTGATCGCTAACCTTGTATACAAAACCATATGTGTCTATCTC
CCTATGCATATTGGATGCTTACATATTCATAACAGATGCGTACATATATCTGCTCAAGAAATCCATCCAG
CAAATATTTATTCAGTGTTCACCTTGTGCAGGGTGTGCAGATGGGGTGTGCAGATAGGAGAAGGAAT
ACGTGTTCATACATAAATAATGTATACACGTAGCTGATTAGACCAGAAGCCAACCAAATATCTAGATGCC
AGTGTGGGAGCATGGCTGTTGGAAAGCCATATACTTCAAATTCCCTGGCTGGGAACAGGCCGGAGCCTGG
AGGTGAGCTGAGCCCCCAAATGAGAGAGGGGTCAGCACAGGGCAGACAGCTGGGGCGGGAGGAAGGCCTT
GGGCCCCCTCTAATGCCATCGGGGTGAGGCTTGGGGCTCCCAGCCCCTTCTGGTCAGTTGTCCCCAAGCT
GTCACTCTCTCTGTCTTTGTGGGGACTTGGAACGGAAACCCATTTTGAGAAGAGTAGCATCTAGGGGCAC
GGCGACCTGTTCCTGTTCTCTCCCACTCTGAGCATCCTCAGAGTGGGATGTATCCTCTCTGGATACAGGG
GCGCTGGATGCTTTGCTGGCCCCAGCACCACTTTGGAGACCTGCTGTGTGCTTCTCAATGCCACCCCCTC
CCTGATGGCACTTCTCTCCGTGAAGGGGCCAGGCCGGGGAAGGGCTGCTCTGCTGTCACGCTTCCTTTCG
```

TABLE 3A-continued

SEQ ID NOs: 1-2, BOVINE EXT2 AND ALX4 GENES

```
TAACTGAAGTGATACAATCTCCGCCTGCCCCGCCTGCTGGACTCCAAGGGTGCTGTTGGGACATGGCTGC
TCTTCCTCCACAGCCCAGCCCAGAGTCTGCTTCCTAGGAGGCCCTTCGTAAAATCTGGGGCACTCAGGGG
TTTAGCCAGGTGAAGGGGTGTGTCCAGGGCCGCCAGGCAGTGGAGGGAGGCTTATGCAAACACGCCCTGA
CTCAGCAGACTCCCTGCTCCAGAAATGCTGCAGCTCACCCACCCGCCTTGGACCAGGACCTCCCTGTGCCA
CGGACCTTGTCTGACCCTGCCAACCGGAGAGGGGAATGCCTGGGGTGGCCCTTGTATGGCACTTTCATAT
CTGAATTTCCAGTAACCAGCATGCCAACCTGCATACAGTAGGCAATCAGCTGGTGTTTGCTGAAAGAATT
AATGACTTCAAGGCCTGGGTATACAGCTCTGGGCCCTCGGGACTGTGAGGGCTCAGAGGAGCAGTGTTTT
TGCCCTGGTAGACGGCGAATTCTCTGCTAAGACCCTAAAGCCAATGTGGCGTCTTAGGGGAGAGGTGGGT
GGGCAGTCAGCATGGGGCAGGAATTGGCTGCTGGGTTAACAGAAAATGAACGAGATTTGCCTGTGTCAGA
GGGGCTCTGGTCAAGGACACTTCCTGTAATAAGTAAACATTCCTGAAAGGGTGAGAGCTTAAACACAGTA

AGTGATGCTAAATGGAGGAGAGCAGTTCAAGGAGGGAGATTCTTTCCAGGTGAGGCTTGGAAGGGGAGGG
AAGGAAACGATCTTTCTTTAAGCTCCTGTGAAGACTGATGCTAGAGACTGCACACATGTTCTTCCTGGAA
AAGCAGGTCACTGGAACGATCTCTGTTTAACAGATGAGGACACTGAGGTTCAGAGAGGTAAAGCACCTCG
CTCAAGGTCACACAGCCAGGATGTGGCAACATCGGTCCGACTCAACTCCTGTACTGGTCTGGCTGCTGAA
TCTAGGTAATAGCTATGTATTGCCTGCTTGACCTTCCCTTTTTGTTCTTTTTCTGTGAGGATTTAGTTAT
TCTCTAGAGCAAAAAGAATATGTTTGGGGGTATTCAAGCTTTGGGGATTTTTTTTTCCGTCCTCTGGTA
TATTGTTAGGAGGGCTTCCGTGGTGACTTGGTGGTAAAGAATCTGCTTGCAATGCAGGAGACTTGGATTC
AATCCTTGGGTGGGGAAGATCCCCTGGAAAAAGAAATGGCAACCTACTCTAGTATTCTTACCTGGAGAAT
CCCATGGATAGAGGAGCCTGGTGTGCTACAGTCCATGGGGTAGCAAAGAGTTAGACATGACTGAGCGATC
AAACAACAACCGCAACAAATACCGTTTGGAAGGGTATCAGTTCTGGCCTCTTCCAAAGGCTCCATCAAAG

ATAACGTGGGAGGCTTTCCTGGTGGCTCAGTGGTAAGGAATCCTTCTGCTAGTGCAGGAGACACGGGTTC
AATCCCTGATCCAGGAAAGTCCTGTGAGCCACGACTATTGAGTCTGTGCTCTAGAGCCCCGGAGCTGCAG
CTACTGACTCCGTGCACTGCAGGTATTGAAGTCCACGCCCCTCGAGCCCGAGCTCCACAGCAGGAGAAGC
CATCTCAATGAGAAGCCTGTACATGGCGACTAGAGAGTAGCCCCTGCTCCTCGCAACTGGAGAACAAGCC
CTCGCAGCAACTAAGACCCAGCGAAGGAAAAATAAATAAATAAATGAAATTATTAAAAAAAAAAAGACA
ACATGGGCTTCCTGCAAGGTGCCCCTCCACCATAAACCTATCCTTCCTGCTCCTTCAAGAGCGATCCCTG
GATGCTGTAGTGAGAAGGATGTGTTTTTGAGGGGGCCTCTTCCCAGGTGGTGCTAGAGGTAAAGAACCCA
CCTGCCAATGCAGGAGGCATAAGAGACGCCAGTTCGATCCCTGGGCCGGGAAGATCCCCTGGAGGAGGGC
ATGGCCACCCACTCCAGTATTTTTGCCTGGAGAATCCCGTGGACAGAGAAGCCTGGTGGGCTACACAATC
CATGAGGTCCCAAAGAGCCAGACACGACTAAAGCGACTTAGAACAGCACAGCTCATCCCTGTCAACTGGT

ATAAAAGCAAATTGTTTGCAAACTTAGATGCTGGAGAGATCAATGAAAGAACTAAAAGTGTTTCCGCGCT
GATCCCATAATCAACACACGTCTGGGGACTGATCCGACCGAGCCTGTGCTAGTGGCATGTGTTCGACTAT
CCCCAGGACGAGGCCCCTGCAGGTCACACCGGTGTCCCCTTCCCCCAGAATCCCAGGTAAGTGGCAGAGA
GCCTTGGCAGACAAACCTGGTCGAAAACACTTCCTGTAATAACTAAGCCAGTCTGTTTATCTAGCTTCTT
GGCTACTAAACAGGCATTGTGAGGGAGGGGGCCCTTCGTCACTAAATCCCCACGCCCCTTTGTAGCGAGT
GATGTCCTTTGTAAGTTGCTGGGTGTCCCTGAACAAGTTACTCCAGCCCTCTCTTCCTCATCTGTTTAAA
AGGGGATTATATTACCACTCCTACGTGCTGTGAAGTTTTAGCCCAAGCACTTAGCACAGAGCCGGGCAC
CTGGGAAGCTCTGAATGAACATTAGCTGTTAGGACCACAGTTAGCATCATCTGCCGGGCAGGGCTGATGG
AAGAGCTGGTGAGTGGAGGTGAGTGTCCCTGTGTGAGGGTGGGAGGGTGTGTGACCCCTGCCTCTGCT
CTGGGGACACTGAGGCCCTAGGGCAGACTCTGGAGGGATATGGATAAGTCTCCTGTCTTGCTTGGGCAGA

CTCTGGAGGCATACAGATGAGTCTCCCGTCTTTGCTCCAGCGAGGAGGAACTTTGTCCTCCCGCACAGGC
TGCCTCCTGCAGACTCTGTCCTCTGGACCCGCTGCCTGTCCCTTCCCTGGCGAGGGCGGGAGGAGGCCC
AGCCACGGGGCCCTGGCCCCCGGGCCGCTGGCCCAGCAGGCCAAGGACTCTGTGTCCTGGGAGGGGAGC
AGCCCTGCGCCGCAGCTGCTCCTCCTGGGAGGGGCTGGGGCAGCAATCTCATCTCTCAGCAGAGACCTCT
CAACCCAGGGGGCAGTGCCCCAGAAAGGGCACAACCCCGAGACCCGCTCAGAGCTGCTTCCTCCTCCTGT
TCATGTGTCCCAGAAACCTGAGAAAATGAGCCAAGTCCTGGGGAGAGGGGGCTCCAGCTGGGGGACCCGG
TCCTCCTTGACCCCCACTTACTGCCGCTTGGGGGTGGGGAGAGCGGTCGTCCGCCCTCCACCCTCCGGAG
GTCCCCTCCGCGTCCCGCCCTCCCTCTCAGGCCACGGGCCGGTTTTCCAGACTTCTCCCTTTCCCACACT
CTTTCCCCGAAGCCTCCTTCACACACCCAGTTCTTCTTAAAGGGGTTCTAAGAAGAACGAATTTCCTATG
AACAGAACAATGCCCTATTAATCTTACGAGGGATTTGAACTTGGCCACATTTCAGCTTTTGATTTAAATA

TCATTTTGGTAATGGGGGAGAAAAAAAAGAAGGCTGACTCTTGGACAGCCCGAGTTTCCAATACCTTCT
GAGCATGAGACGATTTCAAATATAAAATTAAATCCAACTCCCTTCTGCCTCCCCCCTCCCCCCACCGTCC
CCTTCCCCCGCTTTCACTCAGACAAAAAAGCTCACGTCCCACATACTTCATGGGGATATTTCAAGTTAAA
GTTTTGTTTACCTTATAGAAAAGTTAATTAGTTCCTTTTGATCTCACGGGGAAAACCACACAGGAAATTT
TTCTTCAGAAAGTGTACACACGAAGGCATGCTTTACCCTCATAACCAGAGATATTCATTAAAACAATTCG
TTTCGATTTTTAATTTAAAGAAAACATTTTACATTTTCCTGATTTATTATTAAGAGAGTAGTTGTCCCTG
GGGCAGAGCGTGAAGGGGGTCGGCTGAAGTGTTTTTGCTGTGCTGGCAGCCAGCATTGGGCAGTTTGTTT
TGCTACTTTGGATAACAAGAGACTTCTGCAGAGAGGCAAACCTTCAAACACGCCAGATTTCAGTCGCCAA
AATATTAAAAATCCAGGGTTTGGGAGATTGGACTGTATGGTTTAAATAAAGATATTTAAGTTCTGAAAT

ATAAATATTCGAGATCCTGAAAAAACATATCATTGCATTAAAATCTGAAACAGGCAATGGGTGAATCGAG
GGGAGAAAATGTTTACTTTTTTGAGGTTTATCTAATGAAATATAATAAATAGTACATCATGCTCTTTTTT
TTTTTTAACCCCTAGAGATATTTAAGCAATACCTGGATTTGTACAATAAGCTGCTTAGGAAAAGTCTAGA
AAGAGAAACGTTTGGATTTTCGAAATGCGATTTTCAACCTTAAGCACATTTTCCACATCTTGTATTGTTA
TGGGATGAGGGATGCAGAGGACCCTGTAAATTGTGGAACTCATTTCCAGCCCAGACCAATTGAAAAAGA
AATAGTATGGCTTCCCCGAGGTTGAAAGAACAAATTAAAAGATATTGCTGATGGAGCAGCCAAAAGCTGT
GGTCCCCATTACTGCAAGGAAAAAAATCTTAAATAGATATGGTATGGAGACAAAAAGCCTGTGGAAGAGATG
TTTTTTACTAAAGCAAAACCGCTAAAGCAAAACAGCTCTAAAGAGTGGTGTTGACATCAGTATACGATTTT

GAGGGTATTTTTGGGTGCGTATCCCTTTCCTGCCCCTGACACAAATATTTGGAGATTGGGACTGTCATTG
TTGATAAAAATTAAATTGATGCCGCATACAAAAGATATATAAAAACCATGTTAACATATGGGGCGACTTT
GATGATGTTCTGTACACAGCAAAAGTATAAAAATCTGATGACATTTTATTGTCACCAATTTGCTTTTTAA
TCTGTCCCAACCACTGCTTTTAAAAACAGAACTCTTAATATAGATTTCTTTATCAAAAGTTTGCACCTGA
AGATAAATTTTCTGATTTAAATGTATTCCACTCTCTATTTTTTATTTTTGTTTTTTGGTAAATGGTGAA
GGTGTGTGACAGTCCGTTTGTGAAGTTAGGGAAGAATGCATTTATTTTGAAGAGGGATTTAAAAATGCTG
GCTGTAGGAGCAGATTCCTACAAATGAAGCCAGTTCTTAAGGCAAGTTTCCAAAATCTTTCTGTTCAAAT
ACAGAGTCTGAAATCTTTTTAAAAAATTGTCCTTCTACAACACAATTAGTTTTATTTCCTGCCTAAGAT
ACCTTTGTATTTTCTTCTGAAGAAGGATTTACCTTTTTTTTTAGAGCTGGAAATATTCCCTTTTTTCTTCT
```

TABLE 3A-continued

SEQ ID NOs: 1-2, BOVINE EXT2 AND ALX4 GENES

```
TTTCCTGGAGGAAAATGGTTTAATGTAAAGTTTAAGGGAGGGAGAGAGATGTATGGAAATGAATGGAAAA
CAGAAGCTTCAAACGGCTACCCAATTCCCTCTTTGGATTTGCCAAATAACAACTCAAAAATCAGATACTT
CCCATAAGACCATTGATGGGAGACCTTCCCAATAAATATGCATCTATTCCTGTTTTCATCAAAACAAATA
ATTTTCTCTGCTGATTAGGGGCCCTTCCTTCTCCAGTACCCATCATTGGGAACTTTGAGATTTCACTAAA
CATATATACATATATATATATATATATATATATATATATATATAATTTTCCTTTCCGTGAATTTCTACGAAG
TTGGCTTTCTTTCTCCAGGAGGCTGGAGTAGAGTCGGGACCCTGGGTAGACACTTCATTGGTCTGAATGC
AAGAGGGAAAGGGGTGACACTCTAAAGGGAAAGCCACGACCCCAAAGGAGAAAGCACGGACAGATAAAAA
GAACAAGACAAGTAAATATTTTCCTAGCGCGTTTCCAAGTTAAAACCGATCAAGCTACCCGGTTAAAGAA
AGGCAAAAACAAAATTCGTCCCTACCTTTGTCAGATGCAAAGTAATGAGGGGTTGTTCCCAGAGTGGTTA
TGACCTACACAGAGCTTCTTACCTTAAATCTATACATTTTGAACAAAAACAGCTTGGAGCAATTCTCTCC

AAACAACCCCAAATGTTAACCATTCCAACTCAAGATCGGGTTTCTCCTTCAGCCTAGACGGTGATATCAG
TTGGGTTTTCTTTTCTTTTCTTTCTTTCTTTCTTTTTTTTAAAATATGTATTCTTATGTTTCCAATCCT
CAAACATACTTTTTTCATCTTTGTTAAGGCTCCTTCTGGCTGCTGGATGGGCTGGGAGTCGCAGGAGTCC
TTCTCTTCGGGACAATTAGTCTCTCACTTGATCACTTGAAAACGGAATGATTGTCGTGGTCACTGAGTG
GGGCTCTCTCCCTCTTTCCTCTAATATTGTTGCAGATACGTAAAGTTTACTGCGTGCTGTAAATATGTCA
GCTTTTGCCAGGGAGTTTGCTAATAAAGAACCTAGAGGTATTATTGATGGAAAAGATAATGTTTTCAATA
AGACTGGCCCGGGCTAAAGTCTGAGACATTCCACACCCAGCCAAGCATAGGCGTTTGAGACGCCGACCCC
CTGGCCGAGGTGCCGGGCTGGTTTACCGGCCACAGGCCGGCCGTGCTGCCTGCTTCTCCGTGGTCCCCGT
GACTGTTTATTCAGCGCAGTTTTAAACGCCCGACTGGTTTTAGGAGCTCTGTCCTTTCTGAAAAAATGG

CCTTCCTGACCGTCAGGAATAGGTGAACTTATCAGAGAATCATGAGATACGCTTGCCCAGATTGATCTCT
TTGGGGATTTATCAGCTCACCCATGCTGAGAGCAGAGGAAAAAAAAGAAGTCCACCCTTTTCTGTTTGAT
GCTCACTCACATTTTCATTTGTCGTGACAACTTCTGAGTGTAAATTGGATTCATTTTTTTTCCTGGATGT
TCGTTTGTGGAGGATTGTTGGCTTCCCTCTCTTAAAGGAAAAAAAAAAAAGAAATCGCAGAAAGCTTGG
CGTCCGTCTGCCCCACGGCCCTGGCTCCCCTGATTTCAGTCTCCTGGTCTCGGTGTTTTGTCACATCACCC
ACATGACAGTTTCATCTGGTGCTAATGTGGCCGTCACATGGGTTGGTCGTCAGAATTCCATGCTCATTTA
CCATTAATCAAATGCATCATTATGAATTGTGTATGCATTTTAGGGCAGACCCAAACCCGGCTTGATAGG
AAAGTGTTTTTGTTTTTTCCACTTAACGTTCGGCAACGGCAGATGAATGGCAAGGCCAAAGTGACACTC
TTTGTGTTTGCTTAGCCCAGAAATCAACAACCCTAAATTACAGGTTGGTAAGCTATGTCCAGGTAGCATT

AGCTTCTCTGGGTGATTATTATTACTTAAGGGCGGCCACAGTCAGCGCCAGCAAACTGAAGCTGGCCAGA
GGGAGGGCAGACAAGGCGAGCAGAGAGCAGGGTCTCGGCTTCCAAGGGGCCCGGTGCCTCCTTTTGACTG
GGGGGATTTTAGTCTTAGATTGCATTTTCCTGGAAATAGGGACTGGCCCTTCTAATTTGGAAGAATGTGA
GGTATTTGCAGGGCGAGTTCGGATGAGTGGGGGTGGGACGGGTTACCACTGGATGCTTTTGGCAATTTG
TGCACTCTACTTCCCCAGGACTCACTTGCCAGCTTGGCCTCTGTGGGAACATTCCAAGTTCTGGAACCTT
CCTTGGAAGGCCTGACTCCTGTTGGTTGGTGGGGACCTGGCGTCCTGGGCGTATAAAGACGGTTTTCA
TTGGGAGTTTTCAGTGATTAAAGTCTTTCCTGAGGACGGGGGACTGTGTTTCAGGTAAAAACCCTTTCCT
GAGCTGTCACAATAGTTCTGGGAATGGGGGGCCTGGTGCCTGAGACCGGAGGGCCCAACCTGACCCCT
CTCCCCCAGCGAGCCTTGGGAGACAGATCTGACCTGGGCTTAGCTCCCATTCGTTGTCTAACTGCCAGCC
GTCCCAGGCCAGATCGGGAACAGGGAAGGAGGTTGGTCCCGAAAAGCGATCAGAGACGGGGTACAGGGGC

TGCGGTGCTGGCTTATTTGATGGCGCAATTTTTTTTTTCCTTCCCAGCAGACAGCTGGGCCTGGTTGGTG
GCTTGGAGGCCTCTCCCAGGGAAGCGGCGGAGCACTCTTGCCCCCAGGAATGTCTCTTATTTGTGAGGCT
GTCCTGGGCTACTTGGGAGCTCAGGATGTTAGGAAAGCCTGTTAAAAGATAAATACCTTTTCAGAATAAG
CTGCTCAGGATCCACCTTAGCCTGCGGTGGGGAGGCTCCAGGAGAGGCAGAGAGTGCAGTGCTGGGGGG
CCAGGGTCTCTCATGAGGCCTCCTGGGCTGGCTTTGGGAATGTTCCTCCCTTCAAAGCCCCACTTCAGCC
TGGAAGGGCTGAGCCGCTTCCCCAGAGGGCAGTCCAGGGCCGCGGCACACAGACTTCAGCCCTTCTCCCC
TCTTCTCCTGGTCAGCAGGGAGAGATGGGGCTCCCGAGAGCTGGGTCGGGTGGCAGCTGCTGGCAGAGGC
CTCAGAGGTGGGCCCTATGCATAGGGCTGGGGCCAGGGGAGTGTGTGAGTGTGGGTGAAGGGGTGTGTGA
GGGGCAGGTGTGACCTCAGGAAGGAGGGCTACTGGGGTCGCATTGCTTCTCCTCCCAGCCCGTGACCTTC
GGGGCCTGGAACCAGGCAGTAGCATCCAGCCTCTGAGCCCAGGCTCTGAGCCCAGGCTCCGAGCGGCTTT

GAAGAGGCCTGTGGGTCAGCGCTGAGGGTGCTGTTTTTTGAGGCCTTAGGCTCCACTAGCCGGGTCTGTG
TCTTCATCCCAGAATGAGCTGTGGCTTCACCAAGGGGCTCAGAACGGTTTTCCACTCATTCAAGGTCACC
TCAAGCCCAGGGCTTTCTCATCTGAATCTTGAACCCTAGCTCTGTGAAGGATGTCCTGAGCTGTCACCCT
GCTGACAAAAATGCTGGGCCCTGAGACCCTGAAATAGAGCTTCTCAGACAAAGATTTGAGCAACAGTCTA
ACTGAACTCCTTATGAAAATACAGAGGTCTGGTGCCAGGCCGAGTGGGCGGCCTTGGGAGTTTAAGGAAA
TAGGTCTGGTTCCATGGACTTTTTTTTTTAAATTAGGGTTTGGGTCATTTTGGTTTGAAGTTCAACAAA
TCAGCATGGCTTGTCTGGCTTTTTATCTGCCACCTGGTTTGGTTCAAGGACAGAGAAACGTTTCTGTTTA
TAAAACATGTCAGACGTGGCTGGCCAATGCTGGTGTCATTTCTCCTGGCTTCTGCTCCTTTTCAAGGGA
GCTGGTAAAGCTGATCTTCTCCACCTGGGCTGGTCATTTAGCCGGGCCCGGCTGAGGCCCCTGTGTAAT
GGACAACTGCAGCCGGCTGGTAGAGGTGATGGGTGTGTGCGTGCGTACTCAGTTGTGCCCGACTCTTTGT

GACCCCCTGCACTGTAGCCTGCCAGGCCCCTCTGTCCATGGGGTTTTCCAGGCAAGAATACTCGAGTGGG
TTGCCAGTCCCTTCTCCAGGGGATCTTCCTGACCCAGGGATTGCACCCGTGCTCCTATGTCTCCTGCAAC
GGCAGACAGATTCTTTACCACTGATCCACCTGGTAGTATGTAAGATAGATATTATTTGATGTGGAGAGAT
GTTCACTGCAAGCACTAATATAGACTCATTTTTGTAACTGCAAAATAACACATAAATCTGGTAAGAAT
GAAAGCTGTACAGAAGTATTTTTAAAGTAAATGAAATACCTTAATATTTGTACAGTGCTTAGAAGAACAG
TACCTGGCATGTAATAAACACTAGACACACTTAATAAATAAGAGTATATGGAACTAGAAGTCATTTTTCC
TCCCAATTTGGATCTGTAGTCTCCCTCTCCAGAAGCAACCAAATTAATATTTTCTTGCATATTCTTCCAG
AAATTTTATGTGCTTATGAAAGCGTGTCAGCACACATAATTTTACATCGTAAAGAGAAAAGGGTAGG
TTACCAAGTAGCTTTAAAGAGCATAATTCTATTTTTAAAACAAACAAACAAACATGCATAGAAAATAATC
TGGAATCAGATATATCAATCAGGTAAAACTATGATTATCTTCAAAAGGTGGGATCATGGGTGGATTTTCT

TTGTCTTTCTGTTCACTCCTTCTATAATTCTAAAACTTGATTAGAGAAAAACGCATATGAAGAAACACAT
GCATGGATGGGCACATGGACCCTGGTCCTCTTATATAAACGTGTTTAAGAGGGCTGACATCCATGCCAGG
CCCTGGGATCCCATCACAGAACCAGCCTGGACAACCTCCCCTTTGCTCCCTGGGGCCAGCTGCTCTGTTG
CTGACACTGAACCCTGATCTGCGTTTGGCTTTGCCCAGTGGCTCCAGGACTCTCCTGGGGACCCCTGGAC
TGATGATCGAATGAGGATAAGATTTGAGGGACTGTCCAACACATGCATCCCCCTTTAACTGTTTGTTTTG
CTGCTTCTATATCCCTCTGCCAGTTGTGGGGAAGACCCCTTCCTTCCCAGCCTGGGCCTGGGGT
GGCATGCCTAGTTGACCCTGATCTCCCATCAAGGAACAAAGGTGAGCCCCGTTTGAACTTACATGTCCAT
CCTGAGCCCCCGAGTCTCATGGCCTGGGTCCTTTGGACCTATCAGAAGCCCCCTCTGATGTGCCTCTGAG
ATGCAGACAGGCAGGCCGGTGCAGCACTCCAGCTTCCCCACCTGACTTCCTAGAAGCCAGTCTGGTCCCT
GTAATGACCAGTGGAGCAGGGGTCTCGGCCGGTGGTGGTCCTGAGTAGGCACAGTGGACTCCTCTTGACTC
```

TABLE 3A-continued

SEQ ID NOs: 1-2, BOVINE EXT2 AND ALX4 GENES

```
TGTAGACAAGAATGGGGAATCAAACAGACCTGGGCCATGAACCAGCTGCTGTTGCTGTAGGACCTGGGGC
AGATCAGTTCACCTTTCTGAGCCTCAGTTTCCTCATCTCCAAAATGGGTGCACTGAGGGTACCTTCCTCC
TGGGGCTCATATATCTTCATTCTCAATTCATTCCTTTAACACAGATTTTTCTGAGAGCCTTGTGTGCCAA
GCTCTTTACTGGACTCACAAAGGCTCACATATAAGCTTCTACATAAGATACCAGAGAGAACAACAGCAAC
AAAAATGTTTTCCAGAGGTAAAAGCATGGGGAAAGAAGGAGAGGCTTCTTGAAGGATGCATAGGAGTTCT
GACACGGTGAGGGTTGCAGTTGGGAAAGAAAGATGAGGGGTTTCCACAGTCCTTGCATGTGTATGATTTT
GCATATTTCTCACAATACTCTTAGAATTTGAATTTTCTGAGGGTAGGCTGTCATTGTTGCTGGTTGCTAA
GTCTTATCTGATTCTTTTGCGACCTCCGTGGACCTCCATGGCCCACCAGCCTCCTCTGTCCGTGGGACTT
CCTGAGCAAGAATGCGAATGCTGGAGTGAGTTGCCATTTCCTTCTCCAAGAGATCTTCCTAACCCAGGGA

TCAAACCCATATCTCCTGTGTTTGCAGGTGGATCCTTTACCATCTGAGCCACCTAGAAAACTTAGACTGG
ATTCAGCTAGATTGAATCGTAAGCAGAGGGTAATGTGCTAGACAAAACCAAATAATATCGAAGAGTCCAA
TCTCCTGTCTCCTCTGCTCTCATCCTGGGGAATTGGTTGCCTCTTCATTTTTGAGTCAGGGAGAGGTTTC
CCCAGGAGACCTATCTTCCATTTTCCTATTGCTGTTGTTCTCAGGGCTGGAAAGAATAAGGTCTTTAGAC
AGGCTGGCCTCCATCCCTGACTCTGTCACATGTGGGCTGGAGGTCTCCAGCAAGCCTCAGTTTCCTCATC
AGCAAAATGGGCACAGTGGCAATGTCCACCTTGCCAAACTGCTGTGAGACTTCAGATGGGGCAAAGCACC
CACTTAATGCTGGGCACATGCCAGGATGCCTGAGACAGGGCTGAGTCCTCTGCCAGCAGGGCCCAGTGTC
TGGACTCAAGGCATCCTTCTCTTTATTACAAAGCCACACATTGAGTCTGAGCTCATCTGGGGCCCATGTG
GACCCCGGGGAGTCCAGAGATGTTTCATCCCTCTGTTTGGCTTCCATTTTTCCCCACCCTGGCTGAATGCC

TCCAGCCACCTGCCACACCTCCAGATCCCCATCAGGCAGAGAAATTGGTGACCCGTAAGAGCAGAGGGAG
AAGGAAGCTGTGAGGTAGAAACCAGAAGAGATGTGTTTGCAGATGTGAGTCGCAGGGGTGATTAGGACCC
CAGGCACCGTTTCTGCAGGATGGGACCTTCTGGGCGACAGAGCCGACCGTGGAATCTACCCTCCTGGTCC
CAACAGTTCCCAAATCGAGAAGGCAAAGAAGGATTGGCTTTTCCCCCTCCGCCCCTCCCTCCTCTCATCT
GTAAAATTGAGACATTACAGTTCCAAAATGGGCTTTGAGCCTGTAGAAATTAATCTGGTCTGGCAGGAGG
TCTACAAATAAACATATTGTTTCGATTGGTGTTGACATTTGAATTGTGAGAAGGTTTGAAAATGTAACTG
TAGTTGGGATTTTCCAGCCCATCTAAGTTTTTTTCCATGGAGGGGCTCAGTGAATGCCAACTGGGAACCC
AGCAACTGCCCTCTTTAAAAGGACTTGGGCGCTGGGCGAGGCTGCGGATGTCAGGGCTCAGAGCCTGTGC
TGAGGCGGCAGCCCTTTTGTTGGGGGGTGGGCAAGGATTTCAGGAGGCCCAGTGCCTCTGGGCATCTGGG
GCAACCAGCCACTCCAGGAGTGACCTGAAACGTTTAGAGCAACTCCTGTGTGCCCGGAACCTTGTATGTG

AAACCTCACTCAAGTCCTCACACCAGTGCTCTCTGTTGTCCAGTTGCTAAATTGTGTCCGACTCTTTGTG
ACCCCATATACTGTAGCACCAGGCTTCCCAGTTCTTCACCAGCTTCTGGAGTTTGCTCAAACTCATGTCT
ATTGAGTCAGTGATGCCACCCAACCCCCTTATCCTCTGTCGTTCCCTTCTCCTCCTGCCCTCAATCTTTC
CCAGCATCAGGGTCTTTTCCAATGAGTCGGCTGGTCTCATCAGATAGTCAAAGGATTGGGGCTTCAGCTT
CAGCATCAGTCGTTCCAATGAATATTCAGGGTTGGTTTTCTTTAGGATCGACTGGTTTGGTCTCCTTGCA
GTCCAAAGGATTCTAAAGAGTCTTCTCCAGCACCACAGTTGGAAAGCACCAGTTTTTAGTGGTCAGCCTT
CTTTGTGGCCCAACTCTTACATCTGTACATGGCTACTGGGAAAACCATAGCTTTGACTATATGGATCTTT
GTCAGCAAAGTGATGTCTTTCTTTTTTAACACGCGTGTCTAGGCTCTTTATCATAGCTTTCCTTCCAAGAAGCA
AGTGTCTTTTAATTGCTCTTATTATCCCCATTTTACAGACTGGAACACTGAGGAAAAGAGAGGTTAATTT

GCTAAAACCACATAGGAGTAAAATGCAGACTTAGACACAGCCTTCTCTGGCTCTTGGTGTCCTGCCCTAT
ACAATCTACTTTATGCCAGAATTTTCCAGAATGTTGTCTCACCAAGAGAAAGGCTCATTGTCCCAGAAAA
AAGACTGAGCCTTGACTGAGGTGATCTGGTTGTTGAGAACACCAGCTCCATTCTATGTCTGGAACCCTTG
AGGGATTTAAGCCCCACCCCCTTATCTTCCTGCCACCAAGGAAGGGGTCTGTCCTTCTCCCTCCCTCCCCA
CCTCCACGCTCTGGATCTCATCCTTCAGTGGCCTCTGAGTCCCCACTGCCTGCCCATCCCACCTGGCTCC    NW_250796_R1
AGCCTCCCCCCACCGGCCCCACAGGGATGCAGCTAGTTCCCTGTGGGAGGGGCAGCTCTGAGACAGCCCC
CTACTCAGGGGTGAGGTGCACATGGCTTTCAACCACGAACTCAGAGTGCTGGCCGGTTAGGGCAGACACC
TCGTTTTGGGGAAAGGCTTGGTGATTTCTGTACCTGGCAACTTCTGTGTGTGTCAGGCATCATCTCCTGG
CCCCTTAGCTCCAGAGATGCGAAGATCCATCTTCAGGGTCTT<u>AGTCACCTGCTACCATCTCC</u>CTTCTGC    DEL3_308, NW_250796_F1
GCTTCCACACCTACCCCCACAGAGCTGAGCATGGCCGGGAAACACACATGGGAACTATGCTGCCTGCTCC

CCCTTTATCCTCATCATTGGGAGCATCTAAGGGGCCCATCTGGAGAAGCCTTACAAATAGCTGTGAAAAG
AAGAGAAGTGAAAAGCAAAGGAGAAAAGGAAAGATACAAGCATCTGAATGCAGAATTCCAAAGAATAGCA
AGGAGAGATAAGAAAAGCCTTCCTCAGTGATCAATGCAAAGAAATAGAGGAAAATAACAGAATGGGAAAGA
CTAGAGATCTCTTCAAGAAAATTAGAGATACCAAGGGAACTTTTCATACAAAGATGGGCTCGATAAAGGA
CAGAAATGGTATGACCTAACAGAAGCAGAAGATATTAAGAAGAGGTGGCAAGAATACACAGAAGAACTG
TAAAAAGATCTCCACGACCAAAATAATCACAATGGTGTGATCACTCGCCTAGAGCCAGACATCCTGGAAT
GTGAAGTCAAGTGGGCCTTTGAAATCATCCCTACGAACAAAGCTAGTGAGGTGATGGAATTCCAGTTGA
GCTATTTCAAATCCTGAAAGATGATGCTGTGAAAGTGCCGCACTCAATGTGCCAGCAAATTTGGAAAACT
CAGTAGTGGTCACAGGACTGGAAAAGGTCAGTTTTCATTCCAATCCCAAAGAAAGGCAATGCCAAAGAAT

GCTCAAACTACCGCACAATTGCACTCATCTCACACACTAGTAAAGTAATGCTCAAAATTCTCCAAGCCAG
GCTTCAGCAATACGTGAACTGTGAACTTCCAGATGTTCAAGCTGGTTTTAGAAAAGGCAGAGGAACCAGA
GATAGAAAGGCAGAGGAACCAGAGATCAAATTGCCAACATCCGCTGGATCATGGAAAAAGCAAGAGAGT
TCCAGAAAACGTCTGTTTCTGCTTTATTGACTATGCCAAAGCCTTTGACTGTGTGGATCACAATAAACT
GTGGAAAATTCTTTAAGAGATGGGAATACCAGACCACCTGACCTGCCTCTTGAGAAACCTATATGCAGGT
CAGGAAGCAACAGTTAGAACTGGAAATGGAACAACAGACTGGTTCCAAATAGGAAAAGGAGTACGTCAAG
GCTGTATATTGTCACCCTGCTTATTTAACTTATATGCAGGGTACATCACGAGAAACGCTGGGCTGGAAGA
AGCACAAGCTGGAATCAAGATTGCCGGGAGAAATATCAGTAACCTCAGATATGCAGATGACATCATCCTT

ATGGCAGAAAGTGAAGAGGAACTCAAAAGCCTCTTGATGAAAGTGAAAGAGGAGAGTGAAAAGTTGGCT
TAAAGCTCAACATTCAGAAAACGAAGATCATGGCACCTGGTCCCATCACTTCATGGGAAATAGATGGGGA
AACAGTGGAAACAGTGTCAGACTTTATTTATTTTTTGGCTCCAAAATCACTGCAGATGGTGATTGCAGAC
ATGAAATTCAAAGATGCTTACTCCATGGAAGGAAAGTTATAACCAACCTAGACAGCATATTCAAAGCAG
AGACATTACTTTGCCAACAAAGGTCCATCTAGTCAAGGCTATGGTTTTTCCAGTGGTCATGTATGGATGT
GAGAGTTGGACTGTGAAGAAAGCTGAGCGCCAAAGAACTGATGCTTTTGAACTGTGGTGTTGGAGAAGAC
TCTTGAGAGTCCCCTTGGACTGCAAGGAGATCCAACCAGTCCATTCTAAAGGAGATCAGCCCTGGGTGTTC
TTTGGAAGGAATGATGCTACAGCTGAAACTCCAGTACTTTGGCCACCTCATGCGAAGAGTTGACTCATTG
GAAAAGACTCTGATGCTGGGAGGGATTGGGGGCAGGAAGAGAAGGGGACGACAGAGGAGAGATGGCTGG
ATGGCATCACCGACTCAATGGACATGAGTTTGAGTGAACTCGGGGGGCTGGTGATGGACCAGGGAGGCCT
```

TABLE 3A-continued

SEQ ID NOs: 1-2, BOVINE EXT2 AND ALX4 GENES

| | |
|---|---|
| GACGTGCTGTGATTCATGGAGTCACAAAGAGTCGGACACAACTAAGCGACTGAACCGAACTGAACTGACA | TH_BIG_895/DEL3_2389 |
| CTTGCTCCCCCACTGCCTGAGTCCTGTCCTCTCCTATCTCCCCAACAACTATTTACGCAGGGGTCCAAAT | |
| TAGGCCAGATGCGGGAGGAAGGAGTCCTCAAGGGCAGGACCTCTATGCCACCTAGGATGAAGGCTCCCCA | BREAKPOINT B, DEL3_2532C |
| CGCCCATACCTCCCATCCCTTTGATGCCTGGAGGGACAGGAAGCAGGGTGGCAAGATGGTGCCTCTGGTC | |
| TAGTCCACACCCCACACCCCTGGTTTGGTGGTGAGGTGGCCCCATGCCTGACCAGGAAGATGAGTCCTTG | DEL3_2671 |
| GCCACAGACTGGCCTCGCTGCATCCTCTGCTCCCTACCTCTCCTCCTGAGGTCCCTGGGGGTGGGGGGAA | |
| TTGGTGGCCTCCTAGGAAAGAACCCACTTCATCTGTACTACAGATACCACCCCCGACCCTGAGACCACGA | TH_BIGBREAK_R |
| GAGGCCTTGTCTTTGCACCTTAACACACCTCGTCTTTGCTCCTCTGTCTGCCCTGCCCCCAGCCTCCATT | |
| GGTTTGACTCCTCAGTGCCTTCCTCCTCATATTCAAAAGCTCGAAACCATGACCGAAAGTTTGGGGACAC | DEL3_2952C |
| TGGGTTTGTCCTGACACATCTGGGAGCACATGTTCAGGCTTGGATCCGTCTGTCTGGATGTTTTCCGTTT | |
| GTTGGCTGGTTTTGCCTGCAAGAGGTGTGAACCTCTGATTGGCTTTGAGGTTCTGGAAATCAGGAAGGTT | |
| TGTGTTCATTTCAAAGTTCAGAAAAATCACTGTGGTTTTGGGTCACGGTTGGGTTTGCCTGCTTGATGGC | |
| | |
| AGCGGTGGTCTGGGGGGTATCTGAGCTAGGTCTCTGTGGGGTCCCCATGGGGTCTGAGTGTGAGACGCTC | |
| AGGGGGTGGCCCTCTGGGTGGGGCTGATCCTGGACTCAGTGATGGGGTGAGTGGCCAAGGCCGGAGGCAG | DEL3_3269 |
| GGGTAGGGCGCTGTGCTCGCTTAATGAGGTCTGGATGCTCTGGCTTTCCAGCTATGGTTTAAAATCCTCA | |
| GTGCCACTGTCAGCCTAGTGGCCTTGGATTTTGGTCTGTAAATGCCAATATTGGCCTTGACTTACTGACT | |
| TCCTCAACTTTCTGGGCACTGACTTAATCCTCACTGCTGCTGTGGTATGGCATGATAGCACTGTCCTCAT | |
| TTTATAGATGGGAAAATGGAGGCTCAGAGAGGTCAATAACCTGCCCAAGATCACACAGCGTATAGTGGCA | |
| GAGCTGGGACACAAAGCCAGGTCTCTGGCCCATGGTGGACTGTCTGTTCTGCCCCAGACACAGTGCACA | DEL3_3681C |
| GATTGGAACGAGGGAGAGCTGGTGTCCAGAGCTGCTCTCCCTTCAAACTTACTACCAGCACACCTGGATG | |
| TGATTTTTCGTGGACACAGAGAGGTGGTTTGTGGTCAAAGCGTGATGAGAGGGCGGGGCTCAGAGTCTGA | |
| GGGCCCCAGACACGGTGGTGTGAGCAGGCAGTCAGGGGTCTTCTCTGGGGTCTGCCGATGACGGGGCTGC | |
| | |
| TCCTCACTTTTCTGAACCCCAGGTTCCTCCTGCCGCTTCCTAAGGCGGTTCTGAGGCTGCATGGGGATAA | |
| TGTTGATAGAAACTCACAGAGGAGGTCAGAACATATCCGATTTCTGACTCTGCAAAGACGGCTGTGCC | |
| TCGTTAGTCATGTTCTTCCCAAGTTAGCGCAATGCTTGGCCCTGCGCTCGCTAGTAAGCCCTCTTGAAG | DEL3_4068 |
| CCACGTGGGGTCTGGCCTCACAGTCACCGCTGTCAGTTTTAGAGATAAGTCTGTTTCCCTGACCGGCACT | |
| CTGGGTTGGAGTCCCGGATGGCCCCGACTTGTTCTGGAAGGAGCCCCACTGTCTGGGCACAGCAGTCTTC | |
| CTGCAACAGACACGAGCCTTTGGTTGCCTCCCAGGGGTGTTTCCCCTGCCTGCTAAGGCCTGTCACCTCC | |
| TGCCTCTGAACTGACTCTATGCCTTTCCTTCTTCCCAGGGCTGGAGGAGCCTGACTTCCCTCCCCTGTCC | |
| AAGGAGTTCCCACAGTCTTTGGGTTTTCAATTGGAACAATGTGCTAGAGCTTGAGGTGCCTTGAAATTTA | DEL3_4428C |
| AAACAGCTACAGTTTAAAATCCTCAGTGCCAAGGTCCCTGTGTCAGCCTAGTAGCCTTGAATTTGGGTTT | |
| | |
| GTAAATAGCAATATTGGCCTCAACTTACTGACTTAACTTTCTATTCTAGGCTCCTAGTTAATCCTCACGG | |
| CTGCCTCGGTGGGTGGTGTTATAGCATTGTCCCCATTTTATAGATGAGTTTGAAGAGGTCCAGAGAGGTC | |
| AGTAATGTACCCAAGGTCACACAGCTTGCCATGGCAGGGCTGGGACACAAAACCGGCTCTCTGGCCCTGT | |
| GGCCAGCCATCTCTTCTGCCCCAAACACAGCACACAGATCGGAATAATGTGAAGCTGGTGTCCAGCGGAC | NW_197235_R1 |
| CCCTCTGCCTCTGACTTGGTCGGTGACTCAGAGTCTCCCCGGATCCCTTCCCCATCTGGAACAGGGAAGG | |
| CGAGGAATGTGCCCAGCCTTGGGAGACATGAATGGCTGGCTGCTTCGTCAGGCCCGTGGATAGCATCTCT | |
| TTCAGAAGGTGTGACAGTCATGAAAGGTGGCCTGTTCTAAACAGCACTGCCCAGGGCTGTGGCGGGGCT | |
| GCCTTCCCCACAACTGCATGCTGATTAGCTGGTCATGGCCCCCCTCACTCCCCACCCCGCCCAGATCTGTT | NW_197235_F1 |
| CTGCCACCAAAACCACGAGTCTCAGGTCGGCAGCCCCACACCCTGTCCCAGCCATCCTGGCCTTCCTCCT | |
| | |
| GCTTCCCTGGGGACGAGCGGCCCAGGCCCCCCGTCAATGCTGCAGTGTTCCGGGTGGCATTGCCCACGTC | |
| AGGATTGCTTTGCCCTCTTCAAAAAGGATCGGCTGCTACCCCCACGGGGGCCTTACCGGGCTTCGGGGTT | |
| CCCTGGGTGGGAGCACAGAAGGCCTTTTGTGGCTGATGTGAAAAGGCGCTGCCACCTTGGAGGATAAGAA | |
| GCGACCTCTGATGAGAGAGTCACGTTGGCAGACAGAAGGACACAATTTAACTTGTCGAAAAAGATTTTTG | |
| TTTCCCTTCACCCCGTGGGGCGGGAGTGGAATGAGGCAGGAAGGTTCTGTCCCCCTTCGCATGCTCTCCT | |
| AGCTTTCTTCTCCGGCGTCTCCCTTTCCTTTTTCTTGTCCGGCCTCCCTCTTTGCTCTGCTGAGATGTCC | |
| CCCTGTGTGTACCGCCTCTCAAAACGCACCCCTGTCTGTCTGCTTCAGGCCCGTGGATAGCATCTCTCT | |
| TGAGATGCGCCTGCTCTGCGGGCTTCCACTCCTGCTCTCCTTGGATCCTCACAGGGGCCAGGATGACCTT | |
| GAAAAGCACCGGTCTGATTCCATTGGCCTCAACTACCTCCTGGGTCGTCTCCTCCCCTCTTGCCCTTCAG | |
| TTTCTGCTCTGGGGTTCTCCAGGCAGGCTTCAGGCTCAGAGGCTTTGCACATGTGGTTCCTTCTGCCTGG | |
| | |
| AATGCTCTTCCCCCCAGTAACCGCGTGGTTCCCTTATCTCATCTAGGTTTTCCCGAGGTCATCTTCTCAG | |
| ACCCTGCTGGTCTACCCCATTTCAAGTGGCAGCCCCCTTTGCCAACACCACTGATCTCCCTCTGCCCCCA | |
| ACCCCTTGCCTTTCTTCATCACGTGACCACTGTCTGGCTAGAGGTGGAGTTTCTAAGAAGTCAATGATGC | |
| TTAAGCTTCAGAGCCCCTCATCAGTAGGTTCCAAGGCCCGACACCTGAATTGATACTGATAATTTTTCAT | |
| TCTTTTTTCATAAGGAATTCCACTCTCCCCACCAAACTGTATAAGCTTCAGGTCCCACAGAAGCCTGGATC | |
| GACCTGGTCCTATGTCTGACAACGCATCTGTTTTCATTCTACTGGTTCTCTCCCTCTACTGTTAAAAAAC | |
| AAACTCCAAGAGGGCAGAGGGTTTTTTAAAATTATTTATTCGATTTTTGGGGTTGTGCCGGGTCTTCACT | |
| GCTGTGTCTGGGCTTTCTCTAGTTGTGGAGAGCGGGGCTGTTCTCTAGTTTCAGTTCACGAGCTTCTCG | |
| TTGTGGCGGCTTCTCTCGTCGCGGAGCACAGGCTCTAGGGCACGCGGGCTCAGTTGTCGCAACATGCCAG | |
| CTTAGCTGCTTCCTGCCATGTGGAATCGTCCCAGACCAGGGATCGAACGCATGTGCCCGGCACTGGCAGG | |
| | |
| TGGATTCTTAGCCACTCTACCTCCAGGGAAGTCTAGAAGGTAGGTGTTTTTGTCTTTTTTTGTAAAACTA | |
| TTTTATCTCCAGGGTCCAGAACAGTGGCTATGCACAGTAGGAGCTTAATAAATGTTGCTGTATGTACGTA | |
| TATATGACAACTCCAGGTTCATACTTCTTTCAGGGCGTCACATTTCTCTTAGGATAAAGGTCAGCCTCCT | |
| TAACACACCCCACAAGGCCCTGCCCTTCTGCCTGCTCCCAGATGTGCTAGGATTCAGACTCAGGGCCTTT | |
| GCACATGCTCCTTCCTCTGTCTGATGTTCTTTCTCTCCCTGCCTCTGCCTCCATCAGGTCTCTACAGCG | |
| GGCAGTCTGCATCAGTGGGCACTCCACATATGTGGGCTCCACAGCCTCAGATATCGATGGCTGACAGTAC | |
| CACACCATCTTAGCTGAGCGACTTGAACATCCACGGATTTCAGTATCTGCAGAGGTCCTGGAACCAACCC | |
| CCTGTGGAGACTGAGGGACGACTGGACTTGAATGCTGCTTCTCTGTCTGTGCCCAGCCTGGCCCTGGGGA | |
| TACGTGTTCTGGGAGGATCTTGGAGCTTCTGTTGATAGCACTTGCTGCCACCCTCACGTGGTATCCATGC | |
| CATTGCTGGGTTAGTACTTATTTCCCTCCAGGACTGTCAGCTCCATCAGGGCAGGACCGCCTCTTGTGTG | |

TABLE 3A-continued

SEQ ID NOs: 1-2, BOVINE EXT2 AND ALX4 GENES

```
CTCCTGTATCCCCAGCGTAATGCCTGACATGTGCTCGTTTTTACTGACTCAGTCAAGAGCTGCTGAGGAG
ATGTGCAAGATAATAATACTTTAAAAAAAAAAAAAGGGAGGGAAAGACAGAAATCAGGCACAGTTAATAT
GAAAATACACAAAATCACAGACTCTCTGGGGCTTCCCTGGTGGAACAGACAGTAAAGAATCTGCCTGCAG
TGCAGGGGCCCTGGATTTGATGCCTGGCTCAGGAAGATCCCCTGGAGAAGGAAATGGCAACCCATTCCAG
TATTCTTGCCTGGAGAATCCCATGGACAGAGGAGCATGGTGGGCTGCTGTCCATGGGGTTGCAGAGTCAT
ACATGACTGAACGACTTAGCAGCAGCAGTAGCATGTCAAGTCAGAGTCGGGAGGGCATTTGTCCACAGCT
TGTAGACTGTGGTTCCTGGTGCCCTGGGGATGCGCCTCTGGGAATTCTGGGAATTCTATGGAGTGGTCCC
TACAGTCCACTGCTGTGAACGTGCAAGTGTGTGTTCACATGTGCACATATGCGAGTGTGTGTTCACGT
GTGTGTGCTCATGTACACGTATGCAAGCGTGTGTGCACACACACAGGTGTTGTGACTGGGGGTCAGGGAA

GTAGAACGAGCTGCATACGGACAGATCTCAGAGCCCCATTCCCACTTCAGACAGAGCAGTTCTGCTTTTA
CCTGTTGAGGTATTGAACTTCTGCTTCTGATGTTGTTTGAAAAGAAATAAGCTTTCCATCCAAAATCAAA
TTTGGAAATTTCTGATCTGATTTACGGAGAAGGCAATGGCACCCCACTCCAGTACTCTTGCCTGGAAAAT
CCCATGGAAGGAGGAGCCTGGTAGGCTGCAGTCCATGGGGTCGCCAGAGTCGGTCACGACTGAGTGACTT
CACTTTTCACTTTTCACTTTCCTGCATTGGAGAAGGAAATGGCAACCCACTCCAGTGTTCTTGCCTGGAGA
ATCCCAGGGACGGGGAAGCCTGGTGGGCTGCCGTCTATGGGGTCGCACAGAGTTGGACACGACTGAAGTG
ACTTAGCAGATCTGATTTAACGCCCCCTTTCCATTTTAGGGATGAGTAAACTGAGATCTAGAGATGGAGG
TCCTTGTCCTAGATCACAGAGTGAAAGGAGAACAGGACTGGGACCAACCATCAACCCCCTGCCCCACCC
CGAGGCCCTGCCCACGGCCTGTTCCCTGATGCCCAGCCCCTCTTTCTGGTTTTGGTACAGCGCTGCCGC
CTCTCAGCTGTGACCAGGCGGCCGAACACCTGGATGTCCTGGAGCTGATGGAAAAGCTCCAGGGATCCCC

ATGCTTTAATCCCATCATGTAAATCAGGAATCATTTTACTTGCAGAAGACATGACTTCCTACATGTGTGC
TGGAAAATTCACATTGTCTGGTACACCTACTCAGGGGGAAAATCCCAACACACAAAACTAACTTTCCTTT
GAGTCTTTCAGTTGATATCCACTGGCTACCTGTTCATTTATATTATTGTCTGAAAGTGCTCCTAGCAGAC
ACCCAGCAGCAAGCACTGAAGGTTTAGAAAAATCTGTGGGAGCAAAAAGCAAATGATTCCATCCACTAGT
TTCATGGGGGGTGGGGGTGTAGGTGTGAAGATATGAAAAAAAATTAAAAGGATCATTTCCCATATACTT
TGATGCTGGAACAAATACCTCTGGCCAATGTATAGGGGAGAGAAAAACCATTATTTTTTCATTCTTTAAAA
ATAAGTCTTCAATTCATTCTCTGATTACAAAAGTACATCATAGGTACTTCTGGAGAAGTAGAACTTCTAG
AAATGTACATGACTTAGAAAGTAAATATCAGTATTATTCCTAGCCCCTCCCACCAACCACAGCTAATTC
CAATTTGCTTTCAAACCTACTAAGTGTCAGGTTCTATTCTAGGCACTGGAGGGGCAACAGTGAACAAACA

TAGATGACAGTTGTGCCCTGATGGGACTCACAGCTGAATGGAGAAGAGGGGGAAATGGTCACACAATTGT
AAAAAGTCAACTGTGTTTTGCTTTGAAAAGAAGAGATATGAAAGCATAAAATCTGGGGAGAGGACCTTTC
ATGAGGATTTCTGGCGAAGCTTTGTGAGGGAGTCAAGATAGAGTTGGGAATCTCCCACGTTTGTGAAGAT
GGGAAGAAAGAGAGGTCAAGGGAGAAAAAAAACGTCCATGCAAAGGCCTGTGGCAGGAGGGCAAAGAGCG
ACATGACCAGAGGAACTGGTTCAGGCGAAGCGGCAGAGGCTCCTGGGGTTTTGTGAAGACCACGGTAAGA
TTTTTGGGTCTTTGTTCTAAGAGCAAAGAAAGCTATAAACTGTTTAAAGTAACGGTTGCTGTCTAGTCAC
TAAGTCGGGTCCAGTGCTGTTGCAATCTTATGAAATACGGTTCTCCAGGCTCCTCTGTCCGTGGGGTTTC
CCAGGCTAGAATACTGGAGTGGGCTGCCATTCTCTTCTCCAGGGATCTTCCCAACCCAGGGATGGAACAT
GCACCTCCTGTATTGGCAGGTGGATTCTTTACTGCTGAGCCACCAGGGAAGCCCCTTAAATAAGGATGCG

TATGATTATATTTGCATTTGATATATATTCATTCTGATTTTTCTTGATGCATACATGCATCAGCTAATGT      
TGTAGCAGAATGGCTTAAGCAGAAGAGATTCTGAACTGGCTCTTGTGGCTGCAGCTTGATCTGGGGTCTC      288353_R2
AAACAGTGTCTCCAGTTTCTCTCAATTTTCATCCTTTTCATCTGCCCTCCTGACTCTTCCAAGCCCCAT      
GGAGGGCCTCCTGTGGCACCAGGCGTTCATACACTATCTTTCAGCCTGTACCTCAGTGAAAAACGACTAAC      288353_F2
CTGCCTCCGCTGGCATGGCAGTTCTAGCCCTGCTCATCTTCAGCCAACCCCTAAACCAATCACTGTGTTT
AGAGGAATGCGATGCTCTGATTGGCTAGGCCTGAGTCACATGTTTCACAAGGGGCGTGGAATAAACTCT
ACCCAGAGCATATGGCCTGGTAGAGGGAAAATCCTTATGATGAAATTACTTGTAGAATTAGGGCTGAGAT
TGACCAGGAGAGGGCGCAGGGTGTGTTCTAGGAGGGTTGGAAATGTTCTATATTCCTGATCTGGGGGTAG

TTAGGCAGGTATGTGTGTGTATATGTGTGTGTGTCTGTGTGAGTGTATGCTAAGTCACTTCAGTCG
TGTCCAACTCTATGTGATTCTATGGAGTATAGGCCACCAGGTTCCTCTGACCATGGAGTTCTCCAGGCCA
GAATACTGGAGTGGGCAGCCTTTGCCTTCTCAGGGGATCTTCCCAACCCACGGATCGAACTCAAGTCTC
TTGAATTGCAGGCGTATTCTTTACCATCTGAGCTACCAGGGAAGCCTAAGAATACTGGAGTGGGTGATCT
ATCCCTTCTTTAGGGGAACTTCCTGACCCAGGAATTGAACCCAGGTCTCCTACATTGCAGACAGATTCTT
TACCAGCTGAGCTCCCAGGGAAGCCCATGTCCAGCTATACCAAGATTTTAAAAAATACCTCACTGGAGAG
TGGGAAAGAGGAAAATCGGATGTTGTTACCAAGAGGATGGTGAGTGGGTGTTCATTATAATACATTAAT
ATGCTGTGTATATACATTTGCTGTGTCTATACACAGGGTTTCCCAGTTGGCCCTAGTGGCAGAGAATCTG

CCTGCCAATGCAGGAGATGCAAAAGATGTGGGTTCGATTCCTGAGTTGGGAAGATCCCCAGAGTAGGAAA
TGGCAACCTCCTTGAGTATTCTTGCCTGGAAAATACCATGGACAGAGGAGCCTGTTGTTGAGTCGAGTCT
CTGAGTCCCATGGACTGCAGCACACCAGGCTTCCCTGTCCTTCACTATTTTCTGGAGTTTGCTCAAACTC
ATGTCTGTTGTGTCAATGATGCCATCTCACCCCATAATCTCATCCTCTGTCGCCCCCTTCTCCTCCTGCC
TTCAATCTTTCCTAGCATCAGGATCTTTCCCAATGAGTTGGCTCTTCACAGCAGGTGGCCAAAATATTGG
AGCTTCAGCTTCAGCATCAGTCCTTCCAAAGAGTATTCAGGGTTGATTTCCTTTAGGATTTGAGGGCTAC
AGTCCATGGGGCTGCAGAGAGTCGGACATGACTGAGAGATTAAGCCCTCACACACACGTATGTACGACA
TAATATATACATGTATGTTATGTATCAGTTCAGTTCAGTCGCTCAGTCGTGTCCAACTCTTTGCGACCCC
ATGGACTGAAGTATGCCAGGCTTCCCTGTCCATCACCAACTCCTGGAGTTTACTCAAACTCATGTCCATT
```

TABLE 3A-continued

SEQ ID NOs: 1-2, BOVINE EXT2 AND ALX4 GENES

```
GGGTCGATGATGCCATCCAGCCATCTCATCCTCTGTCATCTGCTTCTCCTTCTGCCTTCAATCTTTCCCA
GCATCAGGGTCTTTTCCAATGAGTCAGTTCTTCACATTAGGTGGCAAAGTATTGGAGTCTCAGCTTCAG
CATCAGTCCTTCCAATGAATATTCAGGACTGATTCCTTTAGGATGGACTGGTTGGATCTCCTTGCAGTCC
AAGGGACTCTCTAGAGTCTTCAAGAACACCACAGTTCAAAAGCATCAGTTCTTTGGCACTCAGCTTTCTT
TATAGTTCAACTCTTACATCCATACATGACTACTGGAAAAACCATAGCCTTGACTAGACGGACCTTTGTT
GGCAAAGTAATGTCTCTGCTTTTGAATATGCTGTCTAGGTTGGTCATAACTTTCCTTCCAAGGAGTAAGC
GTCTTTTAATTCCATGGCTGCAATCACCATCTGCAGTGATTTTGGAGCCCCAAAATAAAGTCTGACACT
GTTTCTACTGTTTCCCATCTATTTGTCATGAAGTGATGGGACCAGATGCCATGATCTTAGTTTTGGTTTT

CAGCTTTACTGAGGTATAATTGGCAAATAAAATTATAATACAATAAGTCCCCTATACATGAATCTTCAAG
TTGCAGACTTTCAAAGATGCAAACGTGTGTTCCATCACCGTCAGGTGTGAGTGAAACTGCGGCTTGCCCT
TCATCTCCTATTGTTGACGATCCTTCAGCTCTACTGTCTCCCACCTCCTCTCCCTTCTCCAGTCAGTAAC
TCTTCTTGACTGTTCACTCAGTGCCAGCCCCTGTGTGCCAGCTGTTGTACTGTAGTACTGTACTTTTCAA
GATTCTGTACTGTGAGATTTAAAATGTTTTCTTTATGTTTGTTTTTTAAAATGTATTATTTGTGTGAAA
AGTATTATAAACCTATTACAGTACAGTACTATATAGCTGGGGCTTCCCAATGTCTCAATGGGTAAAGAAT

CTGCCTGCAATGCAGGAGACACAGGAGACTGTGGGTTCAATCTCTGGGTCGGGAAGATCCCTTGGAGGAG
GAAAATGGCAACCCAGCCCAGTATTTTTGCCTGGAAAATCCCATGGGCAGAGAAGCCCAGGCTGTAG
TCCAAAGGGTCACAAAAAGTCAGACACAATATAACTGACTGTGTTAGTTGGGAACCTAGGCTAACTTTTT
TGGACTTACAAACAAACTGAACATAGGAACACACTCTTGGAATGGACCTCATTCGTATGCAGAGAATGTC
CAACGTGATGGTTTGATATATGGCTGCATTATGAAAGGATTCCCACTACCCAGTTAATTAGTGCATCTGT
AAGCTCACGTTTCCCTTTTTTGTTTTGTTTTCGGTGAGAACACTCAAGTTCTACTCTCTTAGCAAATTTT
GGCGTTACGGTACAGGATTTTCAACTATGGACACCGTATTGTATGTAGATAGACATTTGGTGAGAAGTGC
TGTAGCACA
```

TABLE 3B

Sequence no. identifiers for oligonucleotide sequences of Table 3

| Seq. ID | Name in TABLE 3A | Sequence |
|---|---|---|
| Seq ID NO: 8 | TH_MICRO243 | ATATTGGCCAGGTCTTGATG |
| Seq ID NO: 9 | TH_MICRO348C | AAGCTACAGACTGAGGGTTG |
| Seq ID NO: 10 | EXT2_840C | AGTAGAACGAGCTTTGCCAC |
| Seq ID NO: 11 | EXT2_744 | ACTGGGAATTGCTGGCATAG |
| Seq ID NO: 12 | TH_MICRO470C | ATGGACAGTGGAGCCTGAAA |
| Seq ID NO: 13 | TH_MICRO332 | TTCAGATTACTGCCAAGCCC |
| Seq ID NO: 14 | TH_MICRO772C | TGATCCTGGTGATGGTTACA |
| Seq ID NO: 15 | TH_MICRO573 | CTTTGTCATGGACCAGCATC |
| Seq ID NO: 16 | BALX4_4R | GGGAATCTAGCCTCAACTCA |
| Seq ID NO: 17 | ALX4_EXON4 | TGTGGCCCAGGAGATGGCCGCGCTGTGCTCCTTGGCCTTCATGCG GAGGGCCGCGATGCTCGAAGTCTTGCGGTCCGGCTCCCCGTTGAG CTCATAGCCGTTGAGGCCCGGGCTGAGGCCCGCAGCTCCAAACAG GCTGCCCATGTGCGTCTGGCCCACGTGGCTGCCAGCCCCCGAGAC GCTCAGGAAGTCGGTGACGCCGCTGGCCCCGGAGCCGGGGGGGTG GGCGTGAGGGGACATGCAGGCGGGCACCGGGTCACAGGGCACCAC ACAGGCCGGCACGGGCGAGGCGGCCCCATTGTTGCCGATCCAGGA CGGGTTCTGAAT |
| Seq ID NO: 18 | BALX4_4F | TTCCTGAGTGTTTACCTGGG |
| Seq ID NO: 19 | BALX4_3R | CCTGGCCTTCAGCATTCCTC |
| Seq ID NO: 20 | ALX4_EXON3 | CTGGGCATAGTTTTCCGCTCGGGTGAGGAGGGGCAGCTCGTAGGC TGTGGAGAAGTGGGTCCGAACCTGCTGCATTTGCCCGAAGCGTTC CCTCTTCCTCCACTTGGCCCTCCGGTTCTGGAACCAGAC |
| Seq ID NO: 21 | BALX4_3F | AGAGCAGTTGTCGCCAGGGT |
| Seq ID NO: 22 | BALX4_2_1241C | GCAGGATGGGAACGTGAACA |
| Seq ID NO: 23 | BALX4_2_889 | TTGCTCTCCGAGTCGGCCTT |

TABLE 3B-continued

Sequence no. identifiers for oligonucleotide sequences of Table 3

| Seq. ID | Name in TABLE 3A | Sequence |
|---|---|---|
| Seq ID NO: 24 | BALX4_2_836C | CCAGCTTCCTTCACACTGAG |
| Seq ID NO: 25 | ALX4_EXON2 | CTGCACGCGGGCCTCGGTGAGGTCGGTCCTCATGGCCAGCTGCTC CCGCGCGTACACATCGGGGTAGTGGGTCTTCTGGAAGACCTTCTC CAGCTCCTCCAACTGGTAGCTGGTGAAGGTGGTTCTGTTCCGCCG CTTCTTGCCCTTGTTGCTCTCCGAGTCGGCCTTCTCCATTGGGCT GGGGAGGTCGGCGCTGGCCCGGTCCTGGGGCCCCTTCACCCCAGC TTCCTTCACACTGAGGTAGCTGCTGTCCATCCCCACCGTGTCAGA GTCGGGTGGCAACTCTGGCTCACCCAGGGAGCTCTCTTTGG |
| Seq ID NO: 26 | BALX4_2_627 | GAAGCATGGGATGCAAGGTC |
| Seq ID NO: 27 | ALX4_2F | TGGGTGGGTCTGGACATGAGT |
| Seq ID NO: 28 | ALX4_2R | CGTATGGAGCGTCTGTCTAAGG |
| Seq ID NO: 29 | 216232_R | GCTAGAATCCTGAATGGTGC |
| Seq ID NO: 30 | 216232_F | GAGACAGTGTCTAAGACGCA |
| Seq ID NO: 31 | NW_216232_R2 | GCTCTGTGCATACGATGAAG |
| Seq ID NO: 32 | NW_216232_F2 | ACATTCCACAGACCTCCGTC |
| Seq ID NO: 33 | DEL5_699 | GGCATGAAAGGAGGACTCTA |
| Seq ID NO: 34 | DEL5_1109C | CGAGTCTGTTACCACTTCCT |
| Seq ID NO: 35 | DEL5_1389 | AAAGCATTGCCAAGTGTGGA |
| Seq ID NO: 36 | DEL5_1754C | ATCAATTGTGAGGTTGCCAG |
| Seq ID NO: 37 | DEL5_2006 | AGCACAGTGCTTGTCAGGAA |
| Seq ID NO: 38 | DEL5_2497C | CTGTCTGTCAAAGTTTCCGG |
| Seq ID NO: 39 | DEL5_2843 | CATTAGAAGCTGCGCCTGTT |
| Seq ID NO: 40 | DEL5_3292C | ATCTTCAGGACATTCACGGG |
| Seq ID NO: 41 | DEL5_3659 | GGAGTTGAGCAGGATGACTT |
| Seq ID NO: 42 | DEL5_5227C | AAGAGGCTGCACTAAGTCTG |
| Seq ID NO: 43 | DEL5_5516 | TAAGTCCCAGTCCATTCGCA |
| Seq ID NO: 44 | DEL5_5967C | AGCGTCATCAGAAGAACCAG |
| Seq ID NO: 45 | DEL5_6496 | ATCAGAGGTTCTGGCACGAT |
| Seq ID NO: 46 | DEL5_7040C | TATCAGGGAGGCCCACAAAC |
| Seq ID NO: 47 | DEL5_7326 | CAGGCAATTTCCAGGGAAGA |
| Seq ID NO: 48 | DEL5_7683C | TGAGGAGCTGGAATTAGGCA |
| Seq ID NO: 49 | DEL5_7991 | GAGTTCCTGCAATCCCATCA |
| Seq ID NO: 50 | TH_BIGBREAK_F | TGCTCAGGCTGGTTTCTCTTCC |
| Seq ID NO: 51 | DEL5_8750C | AAGACTCTGGTGGTTGCACA |
| Seq ID NO: 52 | TH_BIG_344C | ACGCTGCTGACTATACTGGGTG |
| Seq ID NO: 53 | TH_BIG_478C | AGATGAGTGTGAGCCGGGAACA |
| Seq ID NO: 54 | DEL5_9059 | TCATAGCTTCCTTCCGGACA |
| Seq ID NO: 55 | DEL5_9528C | ATGAAATGCGCACTGACTCC |
| Seq ID NO: 56 | DEL5_9917 | TACGGCGGCAGAATGTTTCA |
| Seq ID NO: 57 | DEL5_10399C | ACTCTAAATTCGCTGGGTGG |
| Seq ID NO: 58 | DEL5_10637 | AGGCATTCTCCCAGATCCAT |

TABLE 3B-continued

Sequence no. identifiers for oligonucleotide sequences of Table 3

| Seq. ID | Name in TABLE 3A | Sequence |
|---|---|---|
| Seq ID NO: 59 | DEL5_10942C | ACAAAGCCGCACGCAGATTT |
| Seq ID NO: 60 | CTG45_R2 | GGTCTGTATCTCCATCCACG |
| Srq ID NO: 61 | CTG45_F2 | GGTTCTTAAGGCTAATGCGC |
| Seq ID NO: 62 | CTG45_R1 | CACAGAGGCCGACGGAAGAA |
| Srq ID NO: 63 | CTG45_F1 | TCAGAGGTGGTGCTCAGAGG |
| Seq ID NO: 64 | BALX4_1_1162C | TTTAACAGCCAACGCTCCGTGC |
| Seq ID NO: 65 | BALX4_1_1068C | CGACCCAAAGTCACAAACCGCT |
| Seq ID NO: 66 | BALX4_1_1116C | ACCTGCAAGGCCGCGCTTGT |
| Seq ID NO: 67 | BALX4_1_1061 | CTGGAGTTTGAGGCTGCCGT |
| Seq ID NO: 68 | BALX4_1_1042C | CGCCTCGTTGCAAGTAGAGA |
| Seq ID NO: 69 | BALX4_1_851C/ BALX4_1_830 | GCTGACAGGAAAGTTGTGCTGA |
| Seq ID NO: 70 | ALX4_EXON1 | CGTAGCAGGGGACCTGCAAGGCCGCGTTGTGGCCGCCGCCGCCT TCCTGGAGTTTGAGGCTGCCGTCCGGGGGCGTCTTGCAGGCGCC TCGTTGCAAGTAGAGATGCGGCTGCGGCGCGGGCGGCTGCGGCT GCGGCGCGGGCGGCTGGGGCTGGAACTTGCTGAAGGAGCCCCGC GCCCCGGCGCCGCTCTCCAGAGGTGCTGCCGGGTCCTGCTGCCC CGCGCCGTAGCGGGCCCGGCTCTTGGCGTCCCCGAATCCCTGCC CTTTGGCGGCGGCTGACAGGAAAGTTGTGCTGAACTTATCACCG CCGGGGTATGCCCTAAAAGGCGACGAGCCCTCCCGGCTCTGCGA CACCGGGCTGTAGTAGGCGTCCATGGCAGCAGCCGGCGACTCGC AGTAAGAGACGCAAGTCTCAGCATT |
| Seq ID NO: 71 | BALX4_1_428 | AGTTGACCAGATCTCCCAAACCCT |
| Seq ID NO: 72 | BALX4_1_426 | AGTTGACCAGATCTCCCAAACCCTCTT |
| Seq ID NO: 73 | BALX4_1_45 | ATTCGGTCGCCACTCC |
| Seq ID NO: 74 | CTG60_F1 | GGAGTTGAGAGACCCGCACC |
| Seq ID NO: 75 | ALX4_68_249 | GGAACAGGACTTCACTACAG |
| Seq ID NO: 76 | CTG60_R1 | CCTTCTACACGGCTAATCAC |
| Seq ID NO: 77 | ALX4_68_1421C | CATCGCACTAGTCTGAGGTT |
| Seq ID NO: 78 | 320933_F2 | GGAATGCAGACACCTAGTCA |
| Seq ID NO: 79 | 320933_R2 | GTTCTAGACGCTTGCACAAC |
| Seq ID NO: 80 | ALX4_33_144 | AGCTCTAGGAAGTTGACAGG |
| Seq ID NO: 81 | ALX4_33_708C | GGTCCAGACTGTCACAGATG |
| Seq ID NO: 82 | 370933_R1 | CCTAAGGAGATGAGAAGCAG |
| Seq ID NO: 83 | 320933_F1 | GTCCTGATCTCTGATGTGCC |
| Seq ID NO: 84 | NW_419640_R1 | TTGGCTCCGCTGTCTAGAAT |
| Seq ID NO: 85 | NW_419640_F1 | TCATCTTGCTGCATGTCGGT |
| Seq ID NO: 86 | NW_250796_R2 | CAGCTTCCTGAGTGTGATCC |
| Seq ID NO: 87 | NW_250796_F2 | CATACAGACCTGGCTCAAGT |
| Seq ID NO: 88 | NW_250796_R1 | ACGCTCTGGATCTCATCCTT |
| Seq ID NO: 89 | DEL3_308 | CTTAGCTCCAGAGATGCGAA |
| Seq ID NO: 90 | NW_250796_F1 | AGTCACCTGCTACCATCTCC |

TABLE 3B-continued

Sequence no. identifiers for oligonucleotide sequences of Table 3

| Seq. ID | Name in TABLE 3A | Sequence |
|---|---|---|
| Seq ID NO: 91 | TH_BIG_895/ DEL3_2389 | CCGAACTGAACTGACACTTGCT |
| Seq ID NO: 92 | DEL3_2532C | ACCTCTATGCCACCTAGGAT |
| Seq ID NO: 93 | DPL3_2671 | AAGATGAGTCCTTGGCCACA |
| Seq ID NO: 94 | TH_BIGBREAK_R | ACGAGAGGCCTTGTCTTTGCAC |
| Seq ID NO: 95 | DEL3_2952C | TCAGTGCCTTCCTCCTCATA |
| Seq ID NO: 96 | DEL3_3269 | TGATCCTGGACTCAGTGATG |
| Seq ID NO: 97 | DEL3_3681C | ACAGATTGGAACGAGGGAGA |
| Seq ID NO: 98 | DEL3_4068 | AGTAAGCCCTCTTGAAGCCA |
| Seq ID NO: 99 | DEL3_4428C | TAGAGCTTGAGGTGCCTTGA |
| Seq ID NO: 100 | NW_197235_R1 | AACACAGCACACAGATCGGA |
| Seq ID NO: 101 | NW_197235_F1 | CTGCATGCTGATTAGCTGGT |
| Seq ID NO: 102 | 288353_R2 | TTCTGAACTGGCTCTTGTGG |
| Seq ID NO: 103 | 288353_F2 | TTCAGCCTGTACCTCAGTGA |

TABLE 4

SEQ ID NO: 3,
TIBIAL HEMIMELIA DELETION BREAKPOINT REGION

GTTTAACGAATTCGCCCTTCAGGCAATTTCCAGGGAAGAGCCAACACATG
AACCCAGAGCTCTTGATGTCCAGAGAAGCCATGGAGTGGGGAAGGAGAAA
GCAAAGAAGCAGCTACTCAGCCACCAGAGAAGATCCAGGTGGTCTGTGGC
AACTCTAAGCCCTCCCCTTACGGGTAAAGCTCCACCCACCTGGGAGCAG
GCTGCCCTTCTCCGCCCAGCCTCTCCAGCACCAATCCATTAACTGCAGTG
AACCAAGCTACTAGTCTGTCTCCCCATCCCGACCTGAAGGCAGAGGCTGT
GTCCAGGGCCTCACAGAATCCCCCAGGAGGCCAGGAACAGGGACAGGCAA
AGTCTGGTGAGGAGCTGGAATTAGGCATTTCAGTCCCCTTCTCTGTGAAA
ACTGGGCATTTGGGCCAGGAGGCGTCTGGCGTCTCTTCCAACACTGGGCG
GGACACCCATCCCGACACCAGGACCCATCATGTTGGAGGGTTGACTTCCG
GGCCTCAACCAAGGTCCCCGACCTGGCAGGTGGTCAGCCTCAGAGGAGGA
AATAAGTCATGTGGCCTCAGCTAACACCCCTTGGGCTCTCACTGCCGGGT
TTCCACACACTTAGGAAACAAAACCCCGGGTCAGGGAGCCCAGCAGAGAG
CAGGAGTCCCTGCCCCACTGGGTCACATTTGGGGATGAGTTCCTGCAATC
CCATCAGGTGCTCTTCTGTTGCCCTGGCAACCCCAGGAGCTCCCAGTGGA
GCCCATCTCATTTCTGAAGGAGGGGGAAAGGGCAAGCATCTGCTGTGCAT
GAGACACAGAGTGTGTGGCCAACTGGATGGATTACAGTGAAAGGAGACGG
TAGGAGAAGGGGCACAGGTACCCCAGCTCCTTCTTCCTTCTCCACCCTCT
GCAGTCCTTCCTTCCTTCCCACTGACTTGCCTGTGGGGTTCCATTCCCCT
TTAGGCCTCAGTTTGTTGTTGATTAGTGGCTAGGTCGTGTCCGACTCTTG
CAACCCTGTGGACTGTAGCCTGCCTCTGTCCATGGGATTTTCCCAGGCAA
GAATACTGGAGGGGGTTGCCATTTCCTTCTCCATGGGGTCTTCCTGACC
CAGGGATCGAGCCCCAGCCCGCGTCTCCTGCATCAGCGGGTGGGTTCTTT
ACCACTGAGCCACCAGAGAAGCCCAGGCCTCCGTTTGCCAAGACGGTGCT
CAGGCTGGTTTCTCTTCCTCAGAACTGAGGAAATGCTCAAGAGCTGGAGG
TGGGAGGAGGCCCCACTGCG▲GTCCTCAAGGGCAGGACCTCTATGCCACC
TAGGATGAAGGCTCCCCACGCCCACACCTCCCATCCCTTTGATGCCTGGA
GGGACAGGAAGCAGGGTGGCAAGATGGTGCCTCTGGTCTAGTCCACACCC
CACACCCCTGGTTTGGTGGTGAGGTGGCCCCATGCCTGACCAGGAAGATG
ACTCCTTGGCCACAGACTGGCCTCGCTGCATCCTCTGCTCCCTACCTCTC
CTCCTGAGGTCCCTGGGGGTGGGGGGAATTGTGGCCTCCTAGGAAAGAA
CCCACTTCATCTGTACTACAGATACCACCCCCGACCCTGAGACCACGAGA
GGCCTTGTCTTTGCACCTTAACACACCTCGTCTTTGCTCCTCTGTCTGCC
CTGCCCCCAGCCTCCATTGGTTTGACTCCTCAGTGCC

▲Indicates position of deleted DNA segment of 45,694 base pairs

TABLE 5

BLAST ANALYSIS OF SEQ ID 2 WITH SEQ ID 1

```
Query= TIBIAL HEMIMELIA DELETION BREAKPOINT
       (1686 letters)

Database: ALX4_supercontig.txt
          1 sequences; 246,969 total letters

Score     E
Sequences producing significant alignments:              (bits)  Value EXT2_ALX4_supercontig                                     2413    0.0

>EXT2_ALX4_supercontig
        Length = 246969

Score = 2413 bits (1217), Expect = 0.0
Identities = 1246/1253 (99%), Gaps = 2/1253 (0%)
Strand = Plus / Plus Query: 20       caggcaatttccagggaagagccaacacatgaacccagagctcttgatgtccagagaagc 79
                ||||||||||||||||||||||||||||||||||||||||||||||||||||||||||||
Sbjct: 189472   caggcaatttccagggaagagccaacacatgaacccagagctcttgatgtccagagaagc 189531

Query: 80       catggagtggggaaggagaaagcaaagaagcagctactcagccaccagagaagatccagg 139
                ||||||||||||||||||||||||||||||||||||||||||||||||||||||||||||
Sbjct: 189532   catggagtggggaaggagaaagcaaagaagcagctactcagccaccagagaagatccagg 189591

Query: 140      tggtctgtggcaactctaagccctcccctta cggggtaaagctccacccacctgggagca 199
                |||||||||||||||||||||||||||||||||||||||||||||||||||||||||||
Sbjct: 189592   tggtctgtggcaactctaagccctcccctta cggggtaaagctccacccacctgggagcg 189651

Query: 200      ggctgcccttctccgcccagcctctccagcaccaatccattaactgcagtgaaccaagct 259
                ||||||||||||||||||||||||||||||| ||||||||||||||||||||||||||||
Sbjct: 189652   ggctgcccttctccgcccagcctctccagcaccaacccattaactgcagtgaaccaagct 189711

Query: 260      actagtctgtctccccatcccgacctgaaggcagaggctgtgtccagggcctcacagaat 319
                ||||||||||||||||||||||||||||||||||||||||||||||||||||||||||||
Sbjct: 189712   actagtctgtctccccatcccgacctgaaggcagaggctgtgtccagggcctcacagaat 189771

Query: 320      cccccaggaggccaggaacagggacaggcaaagtctggtgaggagctggaattaggcatt 379
                ||||||||||| |||||||||||||||||||||||||||||||||||||||||||||||
Sbjct: 189772   cccccaggaggccgggaacagggacaggcaaagtctggtgaggagctggaattaggcatt 189831

Query: 380      tcagtccccttctctgtgaaaactgggcatttgggccaggaggcgtctggcgtctcttcc 439
                ||||||||||||||||||||||||||||||||||||||||||||||||||||||||||||
Sbjct: 189832   tcagtccccttctctgtgaaaactgggcatttgggccaggaggcgtctggcgtctcttcc 189891

Query: 440      aacactgggcgggacacccatcccgacaccaggacccatcatgttggagggttgacttcc 499
                ||||||||||||||||||||||||||||||||||||||||||||||||||||||||||||
Sbjct: 189892   aacactgggcgggacacccatcccgacaccaggacccatcatgttggagggttgacttcc 189951

Query: 500      gggcctcaaccaaggtccccgacctggcaggtggtcagcctcagaggaggaaataagtca 559
                |||||||||||||||| |||||||||||||||||||||||||||||||||||||||||||
Sbjct: 189952   gggcctcaaccaaggtccctgacctggcaggtggtcagcctcagaggaggaaataagtca 190011

Query: 560      tgtggcctcagctaacaccccttgggctctcactgccgggtttccacacacttaggaaac 619
                |||||||||||||||||||||| |||||||||||||||||||||||||||||||||||||
Sbjct: 190012   tgtggcctcagctaacacccc-ttgggctctcactgccgggtttccacacacttaggaaac 190070

Query: 620      aaacccgggtcagggagcccagcagagagcaggagtccctgccccactgggtcacatt 679
                ||||||| ||||||||||||||||||||||||||||||||||||||||||||||||||
Sbjct: 190071   aaaccc-gggtcagggagcccagcagagagcaggagtccctgccccactgggtcacatt 190129

Query: 680      tggggatgagttcctgcaatcccatcaggtgctcttctgttgccctggcaaccccaggag 739
                ||||||||||||||||||||||||||||||||||||||||||||||||||||||||||||
Sbjct: 190130   tggggatgagttcctgcaatcccatcaggtgctcttctgttgccctggcaaccccaggag 190189
```

TABLE 5-continued

BLAST ANALYSIS OF SEQID 2 WITH SEQID 1

```
Query: 740    ctcccagtggagcccatctcatttctgaaggagggggaaagggcaagcatctgctgtgca 799
              ||||||||||||||||||||||||||||||||||||||||||||||||||||||||||||
Sbjct: 190190 ctcccagtggagcccatctcatttctgaaggagggggaaagggcaagcatctgctgtgca 190249

Query: 800    tgagacacagagtgtgtggccaactggatggattacagtgaaaggagacggtaggagaag 859
              ||||||||||||||||||||||||||||||||||||||||||||||||||||||||||||
Sbjct: 190250 tgagacacagagtgtgtggccaactggatggattacagtgaaaggagacggtaggagaag 190309

Query: 860    gggcacaggtaccccagctccttcttccttctccaccctctgcagtccttccttccttcc 919
              ||||||||||||||||||||||||||||||||||||||||||||||||||||||||||||
Sbjct: 190310 gggcacaggtaccccagctccttcttccttctccaccctctgcagtccttccttccttcc 190369

Query: 920    cactgacttgcctgtggggttccattcccctttaggcctcagtttgttgttgattagtgg 979
              ||||||||||||||||||||||||||||||||||||||||||||||||||||||||||||
Sbjct: 190370 cactgacttgcctgtggggttccattcccctttaggcctcagtttgttgttgattagtgg 190429

Query: 980    ctaggtcgtgtccgactcttgcaaccctgtggactgtagcctgcctctgtccatgggatt 1039
              ||||||||||||||||||||||||||||||||||||||||||||||||||||||||||||
Sbjct: 190430 ctaggtcgtgtccgactcttgcaaccctgtggactgtagcctgcctctgtccatgggatt 190489

Query: 1040   ttcccaggcaagaatactggaggggggttgccatttccttctccatgggggtcttcctgac 1099
              ||||||||||||||||||||||||||||||||||||||||||||||||||||||||||||
Sbjct: 190490 ttcccaggcaagaatactggaggggggttgccatttccttctccatgggggtcttcctgac 190549

Query: 1100   ccagggatcgagccccagcccgcgtctcctgcatcagcgggtgggttctttaccactgag 1159
              |||||||||||||||||||||||||||||||||||||||| |||||||||||||||||||
Sbjct: 190550 ccagggatcgagccccagcccgcgtctcctgcatcagcaggtgggttctttaccactgag 190609

Query: 1160   ccaccagagaagcccaggcctccgtttgccaagacggtgctcaggctggtttctcttcct 1219
              ||||||||||||||||||||||||||||||||||||||||||||||||||||||||||||
Sbjct: 190610 ccaccagagaagcccaggcctccgtttgccaagacggtgctcaggctggtttctcttcct 190669

Query: 1220   cagaactgaggaaatgctcaagagctggaggtgggaggaggcccactgcg 1270
              ||||||||||||||||||||||||||||||||||||||||||||||||||
Sbjct: 190670 cagaactgaggaaatgctcaagagctggaggtgggaggaggcccactgcg 190720

Score = 737 bits (372), Expect = 0.0
 Identities = 402/416 (96%)
 Strand = Plus / Plus Query: 1271   gtcctcaagggcaggacctctatgccacctaggatgaaggctccccacgcccacacctcc 1330
              |||||||||||||||||||||||||||||||||||||||||||||||||||| |||||||
Sbjct: 236414 gtcctcaagggcaggacctctatgccacctaggatgaaggctccccacgcccatacctcc 236473

Query: 1331   catccctttgatgcctggagggacaggaagcagggtggcaagatggtgcctctggtctag 1390
              ||||||||||||||||||||||||||||||||||||||||||||||||||||||||||||
Sbjct: 236474 catccctttgatgcctggagggacaggaagcagggtggcaagatggtgcctctggtctag 236533

Query: 1391   tccacaccccacacccctggtttggtggtgaggtggcccatgcctgaccaggaagatga 1450
              ||||||||||||||||||||||||||||||||||||||||||||||||||||||||||||
Sbjct: 236534 tccacaccccacacccctggtttggtggtgaggtggcccatgcctgaccaggaagatga 236593

Query: 1451   ctccttggccacagactggcctcgctgcatcctctgctccctacctctcctcctgaggtc 1510
                |||||||||||||||||||||||||||||||||||||||||||||||||||||||||
Sbjct: 236594 gtccttggccacagactggcctcgctgcatcctctgctccctacctctcctcctgaggtc 236653

Query: 1511   cctnnnnnnnnnnnnnaattggtggcctcctaggaaagaacccacttcatctgtactacag 1570
              |||                  ||||||||||||||||||||||||||||||||||||||||
Sbjct: 236654 cctgggggtgggggaattggtggcctcctaggaaagaacccacttcatctgtactacag 236713

Query: 1571   ataccaccccgaccctgagaccacgagaggccttgtctttgcaccttaacacacctcgt 1630
              ||||||||||||||||||||||||||||||||||||||||||||||||||||||||||||
Sbjct: 236714 ataccaccccgaccctgagaccacgagaggccttgtctttgcaccttaacacacctcgt 236773

Query: 1631   ctttgctcctctgtctgccctgcccccagcctccattggtttgactcctcagtgcc 1686
              ||||||||||||||||||||||||||||||||||||||||||||||||||||||||
Sbjct: 236774 ctttgctcctctgtctgccctgcccccagcctccattggtttgactcctcagtgcc 236829
```

TABLE 6

Summary of PCR product generated by
three primers to determine TH status

| | Normal (−/−) | Hetero Carrier (+/−) | TH phenotype |
|---|---|---|---|
| Primer 1-2 ($L_{12}$) | − | + (from mutant allele) | + |
| Primer 1-3 ($L_{13}$) | + | + (from normal allele) | − |

− no amplified DNA product generated by PCR
+ amplified DNA product generated by PCR
Primer 1: primer binds upstream region
Primer 2: primer binds downstream region
Primer 3: primer binds middle (e.g. mutant) region

We claim:

1. A method of diagnosing a deletion mutation in a bovine genome, said method comprising:
   a) obtaining a DNA sample from the bovine; and
   b) analyzing said DNA sample to determine the presence or absence of a deletion mutation in the Aristaless-like4 (ALX4) gene, wherein said deletion mutation comprises deletion of SEQ ID NO:4 and said deletion mutation is at a breakpoint between nucleotides 1270 and 1271 of SEQ ID NO:3.

2. The method of claim 1, wherein said deletion mutation results in a mutant bovine gene comprising SEQ ID NO:3.

3. The method of claim 1, further comprising identifying the
   DNA sample as from a heterozygous carrier of the Tibial hemimelia (TH) gene.

4. The method of claim 1, wherein the step of analyzing the DNA sample is by polymerase chain reaction (PCR).

5. The method of claim 4, wherein the step of PCR further comprises:
   a) providing a forward primer which binds specifically to a first selected region of SEQ ID NO:2, said first region between base 27,000 and 29,692 of SEQ ID NO:2;
   b) providing a reverse primer which binds specifically to a second selected region of SEQ ID NO:2, said second region between base 75,386 and 78,000; and
   c) performing PCR amplification such that said forward and reverse primer generate an amplified DNA product only in the presence of a DNA sample comprising the deletion mutation.

6. The method of claim 5, wherein the forward primer has a sequence that is SEQ ID NO:5 and the reverse primer has a sequence that is SEQ ID NO:6.

7. The method of claim 5 further comprising providing a third primer, said third primer capable of specific binding to at least a portion of SEQ ID NO:3 and corresponding to a DNA sequence encompassed by bases 29,693 to 75,385 of SEQ ID NO:2, wherein sample DNA that contains SEQ ID NO:3 results in amplification of a first DNA product by said forward primer and said third primer, and wherein DNA that does not contain said SEQ ID NO:3 results in amplification of a second DNA product by said forward primer and said reverse primer, and wherein said forward primer and said third primer binding position are separated by a separation distance that is less than or equal to 4000 base pairs.

8. The method of claim 7, wherein the third primer has a sequence that is SEQ ID NO:7.

9. The method of claim 8, wherein the forward primer has a sequence that is SEQ ID NO:5, and the reverse primer has a sequence that is SEQ ID NO:6.

10. The method of claim 4 further comprising providing a forward primer and a reverse primer, wherein said forward primer and said reverse primer are capable of specific binding to said DNA sample to generate an amplification DNA product only if the DNA sample comprises SEQ ID NO:4.

11. The method of claim 1 further comprising
    a) providing a probe or primer that specifically binds to the sample of DNA having said deletion mutation; and
    b) identifying the sample as containing the deletion mutation for DNA samples that hybridize with said probe or primer;
    wherein said specific binding is at a location that includes nucleotides 1270 and 1271 of SEQ ID NO:4.

12. The method of claim 1, wherein the analyzing the DNA sample further comprises providing a DNA probe or primer, wherein said DNA probe or primer specifically binds to SEQ ID NO:4 and does not specifically bind to bovine DNA comprising SEQ ID NO:3.

13. The method of claim 1, wherein the analyzing the DNA sample further comprises providing a DNA probe or primer, wherein said DNA probe or primer specifically binds to bovine DNA comprising SEQ ID NO:3 and does not specifically bind to bovine DNA comprising SEQ ID NO:4.

14. The method of claim 1, wherein said analyzing the DNA sample comprises DNA sequencing.

15. The method of claim 1, wherein said analyzing the DNA sample comprises providing a probe or primer comprising a purified oligonucleotide, wherein the oligonucleotide has a length between about 15 to 50 nucleotides and specifically binds to a target sequence of SEQ ID NO:4 or complement thereof.

16. The method of claim 1, wherein said analyzing the DNA of the bovine subject comprises providing a probe or primer comprising a purified oligonucleotide, wherein the oligonucleotide has a length between about 15 to 50 nucleotides and specifically binds a breakpoint mutation region in the bovine genome, said breakpoint located between bases 1270 and 1271 of SEQ ID NO:3.

17. The method of claim 1, wherein the bovine is a Shorthorn composite.

18. The method of claim 17, wherein the DNA sample is obtained from blood or semen.

19. A method for screening a bovine to determine if said bovine carries the gene for TH, said method comprising:
    a) providing a biological sample which was removed from said bovine to be screened; and
    b) conducting a biological assay to determine the presence of a mutation in the gene responsible for TH, wherein the mutation comprises a deletion of bases 29,693 to 75,385 in SEQ ID NO:2.

20. A method of diagnosing a mutation in a bovine genome, wherein said mutation is associated with tibial hemimelia (TH), and wherein the mutation is a deletion mutation of SEQ ID NO:4 in the gene that encodes Aristaless-like4 (ALX4) protein, said method comprising:

obtaining a DNA sample from the bovine; and analyzing said DNA sample to determine the presence or absence of the deletion mutation of SEQ ID NO:4 at a breakpoint between nucleotides 1270 and 1271 of SEQ ID NO:3 in the ALX4 gene, wherein said DNA having an upstream region, a downstream region, and a middle region that comprises SEQ ID NO:4 that separates said upstream region from said downstream region indicates absence of the deletion mutation, and wherein said DNA having said upstream region and said downstream region in a contiguous configuration by deletion of SEQ ID NO:4 is identified as having the deletion mutation;

wherein the step of analyzing the DNA sample is by polymerase chain reaction further comprising the steps of:

providing a forward primer which binds specifically to a first selected region of SEQ ID NO:2, said first region between base 27,000 and 29,692 of SEQ ID NO:2;

providing a reverse primer which binds specifically to a second selected region of SEQ ID NO:2, said second region between base 75,386 and 78,000;

performing PCR amplification such that said forward and reverse primer generate an amplified DNA product only in the presence of a DNA sample comprising the deletion of SEQ ID NO:4 from the bovine genome; and providing a third primer, said third primer capable of specific binding to at least a portion of the middle region of DNA, said middle region corresponding to a DNA sequence encompassed by bases 29,693 to 75,385 of SEQ ID NO:2, wherein DNA that contains said middle region results in amplification of a first DNA product by said forward primer and said third primer, and wherein DNA that does not contain said middle region results in amplification of a second DNA product by said forward primer and said reverse primer, and wherein said forward primer and said third primer binding positions are separated by a separation distance that is less than or equal to 4000 base pairs.

21. The method of claim 20, wherein the forward primer has a sequence that is SEQ ID NO:5, the reverse primer has a sequence that is SEQ ID NO:6, and the third primer has a sequence that is SEQ ID NO:7.

22. The method of claim 20, wherein the forward primer has a sequence that is SEQ ID NO:5, and the reverse primer has a sequence that is SEQ ID NO:6.

23. The method of claim 7, wherein:

said forward primer is selected from the group consisting of: TH_BIGBREAK_F (SEQ ID NO:5), DEL5__7991 (SEQ ID NO:49; nucleotides 29109 to 29128 of SEQ ID NO:2), DEL5__7683C (SEQ ID NO:48; nucleotides 28782 to 28801 of SEQ ID NO:2), DEL5__7326 (SEQ ID NO:47; nucleotides 28444 to 28463 of SEQ ID NO:2), DEL5__7040C (SEQ ID NO:46; nucleotides 28139 to 28158 of SEQ ID NO:2), DEL5__6496 (SEQ ID NO:45; nucleotides 27614 to 27633 of SEQ ID NO:2) and DEL5$_{13}$ 5967C (SEQ ID NO:44; nucleotides 27091 to 27110 of SEQ ID NO:2);

said reverse primer is selected from the group consisting of the reverse complement to the sequence of: DEL3__2532C (SEQ ID NO:92; nucleotides 75401 to 75420 of SEQ ID NO:2), DEL3__2671 (SEQ ID NO:93; nucleotides 75559 to 75568 of SEQ ID NO:2), TH_BIGBREAK_R (SEQ ID NO:94; nucleotides 75709 to 75730 of SEQ ID NO:2), DEL3__2952C (SEQ ID NO:95; nucleotides 75794 to 75813 of SEQ ID NO:2), DEL3__3269 (SEQ ID NO:96; nucleotides 76157 to 76176 of SEQ ID NO:2), DEL3__3681C (SEQ ID NO:97; nucleotides 76550 to 76569 of SEQ ID NO:2), DEL3__4068 (SEQ ID NO:98; nucleotides 76956 to 76975 of SEQ ID NO:2), DEL3__4428C (SEQ ID NO:99; nucleotides 77297 to 77316 of SEQ ID NO:2), NW__197235_R1 (SEQ ID NO:100; nucleotides 77626 to 77645 of SEQ ID NO:2) and NW__197235_F1 (SEQ ID NO:101; nucleotides 77895 to 77914 of SEQ ID NO:2); and said third primer is selected from the group consisting of the reverse complement to the sequence of: DEL5__8750C (SEQ ID NO:51; nucleotides 29849 to 29868 of SEQ ID NO:2), TH_BIG__344C (SEQ ID NO:52; nucleotides 29941 to 29962 of SEQ ID NO:2), TH_BIG__478C (SEQ ID NO:53; nucleotides 30075 to 30096 of SEQ ID NO:2), DEL5__9059 (SEQ ID NO:54; nucleotides 30177 to 30196 of SEQ ID NO:2), DEL5__9528C (SEQ ID NO:55; nucleotides 30627 to 30646 of SEQ ID NO:2), DEL5__9917 (SEQ ID NO:56; nucleotides 31035 to 31054 of SEQ ID NO:2), DEL5__10399C, (SEQ ID NO:57; nucleotides 31498 to 31517 of SEQ ID NO:2) DEL5__10637 (SEQ ID NO:58; nucleotides 31755 to 31774 of SEQ ID NO:2) and DEL5__10942C (SEQ ID NO:59; nucleotides 32041 to 32060 of SEQ ID NO:2).

24. The method of claim 7, wherein said first amplified DNA product and said second amplified DNA product have different nucleotide lengths.

* * * * *

UNITED STATES PATENT AND TRADEMARK OFFICE
CERTIFICATE OF CORRECTION

PATENT NO. : 8,158,356 B2  Page 1 of 1
APPLICATION NO. : 11/549888
DATED : April 17, 2012
INVENTOR(S) : Beever et al.

It is certified that error appears in the above-identified patent and that said Letters Patent is hereby corrected as shown below:

In claim 23, column 398, line 10, replace "DEL5$_{13}$5967C" with --DEL5_5967C--.

In claim 23, column 398, line 18, replace "75730of SEQ ID NO:2)" with --75730 of SEQ ID NO:2)--.

Signed and Sealed this
Nineteenth Day of June, 2012

David J. Kappos
*Director of the United States Patent and Trademark Office*